US007947275B2

(12) United States Patent
Sirbasku

(10) Patent No.: US 7,947,275 B2
(45) Date of Patent: *May 24, 2011

(54) COMPOSITIONS AND METHODS FOR DEMONSTRATING SECRETORY IMMUNE SYSTEM REGULATION OF STEROID HORMONE RESPONSIVE CANCER CELL GROWTH

(75) Inventor: David A. Sirbasku, Houston, TX (US)

(73) Assignee: Signe Biopharma, Inc., Irving, TX (US)

( * ) Notice: Subject to any disclaimer, the term of this patent is extended or adjusted under 35 U.S.C. 154(b) by 1010 days.

This patent is subject to a terminal disclaimer.

(21) Appl. No.: 09/852,958

(22) Filed: May 10, 2001

(65) Prior Publication Data

US 2002/0012954 A1 Jan. 31, 2002

Related U.S. Application Data

(60) Provisional application No. 60/203,314, filed on May 10, 2000, provisional application No. 60/208,348, filed on May 31, 2000, provisional application No. 60/208,111, filed on May 31, 2000, provisional application No. 60/229,071, filed on Aug. 30, 2000, provisional application No. 60/231,273, filed on Sep. 8, 2000.

(51) Int. Cl.
| | |
|---|---|
| C07K 16/18 | (2006.01) |
| C07K 16/26 | (2006.01) |
| C12N 5/07 | (2010.01) |
| G01N 33/74 | (2006.01) |
| A61K 31/138 | (2006.01) |
| A61K 35/16 | (2006.01) |
| A61K 39/00 | (2006.01) |

(52) U.S. Cl. ............... 424/155.1; 435/7.23; 514/171
(58) Field of Classification Search ............. 435/4, 7.23; 424/155.1; 514/171
See application file for complete search history.

(56) References Cited

U.S. PATENT DOCUMENTS

| | | | | |
|---|---|---|---|---|
| 4,849,508 | A | 7/1989 | Magnin et al. | 530/387 |
| 4,859,585 | A | 8/1989 | Sonnenschein et al. | 435/29 |
| 5,075,425 | A | 12/1991 | Kotitschke et al. | 530/387 |
| 5,135,849 | A | 8/1992 | Soto et al. | 435/29 |
| 5,405,772 | A | 4/1995 | Ponting | 435/240.31 |
| 6,200,547 | B1 | 3/2001 | Volkonsky et al. | |
| 2002/0006630 | A1* | 1/2002 | Sirbasku | 435/7.23 |

FOREIGN PATENT DOCUMENTS

| | | |
|---|---|---|
| EP | 0702960 A | 3/1996 |
| RU | WO 92/13563 | 8/1992 |
| WO | WO 91/16061 | 10/1991 |
| WO | WO 95/09011 | 4/1995 |
| WO | WO98/04681 | 2/1998 |
| WO | WO98/08934 | 3/1998 |
| WO | WO 00/06723 | 2/2000 |

OTHER PUBLICATIONS

Yildirim (Tr. J. Med. Sci., 1998, 28:383-387.*
Biology online definition of "steroid hormone" (pp. 1-2 ; Nov. 25, 2009).*
MedicineNet.com definition of :thyroid hormone (pp. 1-2; Nov. 25, 2009).*
ATCC website search for "MCF-K" (p. 1; Nov. 25, 2009).*
ATCC website search for "MTW9/PL2" (p. 1; Nov. 25, 2009).*
ATCC website search for"MCF-7A" (p. 1; Nov. 25, 2009).*
ATCC website search for "H-301" (p. 1; Nov. 25, 2009).*
Furuya et al (Cancer Research, Dec. 1989, vol. 49, pp. 6670-6674).*
Hoffman ('The Biochemistry of Clinical Medicine', 1970, pp. 48 and 55).*
Karmanos Cancer Center website search ("MCF-7"; Apr. 20, 2010; pp. 1-2).*
Partial International Search in PCT/US 01/15183, Applicant David A. Sirbasku, International Filing Date Oct. 5, 2001, Date of Mailing Aug. 8, 2002, pp. 4.
Partial International Search in PCT/US 01/15171, Applicant David A. Sirbasku, International Filing Date Oct. 5, 2001, Date of Mailing Aug. 29, 2002, pp. 3.
JP Parisot et al., "Altered Expression of the IGF-1 Receptor in a Tamoxifen-Resistant Human Breast Cancer Cell Line," British Journal of Cancer, vol. 79, No. 5-6, pp. 693-700, 1999.
David Danielpour et al., "Growth of MTW9/PL2 Estrogen-Responsive Rat Mammary Tumor Cells in Hormonally Defined Serum-Free Media," In Vitro Cell. Dev. Biol., vol. 24, No. 1, pp. 42-52, Jan. 1988.
Research Diagnostics Inc., 'Online! Jan. 10, 2000, XP002207863, Retrieved from the Internet: <URL:http://www.researchd.com/rdiabs/igref.ser.htm> 'retrieved on Jul. 29, 2002! The whole document, p. 1.
Jorge E. Moreno-Cuevas et al., "Estrogen Mitogenic Action. I. Demonstration of Estrogen-Dependent MTW9/PL2 Carcinogen-Induced Rat Mammary Tumor Cell Growth in Serum-Supplemented Culture and Technical Implications," In Vitro Cell. Dev. Biol.—Animal, vol. 36, No. 7, pp. 410-427, Jul.-Aug. 2000.
David A. Sirbasku et al., "Estrogen Mitogenic Action. II. Negative Regulation of the Steroid Hormone-Responsive Growth of Cell Lines Derived From Human and Rodent Target Tissue Tumors and Conceptual Implications," In Vitro Cell. Dev. Biol.—Animal, vol. 36, No. 7, pp. 428-446, Jul.-Aug. 2000.
Helenice Gobbi et al., "Transforming Growth Factor-β and Breast Cancer Risk in Women With Mammary Epithelial Hyperplasia," Journal of the National Cancer Institute, vol. 91, No. 24, pp. 2096-2101, Dec. 15, 1999.

(Continued)

*Primary Examiner* — Lynn Bristol
(74) *Attorney, Agent, or Firm* — Woodard, Emhardt, Moriarty, McNett & Henry LLP

(57) ABSTRACT

Serum-containing and serum-free immunoglobulin inhibitors of steroid hormone responsive cancer cell growth are disclosed, along with their methods of production. Also disclosed are defined cell culture media, assay protocols, and model systems using the inhibitors for demonstrating steroid hormone growth effects of natural and synthetic substances, and other cell culture applications. The disclosed compositions and methods employing the immunoglobulin inhibitors are also useful as reagents in research, and for the diagnosis, treatment and prevention of mucus epithelial cancers.

26 Claims, 148 Drawing Sheets

OTHER PUBLICATIONS

Ruth Sager, "Expression Genetics in Cancer: Shifting the Focus from DNA to RNA," Proc. Natl. Acad. Sci. USA, vol. 94, No. 3, pp. 952-955, Feb. 1997.

Sanford D. Markowitz et al., "Tumor Suppressor Activity of the TGF-β Pathway in Human Cancers," Cytokine & Growth Factor Reviews, vol. 7, No. 1, pp. 99-102, 1996.

International Search Report, PCT/US02/36632 dated Jul. 28, 2003 (1 p.).

PCT International Search Report, PCT/US01/15183 dated 20/112002, 3 pages.

Zhihong Chen et al., *A serum-free medium for hybridoma cell culture*, Cytotechnology (1993), vol. 11, pp. 169-174, XP001117870, ISSN: 0920-9069 p. 170, media and additives; pp. 173-174.

Database Biosis 'Online! Biosciences Information Service, Philadelphia, PA US; 1992, Eby J.E. et al., *Preparation of Iron-Deficient Tissue Culture Medium by Deferoxamine-Sepharose Treatment and Application to the Differential Actions of Apotransferrin and Difieric Transferrin*, Database assession No. PREV199294057133, XP002218819 cited in the application abstract & Analytical Biochemistry, vol. 203, No. 2, 1992, pp. 317-325, ISSN:0003-2697.

Database Biosis 'Online! Biosciences Information Service, Philadelphia, PA US 1993, Eby John E. et al., *Apotransferrin stimulation of thyroid hormone dependent rat pituitary tumor cell growth in serum-free chemically defined medium: Role of iron(III) chelation*, Database accession No. PREV199396113609, XP002218820 cited in application abstract & Journal of Cellular Physiology, vol. 156, No. 3, 1993, pp. 588-600, ISSN:0021-9541.

Neumannova Vera et al., *Growth of human tumor cell lines in transferrin-free, low-iron medium*, In Vitro Cellular & Developmental Biology Animal, vol. 31, No. 8, 1995, pp. 625-632, XP001118629, ISSN:1071-2690, the whole document.

C.A. Janeway et al., *Chapter 3: Structure of the Antibody Molecule and the Immunoglobulin Genes: Structural variation in immunoglobulin constant regions; Chapter 9: The Humoral Immune Response: The distribution and functions of immunoglobulin isotypes*, Immuno. Biology—The Immune System In Health and Disease, Fourth Edition, Elsevier Science Ltd./Garland Publishing (1999) pp. 104, 326-327.

R.G. Hamilton, *Chapter 3: Human Immunoglobulins*, Handbook of Human Immunology, CRC Press LLC (1997) pp. 65-109.

A.J. Alberg et al., *Epidemiology, prevention, and early detection of breast cancer [Breast]*, Current Opinion in Oncology (Nov. 1997) vol. 9, 6, pp. 505-511, PMID: 9370070 [PubMed—indexed for MEDLINE); Abstract http://www.ncbi.nlm.nih.gov/entrez/querv.fcgi?cmd=Retrieve&db=PubMed&list_uids=9370070&d... printed on Feb. 15, 2003 (1 page).

A.J. Alberg et al., *Epidemiology, prevention, and early detection of breast cancer [Breast]*, Current Opinion in Oncology (Nov. 1999) vol. 11, No. 6, pp. 435, 13 pages.

J.C. Allegra et al., *Growth of a Human Breast Cancer Cell Line in Serum-Free Hormone-Supplemented Medium*, Cancer Research (Nov. 1978) vol. 38, pp. 3823-3829.

J.F. Amara et al., *17β-Estradiol Has A Biphasic Effect On GH Cell Growth*, Endocrinology, Dept. of Pharm., Endocrinology (Mar. 1983) vol. 112, No. 3, pp. 1141-1143.

T. Anttila et al., *Serotypes of Chlamydia Trachomatis and Risk for Development of Cervical Squamous Cell Carcinoma, JAMA (Jan. 2001) vol. 285, No. 1, pp. 47-51, PMID: 11150108 [PubMed—indexed for MEDLINE); Abstract http://www.ncbi.nlm.nih.gov/entrez/query.fcgi?cmd=Retrieve&db=PubMed&list_uids=11150108&d... printed on Feb. 15, 2003 (2 pages).

T. Anttila et al., *Serotypes of Chlamydia Trachomatis and Risk for Development of Cervical Squamous Cell Carcinoma*, JAMA (Jan. 2001) vol. 285, No. 1, pp. 47-51, (Original Contribution) 11 pages.

J.M. Zenilman, *Chlamydia and Cervical Cancer: A Real Association?* JAMA (Jan. 2001) 285, No. 1, pp. 81-83, (Editorial) 5 pages.

P.E. Gravitt et al., *Chlamydia trachomatis and Cervical Squamous Cell Carcinoma*, JAMA (Apr. 2001) vol. 285, No. 13, pp. 1703-1706, (Letters) 11 pages).

B.A. Arrick, *Therapeutic implications of the TGF-beta system*, J: Mammary Gland Biol. Neoplasia. (Oct. 1996) 1(4):391-7, PMID: 10887513 [PubMed—indexed for MEDLINE); Abstract http://www.ncbi.nlm.nih.gov/entrez/query.fcgi?cmd=Retrieve&db=PubMed&list_uids=10887513&d... printed on Feb. 21, 2003 (1 page).

C.L. Arteaga et al., *Blockade of the Epidermal Growth Factor Receptor Inhibits Transforming Growth Factor α-Induced but Not Estrogen-Induced Growth of Hormone-Dependent Human Breast Cancer*, Molecular Endocrinology (Nov. 1988) vol. 2, No. 1 pp. 1064-1069.

C.L. Arteaga et al., *Blockade of the Type I Somatomedin Receptor Inhibits Growth of Human Breast Cancer Cells in Athymic Mice*, J. Clin. Invest. (Nov. 1989) vol. 84, pp. 1418-1423.

C.L. Arteaga et al., *The multifunctional role of transforming growth factor (TGF)-beta s on mammary epithelial cell biology*, Breast Cancer Res. Treat. 1996; 38(1):49-56, PMID: 8825122 [PubMed—indexed for MEDLINE]; Abstract; http://www.ncbi.nlm.nih.gov/entrez/quety.fcgi?cmd=Retrieve&db=PubMed&list_uids=8825122&d... printed on Feb. 21, 2003 (1 page).

C.L. Arteaga et al., *Transforming Growth factor beta: potential autocrine growth inhibitor of estrogen receptor-negative human breast cancer cells*, Breast Cancer Res Treat. (Jul. 1998) 48(14):3898-904, PMID: 3164252 [PubMed—indexed for MEDLINE]; Abstract; http://www.ncbi.nlm.nih.gov/entrez/query.fcgi?cmd=Retrieve&db=PubMed&list_uids=3164252&d... printed on Feb. 21, 2003 (2 pages).

A.M. Soto, *The Role of Estrogens On The Proliferation of Human Breast Tumor Cells (MCF-7)*, J. Steroid Biochem. (1985) vol. 23, No. 1, pp. 87-94.

M.A. Bakos et al., *Expression and purification of biologically active domain I of the human polymeric immunoglobulin receptor*, Mol. Immunol. (Feb. 1994) 31(2):165-8, PMID: 8309479 [PubMed—indexed for MEDLINE]; Abstract; http://www.ncbi.nlm.nih.gov/entrez/query.fcgi?cmd=Retrieve&db=PubMed&list_uids=8309479&d... printed on Feb. 22, 2003, 1 page.

M.A. Bakos et al., *Characterization of a critical binding site for human polymeric Ig on secretory component*, J. Immunol. (Nov. 1991) 147(10):3419-26, PMID: 1940346 [PubMed—indexed for MEDLINE]; Abstract Http://www.ncbi.nlm.nih.gov/entrez/query.fcgi?cmd=Retrieve&db=PubMed&list_uids=1940346&d... printed on Feb 20, 1003, 1 page.

M.A. Bakos et al., *A Conserved Binding Site on the Receptor for Polymeric Ig Is Homologous to CDRI of Ig Vk Domains*, J. Immunol. (Aug. 1993) vol. 151, No. 3, pp. 1346-1352.

D. Barnes et al., *Growth of a human mammary tumour cell line in a serum-free medium*, Nature, Macmillan Journals Ltd. (Oct. 1979) vol. 281, No. 5730, pp. 388-389.

J. Baselga et al., *Phase II study of weekly intravenous recombinant humanized anti-p185HER2 monoclonal antibody in patients with HER2/neu-overexpressing metastatic breast cancer*, Comment in J. Clin. Oncol. (Mar. 1996) vol. 14, No. 3, pp. 697-699, PMID: 8622019 [PubMed—indexed for MEDLINE]; Abstract, http://www.ncbi.nlm.nih.gov/entrez/query.fcgi?cmd=Retrieve&db=PubMed&list_uids=8622019&dc printed on Feb. 22, 2003, 2 pages.

V. Beral et al., *Overview of the Epidemiology of Immunodeficiency—Associated Cancers*, J. Natl. Cancer Inst. Monogr. (1998) No. 23, pp. 1-6.

P. Brandtzaeg et al., *Immunoglobulin M: Local Synthesis and Selective Secretion in patients with Immunoglobulin A Deficiency*, Science (Mar. 1968) vol. 160, pp. 789-791.

Y. Berthois et al., *Phenol red in tissue culture media is a weak estrogen: Implications concerning the study of estrogen-responsive cells in culture*, Proc. Natl. Acad. Sci. USA (Apr. 1986) vol. 83, No. 8, pp. 2496-2500.

S. Bhatia et al., *Breast Cancer and Other Second Neoplasms after Childhood Hodgkin's Disease*, N. Engl. J. Med., Mar. 21, 1996, vol. 334, No. 12, pp. 745-751 (Original Articles), 15 pages.

S.S. Donaldson et al., *Second Cancers after Hodgkin's Disease in Childhood*, N. Engl. J. Med., Mar. 21, 1996, vol. 334, No. 12, pp. 792-794 (Editorials), 4 pages.

F.E. Mirer et al., *Late Effects of Treatment for Childhood Hodgkin's Disease*, N. Engl. J. Med., Aug. 1, 1996, vol. 335, No. 5, pp. 352-355 (Correspondence), 12 pages.

I. Bieche et al., *Loss and gain of distinct regions of chromosome 1q in primary breast cancer*, Clin. Cancer Res. (Jan. 1995) vol. 1, No. 1, pp. 123-127, PMID: 9815894 [PubMed—indexed for MEDLINE], Abstract, http://www.ncbi.nlm.nih.gov/entrez/query.fcgi?cmd=Retrieve&db=PubMed&list_uids=9815894&dc..., printed on Feb. 21, 2003, 1 page.

I. Bieche et al., *Deletion mapping of Chromosomal Region 1p32-pter in Primary Breast Cancer*, Genes, Chromosomes & Cancer (Mar. 1999), vol. 24, No. 3, pp. 255-263.

R.D. Bindal et al., *Bis(4-hydroxyphenyl)(2-(phenorysulfonyl)phenyl)methane: Isolation and Structure Elucidation of a Novel Estrogen from Commercial Preparations of Phenol Red (Phenolsulfonphthalein)*, J. Med. Chem. (Oct. 1988) vol. 31, No. 10, pp. 1978-1983.

R.D. Bindal et al., *Lipophilic Impurities, Not Phenolsulfonphthalein, Account for the Estrogenic Activity in Commercial Preparation of Phenol Red*, J. Steroid Biochem (Sep. 1988) vol. 31, No. 3, pp. 287-293.

W.P. Bocchinfuso et al., *Mammary gland development and tumorigenesis in estrogen receptor knockout mice*, J. Mammary Gland Biol. Neoplasia (Oct. 1977) vol. 2, No. 4, pp. 323-334, PMID: 10935020 [PubMed—indexed for MEDLINE], Abstract, http://www.ncbi.nlm.nih.gov/enrez/query.fcgi?cmd=Retrieve&db=PubMed&list_uids=109335020&... printed on Feb. 21, 2003, 1 page.

E. Boder, *Ataxia-telangiectasia: some historic, clinical and athologic observations*, Birth Defects Orig. Artic. Ser. 1975;11(1):255-70, PMID: 1096982 [PubMed—indexed for MEDLINE], Abstract, http://www.ncbi.nlm.nih.gov/enrez/query.fcgi?cmd=Retrieve&db=PubMed&list_uids=1096982&... printed on Feb. 21, 2003, 1 page.

P. Bordigoni et al., *Improvement of cellular immunity and IgA production in immunodeficient children after treatment with synthetic serum thymic factor (FTS)*, Lancet (Aug. 1982) vol. 2, No. 8293, pp. 293-297, PMID: 6124716 [PubMed—indexed for MEDLINE], Abstract, http://www/ncbi.nlm.nih.gov/enrez/query.fcgi?cmd=Retrieve&db=PubMed&list_uids=6124716&... printed on Feb. 12, 2003, 1 page.

P.N. Boyaka et al., *Strategies for mucosal vaccine development*, Am. J. Trop. Med. Hyg (Apr. 1999) vol. 4 Supple., pp. 35-45, PMID: 10344675 [PubMed—indexed for MEDLINE], Abstract, http://www.ncbi.nlm.nih.gov/enrez/query.fcgi?cmd=Retrieve&db=PubMed&list_uids=10344675&... printed on Feb. 21, 2003, 1 page.

P. Brandtzaeg, *Role of J Chain and Secretory Component in Receptor-Mediated Glandular and Hepatic Transport of Immunoglobulins in Man*, Scand. J. Immunol. (Aug. 1985) vol. 22, No. 2, pp. 111-146.

P. Brandtzaeg, Part IV. *Transport of IgA and the Role of the Liver: The Secretory Immune System of Lactating Human Mammary Glands Compared With Other Exocrine Organs*, Annals N.Y. Acad. Sciences (Jun. 1983) vol. 409, pp. 353-382.

P. Brandtzaeg, *Immunoglobulin M: local synthesis and selective secretion in patients with immunoglobulin A deficiency*, Science (May 1968) vol. 160, No. 829, pp. 789-791, PMID 4171541 [PubMed—indexed MEDLINE], Abstract, http://www.ncbi.nlm.nih.gov/enrez/query.fcgi?cmd=Retrieve&db=PubMed&list_uids=4171541&... printed on Feb. 21, 2003, 1 page.

P. Brandtzaeg, *The secretory immune system of lactating human mammary glands compared with other exocrine organs*, Annals N.Y. Acad. Sciences (Jun. 1983) vol. 409, pp. 353-382, PMID 6408971 [PubMed—indexed for MEDLINE], Abstract, http://www.ncbi.nlm.nih.gov/enrez/query.fcgi?cmd=Retrieve&db=PubMed&list—uids=6408971&... printed on Feb. 20, 2003, 1 page.

P. Brandtzaeg et al., *Direct evidence for an integrated function of J chain and secretory component in epithelial transport of immunoglobulins*, Nature (Sep. 1984) vol. 311, No. 5981, pp. 71-73.

P. Brandtzaeg, *Molecular and cellular aspects of the secretory immunoglobulin system*, APMIS (Jan. 1995) vol. 103, No. 1, pp. 1-19, PMID 7695886 [PubMed—indexed for MEDLINE], Abstract, http://www.ncbi.nlm.nih.gov/enrez/query.fcgi?cmd=Retrieve&db=PubMed&list_uids=7695886&... printed on Feb. 22, 2003, 1 page.

D.A. Bronzert et al., *Transforming growth factor-beta induces platelet-derived growth factor (PDGF) messenger RNA and PDGF secretion while inhibiting growth in normal human mammary epithelial cells*, Mol. Endocrinol (Jul. 1990) vol. 4, No. 7, pp. 981-989, PMID 2178225 [PubMed—indexed for MEDLINE], Abstract, http://www.ncbi.nlm.nih.gov/enrez/query.fcgi?cmd=Retrieve&db=PubMed&list_uids=2178225&... printed on Feb. 19, 2003, 1 page.

M.G. Brattain et al., *Defects of TGF-beta receptor signaling in mammary cell tumorigenesis*, J. Mammary Gland Biol. Neoplasia (Oct. 1996) vol. 1, No. 4, pp. 365-372, PMID 10887510 [PubMed—indexed for MEDLINE], Abstract, http://www.ncbi.nlm.nih.gov/enrez/query.fcgi?cmd=Retrieve&db=PubMed&Iist_uids=10887510&... printed on Feb. 21, 2003, 1 page.

J.W. Brewer et al., *Mechanism and subcellular localization of secretory IgM polymer assembly*, J. Biol. Chem. (Jun. 1994) vol. 269, No. 25, pp. 17338-17348.

P. Briand et al., *Long-Term Cultivation of a Human Breast Cancer Cell Line, MCF-7, in a Chemically Defined Medium. Effect of Estradiol*, Anticancer Research (Jan.-Feb. 1986) vol. 6, No. 1, pp. 85-90.

J. Brolin et al., *Immunohistochemistry and biochemistry in detection of androgen, progesterone, and estrogen receptors in benign and malignant human prostatic tissue*, Prostate (1992) vol. 20, No. 4, pp. 281-295, PMID 1376911 [PubMed—indexed for MEDLINE], Abstract, http://www.ncbi.nlm.nih.gov/enrez/query.fcgi?cmd=Retrieve&db=PubMed&list_uids=1376911&... printed on Feb. 20, 2003, 1 page.

J.C. Cambier, *Inhibitory receptors abound*? Proc. Natl. Acad. Sci. USA (Jun. 1997) vol. 94, No. 12, pp. 5993-5995.

L.A. Castagnetta et al., *Human prostate cancer: a direct role for oestrogens*, Ciba Found Symp (1995) vol. 191, pp. 269-286; discussion pp. 286-289, PMID 8582203 [PubMed—indexed for MEDLINE], Abstract, http://www.ncbi.nlm.nih.gov/enrez/query.fcgi?cmd=Retrieve&db=PubMed&list_uid=8582203&... printed on Feb. 20, 2003, 1 page.

D. Chakravarthy et al., *Expression and secretion of TGF-beta isoforms and expression of TGF-beta-receptors I, II and III in normal and neoplastic human breast*, Int. J. Oncol. (Jul 1000) vol. 15, No. 1, pp. 187-194, PMID 10375614 [PubMed—indexed for MEDLINE], Abstract, http://www.ncbi.nlm.nih.gov/enrez/query.fcgi?cmd=Retrieve&db=PubMed&Iist_uids=10375614&... printed on Feb. 22, 2003, 1 page.

D. Chalbos et al., *Estrogens stimulate cell proliferation and induce secretory proteins in a human breast cancer cell line (T47D)*, J. Clin. Endocrinol. Metab. (Aug. 1982) vol. 55, No. 2, pp. 276-283.

T.R. Chen et al., *WiDr is a derivative of another colon adenocarcinoma cell line, HT-29*, Cancer Genet Cytogenet (Jul. 1987) vol. 1, pp. 125-134, PMID 3472642 [PubMed—indexed for MEDLINE], Abstract, http://www.ncbi.nlm.nih.gov/enrez/query.fcgi?cmd= Retrieve&db=PubMed&list_uids=3472642&... printed on Feb. 19, 2003, 1 page.

M.E. Conley et al., *Intravascular and mucosal immunoglobulin A: two separate but related systems of immune defense*? Ann Intern Med. (Jun. 1987) vol. 106, No. 6, pp. 892-899, PMID 3579073 [PubMed—indexed for MEDLINE], Abstract, http://www.ncbi.nlm.nih.gov/enrez/query.fcgi?cmd=Retrieve&db=PubMed&list_uids=3579073&... printed on Feb 22, 2003, 1 page.

P. Corvol. et al., *Species Distribution of Testosterone-Binding Globulin*, Biol. Reprod. (Apr. 1973) vol. 8, No. 3, pp. 277-282.

J.F. Couse et al., *Estrogen Receptor Null Mice: What Have We Learned and Where Will They Lead Us*? Endocrine Reviews (Jun. 1999) vol. 20, No. 3, pp. 358-417.

M. Daeron, *Fc Receptor Biology*, Annu. Rev. Immunol. (1997) vol. 15, pp. 203-234.

D.A. Damassa et al., *Biological Effects of Sex Hormone-Binding Globulin on Androgen-Induced Proliferation and Androgen Metabolism in LNCaP Prostate Cells*, Endocrinology (Jul. 1991) vol. 29, No. 1, pp. 75-84.

C.W. Daniel et al., *The role of TGF-beta in patterning and growth of the mammary ductal tree*, J. Mammary Gland Biol. Neoplasia (Oct. 1996) vol. 1, No. 4, pp. 331-341, PMID 10887507 [PubMed—indexed for MEDLINE], Abstract, http://www.ncbi.nlm.nih.gov/enrez/query.fcgi?cmd=Retrieve&db=PubMed&list_uids=10887507&... printed on Feb 21, 2003, 1 page.

D. Danielpour et al., *Growth of MTW9/PL2 Estrogen-Responsive Rat Mammary Tumor Cells in Hormonally Defined Serum-Free Media*, In Vitro Cell Dev. Biol. (Jan. 1988) vol. 24, No. 1, pp. 42-52.

P. Darbre et al., *Effect of Estradiol On Human Breast Cancer Cells in Culture*, Cancer Research (Jan. 1983), vol. 43, No. 1, pp. 349-354.

P.D. Darbre et al., *Effects of Estradiol and Tamoxifen on Human Breast Cancer Cells in Serum-free Culture*, Cancer Research (Jul. 1984) vol. 44, No. 7, pp. 2790-2793.

G. Del Giudice et al., *Mucosal Delivery of Vaccines*, Methods (Sep. 1999) vol. 19, No. 1, pp. 148-155.

R.B. Dickson et al., *Estrogenic Regulation of Growth and Poly peptide Growth Factor Secretion in Human Breast Carcinoma*, Endocrine Reviews (Feb. 1987) vol. 8, No. 1, pp. 29-43.

R.B. Dickson et al., *Induction of epidermal growth factor-related polypeptides by 17 beta-estradiol in MCF-7 human breast cancer cells*, Endocrinology (Jan. 1986) vol. 118, No. 1, pp. 138-142, PMID 3000728 [PubMed—indexed for MEDLINE], Abstract, http://www.ncbi.nlm.nih.gov/enrez/query.fcgi?cmd=Retrieve&db=PubMed&list_uids=3000728&... printed on Feb. 19, 2003, 1 page.

R.B. Dickson et al., *Chapter 8: Estrogen Receptor-Mediated Processes in Normal and Cancer Cells*, J. Natl. Cancer Inst. Monogr. (2000) No. 27, pp. 135-145.

C.T. Eastment et al., *Human Platelet lysate Contains Growth Factor Activities for Established Cell Lines Derived From Various Tissues of Several Species*, In Vitro (1980) vol. 16, No. 8, pp. 694-705.

J.E. Eby et al., *Apotransferrin Stimulation of Thyroid Hormone Dependent Rat Pituitary Tumor Cell Growth in Serum-Free Chemically Defined Medium: Role of FE(III) Chelation*, J. Cellular Physiology (Sep. 1993) vol. 156, No. 3, pp. 588-600.

J.E. Eby et al., *Preparation of Iron-Deficient Tissue Culture Medium by Deferoxamine-Sepharose Treatment and Application to the Differential Actions of Apotransferrin and Differric Transferrin*, Anal. Biochem. (Jun. 1992) vol. 203, No. 2, pp. 317-325.

K. el-Bayoumy et al., *Comparative tumorigenicity of benzo[a]akyrene, 1-nitropyrene and 2-amino-1-methyl-6-phenylimidazo[4,5-b]pyridine administered by gavage to female CD rats*, Carcinogenesis (Feb. 1995) vol. 16, No. 2, pp. 431-434.

L.W. Engel et al., *Establishment and Characterization of Three New Continuous Cell Lines Derived from Human Breast Carcinomas*, Cancer Research (Oct. 1978), vol. 38, No. 10, pp. 3352-3364.

E. Enmark et al., *Oestrogen receptors—an overview*, J. Intern. Med. (Aug. 1999) No. 146, pp. 133-138.

E. Enmark et al., *Human Estrogen Receptor β-Gene Structure, Chromosomal Localization, and Expression Pattern*, J. Clin. Endocrinol. Metab. (Dec. 1997) vol. 82, No. 12, pp. 4258-4265.

R.H. Evans, *The Steroid and Thyroid Hormone Receptor Superfamily*, Science (May 1988) vol. 240, No. 4854, pp. 889-895, PMID 3283939 [PubMed—indexed for MEDLINE], Abstract, http://www.ncbi.nlm.nih.gov/enrez/query.fcgi? cmd=Retrieve&db=PubMed&list_uids=3283939&... printed on Feb. 20, 2003, 1 page.

E. Fallgreen-Gebauer et al., *The covalent Linkage of Secretory Component to IgA. Structure of sIgA*, Biol. Chem. (Nov. 1993) vol. 374, No. II, pp. 1023-1028.

P. Femlund et al., *A Simple Two-Step Procedure for the Simultaneous Isolation of Corticosteroid Binding Globulin and Sex Hormone Binding Globulin from Human Serum by Chromatography on Cortisol-Sepharose and Phenyl-Sepharose*, J. Steroid Biochem (Jun. 1981) vol. 14, No. 6, pp. 545-552.

L. Fiore et al., *Poliovirus Sabin Type 1 Neutralization Epitopes Recognized by Immunoglobulin A Monoclonal Antibodies*, J. Virol. (Sep. 1997) vol. 71, No. 9, pp. 6905-6912.

B. Fisher et al., *Tamoxifen for Prevention of Breast Cancer: Report of the National Surgical Adjuvant Breast and Bowel Project P-1 Study*, J. Natl. Cancer Inst., Articles (Sep. 1998) vol. 90, No. 18, pp. 1371-1388.

W.H. Fridman, *Fc receptors and immunoglobulin binding factors*, FASEB J. (Sep. 1991) vol. 5, No. 12, pp. 2684-2690, PMID 1916092 [PubMed—indexed for MEDLINE], Abstract, http://www.ncbi.nlm.nih.gov/enrez/query.fcgi?cmd= Retrieve&db=PubMed&list_uids=1916092&... printed on Feb. 15, 2003, 1 page.

S.A. Fuqua et al., *Variant human breast tumor estrogen receptor with constitutive transcriptional activity*, Cancer Res. (Jan. 1991) vol. 51, No. 1, pp. 105-109, PMID 1988075 [PubMed—indexed for MEDLINE], Abstract, http://www.ncbi.nlm.nih.gov/enrez/query.fcgi?cmd= Retrieve&db=PubMed&list_uids=1988075&... printed on Feb 20, 2003, 1 page.

S.A. Fuqua et al., *Inhibition of estrogen receptor action by a naturally occurring variant in human breast tumors*, Cancer Res. (Jan. 1992) vol. 52, No. 2, pp. 483-486, PMID 1728420 [PubMed—indexed for MEDLINE], Abstract, http://www.ncbi.nlm.nih.gov/enrez/query.fcgi?cmd= Retrieve&db=PubMed&list_uids=1728420&... printed on Feb. 20, 2003, 1 page.

S.A. Fuqua et al., *Expression of Wild-Type Estrogen Receptor Beta and Variant Isoforms in Human Breast Cancer*, Cancer Res. (Nov. 1999) vol. 59, No. 21, pp. 5425-5428.

R.W. Furlanetto et al., *Somatomedin-C Receptors and Growth Effects in Human Breast Cells Maintained in Long-Term Tissue Culture*, Cancer Res. (May 1984) vol. 44, No. 5, pp. 2122-2128.

V. Giguere et al., *Identification of a new class of steroid hormone receptors*, Nature (Jan. 1988) vol. 331, No. 6151, pp. 91-94, PMID 3267207 [PubMed—indexed for MEDLINE], Abstract, http://www.ncbi.nlm.nih.gov/enrez/query.fcgi?cmd= Retrieve&db=PubMed&list_uids=3267207&... printed on Feb. 12, 2003, 1 page.

H. Gobbi et al., *Transforming Growth Factor-Beta and Breast Cancer Risk in Woman With Mammary Epithelial Hyperplasia*, J. Natl. Cancer Inst. (Dec. 1999) vol. 91, No. 24, pp. 2096-2101.

D. Gospodarowicz et al., *Heparin protects basic and acidic FGF from inactivation*, J. Cell Physiol. (Sep. 1986) vol. 128, No. 3, pp. 475-484, PMID 3528177 [PubMed—indexed for MEDLINE], Abstract, http://www.ncbi.nlm.nih.gov/enrez/query.fcgi?cmd= Retrieve&db=PubMed&list_uids=3528177&... printed on Feb. 20, 2003, 1 page.

M.L. Graham et al., *T47DCO cells, genetically unstable and containing estrogen receptor mutations, are a model for the progression of breast cancers to hormone resistance*, Cancer Res. (Oct. 1990) vol. 50, No. 19, pp. 6208-6217, PMID 2400987 [PubMed—indexed for MEDLINE], Abstract, http://www.ncbi.nlm.nih.gov/enrez/query.fcgi?cmd= Retrieve&db=PubMed&list_uids=2400987&... printed on Feb. 20, 2003, 1 page.

J.A. Gustafsson, *Seeking Ligands for Lonely Orphan Receptors*, Science (May 1999) 284(5418):1285-6, Science (May 1999) 284(5418):1362-5, Science (May 1999) 284(5418):1365-8.

J.A. Gustafsson, *Estrogen receptor beta—a new dimension in estrogen mechanism of action*, J. Endocrinol (Dec. 1999) vol. 163, No. 3, pp. 379-383.

J.A. Gustafsson et al., *Estrogen receptor beta in the breast: role in estrogen responsiveness and development of breast cancer*, J. Steroid Biochem Mol. Biol. (Nov. 2000) vol. 74, No. 5, pp. 245-248.

J.M. Hall et al., *Linkage of Early-Onset Familial Breast Cancer to Chromosome 17q21*, Science (Dec. 1990) vol. 250, No. 4988, pp. 1684-1689.

E. Haug et al., *Receptors for 17beta-estradiol in prolactin-secreting rat pituitary cells*, Mol. Cell Endocrinol (Oct. 1978) vol. 12, No. 1, pp. 81-95, PMID 569089 [PubMed—indexed for MEDLINE], Abstract, http://www.ncbi.nlm.nih.gov/enrez/query.fcgi?cmd= Retrieve&db=PubMed&list_uids=569089&... printed on Feb. 19, 2003, 1 page.

I.C. Henderson et al., *The relationship between prognostic and predictive factor in the management of breast cancer*, Breast Cancer Res. Treat (1998) vol. 52, No. 1-3, pp. 261-288, PMID 10066087 [PubMed—indexed for MEDLINE], Abstract, http://www.ncbi.nlm.nih.gov/enrez/query.fcgi?cmd=Retrieve&db=PubMed&list_uids=10066087&... printed on Feb. 21, 2003. 1 page.

J.S. Horoszewicz et al., *LNCaP model of human prostatic carcinoma*, Cancer Res. (Apr. 1983) vol. 43, No. 4, pp. 1809-1818.

K.B. Horwitz et al., *Steroid Receptor Analyses of Nine Human Breast Cancer Cell Lines*, Cancer Res. (Aug. 1978) vol. 38, No. 8, pp. 2434-2437.

M. Hosobuchi, *Effects of transforming growth factor beta on growth of human mammary epithelial cells in culture*, In Vitro Cell Dev Biol (Aug. 1989) vol. 24, No. 8, pp. 705-713, PMID 2548988 [PubMed—indexed for MEDLINE], Abstract, http://www.ncbi.nlm.nih.gov/enrez/query.fcgi?cmd=Retrieve&db=PubMed&list_uids=2548988&... printed on Feb. 21, 2003, 1 page.

S. Jackson et al., *Normal human sera contain antibodies directed at Fab of IgA*, J Immunol (Apr. 1987) vol. 138, No. 7, pp. 2244-2248, PMID 3494062 [PubMed—indexed for MEDLINE], Abstract, http:// www.ncbi.nlm.nih.gov/enrez/query.fcgi?cmd=Retrieve&db=PubMed&list_uids=3494062&... printed on Feb. 21, 2003, 1 page.

N. Janin et al., *Breast cancer risk in ataxia telangiectasia (AT) heterozygotes: haplotype study in French AT families*, Br J Cancer (Jun. 1999) vol. 80, No. 7, pp. 1042-1045, PMID 10362113 [PubMed—indexed for MEDLINE], Abstract, http://www.ncbi.nlm.nih.gov/enrez/query.fcgi?cmd=Retrieve&db=PubMed&list_uids=10362113&... printed on Feb. 21, 2003, 1 page.

E. Haug, *Progesterone suppression of estrogen-stimulated prolactin secretion and estrogen receptor levels in rat pituitary cells*, Endocrinology (Feb. 1979) vol. 104, No. 2, pp. 429-437, PMID 109280 [PubMed—indexed for MEDLINE], Abstract, http://www.ncbi.nlm.nih.gov/enrez/query.fcgi?cmd=Retrieve&db=PubMed&list_uids=109280&... printed on Feb. 19, 2003, 1 page.

J. Gorski et al., *Hormone receptors: studies on the interaction of estrogen with the uterus*, Recent Prog Horm Res. (1968) vol. 24, pp. 45-80, PMID 4885833 [PubMed—indexed for MEDLINE], Abstract, http://www.ncbi.nlm.nih.gov/enrez/query.fcgi?cmd=Retrieve&db=PubMed&list_uids=4885833&... printed on Feb. 20, 2003, 1 page.

K. el-Bayoumy, *Environmental carcinogens that may be involved in human breast cancer etiology*, Chem Res. Toxicol (Sep.-Oct. 1992) vol. 5, No. 5, pp. 585-590, PMID 1445997 [PubMed—indexed for MEDLINE], Abstract, http://www.ncbi.nlm.nih.gov/enrez/query.fcgi?cmd=Retrieve&db=PubMed&list_uids=1445997&... printed on Feb. 21, 2003, 1 page.

D.F. Easton et al., *The genetic epidemiology of BRCA1. Breast Cancer Linkage Consortium*, Lancet (Sep. 1994) vol. 344, No. 8924, pp. 761, PMID 7915813 [PubMed—indexed for MEDLINE], Abstract, http://www.ncbi.nlm.nih.gov/enrez/query.fcgi?cmd=Retrieve&db=PubMed&list_uids=7915813&... printed on Feb. 15, 2003, 1 page.

S.C. Brooks et al., *Estrogen receptor in a human cell line (MCF-7) from breast carcinoma*, J Biol Chem (Sep. 1973) vol. 248, No. 17, pp. 6251-6253, PMID 4353636 [PubMed—indexed for MEDLINE], Abstract, http://www.ncbi.nlm.nih.gov/enrez/query.fcgi?cmd=Retrieve&db=PubMed&list_uids=4353636&... printed on Feb. 19, 2003, 1 page.

W.S. Bullough, *Chalone control mechanisms*, Life Sci (Feb. 1975) vol. 16, No. 3, pp. 323-330, PMID 123999 [PubMed—indexed for MEDLINE], Abstract, http://www.ncbi.nlm.nih.gov/enrez/query.fcgi?cmd=Retrieve&db=PubMed&list_uids=123999&... printed on Feb. 12, 2003, 1 page.

E.V. Jensen et al., *A two-step mechanism for the interaction of estradiol with rat uterus*, Proc Natl. Acad. Sci USA (Feb. 1968) vol. 59, No. 2, pp. 632-638, PMID 5238991 [PubMed—indexed for MEDLINE], Abstract, http://www.ncbi.nlm.nih.gov/enrez/query.fcgi?cmd=Retrieve&db=PubMed&list_uids=5238991&... printed on Feb. 20, 2003, 1 page.

E.V. Jensen et al., *Estrogen-receptor interaction*, Science (Oct. 1973) vol. 182, No. 108, pp. 126-134, PMID 4354173 [PubMed—indexed for MEDLINE], Abstract, http://www.ncbi.nlm.nih.gov/enrez/query.fcgi?cmd=Retrieve&db=PubMed&list_uids=4354173&... printed on Feb. 20, 2003, 1 page.

F.E. Johansen et al., *Role of J Chain in Secretory Immunoglobulin Formation*, Scand. J. Immunol. (Sep. 2000) vol. 52, No. 3, pp. 240-248.

M.E. Kaighn et al., *Establishment and characterization of a human prostatic carcinoma cell line (PC-3)*, Invest. Urol. (Jul. 1979) No. 1, pp. 16-23, PMID 447482 [PubMed—indexed for MEDLINE], Abstract, http://www.ncbi.nlm.nih.gov/enrez/query.fcgi?cmd=Retrieve&db=PubMed&list_uids=447482&... printed on Feb. 19, 2003, 1 page.

M. Kaufmann, *Review of known prognostic variables*, Recent Results Cancer Res. (1996) vol. 140, pp. 77-87, PMID 8787079 [PubMed—indexed for MEDLINE], Abstract, http://www.ncbi.nlm.nih.gov/enrez/query.fcgi?cmd=Retrieve&db=PubMed&list_uids=8787079&... printed on Feb. 21, 2003, 1 page.

K.P. Karey et al., *Differential Responsiveness of Human Breast Cancer Cell Lines MCF-7 and T47D to Growth Factors and 17 Beta-Estradiol*, Cancer Res. (Jul. 1988) vol. 48, No. 14, pp. 4083-4092.

J.L. Kelsey et al., *Epidemiology of Breast Cancer*, Epidemiol Rev (1990), vol. 12, pp. 228-240.

R. Kemler et al., *In vitro studies on the selective binding of IgG from different species to tissue section s of the bovine mammary glands*, Eur J. Immunol (Sep. 1975) vol. 5, No. 9, pp. 603-608, PMID1993319 [PubMed—indexed for MEDLINE], Abstract, http://www.ncbi.nlm.nih.gov/enrez/query.fcgi?cmd=Retrieve&db=PubMed&list_uids=11993319&... printed on Feb. 15, 2003, 1 page.

N.J. Kenney et al., *Expression of Transforming Growth Factor Alpha Antisense mRNA Inhibits the Estrogen-Induced Production of TGF Alpha and Estrogen-Induced Proliferation of Estrogen-Responsive Human Breast Cancer Cells*, J. Cell Physiol (Sep. 1993) vol. 156, No. 3, pp. 497-514.

R.S. Kerbel et al., *Analysis of established human carcinoma cell lines for lynmphoreticular-associated membrane receptors*, Int. J. Cancer (Nov. 1977) vol. 20, No. 5, pp. 673-679, PMID 924690 [PubMed—indexed for MEDLINE], Abstract, http://www.ncbi.nlm.nih.gov/enrez/query.fcgi?cmd=Retrieve&db=PubMed&list_uids=924690&... printed on Feb. 21, 2003, 1 page.

I. Keydar et al., *Establishment and characterization of a cell line of human breast carcinoma origin*, Eur J. Cancer (May 1979), *vol. 15, No. 5 , pp. 659-670*.

M.S. Khan et al., *Size isomers of testosterone-estradiol-binding globulin exist in the plasma of individual men and women*, Steroids (May 1985), vol. 45, No. 5, pp. 463-472, PMID 3834662 [PubMed—indexed for MEDLINE], Abstract, http://www.ncbi.nlm.nih.gov/enrez/query.fcgi?cmd=Retrieve&db=PubMed&list_uids=3834662&... printed on Feb. 21, 2003, 1 page.

K Kim et al., *Immunoglobulin G Subclasses in Human Colostrum, Milk and Saliva*, Acta Paediatr (Feb. 1992) vol. 81, No. 2, pp. 113-118, PMID 1515753 [PubMed—indexed for MEDLINE], Abstract, http://www.ncbi.nlm.nih.gov/enrez/query.fcgi?cmd=Retrieve&db=PubMed&list_uids=1515753&... printed on Feb. 15, 2003, 1 page.

W.L. Kirkland et al., *Control of Cell Growth. III. Direct Mitogenic Effect of Thyroid Hormones on an Estrogen-Dependent Rat Pituitary Tumor Cell Line*, J. Natl. Cancer Inst. (Jun. 1976) vol. 56, No. 6, pp. 1159-1164.

C. Knabbe et al., *Evidence that transforming growth factor-beta is a hormonally regulated negative growth factor in human breast cancer cells*, Cell (Feb. 1987) vol. 48, No. 3, pp. 417-428, PMID 2879636 [PubMed—indexed for MEDLINE], Abstract, http://www.ncbi.nlm.nih.gov/enrez/query.fcgi?cmd=Retrieve&db=PubMed&list_uids=2879636&... printed on Feb. 19, 2003, 1 page.

H. Kondoh et al., *Jacalin, a jackfruit lectin, precipitates IgA1 but not IgA2 subclass on gel diffusion reaction*, J. Immunol Methods (Apr. 1986) vol. 88, No. 2, pp. 171-173, PMID 3082992 [PubMed—indexed for MEDLINE], Abstract, http://www.ncbi.nlm.nih.gov/enrez/query.fcgi?cmd=Retrieve&db=PubMed&list_uids=3082992&... printed on Feb. 21, 2003, 1 page.

H. Kubagawa et al., *A novel pair of immunoglobulin-like receptors expressed by B cells and myeloid cells*, Proc Natl. Acad. Sci USA (May 1997) vol. 94, No. 12, pp. 5993-5995.

M. Krainer et al., *Differential contributions of BRCA1 and BRCA2 to early-onset breast cancer*, N. Engl J Med (May 1997) vol. 336, No. 20, pp. 1416-1421, (Original Articles) 12 pages.

P. Krajci et al., *Molecular cloning and exon-intron mapping of the gene encoding human transmembrane secretory component (the poly-1g receptor)*, Eur J Immunol (Sep. 1992) vol. 22, No. 9, pp. 2309-2315.

P. Krajci et al., *Secretory component mRNA and protein expression of colorectal adenomas an carcinomas*, Br J Cancer (Jun. 1996) vol. 73, No. 12, pp. 1503-1510.

P. Krajci et al., *The gene encoding human transmembrane secretory component (locus P1GR) is linked to D1S58 on chromosome 1*, Hum Genet (Nov. 1992) vol. 90, No. 3, pp. 215-219, PMID 1487233 [PubMed—indexed for MEDLINE], Abstract, http://www.ncbi.nlm.nih.gov/enrez/query.fcgi?cmd=Retrieve&db=PubMed&list_uids=1487233&... printed on Feb. 21, 2003, 1 page.

P. Krajci et al., *The human transmembrane secretory component (poly-1g receptor): molecular cloning, restriction fragment length*

*polymorphism and chromosomal sublocalization*, Hum Genet (Oct. 1991) vol. 87, No. 6, pp. 642-648.

P. Krajci et al., *Cloning, chromosomal localization, and linkage analysis of the gene encoding human transmembrane secretory component (the poly-1g receptor)*, Adv Exp. Med Biol (1995) No. 371A, pp. 617-623, PMID 8526003 [PubMed—indexed for MEDLINE], Abstract, http://www.ncbi.nlm.nih.gov/enrez/query.fcgi?cmd=Retrieve&db=PubMed&list_uids=8526003&... printed on Feb. 21, 2003, 1 page.

G.G. Kuiper et al., *Cloning of a novel receptor expressed in rat prostate and ovary*, Proc Natl. Acad. Sci USA (Jun. 1996) vol. 93, No. 12, pp. 5925-5930.

G.G. Kuiper et al., *Interaction of estrogen chemicals and phytoestrogens with estrogen receptor beta*, Endocrinology (Oct. 1998) vol. 139, No. 10, pp. 4252-4263.

G.G. Kuiper et al., *Comparison of the ligand binding specificity and transcript tissue distribution of estrogen receptors alpha and beta*, Endocrinology (Mar. 1997) vol. 138, No. 3, pp. 863-870.

R. Kumar et al., *The structure of nuclear hormone receptors*, Steroids (May 1999) vol. 64, No. 5, pp. 310-319.

I. Laursen et al., *Serum albumin as a modulator on growth of the human breast cancer cell line, MCF-7*, Anticancer Res. (Mar.-Apr. 1990) vol. 10, No. 2A, pp. 343-351, PMID 2346307 [PubMed—indexed MEDLINE], Abstract, http://www.ncbi.nlm.nih.gov/enrez/query.fcgi?cmd=Retrieve&db=PubMed&list_uids=2346307&... printed on Feb. 21, 2003, 1 page.

P. Lemieux et al., *The Role of the Estrogen Receptor in Tumor Progression*, J. Steroid Biochem Mol Biol (Jan. 1996), vol. 56, Nos. 1-6, pp. 87-91.

J.J. Letterio et al., *Regulation of Immune Responses by TGF-beta*, Annu Rev Immunol, *No. 16, pp. 137-161*.

C. Lengauer et al., *Genetic instability in colorectal cancers*, Nature (Apr. 1997), vol. 386, No. 6625, pp. 623-627 [Letter] 10 pages.

L.M. Loomes et al., *Purification and characterization of human immunoglobulin IgA1 and IgA2 isotypes from serum*, J Immunol Methods (Aug. 1991) vol. 141, No. 2, pp. 209-218, PMID 1880427 [PubMed—indexed for MEDLINE], Abstract, http://www.ncbi.nlm.nih.gov/enrez/query.fcgi?cmd=Retrieve&db=PubMed&list_uids=1880427&... printed on Feb. 21, 2003, 1 page.

M.L. Loupart et al., *Allelic imbalance on chromosome 1 in human breast cancer. I. Minisatellite and RFLP analysis*, Genes Chromosomes Cancer (Jan. 1995) vol. 12, No. 1, pp. 16-23, PMID 7534106 [PubMed—indexed for MEDLINE], Abstract, http://www.ncbi.nlm.nih.gov/enrez/query.fcgi?cmd=Retrieve&db=PubMed&list_uids=7534106&... printed on Feb. 21, 2003, 1 page.

E. Lullau et al., *Antigen Binding Properties of Purified Immunoglobulin A and Reconstituted Secretory Immunoglobulin A Antibodies*, J Biol Chem (Jul. 1996) vol. 271, No. 27, pp. 16300-0.

S. Mathew et al., *Transforming growth factor receptor gene TGFBR2 maps to human chromosome band 3p22*, Genomics (Mar. 1994) vol. 20, No. 1, pp. 114-115, PMID 8020936 [PubMed—indexed for MEDLINE], Abstract, http://www.ncbi.nlm.nih.gov/enrez/query.fcgi?cmd= Retrieve&db=PubMed&list_uids=8020936&... printed on Feb. 21, 2003, 1 page.

M.I. McBurney et al., *Colonic carcinogenesis: the microbial feast or famine mechanism*, Nutt Cancer (1987) vol. 10, Nos. 1-2, pp. 23-28, PMID 3039469 [PubMed—indexed for MEDLINE], Abstract, http://www.ncbi.nlm.nih.gov/enrez/query.fcgi?cmd=Retrieve &db=PubMed&list_uids=3039469&... printed on Feb. 15, 2003, 1 page.

J. Mestecky et al., *Immunoglobulin A (IgA): Molecular and Cellular Interactions Involved in IgA Biosynthesis and Immune Response*, Adv Immunol (1987) vol. 40, pp. 153-245.

J. Mestecky et al., *Evaluation of monoclonal antibodies with specificity for human IgA, IgA subclasses and allotypes and secretory component. Results of an IUIS/WHO collaborative study*, J Immunol Methods (Jun. 1996), vol. 193, No. 2, pp. 103-148.

J.E. Moreno-Cuevas et al., *Estrogen mitogenic action. III. Is phenol red a "red herring"?*, In Vitro Cell Dev Biol Anim (Jul.-Aug. 2000) vol. 36, No. 7, pp. 447-464.

W.L. McKeehan et al., *Frontiers in Mammalian Cell Culture*, In Vitro Cell Dev Biol (Jan. 1990) vol. 26, No. 1, pp. 9-23.

S. Mosselman et al., *ER beta: identification and characterization of a novel human estrogen receptor*, FEBS Lett (Aug. 1996) vol. 392, No. 1, pp. 49-53, PMID 8769313 [*PubMed—indexed for MEDLINE*], Abstract, http://www.ncbi.nlm.nih.gov/enrez/query.fcgi?cmd=Retrieve&db=PubMed&list_uids=8769313&... printed on Feb 20, 2003, 1 page.

L.C. Murphy et al., *Variant estrogen receptor mRNA species detected in human breast cancer biopsy sample*, Mol Endocrinol (Apr. 1989) vol. 3, No. 4, pp. 687-693, PMID 2725532 [PubMed—indexed for MEDLINE], Abstract, http://www.ncbi.nlm.nih.gov/enrez/query.fcgi?cmd=Retrieve&db=PubMed&list_uids=2725532&... printed on Feb. 20, 2003, 1 page.

A.M. Nakhla et al., *Induction of adenylate cyclase in a mammary carcinoma cell line by human corticosteroid-binding globulin*, Biochem Biophys Res. Commun (Jun. 1988) vol. 153, No. 3, pp. 1012-1018, PMID 2839166 [PubMed—indexed for MEDLINE], http://www.ncbi.nlm.nih.gov/enrez/query.fcgi?Retrieve&db=PubMed&list_uids=2839166&... printed on Feb 19, 2003, 1 page.

A.M. Nakhla et al., *Characterization of ALVA-41 cells, a new human prostatic cancer cell line*, Steroids (Oct. 1994) vol. 10, pp. 586-589.

K.A. Nathavitharana et al., *Presence of secretory IgA antibodies to an enteric bacterial pathogen in human milk and saliva*, Arch Dis Child Fetal Neonatal Ed (Mar. 1995) vol. 72, No. 2, pp. F102-F106, (Original Article) 8 pages.

J.R. Nevens et al., *Affinity Chromatographic Purification of Immunoglobulin M Antibodies Utilizing Immobilized Mannan Binding Protein*, J Chromatogr (Apr. 1992) vol. 597, Nos. 1-2, pp. 247-256.

F.R. Ochsendorf, *Infections in the male genital tract and reactive oxygen species*, Hum Reprod Update (Sep.-Oct. 1999) vol. 5, No. 5, pp. 399-420, PMID 10582780 [PubMed—indexed for MEDLINE], Abstract, http://www.ncbi.nlm.nih.gov/enrez/query.fcgi?cmd=Retrieve&db=PubMed&list_uids=10582780&... printed on Feb 22, 2003, 1 page.

M. Ogasawara et al., *A new serum-free method of measuring growth factor activities for human breast cancer cells in culture*, In Vitro Cell Dev Biol (Sep. 1988) vol. 24, No. 9, pp. 911-920.

J.H. Olsen et al., *Cancer in Patients With Ataxia-Telangiectasia and In Their Relatives in the Nordic Countries*, J Natl. Cancer Inst. (Jan. 2001) vol. 93, No. 2, pp. 121-127.

B.W. O'Malley et al., *Female steroid hormones and target cell nuclei*, Science (Feb. 1974) vol. 183, No. 125, pp. 610-620, PMID 4359082 [PubMed—indexed for MEDLINE], Abstract, http://www.ncbi.nlm.nih.gov/enrez/query.fcgi?cmd=Retrieve&db=PubMed&list_uids=4359082&... printed on Feb. 20, 2003, 1 page.

C.K. Osborne, *Steroid hormone receptors in breast cancer management*, Breast Cancer Res. Treat (1998) vol. 51, No. 3, pp. 227-238, PMID 10068081 [PubMed—indexed for MEDLINE], Abstract, http://www.ncbi.nlm.nih.gov/enrez/query.fcgi?cmd=Retrieve&db=PubMed&list_uids=10068081&... printed on Feb. 21, 2003, 2 pages.

T.D. Pack, *Bacterial binding protein for single-step purification of human IgA*, Application Note (Apr. 1999), pp. 16, 18.

M.A. Palladino et al., *The transforming growth factor-betas. A new family of immunoregulatory molecules*, Ann NY Acad. Sci (1990) vol. 593, pp. 181-187, PMID 2197960 [PubMed—indexed for MEDLINE], Abstract, http://www.ncbi.nlm.nih.gov/enrez/query.fcgi?cmd=Retrieve&db=PubMed&list_uids=2197960&... printed on Feb. 12, 2003, 1 page.

B. Peitersen et al., *Quantitative Determination of Immunoglobulins, Lysozyme, and Certain Electrolytes in breast Milk During the Entire Period of Lactation, During a 24-hour Period, and in Milk from the Individual Mammary Gland*, Acta Paediatr Scand (Sep. 1975), vol. 64, No. 5, pp. 709-717.

U. Pfeffer et al., *Estrogen receptor variant messenger RNA lacking exon 4 in estrogen-responsive human breast cancer cell lines*, Cancer Res. (Feb. 1993) vol. 53, No. 4, pp. 741-743, PMID 7916651 [PubMed—indexed for MEDLINE], Abstract, http://www.ncbi.nlm.nih.gov/enrez/query.fcgi?cmd=Retrieve&db=PubMed& list_uids=7916651&... printed on Feb. 20, 2003, 1 page.

M. Raghavan et al., *Fc Receptors and Their Interactions With Immunoglobulins*, Annu. Rev. Cell Dev. Biol. (1996) vol. 12, pp. 181-220.

R.R. Reddel et al., *Differential Sensitivity of Human Breast Cancer cell Lines to the Growth-Inhibitory Effects of Tomoxifen*, Cancer Res. (Apr. 1985) vol. 45, No. 4, pp. 1525-1531.

C.C. Reese et al., *Alternative models for estrogen and androgen regulation of human breast cancer cell (T47D) growth*, Ann NY Acad. Sci (1988) vol. 538, pp. 112-121, PMID 3190080 [PubMed—indexed for MEDLINE], Abstract, http://www.ncbi.nlm.nih.gov/enrez/query.fcgi?cmd=Retrieve&db=PubMed&list_uids=3190080&... printed on Feb. 12, 2003, 1 page.

I. Laursen et al., *Serum Albumin as a Modulator on Growth of the Human Breast Cancer Cell Line, MCF-7*, Anticancer Research (1990) vol. 10, pp. 343-352.

C.B. Reimer et al., *Specificity and association constants of 33 monoclonal antibodies to human IgA epitopes*, Immunol Lett (Jun. 1989) vol. 21, No. 3, pp. 209-215, PMID 2475439 [PubMed—indexed for MEDLINE], Abstract, http://www.ncbi.nlm.nih.gov/enrez/query.fcgi?cmd=Retrieve&db=PubMed&list_uids=2475439&... printed on Feb. 22, 2003, 1 page.

M. Reiss et al., *Transforming growth factor-beta in breast cancer: a working hypothesis*, Breast Cancer Res. Treat (Aug. 1997) vol. 45, No. 1, pp. 81-95, PMID 9285120 [PubMed—indexed for MEDLINE], Abstract, http://www.ncbi.nlm.nih.gov/enrez/query.fcgi?cmd=Retrieve&db=PubMed&list_uids=9285120&... printed on Feb. 21, 2003, 1 page.

J.M. Renoir et al., *Hormonal and immunological aspects of the phylogeny of sex steroid binding plasma protein*, Proc Natl. Acad. Sci USA (Aug. 1980) vol. 77, No. 8, pp. 4578-4582.

J.L. Reny et al., *Human Serum Does Not Contain a High Affinity Estrogen-Binding Glycoprotein Different From Sex Hormone-Binding Globulin*, J Clin Endocrinol Metab (May 1989) vol. 68, No. 5, pp. 938-945.

S.F. Retta et al., *Purification of fibronectin from human plasma*, Methods Mol Biol (1999) vol. 96, pp. 119-124, PMID 10098128 [PubMed—indexed for MEDLINE], Abstract, http://www.ncbi.nlm.nih.gov/enrez/query.fcgi?cmd=Retrieve&db=PubMed&list_uids=10098128&... printed on Mar. 12, 2003, 1 page.

A. Richardson, *Is breast cancer caused by late exposure to a common virus?* Med Hypotheses (Jun. 1997) vol. 48, No. 6, pp. 491-497, PMID 9247892 [PubMed—indexed for MEDLINE], Abstract, http://www.ncbi.nlm.nih.gov/enrez/query.fcgi?cmd=Retrieve&db=PubMed&list_uids=9247892&... printed on Feb. 22, 2003, 1 page.

T.L. Riss et al., *Rat Pituitary Tumor Cells in Serum-Free Culture. II. Serum Factor and Thyroid Hormone Requirements for Estrogen-Responsive Growth*, In Vitro Cell Dev Biol. (Feb. 1989) vol. 25, No. 2, pp. 136-142.

T.L. Riss et al., *Purification and Identification of Transferrin as a Major Pituitary-Derived Mitogen for MTW9/PL2 Rat Mammary Tumor Cells*, In Vitro Cell Dev Biol (Dec. 1987) vol. 23, No. 12, pp. 841-849.

T.L. Riss et al., *Rat Pituitary Tumor Cells in Serum-Free Culture. I. Selection of Thyroid Hormone-Responsive and Autonomous Cells*, In Vitro Cell Dev Biol (Feb. 1989) vol. 25, No. 2, pp. 127-135.

T.L. Riss et al., *Growth and Continuous Passage of COMMA-D Mouse Mammary Epithelial Cells in Hormonally Defined Serum-Free Medium*, Cancer Res. (Jul. 1987) vol. 47, No. 14, pp. 3776-3782.

T.L. Riss et al., *Human Recombinant Insulin-Like Growth Factor I. I. Development of a Serum-Free Medium for Clonal Density Assay of Growth Factors Using BALB/c 3T3 Mouse Embryo Fibroblasts*, In Vitro Cell Dev Biol (Nov. 1988) vol. 24, No. II, pp. 1099-1106.

M.C. Roque-Barreira et al., *Jacalin: an IgA-binding lectin*, J Immunol (Mar. 1985) vol. 134, No. 3, pp. 1740-1743, PMID 3871459 [PubMed—indexed for MEDLINE], Abstract, http://www.ncbi.nlm.nih.gov/enrez/query.fcgi?cmd=Retrieve&db=PubMed&list_uids=3871459&... printed on Feb. 21, 2003, 1 page.

M.C. Roque-Barreira et al., *IgA-affinity purification and characterization of the lectin jacalin*, Braz J Med Biol Res. (1986) vol. 19, No. 2, pp. 149-157.

W. Rosner et al., *Isolation and Characterization of the Testosterone-Estradiol-Binding Globulin From Human Plasma. Use of a Novel Affinity Column*, Biochemistry (Nov. 1975) vol. 14, No. 22, pp. 4813-4820.

W. Rosner, *The Functions of Corticosteroid-Binding Globulin and Sex Hormone-Binding Globulin: Recent Advances*, Endocr Rev (Feb. 1990) vol. 11, No. 1, pp. 80-91.

W. Rosner et al., *Testosterone-Estradiol-Binding Globulin of Human Plasma: Denaturation and Protection*, Biochim Biophys Acta (May 1974) vol. 351, No. 1, pp. 92-98.

J. Russo et al., *DNA Labeling Index and Structure of the Rat Mammary Gland as Determinants of its Susceptibility to Carcinogenesis*, J Natl. Cancer Inst. (Dec. 1978), vol. 61, No. 6, pp. 1451-1459.

I.H. Russo et al., *Developmental Stage of the Rat Mammary Gland as Determinant of its Susceptibility to 7,12-Dimethylbenz(a)anthracene*, J Natl. Cancer Inst. (Dec. 1978) vol. 61, No. 6, pp. 1439-1449.

M. Sabel et al., *Recent developments in breast imagining*, Phys Med Biol (Mar 1996), vol. 41, No. 3, pp. 315-368, PMID 8778818 [PubMed—indexed for MEDLINE], Abstract, http://www.ncbi.nlm.nih.gov/enrez/query.fcgi?cmd=Retrieve&db=PubMed&list_uids=8778818&... printed on Feb. 21, 2003, 1 page.

R. Sager, *Expression genetics in cancer: shifting the focus from DNA to RNA*, Proc Natl. Acad. Sci USA (Feb. 1997), vol. 94, No. 3, pp. 952-959.

H.H. Samuels et al., *Depletion of L-3,5,3 '-Triiodothyronine and L-Thyroxine in Euthyroid Calf Serum for Use in Cell Culture Studies of the Action of Thyroid Hormone*, Endocrinology (Jul. 1979) vol. 105, No. 1, pp. 80-85.

H. Sato et al., *Iron is deleterious to hormone-responsive pituitary cell growth in serum-free defined medium*, In Vitro Cell Dev Biol (Aug. 1991), vol. 27A, No. 8, pp. 599-602.

H. Sato et al., *Apotransferrins from several species promote thyroid hormone-dependent rat pituitary tumor cell growth in iron-restricted serum-free defined culture*, Mol Cell Endocrinol (Feb. 1992), vol. 83, Nos. 2-3, pp. 239-251.

R.W. Schatz et al., *Effects of Interaction Between Estradiol-17 Beta and Progesterone on the Proliferation of Cloned Breast Tumor Cells (MCF-7 and T47D)*, J Cell Physiol (Sep. 1985) vol. 124, No. 3, pp. 386-390.

A. Segaloff, *Hormone Therapy of Breast Cancer*, Banbury Report; 8 (1981), pp. 229-236.

J. Seidenfeld et al., *Single-Therapy Androgen Suppression in Men With Advanced Prostate Cancer: A Systematic Review and Meta-Analysis*, Ann Intern Med (Apr. 2000) vol. 132, No. 7 pp. 566-577.

G.B. Silberstein et al., *Regulation of Mammary Morphogenesis: Evidence for Extracellular Matrix-Mediated Inhibition of Ductal Budding by Transforming Growth Factor-Beta 1*, Dev Biol (Aug. 1992), vol. 152, No. 2, pp. 354-362.

G.B. Silberstein et al., *Reversible Inhibition of Mammary Gland Growth by Transforming Growth Factor-Beta*, Science (Jul. 1987) vol. 237, No. 4812, pp. 291-293.

D.A. Sirbasku, *Hormone-Responsive Growth In Vivo of a Tissue Culture Cell Line Established From The MT-W9A Rat Mammary Tumor*, Cancer Res. (Apr. 1978) vol. 38, No. 4, pp. 1154-1165.

D.A. Sirbasku et al., *Thyroid Hormone and Apotransferrin Regulation of Growth Hormone Secretion by GH1 Rat Pituitary Tumor Cells in Iron Restricted Serum-Free Defined Medium*, In Vitro Cell Dev Biol (Jan. 1992), vol. 28A, No. 1, pp. 67-71.

D.A. Sirbasku et al., *Thyroid Hormone Regulation of Rat Pituitary Tumor Cell Growth: A New Role for Apotransferrin As An Autocrine Thyromedin*, Mol Cell Endocrinol (May 1991) vol. 77, Nos. 1-3, pp. C47-C55.

D.A. Sirbasku et al., *Purification of an Equine Apotransferrin Variant (Thyromedin) Essential For Thyroid Hormone Dependent Growth of GHI Rat Pituitary Tumor Cells In Chemically Defined Culture*, Biochemistry (Jan. 1991) vol. 30, No. 1, pp. 295-304.

D.A. Sirbasku et al., *Control of Cell Growth. IV. Growth Properties of a New Cell Line Established From An Estrogen-Dependent Kidney Tumor of the Syrian Hamster*, Endocrinology (May 1976) vol. 98, No. 5, pp. 1260-1272.

D.A. Sirbasku et al., *Thyroid Hormone Dependent Pituitary Tumor Cell Growth in Serum-Free Chemically Defined Culture. A New Regulatory Role for Apotransferrin*, Biochemistry (Jul. 1991) vol. 30, No. 30, pp. 7466-7477.

D.A. Sirbasku et al., *Survey of the Mechanisms Regulating Estrogen Promoted Breast Cancer Cell Growth*, DOD Breast Cancer Research (Jun. 2000) Era of Hope, Proceedings vol. II, 2 pages.

D.A. Sirbasku, *Estrogen induction of growth factors specific for hormone-responsive mammary, pituitary, and kidney tumor cells*, Proc Natl. Acad. Sci USA (Aug. 1978) vol. 75, No. 8, pp. 3786-3790.

D.A. Sirbasku et al., *Estrogen mitogenic action. Ii. Negative regulation of the steroid hormone-responsive growth of cell lines derived from human and rodent target tissue tumors and conceptual implications*, In Vitro Cell Dev Biol Anim (Jul.-Aug. 2000) vol. 36, No. 7, pp. 428-446.

D.A. Sirbasku, *New Concepts in Control of Estrogen-Responsive Tumor Growth*, Banbury Report; 8 (1981), pp. 405-443.

E.P. Smith et al., *Estrogen Resistance Caused By A Mutation In The Estrogen-Receptor Gene In A Man*, N. Engl J Med (Oct. 1994) vol. 331, No. 16, pp. 1056-1061.

R.L. Smith et al., *Separation of plasma fibronectin from associated hemagglutinating acivity by elution from gelatin-agarose at pH 5.5*, Thromb Res. (Jan. 1985), vol. 37, No. 1, pp. 91-101, PMID 3983905 [PubMed—indexed for MEDLINE], Abstract, http://www.ncbi.nlm.nih.gov/enrez/query.fcgi?cmd=Retrieve&db=PubMed&list_uids=3983905&... printed on Feb. 20, 2003, 1 page.

M.J. Smyth et al., *A fresh look at tumor immunosurveillance and immunotherapy*, Nat Immunol (Apr. 2001) vol. 2, No. 4, pp. 293-299.

C. Sonneschein et al., *Somatic Mutation Theory of Carcinogenesis: Why It Should Be Dropped and Replaced*, Molecular Carcinogenesis (Dec. 2000) vol. 29, No. 4, pp. 205-211.

C. Sonneschein et al., *Human Serum Albumin Shares the Properties of Estrocolyone-I, The Inhibitor of the Proliferation of Estrogen-Target Cells*, J Steroid Biochem Mol Biol (Oct. 1996) vol. 59, No. 2, pp. 147-154.

A.M. Soto et al., *Cell proliferation of estrogen-sensitive cells: the case for negative control*, Endoc Rev (Feb. 1987), vol. 8, No. 1, pp. 44-52.

A.M. Soto et al., *The role of estrogens on the proliferation of human breast tumor cells*, J Steroid Biochem (Jul. 1985) vol. 23, No. 1, pp. 87-94, PMID 4021494 [PubMed—indexed for MEDLINE], Abstract, http://www.ncbi.nlm.nih.gov/enrez/query.fcgi?cmd=Retrieve&db=PubMed&list_uids=4021494&... printed on Feb. 20, 2003, 1 page.

A.M. Soto et al., *Estrogen-Sensitive Proliferation pattern of Cloned Syrian Hamster Kidney Tumor Cells*, Cancer Res. (Jul. 1988), vol. 48, No. 13, pp. 3676-3680, PMID 3288332 [PubMed—indexed for MEDLINE], Abstract, http://www.ncbi.nlm.nih.gov/enrez/query.fcgi?cmd=Retrieve&db=PubMed&list_uids=3288332&... printed on Feb. 20, 2003, 1 page.

A.M. Soto et al., *Control of Cell Proliferation: Evidence for Negative Control on Estrogen-Sensitive T47D Human Breast Cancer Cells*, Cancer Res. (May 1986) vol. 46, No. 5, pp. 2271-2275.

A.M. Soto et al., *A Plasma-Borne Specific Inhibitor of the Proliferation of Human Estrogen-Sensitive Breast Tumor Cells (Estrocolyone-I)*, J. Steroid Biochem Mol Biol (Dec. 1992) vol. 43, No. 7, pp. 703-712.

H.D. Soule et al., *A human cell line from apleural effusion derived from a breast carcinoma*, J Natl. Cancer Inst. (Nov. 1973) vol. 51, No. 5, pp. 409-416, PMID 4357757 [PubMed—indexed for MEDLINE], Abstract, http://www.ncbi.nlm.nih.gov/enrez/query.fcgi?cmd=Retrieve&db=PubMed&list_uids=4357757&... printed on Feb. 19, 2003, 1 page.

H.L. Spiegelberg, *Biological activities of immunoglobulins of different classes and subclasses*, Adv Immunol (1974) vol. 19, pp. 259-294, PMID 4611172 [PubMed—indexed for MEDLINE], Abstract, http://www.ncbi.nlm.nih.gov/enrez/query.fcgi?cmd=Retrieve&db=PubMed&list_uids=4611172&... printed on Feb. 15, 2003, 1 page.

J.E. Stern et al., *Secretory immune system of the male reproductive tract: effects of dihydrotestosterone and estradiol on IgA and secretory component levels*, J Reprod Immunol (Jun. 1992) vol. 22, No. 1, pp. 73-85, PMID 1522564 [PubMed—indexed for MEDLINE], Abstract, http://www.ncbi.nlm.nih.gov/enrez/query.fcgi?cmd=Retrieve&db=PubMed&list_uids=1522564&... printed on Feb. 22, 2003, 1 page.

J.E. Stern et al.,*Sectetory component in breast cancer. Analysis of the levels in primary and metastatic disease*, Cancer Immunol. Immunother. (1985) vol. 19, No. 2, pp. 226-230, PMID 3847292 [PubMed—indexed for MEDLINE], Abstract, http://www.ncbi.nlm.nih.gov/enrez/query.fcgi?cmd=Retrieve&db=PubMed&list_uids=3847292&... printed on Feb. 21, 2003, 1 page.

K.R. Stone et al., *Isolation of a Human Prostate Carcinoma Cell Line (DU 145)*, Int. J. Cancer (Mar. 1978), vol. 21, No. 3, pp. 274-281.

J.S. Strobl et al., *Prolonged Retention of Estadiol by Human Breast Cancer Cells in Tissue Culture*, Cancer Res. (Sep. 1979) vol. 39, No. 9, pp. 3319-3327.

R.L. Sutherland et al., *High-Affinity Anti-Oestrogen Binding Site Distinct From The Oestrogen Receptor*, Nature (Nov. 1980) vol. 288, No. 5788, pp. 273-275, PMID 7432524 [PubMed—indexed for MEDLINE], Abstract, http://www.ncbi.nlm.nih.gov/enrez/query.fcgi?cmd=Retrieve&db=PubMed&list_uids=7432524&... printed on Feb. 20, 2003, 1 page.

M. Swift, *Public health Burden of Cancer in Ataxia-Telangiectasia Heterozygotes*, J. Natl. Cancer Inst. (Jan. 2001), vol. 92, No. 2, pp. 84-85.

M. Tanji et al., *A Steroid-Binding Protein Mediates Estrogen-Dependent Inhibition of Growth of MCF-7 Breast Cancer Cells*, Anticancer Res. (Jul.-Aug. 2000) vol. 20, No. 4, pp. 2785-2789.

M. Tanji et al., *Growth Inhibition of MCF-7 Cells by Estrogen Is Dependent Upon a Serum Factor*, Anticancer Res. (Jul.-Aug. 2000) vol. 20, No. 4, pp. 2779-2783.

A.H. Tashjian, *Clonal Strains of Hormone-Producing Pituitary Cells*, Methods Enymol (1979) vol. 58, pp. 527-535.

S.V. Tavtigian et al., *The Complete BRCA2 Gene and Mutations in Chromosome 13q-Linked Kindreds*, Nat. Genet (Mar. 1996) vol. 12, No. 3, pp. 333-337, PMID 8589730 [PubMed—indexed for MEDLINE], Abstract, http://www.ncbi.nlm.nih.gov/enrez/query.fcgi?cmd=Retrieve&db=PubMed&list_uids=8589730&... printed on Feb. 15, 2003, 1 page.

M.J. Tsai et al., *Molecular mechanisms of action of steroid/thyroid receptor superfamily members*, Annu. Rev. Biochem (1994) vol. 63, pp. 451-486, PMID 7979245 [PubMed—indexed for MEDLINE], Abstract, http://www.ncbi.nlm.nih.gov/enrez/query.fcgi?cmd=Retrieve&db=PubMed&list_uid7979245&... printed on Feb. 21, 2003, 1 page.

J.P. Vaerman et al., *Antibody against the human J chain inhibits polymeric Ig receptor-mediated biliary and epithelial transport of human polymeric IgA*, Eur. J. Immunol. (Jan. 1998) vol. 28, pp. 171-182.

S. Valtanen et al., *Poliovirus-Specific Intestinal Antibody Responses Coincide With Decline of Poliovirus Excretion*, J. Infect. Dis. (Jul. 2000) vol. 182, pp. 1-5.

J. Veldscholte et al., *A mutation in the ligand binding domain of the androgen receptor of human LNCaP cells affects steroid binding characteristics and response to anti-androgens*, Biochem Biophys Res. Commun (Dec. 1990) vol. 173, No. 2, pp. 534-540.

J. Veldscholte et al., *Unusual specificity of the androgen receptor in the human prostate tumor cell line LNCaP: high affinity for progestagenic and estrogenic steroids*, Biochim Biophys Acta (Apr. 1990) vol. 105, pp. 187-194.

F. Vignon et al., *Effects of Plasma Estrogen Sulfates in Mammary Cancer Cells*, Endocrinology (Apr. 1980) vol. 106, No. 4, pp. 1079-1086.

F. Vignon et al., *Antiestrogens inhibit the mitogenic effect of growth factors on breast cancer cells in the total absence of estrogens*, Biochem Biophys Res. Commun (Aug. 1987) vol. 146, No. 3, pp. 1502-1508, PMID 3304294 [PubMed—indexed for MEDLINE], Abstract, http://www.ncbi.nlm.nih.gov/enrez/query.fcgi?cmd=Retrieve&db=PubMed&list_uids=&3304294... printed on Feb. 20, 2003, 1 page.

J.F. Viret et al., *Mucosal and systemic immune responses in humans after primary and booster immunizations with orally administered invasive and noninvasive live attenuated bacteria*, Infect Immun (Jul. 1999) vol. 67, No. 7, pp. 3680-3685.

I Vorechovsky et al., *the ATM gene and susceptibility to breast cancer: analysis of 38 breast tumors reveals no evidence for mutation*, Cancer Res. (Jun. 1996) vol. 56, No. 12, pp. 2726-2732, PMID 8665503 [PubMed—indexed for MEDLINE], Abstract, http://www.ncbi.nlm.nih.gov/enrez/query.fcgi?cmd=Retrieve&db=PubMed&list_uids=8665503&... printed on Feb. 21, 2003, 1 page.

Y. Wang et al., *Identification of a dominant negative form of the human estrogen receptor*, Mol. Endocrinol (Nov. 1991) vol. 5, No. 11, pp. 1707-1715, PMID 1779972 [PubMed—indexed for MEDLINE], Abstract, http://www.ncbi.nlm.nih.gov/enrez/query.fcgi?cmd=Retrieve&db= PubMed&list_uids=1779972&... printed on Feb. 20, 2003, 1 page.

C.W. Welsch, *Host Factors Affecting the Growth of Carcinogen-induced Rat Mammary Carcinomas: A Review and Tribute to Charles Brenton Huggin*, Cancer Res. (Aug. 1985) vol. 45, No. 8, pp. 3415-3443.

R.V. Wenn et al., *Distribution of Testosterone-Estradiol Binding Globulin (TeBG) In The Higher Vertebrates*, Endokrinologie (Jul. 1977) vol. 69, No. 2, pp. 151-156.

T.E. Wiese et al., *Optimization of estrogen growth response in MCF-7 cells*, In Vitro Cell Dev Biol (Sep.-Oct. 1992) vol. 28A, No. 9-10, pp. 595-602.

R. Wooster et al., *Identification of the breast cancer susceptibility gene BRCA2*, Nature (Dec. 1995) vol. 378, No. 6559, pp. 789-792, PMID 8524414 [PubMed—indexed for MEDLINE], Abstract, http://www.ncbi.nlm.nih.gov/enrez/query.fcgi?cmd=Retrieve&db=PubMed&list_uids=8524414&... printed on Feb. 15, 2003, 1 page.

J. Yang et al., *Estrogen receptor variants in epithelial compartment of normal human breast*, Endocrine (Jun. 2000), vol. 12, No. 3, pp. 243-247, PMID 10963044 [PubMed—indexed for MEDLINE], Abstract, http://www.ncbi.nlm.nih.gov/enrez/query.fcgi?cmd=Retrieve&db= PubMed&list_uids=10963044&... printed on Feb. 12, 2003, 1 page.

K.R. Yamamoto, *Steroid receptor regulated transcription of specific genes and gene networks*, Annu Rev Genet (1985) vol. 19, pp. 209-252, PMID 3909942 [PubMed—indexed for MEDLINE], Abstract, http://www.ncbi.nlm.nih.gov/enrez/query.fcgi?cmd=Retrieve&db= PubMed&list_uids=3909942&... printed on Feb. 21, 2003, 1 page.

D.A. Zajchowski et al., *Estrogen inhibits the growth of estrogen receptor-negative, but not estrogen receptor-positive, human mammary epithelial cells expressing a recombination estrogen receptor*, Cancer Res. (Oct. 1993) vol. 53, No. 20, pp. 5004-5011, PMID 8402691 [PubMed—indexed for MEDLINE], Abstract, http://www.ncbi.nlm.nih.gov/enrez/query.fcgi?cmd=Retrieve&db= PubMed&list_uids=8402691&... printed on Feb. 21, 2003, 1 page.

Feng et al. (Journal Dairy Science 78:2352-2357 (1995)).
Hallaway et al. (Proc. Nat'l. Acad. Sci. 85:10108-10112 (1989)).
Jiang et al. (Anticancer Research 22:2685-2692 (2002)).
Kresse et al (Magnetic Resonance in Medicine 40(2):236-242 (1998)).
Larson et al. (J. Nat'l. Cancer Inst. 64(1): 41-53 (1980)).
Mathias et al. (J. Nuclear Medicine 37(6): 1003-1008 (1996)).
Murphy (The Oncologist 3: 129-130 (1998)).
Patel et al. (Proc. Nat'l. Acad. Sci. 80:6518-6522 (1983)).
Reddel et al (Exp. Cell Research 161:277-284 (1985)).
Sato (Nippon Gan Chiryo Gakkaisi 28(10): 1716-1723 (1993)).
Wang et a.. (Anticancer Research 19:445-450 (1999)).

* cited by examiner

EFFECT OF TEMPERATURE ON THE SPECIFIC
BINDING OF 5 nM $^3$H-E$_2$ TO MTW9/PL2 CELLS

The kinetics are shown (± SD of triplicates) at 37°C (closed circles), 23°C (open circles), and at 4°C (open triangles).

Specific binding was determined in phenol red-free D-MEM/F-12. Each assay sample contained 300,000 CPM and 1.0 x 10$^6$ cells.

FIGURE 2

EFFECT OF CONCENTRATION ON THE SPECIFIC BINDING OF $^3$H-E$_2$ TO MTW9/PL2 CELLS AND A SCATCHARD ANALYSIS OF THE BINDING

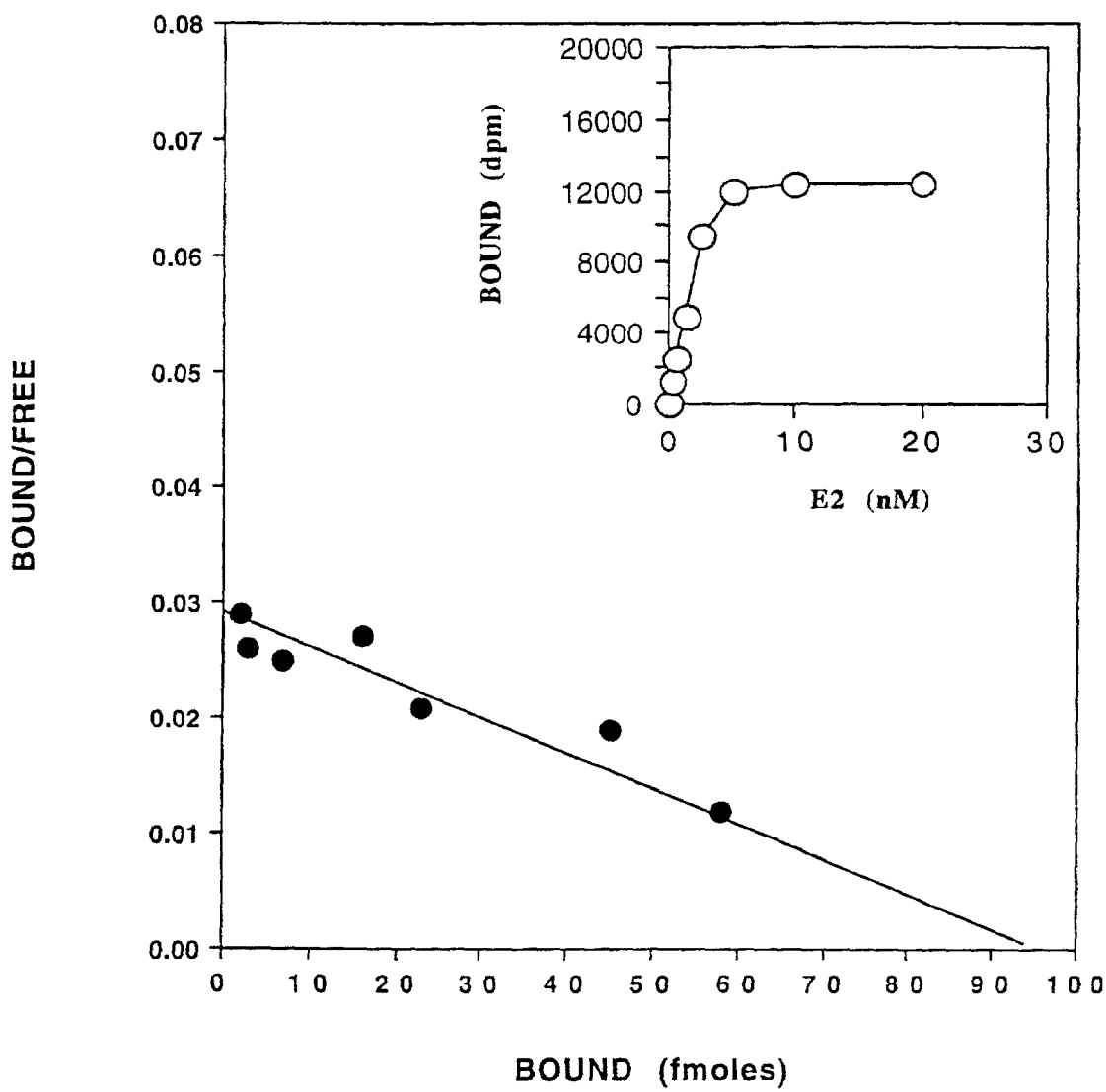

Scatchard analysis of $^3$H-E$_2$ binding (closed circles) was conducted using the traditional method with labeled-unlabeled mixtures of hormone and DES (100-fold excess) over the concentration range 37 pM to 5.0 nM $^3$H-E$_2$. In both experiments, 5 nM $^3$H-E$_2$ was 300,000 DPM. Each assay sample contained 1.0 x 10$^6$ cells.

INSERT: The insert shows a separate experiment in which the effect of $^3$H-E$_2$ concentration was measured on specific binding (DPM) after 2 h at 37° C in phenol red-free D-MEM/F-12.

EFFECT OF OTHER STEROID HORMONES ON THE
BINDING OF $^3$H-E$_2$ TO MTW9/PL2 CELLS

NON-RADIOACTIVE LIGAND EXCESS (A) shows the effects of unlabeled DES (open triangles),
unlabeled DHT (open circles), and unlabeled T (closed circles).

(B) shows the effects of unlabeled DES (open triangles),
unlabeled progesterone (open circles), and unlabeled
cortisol (closed circles).

EFFECT OF TEMPERATURE ON THE SPECIFIC
BINDING OF 5 nM $^3$H-PROGESTERONE TO
MTW9/PL2 CELLS

The kinetics are shown ( SD of triplicates) at 37° C (closed circles), 23° C (open circles), and at 4° C (open triangles). Specific binding was determined in phenol red-free D-MEM/F-12. Each assay sample contained 287,000 CPM $^3$H-progesterone and $1.0 \times 10^6$ cells.

FIGURE 5

EFFECT OF CONCENTRATION ON THE SPECIFIC BINDING OF $^3$H-PROGESTERONE TO MTW9/PL2 CELLS

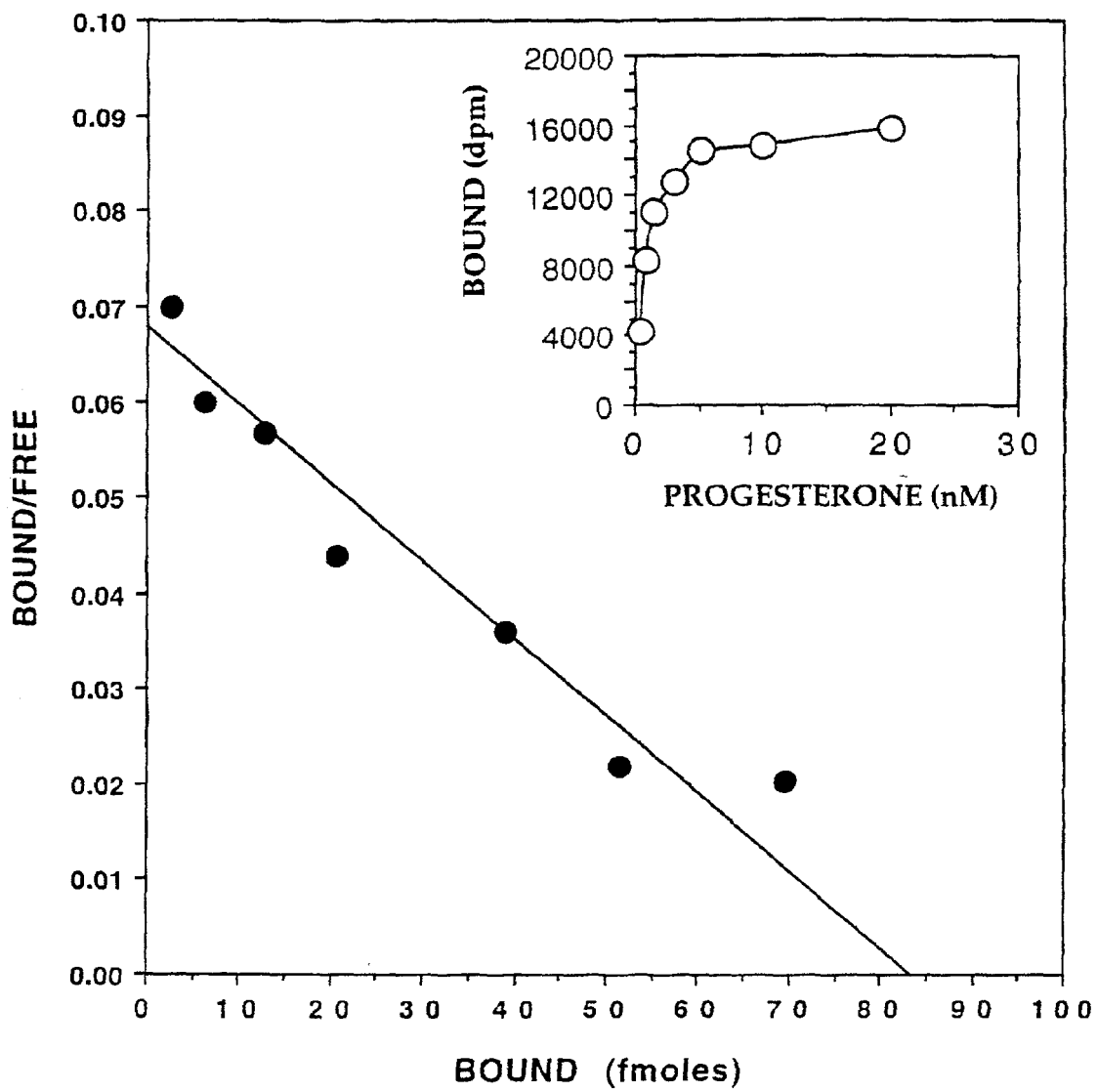

A Scatchard analysis of $^3$H-progesterone binding (closed circles) was conducted using the traditional method with labeled-unlabeled mixtures of hormone and R5020 (100 fold excess) over the concentration range 37 pM to 5.0 nM $^3$H-progesterone. In both experiments, 5.0 nM $^3$H-progesterone was 287,000 CPM. Each assay sample contained 1.0 x 10$^6$ cells.

INSERT: The insert shows a separate experiment in which the effect of $^3$H-progesterone concentration was measured on specific binding (bound dpm) after 2 h at 37° C in phenol red-free D-MEM/F-12.

FIGURE 6

EFFECT OF STEROID HORMONES ON THE BINDING OF $^3$H-PROGESTERONE TO MTW9/PL2 CELLS

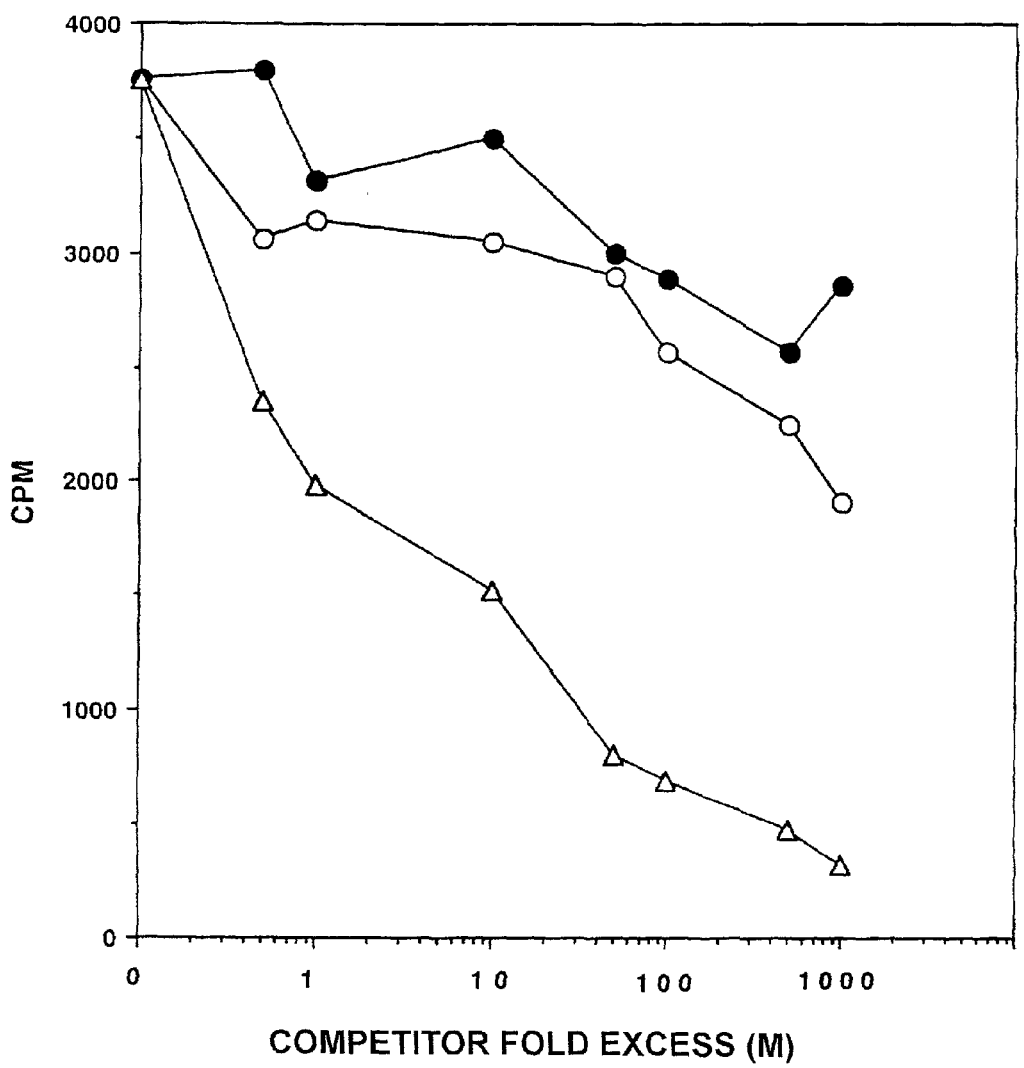

The cells were incubated at 37°C for 2 h in the presence of 5 nM $^3$H-progesterone (287,000 CPM) alone or in the presence of the labeled hormone plus the designated fold excess (M) of unlabeled R5020 (open triangles), unlabeled DHT (open circles), or unlabeled T (closed circles). Each assay sample contained $1.0 \times 10^6$ cells.

EFFECT OF $E_2$ ON THE PROGESTERONE RECEPTOR
CONTENT OF MTW9/PL2 CELLS

Each specific binding presented is the average of
triplicate incubations ± SD (closed circles).

INSERT: The insert shows the effect of $E_2$ concentration
in the culture medium for 2 d prior to the assay of
progesterone receptors (open circles).

WESTERN IMMUNOBLOTTING OF STEROID HORMONE RECEPTORS

FIGURE 9

MTW9/PL2 CELL GROWTH IN 50% CDE - HORSE SERUM

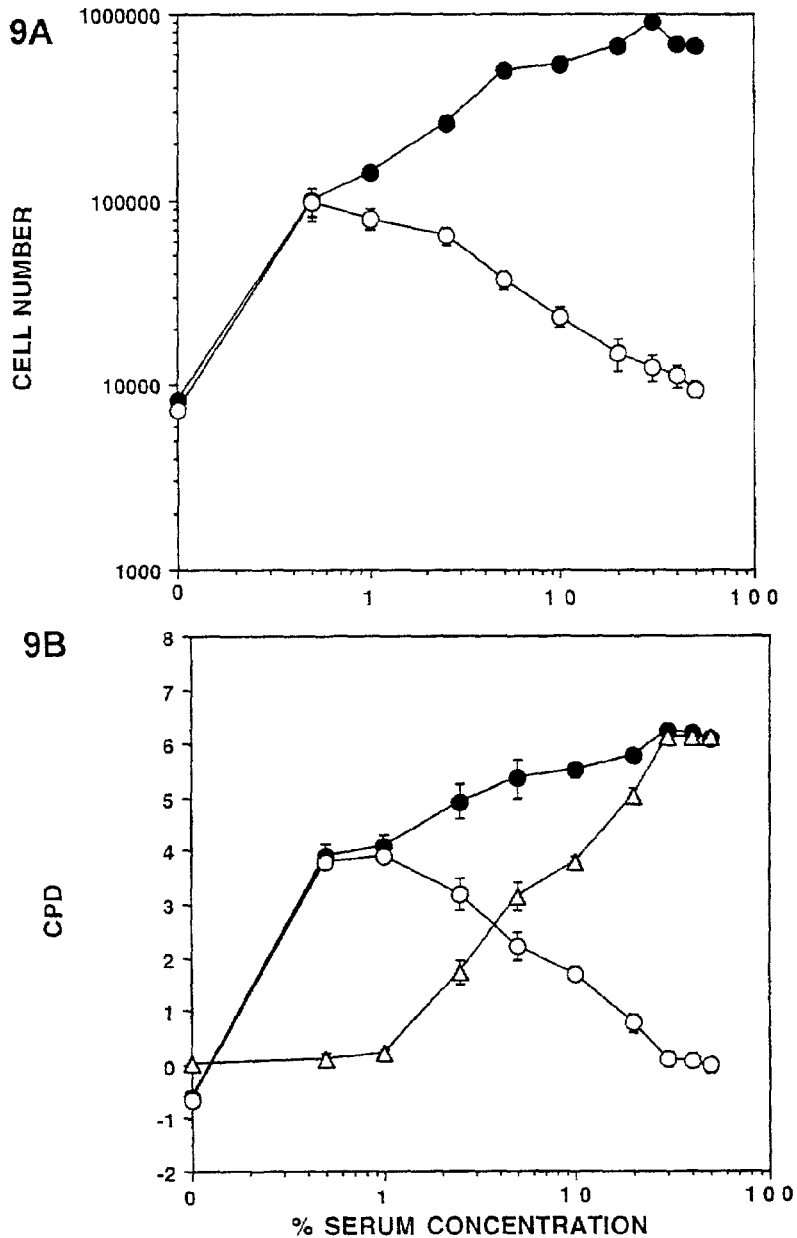

A: DATA EXPRESSED AS CELL NUMBER AFTER 7 DAYS
Growth with 1.0 x 10 M E (closed circles) and without hormone (open circles) in medium containing the designated concentrations of serum.

B. DATA IN (A) EXPRESSED AS CPD
The symbols indicate the same conditions as (A) except the open triangles show CPD differences between growth in dishes with and without the hormone (Difference = estrogenic effect on growth).

MTW9/PL2 CELL GROWTH IN 50% CDE - HORSE SERUM WITH ESTROGENS ADDED AT VARIOUS TIMES AFTER SEEDING

LEGEND:

Control growth in the absence of exogenous estrogen is shown by (triangles). In other dishes, 1.0 x 10$^{-8}$ M E$_2$ was added at the beginning of the experiment (closed circles), after 48 h (open circles), after 96 h (closed squares), or after 144 h (open squares).

STEROID HORMONE DOSE RESPONSE EFFECTS WITH
MTW9/PL2 CELLS IN 50% CDE - HORSE SERUM

LEGEND:

Closed circles = $E_2$
Open circles = $E_1$
Closed squares = $E_3$
Open squares = Progesterone
Closed triangles = DHT
Open triangles = T

MTW9PL2 CELL GROWTH IN CDE SERUM FROM DIFFERENT SPECIES

LEGEND: Open circles = $-E_2$
Closed circles = $+E_2$
Open triangles = Estrogenic effect ZR-75-1 CELLS IN CDE - HORSE SERUM ± 10 nM $E_2$

% SERUM CONCENTRATION

LEGEND:

Closed circles = $+E_2$
Open circles = $-E_2$
Closed triangles = Estrogenic effect MCF7A CELL GROWTH IN CDE - HORSE SERUM $\pm E_2$

% SERUM CONCENTRATION

LEGEND:

Closed circles = $+E_2$
Open circles = $-E_2$
Closed triangles = Estrogenic effect

FIGURE 16

GROWTH KINETICS OF T47D HUMAN BREAST CANCER CELLS IN CDE - HORSE SERUM ±10 nM $E_2$

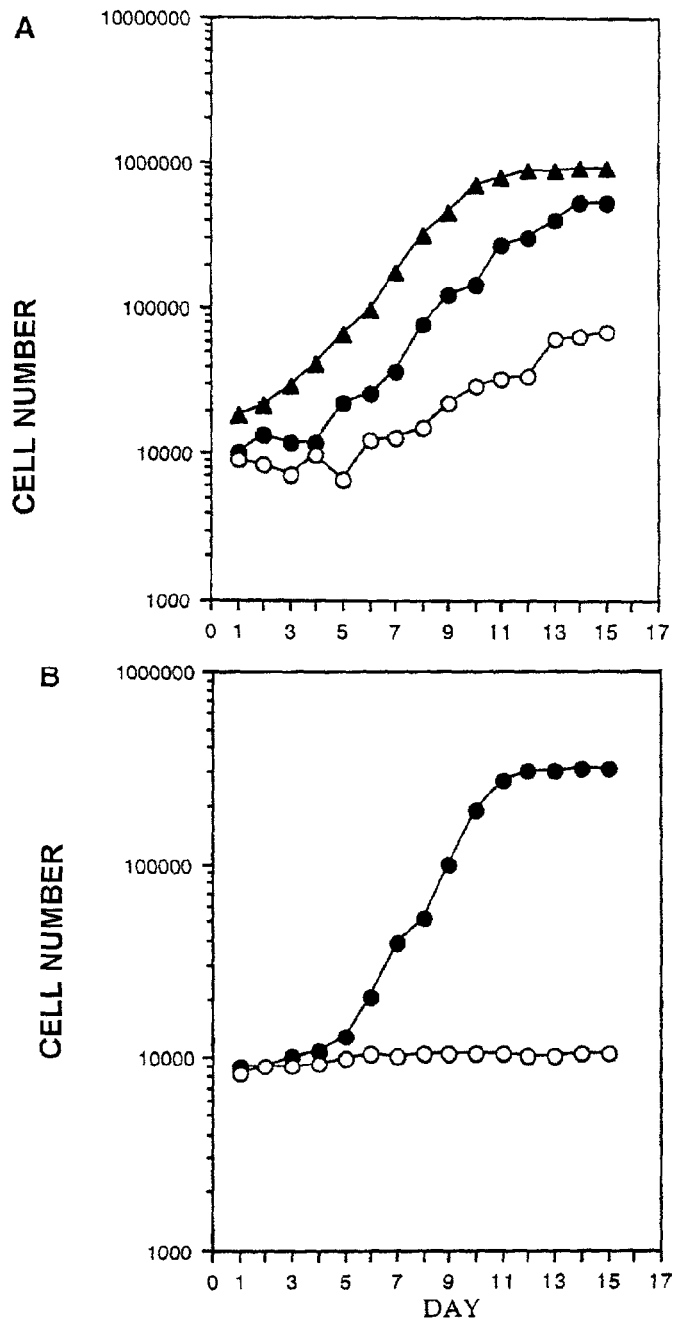

(A) The growth of the cells in medium with 20% (v/v) serum with 10 nM $E_2$ (closed circles) and without the steroid (open circles). As comparison, growth is shown in medium containing 10% (v/v) FBS (triangles).

(B) T47D cell growth kinetics in medium with 50% (v/v) serum with $E_2$ (closed circles) and without the steroid (open circles).

GROWTH OF HUMAN & RODENT CELL LINES
IN 50% CDE - HORSE SERUM $\pm E_2$ (10 nM)

LEGEND: Closed circles = Medium with 10 nM $E_2$
Open circles = Medium without $E_2$
Triangles = Estrogenic effect

DOSE RESPONSE OF STEROID HORMONES
WITH T47D CELLS IN 50% CDE - HORSE SERUM

LEGEND:
Growth after 14 days is shown in response to:
  Closed circles = $E_2$
  Open circles = $E_1$
  Closed triangles = $E_3$
  Open triangles = DHT
  Closed squares = Testosterone
  Open squares = Progesterone
  Crosses = Cortisol

DOSE RESPONSE OF STEROID HORMONES
WITH $GH_4C_1$ CELLS IN 50% CDE - HORSE SERUM

LEGEND:

Growth after 11 days is shown in response to:

Closed circles = $E_2$
Open circles = $E_1$
Closed triangles = $E_3$
Open triangles = DHT
Closed squares = Testosterone
Open squares = Progesterone
Crosses = Cortisol

DOSE RESPONSE OF STEROID HORMONES
WITH H-301 CELLS IN 50% CDE - HORSE SERUM

LEGEND:

Growth after 9 days is shown in response to:
  Closed circles = $E_2$
  Open circles = $E_1$
  Closed triangles = $E_3$
  Open triangles = DHT
  Closed squares = Testosterone
  Open squares = Progesterone
  Crosses = Cortisol

LEGEND:

Growth after 14 days is shown in response to:
  Closed circles = $E_2$
  Open triangles = $E_1$
  Open squares = $E_3$
  Open circles = DHT
  Closed triangles = Testosterone
  Closed squares = Progesterone
  Crosses = Cortisol $T_3$ TITRATION OF $GH_3$ CELLS GROWN
IN SERUM - FREE MEDIUM (PCM)

$E_2$ TITRATION OF $GH_3$ CELLS GROWN IN SERUM-FREE MEDIUM MINUS $T_3$

EFFECT OF $T_3$ ON GH CELL LINES:
GROWTH IN 2.5% CDE - HORSE SERUM WITH NO $E_2$

FIGURE 26

COMPARISON OF 56°C AND 34°C CHARCOAL EXTRACTED SERUM

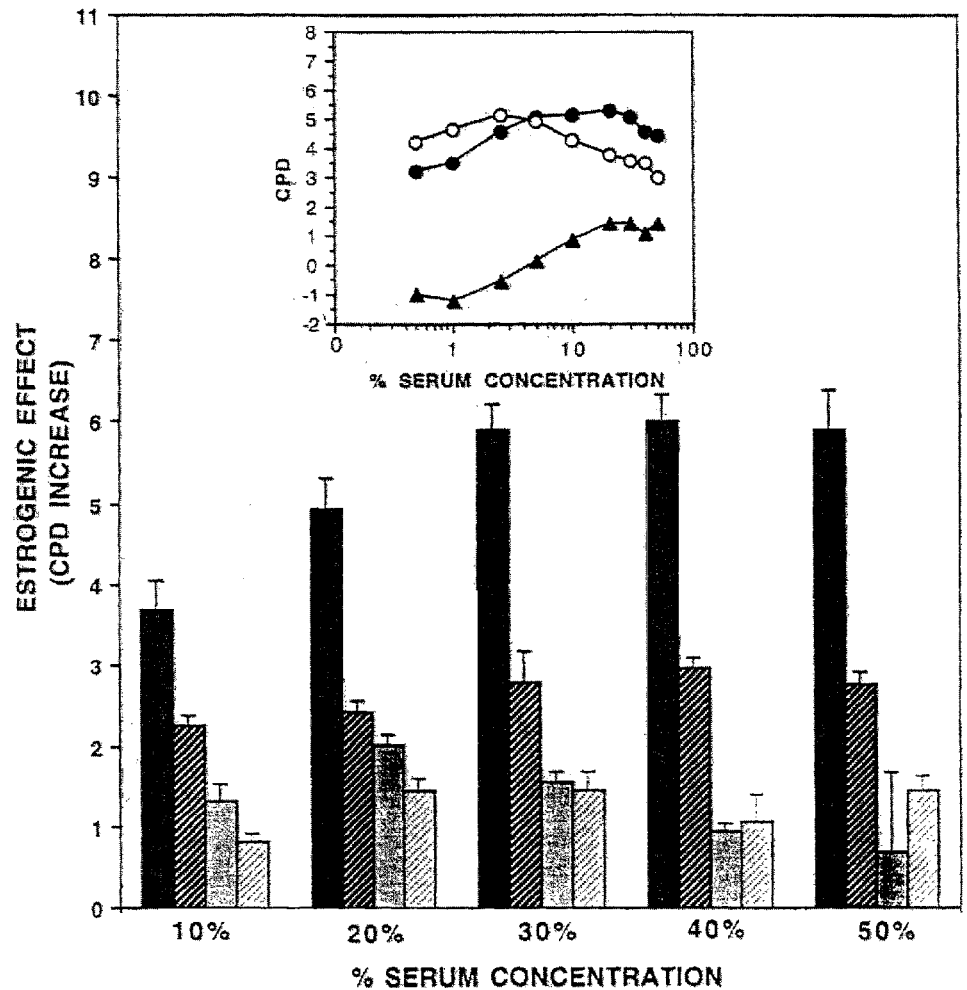

FILLED BARS: Estrogenic effect in 34°C prepared CDE-serum
DARK HATCHED BARS: 56°C prepared CDE-serum
LIGHT SHADED BARS: Charcoal extracted at 34°C then charcoal extraction at 56°C
LIGHT HATCHED BARS: Charcoal extracted at 34°C then incubation for 20 min at 56°C INSERT: Dose-response growth effects of horse serum extracted at 34°C
followed by incubation for 20 min at 56°C
Open circles - Growth without $E_2$
Closed circles - Growth with $1.0 \times 10^{-8} M$ $E_2$
Triangles - Estrogenic effect

HORSE SERUM TITRATION WITH MTW9/PL2 CELLS
EXTRACTION BY XAD-4 RESIN

% SERUM CONCENTRATION

LEGEND:

Open squares = + $E_2$

Closed squares = - $E_2$

HORSE SERUM TITRATION WITH T47D CELLS
EXTRACTION BY XAD-4 RESIN

% SERUM CONCENTRATION

LEGEND:

Open squares = + $E_2$

XXX = - $E_2$

Closed squares = Estrogenic effect

FIGURE 29

MCF-7 CELL GROWTH IN CDE - HORSE SERUM ± PHENOL RED AND ± $E_2$

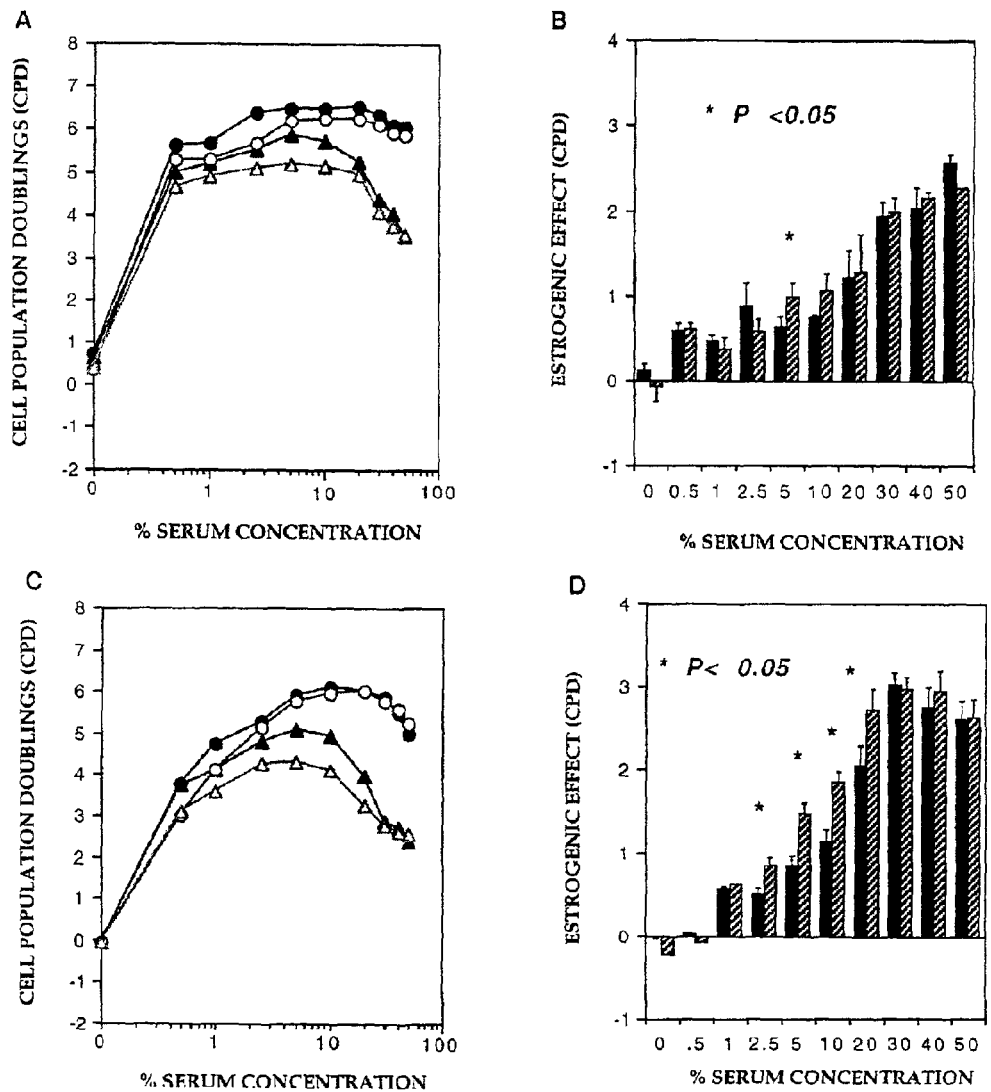

LEGEND:

(A) MCF-7A cell growth in phenol red containing medium with $E_2$ (closed circles) and without $E_2$ (closed triangles), and in phenol red-free medium with $E_2$ (open circles) and without $E_2$ (open triangles).

(B) Estrogenic effects with MCF-7A cells in medium with phenol red (solid bars) and without phenol red (shaded bars) were calculated from (A) and defined as the CPD in medium containing $E_2$ minus the CPD in medium without added $E_2$.

(C) MCF-7K cell growth in phenol red medium with $E_2$ (closed circles) and without $E_2$ (closed triangles), and in phenol red-free medium with $E_2$ (open circles) and without $E_2$ (open triangles).

(D) Estrogenic effects with MCF-7K cells in medium with phenol red (solid bars) and without phenol red (shaded bars), calculated from (C).

FIGURE 30

T47D AND ZR-75-1 CELL GROWTH IN CDE-HS ± PHENOL RED AND ± $E_2$

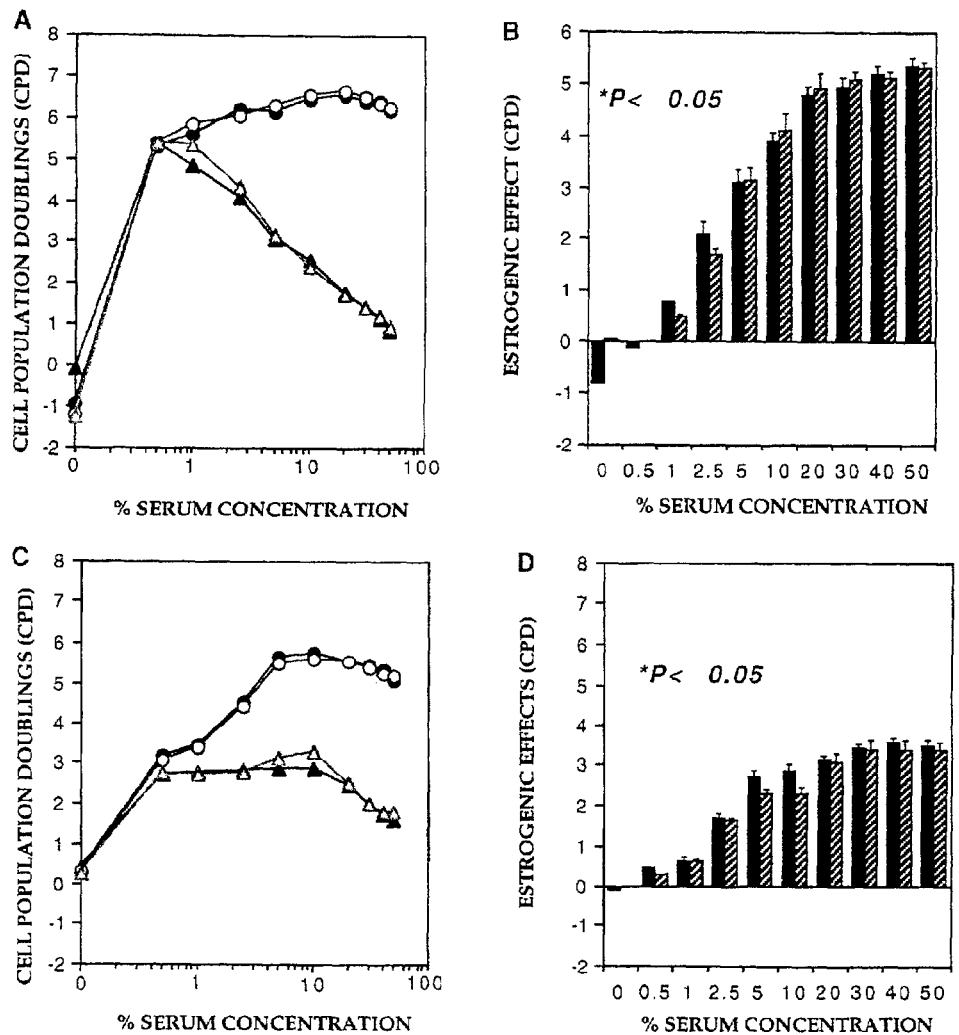

LEGEND:

(A) T47D cell growth in phenol red containing medium with $E_2$ (closed circles) and without $E_2$ (closed triangles), and in phenol red-free medium with $E_2$ (open circles) and without $E_2$ (open triangles).
(B) Estrogenic effects with T47D cells in medium with phenol red (solid bars) and without phenol red (shaded bars) were calculated from (A) and defined as the CPD in medium containing $E_2$ minus the CPD in medium without added $E_2$.
(C) ZR-75-1 cell growth in phenol red medium with $E_2$ (closed circles) and without $E_2$ (closed triangles), and in phenol red-free medium with $E_2$ (open circles) and without $E_2$ (open triangles).
(D) Estrogenic effects with ZR-75-1 cells in medium with phenol red (solid bars) and without phenol red (shaded bars), calculated from (C).

FIGURE 31

MTW9/PL2 CELL GROWTH IN CDE - HORSE SERUM
± PHENOL RED AND ± $E_2$

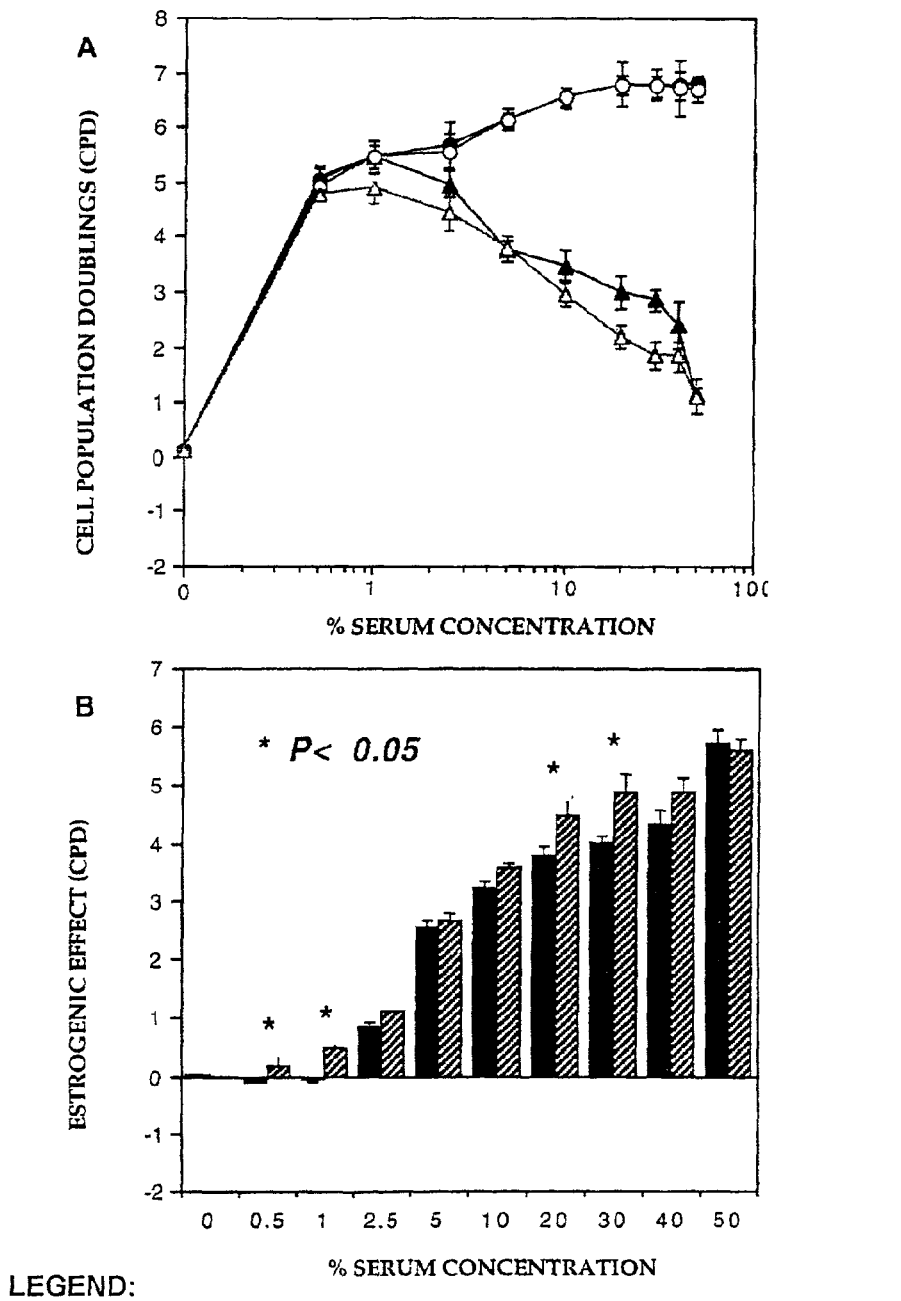

LEGEND:

(A) MTW9/PL2 growth in phenol red medium with $E_2$ (closed circles) and without $E_2$ (closed triangles), and in phenol red-free medium with $E_2$ (open circles) and without $E_2$ (open triangles).

(B) Estrogenic effects with MTW9/PL2 cells in medium with phenol red (solid bars) and without (shaded bars) were calculated from (A).

DOSE RESPONSE TO PHENOL RED AND $E_2$ IN THREE CELL LINES

LEGEND: The growth of the MCF-7A (closed circles), MTW9/PL2 (open circles) and T47D (closed triangles) cell lines was assessed at 14, 7, and 12 days.

FIGURE 33

PROGESTERONE RECEPTOR INDUCTION IN T47D CELLS BY PHENOL RED AND $E_2$

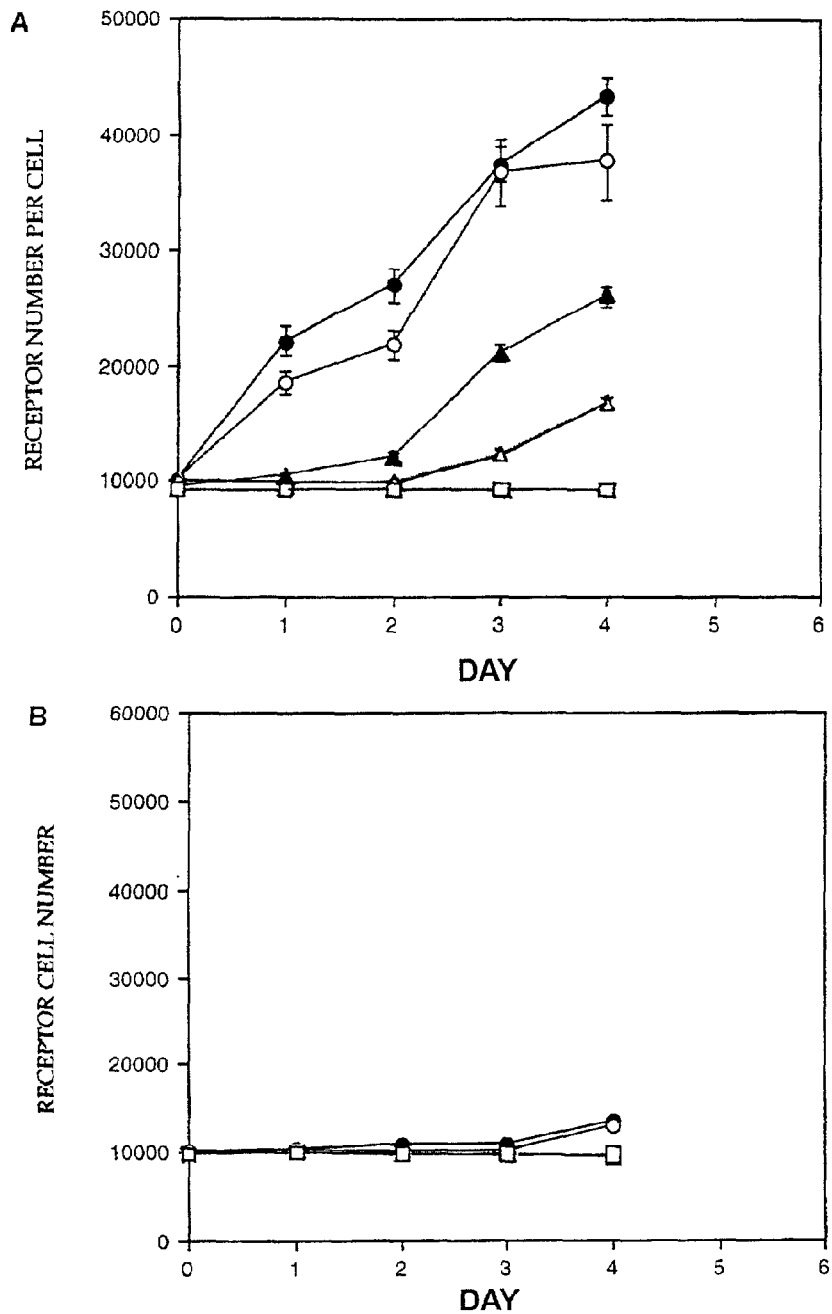

LEGEND:

(A) The effects of $E_2$ at $1.0 \times 10^{-8}$ M (closed circles), $1.0 \times 10^{-10}$ M (open circles), $1.0 \times 10^{-12}$ M (closed triangles), $1.0 \times 10^{-14}$ M (open triangles) and the control without added $E_2$ (open squares).

(B) The effects of phenol red at 16 mg/L (closed circles), 8 mg/L (open circles), 4 mg/L (closed triangles), 2 mg/L (open triangles), and the control without phenol red (open squares).

FIGURE 34

EFFECT OF TGF-beta1 ON THE GROWTH OF
BREAST/MAMMARY ORIGIN CELL LINES

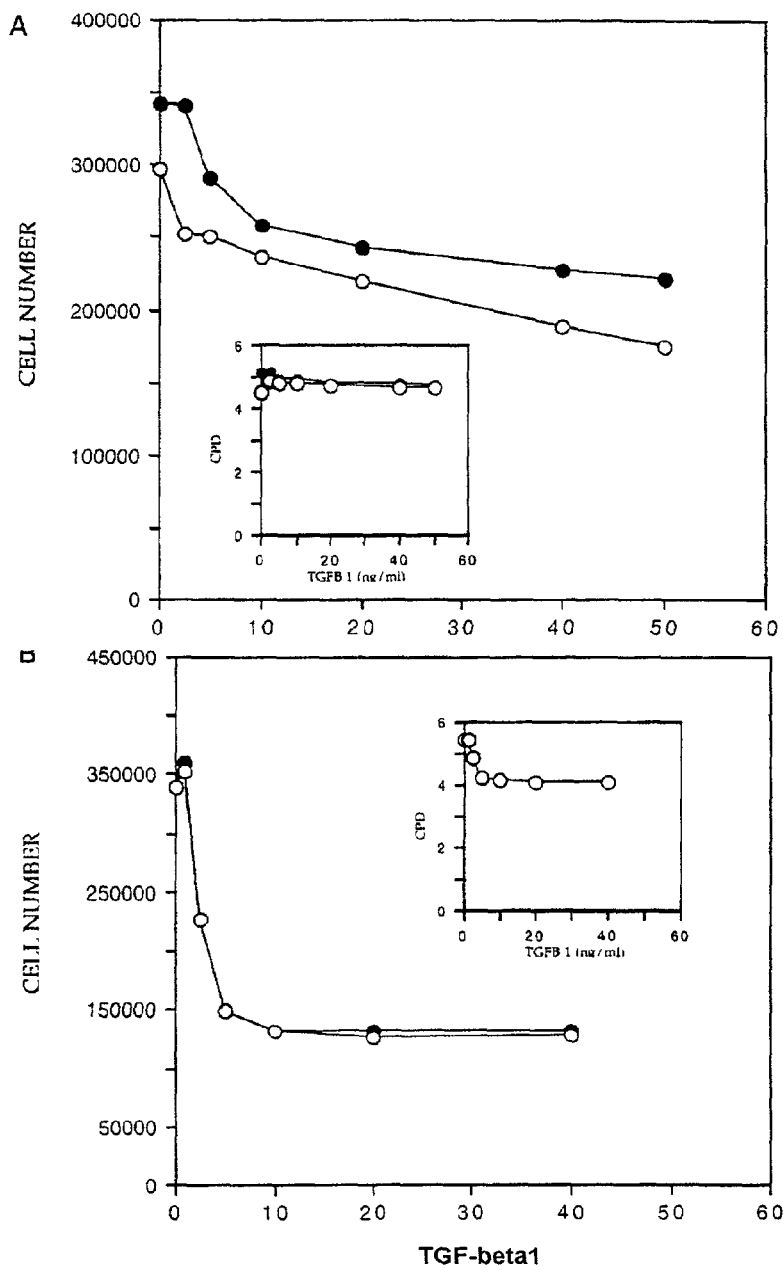

TGF-beta1

LEGEND:

(A) The effect of the transforming growth inhibitor on human breast MCF-7K cell growth as measured after 12 d either with 10 nM $E_2$ (closed circles) or without the hormone (open circles). The insert shows conversion of the cell number results to CPD.

(B) The same experiment with rat mammary MTW9/PL2 cells after 9 d growth.

FIGURE 35

EFFECT OF TGF-beta1 ON THE GROWTH OF CELL LINES FROM BOTH HUMAN AND RODENT TUMORS

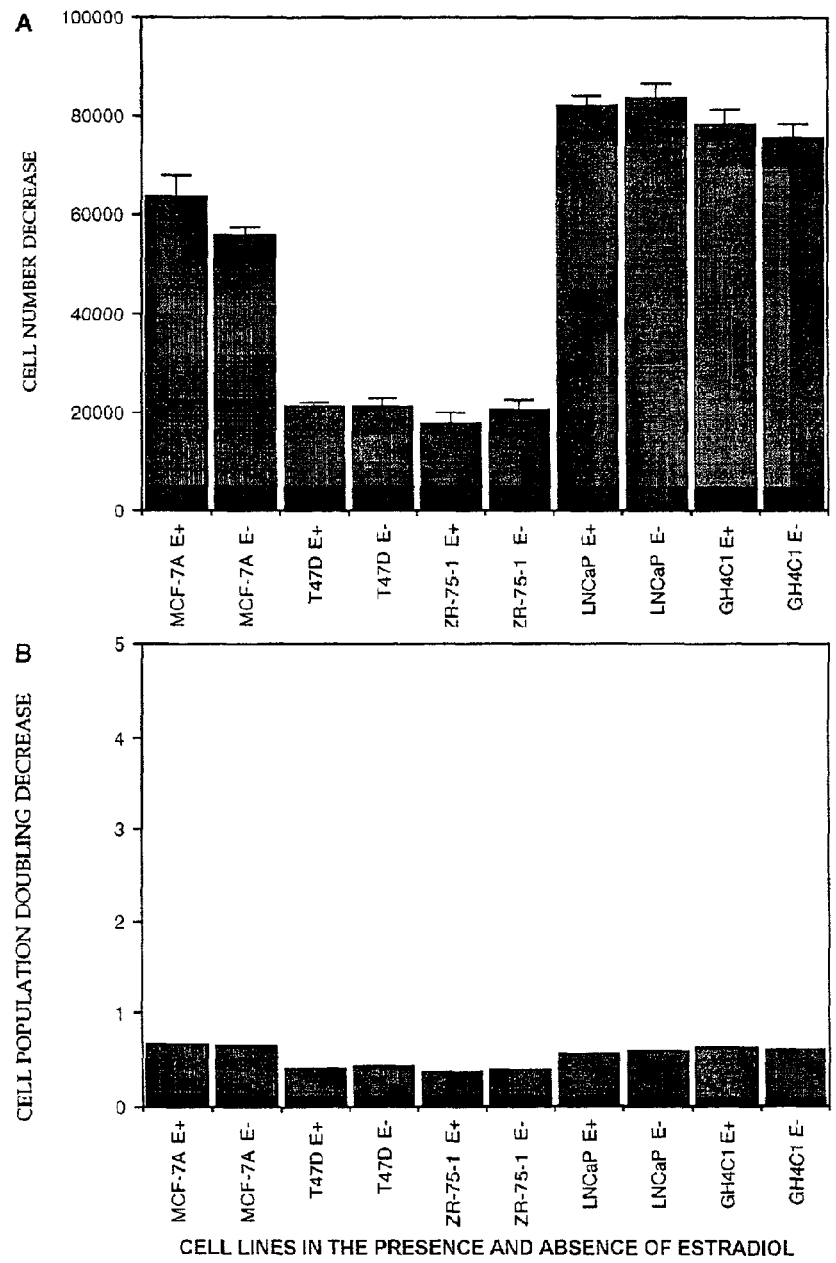

In these studies, TGF-beta1 was added at 40 ng/ml. Estradiol ($\pm$ E) indicates either no added $E_2$ or the steroid at 10 nM.

(A) The effect of TGF-beta1 on five cell lines after 10-14 d growth in medium $\pm E_2$. The results are expressed as cell number decreases caused by TGF-beta1.
(B) The CPD decreases caused by TGF-beta1 $\pm E_2$ with each of the cell lines shown in (A).

FIGURE 36

EFFECT OF EGF AND TGF-alpha ON THE GROWTH
OF HUMAN BREAST CANCER CELLS

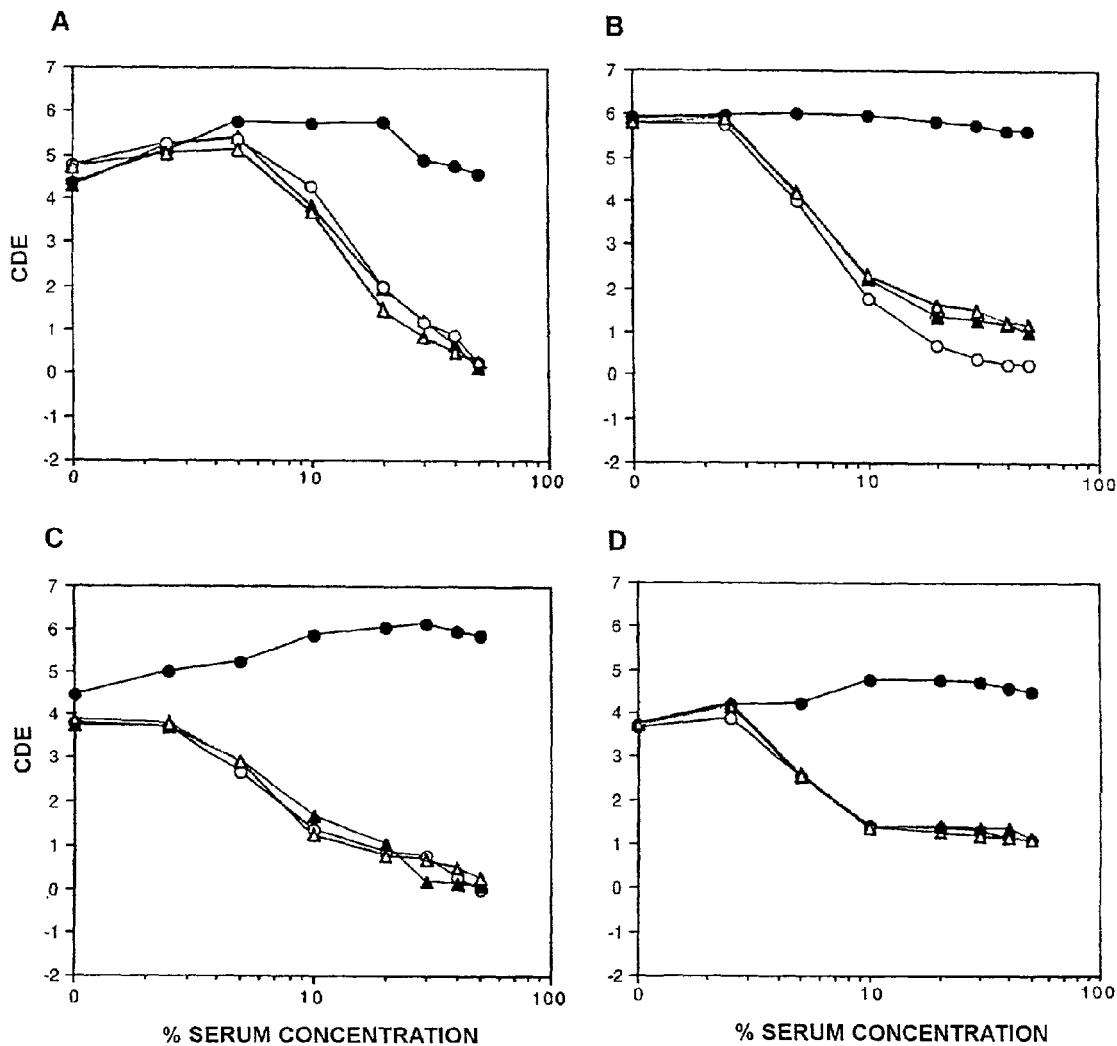

The cells were grown in D-MEM/F-12 supplemented with
increasing concentrations of CDE horse serum. Each line
tested was grown in serum alone (open circles) and in serum
plus 50 ng/ml EGF (open triangles), 50 ng/ml TGF-alpha (closed
triangles), or 10 nM $E_2$ without exogenous growth factors
(closed circles). (A) - (D) show the results with the MCF-7A,
MCF-7K, T47D, and ZR-75-1 cell lines, respectively.

FIGURE 37

EFFECT OF IGF-I ON THE GROWTH OF HUMAN BREAST CANCER CELLS

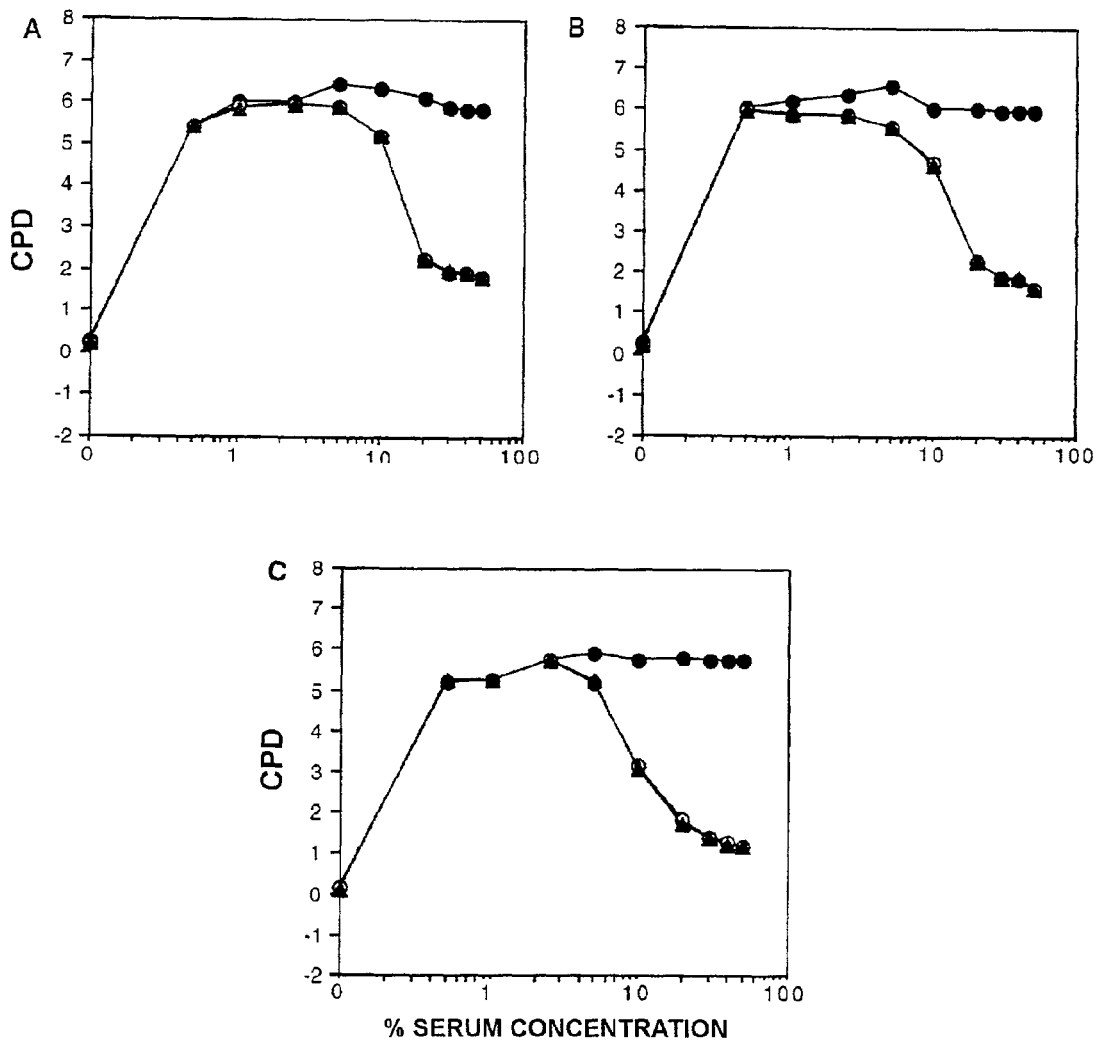

% SERUM CONCENTRATION

Breast cancer cells were grown in D-MEM/F-12 supplemented with increasing concentrations of CDE horse serum. Each cell line tested was grown in serum alone (open circles) and in serum plus 1.0 ug/ml IGF-I (triangles), or in serum with 10 nM $E_2$ without exogenous growth factors (closed circles). (A) - (C) show the results with the MCF-7K, MCF-7A and T47D cells, respectively. Assays were conducted for 12-14 d.

T47D CELLS IN STANDARD D-MEM/F-12 MEDIUM
VS "LOW FE" SERUM-FREE SERUM

LEGEND:
- ■ "STANDARD" MEDIUM
- ▲ "LOW-FE" MEDIUM

LNCaP CELLS IN STANDARD D-MEM/F-12 MEDIUM
VS "LOW-FE" SERUM-FREE MEDIUM

LEGEND:

—○— "STANDARD" MEDIUM

—●— "LOW-FE" MEDIUM

LEGEND:

Closed circles = Fetal bovine serum
Open circles = CAPM + DHT
Closed triangles = CAPM - DHT
Open triangles = D-MEM/F12 only

PC3 AND DU145 GROWTH IN SERUM - FREE
MEDIUM VS MEDIUM WITH 10% FETAL CALF SERUM

LEGEND:

― ◻ ― PC3 IN SERUM-FREE MEDIUM

― ♦ ― DU145 IN SERUM-FREE MEDIUM

― ■ ― PC3 IN 10% FETAL CALF SERUM

― ◇ ― DU145 IN 10% FETAL CALF SERUM

FIGURE 43
DOSE RESPONSE EFFECTS OF CAPM
SERUM - FREE MEDIUM COMPONENTS
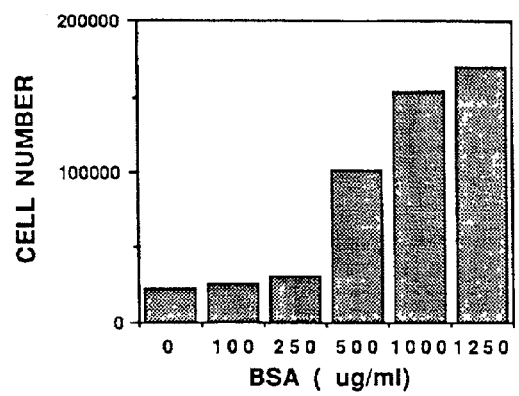
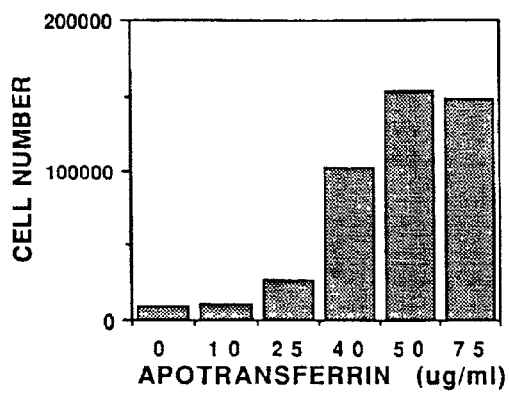
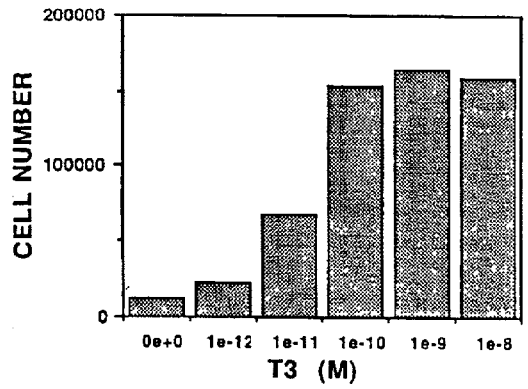
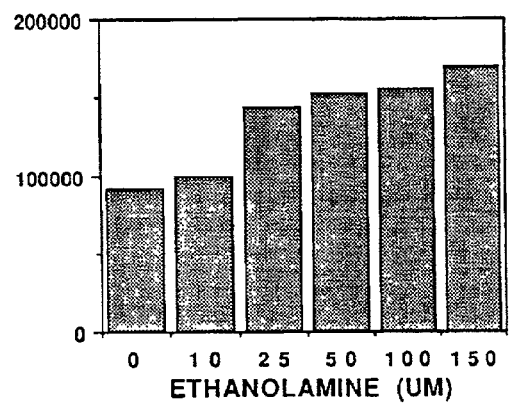
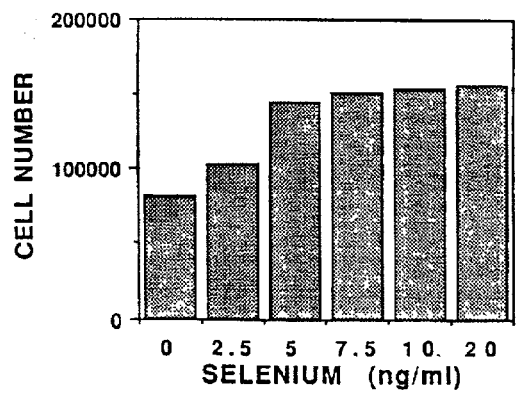
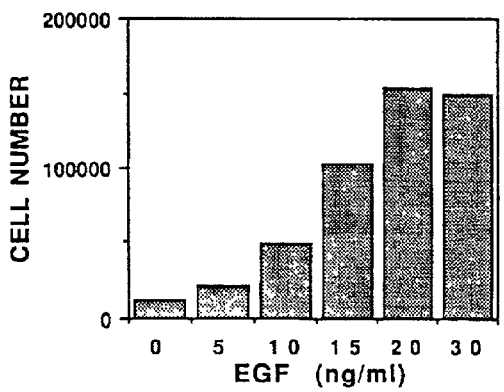

DELETIONS OF INDIVIDUAL COMPONENTS OF CAPM WITH PROSTATE CANCER CELL LINES

EFFECT OF FE (III) IN MCF-7A CELL GROWTH IN DDM-2MF DEFINED MEDIUM

LEGEND:

■ plus $E_2$

▲ minus $E_2$

EFFECT OF FE (III) IN T47D CELL GROWTH
IN DDM-2MF DEFINED MEDIUM

LEGEND:

■ plus $E_2$
▲ minus $E_2$

EFFECTS OF INCREASING CONCENTRATIONS OF
IRON ON LNCaP CELLS GROWN IN SERUM-FREE
MEDIUM WITH APOTRANSFERRIN

EFFECTS OF IRON AND $T_3$ ON THREE PROSTATIC
CELL LINES IN SERUM-FREE MEDIUM

INSERT:

DARK BARS = GROWTH IN CAPM PLUS $T_3$

LIGHT (HATCHED) BARS = GROWTH IN CAPM MINUS $T_3$

NOTE THE STRIKING DEPENDENCE OF LNCaP CELLS ON $T_3$

EFFECT OF CHELATORS ON SERUM-FREE LNCaP
GROWTH UNDER HIGH IRON CONDITIONS

LEGEND:

Closed circles = Deferoxamine

Open circles = Citrate

Closed triangles = EDTA

CDE HORSE SERUM TITRATION ON ALVA-41 CELLS

LEGEND:
● = + 10 nM DHT
○ = STEROID FREE
▲ = ANDROGENIC EFFECT

FIGURE 56

EFFECTS OF ESTROGEN ON STEROID HORMONE-RESPONSIVE HUMAN TUMOR CELL GROWTH

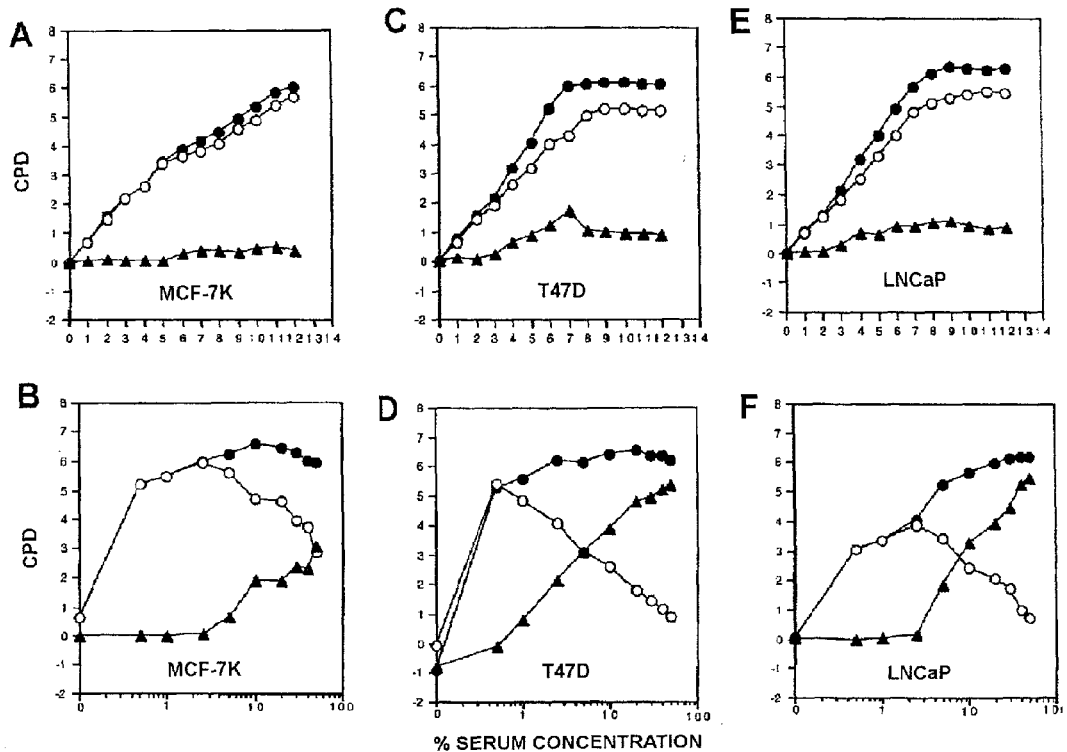

% SERUM CONCENTRATION

The cells were grown in serum-free defined medium and in D-MEM/F-12 supplemented with increasing concentrations of CDE horse serum.

(A) MCF-7K cell growth was measured daily in serum-free defined DDM-2MF with 10 nM $E_2$ (closed circles) and without steroid (open circles) $E_2$. Triangles = estrogenic effect.
(B) MCF-7K cell growth measured after 12 d in D-MEM-F-12 supplemented with the designated concentrations of serum with $E_2$ (closed circles) and without steroid (open circles). The estrogenic effect is shown by triangles.
(C) and (D) show the same experiments as in (A) and (B), respectively, except with T47D cells.
(E) and (F) show the same experiments as in (A) and (B), respectively, except with LNCaP cells. In (E) the serum-free medium was CAPM.

FIGURE 57

EFFECTS OF ESTROGEN ON STEROID HORMONE-RESPONSIVE RODENT TUMOR CELL GROWTH

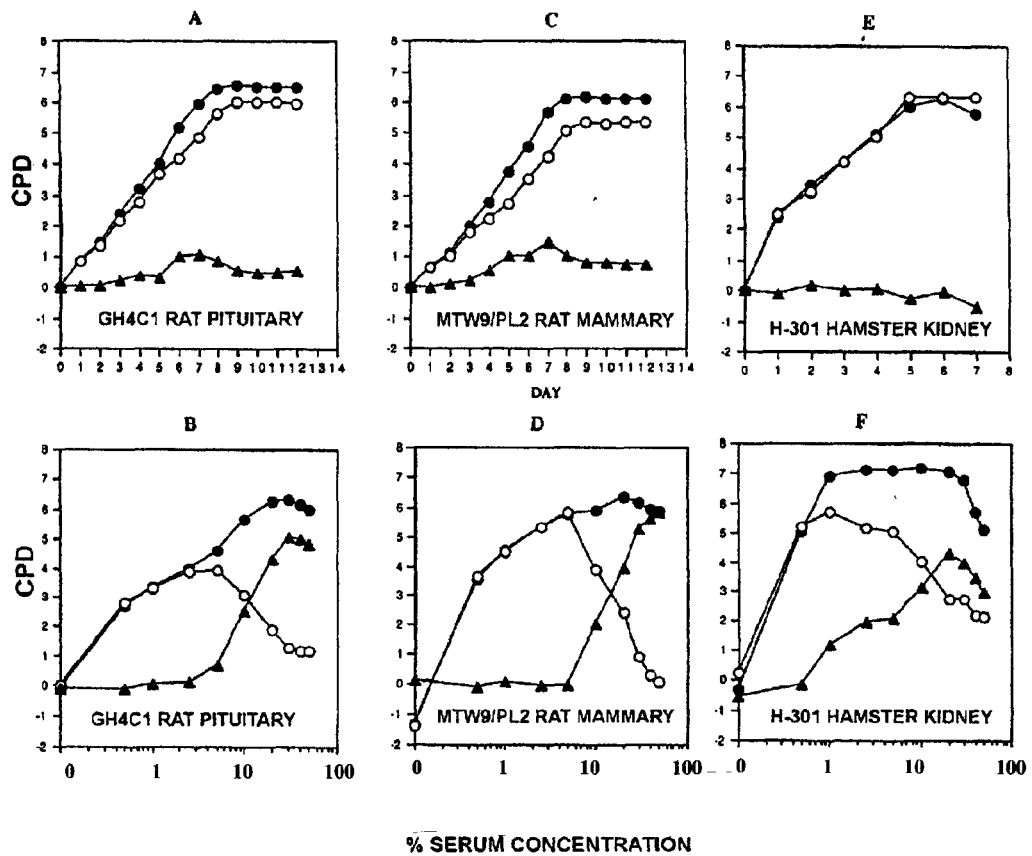

% SERUM CONCENTRATION

Comparison of the effects of estrogen on steroid hormone-responsive rodent tumor cell growth in serum-free defined medium and in D-MEM/F-12 supplemented with increasing concentrations of CDE horse serum.

(A) $GH_4C_1$ rat pituitary tumor cell growth measured daily in serum-free PCM-9 with $E_2$ (closed circles) and without $E_2$ (open circles). The estrogenic effect is shown by triangles.
(B) $GH_4 C_1$ cell growth measured after 9 d in D-MEM-F-12 supplemented with the designated concentrations of CDE horse serum with $E_2$ (closed circles) and without $E_2$ (open circles). The estrogenic effect is shown by triangles.
(C) and (D) show the same experiments as in (A) and (B) respectively, but with the MTW9/PL2 rat mammary tumor cells. The serum-free medium in (D) was DDM-2A.
(E) and (F) show the same experiments as in (A) and (B), respectively, except with the H-301 hamster kidney tumor cells. In (E) the serum-free medium was CAPM.

CDE HORSE SERUM TITRATION ON LNCaP
GROWTH IN SERUM FREE CONDITIONS

LEGEND:

—○— NO STEROID

—●— + $E_2$

—□— + DHT

FIGURE 59

THE EFFECT OF DHT, $E_2$, AND DES ON
LNCaP CELLS GROWN IN CDE HORSE SERUM

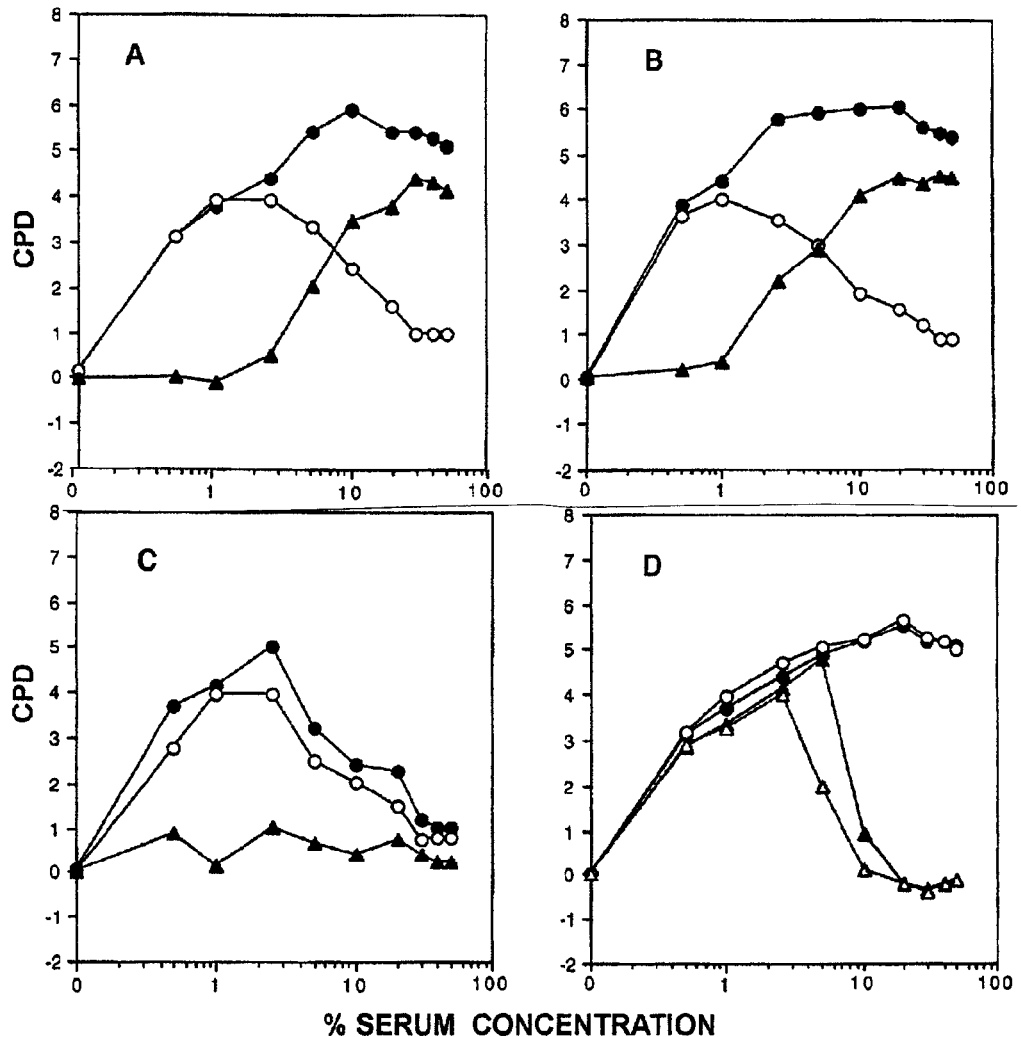

% SERUM CONCENTRATION

LEGEND:

(A) Open circles = - DHT
Closed circles = + DHT
Closed trianges = Androgenic effect (B) Open circles = - $E_2$
Closed circles = + $E_2$
Closed triangles = Estrogenic effect (C) Open circles = - DES
Closed circles = + DES
Closed triangles = Estrogenic effect (D) Open circles = DHT & DES
Closed circles = $E_2$ & DES
Open triangles = No additions
Closed triangles = DES only

TRIS DIALYSIS OF CDE HORSE SERUM
AND ASSAY WITH MTW9/PL2 CELLS

LEGEND:

—●— = + $E_2$

—○— = − $E_2$

—△— = Estrogenic effect

ULTRAFILTRATION OF CDE HORSE SERUM
AND ESTROGENIC EFFECTS WITH MTW9/PL2 CELLS

LEGEND:
  (A) RETENTATE FROM AMICON MEMBRANE
  (B) FILTRATE FROM AMICON MEMBRANE

Open circles = − $E_2$
Closed circles = + $E_2$
Closed triangles = Estrogenic effect

CDE HORSE SERUM TREATED AT 50° C FOR
30 MINUTES AND ASSAYED WITH MTW9/PL2 CELLS

LEGEND:

—○— = + $E_2$

—●— = – $E_2$

—△— = Estrogenic effect

EFFECT OF 50° C INCUBATION ON
ESTROGENIC EFFECT WITH MTW9/PL2

LEGEND:

Closed triangles = Estrogenic effect

CDE HORSE SERUM INCUBATION AT 50° C
FOR 20 HOURS AND ASSAYED WITH MTW9/PL2

LEGEND:

Open circles = $-E_2$

Closed circles = $+E_2$

Closed triangles = Estrogenic effect

CDE HORSE SERUM INCUBATED AT 60° C FOR
90 MINUTES AND ASSAYED WITH MTW9/PL2 CELLS

LEGEND:

Open circles = − $E_2$

Closed circles = + $E_2$

Closed triangles = Estrogenic effect

AFFI-GEL BLUE TREATMENT OF CDE HORSE
SERUM AND ASSAY WITH MTW9/PL2 CELLS

LEGEND:

Open circles = $-E_2$

Closed circles = $+E_2$

Closed triangles = Estrogenic effect

DIALYSIS OF CDE HORSE SERUM AGAINST
6M UREA AND ASSAY WITH MTW9/PL2 CELLS

LEGEND:

—○— = + $E_2$

—●— = − $E_2$ $ED_{50}$ MEASUREMENTS OF THE ESTROGENIC EFFECTS OF CDE HORSE SERUM WITH VARIOUS CELL LINES

LEGEND:
Closed circles = + $E_2$
Open circles = − $E_2$
Closed triangles = Estrogenic effect

ASSAY OF ESTROGENIC ACTIVITY
($ED_{50}$) OF CHROMATOGRAPHIC POOLS

LEGEND:

Closed circles = + $E_2$
Open circles = − $E_2$
Closed triangles = Estrogenic effect

AFFI-GEL BLUE BYPASS FRACTION
ASSAYED WITH MTW9/PL2 CELLS

LEGEND:

Closed circles = + $E_2$

Open circles = − $E_2$

Closed triangles = Estrogenic effect

DEAE SEPHAROSE CHROMATOGRAPHY OF CDE HORSE SERUM

LEGEND:

BARS = FRACTION POOLS

ARROWS = BUFFER CHANGES

Closed circles = Absorbance at 280 nm

Open circles = Conductance

THE ELUTION PROFILE OF PHENYL
SEPHAROSE WITH THE DEAE IV POOL

INSERT: Estrogenic activity with MTW9/PL2

LEGEND:

Closed circles = Absorbance 280 nm

Open circles = Conductance

HTP BIO-GEL CHROMATOGRAPHY OF DEAE POOL IV

BARS = FRACTION POOLS

ARROWS = BUFFER CHANGES

LEGEND:

Open circles = Conductance

Closed circles = Absorbance

THE EFFECT OF CALCIUM ON THE HEAT STABILITY OF THE INHIBITOR IN CDE HORSE SERUM (MTW9/PL2 CELLS)

LEGEND:

—▲— = Chelex treatment only

—△— = CDE horse serum

—■— = Chelex and 1 mM calcium chloride

—○— = Chelex and 10 mM calcium chloride

—●— = Chelex and 50 mM calcium chloride

PROTECTIVE EFFECT OF METAL IONS ON CHELEX TREATED CDE HORSE SERUM INCUBATED AT 37° C AND ASSAYED WITH MTW9/PL2 CELLS

LABELED DHT BINDING TO CDE HORSE SERUM
SATURATION ANALYSIS AND SCATCHARD PLOT

INSERT:

Scatchard analysis of DHT binding

EFFECT OF CALCIUM ON ESTROGENIC EFFECT (A)
AND LABELED STEROID HORMONE BINDING (B)

FIGURE 79
ANTI - HUMAN SHBG PRECIPITATION OF THE
LABELED DHT BINDING ACTIVITY (A) AND THE
ESTROGENIC EFFECT IN CDE HORSE SERUM (B)
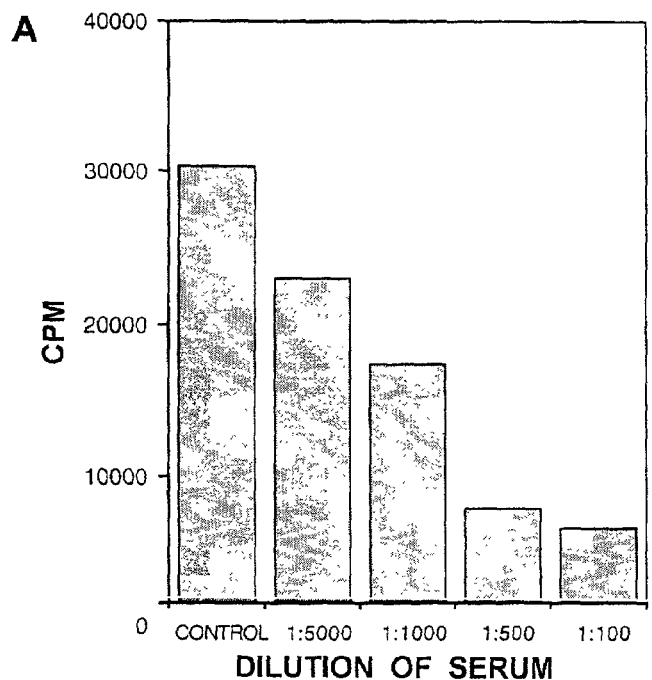
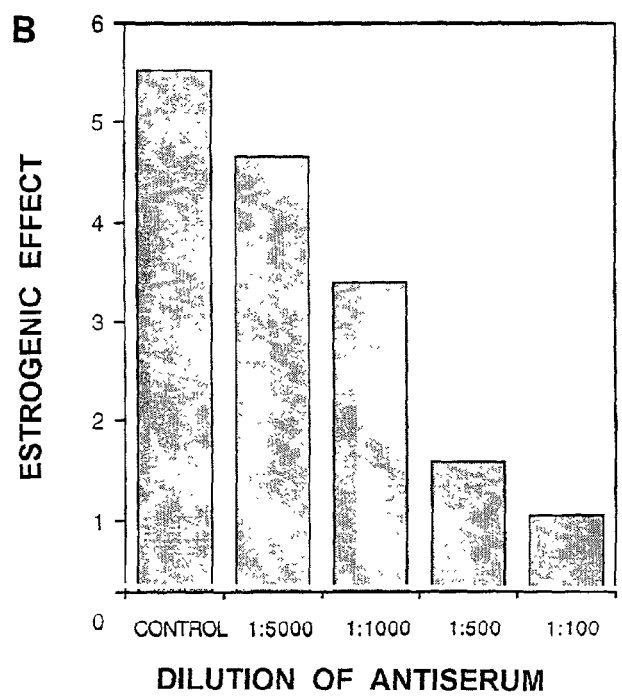

PHENYL SEPHAROSE ELUTION OF

CBG (CA-PS-POOL 1) AND SHBG-LIKE (CA-PS-POOL 11)

ARROW = ELUTION WITH 40% ETHYLENE GLYCOL

INSERT: CORTISOL AFFINITY COLUMN ELUTION

BARS = POOLED ACTIVE FRACTION

SDS PAGE (A) AND WESTERN ANALYSIS (B) OF THREE

PREPARATIONS OF CA-PS-POOL II VS HUMAN SHBG

LANES 1, 2, AND 3 = 10 ug each of CA-PS-POOL II

LANE "SHBG" = 10 mg of purified protein

ASSAY OF CA-PS-POOL II ESTROGEN REVERSIBLE INHIBITORY ACTIVITY WITH SEVERAL ER CELL LINES

LEGEND: Open circles = $-E_2$
Closed circles = $+E_2$
Closed triangles = Estrogenic effect

CORTISOL-AGAROSE AFFINITY REMOVAL
OF THE INHIBITOR FROM CDE-SERUM

LEGEND: Open circles = $-E_2$
Closed circles = $+E_2$
Closed triangles = Estrogenic effect

GROWTH OF ER+ CELL LINES IN SERUM-FREE MEDIUM ± $E_2$

LEGEND:

Closed circles = + $E_2$

Open circles = − $E_2$

EFFECT OF CDE-SERUM ON ESTROGEN RESPONSIVE
GROWTH OF THREE ER+ CANCER CELL LINES IN SFM

A =
T47D IN DDM-2MF

B =
MTW9/PL2 IN DDM-2A

C =
$GH_4 C_1$ IN PCM 9

EFFECT OF CA-PS-POOL II ON ESTROGEN
RESPONSIVE GROWTH IN SERUM FREE MEDIUM

LEGEND: Open circles = − $E_2$
Closed circles = + $E_2$

FIGURE 87

AMINO ACID SEQUENCING - HORSE SHBG

```
                10         20         30         40         50         60         70         80         90        100
hm SHBG  LRPVLPTQSAHDPPAVHLSNGPGGQEPIAVMTFDLTKITKTSSSFEVRFWDPEGVIFYGDTNPKDDWFMLGLRDGRPEIQLHNHWAQLTVGAGPRLDDGRW
rb SHBG              TQRAQDSPAVHLINGLGQEPIQVLTFDLTRIVKASSSFELRTWDSEGVIFYGDTNPKDDWFMLGLRDGRPEIQLHNLWAQLTVGAGPRLDDGSW
rt ABP   LRHIDPIQSAQDSPAKYLSNGPGGQEPVTVLTIDLTKISKPSSSFEFRTWDPEGVIFYGDTNTEDDWFMLGLRDGGQLEIQLHNLWARLTVGFGPRLNDGRW
hs ABP   ..........NGPGGQEPVAVMTIDLTQMSKPYSSFEFRILDPEGVIFYGDTNTKDDWFMLGLRDGGQLEIQMHNPWAQLTVGFGPRLNDGRW
              *   *                       * *   *              ****
         #40:IPGVILVK #25:VVSVLPIQv                     #31:IEGVIPIPSV 110        120        130        140        150        160        170        180        190        200
hm SHBG  HQVEVKMEGDSVLLEVDGEEVLRLRQVSGPLTSKRHPIMRIALGLLFPASNLRLPLVPALDGCLRRDSWLDKQAEISASAPTSLRSCDVESNPGIFLPP
rb SHBG  HQVHVKLRGDSVLLEVDGKEVLRLSQVSGTLHDKPQPVMKIAVGLLFPPSSLRLPLVPALDGCLRRGSWLDPQAQLSASAHLSLRSCDVELQPGLFFPP
rt ABP   HPVELKMNGDSLLLWDGKEMLCLRQVSASLADHPQLSMRIALGGLLPTSKLRFPLVPALDGCIRHDIWLGHQAQLSTSARTSLGNCDVDLQPGLFFPP
hs ABP   HQVELKMSGDSLQLWDGKELLCLRQISGTLANNSWPSMRIALGGLLLPTSSLRFPLVPALDGCLRRDTWLGHQVHLSPSAP.NLGNCDVDLQPGLFFPQ
         *          *    *             * **   *   **   *   *                           * ***      *   ***   *
         #22:SLVYVTNVAK #26:VVVILAIVPK #34:SVPGLVSPSQ     #37:ATVV?LISDF  #20:VQLSPse            #34:SVPGLVSPS
                                                                         #10:VAQFLSTYVIT 210        220        230        240        250        260        270        280        290        300
hm SHBG  GTQAEFNLRDIPQPHAEPWAFSLDLGLKQAAGSGHLLALGTPENPSWLSLHIQDQKVVLSSSGPGLDLPLVLGLPLQLKLSMSRVVLSQGSKMKALALP
rb SHBG  GTHAEFSLQDIPQPQTEPWAFSLDLELKPSEGSGRLLALGTPEDPNWLSLHLQDQKVVLSSGMEPGLDLPLAWGLPLQLKLGVSTAVLSQGSKKKALGLP
rt ABP   GTHAEFSLQDIPQPHTDPWTFSLELGFKLVDGAGRLLTLGTGTNSSWLTLHLQDQTVVLSSEAEPKLALPLAVGLPIQLKLDVFKVALSQGPKMEVLSTS
hs ABP   GTHAEFSLQDIPQPRTDPWSFSFSLELGLKLVDGSGCLLALGTRTNSSWLSLHLQDQKVVLSSGVEPKLVLALDMGLPLQLKLDILKVVLSQGPKTEVLGAS
                                                                                      **    ****
                                                                                 #26:VVVILAIVPK
                                                                                      #9:LAVQVR
         Q
         #41:VFALAPIPGVLK 310        320        330        340        350        360        370
hm SHBG  PLGLAPLLNLWAKPQGRLFLGALPGEDSSTSFCLNGLWAQGQRLDVDQALNRSHEIWTHSCPQSPGNCTDASH
rb SHBG  SPGLGPLLNLWAKPQGRLFLGALPGEDSSASFCLDGLWTVGQKLDMDKALNRSHDIWTHSCPQSPGNGTDASH
rt ABP   LLRLASLWRLWSHPQGRLSLGALPGEDSSASFCLSDLWVQGGRLDIDKALSRSQDIWTHSCPQSPSNDTHTSH
hs ABP   ASRLAALRTLWSHPQGLLSLGALAGDNSSASFCLSDLWVQGGRLDIDQALNRSQNIWTHSCPHSPNNVSHISH
```

WESTERN ANALYSIS OF CBG (POOL I) AND SHBG (POOL II) PREPARATION WITH ANTI-54 kDa

LANES:    1    2    3    4    5    6

1 = CBG PREPARATION #5

2 = CBG PREPARATION #6

3 = SHBG PREPARATION #5.1

4 = SHBG PREPARATION #5.2

5 = SHBG PREPARATION #6.1

6 = SHBG PREPARATION #6.2

ANTIBODY = RABBIT ANTI-54 kDa 1:5000 DILUTION

EFFECT OF ANTI-54kDa ANTISERUM ON MTW9/PL2 CELLS GROWN IN THE PRESENCE OF CA-PS-POOL II

WESTERN BLOT OF COMMERCIAL PREPARATIONS
OF HORSE IgA, IgG AND IgM WITH THE
ANTI-54 kDa ANTIBODY

EFFECT OF COMMERCIALLY PURIFIED HORSE IgG

ON MTW9/PL2 CELL GROWTH IN 2.5% CDE-HORSE SERUM

CONCENTRATION OF HORSE IgG (ug/mL)

LEGEND: ■ plus $E_2$
▲ minus $E_2$

EFFECT OF HORSE IgM ON GROWTH OF THE
MTW9/PL2 CELLS IN 2.5% CDE HORSE SERUM $\pm E_2$

LEGEND:

— ● — = + $E_2$

— ○ — = − $E_2$

— ▼ — = Estrogenic effect

EFFECT OF HORSE IgA ON GROWTH OF THE MTW9/PL2 CELLS IN 2.5% CDE HORSE SERUM $\pm E_2$

LEGEND:

●— = + $E_2$

○— = − $E_2$

▼— = Estrogenic effect

FIGURE 94
SDS PAGE AND WESTERN ANALYSIS OF RAT "SHBG-LIKE" PREPARATIONS
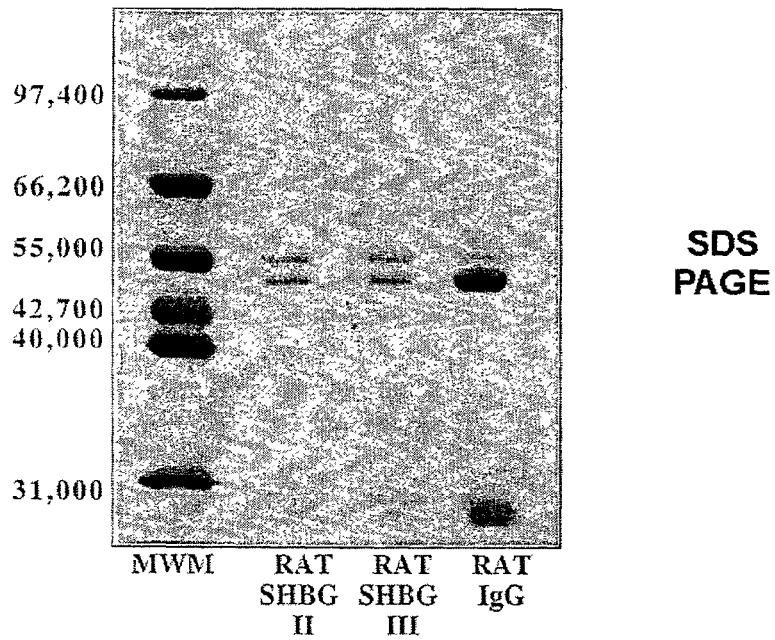
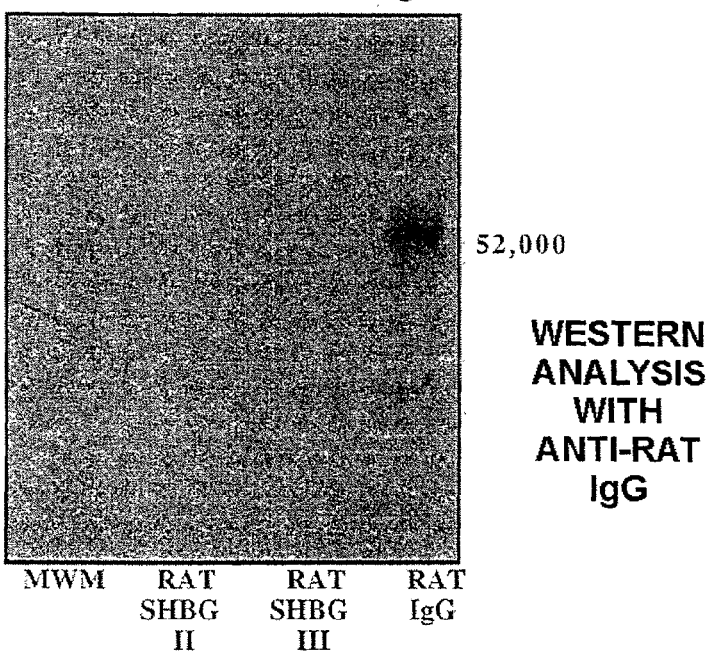

CROSSREACTION OF THE PURIFIED RAT "SHBG-LIKE" PROTEINS
WITH ANTI- IgA, IgG1 AND IgM MONOCLONAL ANTIBODIES

FIGURE 96

AMINO ACID SEQUENCING - RAT SHBG

```
                 10        20        30        40        50        60        70        80        90       100
hmSHBG    ..PVL.T...H.P..VH.......IA.M.F.....T.T.....V.........................PK.............RP......H..Q......A.....D....
rbSHBG      T.R.....VH.I..L....IQ..F....R.V.A.....T.T.....L....S...............PK...................RP..........Q....A....D.S.
hsABP                            ..A.M....QM..Y......L........................K.....................M..P..Q..............
rtABP     LRHIDPIQSAQDSPAKYLSNGPGQEPVTVLTIDLTKISKPSSSFEFRTWDPEGVIFYGDTNTEDDWFMLGLRDGQLEIQLHNLWARLTVGFGPRLNDGRW
                **     ****                ****             *           ***                 **    *         **   **
                       #37':GPFVTPVTVTK    #9:IEQY?STFK                     #29:IFYPI?IYTQ               #21:EVQLVEIGGGLVQPGR
                                P V             LP                               GL   VD  VE
                                                E   #37:DYFR 110       120       130       140       150       160       170       180       190       200
hmSHBG    .Q..V..E...V..E.....E.V.R......GP.TSKRHPI...........F.A.N..L............L...S..DK..EI.A..P...RS...ESN..I.L...
rbSHBG    .Q.HV.LR..V..E.....V.R.S...GT.H.K..PV.K..V....F.P.S..L............L.GS..DP....A..HL..RS...E..............
hsABP     .Q...S.....Q........L....I.GT...NNSWP.............S..........L...T......VII..P..PN-.....................Q
rtABP     HPVELKMNGDSLLLWVDGKEMLCLRQVSASLADHPQLSMRIALGLLLPTSKLRFPLVPALDGCIRRDIWLGHQAQLSTSARTSLGNCDVDLQPGLFFPP
                                                                                                        ***       *
                                                                                                        #18:VVSGLFPVP
                                                                                                        EAPIA
                                                                                                        T 210       220       230       240       250       260       270       280       290       300
hmSHBG    ..Q...N.R.......AE..A.....D..L.QAA..S..H..A....PE..P...S........K.......GSG..G..D....VL..........SMSR..V....S..KA.ALP
rbSHBG    .............Q.E..A.....D.EL.PSE..S.....A...PEDPN..S........K......GM..G..D....W.......G.STAV.......S.KKA.GLP
hsABP                .R...S..........L.....S.C..A....R.......S.......K.....GV...V.A.DM......IL..V......T..GA.
rtABP     GTHAEFSLQDIPQPHTDPWTFSLELGFKLVDGAGRLLTLGTGTNSSWLTLHLQDQTVVLSSEAEPKLALPLAVGLPIQLKLDVFKVALSQGPKMEVLSTS
                                                             ** **   **  *
          ISGAFIAF           #18:VVSGLFPVPISGAFIAF
          K  P V             EAPIA K  P V
                                T 310       320       330       340       350       360       370
hmSHBG    P.G..P.LN...AK.....F..........T......NG..A.....V.Q..N..HE............G.G.DA..
rbSHBG    SPG.GP.LN...AK.....F...........DG..TV..K..M....N..H..............G.G.DA..
hsABP     AS....A.RT......L....A.DN............Q..N....N.........H..N..VS.I..
rtABP     LLRLASLWRLMWSHPQGRLSLGALPGEDSSASFCLSDLWVQGGQRLDIDKALSRSQDIWTHSCPQSPSNDTHTSH
```

FIGURE 97
SDS PAGE (A) AND WESTERN ANALYSIS (B) WITH ANTI-SHBG AND RAT Ig'S
A RAT Igs COMMASSIE STAINED
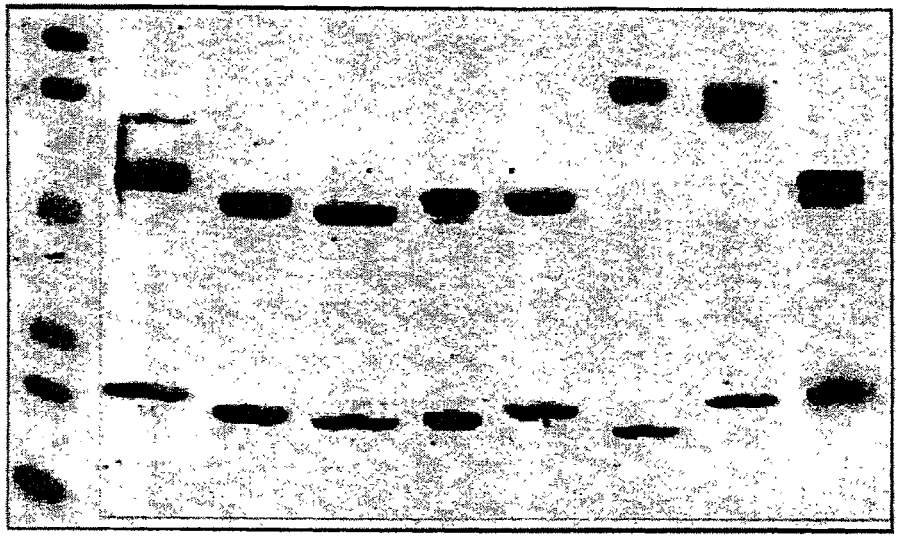
B RAT Igs WESTERN BLOT. ANTI SHBG ANTIBODY
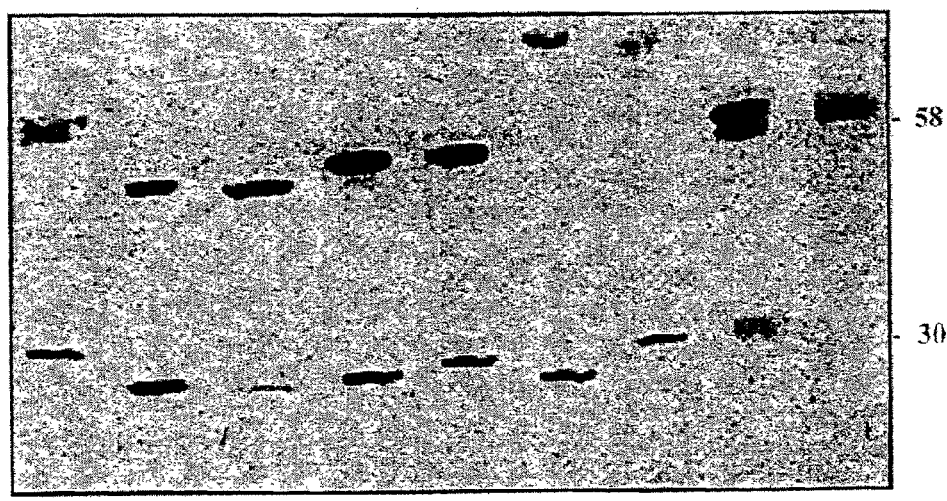

EFFECT OF RAT IgG ON MTW9/PL2 CELL

GROWTH IN 2.5% CDE RAT SERUM

LEGEND:

Closed circles = + $E_2$

Open circles = − $E_2$

Closed triangles = Estrogenic effect

EFFECT OF RAT IgA ON MTW9/PL2 CELL
GROWTH IN 2.5% CDE RAT SERUM

CONCENTRATION OF RAT IgA (ug/mL)

LEGEND:

Closed circles = + $E_2$

Closed squares = − $E_2$

Closed triangles = Estrogenic effect

EFFECT OF RAT IgM ON MTW9/PL2 CELL GROWTH IN 2.5% CDE RAT SERUM

LEGEND:

Closed squares = $-E_2$

Closed circles = $+E_2$

Closed triangles = Estrogenic effect

ELUTION OF IgM FROM MANNAN
BINDING PROTEIN COLUMN

IgM PURIFICATION FROM

PLASMA BY JACALIN

MW    HUMAN    PURIFIED
      IgA      IgA

EFFECT OF IgM ISOLATED FROM HUMAN PLASMA
ON MTW9/PL2 GROWTH IN SERUM-FREE CONDITIONS

LEGEND:

—●— = + $E_2$

——— = − $E_2$

—▼— = Estrogenic effect

THE EFFECT OF VARIOUS IgA AND IgM PREPARATIONS
ON MTW9/PL2 CELLS GROWN IN SERUM-FREE MEDIUM

RAT MYELOMA IgA TITRATION ON $GH_1$ CELLS GROWN IN SERUM-FREE CONDITIONS

LEGEND:

Closed circles = + $E_2$

Open circles = − $E_2$

Closed triangles = Estrogenic effect

HUMAN PLASMA IgA TITRATION ON GH$_1$ CELLS GROWN IN SERUM-FREE CONDITIONS

LEGEND:

Closed circles = + E$_2$

Open circles = − E$_2$

Closed triangles = Estrogenic effect

HUMAN PLASMA IgM TITRATION ON $GH_1$ CELLS
GROWN IN SERUM-FREE CONDITIONS

HUMAN PLASMA IgM CONCENTRATION (ug/mL)

LEGEND:

●— = + $E_2$

■— = − $E_2$

▲— = Estrogenic effect

MECHANISM OF TRANSCYTOSIS OF IgA AND IgM
BY MUCOSAL EPITHELIAL CELLS

FIGURE 110
ESSENTIAL STRUCTURES OF HUMAN PLASMA AND SECRETORY IgA
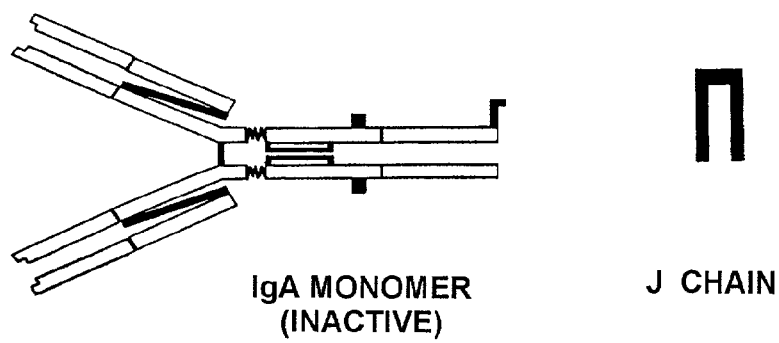
IgA MONOMER (INACTIVE)　　　J CHAIN
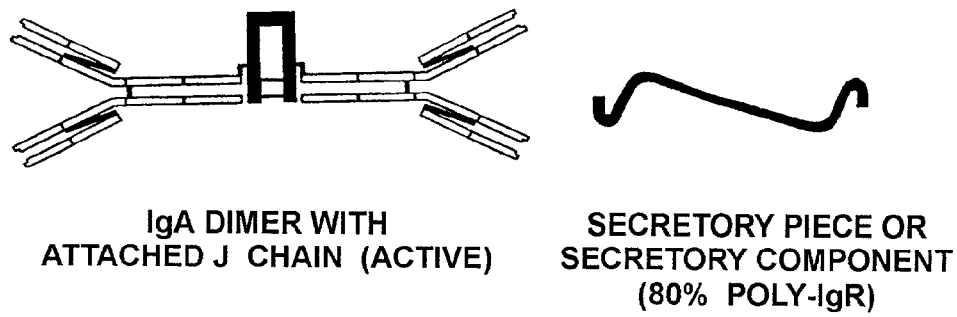
IgA DIMER WITH ATTACHED J CHAIN (ACTIVE)　　　SECRETORY PIECE OR SECRETORY COMPONENT (80% POLY-IgR)
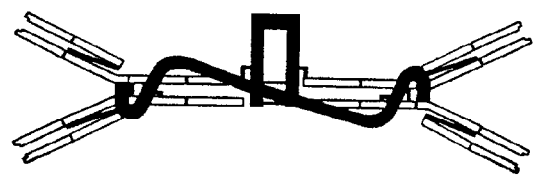
SECRETORY IgA SHOWING J CHAIN AND SECRETORY COMPONENT (INACTIVE)

EFFECT OF RAT MYELOMA IgA ON $GH_3$ CELLS GROWN IN SERUM-FREE MEDIUM

LEGEND:

Closed circles = $+ E_2$

Open circles = $- E_2$

Closed triangles = Estrogenic effect

EFFECT OF RAT IgM ON $GH_3$ CELL GROWTH IN SERUM-FREE MEDIUM

EFFECT OF HUMAN PLASMA IgA ON $GH_3$
CELL GROWTH IN SERUM-FREE MEDIUM

LEGEND:

Closed circles = + $E_2$

Open circles = – $E_2$

Closed triangles = Estrogenic effect

EFFECT OF HUMAN PLASMA IgM ON GH$_3$
CELL GROWTH IN SERUM-FREE MEDIUM

LEGEND:

●— = + E$_2$

■— = − E$_2$

▼— = Estrogenic effect

EFFECT OF RAT MYELOMA IgA ON GH$_4$ CELL GROWTH IN SERUM-FREE MEDIUM

LEGEND:

Closed circles = + E$_2$

Open circles = − E$_2$

Closed triangles = Estrogenic effect

EFFECT OF HUMAN PLASMA IgA ON $GH_4C_1$ CELL GROWTH IN SERUM-FREE MEDIUM

LEGEND:

Closed circles = + $E_2$

Open circles = − $E_2$

Closed triangles = Estrogenic effect

EFFECT OF HUMAN PLASMA IgM ON $GH_4C_1$ CELL GROWTH IN SERUM-FREE MEDIUM

LEGEND:

—●— = + $E_2$

—X— = − $E_2$

—▲— = Estrogenic effect

EFFECT OF HUMAN MILK SECRETORY IgA ON
$GH_4C_1$ CELL GROWTH IN SERUM-FREE MEDIUM

CONCENTRATION OF HUMAN SECRETORY IgA (ug/mL)

LEGEND:

Closed circles = + $E_2$

Open circles = − $E_2$

Closed triangles = Estrogenic effect

EFFECT OF MOUSE IgA ON H301 CELL GROWTH IN SERUM-FREE MEDIUM

LEGEND:

Closed circles = + $E_2$

Open circles = − $E_2$

Closed triangles = Estrogenic effect

EFFECT OF HUMAN PLASMA IgA (A) AND SECRETORY IgA (B) ON H301CELL GROWTH IN SERUM-FREE MEDIUM

LEGEND:  Closed circles = + $E_2$
Open circles = – $E_2$
Closed triangles = Estrogenic effect EFFECT OF ESTRADIOL ON H301 CELL GROWTH IN SERUM-FREE MEDIUM AND 40 ug/mL OF HUMAN IgM EFFECT OF HUMAN PLASMA IgA (A) AND SECRETORY IgA
(B) ON MCF-7A CELL GROWTH IN SERUM-FREE MEDIUM LEGEND:  Closed circles = + $E_2$ Open circles = – $E_2$ Closed triangles = Estrogenic effect EFFECT OF HUMAN IgM ON MCF-7A CELL GROWTH IN SERUM-FREE MEDIUM

LEGEND:

—●— = + $E_2$

—○— = − $E_2$

—▼— = Estrogenic effect

EFFECT OF HUMAN IgM ON MCF-7K
CELL GROWTH IN SERUM-FREE MEDIUM

LEGEND:

—●— = + $E_2$

—○— = − $E_2$

—▼— = Estrogenic effect

EFFECT OF ESTRADIOL ON MCF-7K CELL GROWTH IN SERUM-FREE MEDIUM WITH 40 ug/mL HUMAN IgM

EFFECT OF HUMAN PLASMA IgA (A) AND SECRETORY IgA (B) ON T47D CELL GROWTH IN SERUM-FREE MEDIUM

LEGEND: Closed circles = + $E_2$
Open circles = − $E_2$
Closed triangles = Estrogenic effect

EFFECT OF HUMAN IgM ON T47D CELL GROWTH IN SERUM-FREE MEDIUM

LEGEND: Closed circles = + $E_2$

Open circles = − $E_2$

Closed triangles = Estrogenic effect

EFFECT OF ESTRADIOL ON T47D CELL GROWTH IN SERUM-FREE MEDIUM WITH 40 ug/mL HUMAN IgM

EFFECT OF HUMAN PLASMA IgA (A) AND SECRETORY
IgA (B) ON ZR-75-1 CELL GROWTH IN SERUM-FREE MEDIUM

LEGEND:  Closed circles = + $E_2$
Open circles = − $E_2$
Closed triangles = Estrogenic effect

EFFECT OF HUMAN PLASMA IgM ON
ZR-75-1 CELL GROWTH IN SERUM-FREE MEDIUM

LEGEND:

—●— = − $E_2$

—○— = + $E_2$

EFFECT OF HUMAN IgM ON HT-29 CELL GROWTH IN THE PRESENCE OF INCREASING CONCENTRATIONS OF $T_3$

LEGEND:

☐ = $T_3$ Titration

■ = $T_3$ Titration + 40 ug/mL IgM

EFFECT OF HUMAN PLASMA IgA (A) AND SECRETORY
IgA (B) ON LNCaP CELL GROWTH IN SERUM-FREE MEDIUM

LEGEND: Closed circles = + $E_2$
Open circles = − $E_2$
Closed triangles = Estrogenic effect EFFECTS OF HUMAN PLASMA IgM VS IgM DERIVED FROM MYELOMA CELLS ON LNCaP CELL GROWTH IN SERUM-FREE MEDIUM WITH AND WITHOUT DHT

FIGURE 137

ESTROGENIC EFFECT OF 50 ug/mL OF VARIOUS
IgM'S ON SEVERAL DIFFERENT CELL LINES

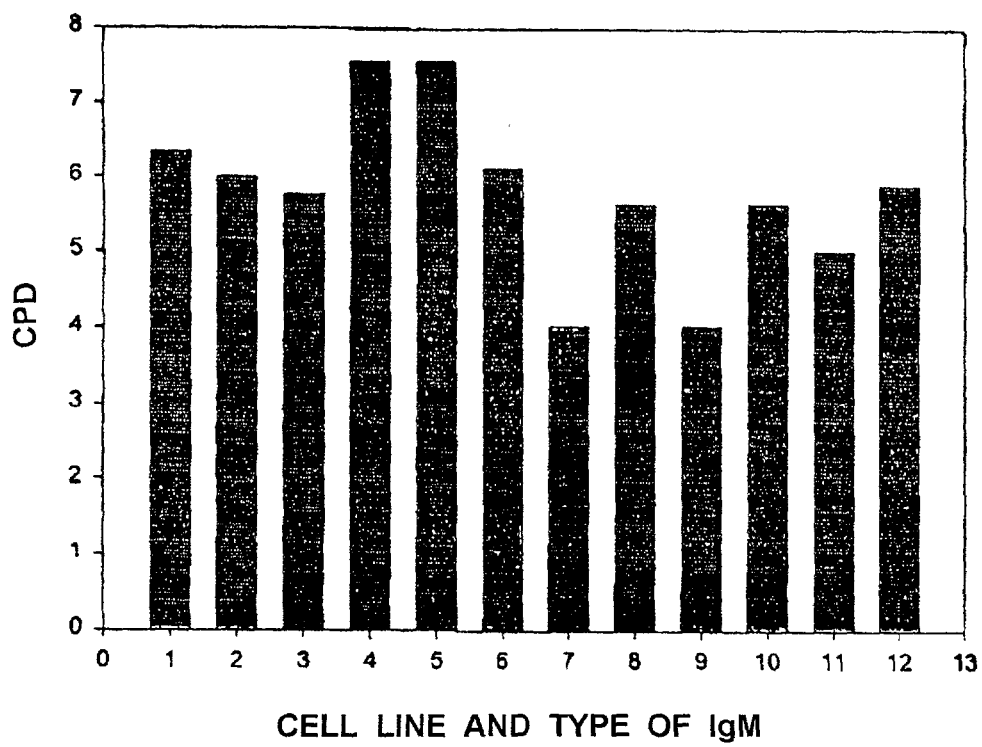

CELL LINE AND TYPE OF IgM

LEGEND:

1. Human IgM on MTW9/PL2 Cells = 6.36 cpd
2. Mouse IgM on MTW9/PL2 Cells = 6.00 cpd
3. Rat IgM on MTW9/PL2 Cells = 5.77 cpd
4. Human IgM on H301 Cells = 7.57 cpd
5. Mouse IgM on H301 Cells = 7.56 cpd
6. Rat IgM on H301 Cells = 6.11 cpd
7. Human IgM on GH1 Cells = 4.12 cpd
8. Rat IgM on GH1 Cells = 5.83 cpd
9. Human IgM on GH3 Cells = 4.09 cpd
10. Human IgM on GH4 Cells = 5.41 cpd
11. Human IgM on MCF-7A Cells = 5.01 cpd
12. Human IgM on MCF-7K Cells = 5.89 cpd

EFFECT OF TAMOXIFEN ON T47D CELL GROWTH
IN DDM-2MF DEFINED MEDIUM

LEGEND:
- ■ SFM + $E_2$
- ▲ SFM - $E_2$
- ▼ SFM + $10^{-9}$ M TAM
- ♦ SFM + $10^{-8}$ M TAM
- ● SFM + $10^{-7}$ M TAM
- □ SFM + $10^{-6}$ M TAM
- △ SFM + $10^{-5}$ M TAM

EFFECT OF INCREASING ESTRADIOL CONCENTRATIONS
ON T47D CELL GROWTH IN SERUM-FREE AND
PHENOL- RED FREE MEDIUM WITH $10^{-7}$ TAMOXIFEN

NOTE:

DATA ARE EXPRESSED AS BOTH CELL NUMBER AND CPD

ESTROGENIC EFFECT GENERATED BY IMMUNOGLOBULINS

WITH T47D CELLS IN SERUM-FREE MEDIUM

EFFECT OF IgG ISOTYPES (40 ug/mL) ON LNCaP CELL GROWTH IN SERUM-FREE MEDIUM

LEGEND:  + = DHT Added
— = No DHT Added

DETECTION OF SECRETORY COMPONENT
IN SECRETORY IgA WITH ANTI-SC ANTIBODY

IgA = Human Plasma

IgG = Human Plasma

Secretory IgA = IgA from Milk

Albumin = Human

HUMAN IgM TITRATION ON T47D CELLS GROWN IN SERUM-FREE MEDIUM WITH DIFFERENT DILUTIONS OF ANTI-SC ANTIBODY

LEGEND: —●— = + $E_2$
—○— = − $E_2$
—▲— = 1:5000 Dilution of Anti-SC Antibody
—△— = 1:1000 Dilution of Anti-SC Antibody
—■— = 1:500 Dilution of Anti-SC Antibody INSERT: EFFECT OF RABBIT SERUM ON T47D CELLS INCUBATED WITH 40 ug/mL HUMAN IgM EFFECT OF IgA ON LNCaP GROWTH IN THE PRESENCE OF ANTI-SECRETORY COMPONENT ANTIBODY AT DIFFERENT DILUTIONS LEGEND:
1. MW
2. ALVA 41: 40 ug
3. ALVA 41: 20 ug
4. DU 145: 40 ug
5. DU 145: 20 ug
6. HUMAN FIBROBLAST: 40 ug
7. HUMAN FIBROBLAST: 20 ug
8. LNCaP: 40 ug
9. LNCaP: 20 ug
10. MDCK1: 20 ug
11. MDCK1: 10 ug
12. PC3: 40 ug EFFECT OF HUMAN PLASMA IgA ON DU145 CELL GROWTH WITH AND WITHOUT DHT EFFECT OF HUMAN PLASMA IgA ON PC3 CELL GROWTH WITH AND WITHOUT DHT

COMPOSITIONS AND METHODS FOR DEMONSTRATING SECRETORY IMMUNE SYSTEM REGULATION OF STEROID HORMONE RESPONSIVE CANCER CELL GROWTH

CROSS-REFERENCE TO RELATED APPLICATIONS

This application claims the benefit under 35 U.S.C. §119 (e) of U.S. Provisional Patent Application Nos. 60/203,314 filed May 10, 2000; 60/208,348 filed May 31, 2000; 60/208,111 filed May 31, 2000; 60/229,071 filed Aug. 30, 2000; and 60/231,273 filed Sep. 8, 2000, now U.S. application Ser. Nos. 09/852,547 filed May 10, 2001; 10/293,019 filed May 10, 2001; 10/293,439 filed Nov. 13, 2002; and 10/293,440 filed Nov. 13, 2002.

STATEMENT REGARDING FEDERALLY SPONSORED RESEARCH OR DEVELOPMENT

Research leading to the present invention was supported in part by the federal government under Grant Nos. DAMD17-94-J-4473, DAMD17-98-8337 and DAMD17-99-1-9405 awarded by the Defense Department through the US Army Medical Research and Materiel Command, Breast Cancer Research Program. The United States government may have certain rights in the invention.

BACKGROUND OF THE INVENTION

1. Field of the Invention

The present invention generally relates to the regulation of steroid hormone responsive cancer cell growth, and more particularly to compositions and in vitro methods and models for demonstrating secretory immune system immunoglobulin regulation of mucosal epithelial cancer cell growth.

2. Description of Related Art

Steroid Hormone Responsive Tumor Cell Growth

In 1896, a physician named Beatson reported in the medical journal *Lancet* (Beatson G T (1896) *Lancet* (Part 1, July 11), 104-107 and *Lancet* (Part 2, July 18), 162-165) that removal of the ovaries from breast cancer patients slowed or stopped the growth of their tumors. As medical science has moved forward, it is now understood that Dr. Beatson had found that the estrogens made by the ovaries promoted the growth of breast cancers. In the 1940s and 1950s, work by Professor Charles Huggins (Huggins C B and Hodges C V (1941) *Cancer Res* 1, 293-297; Huggins et al. (1941) *Arch Surg* 43, 209-223) proved that surgical or chemical castration very substantially reduced the growth of prostate cancers. These results indicated that testicular androgens were important promoters of the growth of tumors of this male accessory organ. In subsequent work, researchers have established that estrogens and androgens act on breast and prostate cancer cells via receptors within the cell nucleus (Tsai M-J and O'Malley B W (1994) *Annu Rev Biochem* 63, 451-486; Evans R E (1988) *Science* (Wash D.C.) 240, 889-895). In fact, estrogen receptors are now commonly measured in breast cancer specimens to assist in decisions regarding the most effective therapies for each patient, and chemical and surgical castration are common treatments for prostate cancer. The regulation of estrogen target tissue cell growth has been a topic of dynamic experimental interest for several years (Jensen E V and DeSombre E R (1973) *Science* (Wash D.C.) 182, 126-134; O'Malley B W and Means A R (1974) *Science* (Wash D.C.) 183, 610-620). Today, it is generally accepted that estrogen interaction with specific nuclear located DNA binding receptors is necessary to initiate critical cell cycle events (Dickson R B and Stancel G M (2000) *J Natl Cancer Inst Monogr* No 27, 135-145). It is also highly likely that other non-steroid factors are essential participants in this process (Sirbasku D A (1978) *Proc Natl Acad Sci* USA 75, 3786-3790; Sirbasku D A (1981) *Banbury Report* 8, 425-443; Dickson R B and Lippman M E (1987) *Endocr Rev* 8, 2943; Soto A M and Sonnenschein C (1987) *Endocr Rev* 8, 44-52). Many of these new regulators fall into the general class of positive acting substances called growth factors (Gospodarowitz D and Moran J S (1976) *Annu Rev Biochem* 45, 531-558; Goustin A S et al. (1986) *Cancer Res* 46, 1015-1029). Simply stated, these agents cause cells to undergo cell division and thereby lead to growth. Because the hallmark of cancer is uncontrolled cell division, understanding these molecules and how they act is of vital importance. Other members of this regulatory family include negative acting agents called growth inhibitors (Knabbe et al. (1987) *Cell* 48, 417-428; de Jong J S et al. (1998) *J Pathol* 184, 44-52). They block cell division, and because of this, are important targets for new anticancer therapies. A great deal of study has focused on cellular site(s) of estrogen action, and various models have been proposed attempting to explain how estrogen participates with these additional factors to regulate growth.

The relative merits of positive versus negative regulation of cell growth have been debated (Dickson R B and Lippman M E (1987) *Endocr Rev* 8, 2943; Soto A M and Sonnenschein C (1987) *Endocr Rev* 8, 44-52). Although the positive direct and positive indirect models (as defined by Soto A M and Sonnenschein C (1987) *Endocr Rev* 8, 44-52) have received the most attention, the concept of negative regulation has intrinsic appeal because its loss offers a ready explanation for the uncontrolled replication of cancer cells. Factors that negatively regulate cell proliferation are now classified as members of the "tumor suppressor" family (Sager R (1997) *Proc Natl Acad Sci* USA 94, 952-955). Defining and understanding this family of intracellular and extracellular growth regulators is a primary focus of current cancer research.

A number of years ago, studies were reported which indicated that serum-borne inhibitors, later named "estrocolyones," had an important if not essential role in steroid responsive cell growth (Soto A M and Sonnenschein C (1987) *Endocr Rev* 8, 44-52; Soto A M et al. (1992) *J Steroid Biochem Mol Biol* 43, 703-712; Soto A M et al. (1986) *Cancer Res* 46, 2271-2275; Soto A M and Sonnenschein C (1984) *Biochem Biophys Res Commun* 122, 1097-1103; Schatz R W et al. (1985) *J Cell Physiol* 124, 386-390; Soto A M and Sonnenschein C (1985) *J Steroid Biochem* 23, 87-94). Estrocolyones appeared to act as estrogen reversible inhibitors of steroid hormone target tissue cell growth. Subsequently, the inhibitor has been variously identified as an unstable $M_r$ 70,000 to 80,000 protein (Soto A M et al. (1992) *J Steroid Biochem Mol Biol* 43, 703-712), the intact serum albumin molecule (Laursen I et al. (1990) *Anticancer Res* 10, 343-352; Sonnenschein C et al. (1996) *J Steroid Biochem Mol Biol* 59, 147-154), two domains of serum albumin (Sonnenschein C et al. (1996) *J Steroid Biochem Mol Biol* 59, 147-154), and the plasma steroid carrier protein sex hormone binding globulin (SHBG) (Reese C C et al. (1988) *Ann N.Y. Acad Sci* 538, 112-121; Fissore F et al. (1994) *Steroids* 59, 661-667; Fortunati N et al. (1993) *J Steroid Biochem Mol Biol* 45, 435-444). Other investigators also thought it possible that SHBG, as well as the other major plasma steroid hormone carrier protein corticosteroid-binding globulin (CBG), were potential growth regulators independent of their steroid hormone binding capacity. This conclusion was based on the fact that specific cellular membrane receptors have been identified for steroid free CBG and SHBG (Hryb D J et al. (1986) *Proc Natl Acad Sci* USA 83, 3253-3256; Hryb D J et al. (1990) *J Biol Chem* 265, 6048-6054) and that binding of SHBG and CBG to cells caused changes to cell growth mediators such as cyclic AMP and protein kinase A (Rosner W (1990) *Endocrine Rev* 11, 80-91; Fortunati N et al. (1996) *Endocrinology* 137, 686-692; Rosner W et al. (1991) *J Steroid Biochem Mol Biol* 40, 813-820; Nakhla A M et al. 153, 1012-1018; Rosner W (1992) *J Andrology* 13, 101-106).

Nonetheless, the roles of both albumin and SHBG as estrogen reversible serum-borne growth regulators have been challenged by the present Inventor, and others (Soto A M et al. (1992) *J Steroid Biochem Mol Biol* 43, 703-712; Damassa D A et al. (1991) *Endocrinology* 129, 75-84). In fact, in one report, SHBG stimulated growth of the androgen responsive ALVA-41 human prostate cancer cell line (Plymate S R et al. (1991) *J Steroid Biochem Mol Biol* 40, 833-839). In 1997, Sirbasku et al. reported that nearly pure CBG and an approximately 85% homogeneous SHBG-like protein were obtained from horse serum (Sirbasku D A et al. "Serum factor regulation of estrogen responsive mammary tumor cell growth." Proceedings of the 1997 Meeting of the "Department of Defense Breast Cancer Research Program: An Era of Hope", (Abstract) pp. 739-740, Washington, D.C., Oct. 31-Nov. 4, 1997) by employing a procedure similar to that described for use with human cord serum (Fernlund P and Laurell C-B (1981) *J Steroid Biochem* 14, 545-552). The Femlund and Laurell procedure was stated to produce human CBG and SHBG in pure or very nearly pure states using cortisol-agarose affinity chromatography at pH 5.5 followed by Phenyl Sepharose™ chromatography at pH 7.4. Under serum-free defined cell culture conditions, the partially purified SHBG-like fraction obtained by Sirbasku et al. demonstrated progressive inhibition of cell growth in a rat mammary tumor cell line (MTW9/PL2) with increasing concentration of the SHBG-like fraction. Addition of 17 β-estradiol ($E_2$) completely reversed even the maximum inhibition. Sirbasku et al. found that the active SHBG-like fraction contained little or no serum albumin as judged by immunological methods and by standard polyacylamide gel electrophoresis in the presence of reducing agents and sodium dodecyl sulfate (SDS-PAGE) (Laemmli U K (1976) *Nature* (Lond) 227, 680-685). Although the SHBG-like inhibitor displayed certain immunological similarities to SHBG, it was clearly distinguishable from SHBG based on physiologic, physical and biochemical analyses. Despite its first proposal more than fifteen years ago, the purified estrogen reversible serum-borne inhibitor has yet to be described. *Sirbasku* et al., as well as others (Soto A M et al. (1992) *J Steroid Biochem Mol Biol* 43, 703-712), has observed that the estrogen reversible inhibitory activity of serum was very labile during isolation by conventional protein purification methods. Other investigators have used a combination of cortisol affinity chromatorgraphy and an ammonium sulfate precipitation to isolate a cell growth inhibitor from human serum. These studies (Tanji M et al. (2000) *Anticancer Res.* 20, 2779-2783; Tanji M et al. (2000) *Anticancer Res.* 20, 2785-2789) describe estrogen inhibition of MCF-7 human breast carcinoma cells that had been maintained at least 3 months in serum-free medium, but no estrogenic effect was observed with normally cultured MCF-7 cells (i.e., cells not long term conditioned to serum-free medium). An isolated steroid-binding protein was stated to mediate an estrogen-dependent inhibition of cell growth. Other serum-borne inhibitors also have been separated from whole serum by diethylaminoethyl (DEAE) chromatography (Dell' Aquila M L and Gaffney E V (1984) *J Natl Cancer Inst* 73, 397-403). The properties of these inhibitors have not been defined further nor have they been shown to act as estrogen-reversible inhibitors.

Carcinogen-induced rat mammary tumors have been studied extensively as models for the in vivo role of hormones in the induction and growth of breast cancer (Welsch C W (1985) *Cancer Res* 45, 3415-3443). Despite ample evidence of hormone dependence in vivo, the carcinogen-induced tumors have not yet yielded permanent tissue culture cell lines that show the same responsiveness to steroid hormones in in vitro culture. Typically, cultures initiated from primary tumors very quickly lose hormone responsiveness. Because of this, the earliest endocrine studies were done with organ cultures (Welsch C W and Rivera E M (172) *Proc Soc Exp Biol Med* 139, 623-626; Lewis D and Hallowes R C (1974) *J Endocrinol* 62, 225-240; Chan P-C et al. (1976) *Proc Soc Exp Biol Med* 151, 362-365; Pasteels J-L et al. (1976) *Cancer Res* 36, 2162-2170) and short-term cultures of dissociated cells (Chan P-C et al. (1976) *Proc Soc Exp Biol Med* 151, 362-365). Now investigators recognized that those approaches were inadequate. More recently, cell lines have been developed from carcinogen-induced rat mammary tumors (Bennett D C et al. (1978) *Cell* 15, 283-298; Rudland P S (1987) *Cancer Metast Rev* 6, 55-83; Webster M K et al. (1990) *J Biol Chem* 265, 4831-4838; Lichtner R B et al. *Cancer Res* 51, 5943-5950; Lichtner R B et al. (1995) *Oncogene* 10, 1823-1832). Although these lines have been useful for investigations related to breast properties, investigators have found that in general they do not display steroid hormone responsiveness in cell culture. To compound the difficulties, most of these lines could not be evaluated for hormone responsiveness in vivo because they were derived from outbred rats. Simply stated, they lack the syngeneic inbred hosts absolutely required for in vivo transplantation.

One of the basic tenets of endocrine physiology is that estrogens and androgens cause coordinate growth of several target tissues (Clark J H et al. (1992) In: *Williams Textbook of Endocrinology*, $8^{th}$ Edition, W B Saunders, Philadelphia, pp 35-90). A partial list of estrogen target tissues includes breast, uterus, cervix, vagina, ovary, pituitary, liver, leukocytes and kidney. A partial list of androgen target tissues includes the male reproductive tract (e. g. prostate, epididymus, and testis), kidney, bladder, liver and muscle. Whatever mechanism is proposed to explain sex steroid dependent growth, one would expect it to be applicable to cells from several of the major target tissues.

The history of attempts to demonstrate steroid hormone responsive tumor cell growth in culture has led to two important conclusions. First, demonstration of estrogen and androgen responsive cell growth in culture required the presence of hormone deficient/depleted serum. One of the first studies to demonstrate this requirement was done with human breast cancer cells (Page M J et al. (1983) *Cancer Res* 43, 1244-1250). Some notable examples of demonstration by others of estrogen responsiveness in serum containing culture include studies with the MCF-7 human breast cancer cells (Lippman M E et al. (1977) *Cancer Res* 37, 1901-1907; Soto A M and Sonnenschein C (1985) *J Steroid Biochem* 23, 87-94; Wiese T E et al. (1992) *In Vitro Cell Dev Biol* 28A, 595-602), the T47D human breast cancer cells (Chalbos D et al. (1982) *J Clin Endocrinol Metab* 55, 276-283; Schatz R W et al. (1985) *J Cell Physiol* 124, 386-390; Soto A M et al. (1986) *Cancer Res* 46, 2271-2275), the ZR-75-1 human breast cancer cells (Darbre P et al. (1983) *Cancer Res* 43, 349-355), the $GH_4C_1$ rat pituitary tumor cells (Amara J F and Dannies P S (1983) *Endocrinology* 112, 1141-1143), and the H-301 Syrian hamster kidney tumor cell line (Soto A M et al. (1988) *Cancer Res*

48, 3676-3680). Two reports have proposed that estrogen responsiveness can be observed in serum-free defined medium with ZR-75-1 cells (Allegra J C and Lippman M E (1978) *Cancer Res* 38, 3823-3829; Darbre P D et al. (1984) *Cancer Res* 44, 2790-2793). However, in both of those studies, the cells were first incubated for several days in medium supplemented with serum before changing to serum-free defined medium conditions. M Ogasawara and D A Sirbasku previously demonstrated that this approach leaves a problematic serum factor "memory" with cells (Ogasawara M and Sirbasku D A (1988) *In Vitro Cell Dev Biol* 24, 911-920). When completely serum-free defined medium conditions were applied (Barnes D and Sato G (1980) *Nature* 281, 388-389; Danielpour D et al. (1988) *In Vitro Cell Dev Biol* 24, 42-52; Karey K P and Sirbasku D A (1988) *Cancer Res* 48, 4083-4092; Ogasawara M and Sirbasku D A (1988) *In Vitro Cell Dev Biol* 24, 911-920; Riss T L and Sirbasku D A (1989) *In Vitro Cell Dev Biol* 25, 136-142), no growth effects of estrogens were observed. Comparison of the observations in serum-free defined medium versus those in medium with serum led to the second important conclusion. Serum contains a mediator(s) that is required for steroid hormone responsiveness in culture. When the mediator is completely purified and defined chemically, its addition to serum-free defined medium will be expected to provide unequivocal confirmation of its role in hormone dependent cell growth.

The purification of the serum-borne mediator has been a challenging undertaking. Sirbasku et al. originally proposed that estrogens per se were not mitogenic, but instead caused the production of endocrine, paracrine or autocrine "estromedins" that were themselves the promoters of target tissue cell growth (Sirbasku D A (1978) *Proc Natl Acad Sci* USA 75, 3786-3790; Sirbasku D A (1981) *Banbury Report* 8, 425-443; Ikeda T et al. (1982) *In Vitro* 18, 961-979; Sirbasku D A and Leland F E (1982) *Biochemical Action of Hormones* 9, 115-140; Leland F E et al. In: *Cold Spring Harbor Conferences on Cell Proliferation*, Volume 9, Books A and B, *Growth of Cells in Hormonally Defined Media*, Cold Spring Harbor, N.Y., pp 741-750). From 1970 through 1984, estrogenic mitogenic effects were most often not seen in culture. Although some laboratories were reporting positive results in serum containing medium, as cited above, others were at the same time recording negative results using the same or related cell lines (Sirbasku D A (1978) *Proc Natl Acad Sci* USA 75, 3786-3790; Sirbasku D A and Kirkland W L (1976) *Endocrinology* 98, 1260-1272; Kirkland W yL et al. (1976) *J Natl Cancer Inst* 56, 1159-1164; Ikeda T et al. (1982) *In Vitro* 18, 961-979; Butler W B et al. (1983) *Cancer Res* 41, 82-88; Edwards D P et al. (1980) *Biochem Biophys Res Commun* 93, 804-812; Shafie S M (1980) *Science* (Wash D.C.) 209, 701-702). Part of the problem may have been due to culture conditions (Ruedl C et al. (1990) *J Steroid Biochem Mol Biol* 37, 195-200; Zugmaier G et al. (1991) *J Cell Physiol* 141, 353-361) or possibly caused by differences that arose because of variations in the properties of cell lines in different laboratories (Seibert K et al. (1983) *Cancer Res* 43, 2223-2239). In addition, there are other more technical issues that are well known in this field, have been described in the literature, and which are addressed in more detail elsewhere herein and in subsequent publications (Moreno-Cuevas J E and Sirbasku D A (2000) *In Vitro Cell Dev Biol* 36, 410-427; Sirbasku D A and Moreno-Cuevas J E (2000) *In Vitro Cell Dev Biol* 36, 428-446; and Moreno-Cuevas J E and Sirbasku D A (2000) *In Vitro Cell Dev Biol* 36, 447-464.) Another vital matter has been how "growth" is defined. Sonnenschein and Soto (Sonnenschein C and Soto A M (1980) *J Natl Cancer Inst* 64, 211-215) have addressed this issue very effectively. To be accepted as valid, sex steroids must cause significant changes in cellular logarithmic growth rates. Elucidation of the nature and activity of the estrogen reversible serum inhibitor(s) continues to be an area of intense experimental interest.

As cited above, A M Soto and C Sonnenschein have proposed that the serum mediator is an estrogen reversible inhibitor they have named estrocolyone. They have alternately described the inhibitor as a pituitary factor (Sonnenschein C and Soto A M (1978) *J Steroid Biochem* 6, 533-537), α-fetoprotein (Sonnenschein C et al. (1980) *J Natl Cancer Inst* 64, 1141-1146; Sonnenschein C et al. (1980) *J Natl Cancer Inst* 64, 1147-1152; Soto A M and Sonnenschein C (1980) *Proc Natl Acad Sci* USA 77, 2084-2087), a serum protein different than human serum albumin (Soto A M et al. (1992) *J Steroid Biochem Mol Biol* 43, 703-712), and in a later reversal of this view, stated that estrocolyone 1 (i.e. the serum-borne estrogen reversible inhibitor) was human serum albumin or a combination of two domains of albumin (Sonnenschein C (1996) *J Steroid Biochem Mol Biol* 59, 147-154). They have also sought the inhibitor as an estrogen-binding glycoprotein different than SHBG using Concanavalin-A chromatography (Reny J-L and Soto A M (1989) *J Clin Endocrinol Metab* 68, 938-945). The outcome of this effort did not identify the inhibitor. The exact chemical nature of the inhibitor was even further complicated by U.S. Pat. No. 4,859,585 (Sonnenschein) and U.S. Pat. No. 5,135,849 (Soto) describing an inhibitor that was derived from heat inactivated serum depleted of its endogenous estrogens and androgens by a 37.5° C. charcoal-dextran procedure. Alternatively, the inhibitor was obtained from serum by ammonium sulfate precipitation. This inhibitor is said to be useful for in vitro testing of substances of interest for activity as an estrogen or androgen agonist or antagonist using the MCF-7 cell line grown in Dulbecco's modified Eagle minimal essential medium supplemented with 5% (v/v) fetal bovine serum. However, the two above-mentioned U.S. patents do not address the issues of (i) whether there are one or more inhibitors, (ii) what is/are the exact chemical composition of the inhibitor(s), and (iii) what conditions were required to yield the long term stable product(s) necessary for the commercial application of the testing methodology described.

Steroid Hormone Receptors

As the matter stands today, it has not been established beyond doubt which of the many estrogen receptors and/or variants is the one that regulates the estrogen induced mitogenic effect. It is generally assumed that the ERα is the most likely positive growth mediator. Estrogens, androgens, progestins, corticosteroids, mineral steroids, vitamin D, retinoic acid and thyroid hormone receptors all belong to a family of DNA binding intracellular receptors that are activated by binding of the appropriate hormone/ligand (Evans R M (1988) *Science* (Wash D.C.) 240, 889-895; Giguere V (1990) *Genetic Eng* (NY) 12, 183-200; Williams G R and Franklyn J A (1994) *Baillieres Clin Endocrinol Metab* 8, 241-266; Kumar R and Thompson E B (1999) *Steroids* 64, 310-319; Pemrick S M et al. (1994) *Leukemia* 8, 1797-806; Carson-Jurica M A et al. (1990), *Endocr Rev* 11, 201-220; Tsai M J and O'Malley B W (1994) *Annu Rev Biochem* 63, 451-486; Alberts B et al. (1994) *Molecular Biology of The Cell*, 3rd edition, Garland Publishing, New York, pp 729-731). The estrogen receptor described in the citations above is now designated the classical estrogen receptor alpha (ERα). Its role in steroid regulated gene expression has been studied extensively and often reviewed (Yamamoto K R (1985) *Annu Rev Genet* 19, 209-252; Green S and Chambon P (1991) In: *Nuclear Hormone Receptors*, Academic Press, New York, pp 15-38; Tsai M-J and O'Malley B W (1994) *Annu Rev Bio-* chem 63, 451-486; McDonnell D P et al. (1992) *Proc Natl Acad Sci* USA 89, 10563-10567; Landel C C et al. (1994) *Mol Endocrinol* 8, 1407-1419; Landers J P and Spelsberg T C (1992) *Crit Rev Eukary Gene Exp* 2, 19-63; Cavailles V et al. (1994) *Proc Natl Acad (Sci* USA 91, 10009-10013; Halachmi S et al. (1994) *Science (Wash D.C.)* 264, 1455-1458; Brasch K and Ochs R L (1995) *Int rev Cyto* 159, 161-194; Härd T and Gustafsson J-Å (1993) *Acc Chem Res* 26, 644-650).

It is noteworthy that estrogen resistance in man is caused by a mutation in the ERα (Smith E P et al. *N Eng J Med* 331, 1056-1061). The most startling fact is that this point mutation (i.e. cytosine→thymidine) generated a premature stop codon, but was not lethal. Although many metabolic abnormalities were noted, development into adulthood was observed without expression of a functional ERα. This fact is further strengthened by the experiments with ERα gene knockout mice (Couse J F and Korach K S (1999) *Endocr Rev* 20, 358-417). The authors state "the list of unpredictable phenotypes in the αERKO (estrogen receptor knockout) must begin with the observation that generation of an animal lacking a functional ER α gene was successful and produced animals of both sexes that exhibit a life span comparable to wild-type". Furthermore, in the review of the ERKO results, it was not possible to conclude that the ERα regulated estrogen responsive cell growth. Indeed, functions normally ascribed to the ERα seemed unaffected. In fact, only relationships to development in tissues such as breast seemed best correlated (Boccchinfuso W P and Korach K S (1997) *J Mammary Gland Biol Neoplasia* 2, 323-334). The situation with ERKO mice and ERβ is similar (Couse J F and Korach K S (1999) *Endocr Rev* 20, 358-417). The results from ERβ knockout suggest an indirect role of this receptor via stromal tissue (Gustafsson J-Å and Warner M (2000) *J Steroid Biochem Mol Biol* 74, 254-248). Certainly a direct growth role for ERβ in breast epithelial cells was not established. The results available from ERKO do not yet provide confidence that either the ERα or the ERβ mediate estrogen responsive cell growth.

There are other pertinent lines of evidence that relate to the role of the ERα and growth. The first is from a study of transfection of estrogen receptor negative cells with the full length functional ERα (Zajchowski D A et al. (1993) *Cancer Res* 53, 5004-5011). Those investigators arrived at a remarkable result. They had expected to regain estrogen responsive growth in the transfected hormone independent cells. This was definitely not the case. Instead, addition of $E_2$ caused cell growth inhibition. Their results indicated that ERα was not a positive mediator, but instead a negative regulator. However, similarly transfected estrogen responsive cell lines such as MCF-7 and T47D were not $E_2$ inhibited in those studies.

More recently, another estrogen receptor has been cloned and cDNA sequenced from rat prostate and ovary (Kuiper G G et al. (1996) *Proc Natl Acad Sci* USA 93, 5925-5930). It has now also been cloned from mouse (Tremblay G B et al. (1997) *Mol Endocinol* 11, 353-365) and human (Mosselman S et al. (1996) *FEBS Lett* 392, 49-53). This new receptor has been named estrogen receptor beta (ERβ). Evidence that ERβ is separate from ERα comes from the fact that the genes are located on different chromosomes (Enmark E et al. (1997) 82, 4258-4265). Therefore, ERβ is not simply an alternate splicing product of the ERα gene. Furthermore, ERβ is distinguishable from ERα based on critical differences in the amino acid sequences of functional domains (Kuiper G G et al. (1996) *Proc Natl Acad Sci* USA 93, 5925-5930; Enmark E et al. (1997) 82, 4258-4265; Dickson R B and Stancel G M (2000) *J Natl Cancer Inst Monogr* No. 27, 135-145). For example, the sequence homology between the two receptors is 97% in the DNA binding domain, but 59% in the C-terminal ligand-binding (i.e. steroid hormone-binding) domain, and only 17% in the N-terminal domain. The ERβ N-terminal domain is much abbreviated compared to the ERα (Enmark E et al. (1997) 82, 4258-4265). Rat ERβ contains an 18 amino acid insert in the domain binding the ligand. Despite the significant differences in structure, ERα and ERβ bind $E_2$ with the same affinity (Kuiper G G et al. (1996) *Proc Natl Acad Sci* USA 93, 5925-5930; Dickson R B and Stancel G M (2000) *J Natl Cancer Inst Monogr* No. 27, 135-145). In fact, others (Tremblay G B et al. (1997) *Mol Endocrinol* 11, 353-365) have stated that ERβ has a slightly lower affinity for $E_2$ than ERα (Tremblay G B et al. (1997) *Mol Endocrinol* 11, 353-365). Therefore, if either of these receptors mediates estrogen-induced growth, the steroid hormone concentrations required for one-half maximum growth (i.e. $ED_{50}$), or for optimum growth (i.e. $ED_{100}$), are expected to be about the same.

It is thought that ERα and ERβ are functionally interrelated (Kuiper G G et al. (1998) *Endocrinology* 139, 4252-4263) and that one role of ERβ is to modulate the transcriptional activity of ERα (Hall J M and McDonnell D P (1999) *Endocrinology* 140, 5566-5578). Clearly however, there are significant functional differences between ERα and ERβ, which have been discussed (Gustafsson J-Å (1999) *J Endocrinol* 163, 379-383). Also, there are functional differences expected because of the different pattern of steroid hormone binding shown by ERβ (Kuiper G G et al. (1996) *Proc Natl Acad Sci* USA 93, 5925-5930). For example, ERβ binds androgens whereas ERα does not. This fact, plus the location of ERβ in prostate indicates a new function that may be androgen related.

It should also be noted that there have been "estrogen related receptors" (ERR 1 and 2) or "orphan" receptors identified that share properties with ERα but do not have a known function and do not have a known ligand (Giguere V et al. (1988) *Nature* (Lond) 331, 91-94; Gustafsson J-Å (1999) *J Endocrinol* 163, 379-383). In fact, today, there are more than 70 "orphan" receptors seeking ligands and functions (Gustafsson J-Å (1999) *Science* (Wash D.C.) 284, 1285-1286).

The Secretory Immune System

Turning now to discussion of a separate body of work from that described above, as further background for understanding the present invention, it should be noted that the immunological function and physiological properties of the body's secretory immune system have been recognized for many years (Tomasi T B et al. (1965) *J Exp Med* 121, 101-124; Brandtzaeg P and Baklien K (1977) *Ciba Foundation Symposium* 46, 77-113; Tomasi T B (1970) *Ann Rev Med* 21, 281-298; Spiegelberg H L (1974) *Adv Immunol* 19, 259-294; Tomasi T B (1976) *The Immune System of Secretions*, Prentice-Hall, Englewood Clifts, N.J.; Mestecky J and McGhee J R (1987) *Adv Immunol* 40, 153-245). The major immunoglobulins secreted as mucosal immune protectors include IgA, IgM and IgG. In human serum, the percent content of IgG, IgA and IgM are 80, 6 and 13%, respectively. In humans, the major subclasses of IgG are IgG1, IgG2, IgG3 and IgG4. These are 66, 23, 7 and 4% of the total IgG, respectively. The relative content of human immunoglobulin classes/subclasses in adult serum follow the order IgG1>IgG2>IgA1>IgM>IgG3>IgA2>IgD>IgE (Spiegelberg H L (1974) *Adv Immunol* 19, 259-294). When the serum concentrations of immunoglobulins are compared to those in exocrine secretion fluids, the relative contents change dramatically (Brandtzaeg P (1983) *Ann N.Y. Acad Sci* 409, 353-382; Brandtzaeg P (1985) *Scand J Immunol* 22, 111-146). For example in colostrum (a breast fluid secretion), IgA is≧80% of the total immunoglobulins. IgM is ≦10% of the total. IgG represents a few percent. In human colostrum and milk, IgG1 and IgG2 are the major subclasses of IgG (Kim K et al. (1992) *Acta Paediatr* 81, 113-118). Clearly, comparison of serum and mucosal fluid concentrations indicate selective immunoglobulin secretion.

Immunoglobulin Function. All human mucus membranes are protected by the secretory immune system (Hanson L Å and Brandtzaeg P (1989) In: *Immunological Disorders in Infants and Children*, 3$^{rd}$ edition, Stiehm E R, ed, Saunders, Philadelphia, pp 169-172). The primary protector is sIgA that is produced as dimers and larger polymers. A single joining "J" chain connects IgA monomers to form the dimers and polymers (Garcia-Pardo A et al. (1981) *J Biol Chem* 256, 11734-11738), and connects monomers of IgM to give pentamers (Niles M J et al. (1995) *Proc Natl Acad Sci USA* 92, 2884-2888). This critical joining endows these structures with a very important immunological property. IgA and IgM are known to bind to bacterial, parasite and viral surface antigens. These complexes bind to receptors on inflammatory cells leading to destruction of the pathogen by antibody-dependent cell-mediated cytotoxicity (Hamilton R G (1997) "Human Immunoglobulins" In: *Handbook of Human Immunology*, Leffell M S et al., eds, CRC Press, Boca Raton, Chapter 3). Dimeric and polymeric sIgA have a high antigen binding valence that effectively agglutinates/neutralizes bacteria and virus (Janeway C A Jr et al. (1999) *Immunobiology, The Immune System in Health and Disease*, 4$^{th}$ edition, Garland Publishing, New York, pp 326-327). Also, sIgA shows little or no complement activation. This means that it does not cause inflammatory responses (Johansen F E et al. (2000) *Scand J Immunol* 52, 240-248). In addition, the fact that IgA exists as two separate forms is significant (Loomes L M et al. (1991) *J Immunol Methods* 141, 209-218). The IgA1 predominates in the general circulation. In contrast, IgA2 is often higher in mucosal secretions such as those from breast, gut, and respiratory epithelium, salivary and tear glands, the male and female reproductive tracts, and the urinary tracts of both males and females. This difference in proportions is important to immune protection of mucosal surfaces. Although the secretory form of IgA1 is by and large resistant to proteolysis (Lindh E (1975) *J Immunol* 114, 284-286), a number of different bacteria secrete proteolytic enzymes that cleave it into Fab and Fc fragments (Wann J H et al. (1996) *Infect Immun* 64, 3967-3974; Poulsen K et al. (1989) *Infect Immun* 57, 3097-3105; Gilbert J V et al. (1988) *Infect Immun* 56, 1961-1966; Reinholdt J et al. (1993) *Infect Immun* 61, 3998-4000; Blake M S and Eastby C (1991) *J Immunol Methods* 144, 215-221; Burton J et al. (1988) *J Med Chem* 31, 1647-1651; Mortensen S B and Kilian M (1984) *Infect Immun* 45, 550-557; Simpson D A et al. (1988) *J Bacteriol* 170, 1866-1873; Blake M S and Swanson J et al. (1978) *Infect Immun* 22, 350-358; Labib R S et al. (1978) *Biochim Biophys Acta* 526, 547-559). In effect, the bacterial proteinases negate the neutralizing effects of multivalent sIgA1. In contrast, because of structural differences (Chintalacharuvu K R and Morrison S L (1996) *J Immunol* 157, 3443-3449), IgA2 lacks sites required for proteolysis. This makes IgA2 more resistant to bacterial digest than IgA1 (Hamilton R G (1997) "Human immunoglobulins" In: *Handbook of Human Immunology*, Leffell M S et al., eds, CRC Press, Boca Raton, Chapter 3).

With regard to IgM, its function is somewhat different. IgM antibodies serve primarily as efficient agglutinating and cytolytic agents. They appear early in the response to infection and are largely confined to the bloodstream. Whether secreted or plasma-borne, IgM is a highly effective activator of the classical complement cascade. It is less effective as a neutralizing agent or an effector of opsinization (i.e. facilitation of phagocytosis of microorganisms). Nonetheless, IgM complement activation causes lysis of some bacteria. The effects of the IgG class are more encompassing. All four subclasses cause neutralization, opsinization and complement activation to defend against mucosal microorganisms. IgG1 is an active subclass in this regard (Janeway C A Jr et al. (1999) *Immunobiology, The Immune System in Health and Disease*, 4$^{th}$ edition, Garland Publishing, New York, pp 326-327).

Immunoglobulin Structure. It was established that immunoglobulin A (IgA) represents 5 to 15% of the total plasma immunoglobulins in humans (Spiegelberg H L (1974) *Adv Immunol* 19, 259-294). IgA has a typical immunoglobulin four-chain structure ($M_r$ 160,000) made up of two heavy chains ($M_r$ 55,000) and two light chains ($M_r$ 23,000) (Fallgreen-Gebauer E et al. (1993) *Biol Chem Hoppe-Seyler* 374, 1023-1028; Kratzin H et al. (1978) *Hoppe-Seylers Z Physiol Chem* 359, 1717-1745; Yang C et al. (1979) *Hoppe-Seylers Z Physiol Chem* 360, 1919-1940; Eiffert H et al. (1984) *Hoppe-Seylers Z Physiol Chem* 365, 1489-1495). In humans, there are two subclasses of IgA. These are IgA1 and IgA2 that have 1 and 2 heavy chains, respectively. The IgA2 subclass has been further subdivided into $A_2m(1)$ and $A_2m(2)$ allotypes (Mestecky J and Russell M W (1986) *Monogr Allergy* 19, 277-301; Morel A et al. (1973) *Clin Exp Immunol* 13, 521-528). IgA can occur as monomers, dimers, trimers or multimers (Lüllau E et al. (1996) *J Biol Chem* 271, 16300-16309). In plasma, 10% of the total IgA is polymeric while the remaining 90% is monomeric. Formation of dimeric or multimeric IgA requires the participation of an elongated glycoprotein of approximately $M_r$ 15,000, designated the "J" chain (Mestecky J et al. (1990) *Am J Med* 88, 411-416; Mestecky J and McGhee J R (1987) *Adv Immunol* 40, 153-245; Cann G M et al. (1982) *Proc Natl Acad Sci USA* 79, 6656-6660). Structurally, the J chain is disulfide linked to the penultimate cysteine residue of heavy chains of two IgA monomers to form a dimeric complex of approximately $M_r$ 420,000. The general structure of the dimer has been well described in the literature (Fallgreen-Gebauer E et al. (1993) *Biol Chem Hoppe-Seyler* 374, 1023-1028). Multimeric forms of IgA and IgM require only a single J chain to form (Mestecky J and McGhee J R (1987) *Adv Immunol* 40, 153-245; Chapus R M and Koshland M E (1974) *Proc Natl Acad Sci USA* 71, 657-661; Brewer J W et al. (1994) *J Biol Chem* 269, 17338-17348). The structures and chemical properties of IgA and IgM have been described in detail (Janeway C A Jr et al. (1996) *Immunobiology, The Immune System in Health and Disease*, Second edition, Garland Publishing, New York, pp 3-32 and pp 8-19).

Immunoglobulin Production. Dimeric and multimeric IgA and IgM are secreted by a number of exocrine tissues. IgA is the predominant secretory immunoglobulin present in colostrum, saliva, tears, bronchial secretions, nasal mucosa, prostatic fluid, vaginal secretions, and mucous secretions from the small intestine (Mestecky J et al. (1987) *Adv Immunol* 40, 153-245; Goldblum R M, et al. (1996) In: Stiehm E R, ed, *Immunological Disorders in Infants and Children*, 4$^{th}$ edition, Saunders, Philadelphia, pp 159-199; Heremans J F (1970) In: *Immunoglobulins, Biological Aspects and Clinical Uses*, Merler E, ed, National Academy of Sciences, Wash D.C. pp 52-73; Tomasi T B Jr (1971) In: *Immunology, Current Knowledge of Basic Concepts in Immunology and their Clinical Applications*, Good R A and Fisher D W, eds, Sinauer Associates, Stanford, Conn., p 76; Brandtzaeg P (1971) *Acta Path Microbiol Scand* 79, 189-203). IgA output exceeds that of all other immunoglobulins, making it the major antibody produced by the body daily (Heremans J F (1974) In: *The Antigens*, Vol 2, Sela M, ed, Academic Press, New York, pp 365-522; Conley ME et al. (1987) *Ann Intern Med* 106, 892-899. IgA is the major immunoglobulin found in human milk/whey/colostrum (Ammann A J et al. (1966) *Soc Exp Biol Med* 122, 1098-1113; Peitersen B et al. (1975) *Acta Paediatr Scand* 64, 709-717); Woodhouse L et al. (1988) *Nutr Res* 8, 853-864). IgM secretion is less abundant but can increase to compensate for deficiencies in IgA secretion.

During passage of IgA through the cell, its structure is modified. A $M_r$ 80,000 fragment of the receptor containing all five of the extracellular domains becomes covalently attached to dimeric IgA to form secretory IgA (sIgA) (Fallgreen-Gebauer E et al. (1993) *Biol Chem Hoppe-Seyler* 374, 1023-1028). The receptor that mediates the translocation has been interchangeably called the "poly-Ig receptor" (poly-Ig receptor) or the "secretory component" (Krajči P et al. (1992) *Eur J Immunol* 22, 2309-2315). For the purposes of the present disclosure, however, the term "poly-Ig receptor" refers to the full length $M_r$ 100,000 transmembrane protein and the term "secretory component" denotes only the $M_r$ 80,000 extracellular five domains of the receptor that become covalently attached to IgA in forming the sIgA structure (Fallgreen-Gebauer E et al. (1993) *Biol Chem Hoppe-Seyler* 374, 1023-1028; Krajči P et al. (1992) *Eur J Immunol* 22, 2309-2315). Because of the unique structure of sIgA, it is highly resistant to acid and proteolysis (Lindh E (1975) *J Immunol* 114, 284-286) and therefore remains intact in secretions to perform extracellular immunological functions. IgM also binds secretory component, but not covalently (Lindh E and Bjork I (1976) *Eur J Biochem* 62, 271-278). However, IgM is less stabilized because of its different association with the secretory component, and therefore has a shorter functional survival time in acidic secretions (Haneberg B (1974) *Scand J Immunol* 3, 71-76; Haneberg B (1974) *Scand J Immunol* 3, 191-197).

The secretion mechanism for IgA and IgM are well described. Conversely, there is a fundamental question surrounding IgG secretion. There is no "J" chain present in IgG1 and IgG2. From the known facts of transcytosis/secretion of immunoglobulins (Johansen F E et al. (2000) *Scand J Immunol* 52, 240-248), it is unlikely that IgG secretion is mediated by the poly-Ig receptor. An epithelial receptor specific for IgG1 has been reported in bovine mammary gland (Kemler R et al. (1975) *Eur J Immunol* 5, 603-608). Apparently, it preferentially transports this class of immunoglobulins from serum into colostrum. Despite this 1975 report however, the receptor has not been chemically or structurally identified nor has the mechanism of transport of IgG monomers been satisfactorily defined. It is possible that this receptor is a member of a large group now designated as Fc receptors (Fridman W H (1991) *FASEB J* 5, 2684-2690), but there is one study with IgG showing that of 31 different long-term human carcinoma cell lines including breast "all lines were found to be consistently Fc receptor negative" (Kerbel R S et al. (1997) *Int J Cancer* 20, 673-679). One possible candidate for the epithelial transport of IgG1 is the neonatal Fc receptor (Raghavan M and Bjorkman P J (1996) *Annu Rev Cell Dev Biol* 12, 181-220). However, there is no indication yet of the presence of this receptor in adult mucosal tissues.

Transcytosis Mediating Receptors. J chain-containing IgA is produced and secreted by plasma B immunocytes located in the lamina propria just beneath the basement membrane of exocrine cells (Brandtzaeg P (1985) *Scan J Immunol* 22, 111-146). The secreted IgA binds to a $M_r$ 100,000 poly-Ig receptor positioned in the basolateral surface of most mucosal cells (Heremans J F (1970) In: *Immunoglobulins, Biological Aspects and Clinical Uses*, Merler E, ed, National Academy of Sciences, Wash D.C., pp 52-73; Brandtzaeg P (1985) *Clin Exp Immunol* 44, 221-232; Goodman J W (1987) In: *Basic and Clinical Immunology*, Stites D P, Stobo J D and Wells J V, eds, Appleton and Lange, Norwalk, Conn., Chapter 4). The receptor-IgA complex is next translocated to the apical surface where IgA is secreted. The binding of dimeric IgA to the poly-Ig receptor is completely dependent upon the presence of a J chain (Brandtzaeg P (1985) *Scan J Immunol* 22, 111-146; Brandtzaeg P and Prydz H (1984) *Nature* 311:71-73; Vaerman J-P et al. (1998) *Eur J Immunol* 28, 171-182). Monomeric IgA will not bind to the receptor. The J chain requirement for IgM binding to the poly-Ig receptor is also true for this immunoglobulin (Brandtzaeg P (1985) *Scan J Immunol* 22, 111-146; Brandtzaeg P (1975) *Immunology* 29, 559-570; Norderhaug I N et al. (1999) *Crit Rev Immunol* 19, 481-508). Because IgA and IgM bind to the poly-Ig receptor via their Fc domains, and because of a repeating Ig-like structure in the extracellular domains, the poly-Ig receptor classifies as a member of the Fc superfamily of immunoglobulin receptors (Krajči P et al. (1992) *Eur J Immunol* 22, 2309-2315; Daëron M (1997) *Annu Rev Immunol* 15, 203-234).

The poly-Ig receptor and the secretory component from human has been cDNA cloned and DNA sequenced (Krajči P et al. (1992) *Eur J Immunol* 22, 2309-2315; Krajči P et al. (1995) *Adv Exp Med Biol* 371A, 617-623; Krajči P et al. (1991) *Hum Genet* 87, 642-648; Krajči P et al. (1989) *Biochem Biophys Res Commun* 237, 9-20) as has the poly-Ig receptor from mouse (Kushiro A and Sato T (1997) *Gene* 204, 277-282; Piskurich J F et al. (1995) and bovine tissue (Verbeet M P et al. (1995) *Gene* 164, 329-333). Altogether, the human poly-Ig receptor coding sequence encompassed 11 exons. The extracellular five domains originate from exons 3 (D1), exon 4 (D2) exon 5 (D3 and D4), exon 6 (D5), exon 7 (the conserved cleavage site to form the secretory component), exon 8 (the membrane spanning domain), exon 9 (a serine residue required for transcytosis), exon 9 (sequence to avoid degradation), exon 10, no known function) and exon 11 (sequence contains a threonine residue and the COOH terminus) (Krajči P et al. (1992) *Eur J Immunol* 22, 2309-2315). With the exception of domains 3 and 4 (both from one exon), the receptor structure follows the rule of one domain/one exon. The poly-Ig receptor binds IgA and IgM via their Fc domains, and more particularly, via a specific amino acid sequence (15→37) of domain 1 (Bakos M-A et al. (1991) *J Immunol* 147, 3419-3426). Of the other extracellular domains, only D5 is known for a specific function. It contains the disulfide bonds that covalently attach to IgA to for sIgA during transcytosis. The role of this receptor in transcytosis of IgA/IgM has been well studied with mucosal tissues and epithelial cells in culture (Vaerman J P et al. (1998) *Eur J Immunol* 28, 171-182; Fahey J V et al. (1998) *Immunol Invest* 27, 167-180; Brandtzaeg P (1997) *J Reprod Immunol* 36, 23-50; Loman S et al. (1997) *Am J Physiol* 272, L951-L958; Mostov K E et al. (1995) *Cold Spring Harbor Symp Quant Biol* 60, 775-781; Schaerer E et al. (1990) *J Cell Biol* 110, 987-998).

During passage of IgA through the cell, its structure is modified. A $M_r$ 80,000 fragment of the receptor containing all five of the extracellular domains becomes covalently attached to dimeric IgA to form secretory IgA (sIgA) (Fallgreen-Gebauer E et al. (1993) *Biol Chem Hoppe-Seyler* 374, 1023-1028). The receptor that mediates the translocation has been interchangeably called the "poly-Ig receptor" (poly-Ig receptor) or the "secretory component" (Krajči P et al. (1992) *Eur J Immunol* 22, 2309-2315). For the purposes of the present disclosure, however, the term "poly-Ig receptor" refers to the full length $M_r$ 100,000 transmembrane protein and the term "secretory component" denotes only the $M_r$ 80,000 extracellular five domains of the receptor that become covalently attached to IgA in forming the sIgA structure (Fallgreen-Gebauer E et al. (1993) *Biol Chem Hoppe-Seyler* 374, 1023-1028; Krajči P et al. (1992) *Eur J Immunol* 22, 2309-2315). Because of the unique structure of sIgA, it is highly resistant to acid and proteolysis (Lindh E (1975) J Immunol 114, 284-286) and therefore remains intact in secretions to perform extracellular immunological functions. IgM also binds secretory component, but not covalently (Lindh E and Bjork I (1976) *Eur J Biochem* 62, 271-278). However, IgM is less stabilized because of its different association with the secretory component, and therefore has a shorter functional survival time in acidic secretions (Haneberg B (1974) *Scand J Immunol* 3, 71-76; Haneberg B (1974) *Scand J Immunol* 3, 191-197).

While the secretion mechanism for IgA and IgM are well described, conversely, a fundamental question surrounds IgG secretion. There is no "J" chain present in IgG1 and IgG2. From the known facts of transcytosis/secretion of immunoglobulins (Johansen F E et al. (2000) *Scand J Immunol* 52, 240-248), it is unlikely that IgG secretion is mediated by the poly-Ig receptor. An epithelial receptor specific for IgG1 has been reported in bovine mammary gland (Kemler R et al. (1975) *Eur J Immunol* 5, 603-608). Apparently, it preferentially transports this class of immunoglobulins from serum into colostrum. Despite this 1975 report however, the receptor has not been chemically or structurally identified nor has the mechanism of transport of IgG monomers been satisfactorily defined. It is possible that this receptor is a member of a large group now designated as Fc receptors (Fridman W H (1991) *FASEB J* 5, 2684-2690), but there is one study with IgG showing that of 31 different long-term human carcinoma cell lines including breast "all lines were found to be consistently Fc receptor negative" (Kerbel R S et al. (1997) *Int J Cancer* 20, 673-679). One possible candidate for the epithelial transport of IgG1 is the neonatal Fc receptor (Raghavan M and Bjorkman P J (1996) *Annu Rev Cell Dev Biol* 12, 181-220). However, there is no indication yet of the presence of this receptor in adult mucosal tissues.

Fc receptors are so named because they bind specific heavy chains (Fc domains). However, before coming to this conclusion, it should be emphasized strongly that the Fc family represented by Fcγ (IgG), Fcα (IgA), and Fcμ (IgM) have traditionally been considered to be located on lymphoid series cells (Fridman WH (1991) FASEB J 5, 2684-2690; Raghavan M and Bjorkman PJ (1996) *Annu Rev Cell Dev Biol* 12, 181-220). There is only limited experimental support for the concept that these receptors are located on epithelial cells (Tonder O et al. (1976) *Acta Pathol Microbiol Scand* 84, 105-111). For the family of leukocyte IgG receptors, 12 transmembrane or soluble receptor isoforms are known. These are grouped into three classes FcγR1 (CD64), Fcγ RII (CD32) and Fcγ RIII (CD16) (Valerius T et al. (1997) Blood 90, 4485-4492). For IgA, there is one gene that encodes several receptors) (i.e. Fcα) by alternate splicing to yield forms from $M_r$ 55,000 to 110,000 (Pleass RJ et al. (1996) *Biochem J* 318, 771-777; van Dijk TB et al. (1996) Blood 88, 4229-4238; Morton HC et al. (1996) *Immunogenetics* 43, 246-247). One of these, FcαR1 is constitutively expressed on monocytes and macrophages and other leukocytes. It binds IgA1 and IgA2 with about the same affinity. The receptor for IgM (i.e.Fcμ) is less well defined, but still has been partially characterized as a $M_r$ 60,000 protein present on activated B cells and other B series cells (Ohno T et al. (1990) *J Exp Med* 172, 1165-1175). The Fc superfamily has another very important aspect pertinent to this disclosure. Receptors of this family mediate negative effects on cells (Cambier JC (1997) *Proc Natl Acad Sci USA* 94, 5993-5995). These receptors have an intracellular amino acid sequence motif I/VxYxxL (SEQ ID NO:1 and SEQ ID NO:2) described as an immunoreceptor tyrosine-based inhibitory motif (ITIM) that signals cell growth shutdown after ligand binding. These signals have been characterized in the FCγRIIB1 receptors of human and mouse (Olcese L et al. (1996) *J Immuno* 156, 4531-4534). The hallmark of these ITIM receptors is that they shut off growth factor dependent growth.

Although the advances and teachings in the prior art have indicated that a serum-borne inhibitor of steroid hormone responsive tumor cell growth exists, until now there has been no adequate isolation or identification of such an inhibitor, and very little understanding of its mode of action has been gained. There is no satisfactory in vitro testing model presently available for demonstrating steroid hormone responsive cell growth that can be correlated to the in vivo situation, or for testing drugs, or other natural or synthetic substances for possible hormone-mimicking or anti-hormone effects.

SUMMARY OF THE INVENTION

The compositions, methods and models of the present invention overcome major shortcomings of the prior art and satisfy long-felt needs for, among other things, a sensitive way to screen substances for estrogenic and androgenic effects. It was discovered, and the embodiments herein demonstrate, that the immune system plays a major role in the growth of estrogen responsive breast and androgen responsive prostate cancers, as well as cancers of other steroid and thyroid hormone responsive mucosal epithelial tissues. IgA, IgM and certain IgGs provide negative regulation of steroid hormone responsive mucosal epithelial cancer cell growth, including breast, prostate, pituitary, kidney and other glandular cancer cells. For the purposes of this disclosure, "cell growth" means cell proliferation or an increase in the size of a population of cells through mitogenesis and cell division rather than an increase in cytoplasmic volume of an individual cell. Prior to the present disclosure, no growth regulating role was known for the secretory immune system, which produces predominantly immunoglobulin A (IgA) and immunoglobulin M (IgM) and lesser amounts of immunoglobulin G (IgG). The discovery that IgA and IgM are the major negative regulators of steroid hormone responsive cell growth arose out of the Inventor's work directed at purifying breast cancer regulatory factors from biological fluids, as described in the following Examples. This discovery and the present invention constitute a major breakthrough in the understanding of these cancers, and other glandular/mucosal tissues that secrete or are bathed by polymeric IgA, secretory IgA (sIgA), IgM and certain IgGs. For the first time, a direct link has been established between the secretory immune system (IgA and IgM) and the most prevalent types of cancer that occur throughout the world. Binding of IgA and IgM to the poly-immunoglobulin receptor (i.e. poly-Ig receptor or poly IgR) is an important step in carrying out the regulatory function of IgA and IgM, and initial indications are that poly IgR mediates the negative regulation of steroid hormone dependent cell growth. Application of these scientific breakthroughs to the detection, diagnosis, prognosis, treatment and deterrence or prevention of cancer of mucosal epithelial tissues (e.g., breast, prostate, kidney, pituitary, thyroid and colon) is described in U.S. patent application Ser. No. 09/852,547PCT/US2001/015171 entitled "Compositions and Methods for the Diagnosis, Treatment and Prevention of Steroid Hormone Responsive Cancers," which is hereby incorporated herein by reference.

No such serum-derived inhibitor has been previously isolated or identified that replicates the large magnitude estrogen reversible inhibitory effects demonstrated in the present investigations using hormone depleted full serum. The serum-borne inhibitor(s) are ubiquitous in mammals and lack species specificity. Their inhibitory activity is completely reversible by picomolar concentrations of steroid hormones when assayed in the new in vitro conditions. Moreover, before the surprising discovery that the serum-borne inhibitor(s) are secretory immunoglobulins, there has been no previous report that IgA, IgM or IgG play any role in the negative regulation of steroid hormone responsive (SHR) mucosal epithelial cell growth, or that binding of IgA and IgM to a polyimmunoglobulin receptor (poly-Ig receptor) is instrumental in carrying out such growth regulation. Prior to the present disclosure, a cell growth related function for the poly-Ig receptor transcytosis receptor, or a poly IgR-like receptor, has not been recognized, nor had such a role ever been attributed to an IgG Fcγ receptor.

In accordance with certain embodiments of the present invention, an immunoglobulin inhibitor of in vitro steroid hormone-responsive steroid hormone responsive cancer cell growth or proliferation are provided. The cancer cells that are inhibited from proliferating in in vitro culture come from a cell line that is also capable of proliferating in vivo when implanted into a suitable host. This immunoglobulin inhibitor (e.g., one or more of the secretory immunoglobulins IgA, IgM and certain IgG subtypes) is a long sought after serum-derived negative regulator of steroid hormone responsive cancer cell growth that, in impure form, was previously referred to as a steroid hormone binding globulin like ("SHBG-like") fraction. For the first time it is disclosed that, surprisingly, certain immunoglobulins exert a steroid hormone reversible negative regulatory (inhibitory) effect on cancer cell growth that is distinct from their well-established immune functions. In the most preferred embodiments, the inhibitor(s) is/are dimeric IgA (non-sIgA), polymeric IgM, IgG1κ and IgG2.

In some embodiments an isolated steroid hormone reversible inhibitor of steroid hormone-responsive cancer cell growth is provided, the inhibitor comprising a secretory immunoglobulin, such as IgA, IgM or IgG.

In some embodiments a steroid hormone irreversible cell growth inhibitor composition is provided that comprises at least one immunoglobulin inhibitor that is active with respect to the ability to inhibit steroid hormone-responsive cancer cell proliferation and inactive with respect to steroid hormone reversibility of the inhibition, and a carrier.

In some embodiments a method of making a steroid hormone irreversible cancer cell growth inhibitor composition comprising exposing an above-described inhibitor composition to calcium depleted conditions for a defined period of time sufficient to render the immunoglobulin irreversibly inhibitory of steroid hormone responsive cancer cell growth in vitro.

According to still other embodiments of the present invention an immunoglobulin inhibitor mimicking substance is provided. In certain embodiments the mimicking substance is tamoxifen.

In certain other embodiments of the present invention a negative control serum is provided which contains steroid hormone depleted blood plasma or serum and is inactive with respect to the ability to inhibit steroid hormone-responsive cell proliferation in the absence of steroid hormone. Some embodiments of the invention provide a method of making a negative control serum, preferably comprising heat treatment at about 50-60° C. for about 90 minutes to about 30 hours.

Also provided in accordance with certain other embodiments of the present invention is a control serum composition containing plasma or serum and containing a reactivatible immunoglobulin inhibitor that is inactive with respect to the ability to inhibit steroid hormone-responsive cell proliferation in the absence of the steroid hormone and in the absence of an activating amount of calcium. In some embodiments the control serum is reactivated and contains calcium ion.

These immunoglobulin inhibitors have many immediate and potential applications as reagents for cell growth assays and therapeutic agents. For example, they are useful for in vitro testing of substances for estrogenic effects (or other steroid hormone-like effects) on steroid hormone responsive cell growth, in a suitable assay system. They are useful for demonstrating steroid hormone reversible inhibition or arrest of cancer cell growth in a variety of in vitro cell culture models employing cancer cell lines that are capable of in vivo tumor growth when implanted into a compatible host. The immunoglobulin inhibitors are also useful as an aid in assessing risk of cancer development or growth in a mucosal epithelial tissue (i.e., glands and tissues that secrete or are bathed by secretory immunoglobulins). Some of these tissues are breast, prostate, oral cavity mucosa, salivary/parotid glands, esophagus, stomach, small intestine, colon, tear ducts, nasal passages, liver and bile ducts, bladder, pancreas, adrenals, kidney tubules, glomeruli, lungs, ovaries, fallopian tube, uterus, cervix, vagina, and secretory anterior pituitary gland cells. The immunoglobulin inhibitors are also expected to be useful in the detection, diagnosis, prognosis, treatment and prevention of steroid hormone responsive cancers of the mucosal epithelial tissues.

In some embodiments of the present invention, a steroid hormone reversible, steroid hormone responsive cancer cell growth inhibitor composition is provided that contains at least one of the above-described immunoglobulin inhibitors together with a carrier, which preferably includes an inhibitor stabilizing medium. Such a composition is especially useful for storing and shipping preparations of the inhibitors without loss of activity. Preferably the stabilizing medium also contains an activity-stabilizing amount of calcium ion, a steroid hormone such as (DHT), and a substance that depresses the freezing point of the composition below about −20° C. (e.g., glycerol). In some embodiments the composition contains steroid hormone depleted body fluid such as blood plasma or serum.

In some embodiments of the present invention, an immunoglobulin inhibitor composition containing steroid-hormone depleted blood plasma or serum is provided. For many in vitro tests of steroid hormone responsive cancer cell growth, it is especially desirable to more closely approximate the in vivo condition by employing serum-containing assay medium instead of completely serum-free medium. In some embodiments this steroid hormone depleted serum-based immunoglobulin inhibitor composition is supplemented or "spiked" with a predetermined amount of certain inhibitors (e.g., IgA or IgM). Such serum-containing compositions are especially useful in assaying for estrogen-like cell growth stimulating effects by a substance of interest. These serum based compositions will also facilitate identification of substances that demonstrate a steroidogenic effect (e.g., estrogen-like stimulation of cell proliferation) in serum-free cell growth assays, but which do not demonstrate the same estrogenic effect in the presence of serum (i.e., when tested in a similar cell growth assay medium that contains serum.) The ability to determine whether a new drug, or other substance of interest, is likely to be non-estrogenic in vivo due to the presence or ameliorating effect of serum factors is of value to the medical profession and the pharmaceutical industry, in particular.

Accordingly, certain embodiments of the present invention provide methods of testing substances of interest, such as drugs or environmental chemicals, for their steroid hormone-like effects on cell growth stimulation employing one of the above-described immunoglobulin inhibitors or serum-based immunoglobulin inhibitor compositions with an appropriate steroid hormone responsive cell line and nutrient medium.

Certain embodiments of the present invention provide methods of testing substances of interest, such as drugs or environmental chemicals, to distinguish cytotoxic effects from anti-estrogenic effects on cell growth. These methods employ one of the above-described immunoglobulin inhibitors or serum-based immunoglobulin inhibitor compositions in an appropriate steroid hormone responsive cell line maintained in a suitable nutrient medium.

In still other embodiments of the present invention a non-inhibitory steroid hormone depleted serum composition is provided that contains steroid hormone-depleted blood plasma or serum, similar to certain of the above-described steroid hormone depleted serum-based immunoglobulin inhibitor compositions, except in this embodiment it contains either no immunoglobulin inhibitor(s) or it contains the immunoglobulin inhibitor(s) in inactive form with respect to ability of the immunoglobulin(s) to inhibit steroid hormone responsive cell proliferation in serum-free cell culture in the absence of a cell growth stimulating amount of steroid hormone. A non-inhibitory steroid hormone depleted serum composition is useful for many in vitro testing situations utilizing serum or plasma, in which the presence of steroid hormones is undesirable. For example, such a serum composition, prepared from a mature animal source, may be advantageously substituted for conventional fetal bovine serum to provide the in vitro growth promoting factors found in serum without introducing spurious amounts of steroid hormone.

In some embodiments, a non-inhibitory steroid hormone depleted serum composition comprises steroid hormone depleted blood plasma or serum plus an immunoglobulin inhibitor in a reactivatibly inactive form with respect to ability of the immunoglobulin to inhibit steroid hormone responsive cell proliferation in a suitable cell growth assay absent an inhibition-reversing amount of the steroid hormone. In certain embodiments the non-inhibitory steroid hormone depleted serum composition contains less than an inhibitor activating amount of calcium ion. In certain embodiments an active immunoglobulin inhibitor containing steroid hormone depleted serum composition is provided that is in reactivated form and contains an immunoglobulin inhibitor reactivating amount of calcium ion.

In accordance with certain other embodiments of the invention, a method of making a steroid hormone-depleted serum extract comprising a steroid hormone reversible inhibitor of steroid hormone responsive cell growth is provided. In some embodiments the method comprises (a) obtaining a non-heat-inactivated fresh or frozen serum specimen; (b) performing a first charcoal-dextran extraction on the specimen at about 30-37° C., preferably 34° C., to yield a first extract; and (c) performing a second 30-37° C., preferably 34° C., charcoal-dextran extraction on the first extract to yield a substantially steroid hormone-depleted serum extract.

In another embodiment of the present invention, an alternative method of making a substantially steroid hormone-depleted serum extract comprising a steroid hormone reversible inhibitor of steroid hormone responsive cell growth is provided. In certain embodiments this method comprises obtaining a non-heat-inactivated fresh or frozen serum specimen and performing an XAD™-4 extraction of the specimen.

In still another embodiment of the invention, a method of making a purified immunoglobulin inhibitor of steroid hormone responsive cancer cell growth is provided. This method includes (a) obtaining a substantially steroid hormone-depleted serum comprising an inhibitor of steroid hormone responsive cancer cell growth; (b) loading the depleted serum onto an agarose-based affinity matrix and eluting a fraction comprising the inhibitor; (c) loading the fraction onto a phenyl-Sepharose™ matrix and eluting a substantially purified inhibitor pool with a suitable buffer containing ethylene glycol; and concentrating the pool to yield a substantially purified inhibitor.

Certain embodiments of the present invention provide in vitro assay methods for detecting steroid hormone-like cell growth stimulation by a substance of interest. In some embodiments, the assay method comprises maintaining a predetermined population of steroid hormone-responsive cells in a nutrient medium comprising a quantity of an immunoglobulin cell growth inhibitor sufficient to inhibit cell growth in the absence of an inhibition-reversing amount of the steroid hormone. In some embodiments the medium is serum-free and the cells themselves are serum free and obtained from a stable steroid hormone-responsive cell line. The method also comprises adding a substance of interest to the cells and medium to yield a test mixture. The test mixture is then incubated for a predetermined period of time under cell growth promoting conditions. "Cell growth promoting conditions" refer to general environmental conditions, other than defined medium components, and include such things as favorable conditions of gaseous atmosphere, temperature and pH. For example, cell growth promoting conditions could include incubation at 37° C. in a humid atmosphere of 5% (v/v) $CO_2$ and 95% (v/v) air in a defined nutrient medium at pH 7.4. After incubation for the desired period of time, it is determined whether the cell population in the test mixture has measurably increased, an increase indicating a steroid hormone-like cell growth stimulating effect by the substance of interest. An assay procedure such as this can be used for in vitro screening of drugs or other body-affecting substances for unwanted cell growth stimulating properties as an aid to avoiding undesirable side effects of such drug or substance in vivo. In certain alternative embodiments, the assay method includes adding to the nutrient medium a defined amount of steroid-hormone depleted serum, which contains the inhibitor(s), and which is obtained from non-heat inactivated serum.

In some embodiments of the assay method, in which the substance of interest contains or is suspected of containing proteolytic activity, the method includes selecting an immunoglobulin inhibitor such as IgA2, which resists protease degradation.

In some embodiments of the assay method an inactive inhibitor-containing control serum is substituted for an active inhibitor-containing serum, to evaluate a substance of interest for cytotoxicity.

In certain embodiments, the assay method comprises an assay procedure similar to the one previously described except that a defined amount of inactive immunoglobulin cell growth inhibitor (i.e., incapable of inhibiting steroid hormone responsive cell growth in the absence of an inhibition-reversing amount of the steroid hormone) is substituted for the active (inhibitory) immunoglobulin inhibitor. In some embodiments a test substance is included in the test mixture. As assay of this type is particularly useful for determining a maximum (uninhibited) level of steroid hormone responsive cell growth stimulation by a test substance. Alternatively, this type of assay can be used to distinguish cytotoxic effects of a test substance from anti-estrogen activity, for example.

In accordance with certain embodiments of the invention, a method of detecting a steroid hormone antagonistic substance is provided. The method comprises (a) maintaining a predetermined population of steroid hormone responsive cancer cells in a nutrient medium comprising a quantity of immunoglobulin inhibitor sufficient to inhibit cell growth in the absence of an inhibition-reversing amount of the steroid hormone, the cells also being steroid hormone responsive for in vivo proliferation; (b) adding a defined amount of the substance of interest to the cells and medium; (c) adding to the cells and medium a defined amount of steroid hormone sufficient to stimulate cell growth in the presence of the inhibitor and in the absence of the substance of interest, to yield a test culture; (d) incubating the test culture for a predetermined period of time under cell growth promoting conditions; (e) testing the substance of interest for cytotoxic effects on the cells; and (f) determining the cell population in the test culture after the predetermined period of time, a lack of measurable increase in the cell population not attributable to cytotoxic effects of the substance indicating a steroid hormone antagonistic effect by the substance of interest.

In accordance with certain embodiments of the invention, cell culture media are provided that comprise a basal nutrient fluid, such as D-MEM/F12, and are substantially devoid of unbound Fe (III), i.e., preferably containing less than 1 μM Fe (III), and more preferably containing 0.15 μM or less. In certain preferred embodiments, the amount of free, or active Fe (III) in the medium is less than a cell growth inhibiting concentration. The media also contain calcium ion, preferably about 0.6 mM to 1.0 M, and more preferably about 0.6 to 10 mM calcium. In certain preferred embodiments, the concentration of calcium ion in the nutrient medium is preferably sufficient to maintain the inhibitory activity of any immunoglobulin inhibitors present in the media. In certain embodiments, a cell culture medium that is especially suited for use in serum-free cell growth studies also includes a Fe (III) chelating agent, preferably deferoxamine, and a cell attachment promoting protein, preferably fibronectin. In certain preferred embodiments the defined composition medium is DDM-2MF, CAPM, DDM-2A or PCM-9, the compositions of which are set out in the Examples below. In preferred embodiments, the cell culture media comprise 100 ng/mL to 10 μg/mL insulin, 0.3-10 nM triiodothyronine, 2-50 μg/mL diferric transferrin, 5-100 μM ethanolamine, 0.2-5.0 mg/mL bovine serum albumin (BSA), 5-20 ng/mL selenium, 2-10 μM deferoxamine. Depending on the requirements of the selected cells to be cultures, the medium may also contain at least one of the following components: 1-50 ng/mL EGF, 0.2-20 ng/mL aFGF, 5-50 μM phosphoethanolamine, 50-500 μg/mL linoleic acid-BSA, 1-50 μg/mL reduced glutathione, 0.5-2.0 mM glutamine, 1-10 μg/mL heparin, and 20-50 μg (per 35-mm diameter culture dish) human fibronectin. In some embodiments the cell culture medium also includes steroid hormone depleted serum.

According to other embodiments of the present invention an in vitro method of culturing steroid hormone responsive cancer cells or autonomous cancer cells is provided. The method comprises (a) maintaining a predetermined population of steroid hormone responsive cells or steroid hormone-independent cancer cells in a steroid hormone-free nutrient medium comprising an above-described cell culture medium and a quantity of immunoglobulin inhibitor sufficient to inhibit cell growth of steroid hormone responsive cancer cells in the absence of an inhibition-reversing amount of the steroid hormone, to provide an incubation mixture, the steroid hormone responsive cells also being steroid hormone responsive for proliferation in vivo when implanted into a suitable host, and the steroid hormone independent cancer cells also being steroid hormone independent for proliferation in vivo when implanted into a suitable host; (b) optionally, adding an inhibition-reversing amount of the steroid hormone to the incubation mixture; (c) incubating the incubation mixture under cell growth promoting conditions; (d) optionally, determining the cell population in the reaction mixture after incubation for a predetermined period of time.

According to certain embodiments of the invention an in vitro method of detecting a cell growth stimulatory or inhibitory effect of a substance of interest on steroid hormone independent cancer cells is provided. The method includes (a) maintaining a predetermined population of steroid hormone independent cancer cells in a nutrient medium as described above, optionally, devoid of the steroid hormone, and, optionally, containing a predetermined quantity of immunoglobulin inhibitor, the steroid hormone independent cells also being steroid hormone independent for proliferation in vivo when implanted into a suitable host; (b) adding a predetermined quantity of the substance of interest to the cells and medium to yield a test mixture; (c) incubating the test mixture for a predetermined period of time under cell growth promoting conditions; (d) optionally, assessing cytotoxicity of the substance of interest; and (e) determining the cell population in the test mixture after the incubation for the predetermined period of time, a measurable increase in the cell population indicating a cell growth stimulating effect by the substance of interest, and an absence of increase in the cell population, not attributable to cytotoxic effects, indicating a cell growth inhibitory effect by the substance of interest.

In accordance with still another embodiment of the present invention, an in vitro method of detecting an immunoglobulin inhibitor-like cancer cell growth inhibitory effect by a substance of interest is provided which comprises (a) maintaining a predetermined population of steroid hormone responsive cancer cells in a nutrient medium as described above, optionally, devoid of the steroid hormone, and, optionally, containing a predetermined quantity of inactivated immunoglobulin inhibitor, the steroid hormone responsive cells also being steroid hormone responsive for proliferation in vivo when implanted into a suitable host; (b) adding a predetermined quantity of the substance of interest to the cells and medium to yield a test mixture; (c) adding to the test mixture an amount of the steroid hormone that would be sufficient to induce cell growth in the absence of an active immunoglobulin inhibitor; (d) incubating the test mixture for a predetermined period of time under cell growth promoting conditions; (e) optionally, assessing cytotoxicity of the substance of interest; and (f) determining the cell population in the test mixture after the predetermined period of time, a measurable increase in the cell population indicating a lack of cell growth inhibitory effect by the amount of the substance of interest, and no increase in the cell population, not attributable to a cytotoxic effect, indicating a cell growth inhibitory effect by the amount of the substance of interest.

In accordance with another embodiment, a method of producing a quantity of a biomolecule, of interest such as a protein, peptide or polynucleotide. The method includes, in a serum-free nutrient medium as described above, culturing a population of cells expressing the biomolecule of interest, harvesting and recovering the biomolecule from the medium. In certain preferred embodiments the protein is a monoclonal antibody.

In accordance with another embodiment, a method of propagating a virus of interest is provided which comprises culturing a population of virus infected cells in an above-described serum-free nutrient medium, harvesting and recovering viruses from the medium.

Further provided in accordance with certain embodiments of the invention is an assay kit for detecting in vitro steroid hormone reversible steroid hormone-responsive cell growth by a substance of interest. In some embodiments such a kit comprises a serum-free defined nutrient cell culture medium substantially free of unbound Fe (III) and containing calcium ion. The kit also contains a substantially steroid hormone-depleted serum comprising a steroid hormone reversible immunoglobulin inhibitor of steroid hormone responsive cell growth. In certain preferred embodiments the extract is prepared by either a double charcoal-dextran extraction method or the XAD-4™ extraction method, described above. In some embodiments the kit also includes a control serum composition comprising an inactivated immunoglobulin inhibitor. In some embodiments the kit also includes a population of cultured steroid hormone responsive cancer cells that are also steroid hormone responsive for proliferation in vivo, preferably MTW9/PL2 rat mammary tumor cells.

In alternative embodiments, assay kits for detecting in vitro steroid hormone reversible steroid hormone-responsive cell growth by a substance of interest are provided. In certain embodiments the kit, which is similar to the one described above, isolated immunoglobulin inhibitors (e.g., IgA, IgM and/or IgG1) are included in addition to, or instead of, the serum-based inhibitor composition(s). Use of this kit will be preferred when the user requires a totally serum-free assay system. In some situations both the steroid hormone depleted serum-containing and the serum-free assay systems are employed in order to detect serum factor effects or to distinguish the influence of serum on detection of cytotoxic effects of a chemical, for example.

In some embodiments the kit also contains other components such as various steroid hormones, or agonists or antagonists thereof, that may be desired for adding to the medium in particular test situations.

In certain embodiments of the invention in vitro assay methods for detecting an immunoglobulin inhibitor of steroid hormone responsive cell growth in a sample of interest, such as a drug or environmental substance, blood serum or another body fluid, are provided. In some embodiments the method comprises (a) maintaining a predetermined population of steroid hormone-responsive culture cells in a nutrient medium, the cells also being steroid hormone dependent for proliferation in vivo when implanted into a suitable host; (b) adding a quantity of steroid hormone to the medium sufficient to stimulate proliferation of the cells under cell growth promoting culture conditions; (c) adding a predetermined quantity of the sample of interest to the medium to yield a test mixture; (d) incubating the test mixture for a predetermined period of time under cell growth promoting culture conditions; (e) optionally, testing the sample for cytotoxic effects on the cells; and (f) determining the cell population in the test mixture after the predetermined period of time, a measurable decrease in the cell population not attributable to cytotoxic effects indicating inhibition by the amount of sample of steroid hormone responsive cell growth.

In some embodiments the assay method also includes adding to the test mixture an amount of the steroid hormone in excess of the minimum amount necessary to maximally stimulate proliferation of the cells; and determining the cell population of the test mixture after the predetermined period of time, a measurable increase in the cell population indicating reversal by the excess amount of steroid hormone of steroid hormone responsive cell growth inhibition.

In accordance with still other embodiments of the present invention, in vitro cell culture models for predicting an in vivo steroid hormone-responsive cancer cell growth effect of a defined stimulus, such as an estrogen, an anti-estrogen, androgen, or other steroid hormone, or a steroid hormone mimicking compound, are provided. In certain embodiments the model includes steroid hormone-responsive cancer cells maintained in a growth medium containing a basal nutrient fluid substantially free of unbound Fe (III), containing calcium ion, and containing an amount of steroid hormone reversible immunoglobulin inhibitor sufficient to arrest cancer cell growth in the absence of an inhibition-reversing amount of the steroid hormone. The cells are also steroid hormone responsive for proliferation in vivo, when implanted into a suitable host. The immunoglobulin inhibitor is chosen from among IgA, IgM and IgG, and combinations thereof. In some embodiments the nutrient medium is serum free, and in others it contains steroid hormone depleted blood plasma or serum. In certain embodiments the steroid hormone responsive culture cells are MTW9/PL2 (rat mammary cancer), T47D (human breast carcinoma), MCF-7 (human breast carcinoma), MCF-7A (human breast carcinoma), MCF-7K (human breast carcinoma), LNCaP (human prostatic carcinoma), ZR-75-1 (human prostatic carcinoma), H-301 (Syrian hamster kidney tumor), $GH_1$ or $GH_3$ (rat pituitary tumor), $GH_4C_1$ (rat pituitary tumor), or HT-29 (human colonic cancer).

In still other embodiments of the present invention an isolated estrogen receptor gamma (ERγ) is provided. In certain embodiments the (ERγg) has an estradiol binding affinity greater than that of estrogen receptor alpha (ERα) or estrogen receptor beta (ERβ) preferably having a $K_d$ for $E_2$ on the order of $>10^{-9}$ M. The ERγ also preferably has specificity for steroid hormone binding in the order estradiol>> diethylstilbestrol >>testosterone=dihydrotestosterone,and has a molecular weight of approximately 50 kDa.

In certain embodiments a mediator of estrogen responsive cell growth comprises ERγ, and in certain embodiments a mediator of estrogen reversal of immunoglobulin inhibition of estrogen responsive cell growth comprises ERγ.

Also provided by the present invention are methods of detecting an estrogenic substance. According to certain embodiments, the method comprises (a) maintaining a predetermined population of estrogen responsive cancer cells in a steroid hormone-free nutrient medium comprising a quantity of immunoglobulin inhibitor sufficient to inhibit cancer cell growth in the absence of an inhibition-reversing amount of estrogen, the cells also being estrogen responsive for proliferation in vivo when implanted into a suitable host; (b) adding a defined amount of the substance of interest to the cells and medium, to yield a test culture; (c) incubating the test culture for a predetermined period of time under cell growth promoting conditions; and (d) determining the cell population in the test culture after the predetermined period of time, a measurable increase in the cell population indicating an estrogen-like cell growth stimulating effect by the substance of interest. In some embodiment the method also includes testing the substance of interest for binding to estrogen receptor gamma and/or testing for cytotoxic effects. In certain embodiments, the method includes selecting estrogen responsive cancer cells containing estrogen receptor gamma.

Also provided by the present invention are methods of detecting an anti-estrogenic substance, such as an antagonist. According to certain embodiments, the method comprises (a) maintaining a predetermined population of estrogen responsive cancer cells in a nutrient medium comprising a quantity of immunoglobulin inhibitor sufficient to inhibit cell growth in the absence of an inhibition-reversing amount of estrogen, the cells being capable of growing in vivo; (b) adding a defined amount of the substance of interest to the cells and medium; (c) adding a defined amount of an estrogen sufficient to stimulate cell growth in the presence of the inhibitor and in the absence of the substance of interest to the cells and medium, to yield a test culture; (d) incubating the test culture for a predetermined period of time under cell growth promoting conditions; (e) testing the substance of interest for cytotoxic effects on the cells; and (f) determining the cell population in the test culture after the predetermined period of time, a lack of measurable increase in the cell population not attributable to cytotoxic effects of the substance indicating a steroid hormone antagonistic effect by the substance of interest. In some embodiments the method also includes testing the substance of interest for binding to estrogen receptor gamma and/or testing for cytotoxic effects. In certain embodiments, the method includes selecting estrogen responsive cancer cells containing estrogen receptor gamma.

Also provided in accordance with the present invention are methods of identifying an estrogen responsive cell that is capable of being inhibited or prevented from proliferating by an estrogen reversible inhibitor of estrogen responsive cell growth. In certain embodiments the method comprises detecting estrogen receptor gamma in the cell.

According to the present invention, methods of inhibiting in vitro cancer cell growth are provided. In certain embodiments the method comprises (a) maintaining a predetermined population of cancer cells in an above-described nutrient medium; (b) adding an effective amount of an iron compound to the medium, to provide an incubation mixture comprising unbound Fe (III), preferably at least about 1 µM Fe (III); (c) incubating the incubation mixture for a predetermined period of time under cell growth promoting conditions; and (d) determining the cell population in the incubation mixture after the predetermined period of time, an increase in cell population indicating lack of inhibition by the Fe (III), and the absence of an increase in cell population indicating inhibition of cell growth by the Fe (III).

In certain embodiments of the present invention, a method of killing cancer cells in vitro is provided. In some of those embodiments a concentration of at least about 10 µM unbound Fe (III) is maintained in the nutrient medium. Alternatively, extended arrest of cancer cell growth by an immunoglobulin inhibitor can also serve to kill steroid hormone responsive cancer cells in culture.

Accordingly, in certain embodiments of the present invention, a method of killing steroid hormone responsive cancer cells in culture is provided which comprises (a) combining a predetermined population of steroid hormone responsive cancer cells with a nutrient medium comprising an above-described cell culture medium and a quantity of steroid hormone irreversible immunoglobulin inhibitor sufficient to inhibit cell growth of steroid hormone responsive cancer cells, to provide an incubation mixture, the steroid hormone responsive cells also being steroid hormone responsive for proliferation in vivo when implanted into a suitable host; (b) incubating the incubation mixture for a predetermined period of time under cell growth promoting conditions; and (c) optionally, determining the cell population in the reaction mixture after the incubation for the predetermined period of time. In some embodiments the immunoglobulin inhibitor is irreversibly, or permanently inhibitory (i.e., the inhibitor is active with respect to the ability to inhibit steroid hormone-responsive cell proliferation and inactive with respect to steroid hormone reversibility of the inhibition.)

Another embodiment of the present invention provides a method of killing a mixed population of steroid hormone responsive cancer cells and autonomous cancer cells. The method comprises contacting the mixed population of cells with an amount of an iron depleting substance sufficient to substantially deprive the autonomous cells of Fe (III), and then maintaining the cells in an iron depleted environment for a sufficient period of time for the autonomous cells to die. The method also includes contacting the mixed population of cells with an amount of a Fe (III) containing substance sufficient to inhibit cell growth and/or kill the steroid hormone responsive cells, and then maintaining the cells in a Fe (III)-enhanced environment for a predetermined period of time sufficient to inhibit cell growth and/or kill the steroid hormone responsive cancer cells. In certain embodiments, the method also includes contacting the mixed population of cells with an amount of immunoglobulin inhibitor sufficient to inhibit proliferation of the steroid hormone responsive cells.

Still other embodiments provided by the present invention are methods of determining the concentration of a steroid hormone in a defined amount of a body fluid. In certain embodiments the method comprises assaying the body fluid for binding of steroid hormone to an immunoglobulin inhibitor of steroid hormone responsive cancer cell growth.

These and other embodiments, features and advantages of the present invention will become apparent with reference to the following description and drawings.

BRIEF DESCRIPTION OF THE DRAWINGS

For the detailed descriptions of the preferred embodiments, reference will now be made to the accompanying figures which include graphs, charts, and test results:

FIG. 2. Scatchard Analysis and Saturation Binding Analysis of $^3$H-$E_2$ Binding to MTW9/PL2 Cells.

FIG. 5. Scatchard Analysis and Saturation Binding Analysis of $^3$H-Progesterone to MTW9/PL2 Cells.

FIG. 6. Effect of Unlabeled Competitor Steroids on $^3$H-Progesterone Binding to MTW9/PL2 Cells.

FIG. 9. CDE-horse Serum Effect on MTW9/PL2 Cell Growth±10 nM $E_2$ for 7 days. (A) Dose-response data expressed as cell numbers; (B) Dose-response data expressed as cell population doublings (CPD) per 7 days.

FIG. 16. Kinetics of T47D Cell Growth in CDE-horse Serum±10 nM E2. (A) Growth Kinetics in 20% CDE-horse±$E_2$ versus 10% Fetal Bovine Serum; (B) Growth Kinetics in 50% CDE-horse Serum±$E_2$.

FIG. 26. Effect of 56° C. versus 34° C. CDE-horse Serum on MTW9/PL2 Cell Growth.

FIG. 29. Effect of Phenol Red on Estrogen Responsive MCF-7 Cell Growth. (A) MCF-7A Cell Growth in CDE-horse Serum±Phenol Red and±$E_2$; (B) Estrogenic Effects with MCF-7A Cells±Phenol Red; (C) MCF-7K Cell Growth in CDE-horse Serum±Phenol Red and±$E_2$ (D) Estrogenic Effects with MCF-7K Cells±Phenol Red.

FIG. 30. Effect of Phenol Red on Estrogen Responsive T47D and ZR-75-1 Cell Growth. (A) T47D Cell Growth in CDE-horse Serum±Phenol Red and±$E_2$; (B) Estrogenic Effects with T47D Cells±Phenol Red; (C) ZR-75-1 Cell Growth in CDE-horse Serum±Phenol Red and $E_2$; (D) Estrogenic Effects with ZR-75-1 Cells±Phenol Red.

FIG. 31. Effect of Phenol Red on Estrogen Responsive MTW9/PL2 Cell Growth. (A) MTW9/PL2 Cell Growth in CDE-horse Serum±Phenol Red and $E_2$; (B) Estrogenic Effects with MTW9/PL2 Cells±Phenol Red.

FIG. 33. Estrogen Induction of Progesterone Receptors by Phenol Red versus $E_2$. (A) Induction by $E_2$ with T47D Cells; (B) Induction by Phenol Red with T47D Cells.

FIG. 34. Effects of TGFβ1 on Cell Growth in 2.5% CDE-horse Serum±$E_2$. (A) MCF-7K Cell Growth; (B) MTW9/PL2 Cell Growth.

FIG. 35. TGFβ1 Inhibition of $ER^+$ Rodent and Human Cell Line Growth±$E_2$. (A) Inhibition Data±$E_2$ Presented in Cell Number; (B) Inhibition Data±$E_2$ Presented in CPD.

FIG. 36. EGF and TGFα as Substitutes for the Effects of $E_2$ in CDE-horse Serum. (A) MCF-7A Cell Growth; (B) MCF-7K Cell Growth; (C) T47D Cell Growth; (D) ZR-75-1 Cell Growth.

FIG. 37. IGF-I as a Substitute for the Effects of $E_2$ in CDE-horse Serum. (A) MCF-7K Cell Growth MCF-7A Cell Growth; (B) T47D Cell Growth.

FIG. 43. Dose-Response Effects of Individual Components of CAPM Serum-free Defined Medium on LNCaP Cell Growth.

FIG. 56. Comparison of Estrogenic Effects in Serum-free Defined Medium and in D-MEM/F-12 Medium Supplemented with CDE-Horse Serum. (A) MCF-7K Cell Growth in Serum-free Defined Medium±$E_2$; (B) MCF-7K Cell Growth in D-MEM/F-12 with CDE-horse Serum±$E_2$; (C) T47D Cell Growth in Serum-free Defined Medium±$E_2$; (D) T47D Cell Growth in D-MEM/F-12 with CDE-horse Serum±E$_2$; (E) LNCaP Cell Growth in Serum-free Defined Medium±E$_2$; (F) LNCaP Cell Growth in D-MEM/F-12 with CDE-horse Serum±E$_2$.

FIG. 57. Comparison of Estrogenic Effects in Serum-free Defined Medium and in D-MEM/F-12 Medium Supplemented with CDE-Horse Serum. (A) GH$_4$C$_1$ Cell Growth in Serum-free Defined Medium±E$_2$; (B) GH$_4$C$_1$ Cell Growth in D-MEM/F-12 with CDE-horse Serum±E$_2$; (C) MTW9/PL2 Cell Growth in Serum-free Defined Medium±E$_2$; (D) MTW9/PL2 Cell Growth in D-MEM/F-12 with CDE-horse Serum±E$_2$; (E) H301 Cell Growth in Serum-free Defined Medium±E$_2$; (F) H301 Cell Growth in D-MEM/F-12 with CDE-horse Serum E$_2$.

FIG. 59. Comparison of the Inhibitor Reversing Effects of DHT, E$_2$, and DES on LNCaP Cell Growth in CDE-horse Serum Containing Medium. (A) Effect of DHT as an Inhibitor Reversing Steroid; (B) Effect of E$_2$ as an Inhibitor Reversing Steroid; (C) Effect of DES as an Inhibitor Reversing Steroid; (D) Effect of Combinations of DHT, E$_2$, and DES as Inhibitor Reversing Steroids.

FIG. 79. Immunoprecipitation of $^3$H-DHT Binding and Estrogenic Activity of CDE-horse Serum by Anti-Human SHBG. (A) $^3$H-DHT Binding Reduction; (B) Estrogenic Activity Reduction.

FIG. 87. Protein Sequencing Results with CA-PS-Pool II Peptides and Homology to Human SHBG, Rabbit SHBG and Rat and Hamster Androgen Binding Protein (SEQ ID NOS: 3-19).

FIG. 94. SDS-PAGE with Coomassie Staining and Western Analysis of Rat Purified "SHBG-like" Proteins. (A) SDS-PAGE of Purified Rat Preparations; (B) Western Analysis with Anti-rat IgG.

FIG. 96. Protein Sequencing Results with Rat "SHBG-like" Peptides and Homology to Human SHBG, Rabbit SHBG and Rat and Hamster Androgen Binding Protein (SEQ ID NOS:36 and 20-26).

FIG. 97. Comparison of Rat IgG Subclasses. (A) SDS-PAGE with Comassie Blue Stainining; (B) Western Analysis with Rabbit Anti-Human SHBG.

FIG. 110. Essential Structures of Human Plasma and Secretory IgA.

Figure 120:
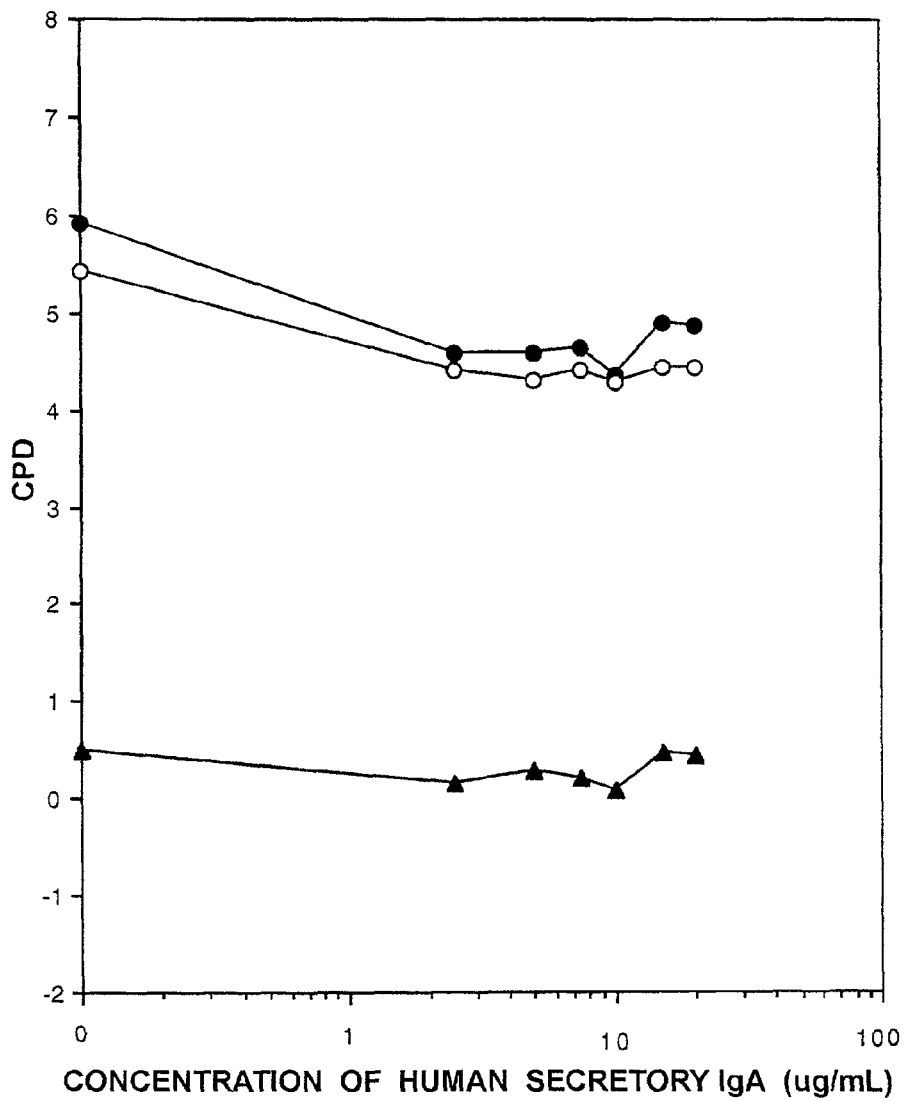

FIG. 120. Effect of Human Secretory IgA on $GH_4C_1$ Cell Growth in Serum-free Defined Medium±$E_2$.

Figure 121:
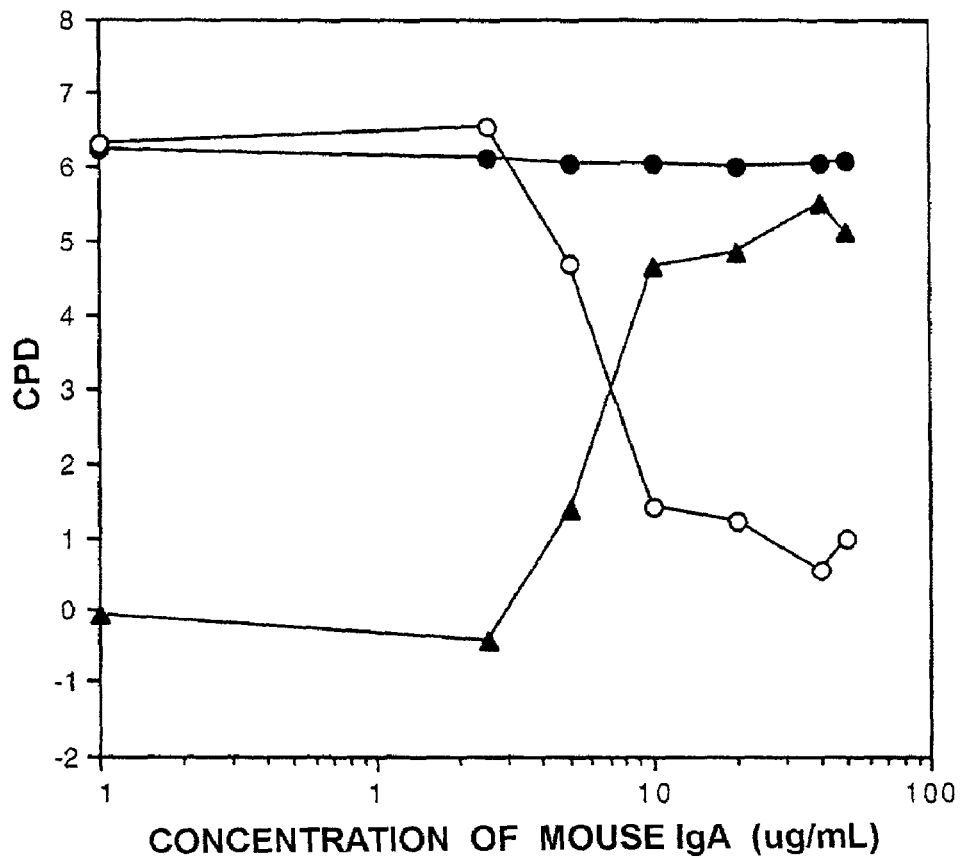

FIG. 121. Effect of Mouse IgA on H301 Cell Growth in Serum-free Defined Medium±$E_2$.

Figure 122:
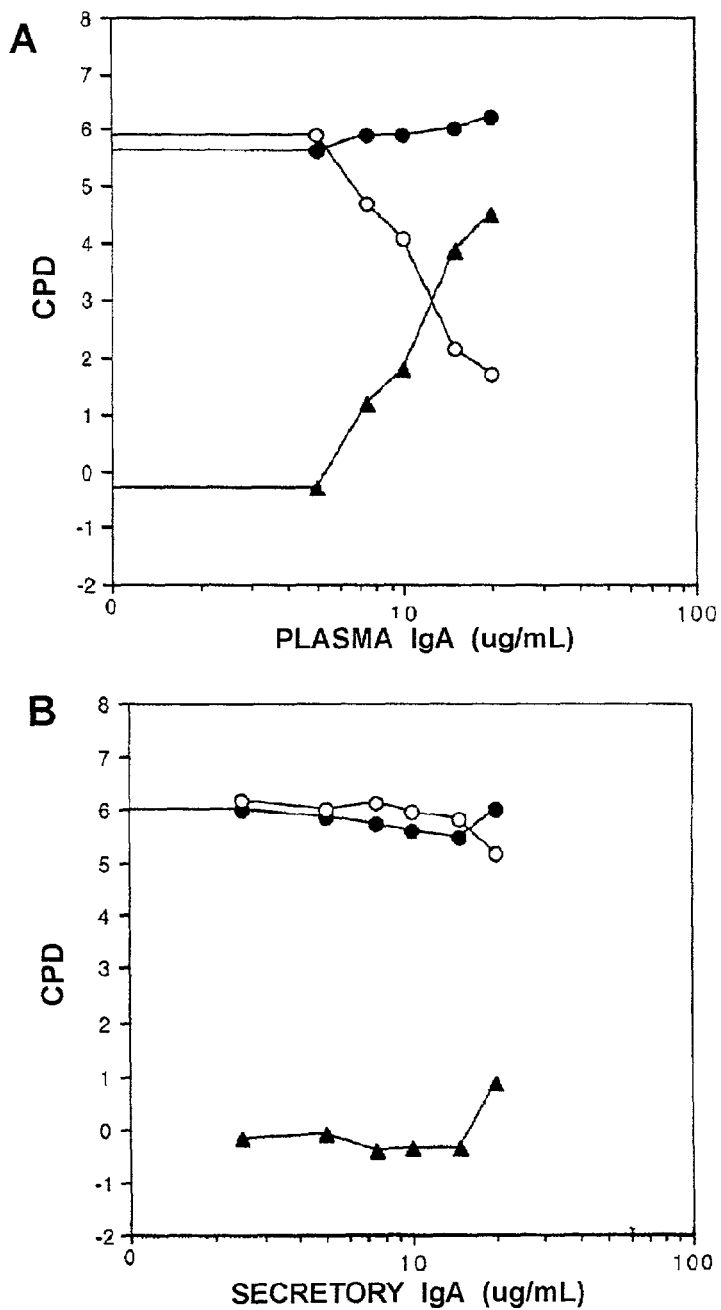

FIG. 122. Effect of Human IgA on H301 Cell Growth in Serum-free Defined Medium±$E_2$ (A) Plasma IgA Effects; (B) Secretory sIgA Effects.

Figure 123:
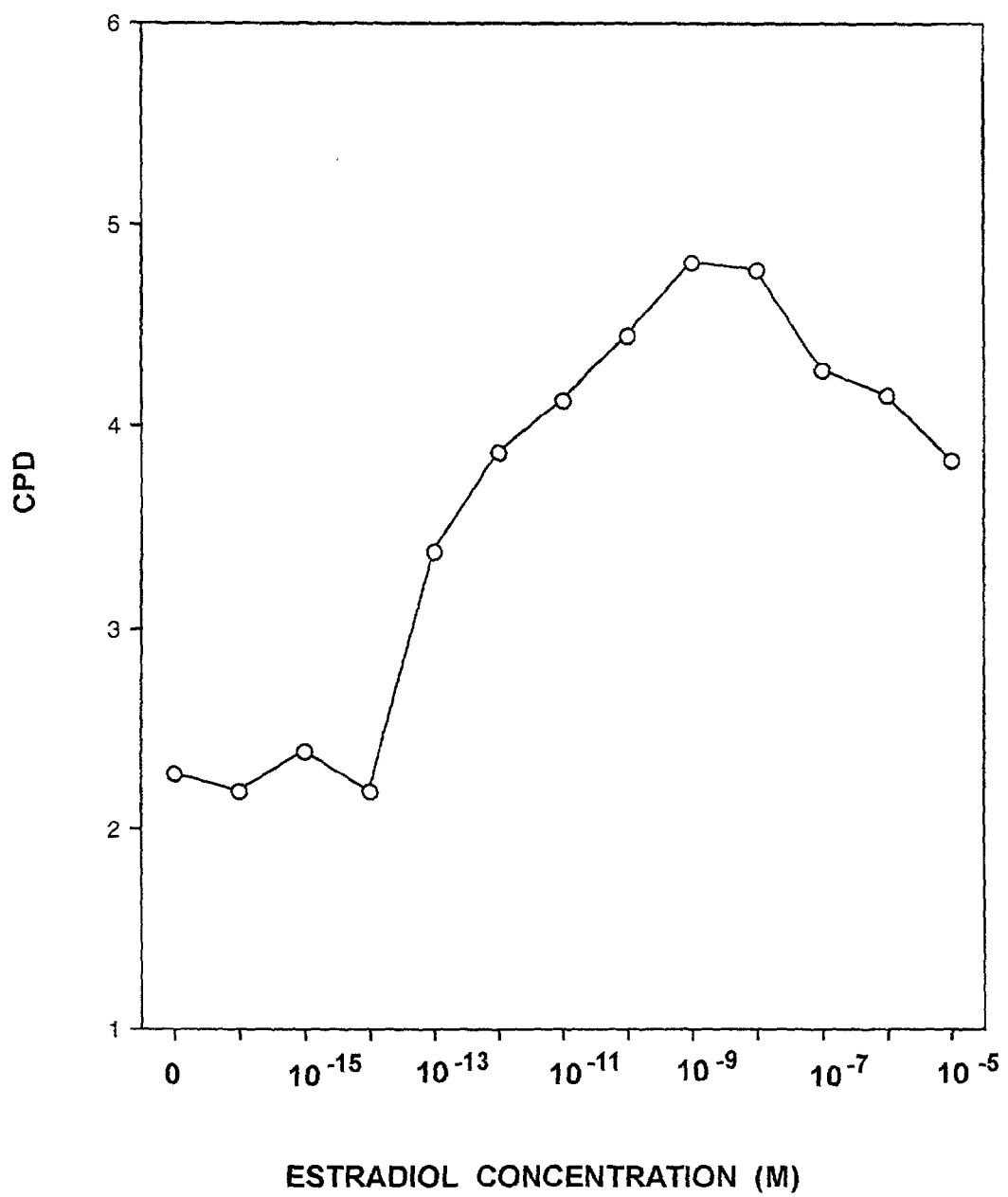

FIG. 123. Dose-Response Effects of $E_2$ on H301 Cell Growth in Serum-free Defined Medium Containing 40 μg/mL Human Plasma IgM.

Figure 124:
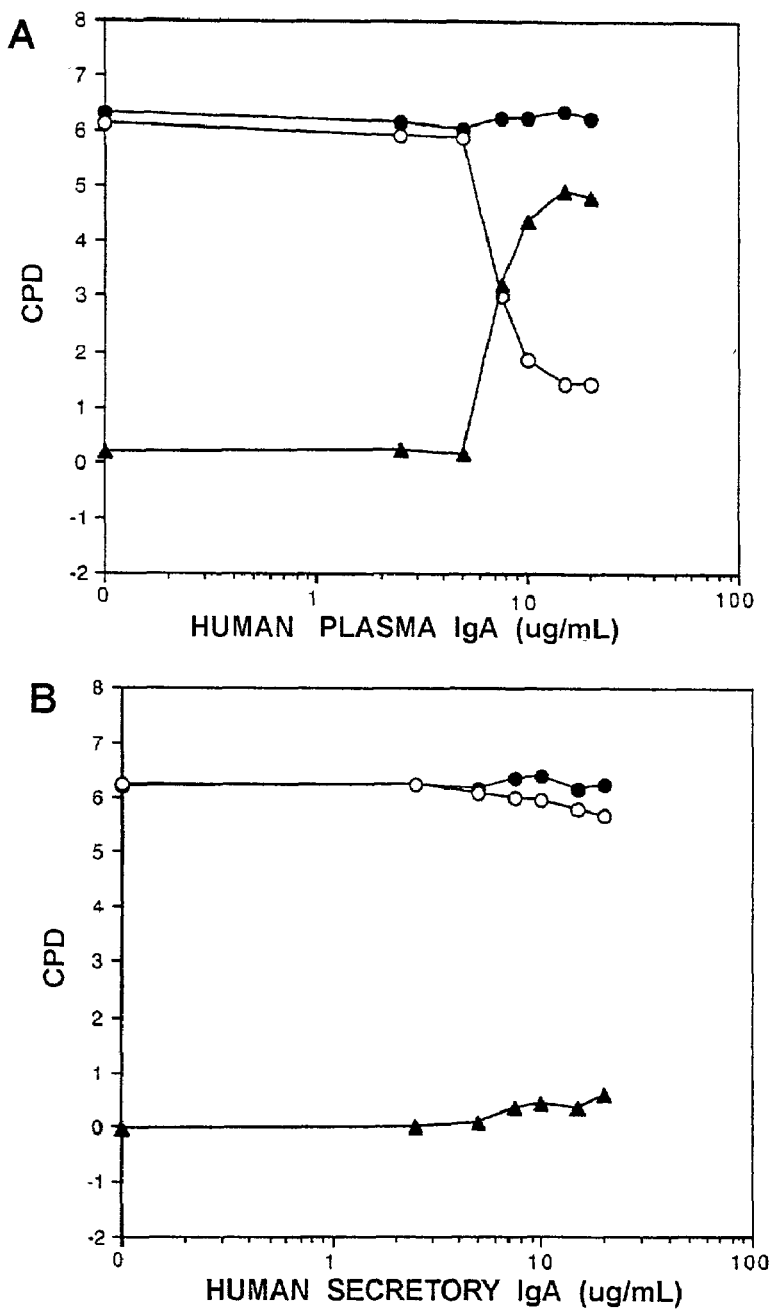

FIG. 124. Effect of Human IgA on MCF-7A Cell Growth in Serum-free Defined Medium±$E_2$. (A) Plasma IgA Effects; (B) Secretory sIgA Effects.

Figure 125:
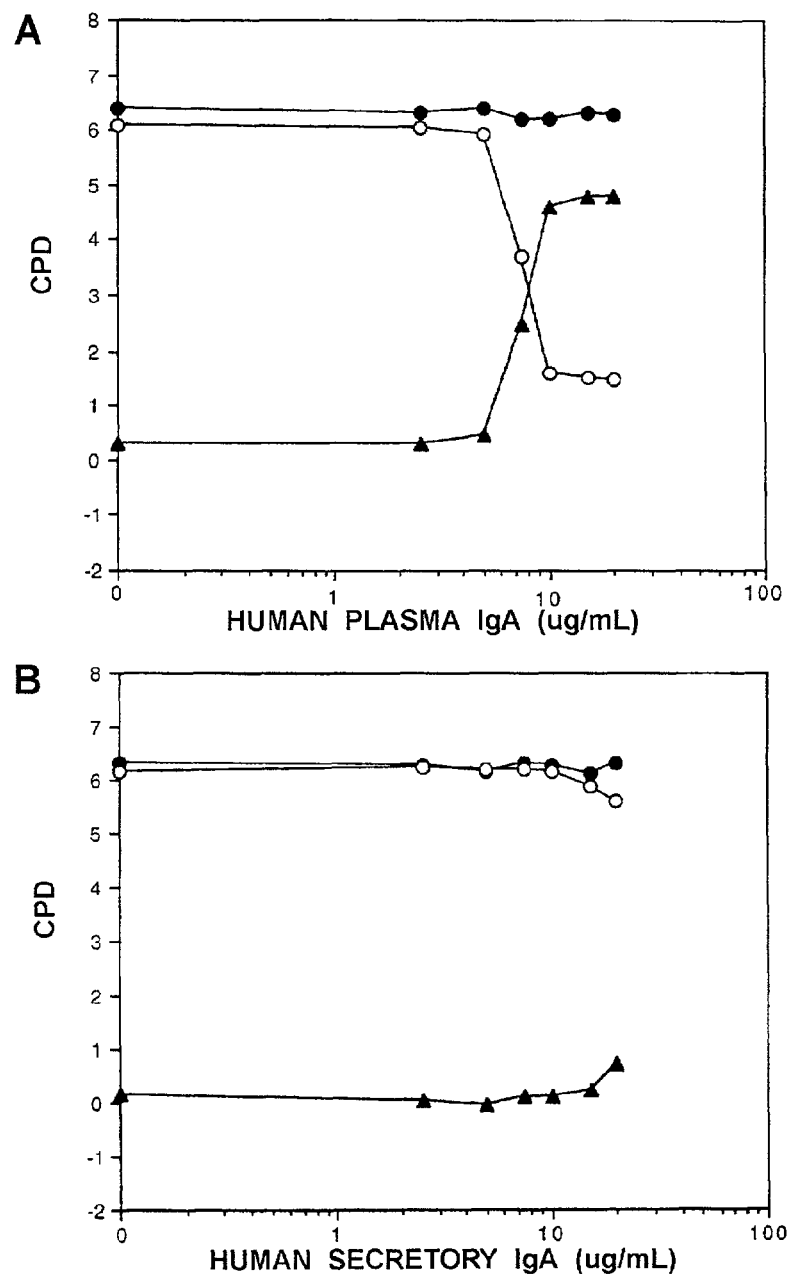

FIG. 125. Effect of Human IgA on MCF-7K Cell Growth in Serum-free Defined Medium±$E_2$. (A) Plasma IgA Effects; (B) Secretory sIgA Effects.

Figure 126:
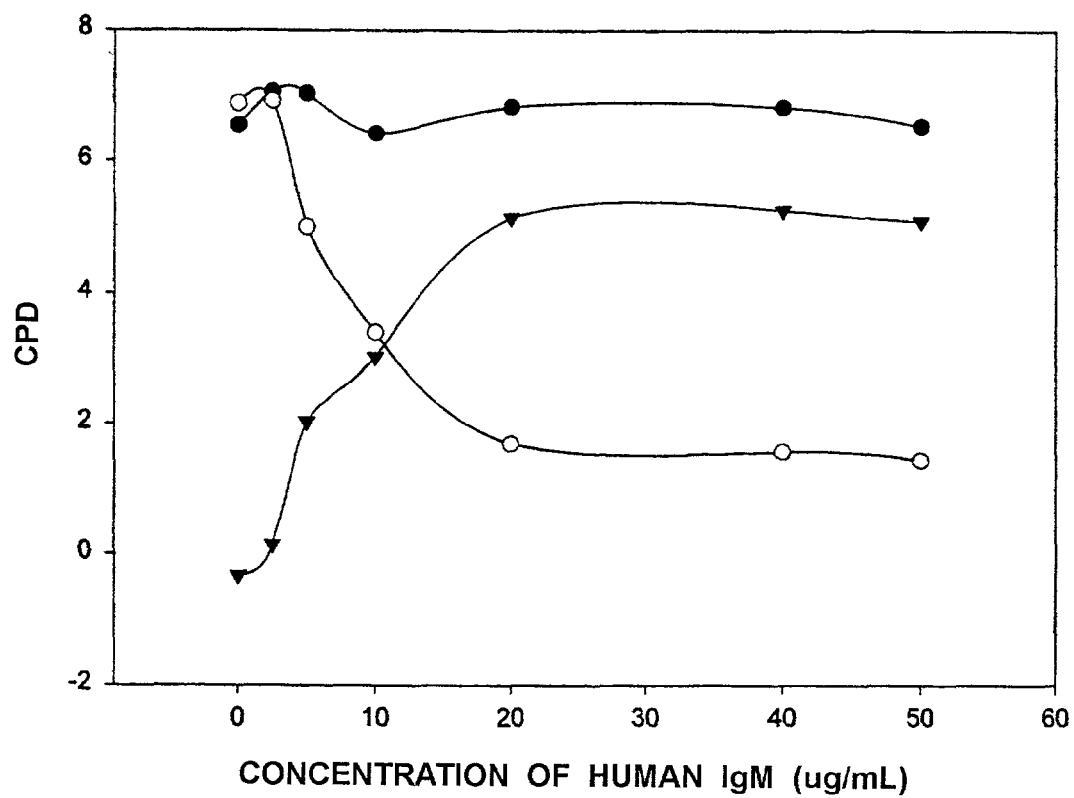

FIG. 126. Effect of Human IgM on MCF-7A Cell Growth in Serum-free Defined Medium±$E_2$.

Figure 127:
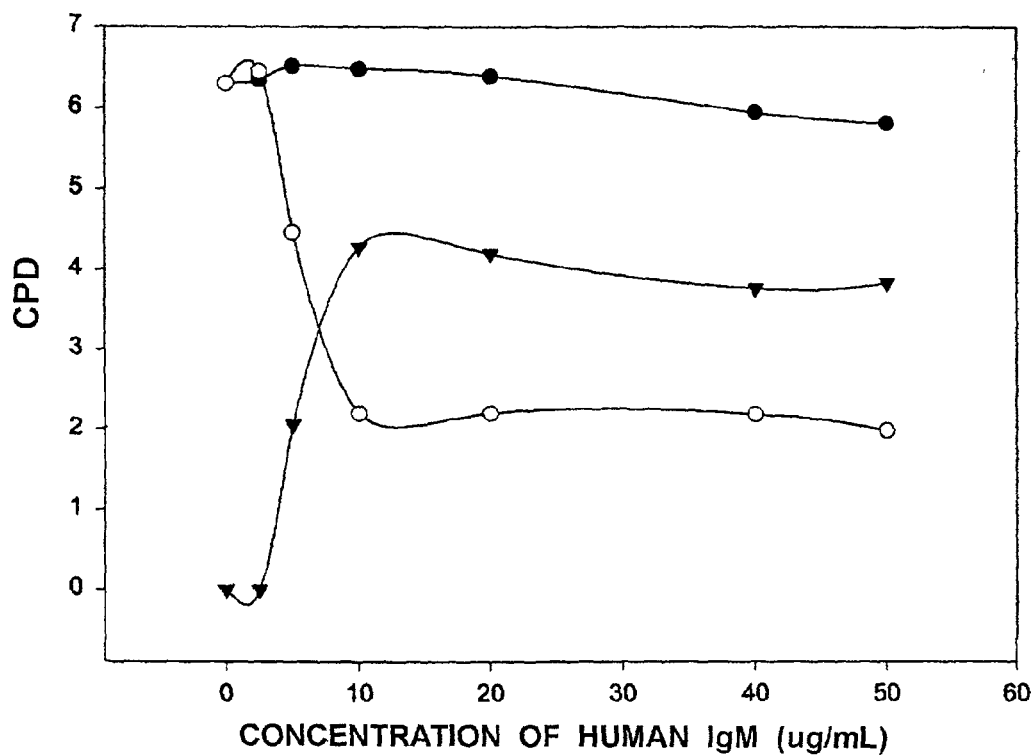

FIG. 127. Effect of Human IgM on MCF-7K Cell Growth in Serum-free Defined Medium±$E_2$.

Figure 128:
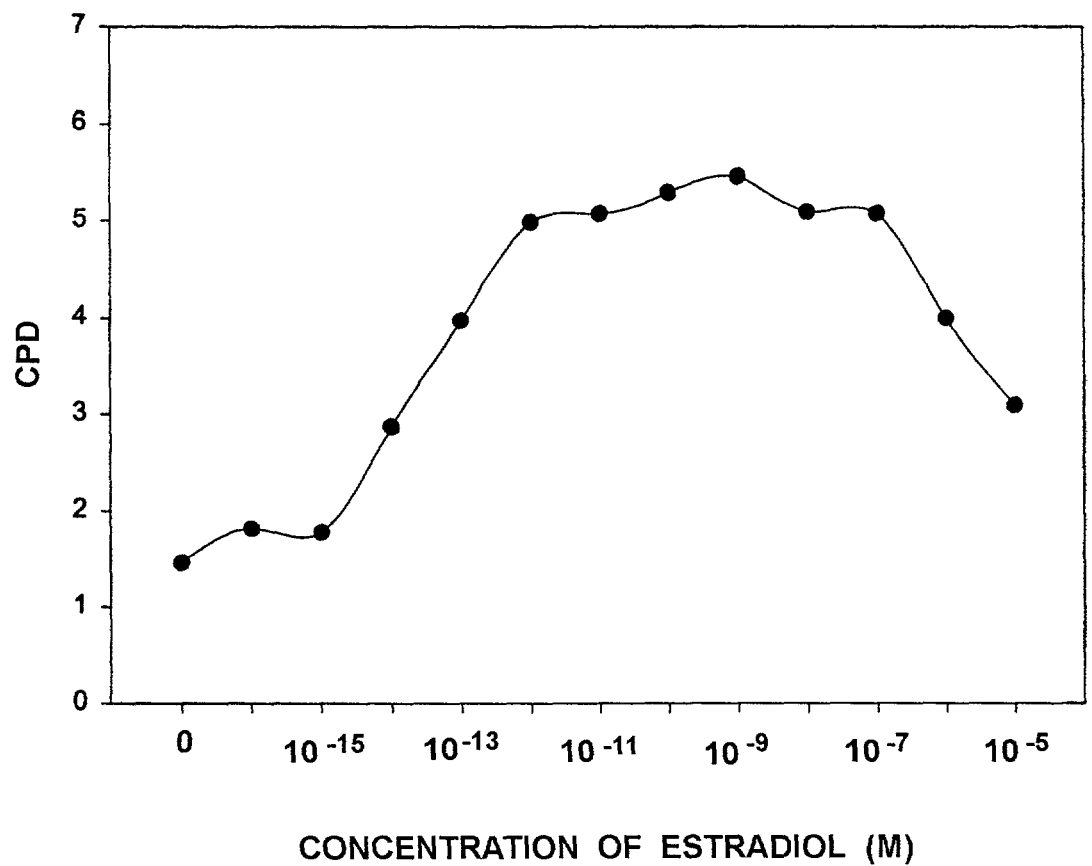

FIG. 128. Dose-Response Effects of $E_2$ on MCF-7K Cell Growth in Serum-free Defined Medium Containing 40 μg/mL Human Plasma IgM.

Figure 129:
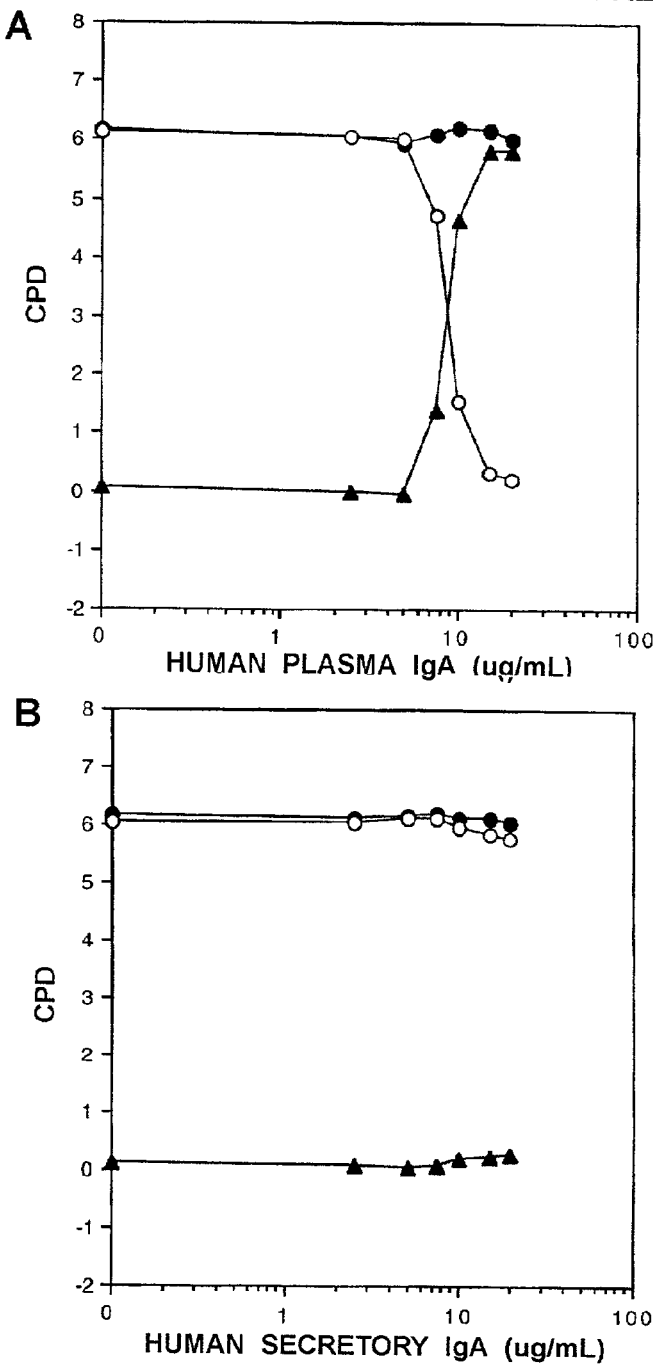

FIG. 129. Effect of Human IgA on T47D Cell Growth in Serum-free Defined Medium±$E_2$. (A) Plasma IgA Effects; (B) Secretory sIgA Effects.

Figure 130:
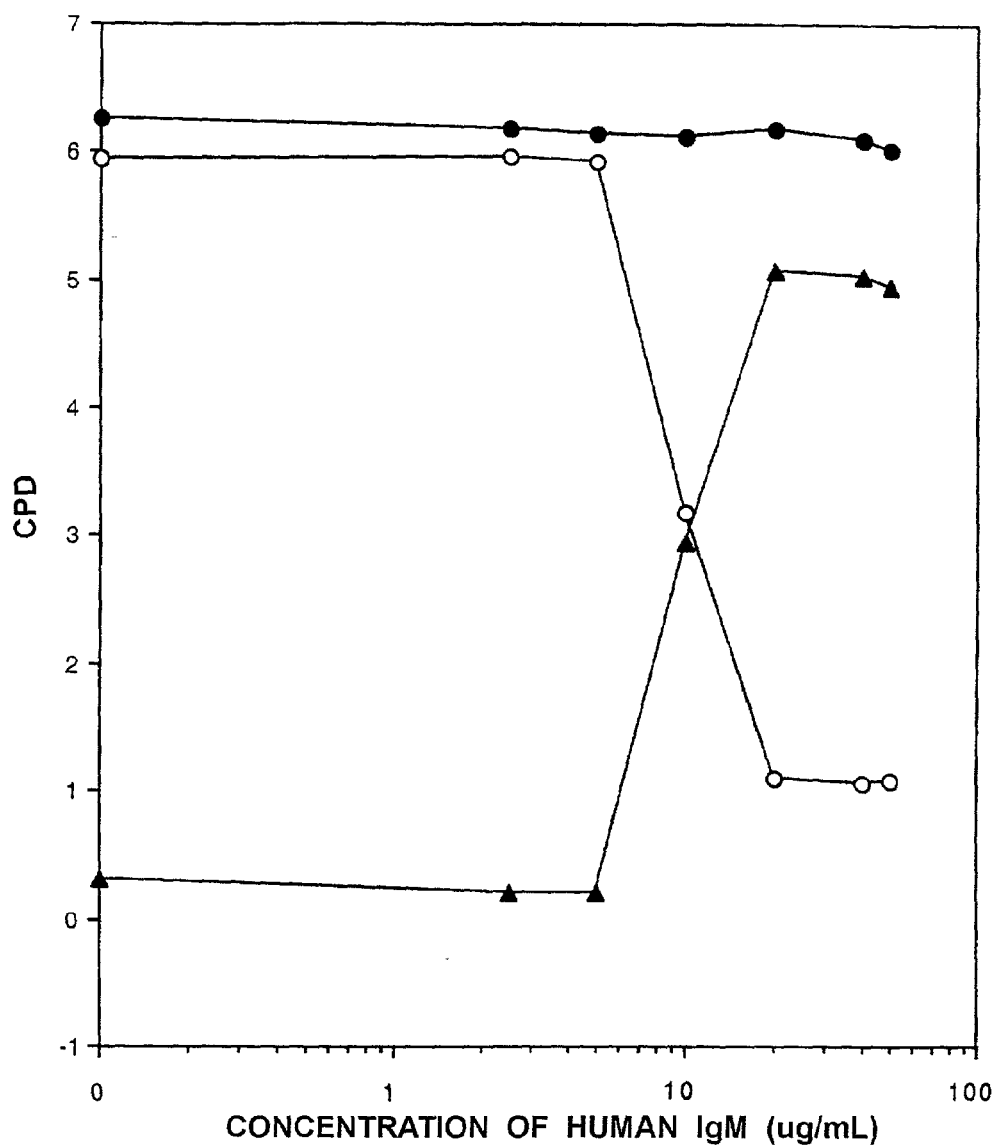

FIG. 130. Effect of Human IgM on T47D Cell Growth in Serum-free Defined Medium±$E_2$.

Figure 131:
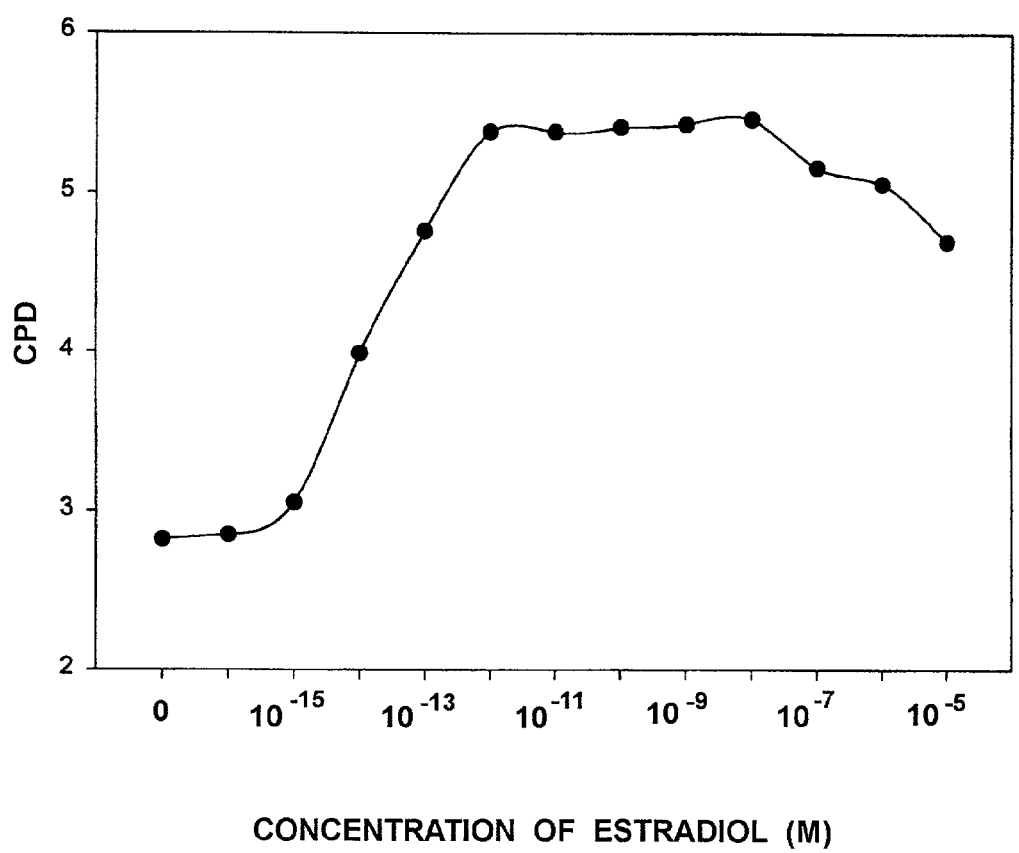

FIG. 131. Dose-Response Effects of $E_2$ on T47D Cell Growth in Serum-free Defined Medium Containing 40 μg/mL Human Plasma IgM.

Figure 132:
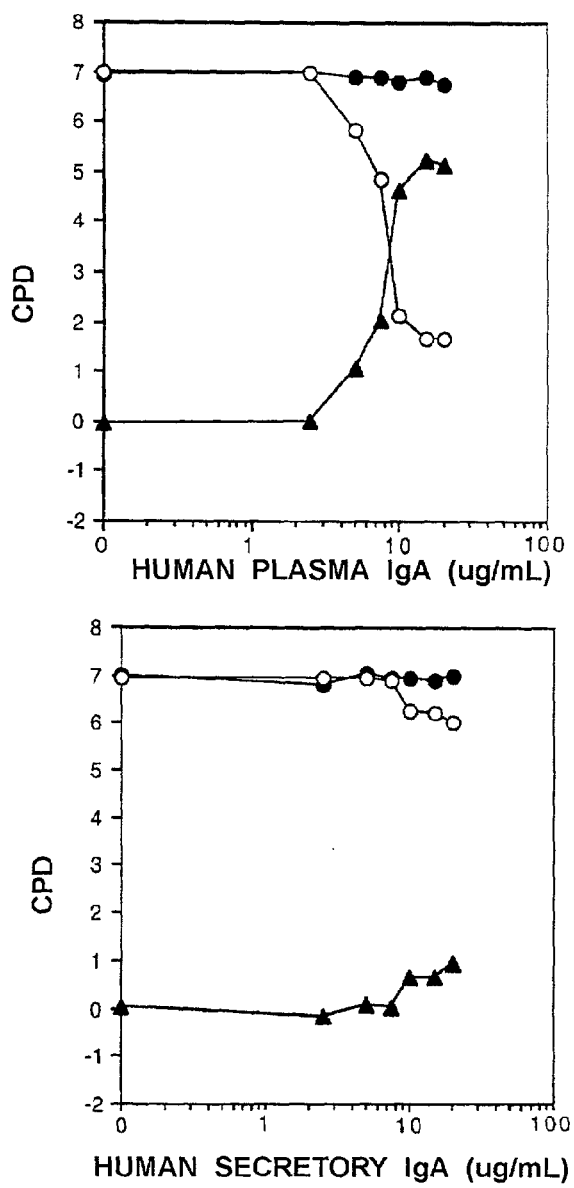

FIG. 132. Effect of Human IgA on ZR-75-1 Cell Growth in Serum-free Defined Medium $E_2$. (A) Plasma IgA Effects; (B) Secretory sIgA Effects.

Figure 133:
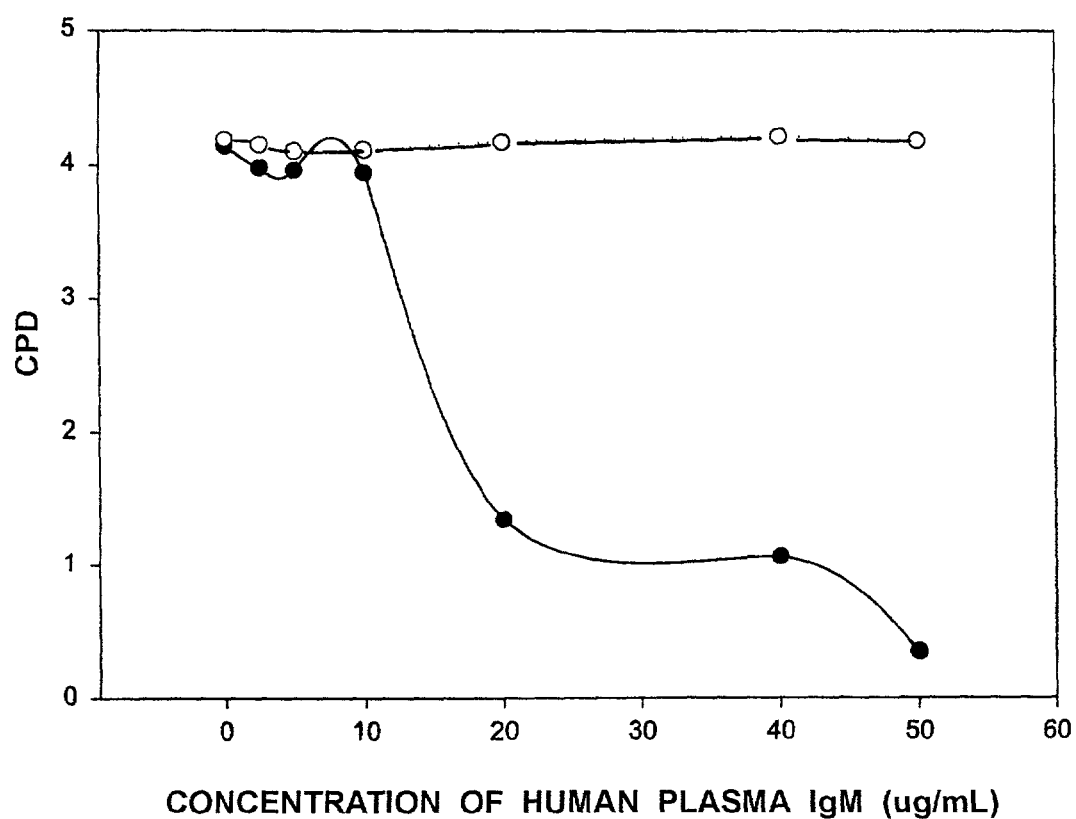

FIG. 133. Effect of Human IgM on ZR-75-1 Cell Growth in Serum-free Defined Medium±$E_2$.

Figure 134:
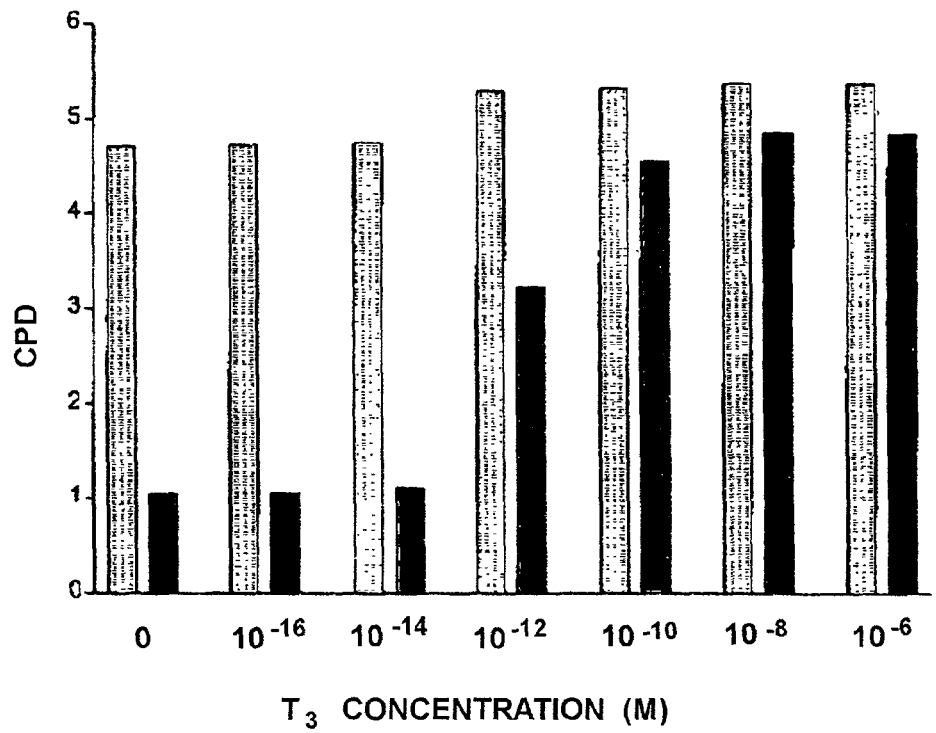

FIG. 134. Effect of Human IgM on HT-29 Cell Growth in Serum-free Defined Medium±$T_3$.

Figure 135:
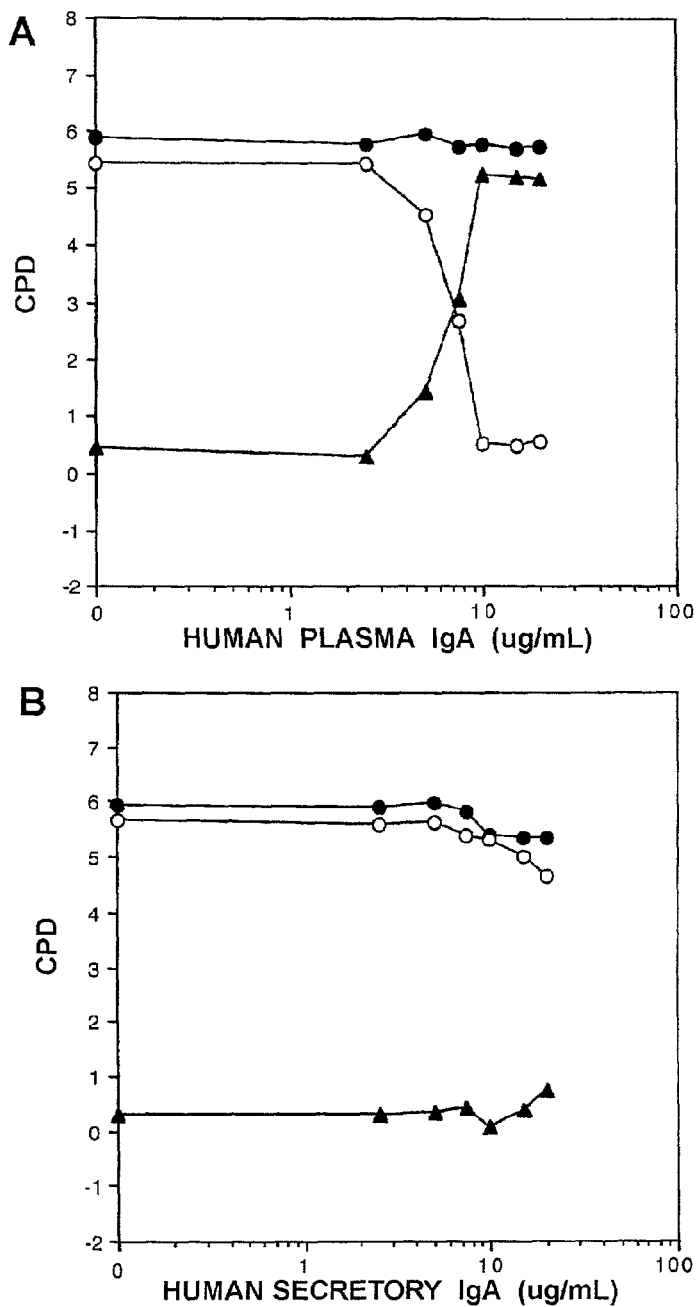

FIG. 135. Effect of Human IgA on LNCaP Cell Growth in Serum-free Defined Medium±$E_2$. (A) Plasma IgA Effects; (B) Secretory sIgA Effects.

Figure 136:
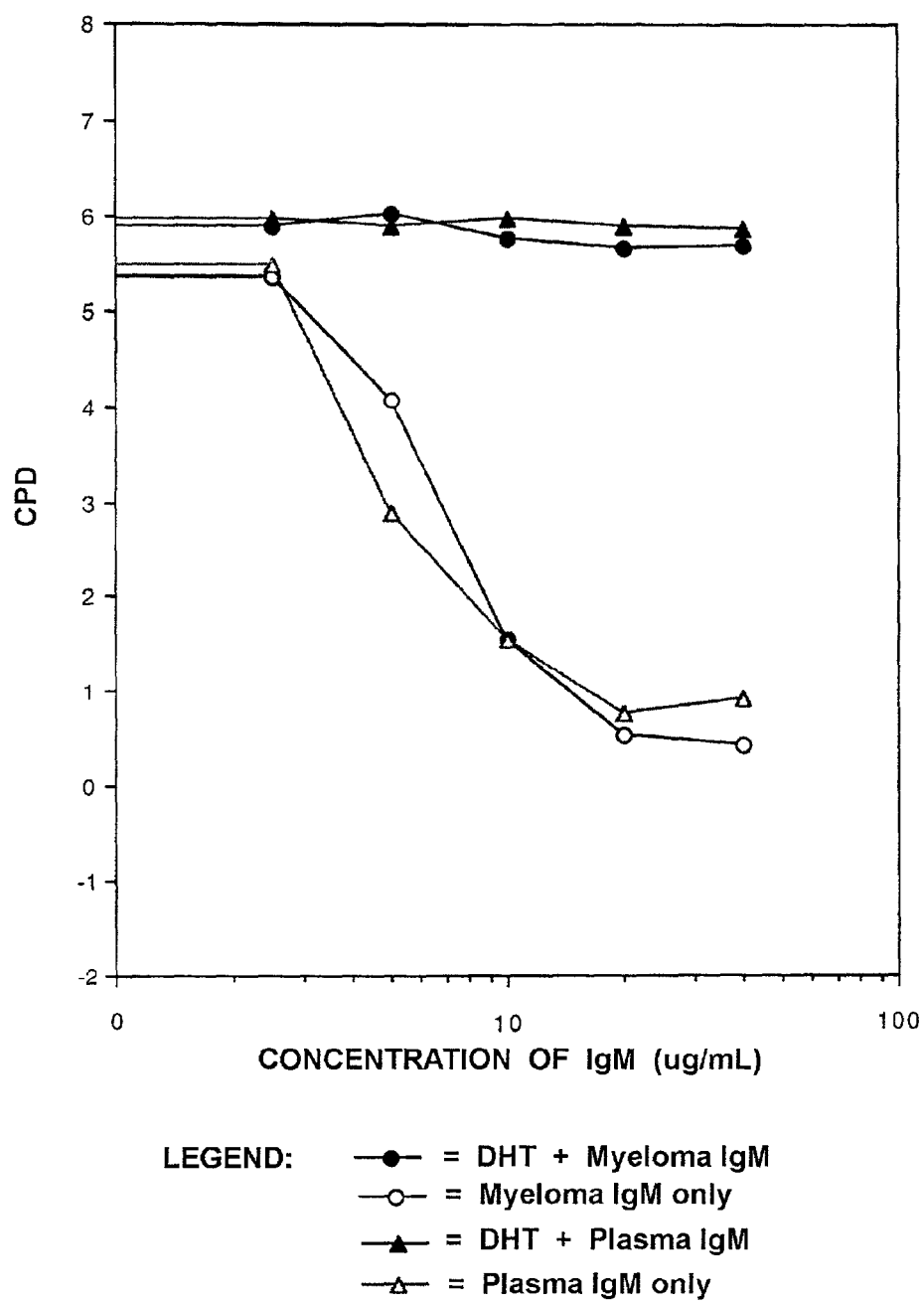

FIG. 136. Effects of Human Plasma versus Human Myeloma IgM on LNCaP Cell Growth in Serum-free Defined Medium±DHT.

FIG. 137. Summary of Estrogenic Effects with Various $ER^+$ Cell lines and Different Ig Sources.

Figure 138:
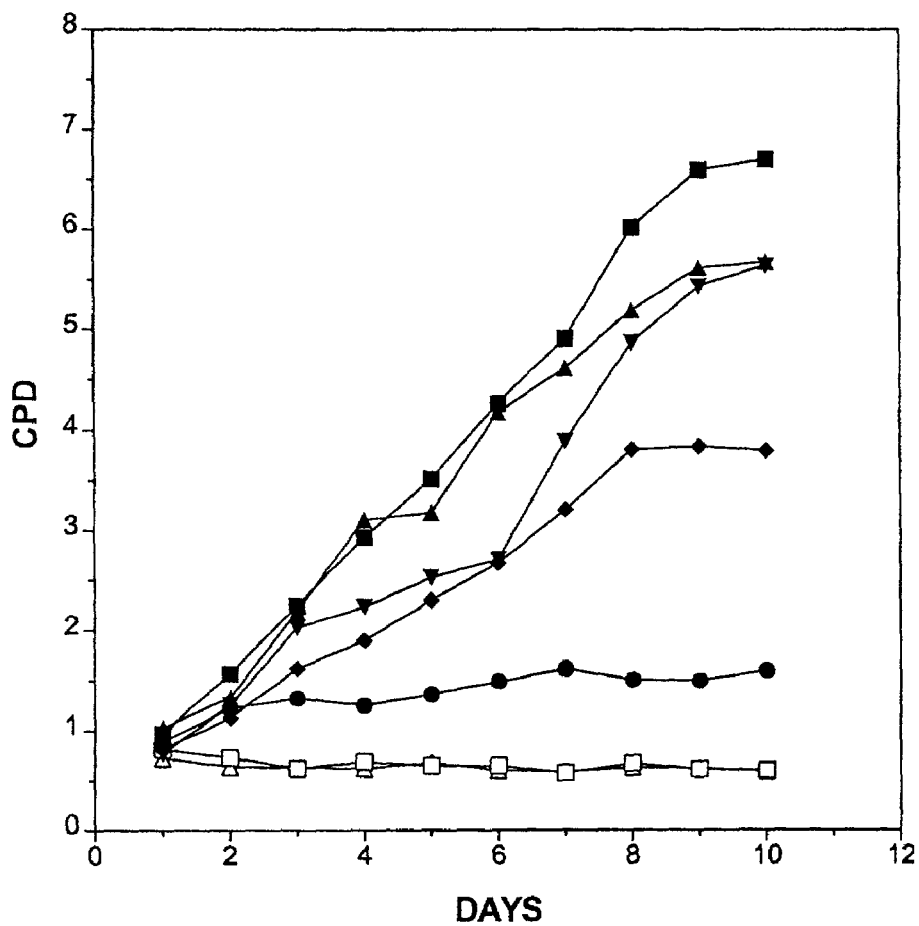

FIG. 138. Effect of Tamoxifen on T47D Cell Growth in Serum-free Defined Medium

Figure 139:
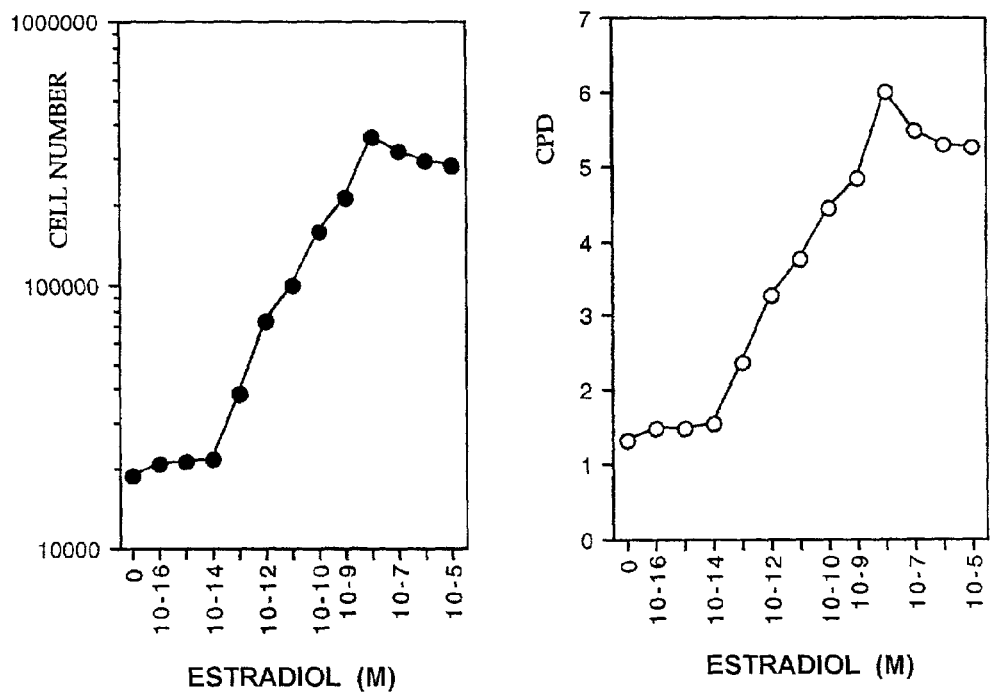

FIG. 139. Estrogen Reversal of Tamoxifen Inhibition of T47D cells in Serum-free Defined Medium FIG. 140. Effect of Rat Immunoglobulins on Estrogen Responsive Growth of MTW9/PL2 Cells In Serum-free Defined Medium.

Figure 141:
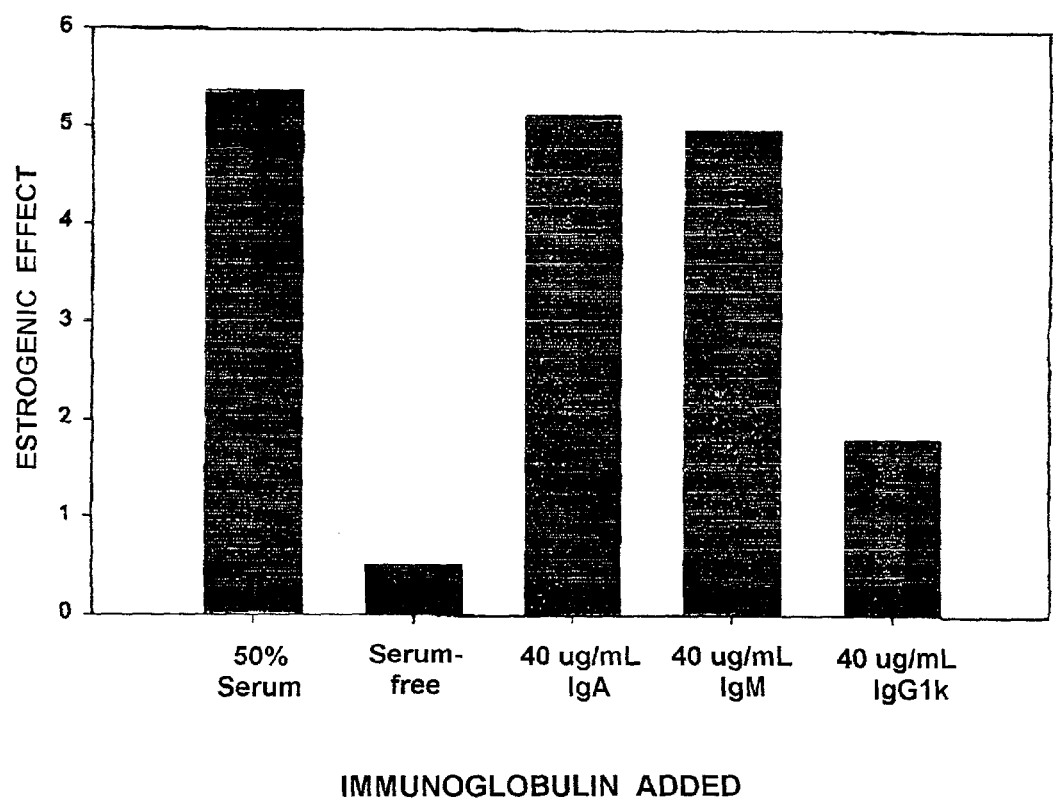

FIG. 141. Comparison of the Estrogenic Effects of Human Immungobulin with T47D Cells in Serum-free Defined Medium.

Figure 142:
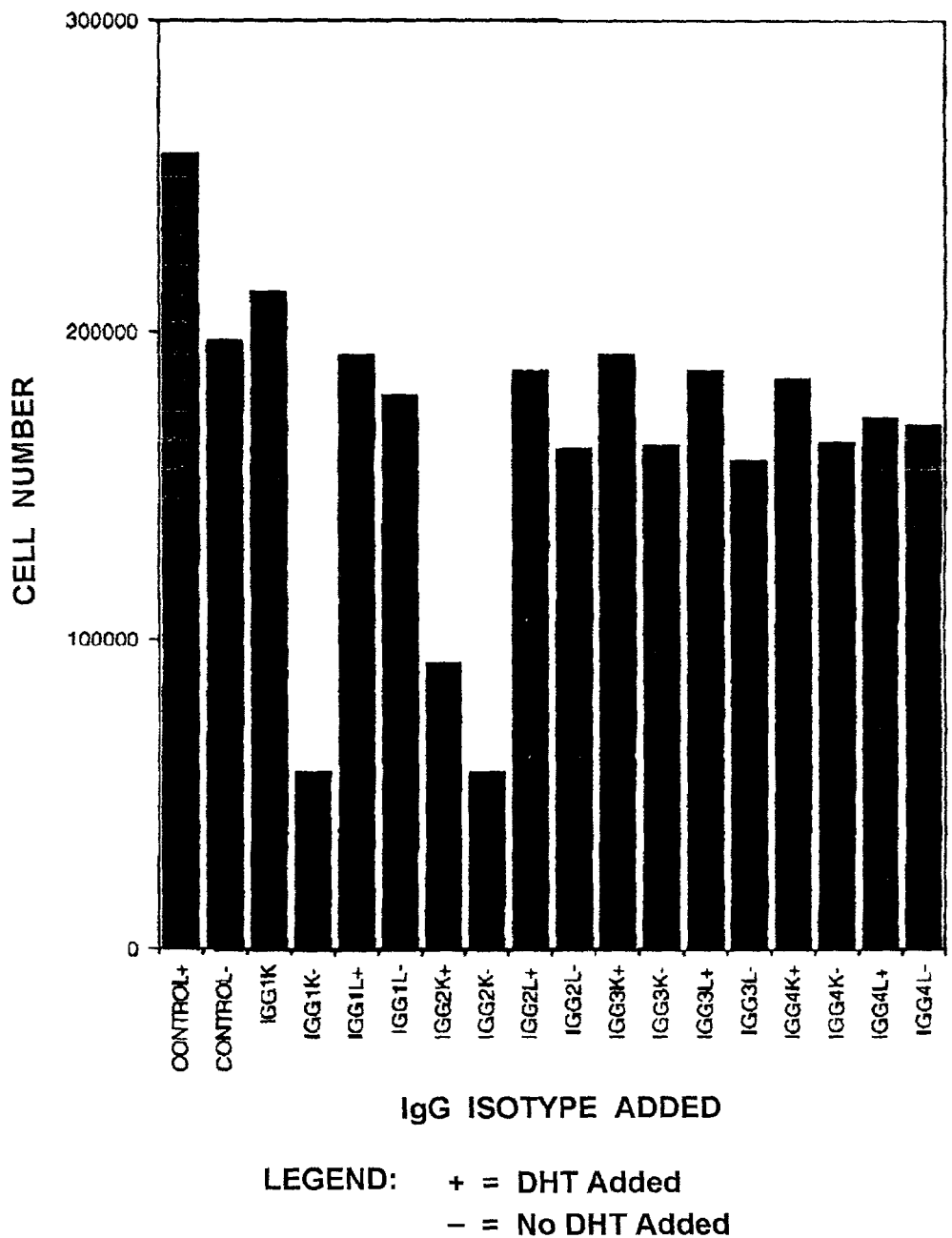

FIG. 142. Effect of Human IgG Isotypes on LNCaP Cell Growth in Serum-free Defined Medium±DHT.

Figure 143:
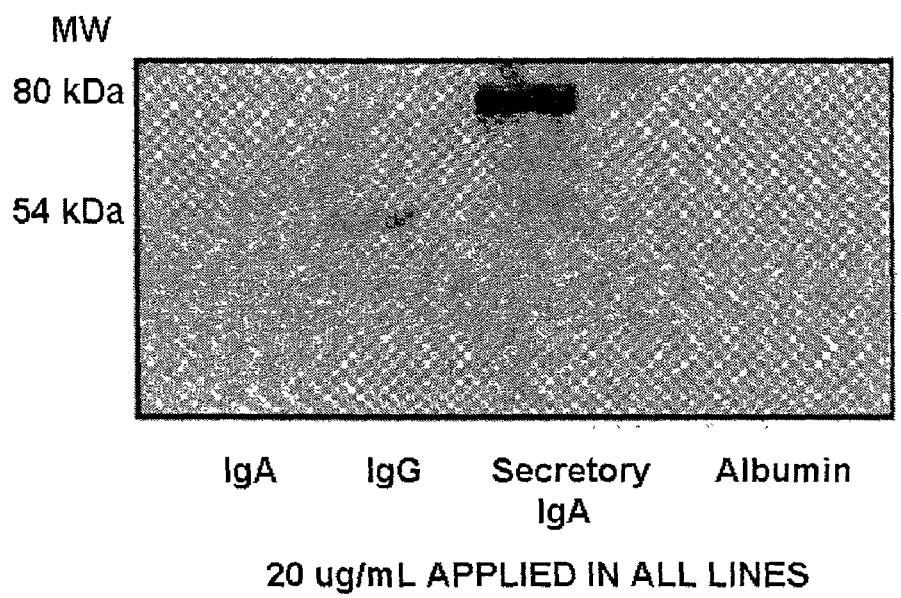

FIG. 143. Western Detection of the Secretory Component of Human Milk sIgA.

Figure 144:
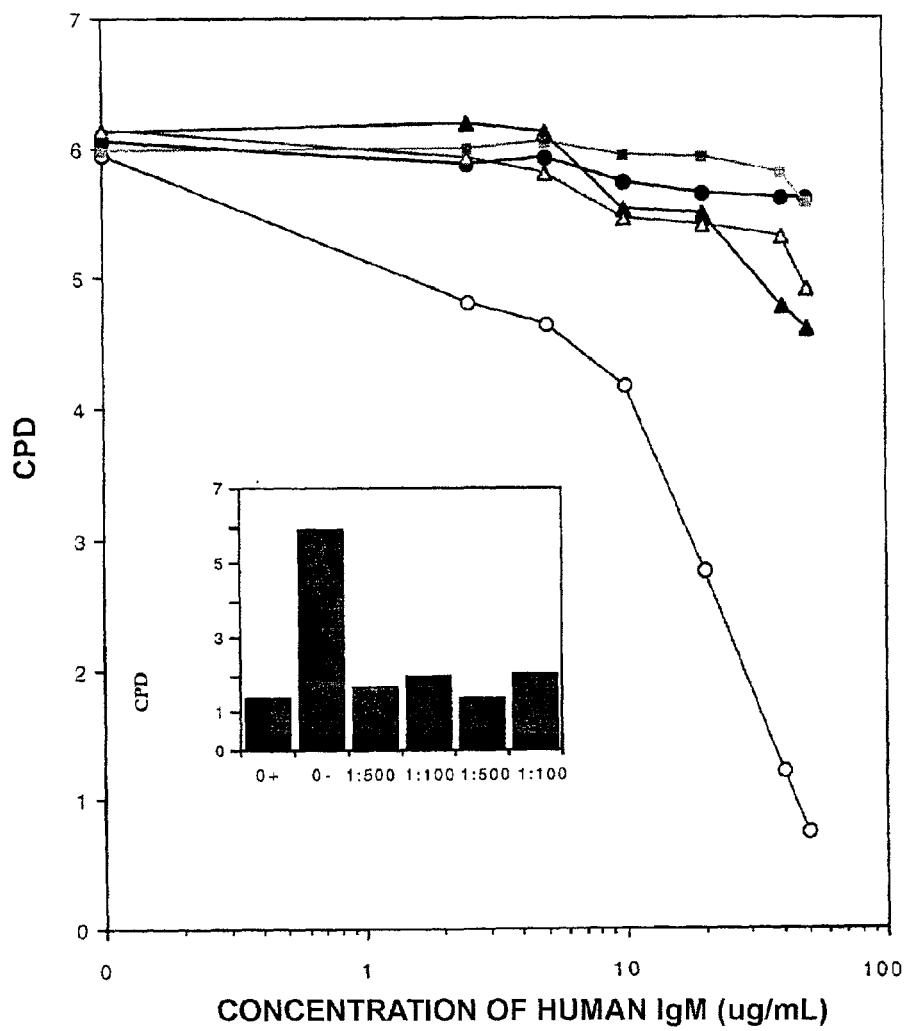

FIG. 144. Effect of Anti-Secretory Component on IgM Inhibition of T47D Cell Growth in Serum-free Defined Medium.

Figure 145:
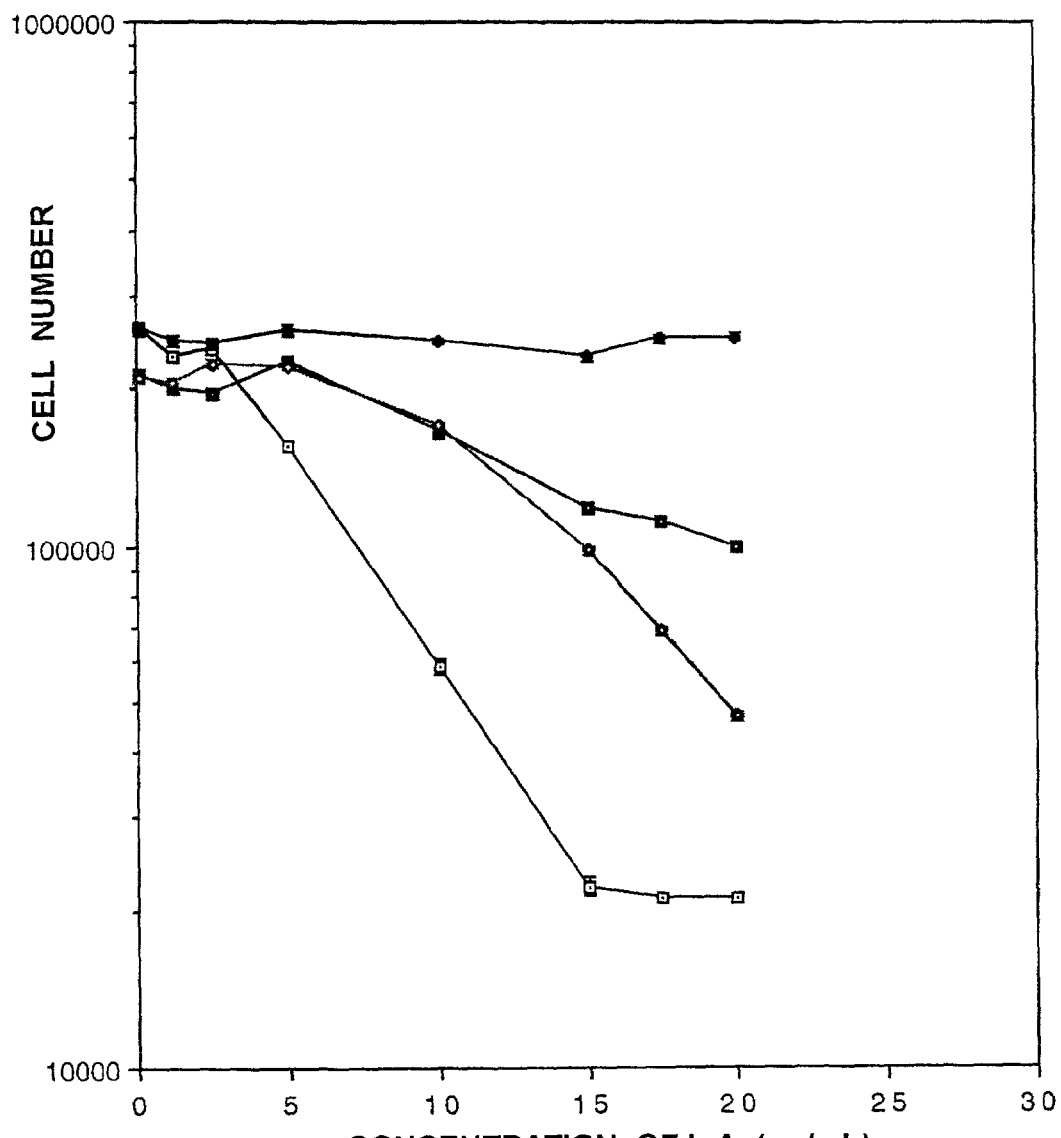

FIG. 145. Effect of Anti-Secretory Component on pIgA Inhibition of LNCaP Cell Growth in Serum-free Defined Medium.

Figure 146:
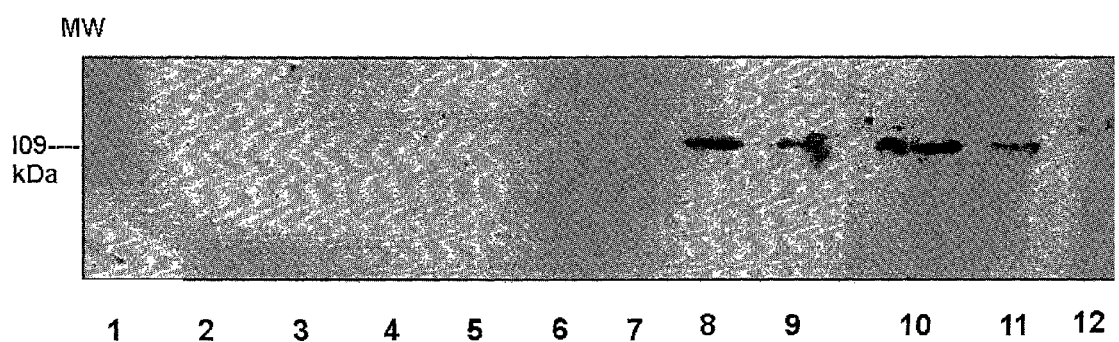

FIG. 146. Western Analysis with Anti-Secretory Component to Detect the Poly-Ig Receptor in $AR^+$ and $AR^-$ Prostate Cancer Cells plus Control Cell Lines.

Figure 147:
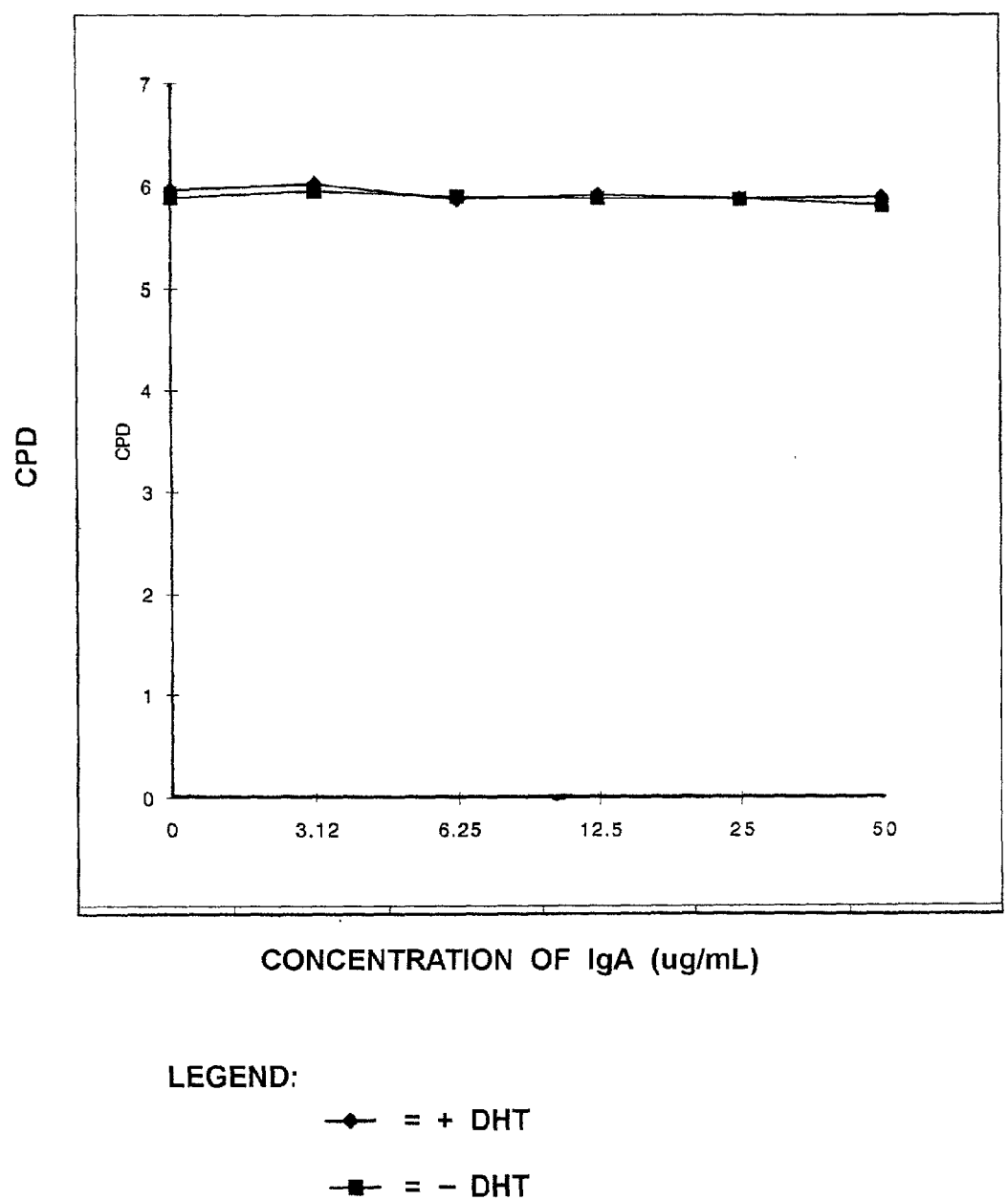

FIG. 147. Effect of Human pIgA on DU145 Cell Growth in Serum-free Defined Medium±DHT.

Figure 148:
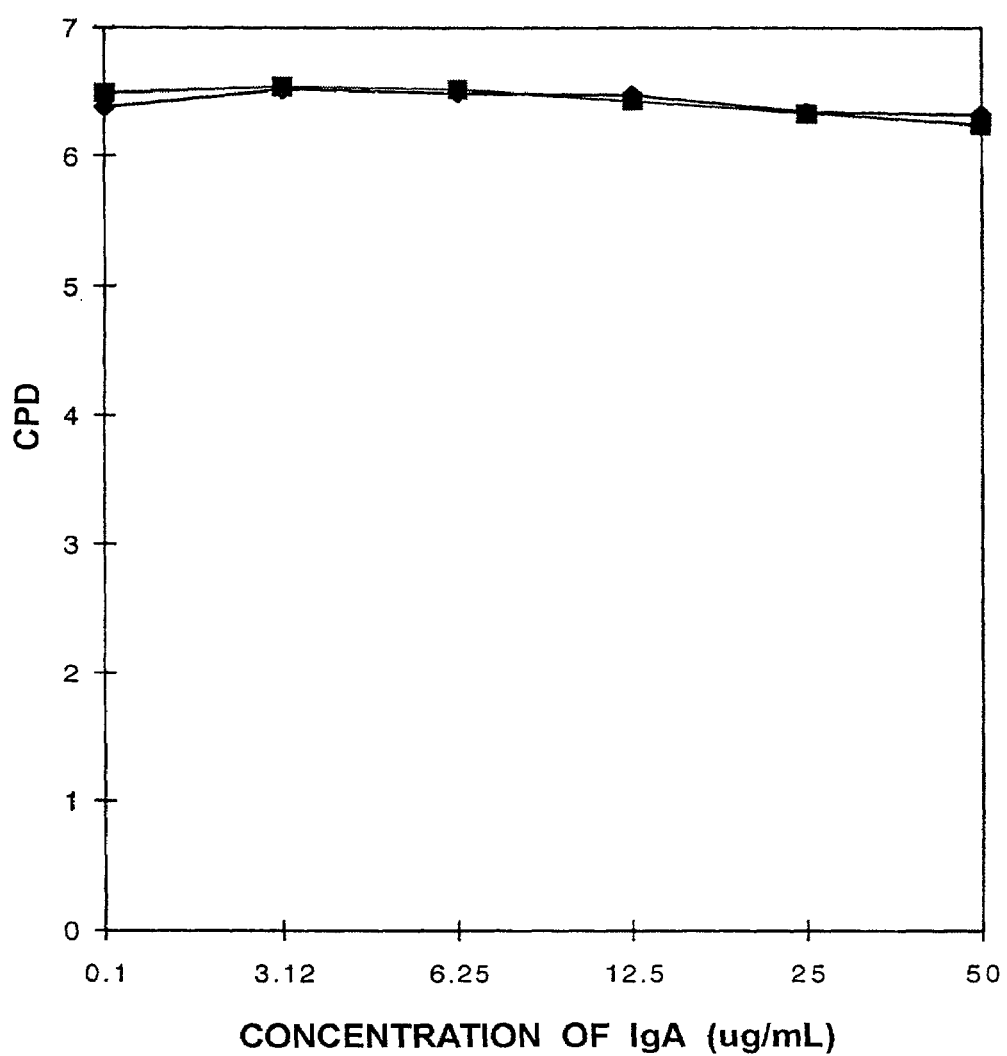

FIG. 148. Effect of Human pIgA on PC3 Cell Growth in Serum-free Defined Medium±DHT.

DETAILED DESCRIPTION OF PREFERRED EMBODIMENTS

To facilitate review of the detailed description of preferred embodiments, a Table of Contents is provided. The titles used for the various subsections and examples are not intended to be limiting and are only an aid to locating certain subject matter. In addition, each Example begins with a short summary of that Example, which is intended merely to facilitate review and is not limiting on the disclosure contained in the full Example, and ends with a Discussion of some conclusions that may be drawn from that Example.

Table of Contents

Subsection

I. Introduction ...
II. General Materials and Methods ...
III. Examples ...
Example 1. Identification of Steroid Hormone Receptors in MTW9/PL2 Cells ...
Example 2. Three Preparations of Steroid Hormone Depleted Serum and Examples of Support of Estrogen Responsive Cell Growth in Culture ...
  A. Charcoal-dextran Extraction at 34° C. ...
  B. Charcoal-dextran Extraction at 56° C. ...
  C. Amberlite™TM XADTM-4Resin Treatment ...
Example 3. Cancer Cell Line MTW9/PL2 Exhibits Estrogen Responsiveness in 34° C. Charcoal-dextran Extracted Serum
Example 4. Estrogen Responsive Growth of Additional Rodent and Human Cell Lines In 34° C. Charcoal-dextran Extracted Horse and Human Serum
Example 5. Thyroid Hormone Growth Effects in CDE-Horse Serum Prepared at 34° C. ...
Example 6. Effect of 56° C. Versus 34° C. CDE-horse Serum on MTW9/PL2Cell Growth
Example 7. Demonstration of Estrogenic Effects in XAD-4 Resin Treated Horse Serum. ...
Example 8. Testing of Substances for Estrogenic Activity. ...
Example 9. Testing of Substances for Inhibitor-like Activity...
Example 10. Serum-free Defined Culture Medium Formulations...
Example 11. Serum-free Defined Medium that Supports Hormone Sensitive and Autonomous Cancer Cell Growth...
Example 12: Differential Effects of Fe (III) on the Growth of Hormone Responsive and Autonomous Human Breast and Human Prostate Cancer Cells...
Example 13: Growth in Serum-free Defined Medium versus Growth in CDE-Serum ±E2...
Example 14: Action of DES on Human AR +LNCaP Prostate Cancer Cells...
Example 15: Preparation of Inhibitor Depleted Serum for Control Studies and Stability Properties of the Inhibitor...
Example 16: Effects of Conventional Purification Methods and Properties of the Estrogen Reversible Serum-borne Inhibitor...
Example 17: Calcium Stabilization and Correlation with 3H-DHT Binding and Immunoprecipitation by Antibodies Raised to Human SHBG...
Example 18: Cortisol Affinity and Phenyl Sepharose Isolation of the "SHBG-like" Estrogen Reversible Inhibitor from CDE-Horse Serum...
Example 19: Serum-free Assay Systems for Measuring Large Magnitude Steroid Hormone Mitogenic Responses with the Two-Step Purified Inhibitor...
Example 20: Chemical and Immunological Properties of the Partially Purified CA-PS-Pool II Inhibitors and Identification as IgA and IgM...
Example 21: Regulation of Steroid Hormone-responsive and Thyroid Hormone-responsive Cancer Cell Growth in Serum-free Defined Medium by Secretory and Plasma Forms of IgA and Plasma and Cell Culture Derived IgM...
  A. MTW9/PL2 Cells - ER+rat mammary tumor...
  B. GH1, GH3, and GH4C1 Cells - ER+rat pituitary tumor...
  C. H301 Cells - ER+Syrian hamster kidney tumor...
  D. MCF-7A and MCF-7K Cells - ER+human breast cancer...
  E. T47D Cells - ER+human breast cancer...
  F. ZR-75-1 Cells - ER+human breast cancer...
  G. HT-29 Cells Thyroid hormone responsive human colon cancer...
  H. LNCaP Cells - AR+human prostate cancer...
Example 22: Effect of Tamoxifen Antiestrogen in Serum-free Defined Medium...
Example 23: IgG1 and IgG2 as an Immunoglobulin Regulators of Estrogen and Androgen Responsive Cancer Cell Growth...
Example 24: Mediation of IgA/IgM Effects by the Poly-Ig Receptor...
Example 25: Mediation of IgG1κ Effects by a Fc-like Receptor...
Example 26. Immunoglobulin Inhibitors as Tools for Identifying the Receptors that Mediate the IgA/IgM/IgG Cell Growth Regulating Effects...
Example 27: Conceptual Model for Cascading Loss of Cell Growth Inhibition in Cancer Cells...
Example 28. IgA/IgM Based Test to Detect Lowered Levels of Steroid Hormone Reversible... Cell Growth Inhibitors in Plasma or Body Secretions...

Introduction

Extracellular negative regulation is a key control mechanism of cell proliferation in steroid hormone responsive cancer cells. Sex steroid hormones (both estrogens and androgens) act to reverse the effects of a serum-borne inhibitor(s) that normally blocks target cell proliferation (Moreno-Cuevas J E and Sirbasku D A (2000) In Vitro Cell Dev Biol 36, 410-427; Sirbasku D A and Moreno-Cuevas J E (2000) In Vitro Cell Dev Biol 36, 428-446; Moreno-Cuevas J E and Sirbasku D A (2000) In Vitro Cell Dev Biol 36, 447-464, incorporated herein by reference). As demonstrated in the Examples that follow, these results were obtained with nine different estrogen receptor alpha (ERα) (Kumar V et al. (1987) Cell 51, 941-951) containing cell lines representing four target tissues and three species (Sirbasku D A and Moreno-Cuevas J E (2000) In Vitro Cell Dev Biol 36, 428-446).

As mentioned in the Background of the Invention, the prior art fails to adequately address the issues of (i) whether there are one or more of the serum-derived inhibitors, (ii) what is/are the exact chemical composition of the inhibitor(s), and (iii) what conditions were required to yield the long term stable product(s) necessary for the commercial application of the testing methodology described. Methods and compositions are presented herein that are useful for testing and assessment of compounds and mixtures for estrogenic or androgenic activity as well as others possessing antiestrogenic and antiandrogenic activities. In the Examples that follow, cell culture methodology and compositions are described that permit testing at concentrations lower than was previously possible using existing methodologies. Moreover, the new in vitro model assay systems obviate the need to conduct animal testing to predict in vivo responses. Some practical applications for the model include protecting the human population from unrecognized exposure to hormone-like compounds that present health hazards as well as developing new antihormone compounds to counterbalance these hazards. The testing of these compounds and mixtures are preferably conducted in serum-containing medium to mimic the conditions encountered by a blood borne agent. Testing can additionally be done under completely serum-free defined medium conditions to determine direct actions on cells without serum or non-essential proteins present.

It has been discovered that the negative regulators of steroid hormone responsive cancer cell growth (estrogen reversible inhibitors) in serum are products from the secretory immune system, i.e., the immunoglobulins A (IgA), M (IgM) and IgG1. These "immunoglobulin inhibitors" act as steroid hormone and thyroid hormone reversible inhibitors of mucosal cell growth. There has been no previous identification of secretory immune system immunoglobulins as regulators of epithelial (mucosal) cell growth, and this discovery is unique in the cell growth regulation field. Application of certain of the compositions and methods is expected to relate to 80% of all human cancers because this high incidence rate arises from mucosal tissues. There is no previously reported evidence directly linking the secretory immunoglobulins with regulation of mucosal cell growth.

With regard to applicability to several mucosal tissues, it is recognized that breast and prostate cancers are very similar diseases. Aside from tissue specific epidemiological and social factors, breast and prostate cancers have remarkable parallels (Grody W W et al. (1994) *Am J Clin Pathol* 102, S1-S67). The secretory immune system acts as a sex steroid hormone reversible inhibitor with target tumor cells from both of these cancers. Both are adenocarcinomas arising from sexually differentiate tissues. Certainly both cancers are very common in North America and northern Europe compared to the rest of the world. Both are strongly influenced by steroid hormones. Both increase in incidence with age. Both are thought to have at least some genetic component. Finally, both have very similar patterns of development when examined histologically.

These facts also have implications with regard to colon, uterine and ovarian cancers. These cancers show familial clustering with breast cancer (Nelson C L et al. (1993) *Genet Epidemiol* 10, 235-244). The aggregation of colon, ovarian, endometrial and breast cancer in families has been described as a "cancer family" which now has the name Lynch Syndrome I and II (Lynch H T et al. (1978) *Cancer* 41, 1543-1549). Other studies have shown links between colorectal cancer and breast cancer (Rozen P et al. (1990) *Cancer Lett* 55, 189-194) and colorectal cancer and breast, uterine and ovarian cancer (Rozen P et al. (1986) *Cancer* 57, 1235-1239). It is clear that the incidence of these several mucosal origin cancers are linked and that this linkage has not been explained.

II. General Materials And Methods

In the Examples below, which describe representative, preferred embodiments of the present invention, the following general materials and methods are employed, except as otherwise noted in the Examples.

Cell Culture Medium. The water used to prepare culture media and all other solutions was purified first by reverse osmosis followed by passage through a U.S. Filter Corporation system with a charcoal filter and two mixed bed ion exchangers. The effluent was distilled using a Bellco glass apparatus with quartz heating elements. The distilled water was stored in airflow restricted glass containers. No metal fittings are allowed in contact with the final purified water. This necessary precaution minimizes recontamination with metal ions. Standard phenol red containing Ham's F12-Dulbecco's modified Eagle's medium (D-MEM/F-12), phenol red-free standard D-MEM/F-12 and a custom-prepared "low-Fe" D-MEM/F-12 medium were supplied by Gibco-BRL (Catalog No. 11330-032) or Bio♦Whittacker (Catalog No. 12-719, liquid). The "low-Fe" medium was standard phenol red containing D-MEM/F-12 from which the usual additions of ferric nitrate and ferrous sulfate had been omitted (Eby J E et al. (1992) *Anal Biochem* 203, 317-325; Eby J E et al. (1993) *J Cell Physiol* 156, 588-600). This medium was a special formulation purchased from Gibco-BRL as a powder and prepared in the highly purified water before 0.2 µm pore filter membrane sterilization. A number of other stock solutions are required for cell culture in either serum containing or serum-free defined medium. Descriptions of each preparation are provided along with specific instructions for their use. The solutions used were designed to minimize the exogenous content of steroid hormone and to minimize the Fe (III) content of the water. Steps are taken for the exclusion of all extraneous sources of steroid hormones and Fe (III). Exclusion of Fe (III) is highly preferred, and in most of the totally serum-free applications, it is considered essential. Wherever possible, disposable plastic ware or glassware is used to minimize potential contamination. It is important to note that excess solutions are preferably discarded after use with each individual cell line to avoid cross-contamination of cell types (Nelson-Rees W A and Fladermeyer R R (1977) *Science* (Wash D.C.) 195, 134-136).

General Cell Culture—Serum. Adult and fetal horse, adult pig, adult sheep and adult and fetal bovine serum were obtained from Gibco-BRL. A mixture of adult male and female rat serum was purchased from Pel-freez, Rodgers, A R. Human serum was purchased from Bio♦Whittacker. Human plasma was a pool of samples collected from pregnant females during routine visits to a local clinic. All serum was stored frozen at −20° C. until used. Repeated freeze-thaw of serum or plasma is avoided. Before charcoal extraction, the EDTA was removed by dialysis at 7° C. for 24 hours against forty volumes of 0.05 M Tris-HCl, pH 7.4, containing 50 mM $CaCl_2$. Dialysis was done with Spectropor 1 membranes (Spectrum Medical Industries, molecular weight cut-off 6,000 to 8,000). The clotted material was removed by centrifugation. This preparation is termed plasma-derived serum. The serum or plasma was not heat pre-treated, or heat inactivated prior to use in the methods described below.

General Cell Culture—Normal Saline. Sterile normal saline (0.15 M NaCl) was prepared in 10 mL aliquots and stored at room temperature. Unused portions are discarded at the end of each experiment. A large supply is sterilized by autoclaving and used to prepare the solutions described below.

General Cell Culture—Trypsin/EDTA for Subculture. Sterile preparations were purchased from Irvine Scientific (Catalog No. 9341) or Bio♦Whittacker (Trypsin-Versene EDTA Mixture) (Catalog No. 17-161F). This preparation contained 0.5 g/L trypsin and 0.2 g/L EDTA in Hank's balanced salts solutions with 10 mg/L phenol red. This preparation does not contain Ca or Mg salts nor does it have $NaHCO_3$. To trypsinize cells, 1.5 mL of this preparation was typically used. Aliquots (2 mL) were stored frozen until used and residual solution discarded at the end of each experiment or application to a cell line.

General Cell Culture—Soybean Trypsin Inhibitor (STI). STI was purchased from Sigma (Catalog No. T9128, Type II-2). An amount of 1.0 mg of this preparation will inactivate 1.0 mg of trypsin activity. The solution is prepared as 0.2% (w/v) in normal saline and sterilized using a 0.2 µm pore diameter filter membranes. Aliquots of 3.0 mL are stored at −20° C. until used. This preparation is used to stop the action of trypsin during harvest of stock cultures for growth assays. STI ensures that all trypsin used to harvest cells for growth assays is inactivated and therefore will not damage the protein additions to serum-free defined medium. Also, use of STI ensures that no extraneous steroid hormones are introduced after harvest of cells from the stock culture dishes.

General Cell Culture—Crude Pancreatic Trypsin for Cell Counting. This trypsin preparation was used to harvest the cells for determining cell numbers. The cells are typically grown in 35-mm diameter dishes. This enzyme was purchased from ICN Biochemicals as the 1-300 porcine pancreatic trypsin preparation (Catalog No. 103140). A stock solution is typically prepared by adding the contents of a preweighed bottle of 1X Dulbecco's modified PBS medium without calcium or magnesium to 800 mL of water. This solution dissolves very gradually with adjustment to pH 7.3 using NaOH. After the solution was clear, 20 g of crude trypsin was added and this mixture stirred for 30 minutes at room temperature. The somewhat cloudy solution was diluted to 1000 mL with water and this volume was stored frozen in bulk overnight at −20° C. to induce cold related precipitation that typically occurs when this preparation was frozen and thawed. After thawing at 37° C. in a water bath, the preparation was filtered through 0.45 µm pore membranes. This preparation was stored at −20° C. in useable portions.

General Cell Culture—EDTA for Cell Counting. The EDTA used is the disodium and dihydrate salt (Sigma Catalog No. E1644). A 0.29 M solution is prepared by adding 107.9 g to 800 mL of water with stirring and adjustment to pH 7.2 with NaOH. The volume is brought to one liter with water and the solution stored at room temperature. Because this solution is used only at the end of the experiments, it does not require sterilization.

General Cell Culture. In TABLE 1 the cell lines used in the described Examples are listed. The abbreviation "KCC" is the Karmanos Cancer Center, Cell Line Repository, Detroit, Mich. The abbreviation "ATCC" is the American Type Culture Collection, Cell Line Repository, Manassas, Va. Professor Armen Tashjian's address is Harvard University, Boston, Mass. Dr. William Rosner's address is Columbia University, New York. Dr. Sirbasku's address is The University of Texas, Houston, Tex. The superscript designations in TABLE 1 for each of the cell lines indicate references that verify that the estrogen and androgen responsive cell lines used in this study are bona fide hormone responsive based on their tumor forming characteristics in host animals. Those reports are clear demonstrations of the reliability of the models used in the present investigations to study sex hormone dependence in culture.

TABLE 1

Cell Lines Employed in the Examples. $ER^+$ indicates receptor containing/$E_2$ sensitive

| CELL LINES | SOURCES | REFERENCES/CELL LINE ORIGIN |
|---|---|---|
| MCF-7K[1] | KCC | Soule HD et al. (1973) J Natl Cancer Inst 51, 1409-1416<br>$ER^+$ human breast cancer |
| MCF-7A[1] | ATCC | Soule HD et al. (1973) J Natl Cancer Inst 51, 1409-1416<br>$ER^+$ human breast cancer |
| T47D[2] | ATCC | Keydar I et al. (1979) Eur J Cancer 15, 659-670<br>$ER^+$ human breast cancer |
| ZR-75-1[3] | ATCC | Engle LW et al. (1978) Cancer Res 38, 3352-3364.<br>$ER^+$ human breast cancer |
| $GH_4C_1$[4] | Dr. A. Tashjian | Tashjian AH Jr (1979) Methods Enzymol 58, 527-535<br>$ER^+$ rat pituitary tumor |
| $GH_3$[5] | ATCC | Tashjian AH Jr (1979) Methods Enzymol 58, 527-535.<br>$ER^+$ rat pituitary tumor |
| $GH_1$ | ATCC | Tashjian AH Jr (1979) Methods Enzymol 58, 527-535<br>$ER^+$ rat pituitary tumor |
| MTW9/PL2[6] | Dr. D. Sirhasku | Danielpour D et al. (1988) In Vitro Cell Dev Biol 24, 42-52<br>$ER^+$ rat mammary tumor |
| H301[7] | Dr. D. Sirbasku | Sirbasku DA and Kirkland WL (1976) Endocrinology 98, 1260-1272<br>$ER^+$ Syrian hamster kidney tumor |
| LNCaP[8] | ATCC | Horoszewicz JS et al. (1983) Cancer Res 43, 1809-1818<br>$AR^+$ human prostatic carcinoma |
| Fibroblasts | Dr. D. Sirbasku | Primary cultures of human foreskin and rat ear cartilage;<br>Eastment CT and Sirbasku DA (1980) In Vitro 16, 694-705 |
| ALVA-41 | Dr. W. Rosner | Nakhla AM and Rosner W (1994) Steroids 59, 586-589<br>$AR^+$ human prostate cancer; androgen growth insensitive |
| DU145 | ATCC | Stone KR et al. (1978) Int J Cancer 21, 274-281<br>$AR^-$ human prostate cancer; androgen growth insensitive |
| PC3 | ATCC | Kaighn ME et al. (1979) Invest Urol 17, 16-23<br>$AR^-$ human prostate cancer; androgen growth insensitive |
| HT-29 | ATCC | Chen TR et al. (1987) Cancer Genet Cytogenet 27, 125-134<br>Thyroid hormone responsive human colon cancer |

[1]The use of two strains of MCF-7 cells has been described (Sirbasku DA and Moreno-Cuevas (2000) In Vitro Cell Dev Biol 36, 428-446). Clonal variations of this line are known (Seibert K et al. (1983) Cancer Res 43, 2223-2239). Demonstration of estrogen responsive MCF-7 tumor formation in vivo (Huseby RA et al. (1984) Cancer Res 44, 2654-2659; Soule HD and McGrath CM (1980) Cancer Lett 10, 177-189; Welsch CW et al. (1981) Cancer Lett 14, 309-316).
[2]Estrogen responsive T47D tumors in vivo (Leung CKH and Shin RPC (1981) Cancer Res 41, 546-551).
[3]Estrogen responsive ZR-75-1 tumors in vivo (Osborne CK et al. (1985) Cancer Res 45, 584-589).
[4]Estrogen responsive $GH_4C_1$ tumors in vivo (Riss TL and Sirbasku DA (1989) In Vitro Cell Dev Biol 25, 136-142).
[5]Estrogen responsive $GH_3$ tumors in vivo (Sorrentino JM et al. (1976) J Natl Cancer Inst 56, 1149-1154).
[6]Estrogen responsive MTW9/PL2 tumors in vivo (Sirbasku DA (1978) Cancer Res 38, 1154-1165; Danielpour D and Sirbasku DA (1984) In Vitro 20, 975-980).
[7]Estrogen responsive H301 tumors in vivo (Sirbasku DA and Kirkland WL (1976) Endocrinology 98, 1260-1272; Liehr JG et al. (1986) J Steroid Biochem 24, 353-356).
[8]Androgen responsive LNCaP tumors in vivo (Sato N et al. (1997) Cancer Res 57, 1584-1589; Gleave M et al (1991) Cancer Res 51, 3753-3761; Horoszewicz JS et al. (1983) Cancer Res 43, 1809-1818; Pretlow TG et al. (1991) Cancer Res 51, 3814-3817; Passaniti A et al. (1992) Int J Cancer 51, 318-324).

General Cell Culture—Cell Passage Method. All stock cultures were grown in medium containing phenol red. Stocks of the cells were maintained at 37° C. in a humid atmosphere of 5% (v/v) $CO_2$ and 95% (v/v) air in 17 to 20 mL of standard D-MEM/F-12 with 2.2 g per liter sodium bicarbonate, 15 mM HEPES (pH 7.4), and serum. With all cell lines except the rat pituitary cells, the serum used for stock culture was 10% (v/v) fetal bovine serum (FBS). For the three rat pituitary tumor cell lines $GH_4C_1$, $GH_1$ and $GH_3$, the medium contained 12.5% (v/v) horse serum and 2.5% (v/v) FBS. To passage the cells, the medium was removed and the dishes washed with 10 mL of saline. Next, the cells were dissociated by incubation at room temperature or at 37° C. for 3 to 10 minutes with 1.5 mL of trypsin/EDTA. The action of the trypsin was stopped by addition of 8 niL of D-MEM/F-12 containing 10% (v/v) FBS or 8 mL of the horse serum/FBS combination. The cells were collected by centrifugation at 1000×g for 5 minutes and suspended in 10 mL of fresh serum containing medium. Aliquots were diluted into Isoton II (Coulter Diagnostics) and cell numbers determined with a Model ZBI or Z1 Coulter Particle Counter. The new dishes (100-mm diameter with 15 to 20 mL of fresh medium) were seeded with $2.0 \times 10^5$ to $1.0 \times 10^6$ cells on an alternating three-four day schedule or weekly as dictated by cell line growth rate. Cultures were used for growth assays between three and six days after passage. Acidic (yellow medium indicator color) cultures are not used for growth assays.

General Cell Culture—Media Types Used. The assays done in the presence of serum were initially in "low-Fe" D-MEM/F-12 containing phenol red (Moreno-Cuevas J E and Sirbasku D A (2000) *In Vitro Cell Dev Biol* 36, 410-427). The issue of the significance of the presence or absence of phenol red, a potential estrogen (Berthois Y et al. (1986) *Proc Natl Acad Sci* USA 83, 2496-2500), has been dealt with in considerable detail (Moreno-Cuevas J E and Sirbasku D A (2000) *In Vitro Cell Dev Biol* 36, 447-464). The Fe (III) content of this medium was $\leq 0.2$ µM (Eby J E et al. (1992) *Anal Biochem* 203, 317-325). Fe (III) levels of $\geq 1.0$ µM interfere with thyroid hormone and estrogen responsive rat pituitary tumor cell growth in culture (Eby J E et al. (1992) *Anal Biochem* 203, 317-325; Eby J E et al. (1993) *J Cell Physiol* 156, 588-600; Sato H et al. (1991) *In Vitro Cell Dev Biol* 27A, 599-602; Sato H et al. (1992) *Mol Cell Endocrinol* 83, 239-251). Although Fe (III) might prevent estrogen responsiveness from being identified in culture with MTW9/PL2 cells, as shown herein and reported (Sirbasku D A and Moreno-Cuevas J E (2000) *In Vitro Cell Dev Biol* 36, 428-446; Moreno-Cuevas J E and Sirbasku D A (2000) *In Vitro Cell Dev Biol* 36, 447464), this is not the case when serum is present. Standard Fe (III)/Fe (II) containing D-MEM/F-12 was as effective as the low-Fe medium. It is clear that the apotransferrin in the serum effectively reduced the free Fe (III) in the medium to less than cytotoxic levels. As stated above, apotransferrin binds Fe (III) with very high affinity at pH 7.4 in plasma. The total concentration of transferrin in serum is about 3 mg/mL. Usually, two-thirds of the total is apotransferrin. This amount is more than adequate to chelate Fe (III) in culture medium (Eby J E et al. (1992) *Anal Biochem* 203, 317-325). However, in assays in serum-free defined medium, as described below, a Fe (III) chelator (e.g. apotransferrin or DFX) is present in the serum-free defined medium at sufficient levels to neutralize the toxic iron.

General Cell Culture—Growth Assay Methods. Cell growth assays were initiated with stock cultures that were harvested by trypsin/EDTA treatment as described above with one exception. It was highly preferred to stop the action of trypsin with 3 mL of soybean trypsin inhibitor (0.5% w/v in saline) instead of medium containing serum. The use of trypsin inhibitor reduced the possibility of contamination of the subsequent assay media by serum-derived steroid hormones. The dissociated cells were collected by centrifugation as described above and washed three times with 10 mL volumes of serum-free standard D-MEM/F-12. After each wash, care was taken to aspirate all medium from the cell pellet and the walls of the centrifuge tubes. This minimized the carry-over of steroid hormones into the experimental test dishes. By taking steps to avoid carryover of serum-containing medium, steroid hormones are prevented from being retained by the cells in culture. It is highly preferred to wash the cells in this way before assaying to measure various steroid hormone effects in culture. It has been reported that steroid hormones are retained long term by breast cancer cells in culture (Strobl J S and Lippman M E (1979) *Cancer Res* 39, 3319-3327). The above-described wash procedure negates this problem. After the final wash, the cells were suspended in 10 mL of serum-free D-MEM/F-12 and cell numbers determined. When cells were to be assayed in medium without phenol red discussed elsewhere herein and reported (Moreno-Cuevas J E and Sirbasku D A (2000) *In Vitro Cell Dev Biol* 36, 447-464), the cells were washed and resuspended in phenol red free D-MEM/F-12 purchased from Gibco-BRL. The growth assays were initiated in 35-mm dishes containing a total of 2.0 mL of medium and the final concentration of all components except steroid hormones. The steroid hormone stocks were diluted to appropriate concentrations in serum-free D-MEM/F-12 and 20 µL aliquots added to each dish. For all growth assays, the medium was not changed after the initial inoculation. Because several of the cell lines described in TABLE 2 grow in serum containing medium and serum-free defined medium as mixtures of suspension and attached cells, removal or changing of the medium during the course of the assays causes substantial cell losses. For all cell growth assays, the initial seed densities ranged from 5,000 to 12,000 cells per 35-mm diameter dish.

General Cell Culture—Steroid Hormone Preparations. A number of hormone preparations are used to supplement the cell cultures. Unlabeled steroid hormones were obtained from Sigma or Steraloids. Stock solutions were prepared in sterile glass containers. The powder (non-sterile) steroid is added to the bottle along with 200 ml of 70% aqueous ethanol (ready as sterile). The steroids dissolve within an hour at room temperature, or when required were dissolved by gentle heating on a hot plate (hand temperature test—no boiling—no open flames). The stock solutions were stored at 4° C. and renewed at six-month intervals. It is not necessary or desirable to filter sterilize these solutions because of steroid hormone loss on filter membranes. Stocks of 1.0 mM steroid hormones were prepared. To prepare diluted stocks for direct use in culture, 10 mL of 1.0 mM steroid hormone is diluted into 10 mL of D-MEM/F-12. This gives a stock of 1.0 µM. It is used in the assay dishes or diluted further in D-MEM/F-12 as needed. The diluted steroids are discarded after each use because they bind to the plastic with storage. The formula weight (FW) of each of the common natural and synthetic hormones used is listed below in TABLE 2 along the abbreviation used for each and the amounts required to prepare 200 mL of stock.

TABLE 2

Preparation of Steroid Hormone Stocks for Cell Culture and Hormone Binding Assays

| STEROID HORMONES | FORMULA WEIGHT (FW) | MILLIGRAMS/200 mL |
|---|---|---|
| 17β-estradiol ($E_2$) | 272.4 | 54.4 |
| Estrone ($E_1$) | 270.4 | 54.1 |
| Estriol ($E_3$) | 288.4 | 57.7 |
| Diethyistilbestrol (DES) | 268.4 | 53.7 |
| Tamoxifen Citrate (TAM) | 563.6 | 112.7 |
| Progesterone (PROG) | 314.5 | 62.9 |
| Hydrocortisone/Cortisol (C) | 362.5 | 72.5 |
| Dexamethasone (DEX) | 392.5 | 78.5 |
| Testosterone (T) | 288.4 | 57.7 |
| Dihydrotestosterone (DHT) | 290.4 | 58.1 |

General Cell Culture—Harvest and Counting Cells. At the termination of the experiments, each plate received 0.4 mL of crude pancreatic trypsin dissolved in phosphate buffered saline was added along with 0.3 mL of 0.29 M EDTA. After 4 to 40 minutes incubation at room temperature or at 37° C., the action of the trypsin was stopped by addition of 0.6 mL of horse serum. The cell clumps were dissociated further by one passage through a 20½ or 23-gauge needle and syringe. This suspension was then diluted to 10 mL with Isoton II and cell numbers determined with a Coulter Counter. The results are presented as the average of triplicate dishes for each test medium. To determine day zero cell numbers, at least triplicate 1.0 mL aliquots of the inoculum were collected for counting during the seeding of the test dishes. Coulter Counter standardization and monitoring were performed by the manufacturer.

General Cell Culture—Quantification of Growth. The cell number results are converted to cell population doublings (CPD) by the following calculation:

$$CPD = \frac{\text{Log}_{10} \text{ Average Cell Number on Collection Day}/ \text{Log}_{10} \text{ Average Cell Number on Day Zero}}{\text{Log}_{10} 2}$$

For the purposes of this Disclosure, the mitogenic response to sex steroid hormones is designated the "steroidogenic effect." For example, the "estrogenic effect" is calculated as the difference between CPD measured in the presence of an estrogen minus CPD in the absence of the steroid. These values equal cell number increases of $2^{CPD}$. The term "androgenic effect" has the same meaning except that it describes growth caused by androgens such as DHT and T. CPD is used herein as a measure of growth because it is a direct calculation of the number of times a cell population undergoes cell division. Furthermore, CPD use permits a direct measure of $ED_{50}$ and $ED_{100}$ Concentrations in different and in replicate assays. The significance of differences between test dishes and controls was evaluated by the student's t test. Values of $p<0.05$ were accepted as significant. Standard deviations ($\pm SD$) are included when appropriate.

CELL LINE AVAILABILITY. The rat breast cancer cell line designated as MTW9/PL2 and the hamster kidney tumor cell line designated as H301 are available from David A. Sirbasku, PhD., Signe Biopharma, Inc., 1717 W Walnut Hill Ln, Suite 104, Irving, Tex. 75038. It should be understood that the availability of a cell line does not constitute a license to practice the subject invention in derogation of patent rights granted by governmental action.

Cell Lines—Budapest Treaty Compliance. Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of each deposit, and in any case, for a period of at least thirty (30) years after the date of deposit or for the enforceable life of any patent which may issue disclosing the cultures. The depositor acknowledges the duty to replace the deposits should the depositor be unable to furnish a sample when requested, due to the condition of the deposit. All restrictions on the availability to the public of the subject culture deposits will be irrevocably removed upon the granting of a patent disclosing it.

Growth of Cells for Steroid Hormone Receptor Assays. Whole cells were assayed for the presence of steroid hormone receptors by a modification of described methods (Baxter J D et al. (1975) *Methods Enzymol* 36, 240-248). The cells (9 to $10 \times 10^6$) were seeded in 850 $cm^2$ roller bottles (Corning) containing 200 mL of standard phenol red containing D-MEM/F-12 supplemented with 2.0% (v/v) charcoal-dextran extracted (CDE) horse serum and grown at 37° C. for five to seven days. The cells were collected from the plastic surface and the medium and concentrated by centrifugation at 1000×g for 15 minutes. The cells were washed with saline, resuspended in 20 mL of saline and treated with 2.0 mL of trypsin/EDTA at room temperature for one minute. The trypsin action was stopped with 6.0 mL of 0.5% (w/v) soybean trypsin inhibitor in saline. The dispersed cells were collected and suspended in phenol red-free D-MEM/F-12 to a density of 0.5 to $1.0 \times 10^6$ per mL. The rationale for measuring steroid hormone binding with whole cells rests with the intent to replicate cell culture conditions. To derive complete information, the use of whole cells avoids the possible loss of a new receptor that might not withstand the cell extraction process or otherwise not be recovered.

Whole Cell Steroid Binding Assays. Total estrogen binding was measured with $^3H-E_2$ (2,4,6,7-$^3H$-17β-estradiol) at specific activity 96 Ci per mmole (Amersham). Non-specific binding was assessed with $^3H-E_2$ plus a 100-fold molar excess of unlabeled DES. Specific binding was total binding minus non-specific binding. To assay specific progesterone binding, the medium contained either $^3H$-progesterone [1,2-$^3H$ (n) progesterone] at specific activity 92 Ci per mmole (ICN) or $^3H$-progesterone plus a 100-fold molar excess of the unlabeled synthetic progestin R5020 (DuPont NEN). Specific androgen binding was measured using [1,2 $^3H$ (N)] DHT at specific activity 45 Ci per mmole (DuPont NEN) and the combination of $^3H$-DHT plus a 100-fold excess of unlabeled DHT. Glucocorticoid specific binding was assayed with [1,2 $^3H$ (N)] hydrocortisone at specific activity 53 Ci per mmole (DuPont NEN) and $^3H$-hydrocortisone plus a 100-fold excess of unlabeled DEX. The steroid hormone binding incubations were done in phenol red free D-MEM/F-12 in a total volume of 1160 μL containing 1000 μL of cells, 100 μL of labeled steroid and 60 μL of unlabeled steroid hormone or medium. The incubations were done in glass tubes for two hours at 37° C. with gentle agitation in an orbital shaker water bath followed by cooling to 0° C. for 15 to 30 minutes. The cells were collected by centrifugation at 7° C. as described above and washed three times with 2 mL portions of ice-cold phenol red-free D-MEM/F-12. The final collected cells were dissolved in 0.5 mL of 0.5N sodium hydroxide and the radioactivity quantified by liquid scintillation counting. All samples were duplicates or triplicates. To obtain dissociation ($K_d$) and association ($K_a$) constants, the data were analyzed by the method of Scatchard (Scatchard G (1949) *Ann N.Y. Acad Sci* 51, 660-672).

Steroid Hormone Receptor Analysis by Western Immunoblotting. The following antibodies were obtained from Affinity Bioreagents: a rabbit polyclonal antibody against a bacterial fusion protein containing the N-terminal domain of the human androgen receptor and a mouse monoclonal antibody against the amino acid sequence 533 through 547 of the DNA binding domain of the progesterone receptor. An affinity-purified rabbit polyclonal antibody corresponding to the amino acid sequence 580 through 599 of the mouse estrogen receptor was obtained from Santa Cruz Biotechnology. To analyze steroid hormone receptor content, both cytosolic and nuclear extracts were prepared. To obtain the cytosol, $20 \times 10^6$ cells were washed with serum-free D-MEM/F-12 and resuspended in 5 mL of 0.01 M Tris-HCl, pH 7.4, containing 0.15 M NaCl and 1 mM EDTA (Tris/EDTA). After cooling to ice-bath temperature, the cells were disrupted by three treatments for ten seconds with a Tekmar Polytron homogenizer. The homogenates were centrifuged at 800×g for 10 minutes followed by centrifugation at 150,000×g for one hour to obtain the cytosolic supernatants. To prepare nuclear extracts, the pellets from the 800×g centrifugation were homogenized again three times with 1.5 mL Tris/EDTA as described above. The centrifugation supernatants from the three homogenizations were combined to give the nuclear extract from each cell line. Protein concentrations were determined using the BCA kit from Pierce Chemical® kit with bovine serum albumin as standard. When required, the samples were concentrated by precipitation with 20% (w/v) trichloroacetic acid. The precipitates were washed once with 500 μL of 70% (v/v) ethanol and twice with 500 μL of water. They were dissolved in 200 μL of 0.01 M Tris-HCl, pH 7.4, containing 1% (w/v) sodium dodecyl sulfate (SDS) by warming to 65° C. SDS-PAGE (Laemmli U K (1970) *Nature* (Lond) 227, 680-685) was done using 8 to 15% (w/v) acrylamide gradient gels with 3% (w/v) acrylamide stacking gels. Each sample was diluted with four volumes of buffer containing 0.3125 M Tris-HCl, pH 6.8, 10% (w/v) SDS, 50% (v/v) glycerol, 25% (v/v) mercaptoethanol and 0.0025% (w/v) bromophenol blue. After heating to 95° C. for five minutes, the samples were applied to the gels and electrophoresis carried out at 7° C. The separated proteins were transferred to nitrocellulose membranes using a Milliblot Graphite Electroblotter I with a transfer buffer containing 1.0 mM (3-[cyclohexylamino]-1-propanesulfonic acid), pH 11, with 10% (v/v) methanol. Transfer was done for 45 minutes at 390 milliamps at room temperature. The receptors were detected by chemiluminescence using a kit from Tropix®. The protocol used was that recommended by the manufacturer. For the detection of androgen receptors, the membranes were incubated at room temperature with a 1:100 dilution of the primary antiserum for one hour and a 1:10000 dilution of second antibody for one hour. To detect estrogen receptors, the primary antiserum was used at a 1:5000 dilution with incubation at room temperature for one hour followed by one hour with a 1:10000 dilution of second antibody. For estrogen and androgen receptors, the second antibody was an affinity purified anti-rabbit immunoglobulin conjugated to alkaline phosphatase. To detect progesterone receptors, the incubations were done with 5 μg/mL primary antibody for 24 hours at 7° C., followed by incubation with a 1:1000 dilution of second antibody for eight hours at room temperature. The second antibody was an affinity purified anti-mouse immunoglobulin conjugated to alkaline phosphatase.

Western Immunoblotting with other Primary Antibodies. The SDS-PAGE and Western Immunoblotting method described above was used throughout the Examples with the only significant modifications being changes in primary antibodies, and if required, changes in the secondary antibody. The changes are noted when introduced.

Labeled Steroid Hormone Binding to Whole Serum and the Purified Inhibitor Including Scatchard Analysis. The binding affinities of tritium labeled steroid hormones (purchased from DuPont NEN) to serum and the purified inhibitor were analyzed by the ion exchange filter method (Mickelson K E and Petra P H (1974) *FEBS Lett* 44, 34-38). Total DHT binding was measured with [1,2-$^3$H(N)] DHT at specific activity 45 Ci/mmole. Nonspecific binding was assessed with $^3$H-DHT plus a 100-fold molar excess of unlabeled DHT. Specific binding was total binding minus nonspecific binding. For $E_2$ specific binding, the incubations contained either $^3$H-$E_2$ [2,4,6,7-$^3$H-17β-estradiol] at specific activity 96 Ci/mmole or $^3$H-$E_2$ plus a 100-fold molar excess of DES. Glucocorticoid specific binding was assayed with [1,2-$^3$H (N)] hydrocortisone at specific activity 53 Ci/mmole and $^3$H-hydrocortisone plus a 100-fold molar excess of unlabeled DEX. Progesterone specific binding was assayed with $^3$H-progesterone [1,2-$^3$H (n) progesterone] alone at specific activity 92 Ci/mmole or $^3$H-progesterone plus a 100-fold molar excess of unlabeled synthetic progestin R5020. The use of 100-fold unlabeled steroids to determine nonspecific binding has been discussed (Chamness G C and McGuire W L (1975) *Steroids* 26, 538-542). Each assay contained 0.01 M Tris-HCl, pH 7.4, with 10 mM $CaCl_2$. The binding conditions were optimized for time and temperature. The incubations were done in glass tubes at 34° C. in a total volume of 660 μL that included 50 μg/mL of the phenyl Sepharose pools and labeled and unlabeled steroid competitor. After two hours, the incubations were cooled to ice bath temperature and 50 to 200 μL aliquots applied to each DEAE-cellulose (DE-81) ion exchange filter (2.3-cm, Fisher) positioned in a Millipore Vacuum Filter Manifold®. Thereafter, the filters were washed with ten one mL portions of ice-cold Tris/$CaCl_2$ buffer. With control incubations minus protein,<3% of the label was retained. Radioactivity was quantified by liquid scintillation methods (Moreno-Cuevas J E and Sirbasku D A (2000) *In Vitro Cell Dev Biol* 36, 410427). To obtain $K_d$ (dissociation constant) and $K_a$ (association constant) values by Scatchard analysis (Scatchard G (1949) *Ann N.Y. Acad Sci* 51, 660-672), the incubations began with 50 nM $^3$H-labeled steroid hormone and included five or six serial two-fold dilutions done both minus and plus 100-fold excesses of unlabeled steroid for each labeled hormone concentration. Data points were the averages of triplicate incubations. $K_d/K_a$ were obtained from plots of (bound/free) versus (bound) hormone. Best-fit slopes were estimated with either Apple MAC computer software or with the PC based Graph Pad program.

Protein Assay and Quantification Methods. For cell growth assays, the protein sample volumes added to the culture medium were≦20%. As required, chromatography samples were concentrated using Amicon Ultrafiltration with YM-10 (molecular weight cut-off 10,000) low protein binding membranes and nitrogen gas pressure (Sirbasku D A et al. (1991) *Biochemistry* 30, 295-304). Before assay, all fractions were dialyzed against 0.05 M Tris-HCl, pH 7.4, with 0.15 M NaCl using Spectropor 1 membranes (molecular weight cutoff 6,000 to 8,000). They were sterilized with 0.2 μm membrane filtration units. The protein concentrations of serum, the ammonium sulfate precipitation and all of the conventional chromatography fractions were estimated as one $A_{280nM}$ equal to one mg/mL. For the cortisol affinity isolated proteins, concentrations were estimated either by the Pierce BCA® method according to the instructions supplied or the dye binding method of Bradford (Bradford M M (1976) *Anal Biochem* 72, 248-254). Trichloroacetic acid (TCA) precipitation was used with BCA to eliminate the interfering cortisol and DHT. With TCA, deoxycholate was used to co-precipitate the protein and ethanol/water washes to eliminate the steroid. Human IgG was used as standard for the colorimetric protein determinations. The protein concentration of several lots of horse serum averaged of 30±5 mg/ml. Ammonium sulfate precipitation was carried out as described (Sirbasku D A et al. (1991) *Biochemistry* 30, 295-304). Before further use, the protein was dissolved in 0.05 M Tris-HCl, pH 7.5, containing either 10 mM $CaCl_2$ or 0.15 M NaCl and dialyzed with Spectropor membranes against several four-liter volumes of the same buffer or a buffer appropriate to the next chromatography step.

III. EXAMPLES

Example 1

Identification of Steroid Hormone Receptors in MTW9/PL2 Cells

In the course of searching for what regulates the growth of estrogen responsive breast cancer and of androgen responsive prostate cancer, an in vitro cell culture system was developed that would serve as an accurate model for predicting in vivo physiological effects. An estrogen responsive rat mammary tumor cell line, the MTW9/PL2 cell line had already been developed (Sirbaska D A (1978) *Cancer Res* 38, 1154-1165). The MTW9/PL2 population is the first highly steroid hormone-responsive rat mammary tumor cell line to be established in culture from a carcinogen-induced tumor. These cells have been shown previously to form estrogen responsive tumors in W/Fu rats (Sirbasku D A (1978) *Cancer Res* 38, 1154-1165; Danielpour D and Sirbasku D A (1984) *In Vitro* 20, 975-980; Riss T L et al. (1986) *J Tissue Culture Methods* 10, 133-150). Nonetheless, they were not estrogen responsive in culture (Sirbasku D A (1978) *Proc Natl Acad Sci USA* 75, 3786-3790). It was thought possible that the cells had lost the estrogen receptors (e.g. dedifferentiation). This Example presents evidence confirming that the cells are estrogen receptor positive and are suitable for use in in vitro and in vivo studies.

Figure 1:
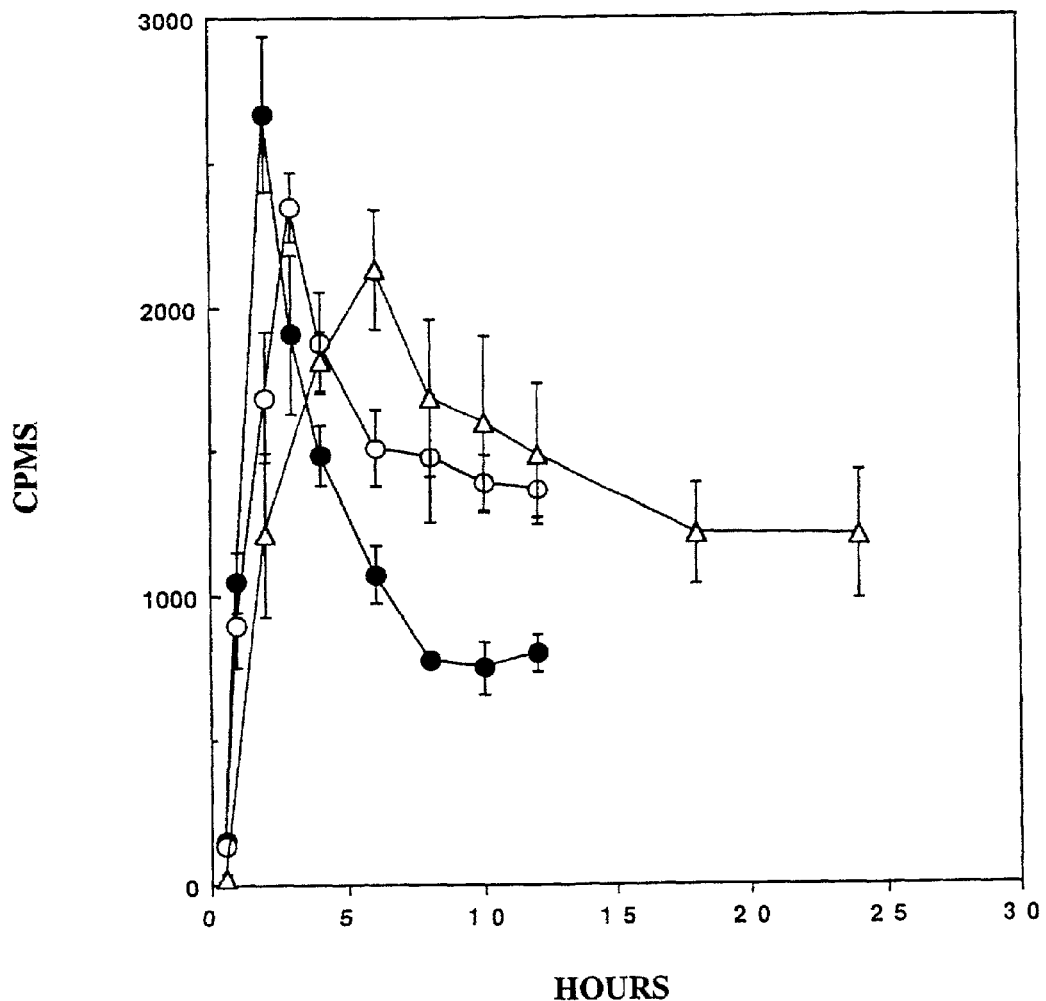
FIG. 1. Effect of Temperature on $^3$H-$E_2$ Binding to MTW9/PL2 Cells.

Identification of MTW9/PL2 Cell Estrogen Receptors by $^3$H-$E_2$ Binding Methods. Examining the MTW9/PL2 cell line anew, the MTW9/PL2 population was examined for $^3$H-$E_2$ binding to whole cells, to determine if estrogen receptors were present. First, the effect of temperature on $^3$H-$E_2$ specific binding was examined (FIG. 1). At 37° C., specific binding reached a maximum in two hours and thereafter decreased rapidly. At 23° C., specific binding reached the same maximum but at three hours. The decay in binding at 23° C. was not as pronounced as at 37° C. At 7° C., the rate of specific binding reached a stable maximum at six hours. Similar temperature effects have been observed for the kinetics of $^3$H-$E_2$ binding to MCF-7 breast cancer cells (Horwitz K B and McGuire W L (1978) *J Biol Chem* 253, 8185-8191; MacIndoe et al. (1982) *Steroids* 39, 245-258).

Effect of $^3$H-$E_2$ Concentration on Binding. Next, the effect of the concentration of $^3$H-$E_2$ on binding at 37° C. was characterized. Specific binding was saturated by $\geq$5 nM $^3$H-$E_2$ (insert FIG. 2). One-half saturation occurred at 2 to 3 nM $^3$H-$E_2$. A Scatchard analysis (Scatchard G (1949) *Ann N.Y. Acad Sci* 51, 660-672) of $^3$H-$E_2$ binding also was done at 37° C. (FIG. 2) (N=2). It indicated a single class of $E_2$ binding sites with a dissociation constant ($K_d$) of $2.78 \times 10^{-9}$ M. This analysis indicated 38,400 estrogen receptors per cell. These values compared closely to a $K_d$ of $1.89 \times 10^{-9}$ M and the estimated 34,000 sites per cell determined for $^3$H-$E_2$ binding to the original MTW9/PL cell population in 1982 (Leland F E et al. (1982) In: *Cold Spring Harbor Conferences on Cell Proliferation*, Volume 9, *Growth of Cells in Hormonally Defined Media*, Sato G, Pardee A B and Sirbasku D A, eds, Cold Spring Harbor, N.Y., pp 741-750). Plainly, the estrogen receptor content of this permanent cell population has remained stable over several years.

Figure 3:
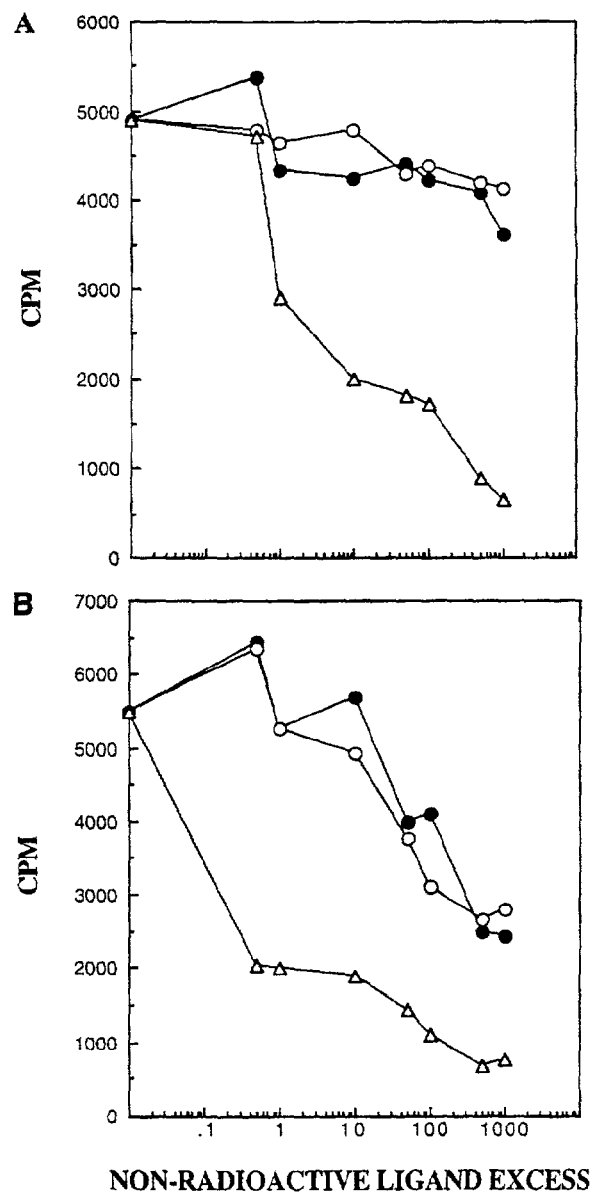
FIG. 3. Effect of Unlabeled Competitor Steroids on $^3$H-$E_2$ Binding to MTW9/PL2 Cells. (A) Competition with Unlabeled Androgens; (B) Competition with Unlabeled Progesterone and Cortisol.

Specificity of $^3$H-$E_2$ Binding. The specificity of $^3$H-$E_2$ binding to MTW9/PL2 cell receptors was examined. The effects of unlabeled DES, DHT or testosterone (T) on binding of 5 nM $^3$H-$E_2$ at 37° C. were examined. The results from one of these experiments (N=3) are shown in FIG. 3A. At 100-fold molar excess, unlabeled DES reduced $^3$H-$E_2$ total binding by 85%. Conversely, 100-fold molar excesses of either DHT or T did not displace $^3$H-$E_2$ total binding significantly. Even at 1000-fold excess, T or DHT only reduced $^3$H-$E_2$ total binding by 15%. Next, the effects of unlabeled progesterone and cortisol on $^3$H-$E_2$ binding to MTW9/PL2 cells were investigated under conditions similar to those used in FIG. 3B. A 100-fold excess of either progesterone or cortisol reduced $^3$H-$E_2$ binding by 30 to 50%. The results of the $^3$H-$E_2$ binding competition studies presented here are nearly identical to those done with cell extracts of the original MTW9/PL population in 1982.

Comparison of the Labeled $E_2$ Binding Dissociation Constants ($K_d$) of Several Estrogen Sensitive Cell Types. Clearly, the assays with extracts measured the same affinity binding sites as analyses with whole cells. This offers reasonable evidence that the standard binding technology employed in these studies is measuring the most common form of receptor present in cells, no matter whether whole cells are assayed or cell extracts. The affinity of the MTW9/PL2 estrogen receptor is that which is characteristic of the ERα. The $K_d$ of the receptor measures the concentration of ligand that one-half saturates the sites. In TABLE 3, the $K_d$ values for labeled $E_2$ are presented as reported and presumably represent the ERα. Only when the measurements are specific for the β form is the designation (ERβ) included.

TABLE 3

Comparison of $E_2$ Binding Affinities Expressed as Dissociation Constants ($K_d$)

| CELL LINES | WHOLE CELLS $K_d$ for $E_2$ | CELL EXTRACTS $K_d$ for $E_2$ | REFERENCES |
| --- | --- | --- | --- |
| MTW9/PL2 | $2.78 \times 10^{-9}$ M | $1.89 \times 10^{-9}$ M | Moreno-Cuevas JE and Sirbasku DA (2000) In Vitro Cell Dev Biol 36, 410-427 |
| MCF-7 | $0.58 \times 10^{-9}$ M | $1.77 \times 10^{-9}$ M | MacIndoe JH et al. (1982) Steroids 39, 247-258 |
| MCF-7-Mason | | $4.0 \times 10^{-9}$ M Unfilled nuclear | Horwitz KB et al. (1978) Cancer Res 38, 2434-2437 |

TABLE 3-continued

Comparison of E₂ Binding Affinities Expressed as Dissociation Constants ($K_d$)

| CELL LINES | WHOLE CELLS $K_d$ for $E_2$ | CELL EXTRACTS $K_d$ for $E_2$ | REFERENCES |
|---|---|---|---|
| MCF-7-Mason | | $0.4 \times 10^{-9}$ M Filled nuclear | Horwitz KB et al. (1978) Cancer Res 38, 2434-2437 |
| MCF-7 | | $0.1 \times 10^{-9}$ M | Reddel RR et al. (1985) Cancer Res 45, 1525-1531 |
| MCF-7-L | | $0.08 \times 10^{-9}$ M | |
| MCF-7-M | | $0.07 \times 10^{-9}$ M | |
| T47D | | $1.0 \times 10^{-9}$ M Unfilled nuclear | Horwitz KB et al. (1978) Cancer Res 38, 2434-2437 |
| T47D | | $4.0 \times 10^{-9}$ M Filled nuclear | Horwitz KB et al. (1978) Cancer Res 38, 2434-2437 |
| T47D | | $0.11 \times 10^{-9}$ M | Reddel RR et al. (1985) Cancer Res 45, 1525-1531 |
| ZR-75-1 | | $0.09 \times 10^{-9}$ M | Reddel RR et al. (1985) Cancer Res 45, 1525-1531 |
| ZR-75-1 | | $1.3 \times 10^{-9}$ M | Engel LW et al. (1978) Cancer Res 38, 3352-3364 |
| H301 | $1.0 \times 10^{-9}$ M | | Liehr JG and Sirbasku DA (1985) In: Tissue Culture of Epithelial Cells, Taub M, ed, Plenum, New York, pp 205-234 |
| H301 | | $0.87 \times 10^{-9}$ M | Soto AM et al. (1988) Cancer Res 48, 3676-3680 |
| GH₃ | | $0.25 \times 10^{-9}$ M | Moo JB et al (1982) In: Growth of Cells in Hormonally Defined Media, Vol. 9, Cold Spring Harbor, New York, pp 429-444 |
| GH₃ | $0.31 \times 10^{-9}$ M | | Haug E et al. (1978) Mol Cell Endocrinol 12, 81-95 |
| Prostate and Ovary | | $0.2 \times 10^{-9}$ M (ERα) $0.5 \times 10^{-9}$ M (ERβ) | Tremblay GB et al. (1997) Mol Endocrinol 11, 353-365 |
| Transfection Studies | | 0.05 to $0.1 \times 10^{-9}$ M (ERβ only) | Kuiper GC et al. (1998) Endocrinology 139, 4252-42-63 |

TABLE 3 presents only a fraction of the estrogen binding data available in the literature. However, the $K_d$ values presented are representative and do show a discernable pattern. The lowest $K_d$ from a literature search was in the range $5 \times 10^{-11}$ M to $1.0 \times 10^{-10}$ M for the ERβ and $7 \times 10^{-11}$ M to $1.1 \times 10^{-10}$ M for the ERα. In general, the binding affinities as estimated by $K_d$ are lower for receptors from human cells than those from rodent lines. It is important to note that the results presented in TABLE 3 indicate that the lower limit of measuring estrogen receptor affinities most likely has been reached. The use of the highest specific activity tritium labeled steroids has been optimized and simply cannot be used to measure 10 to 100-fold lower $K_d$ concentrations. This opens the possibility of an as yet unrecognized ER that mediates growth effects at lower concentrations of estrogen than either the ERα or the ERβ.

Figure 4:
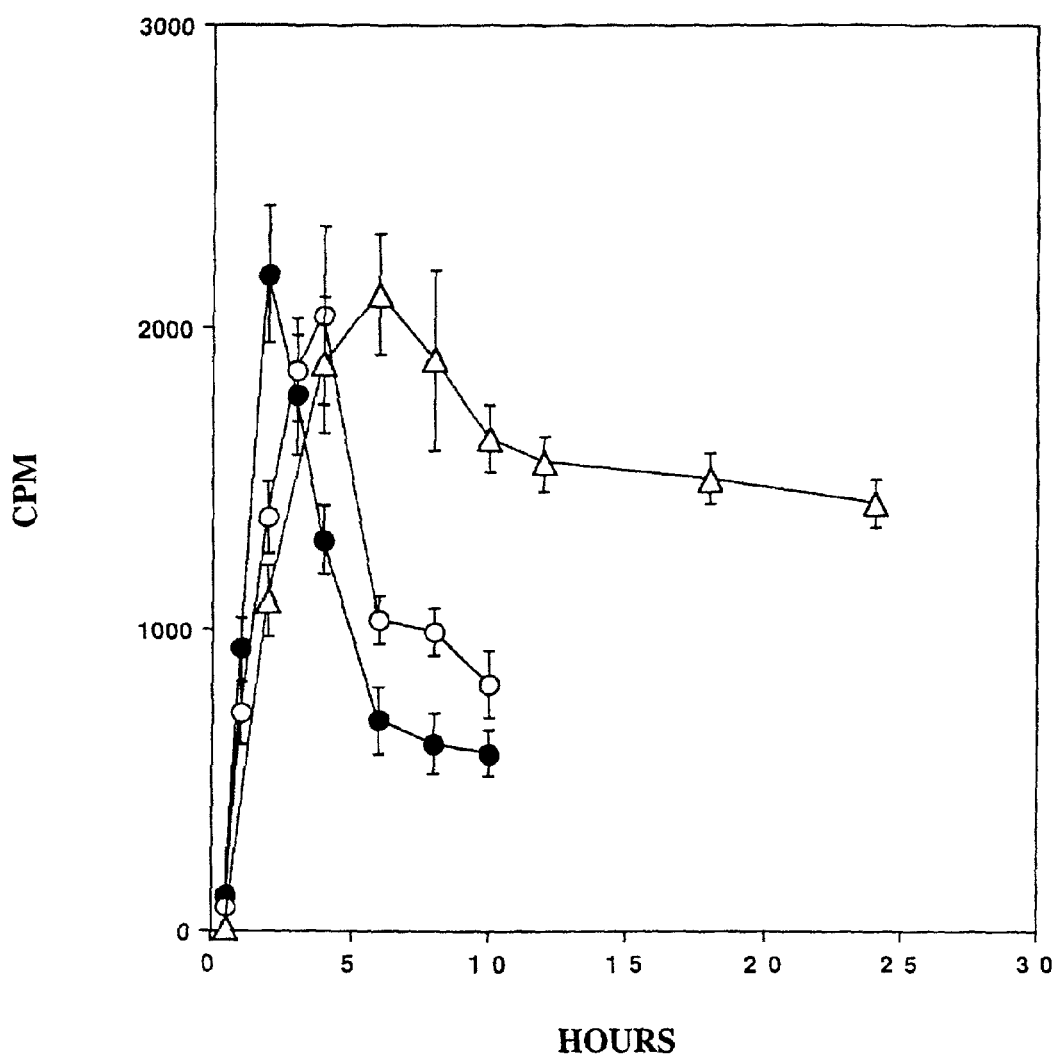
FIG. 4. Effect of Temperature on $^3$H-Progesterone Binding to MTW9/PL2 Cells.

Effect of Temperature on ³H-Progesterone Binding. Progesterone receptors in MTW9/PL2 cells were sought using the same series of experiments done to identify estrogen receptors. The effect of temperature on progesterone specific binding with MTW9/PL2 cells is shown in FIG. 4. Maximum ³H-progesterone binding at 37°, 23° C. and 7° C. occurred at 2, 4 and 6 hours, respectively. fter reaching an optimum, the binding decayed at 37° C. and 23° C. but not at 7° C.

Effect of ³H-Progesterone Concentration on Binding. The saturability of ³H-progesterone binding was examined at 37° C. Labeled progesterone specific binding was saturated at ≧5 nM (insert FIG. 5). One-half saturation occurred at 0.5 to 1 nM ³H-progesterone. Scatchard analysis (N=2) identified a single class of binding sites with a $K_d$ of $1.02 \times 10^{-9}$ M and yielded an estimated 26,800 sites per cell, as shown in FIG. 5. Previous studies in 1982 with extracts of the original MTW9/PL cell population had given a $K_d$ of $3.29 \times 10^{-9}$ M for ³H-progesterone binding and an estimated 180,000 sites per cell (data not shown). Comparison of the number of progesterone sites then and now indicates a decrease. However, a sufficient number remain to expect progesterone specific gene expression or growth regulation (Alexander I E et al. (1989) *Mol Endocrinol* 3, 1377-1386; Keydar I et al. (1979) *Eur J Cancer* 15, 659-670).

Effect of Other Steroid Hormones on ³H-Progesterone Binding. The effect of non-progestins on ³H-progesterone binding was investigated (FIG. 6). As control, the binding was studied in the presence of increasing concentrations of the synthetic progestin R5020. A 100-fold excess of the unlabeled R5020 reduced ³H-progesterone binding by 82%. A 100-fold excess of unlabeled DHT or T reduced binding by ≦20%. A 100-fold excess of unlabeled $E_2$ reduced progesterone binding by a maximum of 20% (data not shown).

Assays for Androgen and Cortisol Receptors. Experiments (N=3) were carried out to seek specific saturable binding sites for androgens using ³H-DHT. In experiments not shown, incubation of MTW9/PL2 cells at 37° C. for two hours with ≦20 nM labeled DHT did not reveal saturable specific binding sites. Studies using ≦20 nM ³H-cortisol did not identify specific saturable receptors for this corticosteroid.

Figure 7:
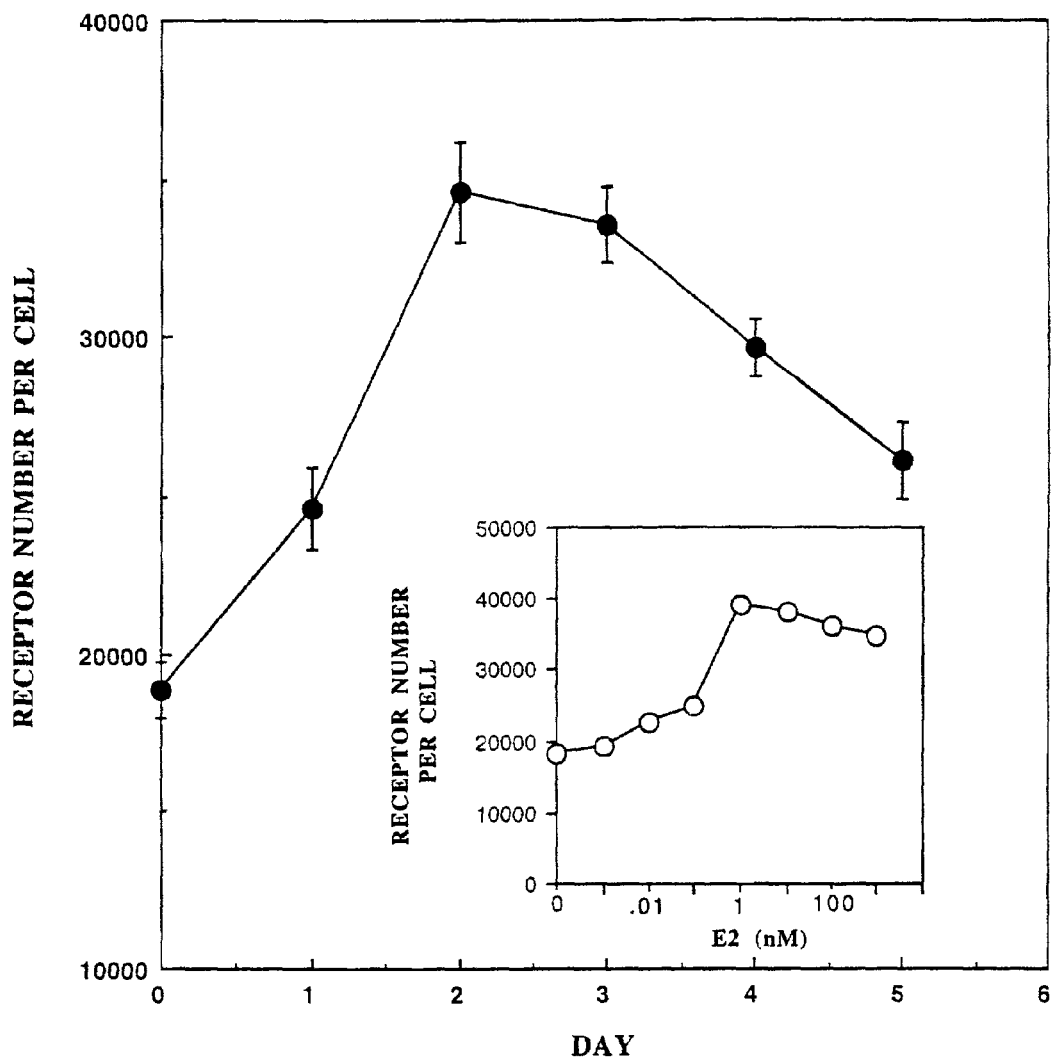
FIG. 7. Estrogen Induction of Progesterone Receptors with MTW9/PL2 Cells.

Estrogen effects on Progesterone Receptor Expression in MTW9/PL2 Cells. Estrogens induction of progesterone receptors in target cells is generally taken as strong evidence of sex steroid responsiveness by the criteria of regulation of gene expression (Leavitt W W et al. (1977) *Ann N.Y. Acad Sci* 286, 210-255; Toft D O and O'Malley B W (1972) *Endocrinology* 90, 1041-1045; Horwitz K B and McGuire (1978) *J Biol Chem* 253, 2223-2228; Haslam S Z and Shyamala G (1979) *Biochem J* 182, 127-131; Haslam S Z and Shyamala G (1979) *Endocrinology* 105, 786-795). In the next study, it was asked whether this was the case with MTW9/PL2 cells. The cells were grown for five to seven days in the absence of estrogens in standard phenol red containing D-MEM/F-12 plus 2% (v/v) charcoal-dextran extracted (CDE) horse serum. Thereafter, they were harvested and inoculated into phenol red free medium in 100-mm diameter dishes containing $1.0 \times 10^{-8}$ M $E_2$. Beginning at day 0 (inoculation day) and for each of the next five days, the cells were assayed for progesterone receptors as described (Moreno-Cuevas J E and Sirbasku D A (2000) *In Vitro Cell Dev Biol* 36, 410-427). All results were normalized to "receptors per cell" to correct for growth over the duration of the experiment. The number of progesterone receptors increased 1.8-fold within two days after exposure to $E_2$ (FIG. 7). In a replicate experiment, the induction was 2.0-fold in two days. The effect of estrogen concentration on progesterone receptor induction also was evaluated (insert FIG. 7). Maximum induction occurred at 1.0 nM $E_2$. These results confirm that MTW9/PL2 cells are $E_2$ responsive by a criterion separate from growth.

Western Analysis for Androgen, Estrogen and Progesterone Receptors. Western immunoblotting was used to analyze the MTW9/PL2 cells for the presence of steroid hormone receptors. Nuclear and cytosolic extracts were compared to those from negative control rat and human diploid fibroblasts and positive control T47D and LNCaP cells. The T47D cells have androgen (Keydar I et al. (1979) *Eur J Cancer* 15, 659-670; Horwitz K B et al. (1978) *Cancer Res* 38, 2434-2437), progesterone (Horwitz K B et al. (1978) *Cancer Res* 38, 2434-2437; Horwitz K B and Alexander P S (1983) *Endocrinology* 113, 2195-2201; Lessey B A et al. (1983) *Endocrinology* 112, 1267-1274) and estrogen (Horwitz K B et al. (1978) *Cancer Res* 38, 2434-2437; Keydar I et al. (1979) *Eur J Cancer* 15, 659-670; Soto A M et al. (1986) *Cancer Res* 46, 2271-2275) receptors. The androgen receptors of LNCaP cells previously have been characterized by labeled hormone binding analysis (Veldscholte J et al. (1990) *Biochem Biophys Res Commun* 173, 534-540; Veldscholte J et al. (1990) *Biochim Biophys Acta* 1052, 187-194) and Western immunoblotting (Prins G S et al. (1991) *Endocrinology* 129, 3187-3199). Although the LNCaP cells were initially reported to not have progesterone or estrogen receptors (Schuurmans A L et al. (1988) *Int J Cancer* 42, 917-922; Brolin J et al. (1992) *The Prostate* 20, 281-295), more recent evidence indicates that they express significant levels of both (Castagnetta L et al. (1995) *Endocrinology* 136, 2309-2319).

Figure 8:
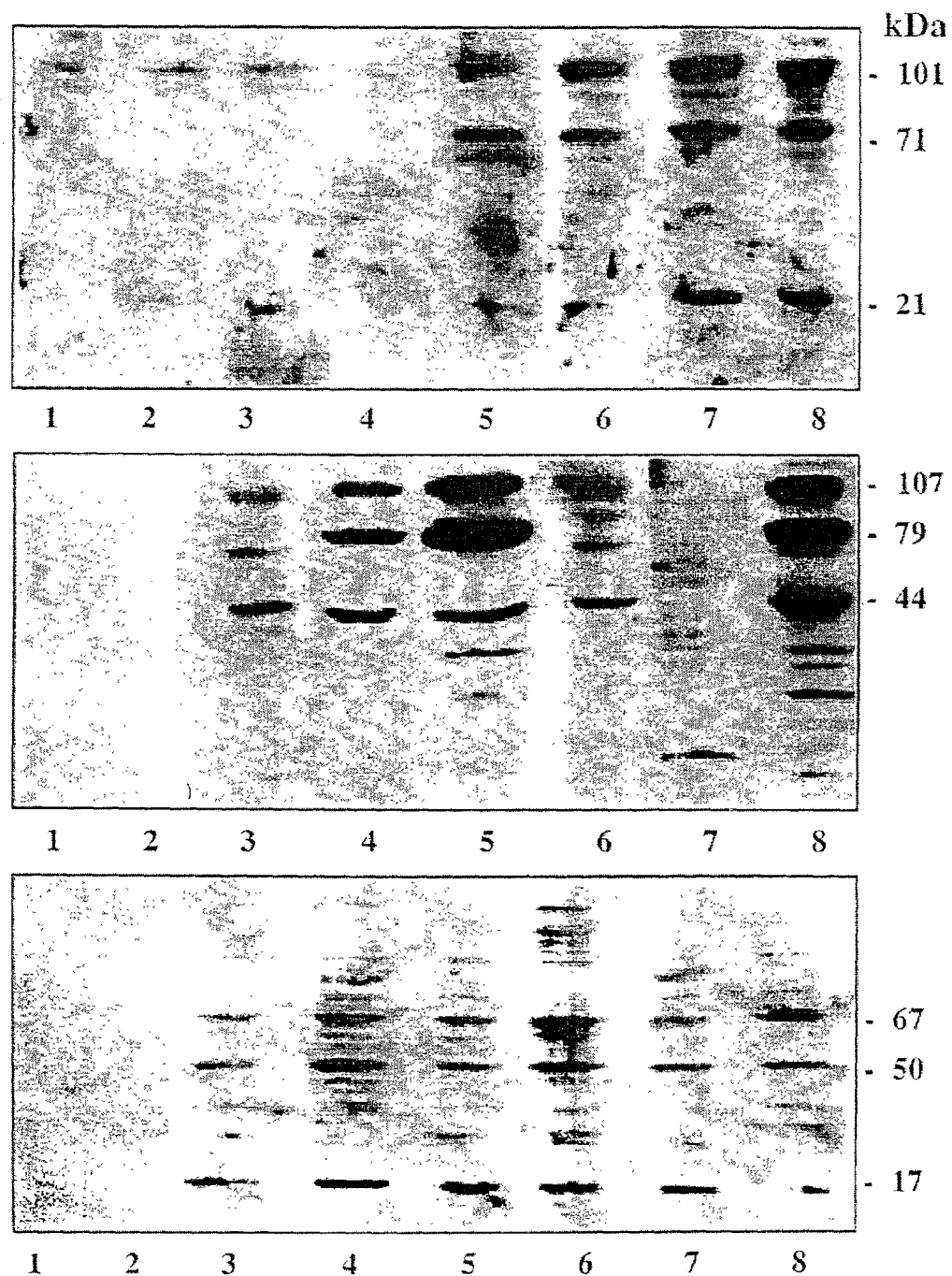
FIG. 8. Western immunoblotting Analysis of Androgen, Progesterone and Estrogen Receptors in MTW9/PL2 cells. Lanes 1 through 8 contain 10 µg of the following cell extract protein: Lanes 1 and 2, cytosolic extracts of rat and human fibroblasts, respectively; Lanes 3 and 4, cytosolic and nuclear extracts, respectively, of MTW9/PL2 Cells; Lanes 5 and 6, cytosolic and nuclear extracts, respectively, of 47D Cells; Lanes 7 and 8, cytosolic and nuclear extracts, respectively, of LNCaP cells. Top, Middle and Bottom Panels are Androgen, Progesterone and Estrogen receptors, respectively.

Western Analysis—Androgen Receptors. As shown in (FIG. 8, top panel), nuclear and cytosolic extracts of LNCaP cells gave an intense band at 101 kDa that was the expected mass of the androgen receptor as determined previously by immunoblotting (Prins G S et al. (1991) *Endocrinology* 129, 3187-3199; Berrevoets C A et al. (1993) *J Steroid Biochem Mol Biol* 46, 731-736). It was also nearly the same mass as the 98.5 kDa predicated by molecular cloning (Trapman J et al. (1988) *Biochem Biophys Res Commun* 153, 241-248; Faber P W et al. (1989) *Mol Cell Endocrinol* 61, 257-262). The bands migrating at 79 kDa and 21 kDa may be degradation products, non-specific reactions between the antibody and unrelated proteins, or may represent other forms of the androgen receptor (Prins G S et al. (1991) *Endocrinology* 129, 3187-3199). The T47D cells showed the same androgen receptors as LNCaP cells. In contrast, there was little androgen receptor in the nuclear or cytosolic extracts of MTW9/PL2 cells. The faint band identified was the same intensity as an equivalent component seen in the extracts of fibroblasts (FIG. 8, top panel). Fibroblasts have been reported to have low levels of androgen receptors (Eil C et al. (1983) *Clin Endocrinol* 19, 223-230; Eil C et al. (1980) *Steroids* 35, 389404).

Western Analysis—Progesterone Receptors. Similar experiments were done to identify progesterone receptors with MTW9/PL2 cells. Receptors of 79 kDa (A form) and 107 kDa (B form) were immunostained with both the cytosolic and nuclear extracts (FIG. 8, middle panel). Another possible form was identified at 44 kDa. The progesterone receptors of MTW9/PL2 cells were the same molecular mass as the A and B forms from chick oviduct (Dure L S et al. (1980) *Nature* (Lond) 238, 784-786; Bimbaumer M et al. (1983) *J Biol Chem* 258, 1637-1644). The forms in MTW9/PL2 cells also compared closely to the 85.6 kDa and 109.6 kDa masses reported for progesterone receptors of rat uterus (Ilenchuk T T et al. (1987) *Endocrinology* 120, 1449-1456). Furthermore, the 79kDa component (A form) was the more abundant of the two receptors in MTW9/PL2 cells. This was also the case for rat uterus (Ilenchuk T T et al. (1987) *Endocrinology* 120, 1449-1456). The T47D positive controls showed the same molecular masses of progesterone receptors although there was greater immunostaining with the cytosolic extracts than with the nuclear preparations. This receptor distribution between cytosol and nucleus was similar to that found when T47D cells were examined by labeled hormone binding (Horwitz K B et al. (1978) *Cancer Res* 38, 2434-2437). The T47D progesterone receptor masses observed in the present study were similar to those reported by others studying human breast cancer cells (Horwitz K B and Alexander P S (1983) *Endocrinology* 113, 2195-2201; Lessey B A et al. (1983) *Endocrinology* 112, 1267-1274; Horwitz K B et al. (1985) *Recent Prog Hormone Res* 41, 249-316). Additionally, the LNCaP cells showed intense nuclear extract staining for the same forms of progesterone receptors seen in extracts of MTW9/PL2 and T47D cells. No progesterone receptors were identified in the negative control rat or human fibroblasts.

Western Analysis—Estrogen Receptors. In the final study, the estrogen receptors in MTW9/PL2 were sought (FIG. 8, bottom panel). The major form of estrogen receptor in MTW9/PL2 cells was molecular mass 67 kDa. Two presumed degradation products of 50 kDa and 17 kDa were also observed. The results with MTW9/PL2 cells were in agreement with the expected mass of the rat estrogen receptor estimated at 67 kDa by molecular cloning (Koike S et al. (1987) *Nucleic Acid Res* 15,2499-2513). The extracts from T47D and LNCaP cells showed a similar estrogen receptor pattern. Control fibroblasts showed no estrogen receptors. Initially, the band identified at 50 kDa was thought to be a degradation product of the 67kDa intact form of ERα (Moreno-Cuevas J E and Sirbasku D A (2000) *In Vitro Cell Dev Biol* 36, 410427); however, it may be an ERβ because that new receptor has a mass of 54 kDa (Enmark E et al. (1997) *J Clin Endocrinol Metab* 82, 4258-4265). The 50 kDa band may also represent a variant form of ERβ (Gustafsson J-Å and Warner M (2000) *J Steroid Biochem Mol Biol* 74, 245-248). Alternately, this band may represent a new estrogen receptor that regulates growth, hereby designated as estrogen receptor gamma (ERγ).

Thus, it is concluded that another positive acting ER exists in the MCF-7 and T47D cells and its function is dominant and sustains growth related gene expression even with the inhibitory ERα present. The existence of two ER receptors is also indicated in an older study of the growth of the $GH_4C_1$ rat pituitary tumor cells in culture (Amara J F and Dannies P S (1983) *Endocrinology* 112, 1141-1143). These investigators demonstrated a biphasic effect of $E_2$ on these cells. At picomolar concentrations, $E_2$ caused growth. At higher concentrations, $E_2$ induced prolactin production secretion and inhibited growth. If two receptors are operating, the growth receptor is more sensitive to $E_2$ whereas the ER regulating gene expression (e.g. prolactin mRNA production) is activated by higher concentrations of estrogen. This same biphasic action of estrogen on the growth of T47D human breast cancers cells has also been noted (Chalbos D et al. (1982) *J Clin Endocrinol Metab* 55, 276-283). Low concentrations promoted growth, whereas higher levels were inhibitory. Indeed, a biphasic effect also was noted with the MCF-7 cell line (Soto A M and Sonnenschein C (1985) *J Steroid Biochem* 23, 87-94). When this observation is coupled with the clear statements of Soto et al. (Soto A M et al. (1986) *Cancer Res* 46, 2271-2275) that "the free estradiol levels needed for maximum response are significantly lower than estrophilin (i.e. ERα) $K_d s$", there is further support for the view that an ER exists that regulates growth and is more estrogen sensitive (i.e. lower $K_d$) than the classical ERα. While those investigators conclude that the results exclusively supported their estrocolyone hypothesis, and excluded ERα as the positive growth regulator, there was no recognition of the possibility of a much higher affinity receptor different than ERα. Finally, there is one other issue that has perplexed endocrinologists and cancer biologists for several years. Breast cancer is sometimes treatable with high doses of estrogen (Segaloff A (1981) *Banbury Report* 8, 229-239). If the ERα is the only growth mediator, one is forced into many other postulates to explain this observation (Reese C C et al. (1988) *Ann N.Y. Acad Sci* 538, 112-121). Indeed, this may actually represent evidence that full occupation of ERα is inhibitory and that another receptor is the positive signal.

Variant estrogen receptors have been identified previously by others. For example from the estrogen growth responsive T47D human breast cancer cell line, there have been three isoforms of the ERα identified in one study (Wang Y and Miksicek R J (1991) *Mol Endocrinol* 5, 1707-1715) and another three in a different study (Graham M L et al. (1990) *Cancer Res* 50, 6208-6217). With another two estrogen growth responsive human breast cancer cell lines, the MCF-7 and ZR-75-1, another ERα variant was identified that lacked the entire exon 4 of the receptor (Pfeffer U et al. (1993) *Cancer Res* 53, 741-743). Variant receptors have also been identified from human breast cancer biopsy specimens (Murphy L C and Dotzlaw H (1989) *Mol Endocrinol* 3, 687-693). Another truncated variant of ERα acts as a natural inhibitor of the action of the wild-type ERα (i.e. unchanged receptor) (Fuqua S A et al. (1992) *Cancer Res* 52, 483-486). Another type of variant has received wide attention because it has constitutive transcriptional activity without the steroid hormone ligand bound (Fuqua S A et al. (1991) *Cancer Res* 51, 105-109). Even normal human breast epithelial cells show several natural variants of ERα (Yang J et al. (2000) *Endocrine* 12, 243-247). When all of these results are considered as a group, it is clear that different forms of the ERα are possible in cells. It is reasonable to conclude that an alternate form of ERα, possibly formed by alternate splicing, or possibly arising from an as yet unrecognized gene, may regulate estrogen dependent/responsive tumor cell growth. Upon further investigation ERγ may prove to be such a variant.

Whatever mechanism is proposed for the action of the steroid hormone (i.e. on growth), it can be seen from the data presented herein, and subsequently reported elsewhere (Sirbasku D A and Moreno-Cuevas J E (2000) *In Vitro Cell Dev Biol* 36, 428-446), it takes a significant period to reverse the effects of the inhibitor. This process cannot be simply due to a rapid effect on transcription caused by steroid hormones (e.g. via a known estrogen receptor). Cellular metabolic events, including the transformation of $E_2$ to an active steroid metabolite, may provide the growth regulating ligand for one of the "orphan" estrogen receptors. An alternative possibility is that the receptor may be activated by metabolites formed from cholesterol metabolism (Gustafsson J-Å (1999) *Science* (Wash D.C.) 284, 1285-1286).

Discussion of Example 1. The evidence presented verifies that the MTW9/PL2 cells are estrogen receptor positive (ER+) with a significant number of progesterone receptors and possibly low levels of androgen receptors. The estrogen receptor content and affinity characteristics of the MTW9/PL2 cells indicate appropriate stability for use as a testing standard and for commercial applications. The long-term stability of this cell line in culture, without alteration of its cell properties, is further discussed in Example 3. These results and the information provided above, show that this cell line is a unique asset for combination in vitro and in vivo modalities that can be applied to evaluate a multitude of compounds or preparations having, or potentially having, hormone or anti-hormone activities.

Example 2

Preparations of Steroid Hormone Depleted Serum

Three Methods. In this example, evaluations of three methods for preparing steroid hormone depleted serum are described. The primary purpose was to prepare serum that supported large magnitude sex steroid growth effects in culture and to identify the dose-response concentrations that cause the effects, as demonstrated in Examples that follow. This meant preparing serum with ≦5 pg/mL estrogen (and other steroid hormones). This concentration corresponds approximately to the lower limit of detection of steroids by radio immunoassay. The methods tested included (A) a two-step charcoal/dextran extraction of serum at 34° C., (B) a one-step charcoal extraction at 56° C., and (C) a one step treatment with Amberlite™ XAD™-4 resin at 37° C. One advantageous result established by this Example is that sera prepared according to the preferred methods contain significant amounts of active immunoglobulin inhibitors, in contrast to previously known steroid depleted sera.

(A) Charcoal-dextran Extraction at 34° C

1. Preparation of the Charcoal/Dextran Mixture. Activated charcoal, untreated powder (100 to 400 mesh), was obtained from Sigma (Catalog No. C5260). This preparation was done at room temperature. The powder (30 g) was suspended in 600 mL of water and stirred for 20-30 minutes at room temperature. The water used to wash and suspend the charcoal was a purified source made by reverse osmosis/ion exchange treatment/charcoal filtration/0.2 µm pore diameter filtration/distillation into glass (only) containers. Next, 3.0 g of Dextran T70 (Pharmacia) was dissolved in 300 mL of water, added to the charcoal suspension with stirring, and the mixture stirred for 30-60 min at room temperature, preferably 60 min. The mixture was then washed with about 6-8 liters of distilled water in a sintered glass funnel (2000 mL, ASTM 40-60, C#36060). This wash removes impurities as well as fine particles of charcoal that cannot be separated from serum by centrifugation. The charcoal-dextran retentate was suspended in a final volume of 300 mL of distilled water to yield a suspension of 100 mg/mL charcoal and 10 mg/mL dextran. Preferably the mixture is stirred vigorously for about an hour, and then stored at room temperature for no more than about 2-3 weeks prior to use.

2. Charcoal-Dextran Extraction at 34° C. of Horse Serum (CDE-Horse Serum). This serum in 500 mL sterile bottles was removed from the freezer (−17° C.) and thawed at 4° C. for 24 to 48 hours. Alternatively, fresh serum could be used. The thawed serum (still in the 500 mL sterile bottles) was placed in an orbital shaker water bath (Lab-Line Orbit Shaker Water Bath) equilibrated at 34° C. The serum was incubated at 140 RPM for 45-60 minutes to reach 34° C. Approximately 250 mL portions of the 34° C. serum (total volume about 1 liter) were transferred to one-liter Erlenmeyer flasks and tightly capped with aluminum foil. These were incubated for 20-30 minutes (preferably 30 minutes) in the 34° C. orbital shaker water bath at a medium-high rotation speed. Thereafter, 25 mL of the charcoal/dextran suspension was added to each flask. The charcoal-dextran suspension was stirred at room temperature while removing the 25 mL aliquot. The final charcoal concentration in each flask was 10 mg/mL, and the final concentration of dextran was 1 mg/mL. After addition of the charcoal-dextran mixture to each flask, the extraction mixtures were shaken at 140-160 RPM at 34° C. for two hours. After this, the mixture was cooled on ice and the charcoal removed by centrifugation at 10,000×g for about 60 minutes at room temperature. In some preparations the temperature of the mixture gradually warmed to about 40° C. during centrifugation. The supernatants were pooled in a two-liter beaker and 275 mL portions of the supernatant (serum) transferred to fresh one-liter Erlemneyer flasks. These were then incubated in the orbital shaker water bath at 34° C. for 20-30 minutes (preferably 30 min) to re-equilibrate the temperature. A second extraction was done by addition of a fresh aliquot (about 14 mL) of the charcoal-dextran suspension. This re-extraction mixture was incubated with shaking for another 2 hours at 34° C. The final charcoal concentration during this extraction was about 5 mg/mL. Afterward the bulk of the charcoal was removed by centrifugation, as before. In some preparations the temperature of the mixture reached about 41° C., without harming the quality of the serum. The supernatants were collected into a two-liter beaker and filtered through 5 μm pore diameter filters to remove residual charcoal. If it was considered necessary for particular preparations (for example, due to charcoal darkening serum) the serum was also filtered with 0.45 μm Millipore filters. These filtrations were done with plastic reusable filter holders and light vacuum. The steroid hormone depleted serum was then sterilized using 0.2 μm pore diameter filters. After sterilization, aliquots of about 26 mL were dispensed into sterile glass (50 mL) bottles or sterile 50 mL polypropylene tubes and stored frozen at −17° C. Although 34° C. is preferred in the above-described regime, and provides the best results, satisfactory depletion of steroid hormones can be obtained over the temperature range of about 30 to 37° C. The 2 hour incubation times for the extraction and re-extraction mixture (at 34° C.) are preferred, but a time range of 30 minute to 3 hours could also be used with success, employing longer incubation times for the lower temperatures within the 30-37° C. range. A ±25% variation in the charcoal concentration used for each extraction had no detrimental effects on the final product.

(B) Charcoal-Dextran Extraction at 56° C. The preparation of 56° C. charcoal-dextran extracted serum was done as described (Sirbasku D A and Kirkland W L (1976) *Endocrinology* 98, 1260-1272; Riss T L and Sirbasku D A (1989) *In Vitro Cell Dev Biol* 25, 136-142; Kirkland W L et al. (1976) *J Natl Cancer Inst* 56, 1159-1164). Frozen serum was thawed for four hours at 37° C. followed by incubation in an orbital shaker water bath at medium-high speed at 56° C. for 15 minutes. The same charcoal-dextran mixture described above was used in this extraction. One-tenth volume (warmed to 56° C.) was added to the serum. Incubation was continued with shaking at 56° C. for 15 minutes. Thereafter, the flasks were cooled in an ice bath and the charcoal removed by centrifugation at 8,000×g and filtration with 5.0 or 0.45 μm pore membrane filters. The serum was 0.2 μm pore filter sterilized and stored at −17° C.

(C) Amberlite™ XAD™-4 Resin Treatment. In a different procedure carried out to free CBG of storage cortisol, XAD resin has been used to remove the steroid by incubation for 5 hrs at room temperature (A. M. Nakhla, et al. (1988) *Biochem. Biophys. Res. Commun.* 153, 1012-1018). Described as such, this method removed only about 80% of cortisol from the purified protein. Careful application of that method failed to yield serum suitable for the purpose of this study. As an alternative to preparing steroid hormone depleted serum by charcoal-dextran extraction, horse serum was treated by incubation with Amberlite™ XAD™-4 nonionic polymeric absorbent (Aldrich, Catalog. No. 21,648-8; or Sigma Catalog No. XAD-4 37380-42-0). Specifically, a 500 mL bottle of horse serum was thawed at 37° C. and divided into 250 mL portions that were each in a one-liter Ehlenmeyer flask. To each flask was added 25 grams of moist XAD-4 resin. The mixtures of serum and resin were then incubated with shaking in a rotary Labline Orbital Shaker water bath at 34° C. at about two-thirds of the maximum rate for 24 hours (speed adjusted to control foaming). This extraction can be done at temperatures from 30° C. to 37° C. At 30° C., the extraction requires 24 to 36 hours. At 37° C., it requires 18-24 hours to be complete. The 34° C. and 37° C. procedures are preferred. Each flask was tightly capped with aluminum foil and taped. After 24 hrs, the resin is allowed to settle by gravity, the supernatant decanted, and then vacuum filtered using a glass fiber filter in a Buchner funnel. The resulting serum was filter sterilized using 0.2 μm pore filter units. Aliquots of about 26 mL were frozen at −17° C. in 50 mL sterile bottles or tubes.

The charcoal method described above is readily applicable to one to five liter volumes of serum per preparation. With use of ≦50 mL per test substance, this is an adequate supply. To prepare larger volumes of serum (i.e. ≧20 liters) for extensive testing programs or commercial applications, the charcoal-dextran methods will preferably employ industrial filtration or other separation equipment to remove the carbon after each extraction. The XAD-4 resin method as presented is adaptable to one to five liters for testing purposes. For industrial applications, where ≧20 to 100 liter batches are customarily required, the resin method is preferred because of the need for only one separation after extraction. However, where "foaming" of the serum protein is to be avoided completely, charcoal extraction is superior. The materials cost for charcoal-dextran has an advantage when economy is a major consideration. It is less expensive than XAD-4 resin on a per liter basis, although the resin is commercially available at low cost when purchased in large amounts (i.e. ≧50-100 kilograms).

Discussion of Example 2. Each of the methods presented have advantages, depending on the particular needs and desires of the user. The scale procedures described are useful to prepared sufficient serum for testing of hormone activities or antihormone activities or evaluation of toxicity of compounds in cell culture assays. This 34° C. method has been used to prepare CDE human serum, porcine serum, rat serum, hamster serum, ovine serum, fetal bovine serum, new born bovine serum (0 to 10 days old), young donor bovine serum (10 days to 6 moths old) young adult bovine serum (300 to 900 lbs), fetal horse serum, chicken serum, turkey serum, dog serum, goat serum, rabbit serum and monkey serum. Subsequent Examples demonstrate how these stripped sera are preferably employed. The results demonstrate the broad utility of the method of preparing charcoal-dextran extracted serum for testing of cell lines from many species using homologous serum assays. From these results it can also be readily appreciated that these methods are applicable to testing of veterinary medicine samples or compounds of significance to domestic animals, as well as any application where a steroid hormone stripped serum is used.

Example 3

Cancer Cell Line MTW9/PL2 Exhibits Estrogen Responsive Growth in 34° C. Charcoal-Dextran Extracted Serum Estrogenic Effects in Cultures Supplemented with CDE-horse Serum. Unless otherwise stated, references in this and the following Examples to "CDE-horse serum" refer to the 34° C. charcoal-dextran extraction process described in above. The MTW9/PL2 cells were assayed for $E_2$ responsiveness in cultures supplemented with increasing concentrations of CDE-horse serum (FIG. 9A). Concentrations≦5% (v/v) promoted growth. Typically within seven days cell numbers increased from 6,000 per dish to more than 200,000 in 2 to 5% serum. This most likely resulted from stimulation by serum-borne growth factors as well as the mitogenic effect of transferrin (Danielpour D et al. (1988) *In Vitro Cell Dev Biol* 24, 42-52; Riss T L and Sirbasku D A (1987) *In Vitro Cell Dev Biol* 23, 841-849; Riss T L et al. (1986) *J Tissue Culture Methods* 10, 133-150). As serum concentrations exceeded 5% (v/v), the effects of the growth promoters were counteracted by a serum-borne inhibitor(s). At serum concentrations of 30 to 50% (v/v), growth was completely inhibited. Usually only seed density cell numbers were found after seven days in cultures containing 50% (v/v) CDE-horse serum. In contrast, the presence of $1.0 \times 10^{-8}$ M $E_2$ completely reversed the serum dependent inhibition. In cultures supplemented with 20 to 50% (v/v) CDE-serum plus $1.0 \times 10^{-8}$ M $E_2$, cell numbers were≧400,000 per dish. Logarithmic quantifying of cell growth was done by converting the cell number data in FIG. 9A into CPD. A plot of these values is shown in FIG. 9B. The estrogenic effect is also presented. In FIG. 9B, the difference was maximum at 30% (v/v) CDE-horse serum. It was a 6.14 CPD or a 70-fold (i.e. $2^{CPD}$ or $2^{6.14}$) increase in cell numbers in response to $E_2$. In randomly selected replicate experiments (N=9) done over a two-year period with different preparations of CDE-horse serum, the average maximum estrogen effect±SEM was 6.43 CPD±0.49 (range 5.63 to 7.22). This was an 86-fold ($2^{6.43}$) estrogenic effect. The modal concentration of serum that promoted maximum $E_2$ effects was 40% (range 20 to 50%).

Morphology of MTW9/PL2 Cells Growing in CDE-horse Serum±$E_2$. The morphology of the cells growing under the conditions was examined. The photomicrographs (Moreno-Cuevas J E and Sirbasku DA (2000) *In Vitro Cell Dev Biol* 36, 410-427) show cells growing under optimum conditions in medium with 2.5% (v/v) CDE-horse serum with and without $E_2$, respectively. The presence of the hormone had no effect on the appearance of the cultures. The cells grew in clusters in suspension and had the same morphology reported earlier for the parent MTW9/PL line grown in medium containing 10% (v/v) fetal bovine serum (Sirbasku D A (1978) *Cancer Res* 38, 1154-1165). When the concentration of CDE-horse serum was increased to 50% (v/v) without steroid, many fewer cells were present. Despite the near complete inhibition of growth, the morphology of the cells was the same as in rapidly growing cultures. Estrogen addition to this same medium caused substantial growth. The morphology of the estrogen-stimulated cultures in 50% serum was equivalent to that seen with or without estrogen in 2.5% serum. The inhibitor had no effect on the microscopic morphology of MTW9/PL2 cultures nor did it affect cell-cell adhesion or cell-surface adhesion.

Figure 10:
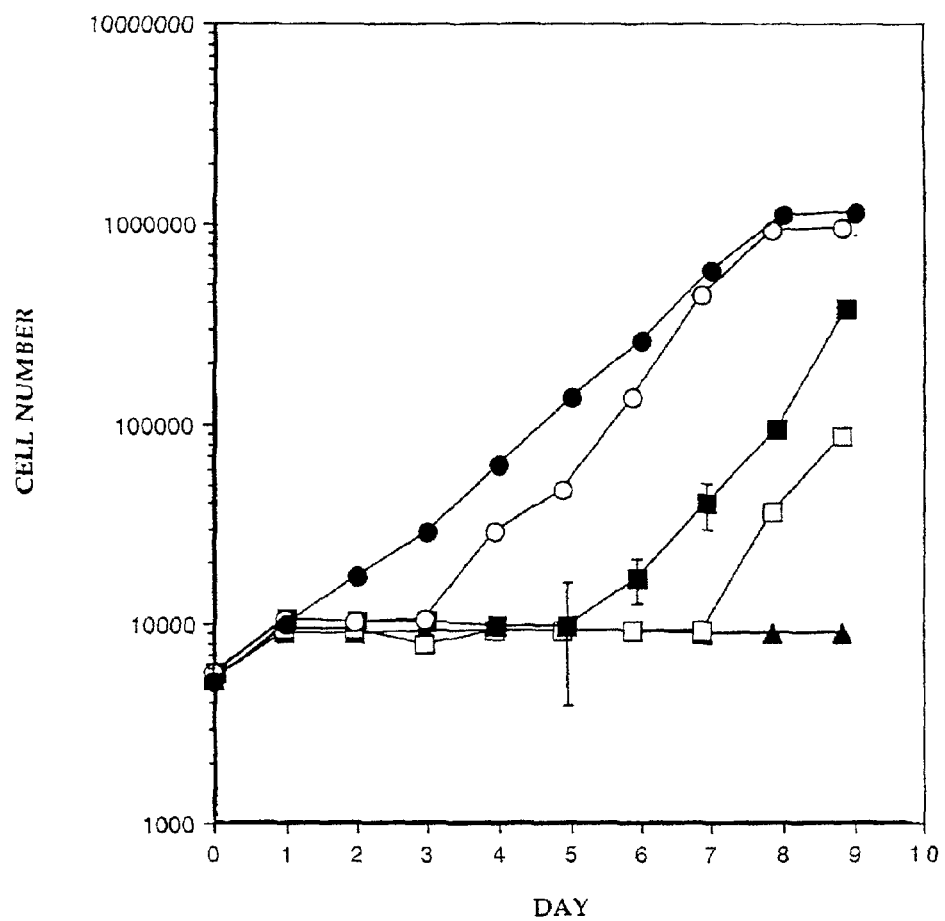
FIG. 10. Restoration of Growth by Addition of 10 nM $E_2$ on days 0, 2, 4 and 6 After Seeding the MTW9/PL2 cells into Fully Inhibitory Medium Containing 50% (v/v) of CDE-horse serum.

Estrogen Reversibility of the Growth Inhibition Caused by CDE-Horse Serum. It was examined whether inhibition caused by CDE-horse serum was reversible even after several days in culture (FIG. 10). The MTW9/PL2 cells were seeded into medium containing 50% (v/v) CDE-horse without $E_2$ and cell numbers monitored daily. Growth ceased within 48 hours; thereafter cell numbers remained static. In parallel cultures, addition of $E_2$ on days two, four, and six after seeding caused resumption of growth (after a lag period) at nearly the same rate as cultures that received hormone at the time of inoculation. These results show that the cells survived in the presence of the inhibitor without $E_2$ for at least six days.

Storage Stability of CDE-Horse Serum. TABLE 4 shows the effect of storage temperature on the estrogen mediating activity of CDE-horse serum. The assays were done with MTW9/PL2 cells as shown in FIGS. 9A and 9B. Stability was assessed by four criteria: (i) the concentration of serum needed to give an estrogenic effect of 2.5 CPD (i.e. $ED_{2.5}$), (ii) the percent serum needed for the maximum estrogenic effect, and the magnitude of the estrogenic effects (CPD) at (iii) 20% and (iv) 30% serum. CDE-horse serum was stable at 23° C. for three weeks without loss of activity as assessed by all four criteria. Storage at 4° C. was detrimental within 24 days as measured by the CPD at 20% and 30% (v/v) serum concentrations. Longer storage at 4° C. was not advisable. Storage at −17° C. was most effective; the activity was unchanged even after 90 days. In experiences not shown, repeated freeze-thaw cycles caused an appreciable loss of inhibitor activity.

TABLE 4

Summary of the Effects of Serum Storage Temperature on Activity.

| Days of Storage | % Serum needed for 2.5 CPD ($ED_{2.5}$) of $E_2$ Induced growth | Maximum $E_2$ Induced CPDs (% serum, v/v, for the maximum) | CPD at 20% (v/v) serum | CPD at 30% (v/v) serum |
|---|---|---|---|---|
| Storage at 23° C. | | | | |
| 1 | 2.1 | 4.9 (10%) | 5.0 | 3.2 |
| 3 | 5.2 | 5.4 (20%) | 6.2 | 5.2 |
| 6 | 5.0 | 4.2 (10%) | 3.5 | 0.9 |
| 14 | 2.9 | 6.0 (10%) | 4.3 | 2.6 |
| 23 | 4.0 | 6.3 (10%) | 3.9 | 2.5 |
| Storage at 4° C. | | | | |
| 1 | 1.8 | 5.9 (10%) | 4.9 | 4.0 |
| 7 | 6.8 | 5.7 (20%) | 6.4 | 5.4 |
| 15 | 3.8 | 4.1 (30%) | 5.5 | 4.2 |
| 24 | 5.3 | 5.3 (10%) | 1.0 | 2.8 |
| 44 | 3.0 | 4.8 (5%) | 0.04 | 0.26 |
| 55 | 2.2 | 5.0 (5%) | 0.00 | 0.24 |
| 90 | >50 | 2.1 (5%) | 0.30 | 0.40 |
| Storage at −17° C. | | | | |
| 1 | 2.6 | 5.2 (10%) | 5.0 | 3.1 |
| 7 | 4.0 | 5.8 (30%) | 6.8 | 5.8 |
| 44 | 3.3 | 5.8 (20%) | 6.0 | 5.4 |
| 90 | 6.1 | 5.2 (30%) | 6.2 | 5.9 |

Dose-Response Effects of Steroid Hormones in CDE-Horse Serum. The dose effects of a number of steroid hormones were evaluated with MTW9/PL2 cells in medium containing 50% (v/v) CDE-horse serum. The results of one of these studies (N=3) are presented in FIG. 11. Estrogens were the most effective mitogens. Their order of potency was $E_2 > E_1 > E_3$. This relative potency was expected based on the affinities of these steroids for the estrogen receptors of other target tissues (Clark J H and Markaverich B M (1983) *Phannacol Ther* 21, 429-453). The cell numbers in dishes containing $1.0 \times 10^{-13}$ M $E_2$ were 32-fold (p<0.01) higher than in dishes without the hormone. Concentrations of $1.0 \times 10^{-12}$ to $1.0 \times 10^{-11}$ M $E_2$ promoted 6.73 CPD that was a 110-fold estrogenic effect in seven days. The $ED_{50}$ of $E_2$ was about 0.5 to $1.0 \times 10^{-12}$ M. Using $E_1$ and $E_3$, optimum growth was achieved at $1.0 \times 10^{-9}$ and $1.0 \times 10^{-8}$ M, respectively. In experiments not shown, the mitogenic potency of the synthetic estrogen DES was assessed. At $1.0 \times 10^{-8}$ M, it caused the same growth as saturating concentrations of the natural estrogens. The DES effect was 6.98 CPD in seven days that was a 126-fold ($2^{6.98}$) increase in cell number. The next most potent hormone was DHT. It caused significant (p<0.05) growth at super physiologic concentrations $\geq 1.0\times10^{-8}$ M. Progesterone also caused significant growth, but only at supraphysiological concentrations $\geq 1.0\times10^{-7}$ M. Cortisol was ineffective at concentrations up to $1.0\times10^{-5}$M.

Figure 12:
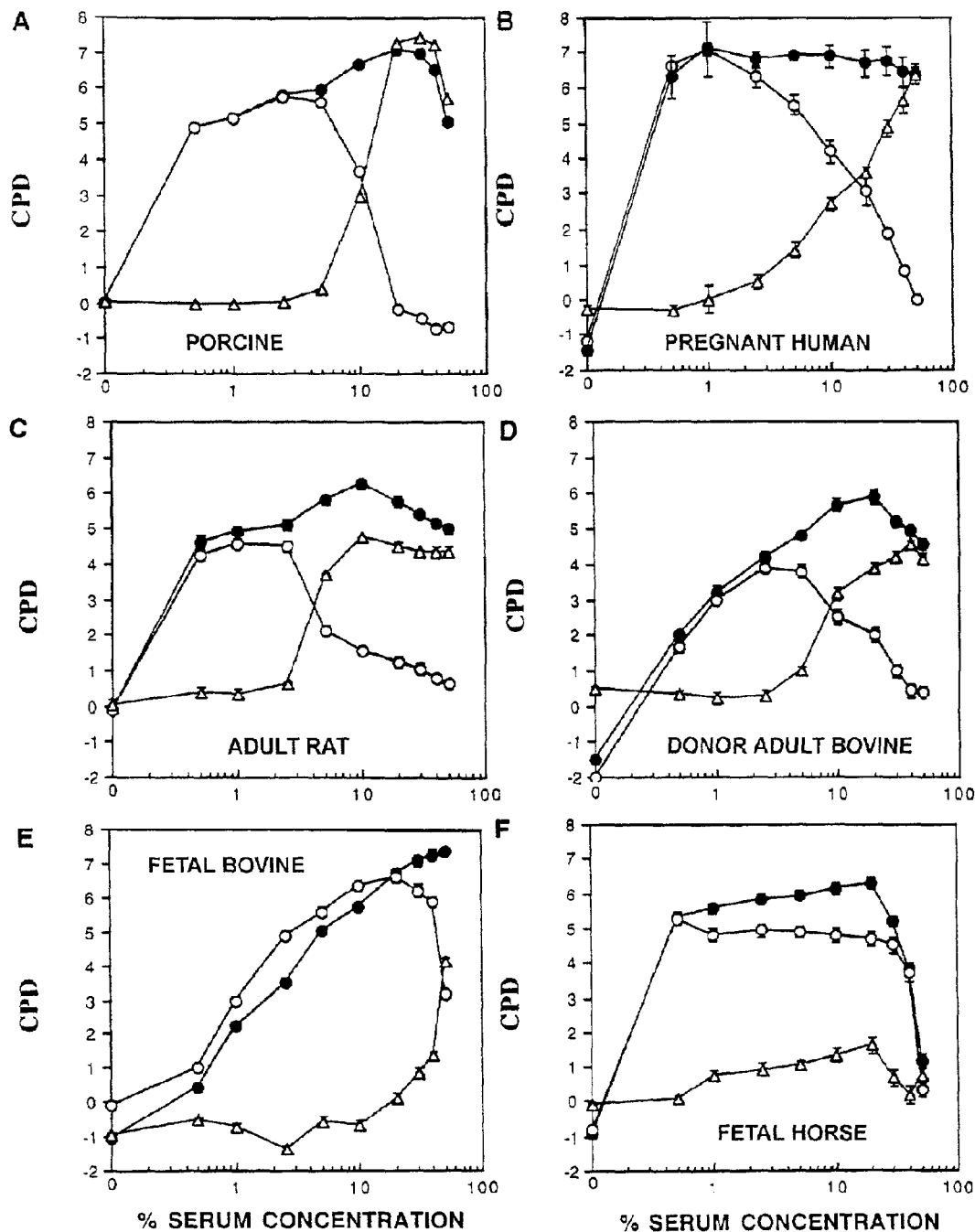
FIG. 12. MTW9/PL2 Cell Growth±$E_2$ in Medium with CDE Sera from Several Species. (A) CDE-porcine Serum; (B) CDE-pregnant Human Serum; (C) CDE-adult Rat Serum; (D) CDE-adult Bovine Serum; (E) CDE-fetal Bovine Serum; (F) CDE-fetal Horse Serum.

Estrogen Mitogenic Effects with MTW9/PL2 Cells in CDE-Serum from Several Species. Serum from species other than horse were examined to determine they also possessed estrogen reversible inhibitory activity with rat MTW9/PL2 cells. These experiments are shown in FIG. 12. All of the sera tested were charcoal dextran extracted at 34° C. CDE-porcine (FIG. 12A), and CDE-human serum (FIG. 12B) showed patterns nearly identical to that of CDE-horse serum. The maximum estrogenic effects with both sera were six to seven CPD (N=3). CDE-rat serum also showed the same pattern of estrogen reversible growth inhibition (FIG. 12C). CDE-ovine serum showed estrogen reversible inhibition equivalent to CDE rat serum (data not shown). With serum from rats, the maximum estrogenic effect was four to five CPD (N=4). CDE-bovine serum (adult donor herd) displayed the same pattern of activity as other sera (FIG. 12D). CDE-fetal bovine serum showed a different pattern (FIG. 12E). Even at 40% (v/v), there was no inhibition. With some batches of this serum, there was no inhibition even at 50% (N=2). With others (N=2), inhibition was found. In these experiments, the estrogenic effects reached three to four CPD in 50% (v/v) CDE-serum. Even with this variability, fetal bovine serum has less activity than the serum from the adults of this species. The assays with CDE-fetal horse serum (N=3) showed inhibition at 50% (v/v) that was not reversible by 10 nM $E_2$ (FIG. 12F). The present study shows very clearly that estrogen growth effects were not found in medium with 5% (v/v) fetal bovine serum, as also reported (Moreno-Cuevas J E and Sirbasku D A (2000) *In Vitro Cell Dev Biol* 36, 410-427). In fact, charcoal-dextran treated fetal bovine serum at concentrations of $\leq$40% (v/v) does not cause inhibition of estrogen target cell growth in culture.

Technical Conditions for Demonstrating Estrogen Responsiveness in Culture and Evidence for a Serum-Borne Inhibitor. Conditions that permit the observation of very large magnitude estrogen mitogenic effects with the permanent MTW9/PL2 cell line in culture are defined herein. As mentioned in the Background of the Invention, most existing rat mammary tumor cell lines are not suitable for use in evaluating hormone responsiveness in vivo because they are derived from outbred animals. This problem was overcome by developing the MTW9/PL2 rat mammary tumor cell line from a carcinogen-induced hormone responsive tumor (i.e. the MT-W9A tumor), first induced and transplanted in an inbred W/Fu rat as described (MacLeod R M et al. (1964) *Cancer Res* 75, 249-258). The MTW9/PL2 cells form hormone responsive tumors when implanted in these rats (Sirbasku D A (1978) *Cancer Res* 38, 1154-1165; Danielpour D and Sirbasku D A (1984) *In Vitro* 20, 975-980; Riss T L et al. (1986) *J Tissue Culture Methods* 10, 133-150). In culture, the MTW9/PL2 cells showed the same hormone responsiveness expected of rat and human breast epithelial cells, as shown herein and subsequently reported (Moreno-Cuevas J E and Sirbasku D A (2000) *In Vitro Cell Dev Biol* 36, 410-427; Sirbasku D A and Moreno-Cuevas J E (2000) *In Vitro Cell Dev Biol* 36, 428-446; Moreno-Cuevas J E and Sirbasku D A (2000) *In Vitro Cell Dev Biol* 36, 447-464).

The effects of the steroid hormones in culture were the same as described for the growth of the original MT-W9A tumor in W/Fu rats (MacLeod et al. (1964) *Endocrinology* 75, 249-258) and tumor formation by the parental MTW9/PL cell line in this same strain of rats (Sirbasku D A (1978) *Cancer Res* 38, 1154-1165). The present embodiment is the first established cell line derived from a carcinogen induced rat mammary tumor that continues to show large magnitude growth responses to estrogens, progesterone and androgens even after extended periods in culture, preferably when cultured under the conditions disclosed herein. Thyroid hormone responsiveness has also been demonstrated for MTW9/PL cells (Leland F E et al. (1981) In: *Functionally Differentiated Cell Lines*, Sato G, ed, Alan Liss, New York, pp 1-46). Of the other important hormones known to influence the growth of the original MT-W9A tumor, only prolactin remains to be investigated. Prolactin is not mitogenic for the parental MT9/PL cells under serum-free defined conditions (Danielpour D et al. (1988) *In Vitro Cell Dev Biol* 24, 42-52). Continuing investigations are directed toward evaluating the possibility that prolactin also reverses the effects of the serum-borne inhibitor or otherwise acts as a cytokine to influence the production of immunoglobulins in breast and other mucosal tissues. The development of this cell line now permits not only sensitive steroid hormone growth analysis in culture, but also direct comparisons to the effectiveness of the same test substances in animals. No other such rat mammary system is currently available.

MTW9/PL2 Receptor Not Lost in Culture. The present results showing an average 86-fold MTW9/PL2 cell number increase in seven days in response to physiological concentrations of $E_2$ have several important technical implications. Most notably, they contradict many earlier explanations for why estrogen stimulated cell growth has been difficult to demonstrate in culture. Originally, the lack of estrogenic effects in culture was thought to be due to a dedifferentiation of cells that resulted in a loss of functional receptors or some other aberration that disrupted the growth response. In light of the present Disclosure, this explanation now seems very unlikely. The present results show the presence of similar levels of estrogen receptors in both the original MTW9/PL cell line reported in 1982 and the current MTW9/PL2 cells. Analyses made by others showing estrogen receptors in established cell lines in culture (Horwitz K B et al. (1978) *Cancer Res* 38, 2434-2437; Haug E (1976) *Endocrinology* 104, 429-437; Soto A M et al. (1988) *Cancer Res* 48, 3676-3680; Keydar I et al. (1979) *Eur J Cancer* 15, 659-670; Engel L W et al. (1978) *Cancer Res* 38, 3352-3364) also mitigate against this explanation. Furthermore, the estrogen receptors of the MCF-7 cells were functional based on the demonstration of estrogen inducibility of the progesterone receptor (Horwitz K B and McGuire W L (1978) *J Biol Chem* 253, 2223-2228). As with the human breast cancer cells, the MTW9/PL2 line was also significantly estrogen responsive by this criterion. When all of the available data is considered in light of the presently disclosed observations, the notion that long-term culture necessarily leads to loss of functional estrogen receptors is laid to rest. A major advantage of the MTW9/PL2 line is its long-term stability permitting series analyses over long periods of time without concern for cell property changes.

Figure 11:
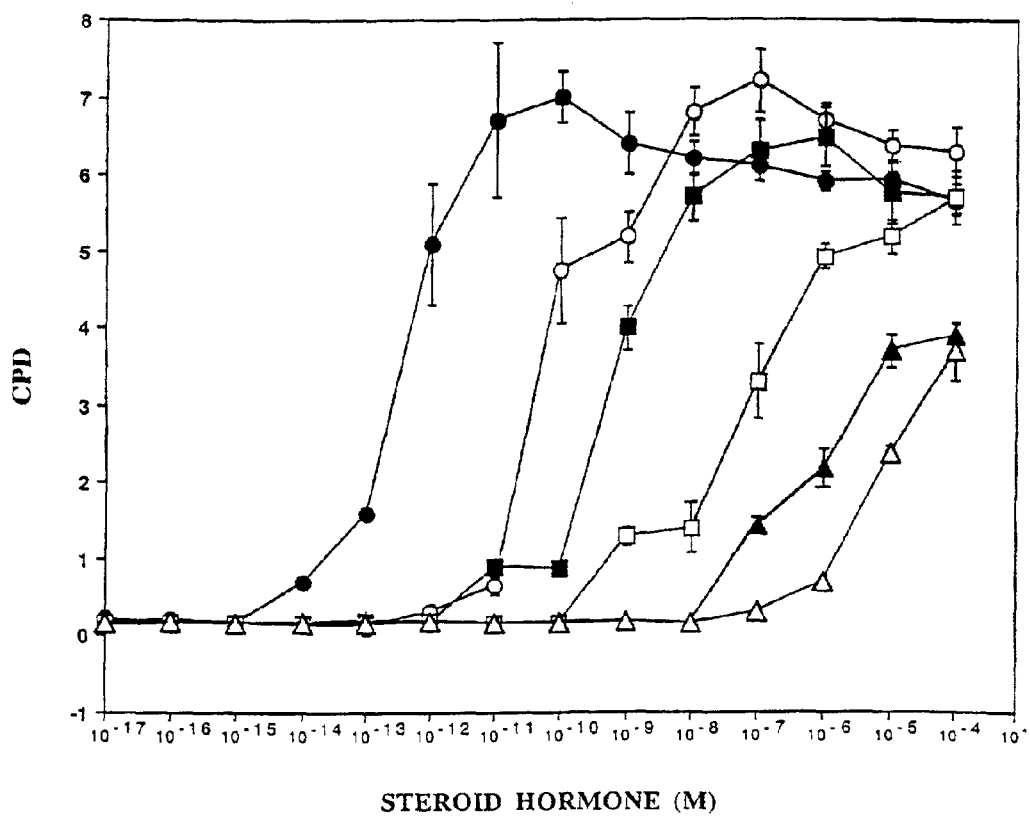
FIG. 11. Dose-Response Effects of Steroid Hormones on Growth of the MTW9/PL2 Cells in Medium Containing 50% (v/v) CDE-horse Serum.

Prolonged Steroid Hormone Retention by Culture Cells. It has been suggested that prolonged retention of estrogens might be the reason for a lack of responsiveness of target cells in culture (Strobl J S and Lippman M E (1979) *Cancer Res* 39, 3319-3327). Investigators have reported that the half-life of loss of specifically bound $^3H$-$E_2$ from MCF-7 cells was about 24 hours at 37° C. (Strobl J S and Lippman M E (1979) *Cancer Res* 39, 3319-3327). Cells from stock cultures grown in untreated/steroid hormone containing serum were proposed to retain stimulating levels of estrogens. Even several washes over 78 hours did not attenuate the problem (Strobl J S and Lippman M E (1979) *Cancer Res* 39, 3319-3327). Conversely, the studies herein did not identify this problem. All the assays reported here were done with cells taken directly from cultures grown in steroid hormone containing serum (e.g. fetal bovine serum). After trypsinization of the MTW9/PL2 cells from stock culture, only three careful washes with serum-free D-MEM/F-12 were performed before initiating the growth assays. The results in FIG. 11 show clearly that $1.0 \times 10^{-12}$ M $E_2$ caused significant MTW9/PL2 cell growth. Also, the results in FIG. 10 show that MTW9/PL2 cells cease proliferation within 48 hours of starting a growth assay. These observations either support the conclusion that prolonged steroid hormone retention by cells is not as serious an issue as first proposed or are evidence that the technical processes described herein to prepare cells for assays have eliminated this problem. With regard to the present investigation, all cell lines studied showed this same property when prepared by the same technical process for growth assays.

Merits of Charcoal Extraction. Other investigators have challenged the use of charcoal extraction to deplete serum of steroid hormones. It has been stated that this procedure absorbs or otherwise alters serum to make it ineffective (Amara J F and Dannies P S (1983) *Endocrinology* 112, 1141-1143; Wiese T E et al. (1992) *In Vitro Cell Dev Biol* 28A, 595-602). To counter this problem, either individual lots of untreated serum were used to seek estrogenic effects (Wiese T E et al. (1992) *In Vitro Cell Dev Biol* 28A, 595-602), or serum was prepared from animals after endocrine ablation surgery (Amara J F and Dannies P S (1983) *Endocrinology* 112, 1141-1143). One of the best examples of use of surgically depleted serum came from the study of the $GH_4C_1$ rat pituitary cells (Amara J F and Dannies P S (1983) *Endocrinology* 112, 1141-1143). They were highly $E_2$ responsive in medium supplemented with the serum from a gelded horse (Amara J F and Dannies P S (1983) *Endocrinology* 112, 1141-1143). However, experience with serum derived by these methods has not been as positive. For example, this issue was inventigated in 1976 with the related $GH_3C_{14}$ rat pituitary tumor cell line (Kirkland W L et al. (1976) *J Natl Cancer Inst* 56, 1159-1164), and found that serum from ovariectomized sheep or adrenalectomized and ovariectomized sheep did not support estrogen effects. Furthermore, unextracted serum from different species can at times support limited estrogenic effects. However, the estrogenic effects are of lower magnitude than those in the CDE-serum described herein. Based on the observation that CDE-serum from a number of species was very effective, it seems highly unlikely that the now-disclosed preferred 34° C. procedure is deleterious. However, it is clear that the 56° C. charcoal method caused a temperature dependent loss of the inhibitor (FIG. 26). The presently described CDE-serum provides greater consistency and reproducibility than the other proposed approaches (Amara J F and Dannies P S (1983) *Endocrinology* 112, 1141-1143; Wiese T E et al. (1992) *In Vitro Cell Dev Biol* 28A, 595-602). Another advantage is that these results do not dependent significantly on the lot of serum purchased. Furthermore, CDE-serum consistently provides larger magnitude estrogenic effects than serum obtained by either of the other approaches discussed above.

Steroid Hormone Conjugates are Non-Problematic. While charcoal treatment can be expected to remove the major classes of steroid hormones from serum, there is a question about its effect on the more soluble and potentially active conjugates. It has been reported that hydrolysis of estrogen sulfates provided free estrogens in human breast cancer cell cultures (Vignon F et al. (1980) *Endocrinology* 106, 1079-1086). This abrogated the effects of exogenous $E_2$. Although the previous investigations did not address estradiol sulfate, it was shown that more than 95% of estrone sulfate and estradiol glucuronide were removed from serum by a single 56° C. charcoal extraction (Sirbasku D A and Kirkland W L (1976) *Endocrinology* 98, 1260-1272). Additionally, in previous studies MTW9/PL cells were incubated with tritium labeled estradiol glucuronide for up to 24 hours under cell culture conditions and found no organic solvent extractable free steroid. Both past and current results indicate that the impact of the estrogen conjugates has been overestimated. In the present study, no precautions were taken to remove the conjugated forms of estrogens from any of the sera tested. Despite this, it was found that many different types of serum were effective after charcoal extraction at 34° C. Thus, it is concluded that removal of steroid conjugates by digestion or any procedure beyond charcoal treatment is unnecessary. This is a further advantage of the new CDE method because the additional treatment to remove the steroid conjugates could be prohibitive for larger scale production than a few liters.

Plastic Product Use for Cell Culture. The present studies were done with plastic ware made of polystyrene. Plastic is manufactured using alkylphenols (Platt A E (1978) In: *Encyclopedia of Chemical Technology*, Kirk R E, Othmer D F, eds, 3$^{rd}$ Edition, Volume 26, Wiley, New York, pp 801-847). One of these compounds, p-nonyl-phenol, has been reported to be estrogenic for MCF-7 cells in culture (Soto A M et al. (1991) *Environ Health Perspect* 92, 167-173). This xenobiotic most likely is present in the cultures used in these studies. No precautions were taken to exclude compounds leaching from plastic. In fact, the bioassay procedures herein are done with polystyrene plastic ware and culture dishes almost exclusively. If there had been a significant contamination of the medium by such compounds, the estrogenic effects reported in this study should not have been seen or should have been markedly attenuated. An advantage of the assay systems described herein is that they have no need for expensive and or exotic substitutes for the common plastic ware used in cell culture laboratories to conduct bioassays. Also, the CDE-serum can be stored and shipped for commercial use in plastic containers without concern for creation of plastic-induced artifacts.

Discussion of Example 3.

Using the present 34° C. CDE and XAD-4 serum, estrogen responsiveness can be demonstrated in rat tumor cells, where no such responsiveness had previously been demonstrated. Further, because estrogen responsiveness and binding affinity can now be compared, data indicating the existence of a heretofore unknown estrogen receptor have been generated.

Example 4

Estrogen Responsive Growth of Additional Rodent and Human Cell Lines In Charcoal-Dextran Extracted Horse and Human Serum In addition to the above-described studies using the MTW9/PL2 rat mammary tumor cell line, several other cell lines were employed to define the conditions for demonstrating estrogen and androgen responsive cell growth. Established cell lines from a number of different steroid hormone target tissues were selected for growth regulation analysis under those defined conditions.

Figure 13:
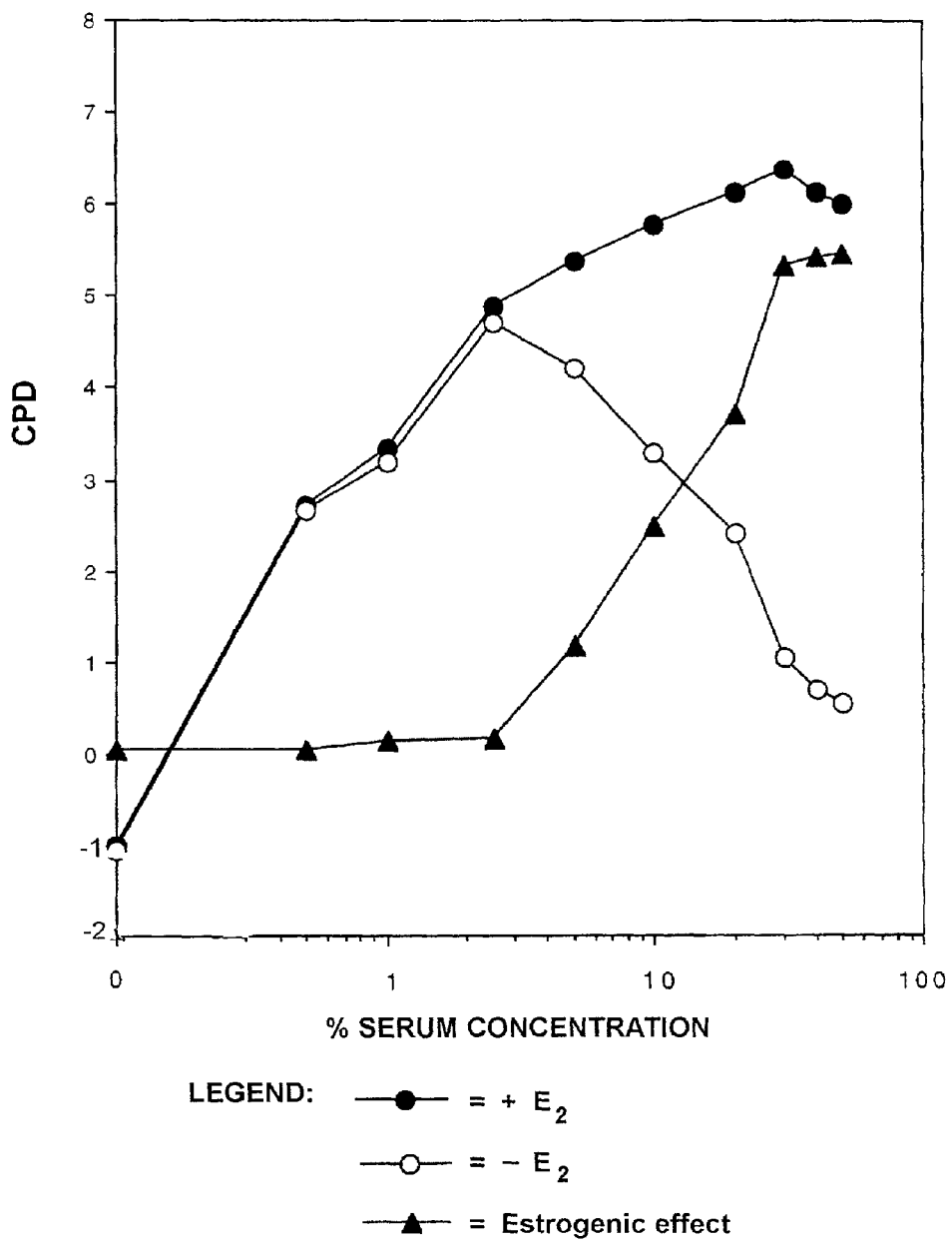
FIG. 13. CDE-horse Serum Effect on $GH_4C_1$ Cell Growth±10 nM $E_2$ for 10 days.
Figure 14:
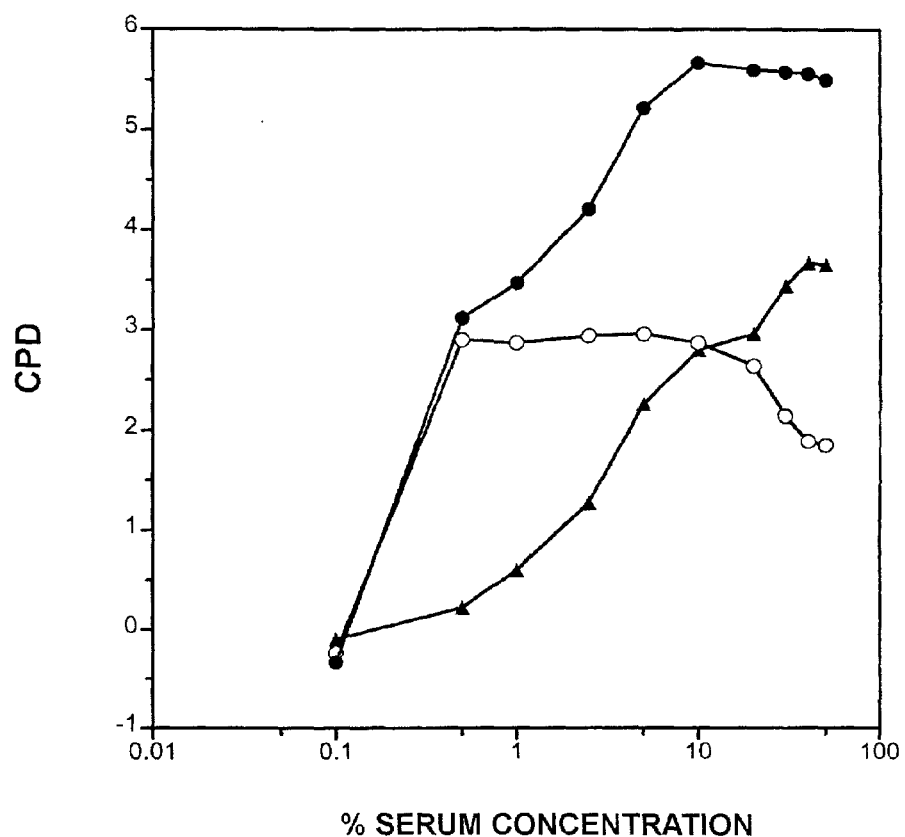
FIG. 14. CDE-horse Serum Effect on ZR-75-1 Cell Growth±10 nM $E_2$ for 14 days.
Figure 15:
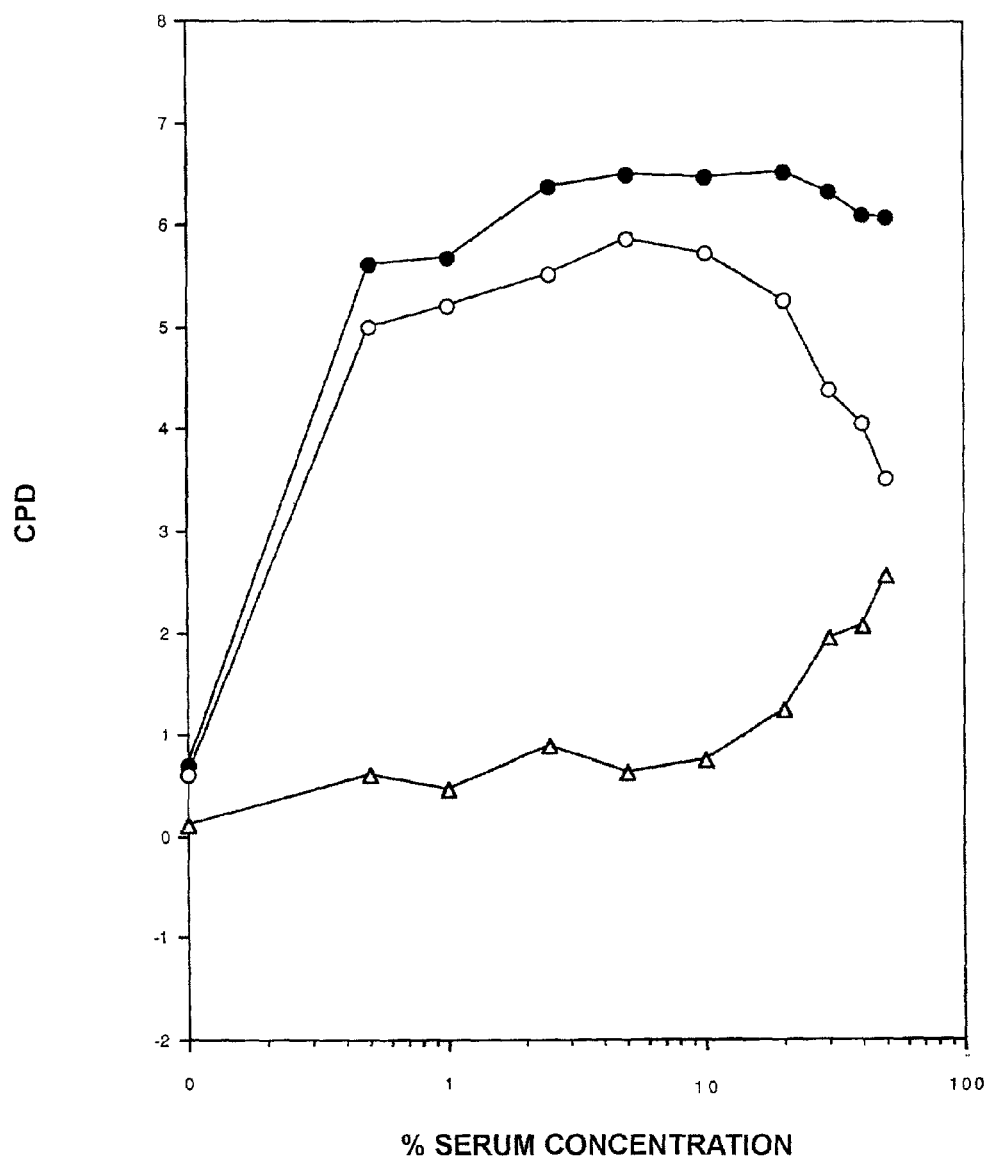
FIG. 15. CDE-horse Serum Effect on MCF-7A Cell Growth±10 nM $E_2$ for 10 days.

Estrogen Mitogenic Effects with Established ER$^+$ Rodent Tumor and Human Carcinoma Cells in CDE-Horse Serum. In the first study of this series, the three GH rat pituitary tumor cell lines were examined for estrogenic effects in CDE-horse serum. This was considered important in light of their clear responsiveness to many hormones (Tashjian A H Jr (1979) *Methods Enzymol* 58, 527-535). Furthermore, these cells are from a tissue that grows coordinately with mammary tissue in castrated rats administered exogenous estrogens. As described above, this suggested a common regulation mechanism. FIG. 13 shows an estrogenic effect≧5 CPD with $GH_4C_1$ cells in 10 days. The results with $GH_3$ and $GH_1$ cells ranged between 4.0 and 5.2 CPD in 10 to 14 day assays (data not shown). The same progressive estrogen reversible CDE-serum inhibition was demonstrable with both rat mammary and rat pituitary tumor cells in CDE-horse serum. To confirm the effectiveness CDE-horse serum with human cells, the ZR-75-1 breast cancer line was selected because of previous attempts to demonstrate its estrogen responsiveness in culture (Allegra J C and Lippman M E (1978) *Cancer Res* 38, 3823-3829; Darbre P D et al. (1984) *Cancer Res* 44, 2790-2793; Darbre P et al. (1983) *Cancer Res* 43, 349-355). The ZR-75-1 cells showed the same CDE-serum caused estrogen reversible inhibition as seen with rodent cell lines in this serum. In 14 days, there was a 3.65 CPD (i.e. 12.5-fold) estrogenic effect (FIG. 14). This was a greater response than recorded in the ZR-75-1 cell studies cited above. Of all of the cell lines studied, the MCF-7A was the least estrogen responsive even in 50% CDE-horse (FIG. 15). The estrogenic effect was 2.65 CPD in 10-12 days. This was still significant ($p<0.01$) as a $2^{2.65}$ or 6.3-fold increase in cell number caused by estrogen. The present serum-derived inhibitor exhibited biological activity exactly opposite the estrogen reversible inhibitors described by M Tanji et al. (Tanji M et al. (2000) *Anticancer Res.* 20, 2779-2783; Tanji M et al. (2000) *Anticancer Res.* 20, 2785-2789).

Additional Cell Lines Evaluated. Evidence is presented herein that the MCF-7K, T47D, LNCaP, and H301cells are highly sex steroid hormone responsive in CDE-horse serum.

Kinetics of Estrogen Responsive Growth in CDE Serum Containing Medium. In the experiments presented in FIGS. 16A and 16B, $ER^+$ cell growth was measured daily for 15 days to determine cell growth kinetics$\pm E_2$. The results with the T47D line are presented as characteristic of human cells. When evaluated in medium with partially inhibitory 20% (v/v) CDE horse serum, the effect of $E_2$ on cell number increase was not apparent until after 4 days (FIG. 16A). Increasing the concentration of CDE serum to 50% (v/v) further delayed the effect of $E_2$ (FIG. 16B). Clearly, whatever mechanism is proposed for the action of the steroid hormone, it takes a significant period to reverse the effects of the inhibitor. This process cannot be simply due to a rapid effect on transcription caused by steroid hormones. The interaction of $^3H$-$E_2$ with intracellular estrogen receptors saturates in≦1 hour at 37° C. (Horwitz K B and McGuire W L (1978) *J Biol Chem* 253, 8185-8191; MacIndoe J H et al. (1982) *Steroids* 39, 245-258; Moreno-Cuevas J E and Sirbasku D A (2000) *In Vitro Cell Dev Biol* 36, 410-427), while de novo hormone induced protein synthesis requires only a few hours (Beato M (1989) *Cell* 56, 335-344). Based on a growth lag of≧4 days, it is likely that steroid hormones initiate a cascade of signaling events that are more complex than recognized today. To demonstrate that the lag period was related to the inhibitor, T47D growth was monitored daily in D-MEM/F-12 supplemented with 10% (v/v) fetal bovine serum (FIG. 16A). This concentration of fetal bovine serum shows no inhibitor (Moreno-Cuevas J E and Sirbasku D A (2000) *In Vitro Cell Dev Biol* 36, 410-427). Cell growth in medium with fetal bovine serum showed at most a one or two day lag period.

Figure 17:
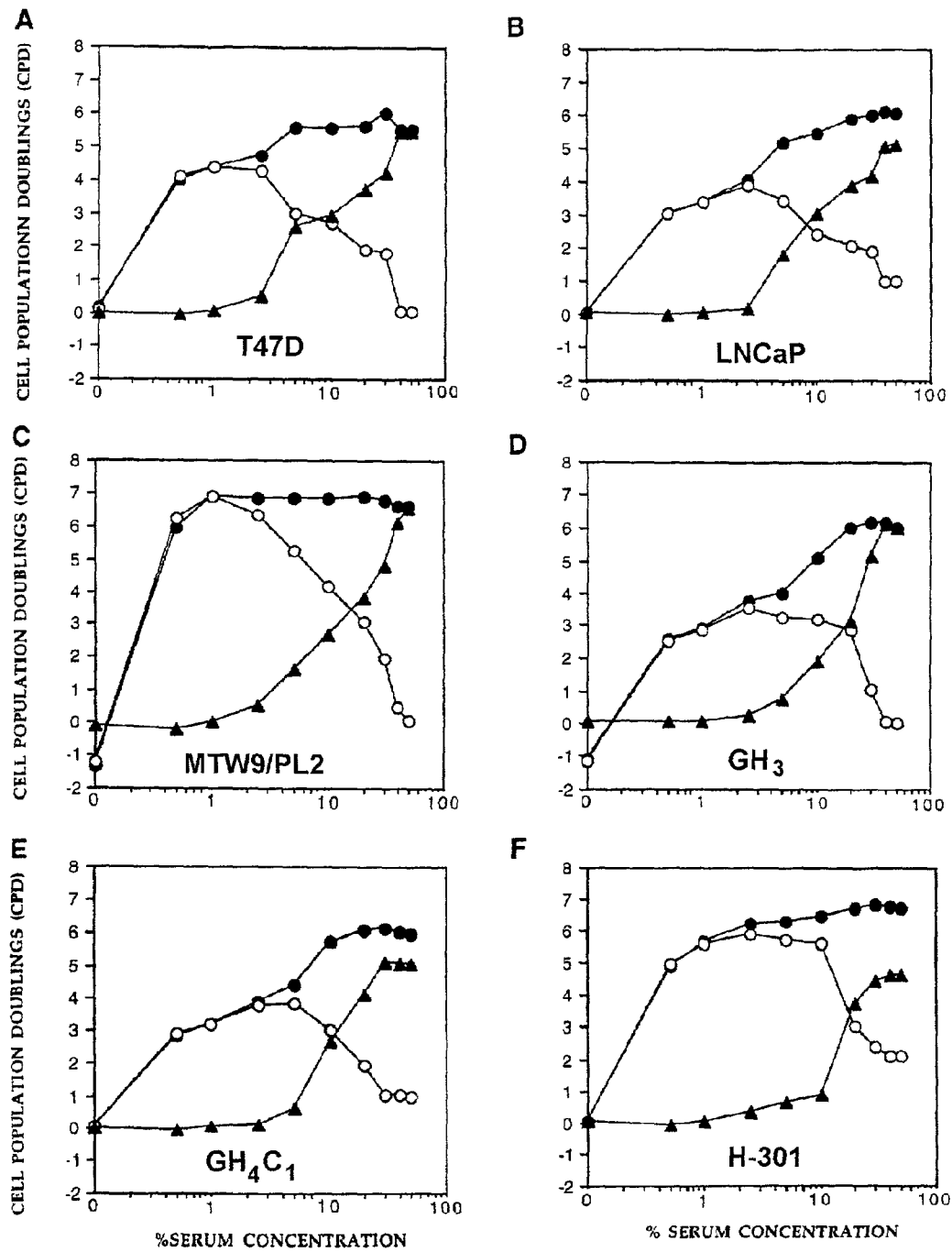
FIG. 17. Rodent and Human $ER^+$ Cell Growth in 50% CDE-human Serum±$E_2$. (A) T47D Human Breast Cancer Cells; (B) LNCaP Human Prostate Cancer Cells; (C) MTW9/PL2 Rat Mammary Tumor Cells; (D) $GH_3$ Rat Pituitary Tumor Cells; (E) $GH_4C_1$ Rat Pituitary Tumor Cells; (F) H301 Syrian Hamster Kidney Tumor Cells.

Effect of CDE-Human Serum on Estrogen Responsive Cell Growth. The next study examined whether human serum was a source of inhibitor for steroid hormone sensitive cell lines from different species and tissues. The results confirm that CDE-human serum contains approximately the same level of inhibitor as CDE-horse serum. Results are shown with T47D human breast cancer cells (FIG. 17A), LNCaP human prostatic carcinoma cells (FIG. 17B), MTW9/PL2 rat mammary tumor cells (FIG. 17C), two GH rat pituitary tumor cell lines (FIGS. 17D and 17E), and the Syrian hamster H301 kidney tumor cells (FIG. 17F). All lines showed the same biphasic response to CDE-human serum. Low concentrations (i.e.≦10%) promoted growth whereas higher concentrations (i.e.≧20%) progressively inhibited growth. Only the absolute magnitudes of the estrogenic effects varied. Replicate assays with MCF-7A, MCF-7K and ZR-75-1 cells gave the same outcomes (data not shown). The experiments reported thus far herein support the conclusion that the inhibitor is ubiquitous in mammals and is not species specific, also subsequently reported (Sirbasku D A and Moreno-Cuevas (2000) *In Vitro Cell Dev Biol* 36, 428-446).

Figure 18:
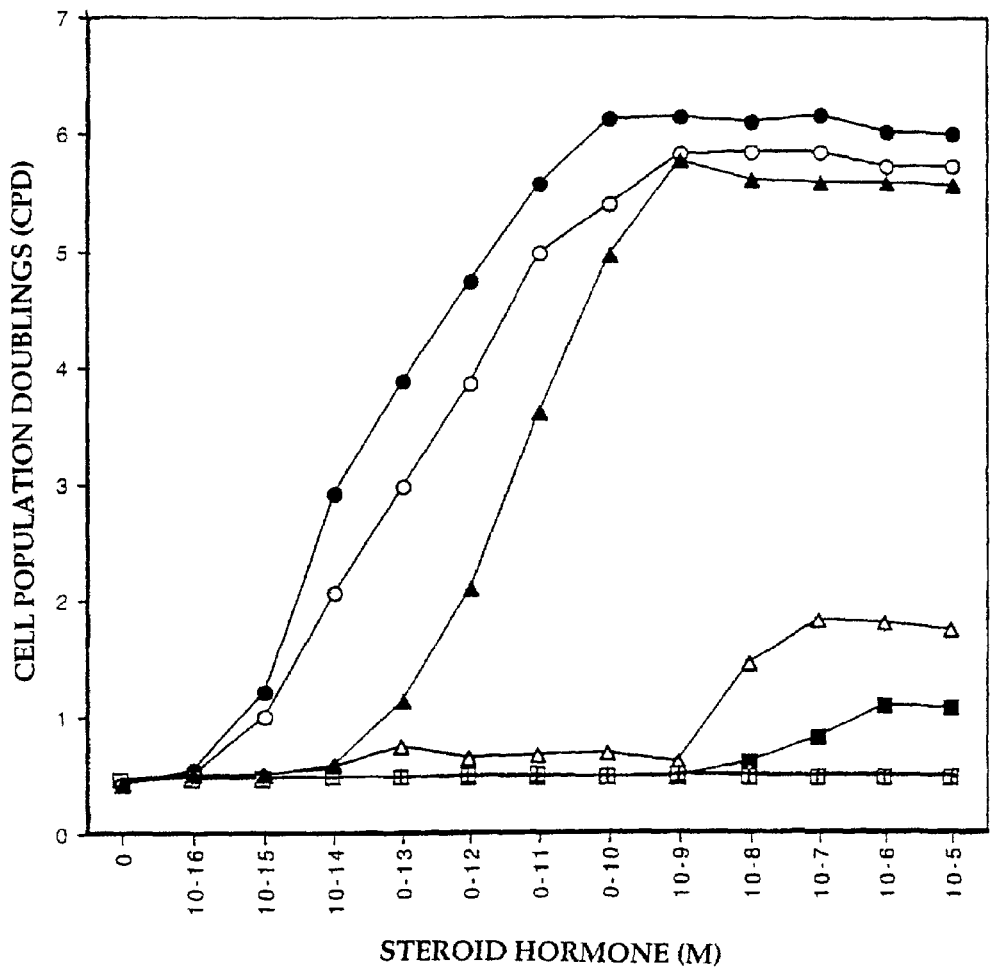
FIG. 18. Dose-Response of Steroid Hormones with T47D Cells in 50% CDE-horse Serum.

Dose-Response Effects of Steroid Hormones with Human Breast Cancer Cells in CDE Serum. The studies presented thus far have assessed estrogen effects using 10 nM $E_2$ Although 10 nM saturates growth, it is decidedly at the high boundary of physiological. It is important to note that circulating estrogens in non-pregnant females are generally thought to be in the range of $10^{-8}$ to $10^{-10}$ M (Clark J H et al. In: *Williams Textbook of Endocrinology* (1992), Saunders, Philadelphia, pp 35-90). Tissue concentrations are generally conceded to be lower due to SHBG that reduces the "free" or "active" form of sex steroid hormones (Rosner W (1990) *Endocr Rev* 11, 80-91). The next studies with T47D cells determined the effective concentration ranges for the three most common estrogens and compared these to non-estrogen steroid hormones. FIG. 18 shows an analysis with T47D cells in D-MEM/F-12 containing 50% (v/v) CDE horse serum for 14 days. Estrogens were the only physiologically relevant activators of T47D growth. As expected from previous studies with breast cancer cells (Lippman M E et al. (1977) *Cancer Res* 37, 1901-1907; Jozan S et al. (1979) *J Steroid Biochem* 10, 341-342; Katenellenbogen B S (1980) *Annu Rev Physiol* 42, 17-35) and other estrogen target tissues (Clark J H and Markaverich B M (1983) *Pharmacol Ther* 21, 429-453), their order of effectiveness was $E_2>E_1>E_3$. $E_2$ caused significant ($p<0.05$) growth when present at $1.0\times10^{-14}$ M and optimum growth at $1.0\times10^{-10}$ M. Higher concentrations were not inhibitory. The $ED_{50}$ concentration of $E_2$ was≦$1.0\times10^{-13}$ M. It is noteworthy that even $E_3$ was remarkably potent. Others also had commented that $E_3$ was more potent than expected (Lippman M E et al. (1977) *Cancer Res* 37, 1901-1907). This observation may have special significance because breast cancers that appear during pregnancy can be particularly life threatening. Human maternal plasma has greatly elevated levels of $E_3$ during the last trimester of pregnancy. Testosterone and DHT promoted growth but only at supraphysiological concentrations (FIG. 18). Other investigators have suggested that supraphysiological concentrations of androgens act through the ER of human breast cancer cells (Zava D T and McGuire W L (1978) *Science* (Wash D.C.) 199, 787-788). However, another group has reported no effect of androgens on human breast cancer cell proliferation (Soto A M and Sonnenschein C (1985) *J Steroid Biochem* 23, 87-94). In the present study, progesterone and cortisol were completely ineffective with T47D cells (FIG. 18). Others have also reported negative results with these hormones and human breast cancer cells (Schatz R W (1985) *J Cell Physiol* 124, 386-390; Soto A M and Sonnenschein C (1985) *J Steroid Biochem* 23, 87-94). The data presented in this Disclosure support the conclusion that the new CDE serum culture conditions yield physiologically relevant information.

Figure 19:
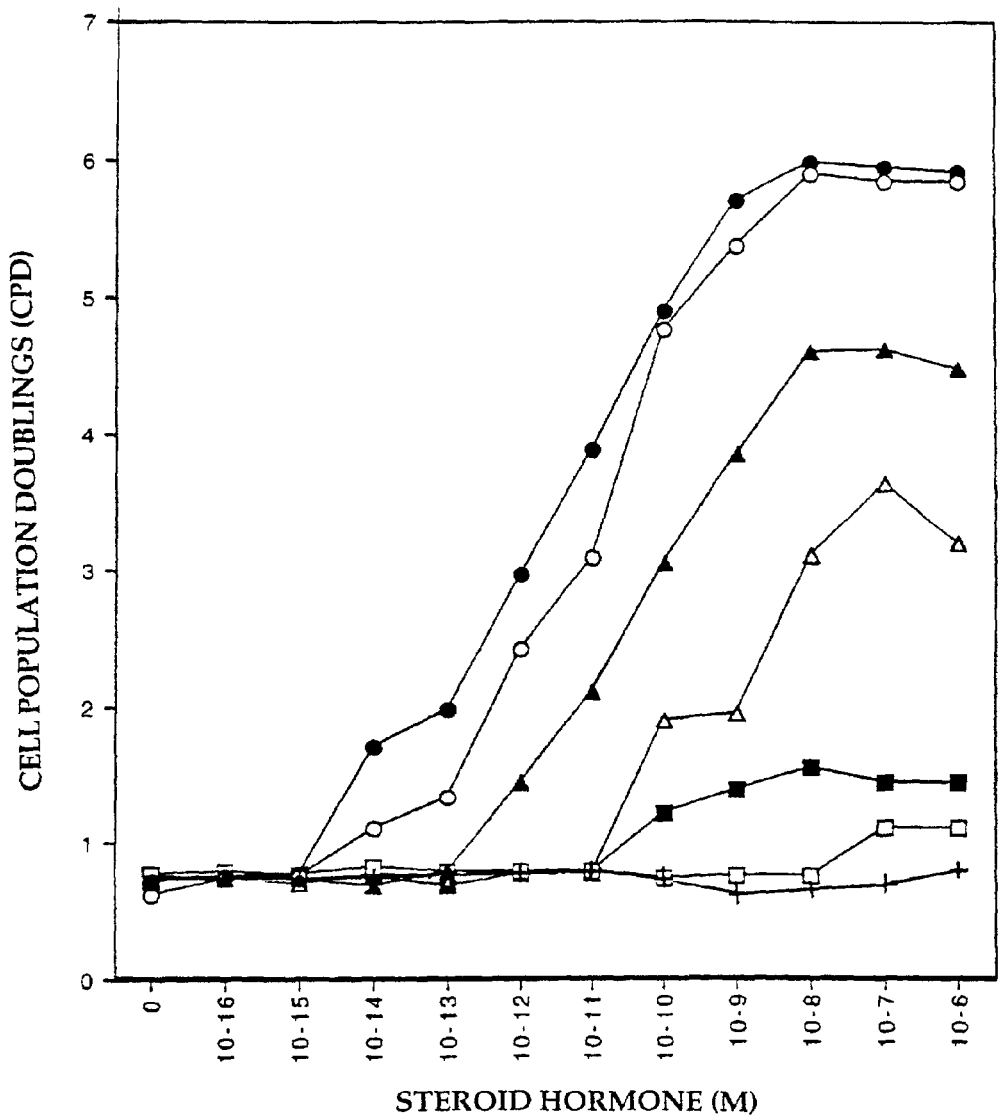
FIG. 19. Dose-Response of Steroid Hormones with $GH_4C_1$ Cells in 50% CDE-horse Serum.

Dose-Response Effects of Steroid Hormones with Rat Pituitary Tumor Cells in CDE Serum. The GH family of related cell lines responds to a number of different classes of hormones (Amara J F and Dannies P S (1983) *Endocrinology* 112, 1141-1143; Tashjian A H Jr et al. (1970) *J Cell Biol* 47, 61-70; Tashjian A H Jr (1979) *Methods Enzymol* 58, 527-535; Haug E (1979) *Endocrinology* 104, 429437; Schonbrunn A et al. (1980) *J Cell Biol* 85, 786-797; Sorrentino J M et al. (1976) *J Natl Cancer Inst* 56, 1159-1164; Ramsdell J S (1991) *Endocrinology* 128, 1981-1990; Hayashi I et al. (1978) *In Vitro* 14, 23-30; Faivre-Bauman A et al. (1975) *Biochem Biophys Res Commun* 67, 50-57). These cells also form steroid hormone responsive tumors in W/Fu rats (Sorrentino J M et al. (1976) *J Natl Cancer Inst* 56, 1149-1154). The $GH_4C_1$ strain was selected as an example for this next study because of its marked $E_2$ responsiveness in culture (Amara J F and Dannies P S (1983) *Endocrinology* 112, 1141-1143; Sirbasku D A and Moreno-Cuevas J E (2000) *In Vitro Cell Dev Biol* 36, 428-446; Sato H et al. (1991) *In Vitro Cell Dev Biol* 27A, 599-602) and estrogen requirement for tumor formation in rats (Riss T L and Sirbasku D A (1989) *In Vitro Cell Dev Biol* 25, 136-142). The dose-response effect of steroid hormones with $GH_4C_1$ rat pituitary tumor cells in 50% CDE-horse serum was analyzed next. FIG. 19 shows the results of these experiments. All three major estrogens promoted growth. The potencies of $E_2$ and $E_1$ were equivalent whereas $E_3$ was substantially less effective. Even at supraphysiologic concentrations, $E_3$ did not promote the saturation densities seen with $E_2$ and El. The lowest concentration of $E_2$ and $E_1$ that gave significant (p<0.05) growth was $1.0 \times 10^{-12}$ M. The $ED_{50}$ of $E_2$ was $\leq 1.0 \times 10^{-11}$ M. Optimum growth required supraphysiological concentrations (i.e. $1.0 \times 10^{-8}$ M) of $E_2$ and $E_1$. In the present studies, the biphasic effect of $E_2$ reported by Amara and Dannies (Amara J F and Dannies P S (1983) *Endocrinology* 112, 1141-1143) was not found. This may be explained by the different conditions used to conduct the assays. The matter of assay culture conditions with $ER^+$ cells has been discussed (Zugmaier G et al. (1991) *J Steroid Biochem Mol Biol* 39, 681-685). Certainly however, the low $E_2$ concentration for $ED_{50}$ still speaks to a problem with $ER\alpha$ as the mediating receptor. Furthermore, the pattern reported in this Example is consistent with physiological facts. Tumor formation by GH cells was greater in W/Fu rats treated with 25 mg estrogen pellets than in untreated intact sexually mature females (Sorrentino J M et al. (1976) *J Natl Cancer Inst* 56, 1149-1154). Without a doubt, supraphysiological levels of estrogens were most effective in vivo. In contrast to estrogens, progesterone and cortisol had no effect on $GH_4C_1$ growth in culture (FIG. 19). These steroids also did not promote GH cell tumor growth in vivo (Sorrentino J M et al. (1976) *J Natl Cancer Inst* 56, 1149-1154). The findings with androgens and $GH_4C_1$ cell growth shown in FIG. 19 revealed another important contribution made by the work in CDE serum supplemented cultures described herein. It has been shown before that T promoted GH tumor growth in vivo (Sorrentino J M et al. (1976) *J Natl Cancer Inst* 56, 1149-1154). It was proposed at that time that T was effective because it was metabolized to estrogens in the rat. Therefore, it was expected that T would be ineffective in culture. The results in FIG. 19 confirm this expectation. In this case, the new culture methods permitted resolution of an issue arising from previous in vivo observations. The dose-response results in FIG. 19 fortify a conclusion arrived at earlier that cell culture can be used to uncover physiologically important new information not accessible by in vitro methods (McKeehan W L et al. (1990) *In Vitro Cell Dev Biol* 26, 9-23).

Figure 20:
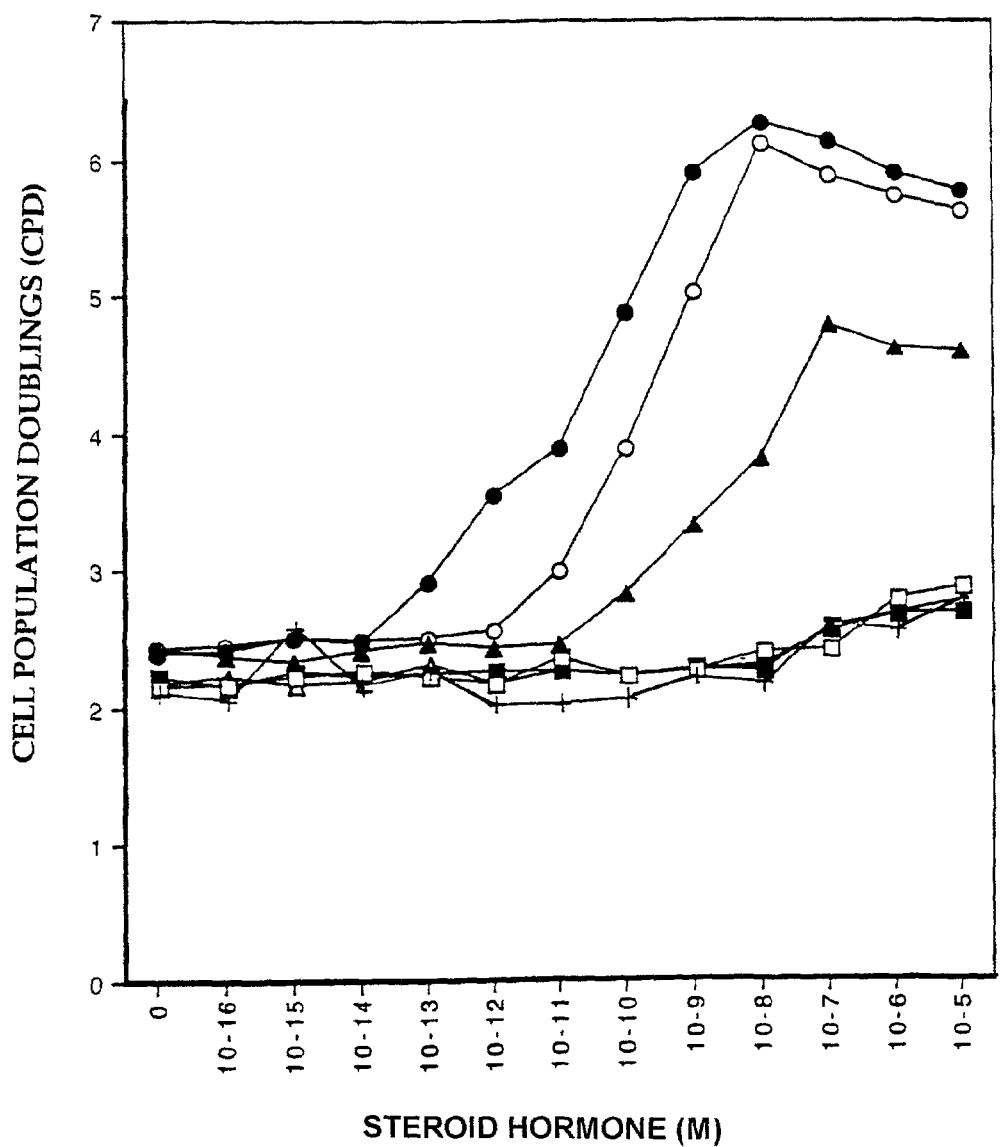
FIG. 20. Dose-Response of Steroid Hormones with H301 Cells in 50% CDE-horse Serum.

Dose-Response Effects of Steroid Hormones with Hamster Kidney Tumor Cells in CDE Serum. To explore the utility of the new culture conditions further, steroid hormone effects on the H-301 Syrian hamster kidney tumor cells in D-MEM/F-12 containing 50% (v/v) CDE-horse serum were investigated. This cell line has two unique characteristics. First, tumors form from H301 cells in Syrian hamsters only in response to exogenous estrogens (Sirbasku D A and Kirkland W L (1976) *Endocrinology* 98, 1260-1272). It is very important to note that normal physiologic levels in intact adult female hamsters do not support tumor formation (Sirbasku D A and Kirkland W L (1976) *Endocrinology* 98, 1260-1272). It is thought that progesterone from the normal estrus cycle suppresses growth in response to physiological levels of estrogen (Kirkman H and Robbins M (1959) In: *National Cancer Institute Monograph No.* 1, National Institutes of Health, Bethesda, Md.). Second, these cells only form tumors in response to estrogens. The other major classes of steroid hormones are ineffective in vivo. The relative effectiveness of the three estrogens with H301 cells was investigated (FIG. 20). Their potency was $E_2 > E_1 > E_3$. As with rat tumor cells, E3 was markedly less effective than $E_2$ or $E_1$. $E_2$ and $E_1$ required $1.0 \times 10^{-11}$ M and $1.0 \times 10^{-10}$ M, respectively, to achieve significant (p<0.05) growth. The $ED_{50}$ concentration of $E_2$ is about 5 to $9 \times 10^{-11}$ M. As expected from in vivo results (Sirbasku D A and Kirkland W L (1976) *Endocrinology* 98, 1260-1272), this concentration was higher than for the rat pituitary tumor cells (FIG. 19) or rat mammary tumor cells (FIG. 11). In fact, they were as much as 100 to 1000-fold higher than for human breast cancer cells (FIG. 18). In other tests shown in FIG. 20, progesterone, cortisol, T and DHT were all inactive. The higher estrogen concentrations required for significant growth of the H-301 cells in culture, coupled with the marked estrogen specificity, indicate that the medium conditions used in this study yielded physiologically germane results.

Figure 21:
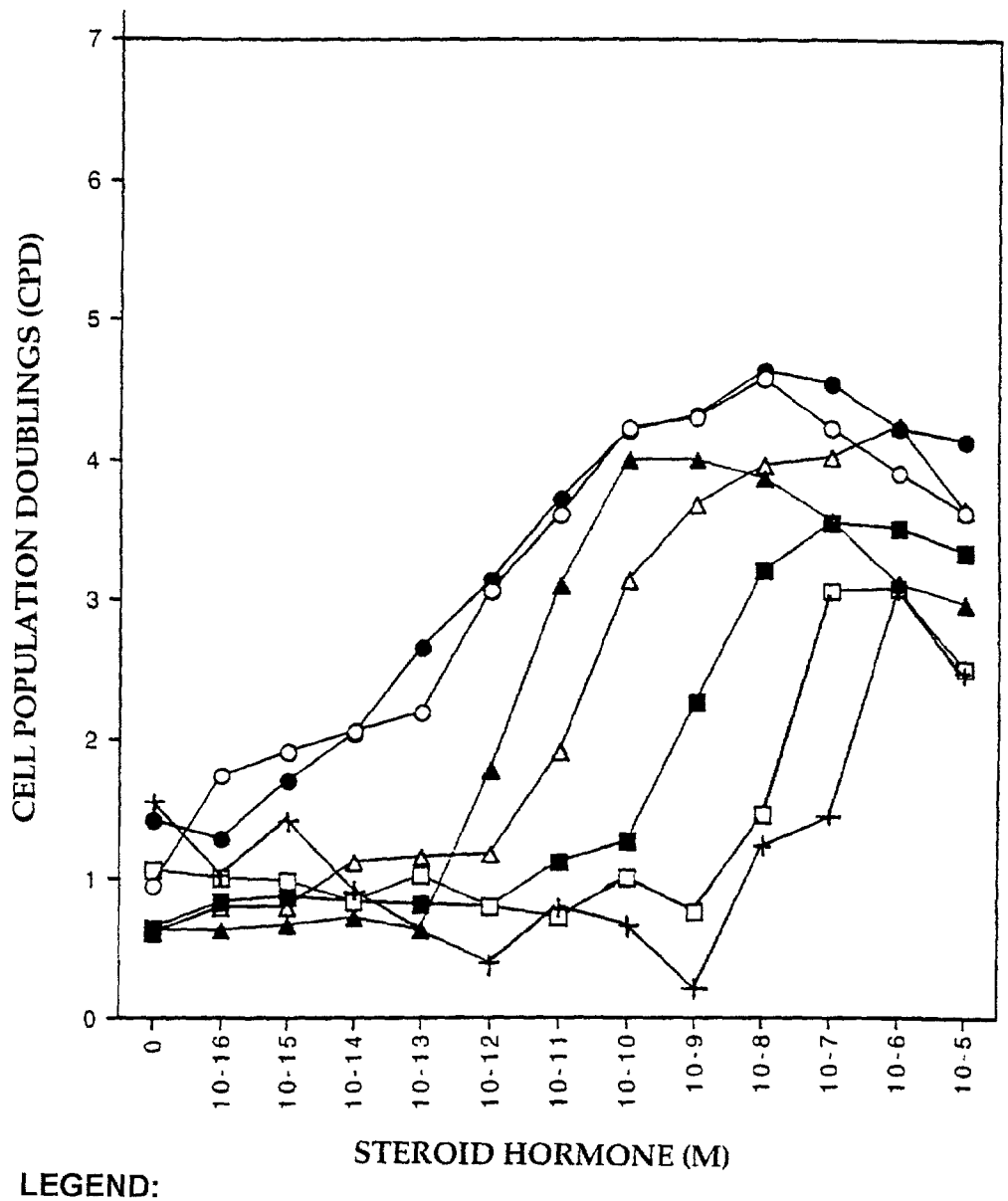
FIG. 21. Dose-Response of Steroid Hormones with LNCaP Cells in 50% CDE-horse Serum.

Dose-Response Effects of Steroid Hormones with Human Prostatic Carcinoma Cells in CDE Serum. In the final dose-response study, the potency of several classes of steroid hormones with the LNCaP cells was analyzed. This was done in D-MEM/F-12 containing 50% (v/v) CDE horse serum. Due to a point mutation which permits binding of both androgen and non-androgen hormones to the AR of LNCaP cells (Veldscholte J et al. (1990) *Biochem Biophys Res Commun* 173, 534-540; Veldscholte J et al. (1990) *Biochim Biophys Acta* 1052, 187-194), the Inventor expected several classes of steroids to promote growth, albeit at concentrations compatible with their known affinities for the mutated receptor. This proved to be the case, as shown in FIG. 21. DHT and $E_2$ were the most potent steroids. In fact, they were equipotent. Both caused significant (p<0.05) growth at $1.0 \times 10^{-12}$ M. Contrary to other reports (Schuurmans A L et al. (1988) *The Prostate* 12, 55-64; Sonnenschein C et al. (1989) *Cancer Res* 49, 3474-3481; de Launoit Y et al. (1991) *Cancer Res* 51, 5165-5170; Lee C et al. (1995) *Endocrinology* 136, 796-803; Kim I et al. (1996) *Endocrinology* 137, 991-999), the present study did not find that high concentrations of DHT inhibited LNCaP growth. The potency of the steroid hormones tested was $DHT=E_2>T>E_1>$progesterone$>E_3>$cortisol. As potencies declined, saturation densities also decreased. The observed relative steroid potencies agreed with those of others (Belanger C et al. (1990) *Ann N.Y. Acad Sci* 595, 399-402), and correlated with the expected binding of the various classes of steroids to the mutated AR of the LNCaP line.

Additionally, the presently disclosed methods offered the advantage of greater growth responses. The results in FIG. 21 not only lend support to the view that cultures containing a high concentration of CDE serum yield physiologically relevant information, but they also demonstrate that the new charcoal extraction method disclosed herein effectively depletes several classes of steroid hormones.

Comparisons of $ED_{50}$ and $K_d$ as Evidence Supporting a New ER Designated ERγ. As mentioned in the Background of the Invention, it is important to recognize that if a given estrogen receptor is in fact a mediator of estrogen-induced growth, then the steroid hormone concentrations required for one-half maximum growth (i.e. $ED_{50}$), or for optimum growth (i.e. $ED_{100}$), should be about the same. According to the theory of hormone binding, the $K_d$ value represents the steroid concentration that one-half saturates the existing receptors. The following TABLE 5 summarizes the $ED_{50}$ concentrations required for a one-half maximum growth and the corresponding lowest $K_d$ measured for the same or closely related cell lines:

TABLE 5

Comparisons of $ED_{50}$ and $K_d$ as Evidence
Supporting a New ER Designated ERγ

| Cell Line | $ED_{50}$ for $E_2$ Induced Growth | $K_d$ for $E_2$ | Fold-higher $K_d$ Concentration Compared to $ED_{50}$ for Growth |
|---|---|---|---|
| MTW9/PL2 | $1 \times 10^{-12}$ M | $1.8 \times 10^{-9}$ M | $1.8 \times 10^3$ |
| T47D | $1 \times 10^{-12}$ M | $0.11 \times 10^{-9}$ M | $1.1 \times 10^3$ |
| $GH_4C_1$ | $1 \times 10^{-11}$ M | $0.25 \times 10^{-9}$ M | 25 |
| H301 | $9 \times 10^{-11}$ M | $0.87 \times 10^{-9}$ M | 10 |

Clearly, to seek the new ERγ, the rat mammary or human breast cells will be the best sources based on the differences between the $ED_{50}$ growth concentrations and the $K_d$ values for ERα or ERβ. Because the ERβ was first obtained from rat tissues, the MTW9/PL2 cells will be the preferred source of ERγ.

One preferred application supported by the data in TABLE 5 is the use of the ERγ for diagnosing and/or screening for breast cancer. Measurement of the ER.gamma. specifically will provide a more accurate determination of estrogen receptor status and therefore permit more precise modeling of the therapy for each patient. ERγ will be identified by immunohistochemical methods, labeled ligand binding with very high specific activity isotopes, and by PCR and other molecular biology analyzes. Other methods will also be applied. Similar analyses are expected to be applicable to other estrogen receptor related or estrogen receptor containing mucosal cancers including ovarian, uterine, vaginal, cervical, colon, lung, stomach, pituitary, liver, pancreas, skin and kidney, as described in co-owned, concurrently filed U.S. patent application Ser. No. 09/852,547 /PCT/US2001/015171 entitled "Compositions and Methods for the Diagnosis, Treatment and Prevention of Steroid Hormone Responsive Cancers," which is hereby incorporated herein by reference.

The dose-response results presented in FIGS. 11, and 18 through 21 demonstrate the usefulness of the extracted sera, assays and cell lines with regard to assessment of estrogenic activity or androgenic activity in industrial, commercial, environmental, medicinal, or other medical samples where activity measurement is required at concentrations below the usual levels detectable by radioimmunoassay. The sensitivity of this bioassay is unique.

Benign prostatic hypertrophy (BPH) is among the most common afflictions of older men. About 50% of 60-year old men have BPH. At 85 years about 90% of men have BPH (Berry S J et al. (1984) *J Urol* 132, 474-479). There is a general view that estrogens may be important in BPH (Henderson D et al. (1987) *Steroids* 50, 219-229; Nakhla A M et al. (1994) *Proc Natl Acad Sci* USA 91, 5402-5405). The paradox involved is that as men age androgen levels fall and SHBG rises. These work in concert to further limit available androgen (Davidson J M et al. (1983) *J Clin Endocrinol Metab* 57, 71-77; Tenover J S et al. (1987) *J Clin Endocrinol Metab* 65, 1118-1126). Furthermore, as part of the weight gain with age, estrogens become more prominent in older men. Although it has been suggested that estrogens cause LNCaP cell growth via an estrogen receptor, it remains to be proven conclusively. Nonetheless, the ERγ may be expressed in BPH and prostatic cancer and therefore its use as a diagnostic tool and a site for development of new antihormone treatments of these diseases has great potential.

Discussion of Example 4. The results presented in this Example have special significance with regard to support for the conclusion that a new ERγ regulates growth and is activated by more than 10-fold at lower concentrations of $E_2$ than expected of the classical EDα. Example 4 also demonstrates the utility of assays using 34° C. CDE serum for demonstrating estrogen responsive cell growth in a variety of tissues.

Example 5

Thyroid Hormone Growth Effects in CDE-Horse Serum Prepared at 34° C.

This Example demonstrates that not only steroid hormone but also thyroid hormone growth effects can be demonstrated in cell growth assays using the present 34° C. CDE serum.

Figure 22:
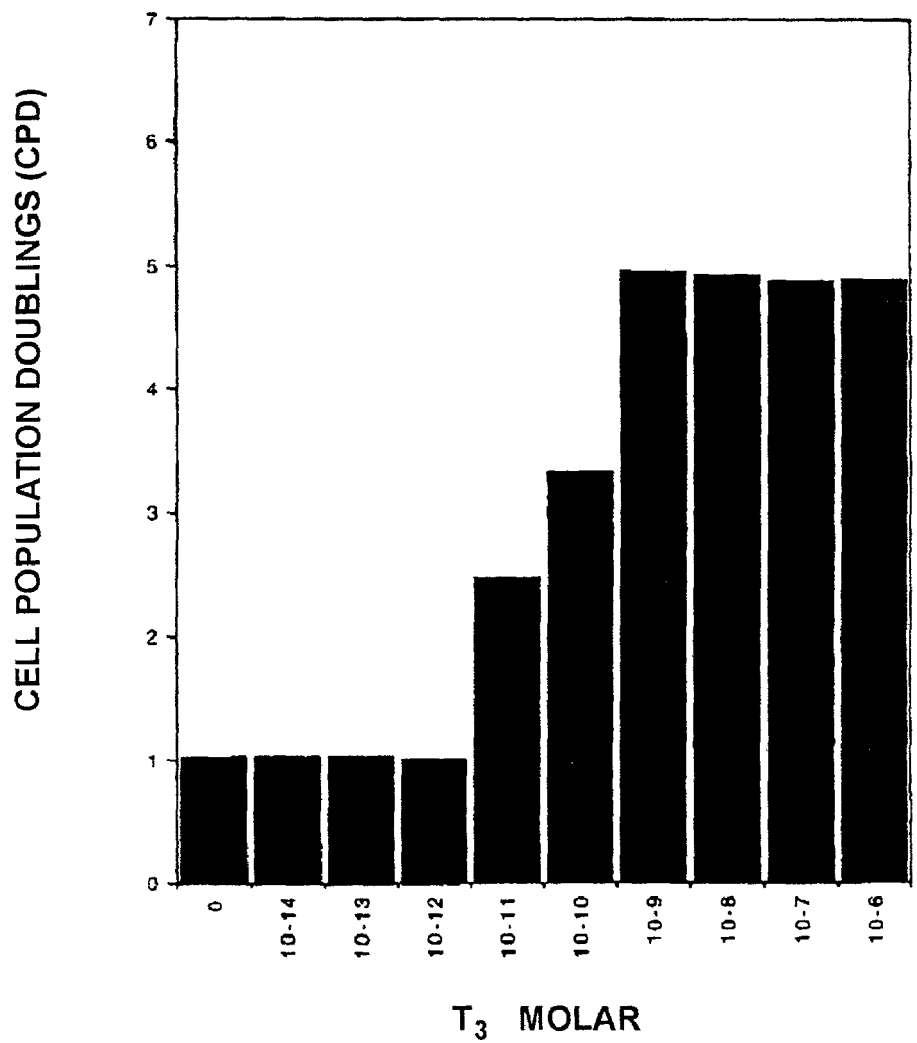
FIG. 22. $T_3$ Growth Effects with $GH_3$ Cells in Serum-free Medium (PCM).
Figure 23:
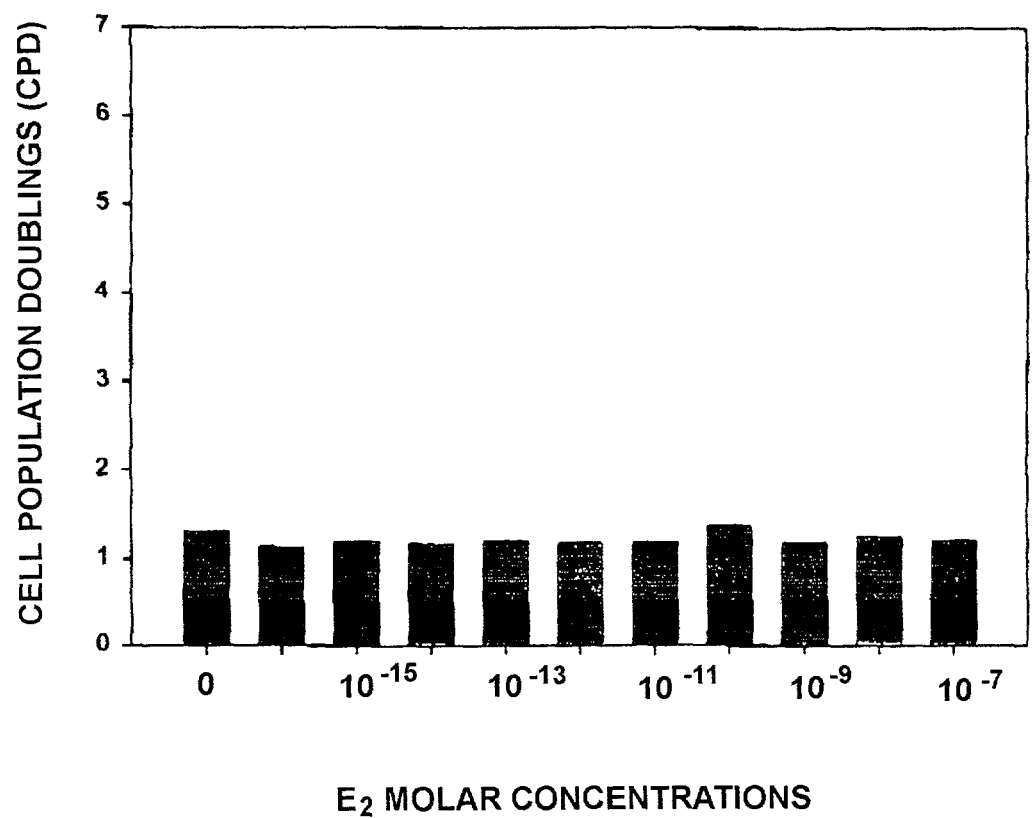
FIG. 23. $E_2$ Growth Effects with $GH_3$ Cells in Serum-free Medium (PCM) Minus $E_2$.
Figure 24:
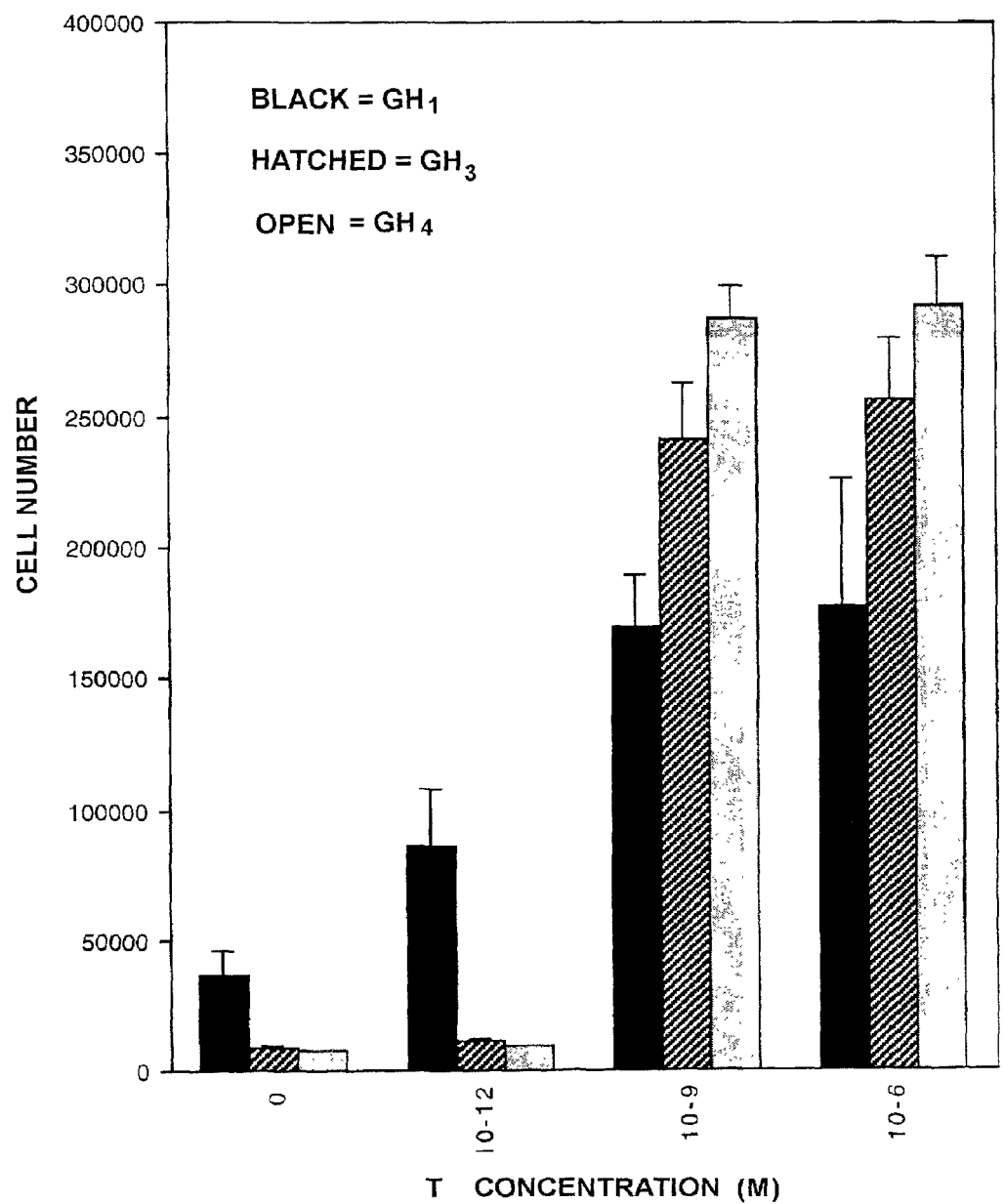
FIG. 24. $T_3$ Growth Effects with Three GH Cell Lines in 2.5% CDE-horse Serum.
Figure 25:
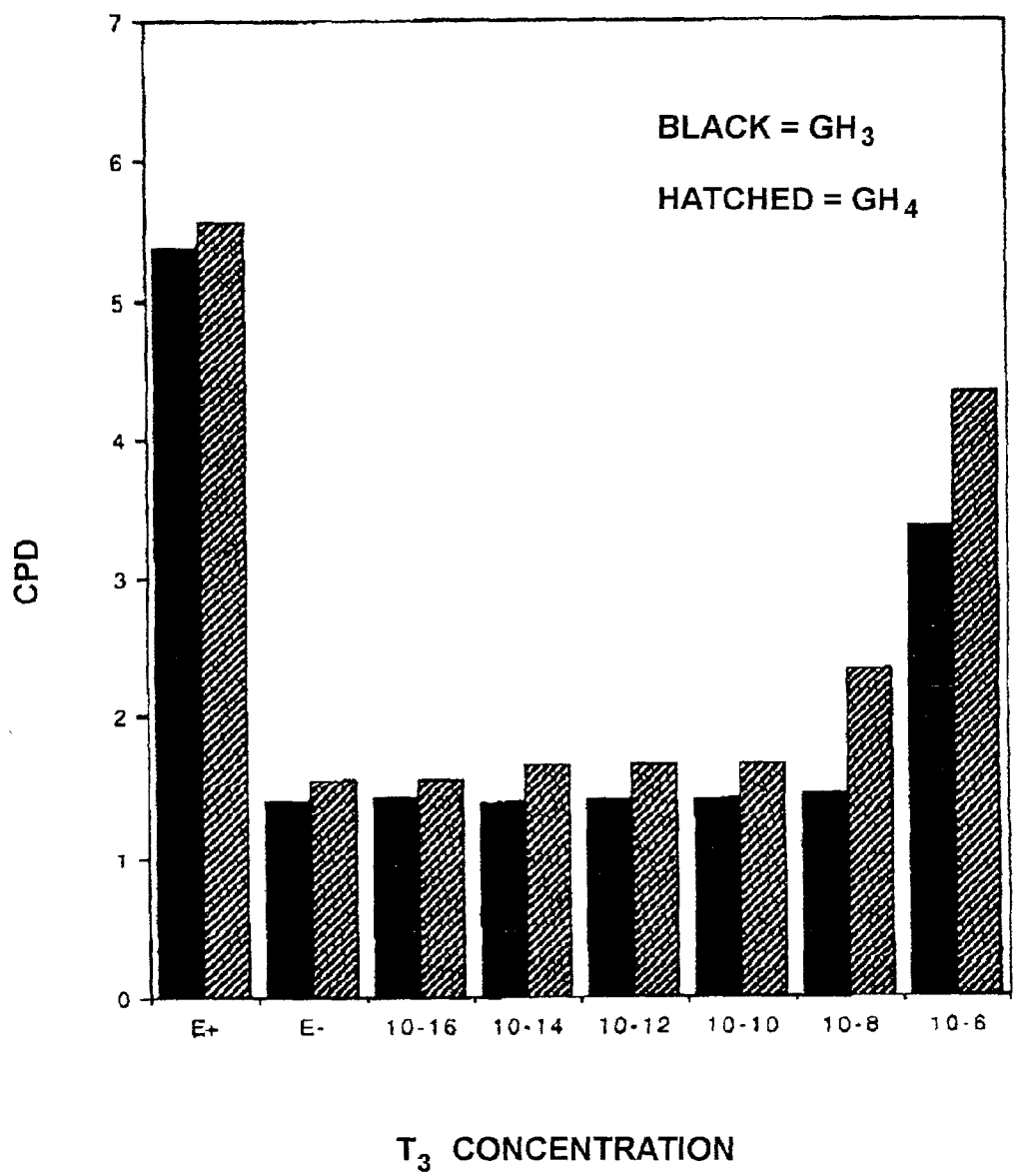
FIG. 25. $T_3$ Growth Effects with Two GH Cell Lines in 50% CDE-horse Serum.

Thyroid Hormone Responsive Pituitary Tumor Cell Growth in CDE-Serum Prepared at 34° C. GH rat pituitary tumor cells are highly thyroid hormone responsive in serum-free defined medium (Eby J E et al. (1992) *Anal Biochem* 203, 317-325; Eby J E et al. (1992) *J Cell Physiol* 156, 588-600; Sato H et al. (1991) *In Vitro Cell Dev Biol* 27A, 599-602). An example of this responsiveness with the $GH_3$ line is shown in FIG. 22. However, in serum-free defined medium, these cells are not $E_2$ responsive when $T_3$ is omitted from the medium (FIG. 23). During evaluation of the role the GH cell lines in CDE-serum, in D-MEM/F-12 with 2.5% (v/v) CDE-horse serum, $T_3$ caused substantial growth of the $GH_4C_1$, $GH_1$ and $GH_3$ rat pituitary tumor cell lines (FIG. 24). However, at 50% (v/v) CDE-horse serum, only supraphysiologic concentrations of thyroid hormone showed growth effects (FIG. 25). Nonetheless, the 34° C. CDE method described in the preceding Examples is clearly functional to demonstrate both steroid hormone and thyroid hormone growth effects in culture. It is known that the thyroid hormone receptor is a member of a superfamily of receptors that also includes the steroid hormone receptors (Evans R M (1988) *Science (Wash D.C.)* 240:889-895). Testing of substances expected to have thyroid hormone like activity can be performed with the GH cell lines in the presence of low concentrations of CDE-serum.

Discussion of Example 5. The removal of thyroid hormones from serum has been described before using the Bio-Rad™ AG-1 X8 ion exchange resin (Samuels H H et al. (1979) *Endocrinology* 105, 80-85). Removal of $T_3/T_4$ by the AG-1 X8 method relies on their negative carboxylic acid charge at neutral pH. However, ion exchange does not remove the uncharged/hydrophobic steroid hormones. This Example demonstrates that the 34° C. CDE method described herein is more effective than the AG-1 X8 method previously known.

Example 6

Effect of 56° C. versus 34° C. CDE-Horse Serum on MTW9/PL2 Cell Growth

Previously, unsuccessful attempts were made to identify estrogen responsive tumor cell growth in cultures supplemented with serum depleted of steroid hormones by a 56° C. charcoal extraction procedure (Kirkland W L et al. (1976) *J Natl Cancer Inst* 56, 1159-1164; Sirbasku D A and Kirkland W L (1976) *Endocrinology* 98, 1260-1272; Sirbasku D A (1978) *Proc Natl Acad Sci* USA 75, 3786-3790; Leland F E et al. (1982) In: *Cold Spring Harbor Conferences on Cell Proliferation*, Volume 9, *Growth of Cells in Hormonally Defined Media*, Cold Spring Harbor, N.Y., pp 741-750; Liehr J G and Sirbasku D A (1985) In: *Tissue Culture of Epithelial Cells*, Taub M, ed, Plenum, N.Y., pp 205-234; Riss T L and Sirbasku D A (1989) *In Vitro Cell Dev Biol* 25, 136-142). In light of the data presented in the foregoing Examples, it appears that the 56° C. method was the major problem. The high temperature may have inactivated the inhibitor. Alternatively, because the 56° C. method was done for only a brief period, it may not have sufficiently removed the steroid hormones. Clearly, from the results presented above, even modest levels of residual estrogens can promote growth. This latter possibility seemed likely because the 56° C. method removed only somewhat more than 90% of the serum steroid hormones (Kirkland W L et al. (1976) *J Natl Cancer Inst* 56, 1159-1164; Sirbasku D A and Kirkland W L (1976) *Endocrinology* 98, 1260-1272). To reevaluate this problem, the $E_2$ effects on MTW9/PL2 cell growth were compared in medium supplemented with either 34° C. or 56° C. CDE-horse serum. As expected, the assay with control 34° C. treated serum, prepared as described in Example 2, showed maximum estrogenic effects of 6.01 CPD (FIG. 26). By comparison, the same lot of serum that had been charcoal extracted at 56° C. showed a maximum estrogenic effect of only 2.96 CPD (FIG. 26). When 34° C. CDE-serum was either charcoal extracted again at 56° C., or heated at this temperature for 20 minutes without charcoal, $E_2$ induced growth was reduced to only 1.47 and 2.01 CPD, respectively (FIG. 26). A typical assay from which these results were calculated is shown in (FIG. 26, insert). This experiment demonstrates that 56° C. treatment results in the loss of the inhibitory activity in serum. It should be noted that many investigators routinely "heat inactivate" serum at 56° C. for 20 to 30 minutes to destroy complement. The results indicate that this heating should be avoided when the serum is to be used in cell culture experiments testing steroid hormone growth responsiveness.

Discussion of Example 6. This example makes clear some major differences between the serum-borne inhibitor presently disclosed and those previously described. Specifically, exposure to heat can inactivate or alter the effect of inhibitors. For example, U.S. Pat. Nos. 4,859,585 (Sonnenschein) and 5,135,849 (Soto) describe an inhibitor that was derived from heat inactivated (i.e. 56° C. treated) serum and thereafter depleted of its endogenous estrogens and androgens by a 37.5° C. single step charcoal-dextran procedure. The facts of that method are also stated in a publication (Soto A M and Sonnenschein C (1984) *Biochem Biophys Res Commun* 122, 1097-1103). In light of the results presented in FIG. 26, it is likely that the inhibitor described by Sonnenschein and Soto is a different molecular entity, as further illustrated in Examples which follow. Among other differences, the serum used to isolate the present active inhibitor has not been inactivated by exposure to heat.

Example 7

Demonstration of Estrogenic Effects in XAD-4 Resin Treated Horse Serum

Figure 27:
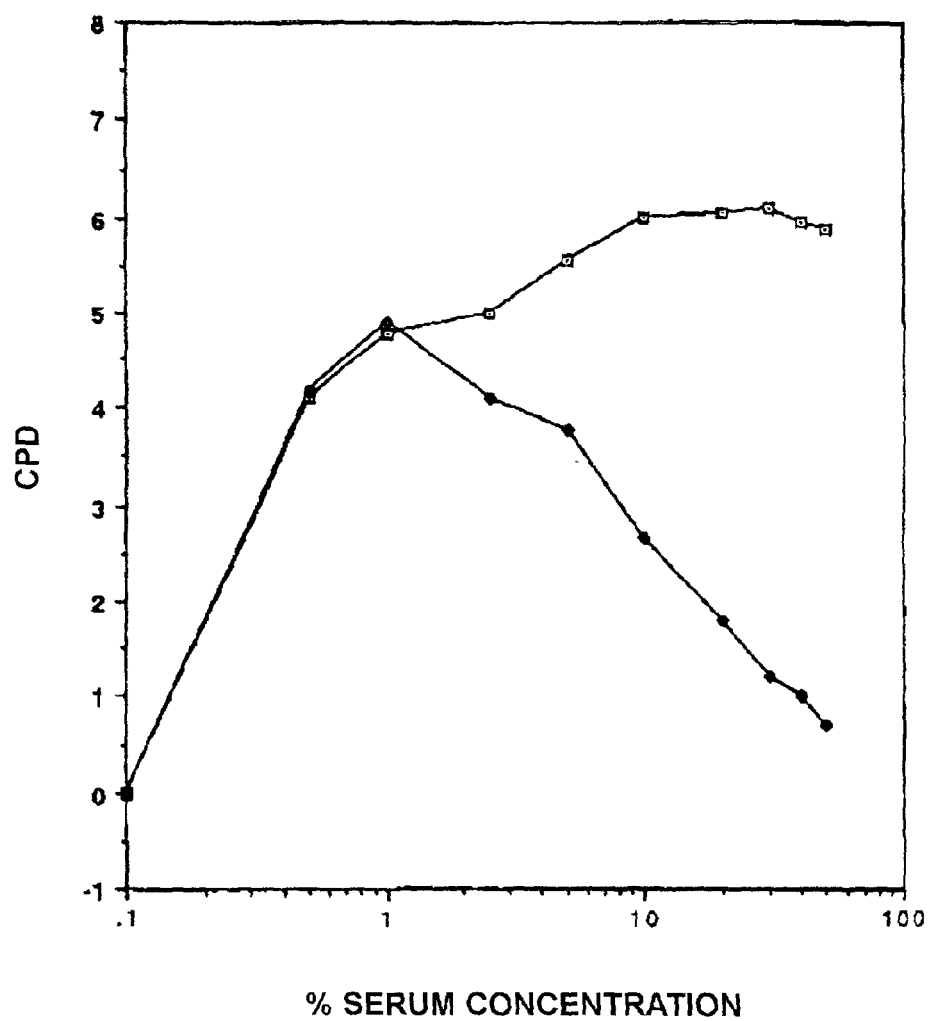
FIG. 27. Effect of XAD-4 Resin Treated Horse Serum on MTW9/PL2 Cell Growth±$E_2$.
Figure 28:
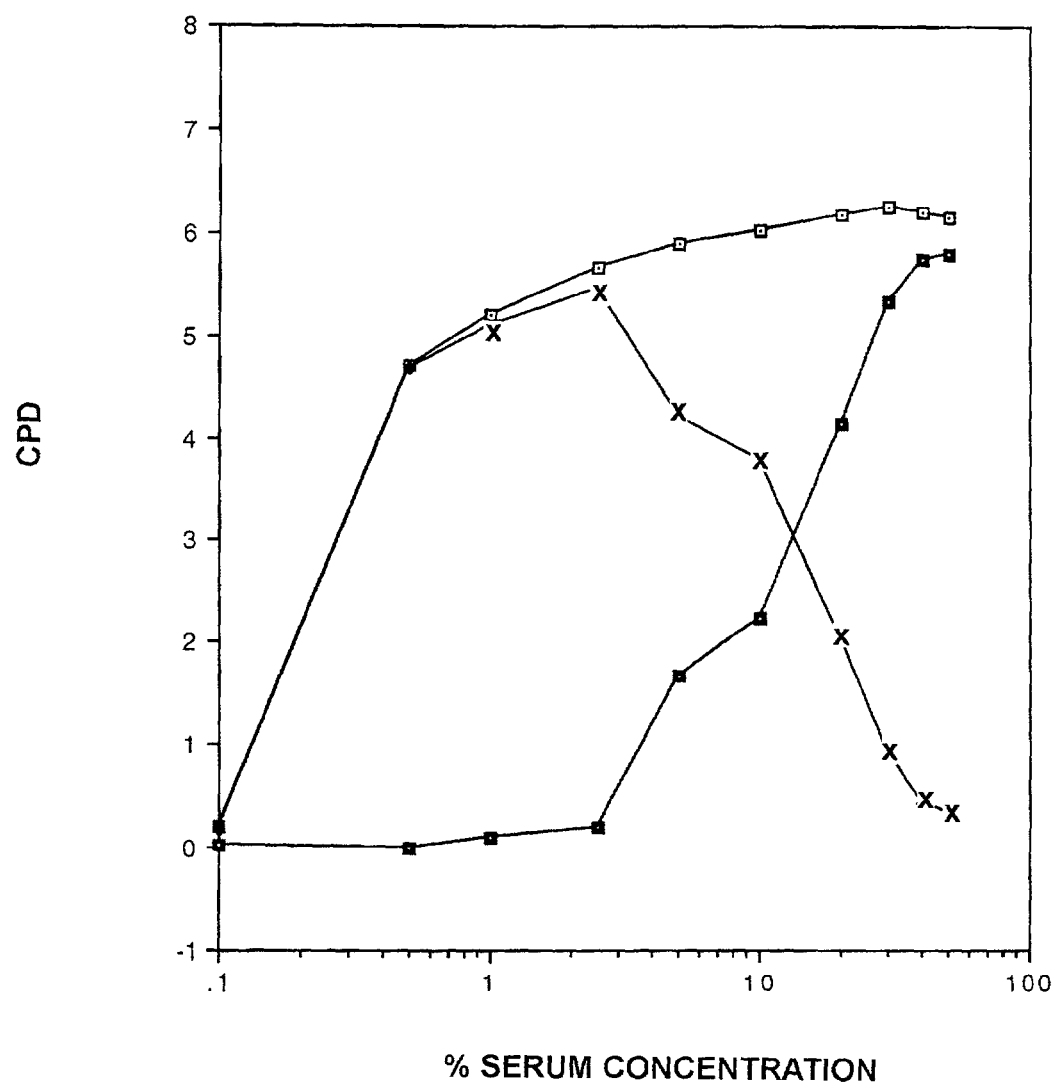
FIG. 28. Effect of XAD-4 Resin Treated Horse Serum on T47D Cell Growth±$E_2$.

Horse serum depleted of steroid hormones by XAD-4™, prepared as described in Example 2.C, was assayed to determine if it demonstrated estrogen reversible inhibition of $ER^+$ cancer cell growth in culture. FIG. 27 shows the effects of XAD-4 treated horse serum±10 nM $E_2$ with the MTW9/PL2 cell line. Unmistakably, the pattern of cell response was the same as seen with CDE-horse serum prepared as described in Example 2.A. At 50% XAD-4 serum (v/v), an estrogenic effect of 5.2 CPD was observed in 7 days. FIG. 28 shows a similar experiment with T47D cells after 14 days. At 50% (v/v) XAD-4 treated serum, an estrogenic effect with T47D cells of 5.3 CPD was observed. The magnitudes of the estrogenic effects with both cell lines were the same as observed with CDE-horse serum. Because both MTW9/PL2 and T47D cells are sensitive to picomolar concentrations of estrogen, it was evident that the $XAD_4$™ resin treatment effectively removed the endogenous sex steroids present in serum.

Discussion of Example 7. There is no previous report of the preparation of steroid depleted serum by this resin treatment method. As indicated in Example 2, the XAD-4™ treatment method has particular applicability for the industrial preparation of large volumes of steroid hormone depleted serum, and will allow the commercial supply of steroid depleted serum at reasonable cost. A preferred application for this steroid hormone stripped serum is in the biotechnology industry, in which cell culture is used to produce medically and otherwise commercially significant proteins and cellular products. Steroid hormone depleted serum has applicability beyond the $ER^+$ and $AR^+$ cells described in this report. For example, hybridoma cells are the sources of many important monoclonal antibodies. Depletion of steroids from the serum used to grow these cells will increase cell viability (cortisol is a potent cytotoxic agent) and therefore increase product yield. These and other applications of the XAD-$_4$™ treated serum for both commercial and diagnostic testing as well as for industrial production of valuable cellular products are foreseen.

Example 8

Testing of Substances for Estrogenic Activity

The purported estrogenic effects of phenol red were tested and proven to be unfounded. Further, the methods described in this Example exemplify methods that are generally effective for assessing the steroidogenic activity of any substance.

Phenol Red as an Estrogen.

It is widely believed that the phenol red indicator in tissue culture medium acts as a weak estrogen (Berthois Y et al. (1986) *Proc Natl Acad Sci* USA 83, 2496-2500). In the first report describing the phenol red problem, the indicator itself was thought to act as an estrogen (Berthois Y et al. (1986) *Proc Natl Acad Sci* USA 83, 2496-2500). At the concentration in standard culture media (e.g. D-MEM/F-12 is 8.1 mg/mL or 22.9 µM), it was believed to stimulate $ER^+$cell growth nearly as well as natural estrogens. Simply stated, this meant that exogenous estrogens would have no effect because the cells were already nearly completely stimulated. Further work by the original investigators later demonstrated that it was the lipophilic impurities in phenol red that were the true culprits (Bindal RD et al. (1988) *J Steroid Biochem* 31, 287-293). The chemical structure of one was determined to be bis(4-hydroxyphenyl) [2-(phenoxysulfonyl)phenyl]methane (Bindal RD and Katzenellenbogen JA (1988) *J Med Chem* 31, 1978-1983). Interfering amounts of the impurities were identified in many different commercially available preparations of phenol red (Bindal RD et al. (1988) *J Steroid Biochem* 31, 287-293; Bindal RD and Katzenellenbogen JA (1988) *J Med Chem* 31, 1978-1983). These investigators concluded that many, if not most, phenol red containing culture media had sufficient contaminants to at least partially mask estrogenic effects. Despite the wide acceptance of phenol red as an estrogen, experience has shown differently. Instead, large estrogen mitogenic effects have been observed in phenol red containing culture medium with $ER^+MCF-7$ human breast cancer cells, T47D human breast cancer cells, MTW9/PL2 rat mammary tumor cells, GH rat pituitary tumor cells, H301 Syrian hamster kidney tumor cells and the androgen receptor positive ($AR^+$) and $ER^+LNCaP$ human prostatic carcinoma cells, as shown herein and subsequently reported (Moreno-Cuevas JE and Sirbasku DA (2000) In Vitro Cell Dev Biol 36, 410-427; Sirbasku DA and Moreno-Cuevas JE (2000) *In Vitro Cell Dev Biol* 36, 428-446, incorporated by reference). In these studies, even when phenol red was present, estrogen-inducible cell number increases of 8 to 80-fold were observed. These responses were as large or larger than any previously reported. They exceeded any reported in phenol red free medium. Also, growth without the natural hormone was very limited even with phenol red present (Moreno-Cuevas JE and Sirbasku DA (2000) *In Vitro Cell Dev Biol* 36, 410-427; Sirbasku DA and Moreno-Cuevas JE (2000) *In Vitro Cell Dev Biol* 36, 428-446).

Phenol Red Indicator is a "Red Herring". Phenol red was further evaluated. Head-on comparisons of the growth of nine different $ER^+$ cell lines representing four target tissues and three species in medium with and without phenol red were performed (Moreno-Cuevas J E and Sirbasku D A (2000) *In Vitro Cell Dev Biol* 36, 447-464). These studies were designed to specifically test various aspects of published reports that phenol red is estrogenic. Considering the results of these head-on comparisons, new conclusions have been reached about the effects of phenol red in culture, especially as they are relevant to experimental conditions available today to most investigators. Even more important, the test assays show the methods that can be used to determine if any commercial preparation or other source material possesses estrogenic activity. To do this, nine cell lines were employed in the tests. Five different experimental protocols were used to investigate phenol red. First, $E_2$ responsive growth of all nine $ER^+$ cells lines was compared in medium with and without the indicator. Second, using representative lines it was asked if phenol red was mitogenic in indicator free medium. The dose-response effects of phenol red were compared directly to those of $E_2$. Third, it was asked if tamoxifen inhibited growth equally in phenol red containing an indicator-free medium, which would also confirm or refute a report indicating that antiestrogen effects should be seen only in phenol red containing medium. Fourth, it was asked if phenol red displaced the binding of $^3H-E_2$ using $ER^+$ intact human breast cancer cells. Fifth, $E_2$ and phenol red were compared as inducers of the progesterone receptor using a human breast cancer cell line. All of the experiments reported (Moreno-Cuevas J E and Sirbasku D A (2000) *In Vitro Cell Dev Biol* 36, 447-464) support the conclusion that the concentration of phenol red contaminants in a standard culture medium available today is not sufficient to cause estrogenic effects. The real issue of how to demonstrate estrogenic effects in culture resides elsewhere than phenol red. Demonstration of sex steroid hormone mitogenic effects in culture depends upon conditions that maximize the effects of a serum-borne inhibitor, as described in foregoing Examples. When the effects of the inhibitor are optimized, the presence or absence of phenol red makes no everyday difference to the demonstration of estrogen mitogenic effects with several target cell types from diverse species.

Phenol Red Testing for Estrogenic Activity with MCF-7A Cells. The original reports of the effect of phenol red or its impurities had used the MCF-7 human breast cancer cells to assess estrogenic activity (Berthois Y et al. (1986) *Proc Natl Acad Sci* USA 83, 2496-2500; Bindal RD et al. (1988) *J Steroid Biochem* 31, 287-293; Bindal R D and Katzenellenbogen J A (1988) *J Med Chem* 31, 1978-1983). The initial study began with the MCF-7A strain of this population. As shown in FIG. 29A, growth was measured in the presence of increasing concentrations of CDE-horse serum with and without phenol red in the medium and$\pm E_2$. Concentrations of $\leq 10\%$ (v/v) CDE-horse serum supported more than 5 CPD. Higher concentrations progressively inhibited in both indicator containing and indicator free medium. In both types of medium, $E_2$ was required to reverse the serum inhibition. To confirm that $E_2$ was equally effective in phenol red free and phenol red containing medium, the estrogenic effects shown in FIG. 29A were compared in both types of medium and at each serum concentration. The results of this analysis are presented in FIG. 29B. The maximum estrogenic effect at 50% (v/v) serum was 2.38 CPD (i.e. $2^{2.38}$ or 5.2-fold) in medium without indicator and 2.56 CPD (i.e. $2^{2.56}$ or 5.9-fold) with phenol red. This difference was not significant. Only at 5% (v/v) serum was there a significantly ($p<0.05$) greater estrogenic effect in phenol red free medium. However, in replicate experiments this<1.0 CPD effect was inconsistent. At all other serum concentrations, the growth differences between plus and minus phenol red were not significant.

Test of Phenol Red Effects with MCF-7K Cells. The MCF-7K strain was routinely more estrogen responsive than the MCF-7A line (Sirbasku D A and Moreno-Cuevas J E (2000) *In Vitro Cell Dev Biol* 36, 428-446). The MCF-7K cells also showed a serum concentration dependent growth inhibition (FIG. 29C). The final degree of inhibition at 50% (v/v) serum was independent of phenol red. Only in the presence of 2.5, 5, 10 and 20% (v/v) CDE-horse serum were the estrogenic effects significantly greater in phenol red free (FIG. 29D). It is important to note that while these differences were identified more often with the MCF-7K strain than the MCF-7A line, they were invariably small. Plainly, no serum concentration supported$\geq 1.0$ CPD estrogenic effects in phenol red free medium compared to indicator free medium (FIG. 29D). In fact, deletion of phenol red improved estrogen responsiveness by an average of only 0.6 CPD with the MCF-7K line. When judged by the maximum estrogenic effects achievable with MCF-7K cells in 50% (v/v) CDE-horse serum, plus and minus phenol red gave indistinguishable results of CPD 3.01 (8.0-fold) and CPD 2.99 (7.9-fold), respectively (FIG. 29D).

Phenol Red Testing for Estrogenic Activity with T47D and ZR-75-1 Cells. The same experiments just described above with the MCF-7 cell strains were repeated with T47D and ZR-75-1 cells. These lines were substantially more estrogen stimulated in CDE-serum than MCF-7 cells (Sirbasku D A and Moreno-Cuevas J E (2000) *In Vitro Cell Dev Biol* 36, 428-446) and hence were expected to be more sensitive to phenol red/contaminants.

Phenol Red and T47D Cells. T47D cells were grown in medium with CDE-horse serum both with and without phenol red (FIG. 30A). Low concentrations of serum (i.e.≦2%) promoted growth. Higher concentrations progressively inhibited growth irrespective of indicator content. In both media, $E_2$ was required to reverse the inhibition (FIG. 30A). In 50% (v/v) CDE-horse serum, the maximum $E_2$ responses were $2^{5.35}$ (41-fold) and $2^{5.29}$ (39-fold) in phenol red containing and indicator free medium, respectively (FIG. 30B). Only at low serum concentrations were phenol red effects observed in any experiment. In some replicates, the phenol red effect was opposite to that expected. For example, in the experiment shown in FIG. 30B, 0.5 to 2.5% serum showed significantly ($p<0.05$) greater estrogenic effects in the presence of phenol red. These results graphically illustrate the hazards of interpreting 1.0 CPD responses either in favor of phenol red/contaminants as estrogens or in opposition to this proposal.

Phenol Red and ZR-75-1 Cells. ZR-75-1 cells showed similar results as the T47D line. Serum caused an inhibition of growth that was undoubtedly unrelated to phenol red (FIG. 30C). In both types of medium, and at every serum concentration tested, $E_2$ was required to reverse the inhibition (FIG. 30C). In 50% (v/v) serum, ZR-75-1 cells showed maximum estrogenic effects of $2^{3.39}$ (10.5-fold) and $2^{3.49}$ (11.2-fold) in medium with and without indicator, respectively (FIG. 30D). As seen with T47D cells, the ZR-75-1 line showed greater estrogenic effects in medium with phenol red than in medium without indicator when the serum was 0.5, 5 or 10% (v/v) (FIG. 30D).

Phenol Red Testing for Estrogenic Activity with MTW9/PL2 Cells The next experiments were done with MTW9/PL2 rat mammary tumor cells (FIG. 31A). They were inhibited by high concentrations of CDE-horse serum with and without indicator. $E_2$ was required to reverse the inhibition in both types of medium (FIG. 31A). The maximum estrogenic effects in 50% serum were $2^{5.82}$ (56-fold) and $2^{5.69}$ (52-fold) with and without phenol red, respectively (FIG. 31B). In the experiment shown in FIG. 31B, estrogenic effects were unpredictably greater in phenol red free medium than in medium with indicator. This was observed at low serum concentrations (i.e. 0.5 and 1.0%) and again at higher levels (i.e. 20 and 30%). Although suggesting a phenol red effect, these results in fact only serve to emphasize the pitfalls of accepting small changes as meaningful even though they are significant at $p<0.05$. When estrogenic effects were found with MTW9/PL2 cells in phenol red free conditions, they invariably were≦1.0 CPD. The sum of the studies with MTW9/PL2 cells did not yield a predictable correlation between estrogenic effects in the absence of the indicator and serum concentrations.

Other Cell Lines Tested for Growth±Phenol Red and±$E_2$. The results presented above were replicated with the $GH_1$ and $GH_4C_1$ rat pituitary tumor cell lines as well as with the H301 cells and the LNCaP cell line (Moreno-Cuevas J E and Sirbasku D A (2000) *In Vitro Cell Dev Biol* 36, 447-464). Again, the presence or absence of the indicator in the medium containing CDE-horse serum had no effect whatever on the demonstration of the usual high estrogenic effects with these cells.

Figure 32:
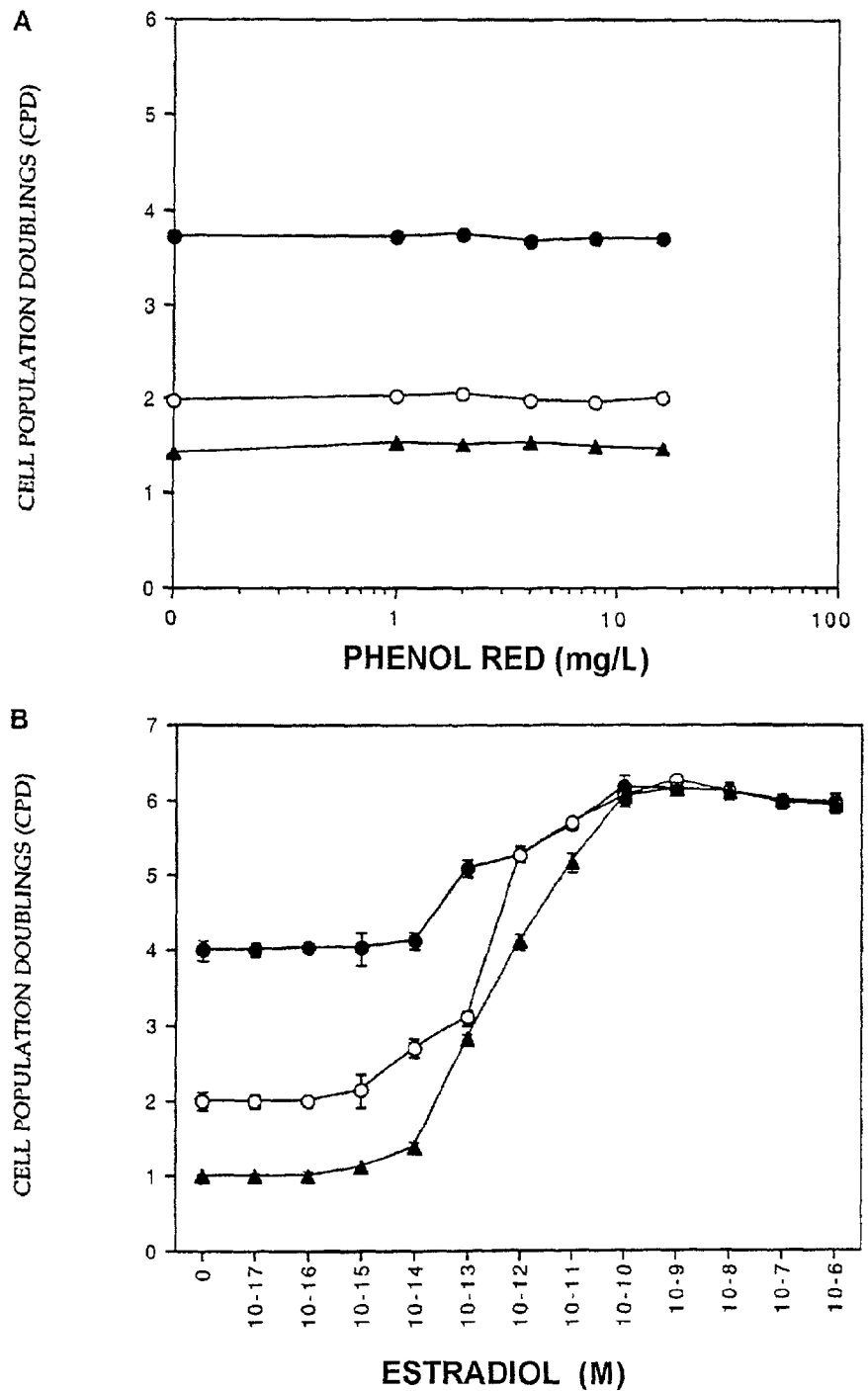
FIG. 32. Dose-Response Effects of Phenol Red versus $E_2$ with Three $ER^+$ Cell Lines. (A) Growth Effects of Phenol Red with MCF-7K, T47D and MTW9/PL2 Cells; (B) Growth Effects of $E_2$ with MCF-7K, T47D and MTW9/PL2 Cells.

Direct Test of Phenol Red Estrogenic Activity. Three cell lines were selected for a direct test of phenol red as a mitogen. The MCF-7A line was used because it most closely approximated the origin and passage age of the cells used to conduct the original study of phenol red as a weak estrogen (Berthois Y et al. (1986) *Proc Natl Acad Sci* USA 83, 2496-2500). The T47D cells were chosen because they are the most estrogen responsive human breast cancer cell line available today (Sirbasku D A and Moreno-Cuevas J E (2000) *In Vitro Cell Dev Biol* 36, 428-446). The MTW9/PL2 cells were chosen as an example of a highly estrogen responsive rodent origin line (Moreno-Cuevas J E and Sirbasku D A (2000) *In Vitro Cell Dev Biol* 36, 410-427; Sirbasku D A and Moreno-Cuevas J E (2000) *In Vitro Cell Dev Biol* 36, 428-446). The assays were done in phenol red free D-MEM/F-12 supplemented with 30% CDE-HS. This concentration was chosen even though it is not as inhibitory as 50% (v/v) serum. This selection was made to reduce possible interactions of the phenol red/contaminant with serum proteins while still retaining a significant inhibitory effect. Phenol red concentrations of up to 16 mg/L were added to this medium. This highest level was twice that in standard commercially formulated Gibco-BRL D-MEM/F-12. Several different manufacturing lots of aqueous phenol red gave equivalent results. The preparations used in this study ranged in age from newly obtained to more than ten year old laboratory stocks. These experiments gave unmistakable results. There was no increase in the growth of any of the cell lines in response to phenol red (FIG. 32A). By comparison, parallel cultures receiving $E_2$ showed sizable 2 to 5 CPD responses to the natural hormone (FIG. 32B). $E_2$ at $1.0 \times 10^{-10}$ M optimized growth of all three cell lines. The $ED_{50}$ concentrations of $E_2$ were $3.0 \times 10^{-12}$ M. Significant ($p<0.05$) estrogenic effects were observed at $1.0 \times 10^{-12}$ M. The results presented in FIG. 32 indicate that the culture conditions used in this study could reasonably be expected to detect responses due to contaminants present at the concentrations indicated in the original reports (Berthois Y et al. (1986) *Proc Natl Acad Sci* USA 83, 2496-2500; Bindal R D et al. (1988) *J Steroid Biochem* 31, 287-293; Bindal R D and Katzenellenbogen J A (1988) *J Med Chem* 31, 1978-1983).

Comparison of $E_2$ Potency in Medium with and without Phenol Red. As described above in TABLE 5, the T47D and MTW9/PL2 cells grow significantly in response to $1.0 \times 10^{-12}$ M $E_2$. The D-MEM/F-12 used in those studies also contained about 23 μM phenol red. When the results of those studies were compared to the experiments in FIG. 32B, done in D-MEM/F-12 without indicator, the estrogen dose response curves were very similar. The conclusion is straightforward. $E_2$ dose-responses were not affected by phenol red. If phenol red lipophilic contaminants were present at the concentrations originally suggested (Berthois Y et al. (1986) *Proc Natl Acad Sci USA* 83,2496-2500; Bindal R D et al. (1988) *J Steroid Biochem* 31,287-293; Bindal R D and Katzenellenbogen J A (1988) *J Med Chem* 31, 1978-1983) they should have masked the observation of picomolar effects of exogenous estrogens.

Effect of Phenol Red on Binding of $^3H$-$E_2$ to Intact Cells. For the next study, intact T47D cells were used to measure the effects of phenol red on estrogen receptor binding. The cells were incubated with 5 nM $^3H$-$E_2$ and the effects of addition of increasing concentrations of unlabeled $E_2$ assessed (TABLE 6). A 100-fold excess of unlabeled $E_2$ displaced 75% of the binding of $^3H$-$E_2$. By this criterion, 75% of the binding of $^3H$-$E_2$ was specific to estrogen receptors (Chamness G C and McGuire W L (1975) *Steroids* 26, 538-542). The same analysis was conducted with aqueous preparations of phenol red. Even at 16 mg/L, the indicator did not reduce the binding of $^3H$-$E_2$ (TABLE 6). This was true no matter which batch of indicator was analyzed (results not shown). The phenol red used for the experiment shown in TABLE 6 was approximately the same age (purchased in 1986) as the date of the original report (Berthois Y et al. (1986) *Proc Natl Acad Sci* USA 83, 2496-2500). These results raise the question how often preparations of phenol red purchased at that time as an aqueous membrane filtered product contained a sufficient level of contaminants to elicit an estrogenic effect.

TABLE 6

Displacement of $^3$H-E$_2$ Binding to Intact T47D Cells by Unlabeled E$_2$ or Unlabeled Phenol Red Indicator Free and Serum-free D-MEM/F-12 for Two Hours at 37° C.

| Additions | Counts per Minute | Percent of Control |
|---|---|---|
| Control - No Additions (5 nM $^3$H-E$_2$ only) | 12,458 ± 1615 | 100% |
| 2.5 nM Unlabeled E$_2$ | 12,177 ± 872 | 98% |
| 5.0 nM Unlabeled E$_2$ | 8,756 ± 588 | 70% |
| 50 nM Unlabeled E$_2$ | 7,898 ± 744 | 63% |
| 250 nM Unlabeled E$_2$ | 4,892 ± 194 | 39% |
| 500 nM Unlabeled E$_2$ | 3,494 ± 127 | 28% |
| 1000 nM Unlabeled E$_2$ | 2,543 ± 304 | 20% |
| 1 mg/L Phenol Red | 12,670 ± 727 | 102% |
| 2 mg/L Phenol Red | 13,874 ± 906 | 111% |
| 4 mg/L Phenol Red | 11,730 ± 566 | 94% |
| 5 mg/L Phenol Red | 12,357 ± 664 | 99% |
| 16 mg/L Phenol Red | 13,748 ± 998 | 110% |

Comparison of the E$_2$ and Phenol Red Induction of Progesterone Receptors. Another putative function of phenol red was to induce progesterone receptors in estrogen sensitive cells. An investigation was made as to whether the indicator induced an increase in the progesterone receptors of T47D cells which contain these sites (Horwitz K B et al. (1978) *Cancer Res* 38, 2434-2437). In a first study, the kinetics of progesterone receptor induction versus estrogen concentration in phenol red free medium were investigated (FIG. 33A). E$_2$ levels as low as $1.0 \times 10^{-12}$ M caused a significant two-fold increase in receptor content in four days. At $1.0 \times 10^{-8}$ M, E$_2$ induced a four-fold increase in progesterone receptors in four days. Clearly, E$_2$ induced a time and concentration dependent increase in the progesterone receptors with T47D cells. Next, this same analysis was done with phenol red over a concentration range of 1 to 16 mg/L (FIG. 33B). Phenol red induced a small increase in progesterone receptors at 8 and 16 mg/L after four days. This induction was about the same as caused by $1.0 \times 10^{-14}$ M E$_2$ (FIG. 33A). These results indicate that if estrogenic contaminants are present in phenol red, they are most likely in the $10 \times 10^{-14}$ M range even assuming equal receptor binding capacity to E$_2$. This point is important because the active agent is thought to be only a trace impurity in many batches of phenol red (Bindal R D et al. (1988) *J Med Chem* 31, 1978-1983). The impurities bind to the estrogen receptor with only 50% of the affinity of E$_2$. The impurity was expected to be 0.002% of the phenol red concentration. Based on test results that employed many different batches of Gibco-BRL D-MEM/F-12, this concentration of the impurity seems highly unlikely in the medium commercially available today.

Discussion of Example 8. The studies of the effects of phenol red or its lipophilic impurities demonstrate the usefulness of the presently disclosed methods for the assessment of estrogenic and androgenic activity of commercially prepared materials, substances present or extracted from environmental or food sources or other sources that are thought to contain such activities. The testing can be approached by three separate methods as shown by examples with phenol red. (1) Compounds or other preparations and substances can be tested for growth activity with human or rodent cell lines depending upon the information sought. Potency can be established as UNITS based on E$_2$ or any other estrogen or androgen required. This permits direct expression of the estrogen like activity or androgen like activity per volume or mass of the substance under evaluation. Levels can be measured without regard for expensive development of a radio immunoassay that in the end still does not yield evidence of biological activity as a sex steroid hormone analog (agonist or antagonist). The use of rodent cell lines opens the possibility of direct comparison to in vivo activity if required. (2) Another form of analysis is direct measure of potency by $^3$H-E$_2$ or $^3$H-DHT binding displacement analysis from whole cells or extracted estrogen receptors. An example with $^3$H-E$_2$ and whole cells is shown in TABLE 6. The two different binding assays offer different information. Whole cells have a predominance of hydrophobic sites (i.e. membranes) that absorb lipophilic substances and therefore may attenuate their activity. Use of cell extracted sex steroid hormone receptors permits direct measure of the potential of a substance to act as a hormone independent of its biological effects. (3) Finally, use of the progesterone receptor analysis permits evaluation of substances and preparations by a method entirely independent of growth. This is a gene expression based analysis that permits evaluation that can be used to supplement growth data or be used in place of growth analysis. The MTW9/PL2 cells have been shown above to be suitable for this purpose.

Example 9

Testing of Substances for Inhibitor-Like Activity

In studies described in this Example, TGFα, TGFβ1, EGF, IGF-I, IGF-II and insulin were tested for inhibitor-like acitivity, using the cell growth assay described in the General Materials and Methods section, and in the foregoing Examples, substituting those proteins for the serum-borne inhibitor contained in the preferred CDE serum.

TGFβ1 as a Substitute for the Serum-Borne Estrogen Reversible Inhibitor. Normal mouse mammary (Silberstein G B and Daniel C W (1987) *Science* (Wash D.C.) 237, 291-293; Silberstein G B et al. (1992) *Dev Biol* 152, 354-362) and normal human breast epithelial cell growth is inhibited by TGFβ (Bronzert D A et al. (1990) *Mol Endocrinol* 4, 981-989). Additionally, human breast cancer cells are inhibited by TGFβ (Knabbe C et al. (1987) *Cell* 48, 417-428; Arteaga C L et al. (1988) *Cancer Res* 48, 3898-3904; Arteaga C L et al. (1990) *Cell Growth Diff* 1, 367-374). TGFβ also inhibits the GH$_4$C$_1$ rat pituitary tumor cells (Ramsdell J S (1991) *Endocrinology* 128, 1981-1990) and the LNCaP human prostatic carcinoma cells (Schuurmans A L et al. (1988) *The Prostate* 12, 55-64; Wilding G et al. (1989) *Mol Cell Endocrinol* 62, 79-87; Carruba G et al (1994) *Steroids* 59, 412-420; Castagnetta L A and Carruba G (1995) *Ciba Found Symp* 191, 269-286; Kim I Y et al. (1996) *Endocrinology* 137, 991-999). In studies presented next, replacement of the serum-borne inhibitor with TGFβ was attempted. A number of related forms of this inhibitor are known (Clark D A and Coker R (1998) *Int J Biochem Cell Biol* 30, 293-298; Massague J (1998) *Annu Rev Biochem* 67, 753-791). TGFβ1 and TGFβ2 are most often studied and commonly have similar potencies. For example, they are equipotent with human breast cancers cells (Zugmaier G et al. (1989) *J Cell Physiol* 141, 353-361). TGFβ1 was chosen for the instant study. Without a doubt, a number of the key cell lines used throughout the Examples were inhibited by TGFβ. It was therefore considered essential to ask if TGFβ was the estrogen reversible inhibitor.

TGFβ1 and MCF-7 Cells. Because MCF-7 cells are probably the most studied human breast cancer line today, this next work began with those cells. TGFβ has been described as a hormone regulated autocrine inhibitor of the ER$^+$ MCF-7 human breast cancer cell growth (Knabbe C et al. (1987) *Cell* 48, 417-428). In the present study, to test if TGFβ1 substituted for the serum-borne inhibitor with these cells, they were grown in D-MEM/F-12 containing 2.5% (v/v) CDE-horse serum plus increasing concentrations of transforming growth factor and±$E_2$. The results in FIG. 34A show that even 50 ng/mL of TGFβ1 caused only a modest inhibition of MCF-7K cell growth. Cell numbers were reduced from 350,000 to 200,000 per dish. This difference was significant (p<0.05). Nevertheless, the estrogen reversal of the inhibition was no larger than the $E_2$ effect observed in D-MEM/F-12 containing 2.5% (v/v) horse serum without TGFβ1 FIG. 34A. Furthermore, when the cell number data were expressed as CPD (insert FIG. 34A), it was definite that TGFβ1 was at best a very modest inhibitor and that there was no TGFβ1 related estrogenic effect.

TGFβ1 and MTW9/PL2 Cells. The next study was performed because the MTW9/PL2 cells are the only known estrogen growth responsive rat cell line derived from a hormone responsive carcinogen induced tumor. A similar analysis was done with the MTW9/PL2 rat mammary tumor cells (FIG. 34B). TGFβ1 reduced cell numbers from 350,000 to 100,000 per dish. This was significant (p<0.05). However, the presentation of cell number results only tends to exaggerate the effects of TGFβ1. When the results were converted to CPD (FIG. 34B, insert), the actual inhibition was 1.5 CPD. This was at most a 25% decrease in growth rate. As shown, there was no estrogen reversal of the TGFβ1 inhibition with MTW9/PL2 cells.

TGFβ1 and other $ER^+$ Cell Lines. The effects of TGFβ1 at 50 ng/mL±$E_2$ were also investigated with the other cell lines used in this study. The MCF-7A, T47D and ZR-75-1 human breast cancer cells were inhibited by TGFβ1 (FIG. 35A). From these results, and those in FIG. 34A, it was clear that the MCF-7 cells were the most sensitive of the $ER^+$ human breast cancer lines tested. Irrespective of the line, $E_2$ had no influence on the TGFβ1 mediated inhibitions (FIG. 35A). The same experiments were done with the LNCaP cells and the $GH_4C_1$ pituitary line (FIG. 35A). They were more sensitive to TGFβ1 than breast cancer cells. Nonetheless, the TGFβ1 effects were not reversed by $E_2$. When the cell number decreases presented in FIG. 35A were converted to CPD, it was clear that the TGFβ1 effects were negligible and that $E_2$ was of no significant consequence (FIG. 35B). Thus, TGFβ1 did not substitute for the estrogen reversible inhibitor(s) in CDE serum with any of the sex steroid sensitive $ER^+$ cell lines tested.

TGFα and EGF as Substitutes for the Estrogen Reversible Inhibitor in CDE Serum. The EGF family of mitogens and receptors has been linked to breast cancer proliferation, invasion and progression (Dickson R B and Lippman M E (1987) *Endocr Rev* 8, 29-43; Normanno N et al. (1994) *Breast Cancer Res Treat* 29, 11-27; Ether S P (1995) *J Natl Cancer Inst* 87, 964-973; de Jung J S et al. (1998) *J Pathol* 184, 44-52 and 53-57). Most prominent among these polypeptide mitogens has been the EGF analogue, TGFα (Dickson R B and Lippman M E (1987) *Endocr Rev* 8, 2943; de Jung J S et al. (1998) *J Pathol* 184, 44-52 and 53-57). Estrogen induced secretion of TGFα is thought to create an autocrine loop that promotes breast cancer cell growth (Dickson R B et al. (1985) *Endocrinology* 118, 138-142; Dickson R B et al. (1986) *Cancer Res* 46, 1707-1713; Dickson R B et al. (1986) *Science* (Wash D.C.) 232, 1542-1543; Dickson R B and Lippman M E (1987) *Endocr Rev* 8, 29-43; Derrick R (1988) *Cell* 54, 593-595; Arrack B A et al. (1990) *Cancer Res* 50, 299-303; Kenney N J et al. (1993) *J Cell Physiol* 156, 497-514; Normanno N et al. (1994) *Breast Cancer Res Treat* 29, 11-27; Dickson R B et al. (1987) *Proc Natl Acad Sci* USA 84, 837-841; Salomon D S et al. (1984) *Cancer Res* 44, 4069-4077; Liu S C et al. (1987) *Mol Endocrinol* 1, 683-692). TGFα is also thought to potentiate estrogen action in uterus (Nelson K G et al. (1992) *Endocrinology* 131, 1657-1664) as well as to regulate the EGF receptor in this tissue (DiAugustine R P et al. (1988) *Endocrinology* 122, 2355-2363; Huet-Hudson Y M et al. (1990) *Mol Endocrinol* 4, 510-523; Mukku V R and Stancel G M (1985) *J Biol Chem* 260, 9820-9824). The culture conditions described herein offer a new opportunity to test the autocrine growth model under conditions not previously available. Application of the new cell growth assays allowed a direct test to determine if an autocrine/intacrine growth factor loop explains the estrogen reversal of the serum inhibition.

EGF and TFGα as Substitutes for $E_2$. Growth of the MCF-7A, MCF-7K, T47D and ZR-75-1 cells was measured in D-MEM/F-12 containing increasing concentrations of CDE horse serum with and without exogenous EGF or TFGα. The results with the four cell lines are shown in FIGS. 36A, 36B, 36C, and 36D, respectively. As expected, CDE horse serum was progressively inhibitory at concentrations>5% (v/v). The addition of growth saturating concentrations (Karey K P and Sirbasku D A (1988) *Cancer Res* 48.4083-4092) of EGF or TGFα did not reverse the effects of the serum-borne inhibitor. In control cultures without added polypeptide mitogens, $E_2$ completely reversed the serum inhibition. These results again confirm the same conclusion arrived at earlier using an entirely different approach (Karey K P and Sirbasku D A (1988) *Cancer Res* 48. 4083-4092). Direct evidence for obligatory EGF/TFGα autocrine loops in estrogen responsive cell growth simply has not yet been established. In fact, there is solid in vivo evidence to challenge EGF/TFGα autocrine loop participation in the action of estrogens (Arteaga C L et al. (1988) *Mol Endocrinol* 2, 1064-1069).

IGF-I, IGF-II and Insulin as Substitutes for Estrogen Action. Insulin-like growth factors I and II (IGF-I and IGF-II) promote breast cancer cell growth (Furlanetto R W and DiCarlo J N (1984) *Cancer Res* 44, 2122-2128; Myal Y et al. (1984) *Cancer Res* 44, 5486-5490; Dickson R B and Lippman M E (1987) *Endocr Rev* 8, 29-43; Karey K P and Sirbasku D A (1988) *Cancer Res* 48, 4083-4092; Ogasawara M and Sirbasku D A (1988) *In Vitro Cell Dev Biol* 24, 911-920; Stewart A J et al. (1990) *J Biol Chem* 265, 2172-2178). IGF-I related proteins (Huff K K et al. (1986) *Cancer Res* 46, 4613-4619; Huff K K et al. (1988) *Mol Endocrinol* 2, 200-208; Dickson R B and Lippman M E (1987) *Endocr Rev* 8, 29-43; Minute F et al. (1987) *Mol Cell Endocrinol* 54, 17-184, as well IGF-II (Yee D et al. (1988) *Cancer Res* 48, 6691-6696; Osborne C K et al. (1989) *Mol Endocrinol* 3, 1701-1709), are thought of as possible autocrine/paracrine mitogens. Their secretion in response to hormones has been proposed (Dickson R B and Lippman M E (1987) *Endocr Rev* 8, 2943; Huff K K et al. (1988) *Mol Endocrinol* 2, 200-208; Osborne C K et al. (1989) *Mol Endocrinol* 3, 1701-1709). Insulin itself is likely an endocrine mediator. In the instant study, it was investigated whether exogenous IGF-I addition to cultures containing CDE-horse serum substituted for the inhibition reversing effects of estrogens with human breast cancer cells. FIGS. 37A and 37B show the results with the MCF-7K and MCF-7A cells, respectively. Clearly, 1.0 μg/mL IGF-I did not reverse the serum inhibition. This was true despite the fact that this concentration of added IGF-I was much more than growth saturating (Karey K P and Sirbasku D A (1988) *Cancer Res* 48, 4083-4092). Duplicate studies with the T47D cells gave the same results (FIG. 37C). It should be noted that IGF-I is active with breast cancer cells even in the presence of serum (Furlanetto R W and DiCarlo J N (1984) *Cancer Res* 44, 2122-2128; Myal Y et al. (1984) *Cancer Res* 44, 5486-5490; Osborne C K et al. (1989) *Mol Endocrinol* 3, 1701-

1709; Stewart A J et al. (1990) *J Biol Chem* 265, 2172-2178; Cullen K J et al. (1990) *Cancer Res* 53, 48-53) that contains specific growth factor binding proteins (Rechler M et al. (1980) *Endocrinology* 107, 1451-1459). Human breast cancer cells also secrete binding proteins for the insulin-like growth factors (Yee D et al. (1991) *Breast Cancer Treat Res* 18, 3-10). Binding of the insulin-like factors to carrier proteins may attenuate activity (Zapf J et al. (1978) *J Clin Invest* 63, 1077-1084), have both inhibiting and activating effects (De Mellow J S et al. (1988) *Biochem Biophys Res Commun* 156, 199-204), or enhance biological action (Elgin R et al. (1987) *Proc Natl Acad Sci* USA 84, 3254-3258; Blum W F et al. (1989) *Endocrinology* 125, 766-772). In parallel studies (data not shown), the effects of IGF-II were assayed with the same breast cancer lines under the conditions used with IGF-I. Even at 500 ng/mL, IGF-II did not reverse the inhibitory effects of 10 to 50% (v/v) CDE serum. In another related test, insulin at 10 ng/mL to 10 µg/mL did not reverse the inhibition caused by 50% (v/v) CDE serum. The results with insulin, IGF-I and IGF-II were mutually supportive because these mitogens promote growth via a common receptor (Rechler M et al. (1980) *Endocrinology* 107, 1451-1459; Karey K P and Sirbasku D A (1988) *Cancer Res* 48, 4083-4092; Osborne C K et al. (1989) *Mol Endocrinol* 3, 1701-1709; Stewart A J et al. (1990) *J Biol Chem* 265, 2172-2178). The insulin results were also important in another way. This hormone does not interact with binding proteins and hence their presence in medium will not influence insulin action. These results again confirm the same conclusion arrived at earlier using an entirely different approach (Karey K P and Sirbasku D A (1988) *Cancer Res* 48, 4083-4092). Direct evidence for obligatory IGF-1/IGF-II autocrine loops in estrogen responsive cell growth simply has not been confirmed yet. In fact, there is solid in vivo evidence to the challenge IGF-1/IGF-II autocrine loop participation in the action of estrogens (Arteaga C L et al. (1989) *J Clin Invest* 84, 1418-1423).

Conceptual Derivations from this Study. These results also have a direct bearing on a number of hypotheses advanced to explain how estrogens cause target tissue cell growth. The development of the new methods herein provided a unique opportunity to reevaluate the most widely cited proposals under consideration. It was concluded that serum contains an inhibitor that effectively blocks ER$^+$ and AR$^+$ cell growth. Furthermore, physiologic concentrations of sex steroid hormones reverse this inhibition. The results were uniformly the same no matter from which species the cell lines were derived or which species was the source of the serum. In every case, the effects of the various classes of steroid hormones on the different cell lines were consistent with their known tumor forming/growth properties in vivo or published responses in vitro. These results provide new insights into the following proposed mechanisms.

Serum Factor Regulation—Demonstration of Estrogen Responsiveness. The literature describing positive sex steroid hormone growth effects is notably weighted in favor of the use of serum-supplemented cultures. In fact, a review made of the literature (Briand P and Lykkesfeldt A E (1986) *Anticancer Res* 6, 85-90; Wiese T E et al. (1992) *In Vitro Cell Dev Biol* 28A, 595-602) indicates that most past studies have used medium containing ≦20% (v/v) steroid hormone depleted serum. Although other investigators have reported estrogenic effects in "serum-free defined culture", these studies actually used conditions that included a prolonged preincubation in the presence of serum (Allegra J C and Lippman M E (1978) *Cancer Res* 38, 3823-3829; Briand P and Lykkesfeldt A E (1986) *Anticancer Res* 6, 85-90; Darbre P D et al. (1984) *Cancer Res* 44, 2790-2793). The results presented in preceding Examples demonstrate clearly that large magnitude effects are readily demonstrable in medium with CDE-serum and that as the CDE-serum concentrations increase to a maximum useable level of 50%, cell growth is inhibited and estrogens invariably reverse these effects. In light of those results, it was clear that the presence of serum, or a factor(s) contained in serum, made possible the demonstration of sex hormone dependent growth in culture.

The Endocrine Estromedin Hypothesis—Positive Indirect Control. In 1978 it was proposed (Sirbasku D A (1978) *Proc Natl Acad Sci* USA 75, 3786-3790) that growth of estrogen target tissues was not mediated directly by these hormones, but was instead controlled indirectly by steroid inducible circulating growth factors (i.e. endocrine estromedins). Estromedins were proposed to be secreted by target tissues such as uterus, kidney and pituitary, and to act in concert to simultaneously promote the growth of all ER$^+$ target tissues (Sirbasku D A (1978) *Proc Natl Acad Sci* USA 75, 3786-3790; Sirbasku D A (1981) *Banbury Report* 8, 425-443; Ikeda T et al. (1982) *In Vitro* 18, 961-979). The estromedin hypothesis arose from the observation that reproducible in vitro direct estrogen mitogenic effects were not identifiable (Sirbasku D A (1978) *Proc Natl Acad Sci* USA 75, 3786-3790; Sirbasku D A (1981) *Banbury Report* 8, 425-443; Ikeda T et al. (1982) *In Vitro* 18, 961-979). It must be emphasized that the original estromedin hypothesis rested entirely upon the failure to demonstrate large magnitude estrogen mitogenic effects in culture with cell lines confirmed to form steroid hormone responsive tumors in host animals. When estrogen effects were clearly observed with the MTW9/PL2 rat mammary tumor cells in culture, as described herein and reported (Moreno-Cuevas J E and Sirbasku D A (2000) *In Vitro Cell Dev Biol* 36, 410-427; Sirbasku D A and Moreno-Cuevas J E (2000) *In Vitro Cell Dev Biol* 36, 428-446), it was apparent that the endocrine estromedin model required further evaluation. It was reasoned that extension of these results to additional ER$^+$ cell lines, including those from other species and diverse target tissues, would either provide important support for the earlier hypothesis or disprove it. In the work disclosed herein, this reassessment has been accomplished. All of the ER$^+$ cells tested, as well as one androgen sensitive AR$^+$ human cancer line, manifested substantial growth in response to the appropriate steroid hormones in cultures containing inhibiting concentrations of CDE serum. There can be no doubt that steroid hormones act positively to promote target tumor cell growth. The results presented in this report plainly nullify the previous endocrine estromedin model of steroid hormone responsive cell growth. The disproval of the earlier endocrine estromedin model reopened the question of how estrogens and other factors regulate sex steroid responsive growth.

Autocrine and Paracrine Models—Positive Indirect Control. In the studies described in this Example, it was asked if exogenous growth factors mimic the inhibitor reversing effects of estrogens. The EGF/TFGα and insulin-like families were focused on because of their high biological potencies and physiologic relevance. These growth factors were expected to substitute for steroid hormones based on the autocrine loop mechanisms proposed earlier. Despite this expectation, polypeptide growth factors did not substitute for the estrogens. They were inactive in the presence of the serum-borne inhibitor. In point of fact, deduction indicates that it makes no practical difference whether the growth factors were autocrine or paracrine in origin. The presence of the serum inhibitor in effect blocks all mitogenic action except that exerted by the steroid hormones. This is a preferred feature of the serum-borne inhibitor(s) disclosed herein, and is further described in Examples which follow, when the use of serum-free defined culture is described. These results also indicate that the search for the regulatory mechanism controlling estrogen dependent growth must seek new directions. Since the estrogenic effects seen in CDE-serum are the largest yet recorded, CDE is the preferred source of the regulator in the cell growth assays.

Culture Parallels in vio Growth Regulation. The results shown in this Example have another important implication. Usually normal in vivo tissues are bathed in growth factor containing fluids. Mitogens within tissues may be of local origin or may be derived from the circulation (Gospodarowitz D and Moran J S (1976) *Annu Rev Biochem* 45, 531-558; Goustin A S et al. (1986) *Cancer Res* 46, 1015-1029). If growth factors have unrestricted freedom to stimulate cell proliferation, normal formation and architecture of the tissues would not develop nor could they be maintained. Manifestly, tissue architecture would be disrupted. In fact, this is one definition of cancer (Sonnenschein C and Soto A M (2000) *Mol Carcinog* 29, 205-211). The properties of a serum-borne inhibitor that counterbalances unrestricted growth merit serious further consideration with regard to how cancers develop in steroid hormone sensitive tissues. Others researchers have also arrived at this conclusion (Soto A M and Sonnenschein C (1985) *J Steroid Biochem* 23, 87-94).

The Estrocolyone Hypothesis—Negative Indirect Regulation. The estrocolyone model (Soto A M and Sonnenschein C (1987) *Endocr Rev* 8, 44-52) is an indirect negative mechanism based on regulation of sex steroid hormone dependent cells via a serum-borne inhibitor. The inhibitor blocks growth promoted by non-steroidal mitogens such as growth factors and diferric transferrin. Sonnenschein and Soto first proposed that estrocolyone acted at the cell surface via specific receptors. The effects of sex steroid hormones were to bind estrocolyone and prevent it from associating with the cells. Only low physiologic concentrations of sex steroid hormones were needed for this function. The special emphasis of this model was that sex steroid hormones did not act through intracellular located DNA binding receptors (i.e. cytosolic or nuclear sites). These intracellular sites had no growth function. Hence, this was an indirect negative mechanism (Soto A M and Sonnenschein C (1987) *Endocr Rev* 8, 44-52). The results presented in this disclosure are in agreement with the serum-borne mediator aspect of the estrocolyone hypothesis. There is no doubt that serum from several species contains a steroid hormone reversible inhibitor and that its isolation and molecular characterization will be a major advance with both practical and conceptual applications. With regard to the action site of the steroid hormones, these results differ from the estrocolyone hypothesis as described (Soto A M and Sonnenschein C (1987) *Endocr Rev* 8, 44-52). As discussed in the Background of the Invention, the tentative identification of several estrocolyone candidates have been described, and in U.S. Pat. Nos. 4,859,585 (Sonnenschein) and 5,135,849 (Soto), the issue of properties was raised again, but with different conclusions than published earlier.

The Positive Direct Model—Steroid Hormone Receptor Mediation. The one mechanism most widely accepted regarding steroid hormones and growth involves the nuclear located DNA binding ERα receptor (Gorski J and Hansen J C (1987) *Steroids* 49, 461-475). Growth is thought to be mediation by specific cytosolic and/or nuclear located receptors that ultimately alter DNA transcription to regulate gene activity. Results from many laboratories support this mechanism (Jensen E V and Jacobson H I (1962) *Recent Prog Horm Res* 18, 387-414; Gorski J et al. (1968) *Recent Prog Horm Res* 24, 45-80; Jensen E V et al. (1968) *Proc Natl Acad Sci USA* 59, 632-638; Jensen E V and DeSombre E R (1973) *Science* (Wash D.C.) 182, 126-134; Anderson J N et al. (1974) *Endocrinology* 95, 174-178; O'Malley B W and Means A R (1974) *Science (Wash D.C.)* 183, 610-620; Lippman M E (1977) *Cancer Res* 37, 1901-1907; Harris J and Gorski J (1978) *Endocrinology* 103, 240-245; Markaverich B M and Clark J H (1979) *Endocrinology* 105, 1458-1462; Katzenellenbogen B S (1980) *Annu Rev Physiol* 42, 17-35; Katzenellenbogen B S (1984) *J Steroid Biochem* 20, 1033 -1037; Clark J H and Markaverich B M (1983) *Pharm Ther* 21, 429-453; Darbre P et al. (1983) *Cancer Res* 43, 349-355; Darbre P D et al. (1984) *Cancer Res* 44, 2790-2793; Huseby R A et al. (1984) *Cancer Res* 44, 2654-2659; Gorski J and Hansen J C (1987) *Steroids* 49, 461-475; Katzenellenbogen B S et al. (1987) *Cancer Res* 47, 4355-4360; O'Malley B W (1990) *Mol Endocrinol* 4, 363-369). As also discussed in Example 1, the preferred positive action of estrogens is activation of a new ERγ that saturates/activates at lower steroid concentrations than the ERα or the ERβ.

Serum Proteins with Estrocolyone Steroid Binding Characteristics. If the estrocolyone mechanism is in fact correct, one must be able to identify at least one serum protein with very high affinity binding (i.e. $K_d$ picomolar) for sex steroids. There is, however, a major unresolved problem with that hypothesis. Other than sex hormone binding globulin (SHBG), additional high affinity estrogen binding in CDE human serum has not been found. SHBG has $K_d$ of $1.7 \times 10^{-9}$ M for $E_2$ at 37° C. (Rosner W and Smith R N (1975) *Biochemistry* 14, 4813-4820). This affinity does not qualify as the high binding expected of estrocolyone. Also, a search for estrocolyone in human serum only resulted in identification of SHBG (Reny J-C and Soto A M (1992) *J Clin Endocrinol Metab* 68, 938-945). No higher affinity binding site/protein was found. The binding of labeled steroid hormones with CDE-horse and CDE-rat serum was studied (results presented in an Example which follows), and $^3H-E_2$ specific binding at $K_d$ of 20 to 50 nM was found. This is a significant matter because estrogenic effects are demonstrated in this disclosure at 1 to 10 picomolar. As further support for this point, the estrocolyone authors found estrogenic effects at 10 to 30 picomolar $E_2$ (Soto A M and Sonnenschein C (1985) *J Steroid Biochem* 23, 87-94; Soto A M and Sonnenschein C (1987) *Endocr Rev* 8, 44-52). The lack of correlation between the concentration of steroid that promotes growth and affinity of sex steroids for serum components raises serious questions about this aspect of the estrocolyone hypothesis. These observations also suggest that a very high affinity intracellular ERγ regulates growth.

A New Model of Steroid Hormone Responsive Cell Growth. A new model best fits the available data. It brings together aspects of both the direct positive mechanism and indirect negative control. According to this model, regulation of steroid hormone target tumor cell growth is a balance between positive and negative control signals. This balance dictates either growth (i.e. cell division) or quiescence (i.e. cell metabolism and tissue specific function but without cell division). The positive mediators are the steroid hormones acting mediated by a high sensitivity intracellular DNA binding sex steroid receptor that ultimately activates gene expression via intracellular located receptors; whereas negative regulation is exerted by a serum-borne inhibitor that acts at the cell surface. The results disclosed herein support the view that growth is controlled directly by both negative and positive mediators. In a subsequent Example, this model of negative and positive response control mechanisms is further described and the mediators are shown to be the secretory immunoglobulins acting on cell surface (membrane) receptors.

TGFβ and Relevant Inhibition. The results presented further define the molecular properties of the serum-borne inhibitor by eliminating TGFβ1 as a candidate. This is an important issue because of the well-known effects of TGFβ on normal breast epithelial cells (Hosobuchi M and Stampfer M R (1989) *In Vitro Cell Dev Biol* 25, 705-713) and ER⁻ estrogen insensitive breast cancer cells (Arteaga C L et al. (1988) *Cancer Res* 48, 3898-3904). The results herein continue to confirm a previously unrecognized entity that serves as the estrogen reversible inhibitor in serum. Inhibitors that lack estrogen reversibility can be eliminated from consideration.

Discussion of Example 9. From this series of experiments, it can be readily appreciated that any other natural or synthetic protein or other substance can be similarly tested for cancer cell growth inhibiting activity akin to the serum-derived inhibitor in the CDE horse serum. Also, the same XAD™-4 and CDE extraction protocols may also be applied to body fluids and secretions other than serum, and the extracted fluids may be assayed as described for inhibitor activity. Such fluids or secretions include plasma, urine, seminal fluid, milk, colostrum, mucus and stool. An XAD™-4 column is especially suited for preparing a steroid hormone depleted specimen from a small sample of body fluid.

Example 10

Serum-free Defined Culture Medium Formulations.

In this Example, formulations of various serum-free defined culture media are discussed. Among other features, the preferred embodiments of the present media provide useful tools for detecting estrogenic effects.

During the course investigations leading to the present invention, serum-free defined medium was used to identify IgA, IgM and IgGs as estrogen and/or androgen reversible inhibitors of target tumor cell growth in culture, as demonstrated in subsequent Examples. However, before the full effects of the immunoglobulins could be measured in serum-free defined medium, another issue had to be resolved. The growth of hormone responsive cancer cell types in serum-free medium based on standard preparations of D-MEM/F-12 was not as vigorous as expected. Despite the extensive purification of the water used for cell culture procedures (Sirbasku D A et al. (1991) *Biochemistry* 30, 295-304; Sirbasku D A et al. (1991) *Biochemistry* 30, 7466-7477) and careful management of technical issues (Moreno-Cuevas J E and Sirbasku D A (2000) *In Vitro Cell Dev Biol* 36, 410-427), it was still apparent that the problem persisted. It was found that thyroid hormone dependent cell growth in culture was being inhibited by a normal component in standard D-MEM/F-12 medium and that a serum-borne factor corrected the problem. This work was done with established rat pituitary tumor cell lines (Tashjian A H Jr (1979) *Methods Enzymol* 58, 527-535) in serum-free defined medium (Sirbasku D A et al. (1991) 77, C47-C55; Sirbasku D A et al. (1991) *Biochemistry* 30, 295-304; Sirbasku D A et al. (1991) *Biochemistry* 30, 7466-7477). As this work developed, it was recognized that the serum factor was apotransferrin and that its addition to serum-free defined medium permitted observation of thyroid hormone dependent pituitary tumor cell growth (Sirbasku D A et al. (1992) *In Vitro Cell Dev Biol* 28A, 67-71; Sato H et al. (1992) *Mol Cell Endocrinol* 83, 239-251). Apotransferrin is a $M_r$ 80,000 bilobular serum protein that binds one Fe (III) in each lobe, albeit with slightly different affinities (Aisen P and Liebman A (1972) *Biochim Biophys Acta* 257, 314-323; Chasteen N D (1983) *Trends Biochem Sci* 8, 272-275; Evans R W and Williams J (1978) *Biochem J* 173, 543-552). When Fe (III) saturated, the protein is called diferric transferrin. This form of transferrin is the major iron delivery system for the body (Young S P and Aisen P (1981) *Hepatology* 1, 114-119; Ciechanover A et al. (1983) *J Biol Chem* 258, 9681-9689). Because apotransferrin possesses very high affinity for Fe (III) (i.e. ~$10^{20}$ at pH 7.4), there is no significant free iron in blood. Considering the extraordinary specificity of apotransferrin for Fe (III), it was concluded that the presence of the ferric (FeIII) form of iron in culture medium was deleterious to hormone responsive rat pituitary tumor cell growth (Sato H et al. (1991) *In Vitro Cell Dev Biol* 27A, 599-602). Additional work with apotransferrin and other Fe (III) chelators, along with direct addition of Fe (III) to culture medium, confirmed that this toxic metal was inhibiting thyroid hormone dependent growth of rat pituitary tumor cells in culture (Eby J E et al. (1992) *Anal Biochem* 203, 317-325; Eby J E et al. (1992) *J Cell Physiol* 156, 588-600). In neutralizing studies, the very specific Fe (III) chelator deferoxamine mesylate (a.k.a. deferoxamine or desferrioxamine) stood out because of its very high affinity for the iron (i.e. ~$10^{30.6}$) (Eby J E et al. (1993) *J Cell Physiol* 156, 588-600) and its lack of toxicity to cells in culture. Its addition to cell culture, at concentrations in small excess of the few μM levels of Fe (III) in medium, essentially neutralized the toxic metal (Eby J E et al. (1992) *Anal Biochem* 203, 317-325). Because deferoxamine is a low molecular weight bacterial product, it is relatively inexpensive compared to serum-derived apotransferrin. But without doubt, it is equally effective (Eby J E et al. (1992) *Anal Biochem* 203, 317-325). Before these studies, deferoxamine had never been used in serum-free defined medium to protect hormone responsive cell growth from the toxic effects of Fe (III). Prior to the present invention, the broad applicability of that information had not yet been discovered nor had it been discovered that some of the tools developed (e.g. a deferoxamine-Sepharose® affinity matrix) were applicable to estimation of the concentrations of biologically active Fe (III) in chemical, industrial, environmental and biological samples. Deferoxamine mesylate is a U.S. FDA approved drug used to treat iron overload and iron toxicity in humans. It is marketed by Novartis Pharmaceuticals, East Hanover, N.J., under the trade name DESFERAL®. Deferoxamine mesylate is sold to researchers by Sigma Chemicals (St. Louis, Mo.).

Serum-free Defined Mammalian Cell Culture—Development Background. The use of serum-free defined medium to grow diverse cell types in culture gained national and international recognition with the publication by Hayashi and Sato (Hayashi I and Sato G H (1976) *Nature* (Lond) 259, 132-134). They demonstrated a breakthrough. The serum supplement commonly used in cell culture medium could be replaceable entirely by mixtures of nutrients and hormones in serum-free medium. This observation was expanded to include cell types from many mammalian tissues (Barnes D and Sato G (1980) *Anal Biochem* 102, 255-270; Barnes D and Sato G (1980) *Cell* 22, 649-655; Bottenstein J et al. (1979) *Methods Enzymol* 58, 94-109; Rizzino A et al. (1979) *Nutr Rev* 37, 369-378). Further development and application of this technology has been reported (Barnes D W, Sirbasku D A and Sato G H (Volume Editors) (1984) *Cell Culture Methods for Molecular Biology and Cell Biology*, Volume 1: *Methods for Preparation of Media, Supplements, and Substrata for Serum-free Animal Cell Culture*; Volume 2: *Methods for Serum-free Culture of Cells of the Endocrine System*; Volume 3: *Methods for Serum-free Culture of Epithelial and Fibroblastic Cells*; Volume 4: *Methods for Serum-free Culture of Neuronal and Lymphoid Cells*, Alan R. Liss/John Wiley, New York). A national symposium organized and directed by Drs. Gordon Sato, Authur Pardee and David Sirbasku was held at the Cold Spring Harbor Laboratory to address the unfolding technology required for serum-free defined medium growth of cells in culture and to discuss its applications (Sato G H, Pardee A B and Sirbasku D A (1982) Volume Editors, *Cold Spring Harbor Conferences on Cell Proliferation*, Volume 9, Books A and B, *Growth of Cells in Hormonally Defined Media*, Cold Spring Harbor, N.Y.).

Serum-free Defined Culture—Nutrient Additions. A number of nutrient additions to D-MEM/F-12 are needed to grow the cells used in the presently described studies. The formulations of serum-free defined medium employed are specific optimizations, modifications, or necessary changes of earlier media that have been described (Riss T L and Sirbasku D A (1987) *Cancer Res* 47, 3776-3782; Danielpour D et al. (1988) *In Vitro Cell Dev Biol* 24, 42-52; Ogasawara M and Sirbasku D A (1988) *In Vitro Cell Dev Biol* 24, 911-920; Karey K P and Sirbasku D A (1988) *Cancer Res* 48, 4083-4092; Riss T L et al. (1988) *In Vitro Cell Dev Biol* 24, 1099-1106; Riss T L et al. 25, *In Vitro Cell Dev Biol* 25, 127-135; Riss T L and Sirbasku D A (1989) *In Vitro Cell Dev Biol* 25, 136-142; Riss T L et al. (1986) *J Tissue Culture Methods* 10, 133-150; Sirbasku D A et al. (1991) *Mol Cell Endocrinol* 77, C47-C55; Sirbasku D A et al. (1991) *Biochemistry* 30, 295-304; Sirbasku D A et al. (1991) *Biochemistry* 30, 7466-7477; Sato H et al. (1991) *In Vitro Cell Dev Biol* 27A, 599-602; Sirbasku D A et al. (1992) *In Vitro Cell Dev Biol* 28A, 67-71; Sato H et al. (1992) *Mol Cell Endocrinol* 83, 239-251; Eby J E et al. (1992) *Anal Biochem* 203, 317-325; Eby J E et al. (1993) *J Cell Physiol* 156, 588-600; Sirbasku D A and Moreno-Cuevas J E (2000) *In vitro Cell Dev Biol* 36, 428-446).

Serum-free Defined Medium Nutrient Supplements—Bovine Serum Albumin. Bovine serum albumin (BSA) (Sigma Catalog No. A3912) was made by "initial fractionation by heat shock and Fraction V", minimum purity 98% (electrophoresis), according to the supplier. A 50mg/mL stock solution of BSA was prepared in normal saline and was sterilized using 0.2 µm pore membrane filters. Aliquots are stored at −20° C. in plastic tubes. As will be discussed below, the "heat shock" step that was used in most albumin preparation methods inactivates the estrogen reversible inhibitor disclosed herein.

Serum-free Defined Medium Nutrient Supplements—Linoleic Acid—Albumin (Lin-Alb). This preparation was purchased from Sigma as Linoleic Acid Albumin Conjugate (Catalog No. L8384). The conjugate is supplied as a powder sterilized by irradiation. The fatty acid content is 1% linoleic acid by weight. A stock solution was typically prepared by dissolving the contents of a 500 mg bottle in 10 mL of sterile normal saline to give a final concentration of 50 mg/mL. Aliquots are stored at 4° C. in polystyrene tubes. This solution is never frozen. Mammalian cells cannot produce polyunsaturated fatty acids. They must be supplied in a soluble form. Fatty acids are carried physiologically bound to albumin.

Serum-free Defined Medium Nutrient Supplements—Ethanolamine (ETN). ETN was purchased from Sigma (Catalog No. A5629) (FW 61). This liquid has a density of 1.0117 grams/mL. Using 0.610 mL in 100 mL of water, a 100 mM stock solution was prepared which was sterilized using the 0.2 µm pore membrane filters. The ETN was stored at −20° C. in polystyrene tubes. This nutrient is required to sustain phospholipid metabolism required for all membrane biosynthesis.

Serum-free Defined Medium Nutrient Supplements—Phosphoethanolamine (PETN). This solid material was purchased as o-phosphoryl-ethanolamine (FW 141) (Sigma Catalog No. P0503). A 10 mM stock of PETN was prepared by dissolving 141 mg in 100 mL of water and sterilizing with 0.2 µm pore membrane filters. Aliquots were stored at −20° C. in polystyrene tubes. This component is an adjunct to ETN.

Serum-free Defined Medium Nutrient Supplements—Glutamine (GLUT). This essential amino acid was purchased from Sigma (Catalog No. G5763). It is "cell culture tested" according to the manufacturer. Addition of glutamine (FW 146.1) to the culture media is necessary because of its relatively short half-life (i.e. about 80% is lost in 20 days at 35° C.). See the Sigma product information for the decay curves at different temperatures and pH. Purchased D-MEM/F-12 stored in the refrigerator for about three weeks lost most of the original glutamine present. For serum-free applications, additional supplementation is required to sustain growth. For a preparation, 11.7 g was dissolved in 400 mL of water to give 200 mM glutamine. This solution was sterilized using 0.2 µm pore filter membranes. Aliquots are stored at −20° C. polystyrene tubes. The final glutamine concentration added to serum-free defined medium is 2 mM. Glutamine is a major metabolite and energy source for cells growing in culture.

Serum-free Defined Medium Nutrient Supplements—Reduced Glutathione (GSH). Crystalline reduced glutathione (FW 307.3) was purchased from Sigma (Catalog No. G4251). A stock of 40 mg/mL was prepared by dissolving 400 mg in 10 mL of water. This stock was very quickly sterilized with a 0.2 µm pore filter unit. Aliquots were quickly stored at −20° C. in polystyrene tubes. According to Sigma technical service, this sulfhydryl (—SH) compound is unstable in aqueous solutions, including tissue culture medium, and is rapidly converted to the oxidized GS-SG form by exposure to air. Addition every two to four days to the culture medium may be required for reducing agent requiring cells. Another reducing agent that also is effective is mercaptoethanol. It is more stable and often effective at lower concentrations than GSH. Reducing agents act as "scavengers" of free radicals generated by the oxygen atmosphere of cell culture.

Serum-free Defined Medium Nutrient Supplements—Selenium (Se). A powder of sodium selenite (100 mg/vial) is obtained from Collaborative Research or Sigma (Catalog No. S5261). It has been sterilized by irradiation. The contents of a single vial are dissolved in 100 mL of sterile water to give final stock of 1.0 mg/mL. This preparation should not be filter sterilized because Se binds to filters. The final volume was diluted to 100 mL with sterile saline. Aliquots are stored at −20° C. in polystyrene tubes. Selenium is an important cofactor for enzyme systems that protect the cells from oxidation effects.

Serum-free Defined Medium Nutrient Supplements—Diferric Transferrin (2FeTf). Iron Fe (III) saturated (98%) human transferrin (diferric transferrin) was purchased from Collaborative Research (Catalog No. 40304) or Sigma (Catalog No. T3309) as bottles containing 1 gram of red colored powder. The contents of one bottle are dissolved in 100 mL of normal saline. This red colored solution is sterilized using 0.2 µM pore membrane filters. This stock is 10 mg/mL. Aliquots are stored at −20° C. in polystyrene tubes. All growing cells require diferric transferrin as a source of iron for a great many metabolic processes.

Serum-free Defined Medium Growth Factor Supplements—Epidermal Growth Factor (EGF). EGF prepared from mouse submaxillary gland (tissue culture grade) was purchased from Collaborative Research (Catalog No. 40001) as 100 µg in a sterile vial or from Sigma (Catalog No. E4127). The original vials are stored at 4° C. according to the manufacturer's instructions. To prepare a stock solution, 5.0 mL of sterile saline was added to a vial to yield a 20 μg/mL EGF solution. Aliquots are stored frozen at −20° C. polystyrene tubes. Repeated freeze-thaw must be avoided. This growth factor is useful because of its very broad cell specificity range.

Serum-free Defined Medium Growth Factor Supplements—Acidic Fibroblast Growth Factor (aFGF). Acidic FGF is purchased from Sigma (Catalog No. F5542). It is the human recombinant product from *E. coli*. This product has very specific handling requirements. It is provided sterilized in 25 μg vials lyophilized from PBS containing 1.25 mg of BSA. The contents of each vial are reconstituted in 25 mL of sterile PBS containing 1.0 mg/mL of BSA and 10 μg/mL of heparin. Filtration of this product at this concentration must absolutely be avoided. This solution is stored at −20° C. in polystyrene tubes. The solutions of aFGF definitely cannot be freeze-thawed more than twice. This growth factor is highly labile. Careless handling will result in problems. Keratinocyte growth factor (KGF) can substitute for aFGF. The fibroblast growth factor family is very important in growth of urogenitial tissues including prostate.

Serum-free Defined Medium Growth Factor Supplements—Heparin. Heparin is used to stabilize FGF in cell culture (Gospodarowitz D and Cheng J (1986) *J Cell Physiol* 128, 475-484). Heparin is obtained from Sigma (Catalog No. H3149) as the sodium salt, Grade 1-A, from porcine intestinal mucosa. A solution of 1.0 mg/mL is made in saline and sterilized with 0.2 μm pore membrane filters. An aliquot of 250 μL is added to the 25 mL of aFGF reconstitution solution used above. Sterile heparin is stored at 4° C.

Serum-free Defined Medium Adhesion Protein Supplement—Fibronectin (Fbn). Human plasma derived Fbn can be purchased from many commercial sources. Bovine Fbn is also available and is effective. Fbn is prepared from units of fresh human plasma (unfrozen) or fresh bovine (unfrozen) plasma by two methods (Retta S F et al. (1999) *Methods in Molecular Biology* 96, 119-124; Smith R L and Griffin C A (1985) *Thrombosis Res* 37, 91-101). Purity is evaluated by SDS-PAGE with Coomassie Brilliant Blue staining or silver staining (Pierce Chemicals® kits). Adhesion activity is confirmed with cells in serum-free defined medium. Vitronectin can substitute for fibronectin.

Serum-free Defined Medium Iron (Fe (III) Chelator Supplements—Deferoxamine Mesylate (DFX). DFX (FW 656.8) is purchased from Sigma (Catalog No. D9533). The stock solution is made at 10 mM by adding 131 mg to 20 mL of highly purified water as described above. The solution is sterilized by filtration with 0.2 μM pore membranes. Aliquots are stored at −20° C. in polystyrene tubes.

Serum-free Defined Medium Iron (Fe (III) Chelator Supplements—Apotransferrin (apoTf). Human serum ApoTf can be purchased from Sigma (Catalog No. T4382). It is minimum 98% iron-free. ApoTf is also prepared as described previously (Sirbasku D A et al. (1991) *Biochemistry* 30, 295-304; Sirbasku D A et al. (1991) *Biochemistry* 30, 7466-7477). ApoTf is prepared by dialysis against citrate buffer pH 5.0-5.5 with 1 μg/mL DFX present to chelate>98% of the iron. Handling and storage were as described for diferric transferrin but with great care to avoid contact with iron sources.

Serum-free Defined Medium Nutrient Supplements—Bovine Insulin (INS). This hormone was purchased from either of two sources. From Gibco-BRL it is Insulin, Bovine Zinc Crystals for Cell Culture Applications (Catalog No. 18125-039). It was also obtained from Collaborative Research (Catalog No. 40305) and stored at 4° C., according to that manufacturer's recommendation. Gibco-BRL recommends solid insulin storage at −5° C. to 20° C. A stock of 10 mg/mL in 0.01 N HCl was prepared by adding 250 mg of insulin to 25 mL of the acid. The HCl was made by adding 172 μL of concentrated (11.6 N) HCl to 100 mL of water. The final stock solution of 10 mg/mL of insulin is filter sterilized using 0.2 μm pore diameter membranes. Aliquots are stored at 4° C. in polystyrene tubes. Care was taken not to freeze-thaw the aliquots of stock solution. Insulin is a very broad range cell growth-stimulating factor as well as a regulator of specific metabolic processes.

Serum-free Defined Medium Nutrient Supplements—Thyroid Hormones. The preferred thyroid hormone is $T_3$ (3', 5-Triiodothyronine, FW 673, purchased from Sigma as Catalog No. T2752). It is stored desiccated at −20 C. To prepare stocks, 0.5 N NaOH was made by addition of 20 grams of pellets to one liter of water. Then, 67.3 mg of $T_3$ was added. After dissolving the $T_3$ with stirring for a few minutes, 25 mL of this stock was diluted up to 250 mL with water, for a final concentration of 0.05 N NaOH. This dilution was sterilized using the 0.2 μm pore diameter filter. At this point, the final stock for storage was 10 μM $T_3$. Aliquots of this final stock are stored in polystyrene tubes at −20° C. The second thyroid hormone, thyroxin ($T_4$, sodium salt, pentahydrate FW 888.9), is prepared by the same procedure. For this stock solution, 88.9 mg of $T_4$ are used. $T_4$ is purchased from Sigma (Catalog No. T2501). $T_4$ is used at 10 to 20 times higher concentrations than $T_3$. Care is taken not to freeze-thaw these preparations. Thyroid hormones have a very broad range of biological effects on metabolism and growth. Many cells in culture require these for growth.

Compositions of Serum-free Defined Media. TABLE 7 presents the formulations of the preferred serum-free defined media developed for use in detecting high-level steroid hormone reversible inhibition by steroid hormone-stripped serum fractions and by purified inhibitors in serum-free cell growth assays. As indicated in the footnotes to the table, when a particular component is included in one of the formulations, the concentration that provides a suitable cell growth medium can fall within the indicated range.

TABLE 7

Composition of Serum-free Defined Media
Based on Standard Gibco-BRL D-MEM/F-12

| | CELL TYPE | | | | |
|---|---|---|---|---|---|
| | Human Breast | Human Prostate | Rat Mammary | Rat Pituitary | Hamster Kidney |
| | MEDIUM NAME | | | | |
| | DDM-2MF | CAPM | DDM-2A | PCM-9 | CAPM |
| COMPONENT FINAL CONCENTRATIONS IN THE DEFINED MEDIA | | | | | |
| Insulin[1] | 500 ng/mL | 10 μg/mL | 10 μg/mL | 10 μg/mL | 10 μg/mL |
| EGF[2] | 20 ng/mL | 20 ng/mL | 20 ng/mL | None | 20 ng/mL |
| AFGF[3] | None | 10 ng/mL | None | None | 10 ng/mL |
| Triiodothyronine[4] | 0.3 nM | 1.0 nM | 0.3 nM | 1.0 nM | 1.0 nM |

TABLE 7-continued

Composition of Serum-free Defined Media
Based on Standard Gibco-BRL D-MEM/F-12

| | CELL TYPE | | | | |
|---|---|---|---|---|---|
| | Human Breast | Human Prostate | Rat Mammary | Rat Pituitary | Hamster Kidney |
| | MEDIUM NAME | | | | |
| | DDM-2MF | CAPM | DDM-2A | PCM-9 | CAPM |
| COMPONENT FINAL CONCENTRATIONS IN THE DEFINED MEDIA | | | | | |
| Diferric transferrin[5] | 10 μg/mL | 10 μg/mL | 10 μg/mL | 10 μg/mL | 10 μg/mL |
| Ethanolamine[6] | 50 μM | 50 μM | 50 μM | 10 μM | 50 μM |
| Phosphoethanolamine[7] | 5 μM | None | 5 μM | None | None |
| Bovine Serum Albumin[8] | 500 μg/mL | 1.0 mg/mL | 500 μg/mL | 500 μg/mL | 1.0 mg/mL |
| Linoleic acid-BSA[9] | 150 μg/mL | None | 150 μg/mL | None | None |
| Selenium[10] | 20 ng/mL | 10 ng/mL | 20 ng/mL | 10 ng/mL | 10 ng/mL |
| Reduced glutathione[11] | 20 μg/mL | None | 20 μg/mL | None | None |
| Glutamine[12] | 2.0 mM | None | 2.0 mM | None | None |
| Heparin[13] | None | 7.5 μg/mL | None | None | 7.5 μg/mL |
| Deferoxamine[14] | 5 μM | 10 μM | 5 μM | 10 μM | 10 μM |
| Human Fibronectin[15] | 25 μg | 20 μg | None | None | 20 μg |

When a component is added, the following are the effective concentration ranges used:
[1]INS range 100 ng/mL to 10 μg/mL
[2]EGF range 1 ng/mL to 50 ng/mL
[3]aFGF range 0.2 ng/mL to 20 ng/mL
[4]$T_3$ range 0.3 nM to 10 nM
[5]2FeTf range 2 μg/mL to 50 μg/mL
[6]ETN range 5 μM to 100 μM
[7]PETN range 5 μM to 50 μM
[8]BSA range 0.2 mg/mL to 5.0 mg/mL
[9]Lin-Alb range 50 μg/mL to 500 μg/mL
[10]Se range 5 ng/mL to 20 ng/mL
[11]GSH range 1 μg/mL to 50 μg/mL
[12]Glut range 0.5 mM to 2.0 mM
[13]Heparin range 1 μg/mL to 10 μg/mL
[14]DFX range 2 μM to 20 μM
[15]Fbn range 15 μg to 50 μg per 35-mm diameter dish Serum-free Media Variations. Standard phenol red-containing Gibco-BRL D-MEM/F-12 is a preferred basal medium to which the defined media components are added. It contains 0.6 mM to 1.0 M $CaCl_2$. D-MEM/F-12 can be purchased from Gibco-BRL in the liquid form or can be prepared from the powder formulation using only highly purified water. Alternatively, another suitable basal medium could be used as long as it provides at least the required minimum amounts of necessary nutrients, vitamins and minerals to maintain cell viability of the desired cell line. The calcium concentration range preferred is 0.6 to 10 mM. Calcium stabilizes the inhibitor in cell culture without impairing cell growth. The human breast cancer cell medium, DDM-2MF, was a modification of the original DDM-2 medium (Danielpour D et al. (1988) In Vitro Cell Dev Biol 24, 42-52) and MOM-1 (Ogasawara M and Sirbasku D A (1988) In Vitro Cell Dev Biol 24, 911-920) and contained modified hormone concentrations, deferoxamine (DFX) and fibronectin. Aqueous salt solutions such as tissue culture medium contain hydrolytic polymeric forms of Fe (III) (Spiro T G et al (1966) J Am Chem Soc 88, 2721-2726). DFX binds this form of Fe (III) with very high affinity (Schubert J (1964) In; Iron Metabolism: The Chemical Basis of Chelation, Springer, Berlin, pp 466-498). If not removed, Fe (III) inhibits hormone-responsive growth in serum-free defined medium (Sirbasku D A et al. (1991) Mol Cell Endocrinol 77, C47-C55; Sato H et al. (1992) Mol Cell Endocrinol 83, 239-251; Eby J E et al. (1993) J Cell Physiol 156, 588-600; Eby J E et al. (1992) Anal Biochem 203, 317-325). Fibronectin was used with DDM-2MF to promote cell attachment. The 35-mm diameter assay dishes were pre-coated by incubation with the designated amount of fibronectin (TABLE 7) for 16 to 48 hours at 37° C. in 2.0 mL of D-MEM/F-12. CAPM human prostatic cancer cell medium was developed to support the growth of tumor cells from this tissue. The composition of CAPM is described in TABLE 7. CAPM also supports the growth of the H301 Syrian hamster kidney tumor cells. DDM-2A, which is a modified form of DDM-2 (Danielpour D et al. (1988) In Vitro Cell Dev Biol 24, 42-52), was preferred for growing MTW9/PL2 cells. PCM-9 defined medium was developed for growing the rat pituitary cell lines. This medium differs from previous PCM formulations (Sirbasku D A et al. (1991) Mol Cell Endocrinol 77, C47-C55; Sato H et al. (1992) Mol Cell Endocrinol 83, 239-251; Eby J E et al. (1993) J Cell Physiol 156, 588-600; Eby J E et al. (1992) Anal Biochem 203, 317-325) in that DFX was substituted for apotransferrin and the triiodothyronine concentration was increased to 1.0 nM. Although DFX and apotransferrin (2 to 50 μg/mL) are the preferred chelators based on their very high specificity and affinities for Fe (III), EDTA at 1 to 10 μM or sodium citrate at 10 to 1000 μM also effectively neutralize the cytotoxic effects of Fe (III) (Eby J E et al. (1993) J Cell Physiol 156, 588-600). Ascorbic acid (vitamin C) also chelates Fe (III), but is used less often because it is unstable in cell culture medium at 37° C. in an oxygen environment in the presence of salts and metals in the medium. Also, at concentrations of 50 to 100 μg/mL, apo-ovotransferrin and apo-lactoferrin also were effective Fe (III) chelators in serum-free defined medium (Eby J E et al. (1993) J Cell Physiol 156, 588-600). Although EGF, aFGF and insulin are the preferred growth factors, several other human recombinant proteins are effective. They have either been purchased or obtained as gifts from Gibco- BRL, Sigma or IMCERA Bioproducts. Insulin-like growth factors I and II (IGF-I and IGF-II) can be used to replace insulin, transforming growth factor α (TFGα) replaces EGF, TGFβ as an inhibitory supplement, and basic fibroblast growth factor (bFGF) partially replaces aFGF. Insulin can be used to replaced IGF-I and IGF-II. All of these protein growth factors are dissolved under sterile conditions according to manufacturers' instructions and stored as indicated.

Discussion of Example 10. The preferred serum-free media described above provide an ideal scenario for the study of growth responses of hormone responsive cancers without the myriad of potential interactions accompanying the presence of serum with its 5000+ proteins and other compounds. The formulations presented permit dissection of growth into its individual parts caused by different stimulators. When of interest, a combination of a few factors can be investigated to achieve an understanding of growth promoter/inhibitor interactions (i.e. cross-talk). This is exceptionally difficult to achieve in the presence of full serum. The serum-free medium described herein provided a tool for the assessment of growth inhibitor(s) isolated from CDE-horse serum, whose actions are reversed by sex-steroid hormones, as mentioned at the beginning of this Example and described in more detail in subsequent Examples. The preferred serum-free media of the present invention raise hope for the provision of new insight that could help to clarify the mechanisms involved in the control of breast, prostatic and other mucosal cancers under conditions not previously available.

Moreover, because of widespread concern today about possible contamination of commercial animal sera by disease causing agents such as bovine spongiform encephalopathy ("mad cow disease"), there is a great need for serum-free cell culture media that can support a variety of cell types. The new media compositions fill that need. The new serum-free media can be used not only for assays but also for large scale testing purposes and industrial uses such as cell culture production of a desirable protein. For example, an antigen for vaccine production, or a monoclonal antibody can be prepared without fear of contamination a by serum-derived infectious agent. They are also useful for producing a quantity of virus for vaccine manufacture or for producing recombinant viruses for gene therapy. Basic cell culture methods for producing quantities of proteins or viruses are well known in the art and have been described in the literature.

Example 11

Serum-free Defined Medium that Supports Hormone Sensitive and Autonomous Cancer Cell Growth In this Example, it is shown that media derived according to the present methods are effective for supporting hormone sensitive and autonomous cancer cell growth.

Selection of Models to Study Hormone Dependence and Autonomy in Serum-free Defined Culture Media. One goal was to develop serum-free defined media that can be used to directly compare negative serum factor regulation with steroid hormone responsive and steroid hormone autonomous cancers of the same tissue. That meant establishing a medium that supported the growth of both cell types. As models, human prostatic carcinoma and human breast carcinoma cells were chosen because responsive and autonomous (unresponsive) cell lines are currently available for both types of cancers. Furthermore, as discussed above, these cancers have many common characteristics including their tendency to pass from steroid hormone receptor positive to steroid hormone receptor negative in a process called tumor progression.

Figure 38:
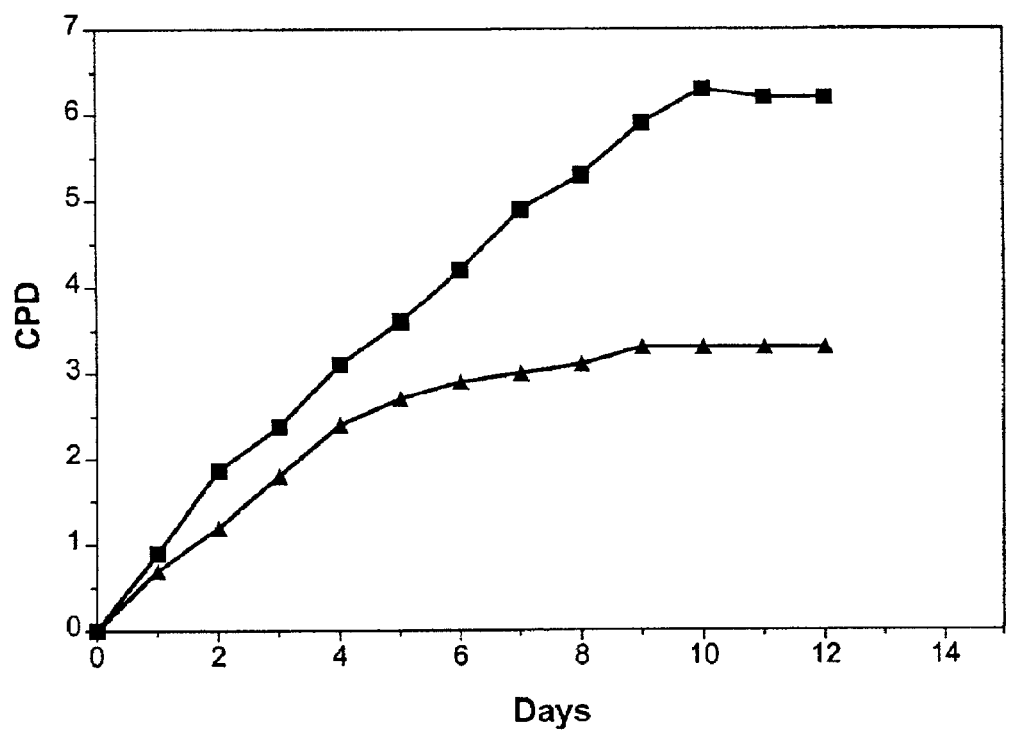
FIG. 38. Growth of T47D Human Breast Cancer Cells in Standard and "low-Fe" D-MEM/F-12.
Figure 39:
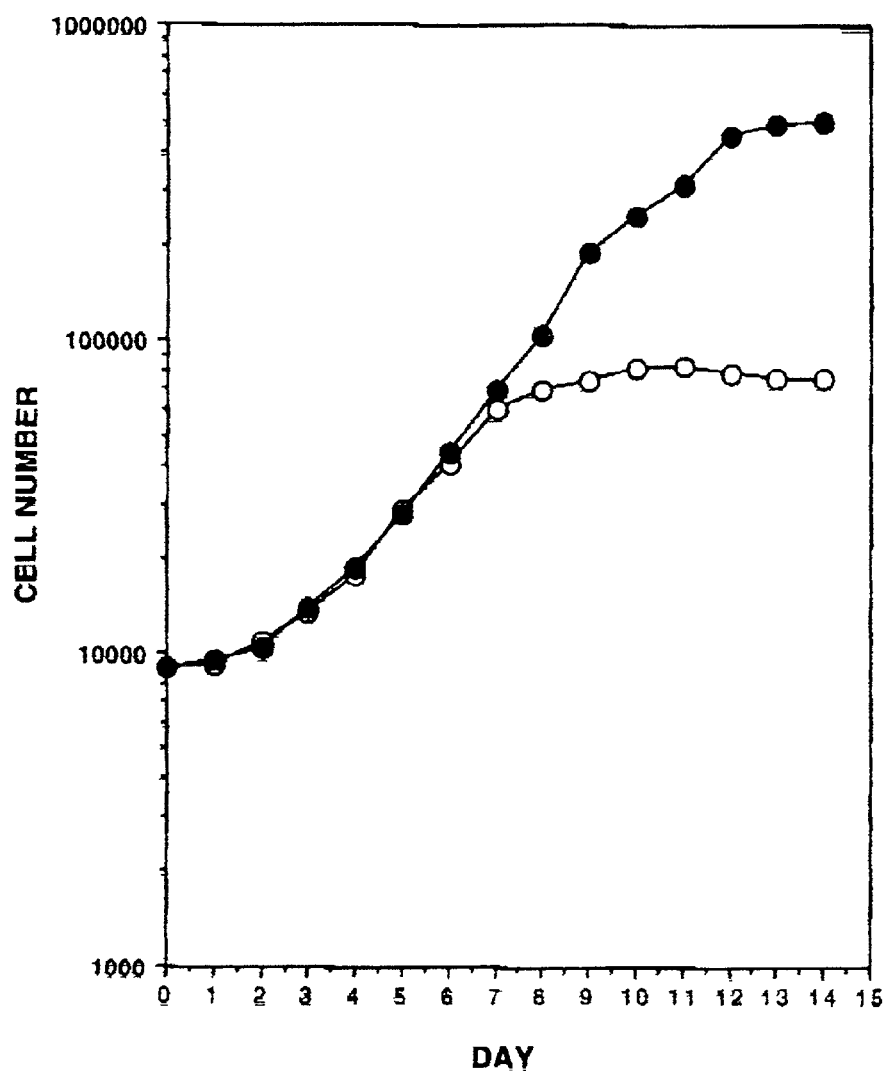
FIG. 39. Growth of LNCaP Human Prostate Cancer Cells in Standard and "low-Fe" D-MEM/F-12.
Figure 40:
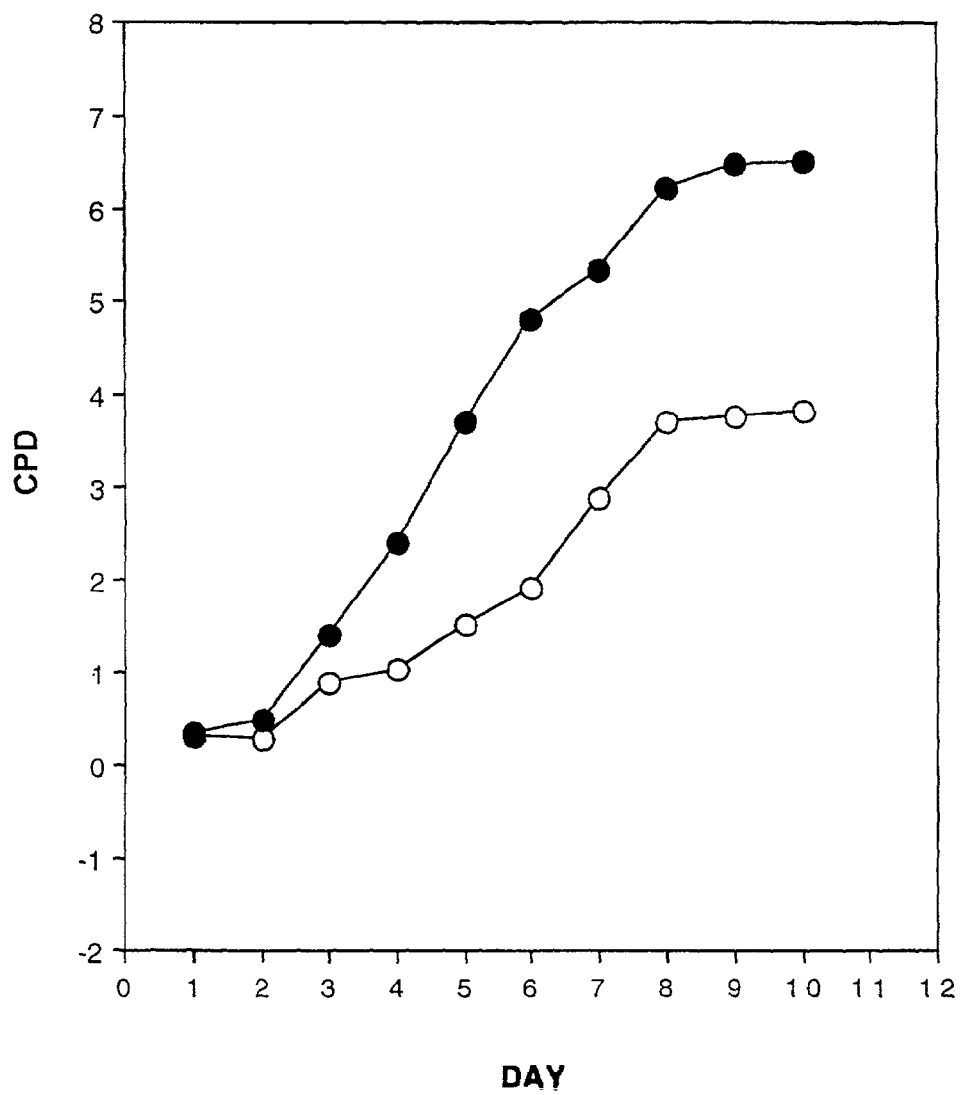
FIG. 40. Growth of MDCK Dog Kidney Tubule Cells in Standard and "low-Fe" D-MEM/F-12.

During the course of development of such defined media, one observation was made consistently: breast cancer cells that were $ER^+$ (i.e. estrogen sensitive) and prostate cancer cells that were $AR^+$ (i.e. androgen sensitive) grew less well in defined medium based on standard D-MEM/F12 than in defined medium based on "low-Fe" D-MEM/F12. The results of an example with T47D cells in DDM-2MF are shown in FIG. 38. The example with LNCaP cells in CAPM is shown in FIG. 39. Another example is the thyroid hormone responsive MDCK kidney tubule epithelial cells in CAPM as shown in FIG. 40. Standard D-MEM/F-12 contains both ferric nitrate and ferrous sulfate as nutrient additions. When purchased without these salts, the medium was designated "low-Fe" D-MEM/F-12. The iron concentrations in standard and "low-Fe" D-MEM/F-12 were 1.0 μM and 0.15 μM, respectively (Eby J E et al. (1992) *Anal Biochem* 203, 317-325). Even in "low-Fe" medium, iron is present as a contaminant in the chemicals used to make the formulation, the 2.2 g/L $NaHCO_3$ added as a metabolic requirement and buffer, and the 15 mM HEPES buffer necessary for stabilizing the pH under serum-free conditions (Eby J E et al. (1992) *Anal Biochem* 203, 317-325). It is noteworthy that as low as 1.0 μM Fe (III) inhibits epithelial cell growth completely within five to seven days. In another test the thyroid hormone responsive human HT-29 colonic carcinoma cells in CAPM also grew better in "low-Fe" than standard D-MEM/F-12 (data not shown). This indicates that restriction of Fe (III) in culture medium will have implications even beyond sex steroid hormone dependent cells.

Modifications of the Usual Growth Assays for Experiments in "Low-Fe" Medium versus "Standard" Medium. Specific modifications of the customary cell growth assays were required for assays done under iron-restricted conditions. For example, the 35-mm assay dishes were incubated for 16 to 24 hours prior with 20 to 25 μg of fibronectin in 2 mL of "low-Fe" D-MEM-F12 medium. Serum-free components were added to "low-Fe" D-MEM/F-12 at double the concentrations needed (2X) or to "standard" D-MEM/F-12 at (2X) as the experiments dictated. Each assay dish received 1.0 mL of this solution. Next, the cells to be used in the assays were washed three times in either "low-Fe" medium or "standard" medium depending upon the experimental protocol. These washes were done with the same care as described above in General Materials and Methods. Each dish received 1.0 mL of cells in the appropriate medium. At this point, the components final concentrations were (1X) as summarized in TABLE 7. Also, TABLE 7 describes medium containing deferoxamine as the Fe (III) chelator. Although less preferred, due in part to cost considerations, specificity, and affinity for Fe (III), as noted above, apotransferrin is also effective, especially at the preferred apotransferrin concentration of 50 μg/mL. When apotransferrin binds Fe (III), it is converted to one of three forms of ferric transferrin (Eby J E et al. (1992) *Anal Biochem* 203, 317-325). These become additional support for cell growth in defined medium, thereby converting a toxic substance to a useable nutrient.

Figure 41:
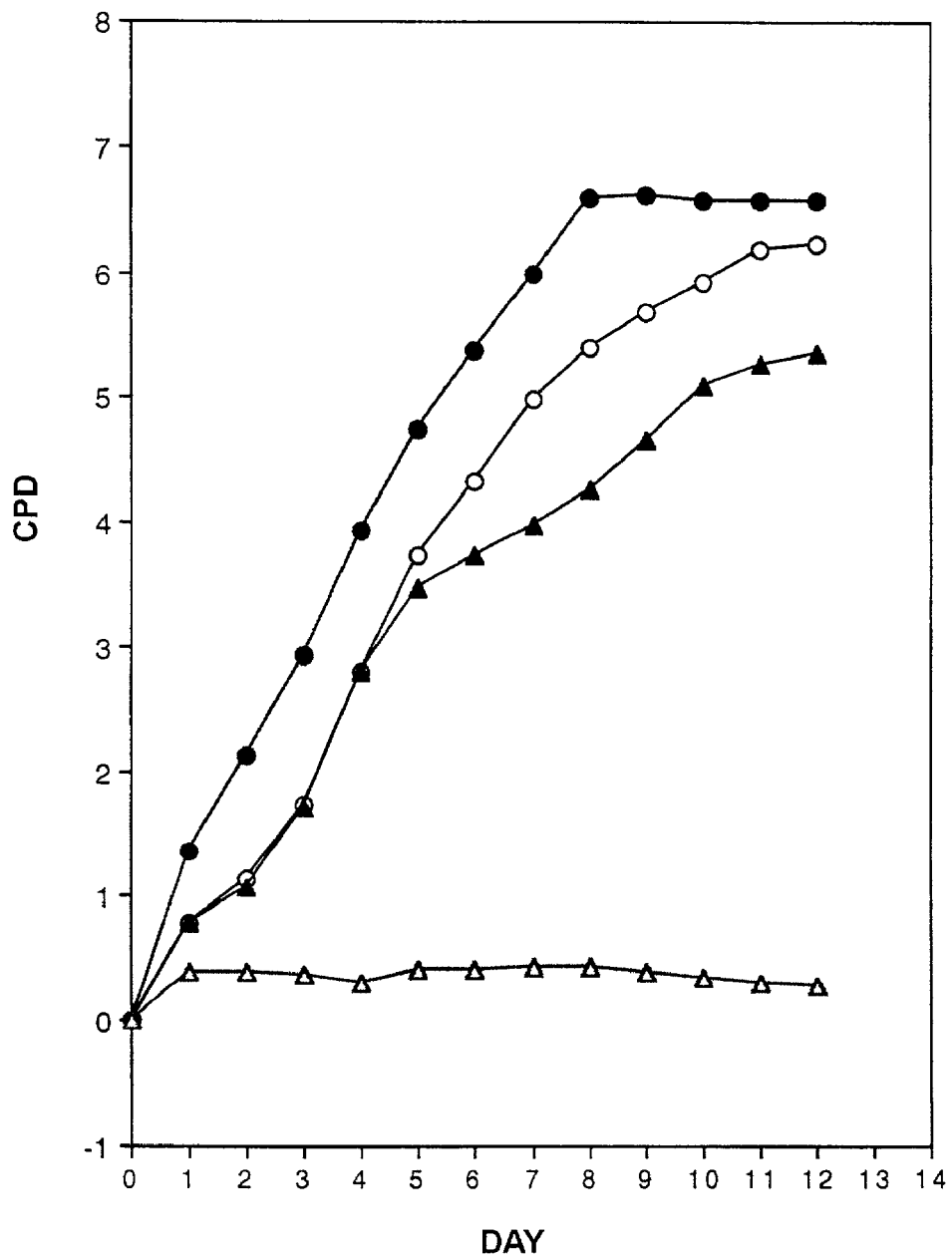
FIG. 41. Growth of $AR^+$ LNCaP Cells in CAPM±DHT versus Growth in D-MEM/F-12 Containing 10% Fetal Bovine Serum.
Figure 42:
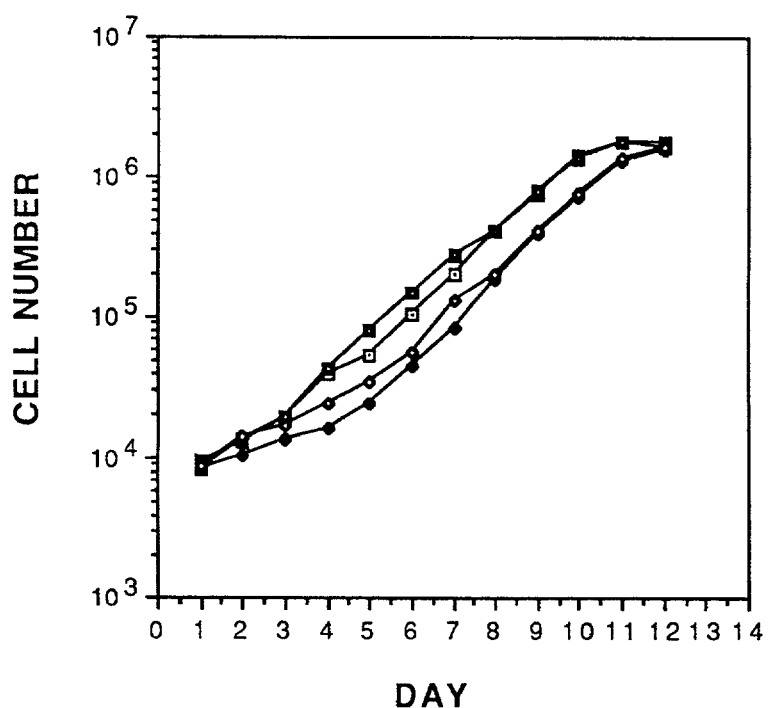
FIG. 42 Growth of the $AR^-$ DU145 and $AR^-$ PC3 Cells in CAPM versus Growth in D-MEM/F-12 Containing 10% Fetal Bovine Serum.

Growth in Serum-free Defined Medium versus D-MEM/F-12 with 10% (v/v) Fetal Bovine Serum. To demonstrate the usefulness of the formulations in TABLE 7, cell growth was compared in serum-free defined medium±steroid hormone versus growth supported by fetal bovine serum. It is generally accepted that fetal bovine serum represents one of the most effective sera for tissue culture. As an example, growth of the LNCaP cells was compared in CAPM±DHT versus growth in 10% (v/v) fetal bovine serum (FIG. 41). CAPM plus 10 nM DHT supported growth at about 80-90% of the rate of fetal bovine serum. Growth promoted by 10% fetal bovine serum obtained from conventional commercial sources reached 6.57 (±0.48) CPD or, a 96-fold increase on cell number in 12 days. By day 12, cell densities in CAPM nearly equaled those in serum. Growth promoted by the serum-free medium reached 6.22 (±0.35) CPD or 84-fold increase. CAPM was able to support LNCaP growth even in the absence of sex-steroid hormones. Maximum growth obtained without sex-steroid hormones was of 5.35 (±0.12) CPD or a 49-fold increase. The androgenic effect is therefore marginal, with differences of less than one CPD between the presence and absence of DHT. Also shown, the cells did not grow in D-MEM/F-12 without any additions (FIG. 41). Similar studies were done with other cell lines to determine growth rates versus serum and to establish the periods for single time assays (e.g. 7, 10,12 or 14 days). FIG. 42 shows the same analysis with DU145 and PC3 cells in CAPM and in D-MEM/F-12 with 10% fetal bovine serum. As the cell number data show, growth was logarithmic. After 12 days, growth in the serum-free medium was identical to that in 10% fetal bovine serum for both cell lines. Growth of PC3 in 10% serum reached 6.98 (±0.71) CPD or a 112-fold increase in cell number versus 6.97 (±0.44) CPD or the same fold increase for cell numbers in serum-free medium. Growth of DU145 in 10% fetal bovine serum was 6.71 (±0.58) CPD versus 6.73 (±0.18) CPD in serum-free conditions. The results in FIGS. 41 and 42 demonstrate by example that the serum-free defined media in TABLE 7 are effective with both hormone sensitive and hormone autonomous cells.

Figure 44:
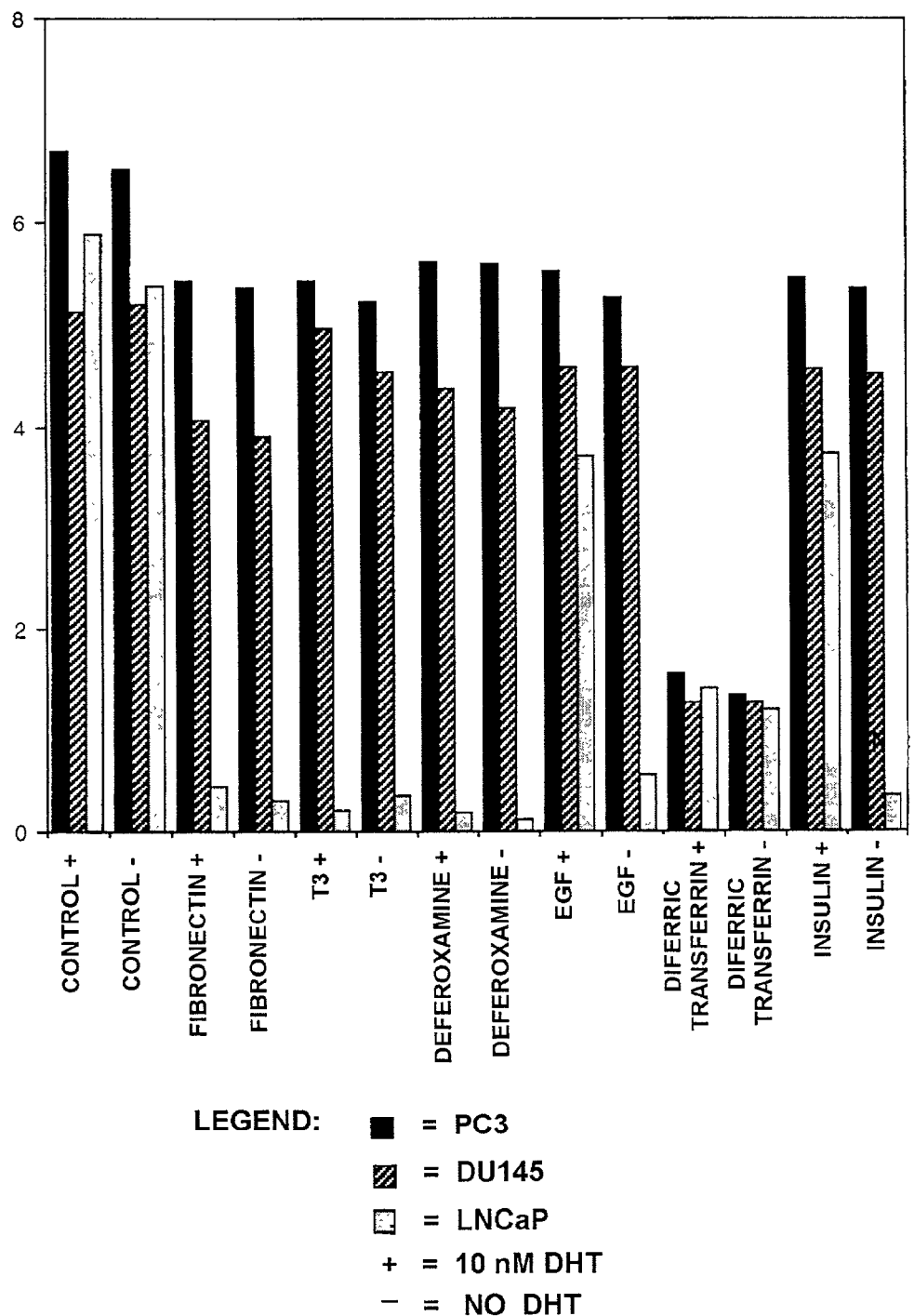
FIG. 44. Effects of Deletion of Individual Components from CAPM Serum-free Medium on LNCaP, DU145 and PC3 Cell Growth±DHT.

Determination of Component Concentrations and the Requirement for a Fe (III) Chelator. The optimum concentration of each single component was determined by dose-response analysis in the presence of other components. The technology used to establish early forms of serum-free defined media has been described (Danielpour D et al. (1988) *In Vitro Cell Dev Biol* 24, 42-52; Ogasawara M and Sirbasku D A (1988) *In Vitro Cell Dev Biol* 24, 911-920). An example of this process is shown in FIG. 43 with LNCaP cells. Dose-response effects of bovine serum albumin, apotransferrin, $T_3$, ethanolamine, selenium, and EGF are shown. The results show clearly that the addition of the iron chelator apotransferrin was required for cell growth. After determining optimum concentrations for each component, the contribution of each to the total was assessed by another assay. Individual components were deleted one at a time. As an example, the three most widely used prostatic carcinoma cell lines were compared (i.e. LNCaP, PC3 and DU145) in CAPM that contained deferoxamine in place of apotransfenin (FIG. 44). The deletions were done±DHT. The first and most striking result was the major differences between the growth requirements of the DHT sensitive LNCaP cells and those of the autonomous DU145 and PC3. Only the deletion of diferric transferrin substantially prevented the growth of autonomous cells. Also, it was clear that deletion of deferoxamine had only a small (i.e.<20%) effect on growth of the DU145 and PC3 cells. The DU145 and PC3 cell lines also were $T_3$, insulin, EGF, fibronectin and deferoxamine independent. As expected±DHT had no significant effect on DU145 or PC3. By contrast, LNCaP growth was significantly (p<0.01) reduced or arrested completely by deletion of fibronectin, T3, diferric transferrin or deferoxamine. LNCaP growth also was inhibited by deletion of EGF or insulin, but these effects were pronounced only in the absence of DHT.

Discussion of Example 11. The media described in TABLE 7 were optimized for the specific cell types designated. Additionally, they were optimized to permit direct comparison of the growth properties of $ER^+$ and $AR^+$ steroid hormone sensitive tumor cell lines to their $ER^-$ and $AR^-$ steroid hormone insensitive (also called autonomous) counterparts. This careful optimization was done originally to study rat mammary tumor cells of both types in DDM-2A defined media. The appropriate cell lines for this approach have been developed from the MTW9/PL2 population and described (Danielpour D and Sirbasku D A (1984) *In Vitro* 20, 975-980). The medium DDM-2MF has been developed for the same purpose only for comparisons of $ER^+$ and $ER^-$ forms of these cancers. TABLE 1 lists the most important $ER^+$ human breast cancer cell lines in use today. In addition a number of other $ER^-$ human breast cancer cells lines have been evaluated. They are the MDA-MB-231 (Cailleau R et al. (1974) *J Natl Cancer Inst* 53, 661-674), BT-20 (Lasfargues E Y and Ozzello L (1958) *J Natl Cancer Inst* 21, 1131-1147), Hs0578T (Hackett A J et al. (1977) *J Natl Cancer Inst* 58, 1795-1806), MDA-MD-330 (Cailleau R et al. (1978) *In Vitro* 14, 911-915), and the myoepithelial HBL-100 (Gaffiey E V (1982) *Cell Tissue Res* 227, 563-568). The demonstration of $ER^-$ status of these lines has been described (Reddel R R et al. (1985) *Cancer Res* 45, 1525-1531). With regard to human prostatic cancer, the only reliable androgen responsive cell line available today is the LNCaP (TABLE 1). Another, the ALVA41, has been described as androgen growth responsive (Nakhla A M and Rosner W (1994) *Steroids* 59, 586-589). However, as shown in subsequent Examples, this line is autonomous by the criterion of lack of DHT effects in CDE-horse serum. Two other human prostate cancer cell lines are commonly used as autonomous examples. These lines are the DU145 (Stone K R et al. (1978) *Int J Cancer* 21, 274-281) and the PC3 (Kaighn M E et al. (1979) *Invest Urol* 17, 16-23). Previously, there was a defined medium established for PC3 cells (Kaighn M E et al. (1981) *Proc Natl Acad Sci* USA 78, 5673-5676). This medium was evaluated and did not support LNCaP cell growth. However, others have reported "serum-free" media that was stated to be effective with LNCaP, DU145, PC3 and ALVA-31 cells (Hedlund T E and Miller G J (1994) *The Prostate* 24, 221-228). The problem was this medium was not serum-free nor was it defined. The experiments began with cells plated into 5% serum and then preceded to use a serum fraction called fetuin to support growth. Fetuin is a complex undefined mixture of ≧4% of the proteins in serum. Under those conditions, an accurate analysis of hormonal and growth factor effects cannot be done satisfactorily. The completely serum-free CAPM in TABLE 7 supports the growth of all of these prostate cell lines. In addition, CAPM has been applied to the $ER^+$ estrogen growth stimulated H301 Syrian hamster kidney cells (Sirbasku D A and Moreno J E (2000) *In Vitro Cell Dev Biol* 36, 428-446) and its autonomous derivative cell line A195. As has been reviewed (Evans R M (1988) *Science (Wash D.C.)* 240, 889-895), steroid hormones and thyroid hormones belong to the same superfamily of receptors. Both are important in growth. Therefore, it was expected that some tissues might be thyroid hormone positive regulated, while others might be positive regulated by steroid hormones. CAPM has also been applied to the study of thyroid hormone reversal of purified inhibitors with the human colonic carcinoma cell line HT-29. Similar use has been made of CAPM with the MDCK dog kidney tubule cell line (Leighton J et al. *Science* (Wash D.C.) 158, 472-473). CAPM replaces a different defined medium prepared for MDCK cells (Taub M et al. (1979) *Proc Natl Acad Sci* USA 76, 3338-3342). It is likely that the prostaglandins in that earlier medium interfere with the action of the thyroid hormones. In any case, that medium was not useful for demonstration of thyroid hormone reversal of purified MDCK cell growth inhibitors. All of these observations support the view that a series of uniquely optimized media have been formulated to define the growth requirements of epithelial cells from several of the very prominent cancers of humans. Furthermore, the technology developed promises application to the optimization of growth of other types of epithelial cells from a variety of target tissues.

Example 12

Differential Effects of Fe (III) on the Growth of Hormone Responsive and Autonomous Human Breast and Human Prostate Cancer Cells This Example demonstrates that iron has an inhibiting effect on steroid responsive cell growth, independent of the above-described immunoglobulin effects, and which is distinguishable from its effect on autonomous cells.

Approaches to Demonstration of Iron Toxicity. The fact that standard D-MEM/F-12 contains sufficient Fe (III) to inhibit cell growth, led to the next series of studies. Other approaches were used to further demonstrate the deleterious effects of Fe (III) on hormone responsive tumor cell growth. To add Fe (III) to culture medium, it must be in a soluble form. Ferric ammonium citrate was selected for use. However, ferric ammonium sulfate is also effective. Ferric ammonium citrate is a mixture that contains 16.6% of ferric iron by weight. The amount of mixture added to each dish was adjusted to achieve the desired Fe (III) concentrations. Due to the light sensitivity of the mixture, the solutions were prepared fresh daily and the experiments carried out under restricted light conditions. Also, the mixture was prepared in water. Buffers without phosphate may be used, but they are generally less effective. The ferric mixtures and the iron chelators EDTA, deferoxamine mesylate and sodium citrate were purchased from Sigma.

Figure 45:
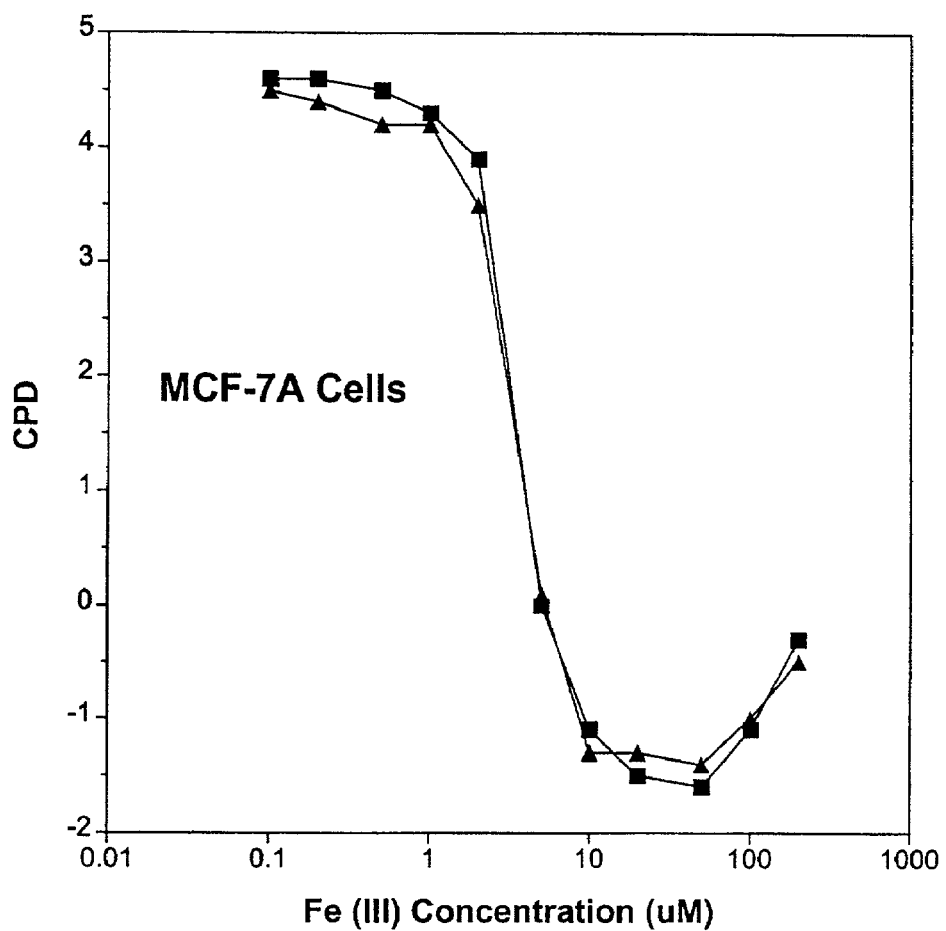
FIG. 45. Effect of Fe (III) on MCF-7A Cell Growth in DDM-2MF Serum-free Defined Medium.
Figure 46:
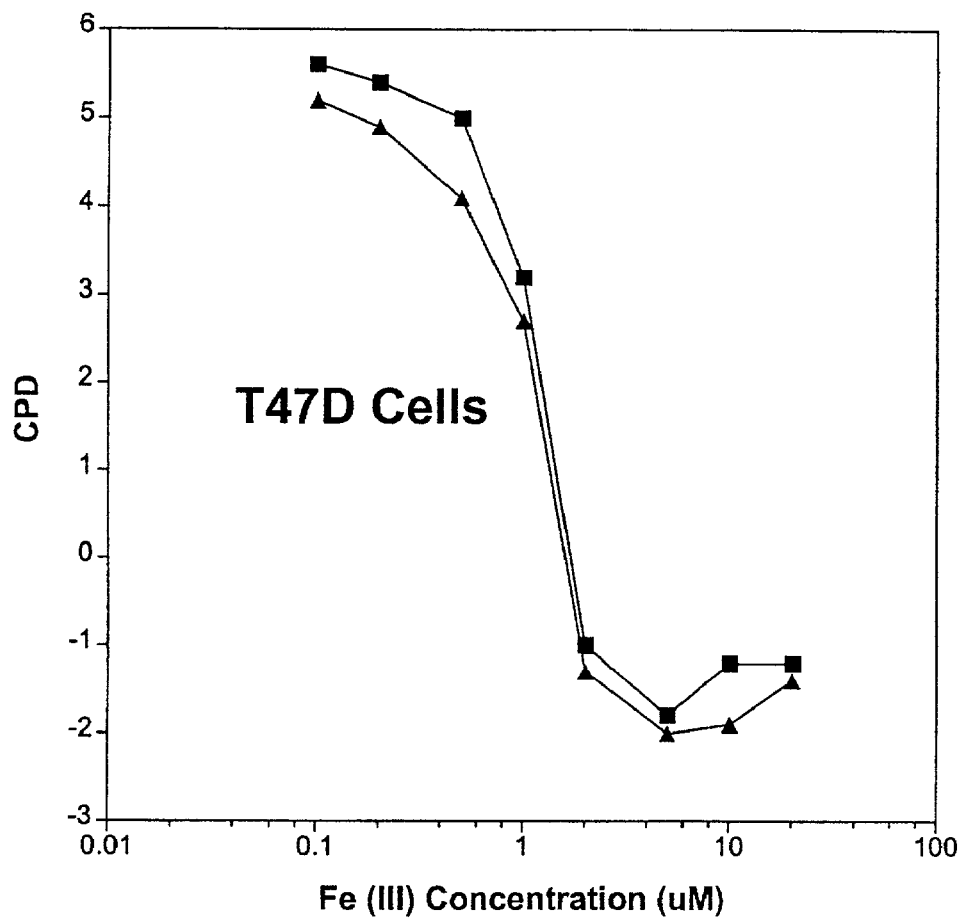
FIG. 46. Effect of Fe (III) on T47D Cell Growth in DDM-2MF Serum-free Defined Medium.

Iron Toxicity with Human $ER^+$ Breast Cancer Cells. In the first experiments, two $ER^+$ cell lines were evaluated for Fe (III) sensitivity in DDM-2MF defined medium prepared with 10 µg/mL apotransferrin in place of the deferoxamine shown in TABLE 7. The effect of addition of ferric ammonium citrate on MCF-7A growth±$E_2$ at 10 days is shown in FIG. 45. Either with or without the steroid, Fe (III) was completely inhibitory at 10 µM. There were no viable cells in the dishes at≧10 µM. The $EI_{50}$ of Fe (III) with MCF-7A cells was 5 to 7 µM. A similar analysis with T47D cells in DDM-2MF with 10 µg/mL apotransferrin instead of deferoxamine showed complete inhibition at 10 days with 2 µM Fe (III) (FIG. 46). At≧2 µM there were no viable cells in the dishes either with or without $E_2$. The $EI_{50}$ of FE (III) with T47D cells was 1 µM.

Figure 47:
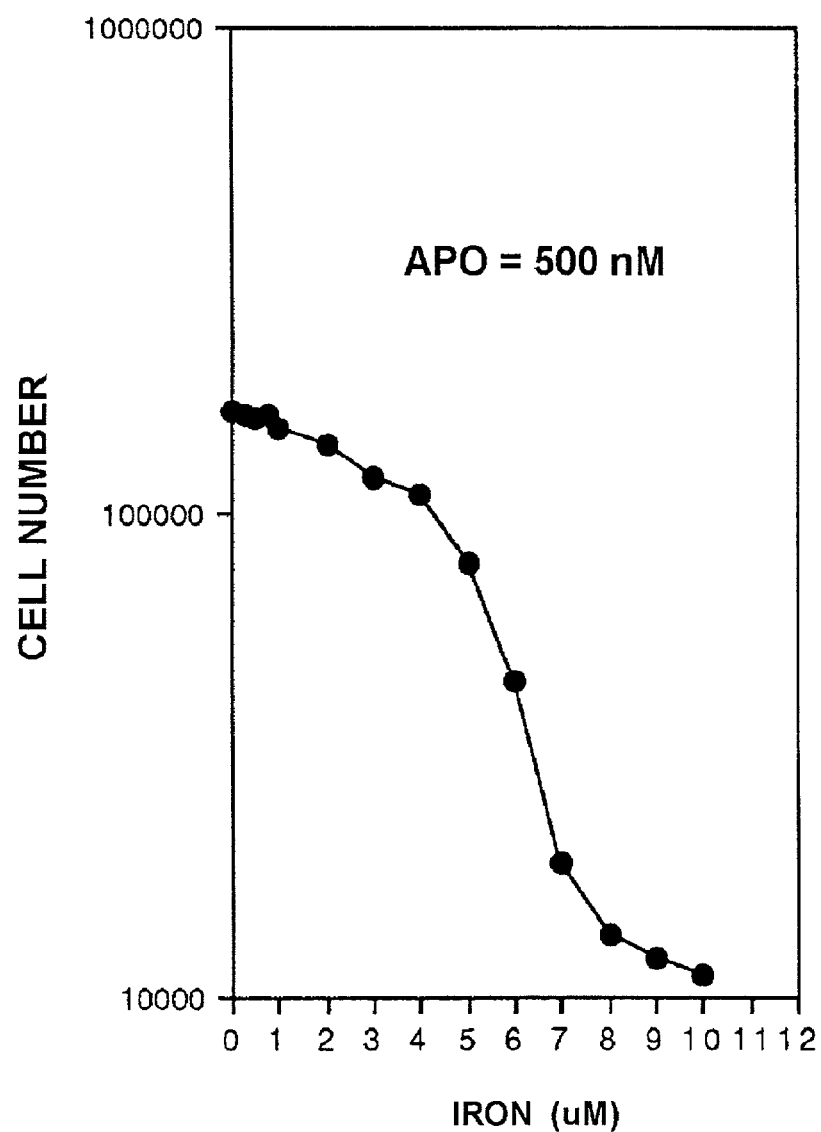
FIG. 47. Effect of Fe (III) on LNCaP Cell Growth in CAPM Plus Apotransferrin.
Figure 48:
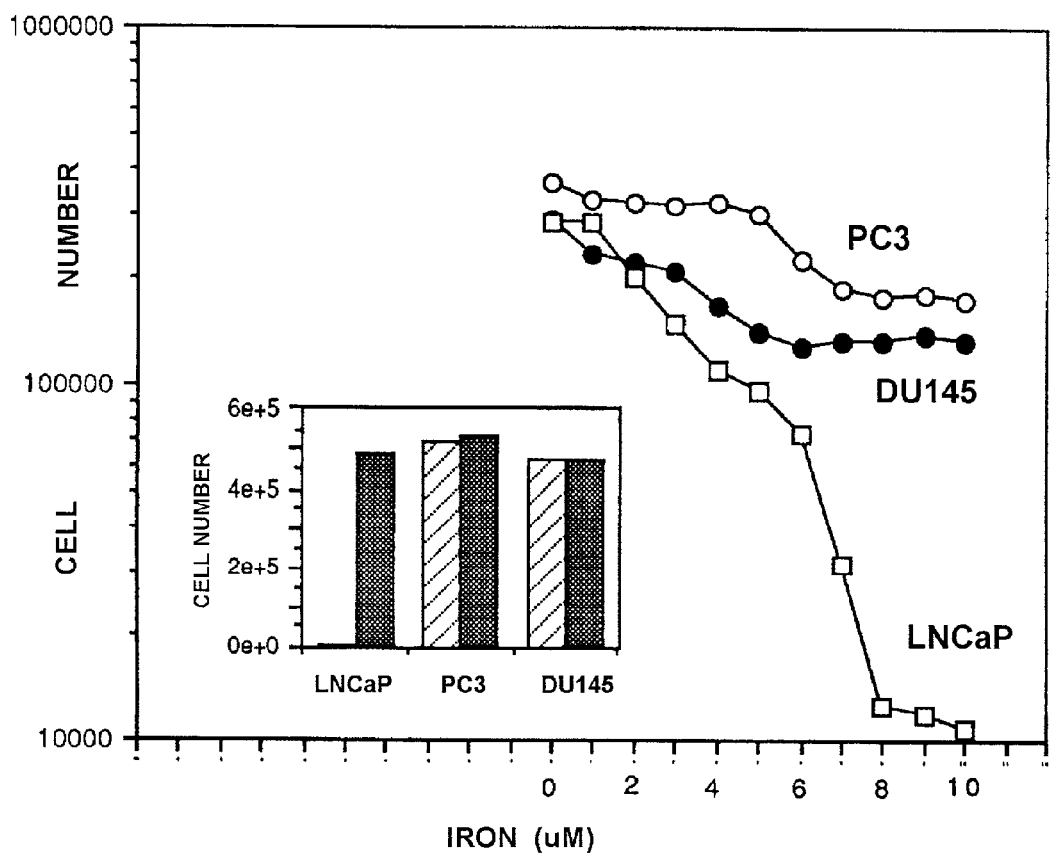
FIG. 48. Comparative Effect of Fe (III) on LNCaP, DU145 and PC3 Cell Growth in CAPM.

Iron Toxicity with $AR^+$ and $AR^-$ Human Prostate Cancer Cell Lines The effect of Fe (III) on $AR^+$ LNCaP cell growth was assessed in CAPM defined medium in which apotransferrin (500 nM) was substituted for deferoxamine, and the results are shown in FIG. 47. Clearly, 10 µM Fe (III) arrested growth to seed density levels (i.e. 12,000 cells per dish) in a 12-day assay. The $EI_{50}$ for LNCaP cells was 5 µM. In another experiment in CAPM, the effects of ferric ammonium citrate were evaluated with $AR^+$ LNCaP cells and $AR^-$ PC3 and DU145 cells (FIG. 48). Again, Fe (III) inhibited LNCaP cells to seed densities levels by 8 to 10 µM. However, effects on the androgen autonomous PC3 and DU145 cells were markedly less (FIG. 48). Reductions of 10 to 30% in cell number for PC3 and DU145, respectively, were observed in 10 µM Fe (III). The inhibitory effects of Fe (III) on the androgen independent PC3, DU145 and ALVA-41 cells were variable, and never as marked as with the steroid hormone responsive LNCaP cells. The insert in FIG. 48 shows a correlation between hormone responsiveness and Fe (III) effects. The results show a correlation between iron effects and thyroid hormone responsiveness. LNCaP cells are $T_3$ responsive whereas PC3 and DU145 are not.

Figure 49:
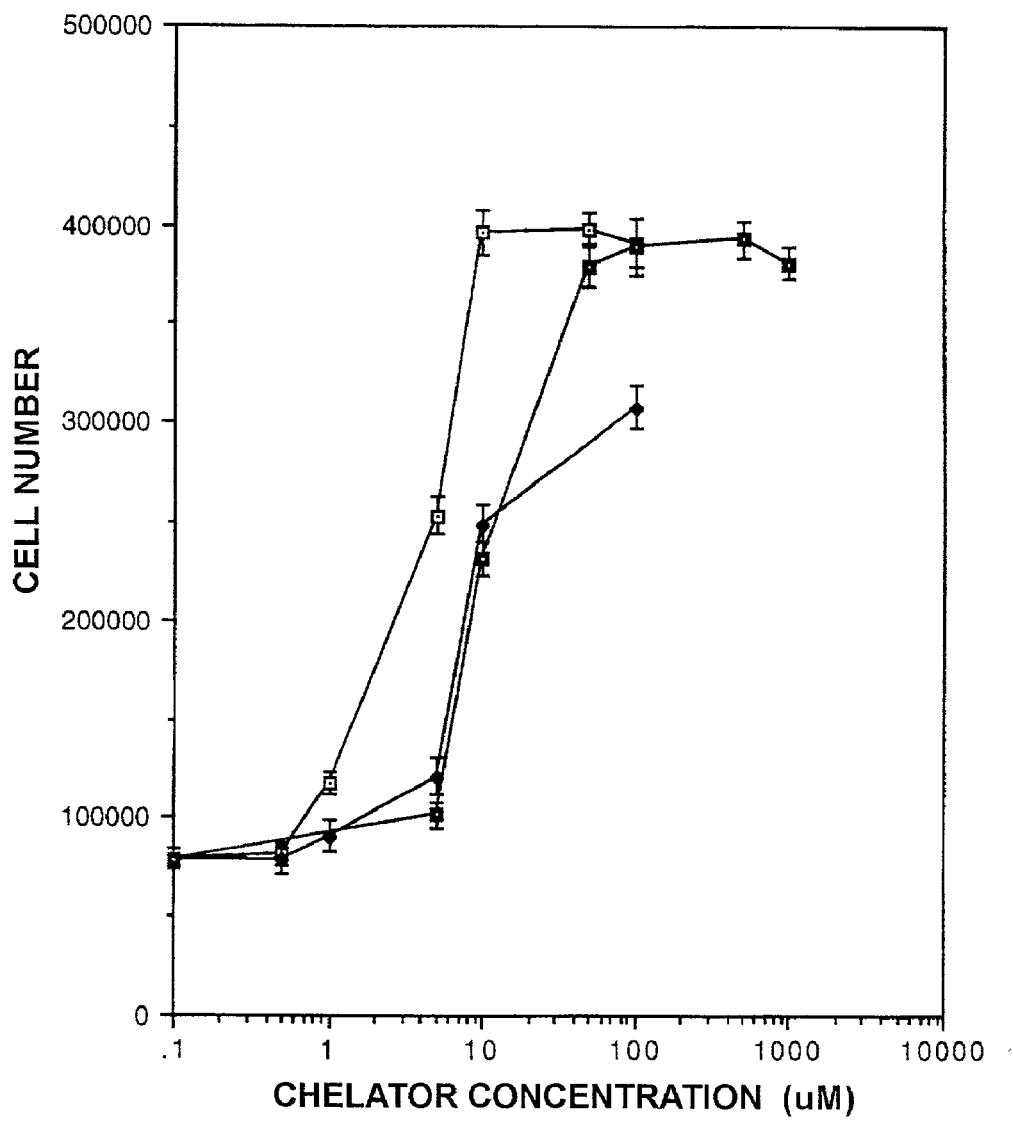
FIG. 49. Growth Restoring Effect of Fe (III) Chelators in serum-free medium with T47D Cells.
Figure 50:
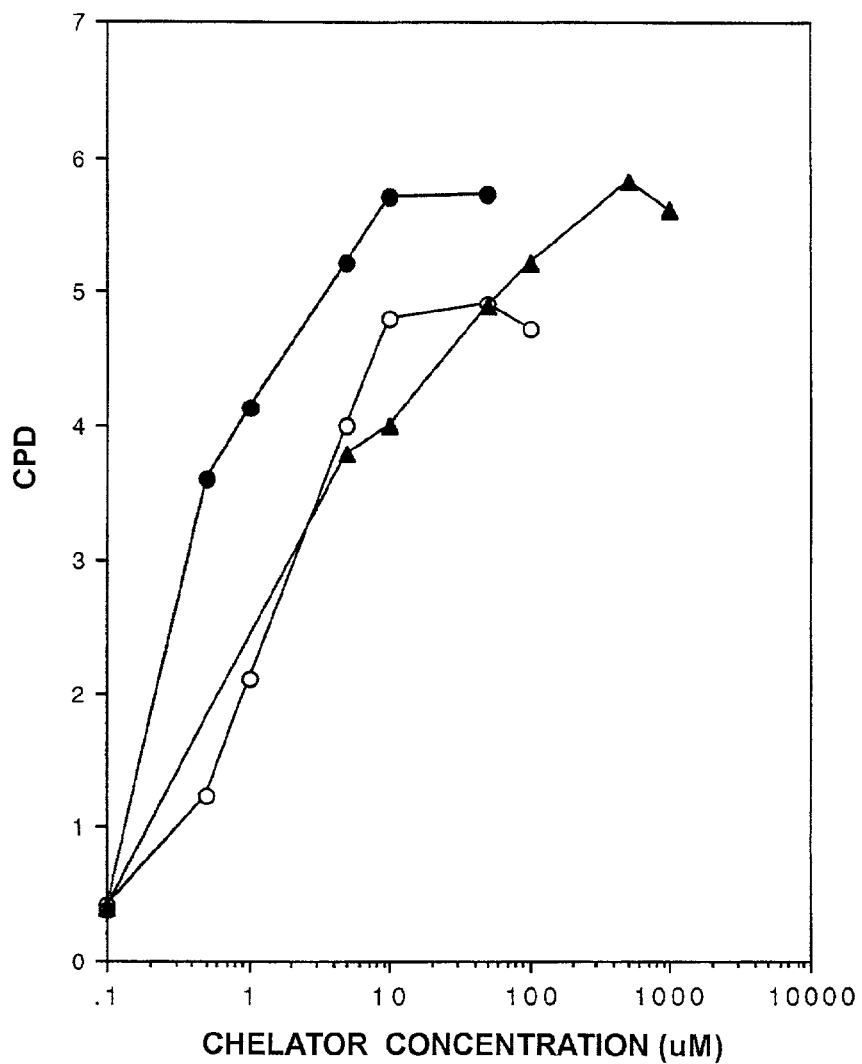
FIG. 50. Growth Restoring Effect of Fe (III) Chelators in serum-free medium with LNCaP Cells FIG. 51. Comparison of DU145 Cell Growth in "low-Fe" and "standard" D-MEM/F-12 Based Serum-free Defined Medium CAPM.

Reversal of Fe (III) Inhibition by Iron Chelators. The inhibitory/cytotoxic effects of Fe (III) were reversible by the addition of iron chelators. Those studied were selected based on data showing their relative affinities and specificities for Fe (III) (Schubert J (1963) In: *Iron Metabolism*, Gross F, ed, Springer-Verlag, Berlin, pp 466-496). Deferoxamine is most specific and has the highest affinity for Fe (III). Citrate is next most effective. EDTA is not as effective nor is it as specific as the first two chelators. In experiments with T47D cells, the eferoxamine usually present in the DDM-2MF medium was removed and an additional 1.5 µM Fe (III) added to ensure complete inhibition of the cells. FIG. 49 shows the relative effects of addition of these three chelators to T47D serum-free defined medium cultures. The order of effectiveness was as expected from the affinities and specificities of these chelators. Clearly, addition of Fe (III) chelators restored growth. FIG. 50 shows a similar study with LNCaP cells in CAPM defined medium from which the deferoxamine also was removed and 1.5 µM Fe (III) added. It was clear that chelation of the Fe (III) restored growth. It should be noted that this conclusion is reasonable based on the fact that deferoxamine has near absolute specificity for Fe (III). Concentrations as low as 0.5 µM of deferoxamine were sufficient to induce 3.5 CPD with LNCaP cells. Maximum growth with this chelator (5.81 CPD) was obtained at 10 µM. Citrate and EDTA were also effective growth stimulators of LNCaP cells incubated at high iron concentrations. Maximum growth was obtained with the addition of 500 µM and 10 µM respectively. The growth induction achieved with EDTA is lower than with citrate or deferoxamine. This probably could be explained by the fact that EDTA is a less discriminatory chelator, and essential metals other than iron were affected. Concentrations of the chelators higher than the ones showed in the FIGS. 49 and 50 were associated with cell damage and death. In particular, chelation of calcium by citrate and EDTA will cause cell death in culture. As controls, stimulation by chelators was prevented by resupply of Fe (III) (data not shown).

Figure 51:
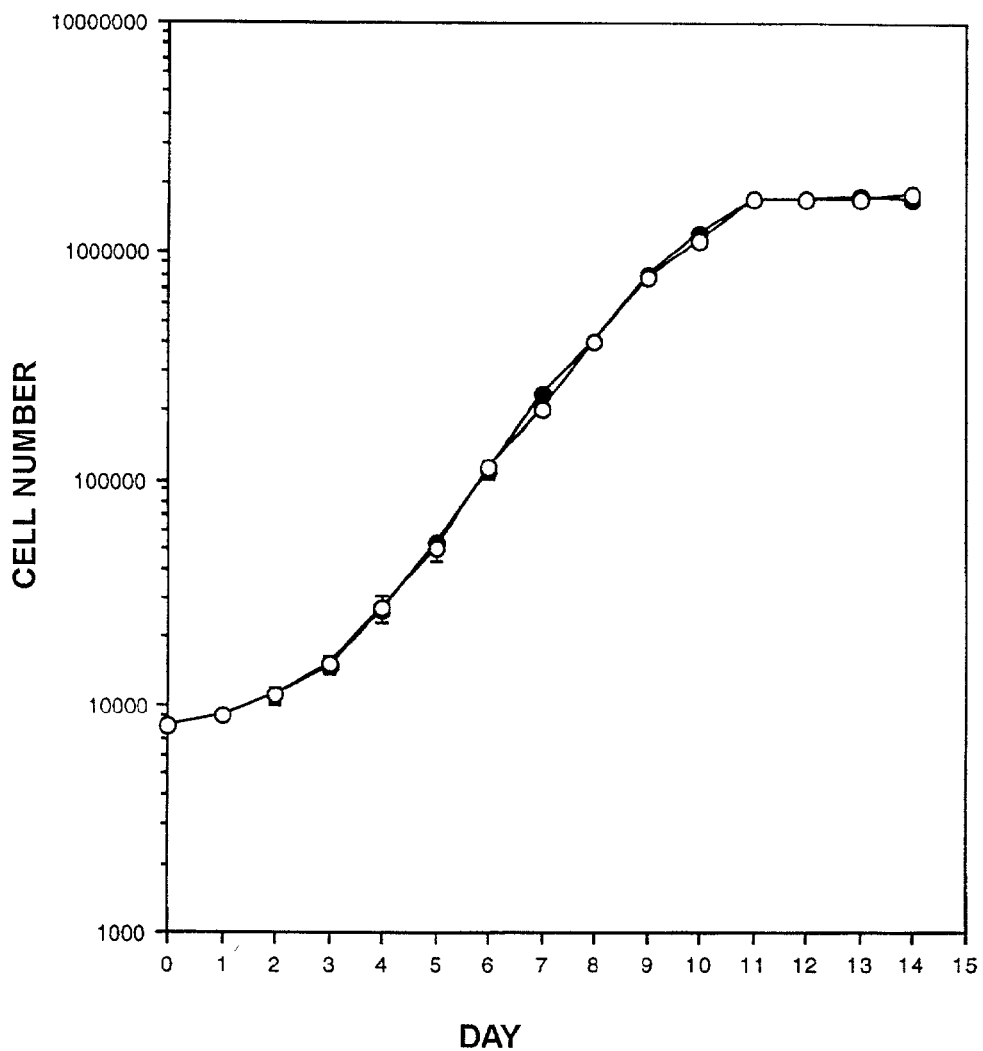
Figure 52:
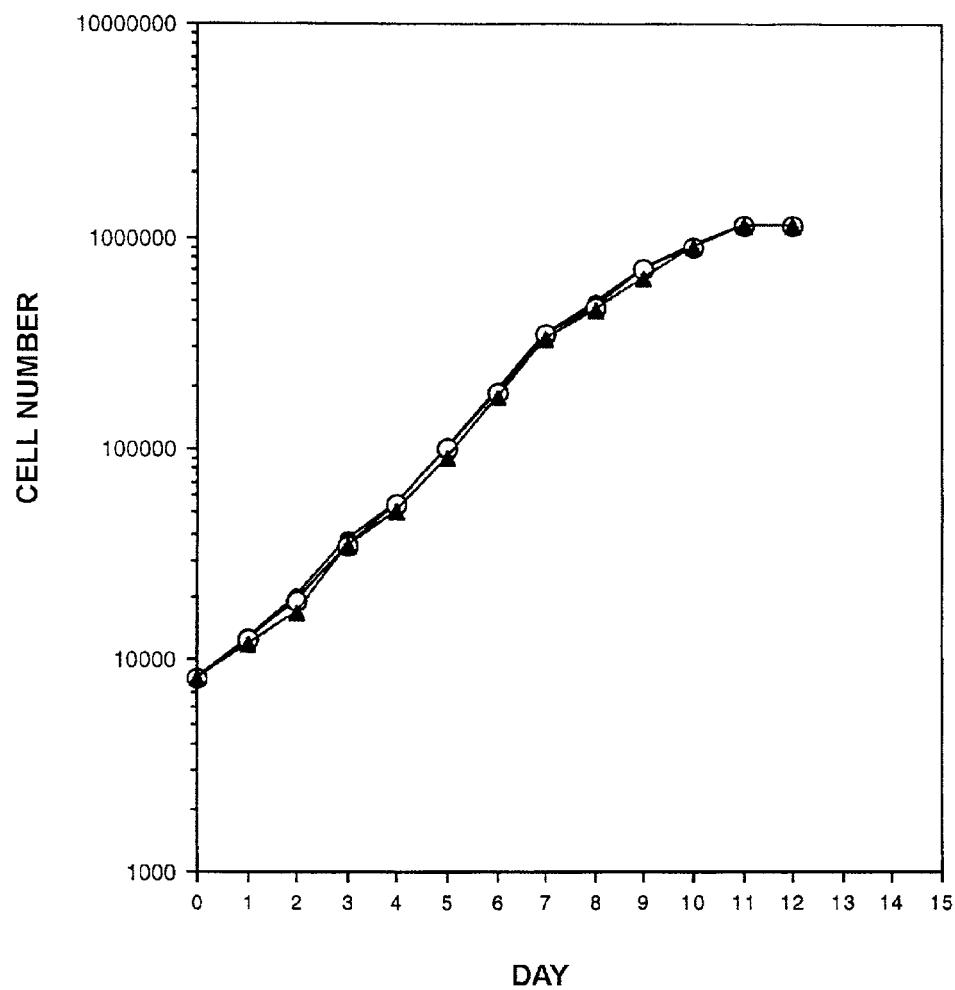
FIG. 52. Comparison of PC3 Cell Growth in "low-Fe" and "standard" D-MEM/F-12 Based Serum-free Defined Medium CAPM.
Figure 53:
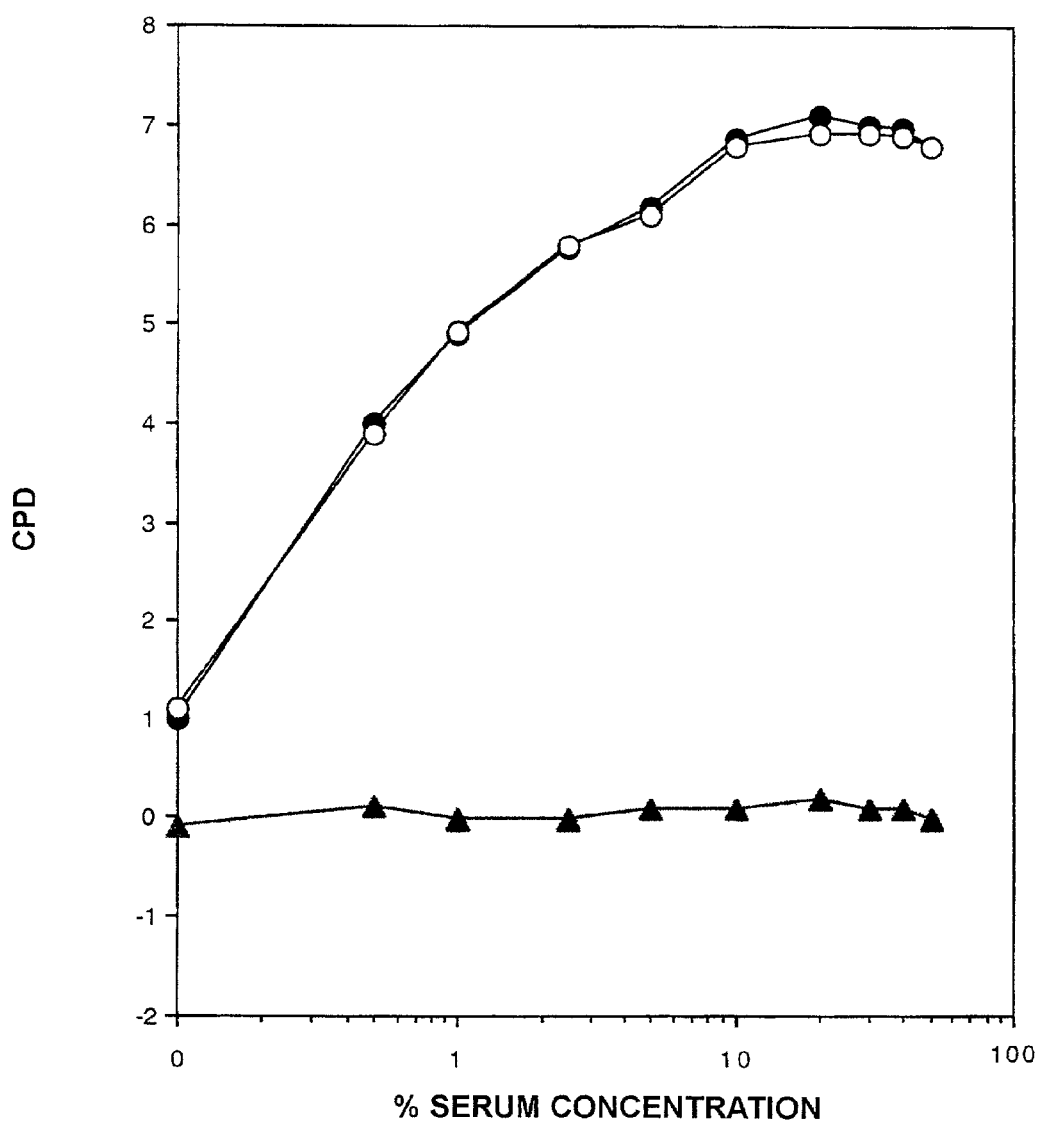
FIG. 53. Growth of the DU145 Cells in CDE-horse Serum±DHT.
Figure 54:
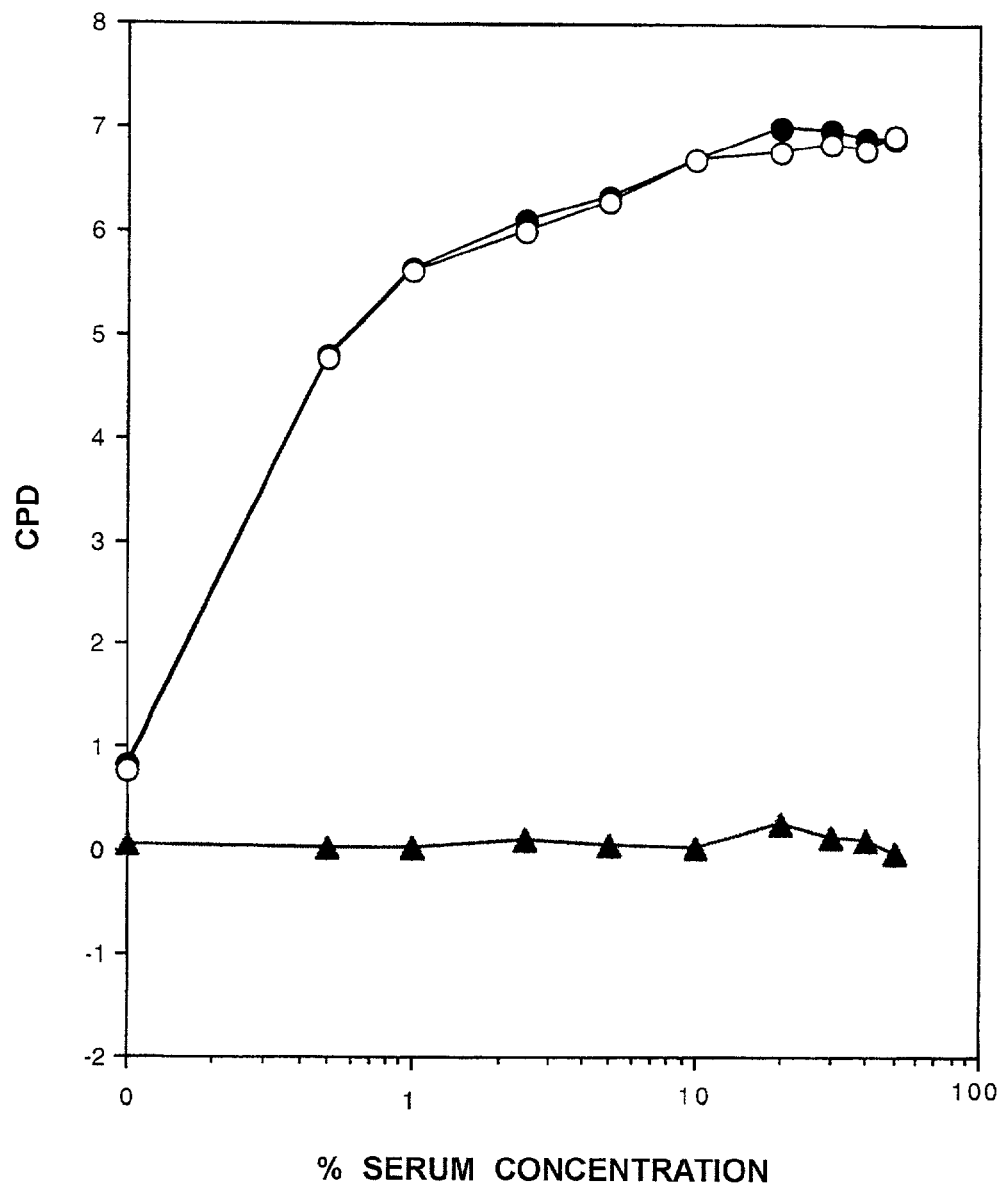
FIG. 54. Growth of the PC3 Cells in CDE-horse Serum±DHT.
Figure 55:
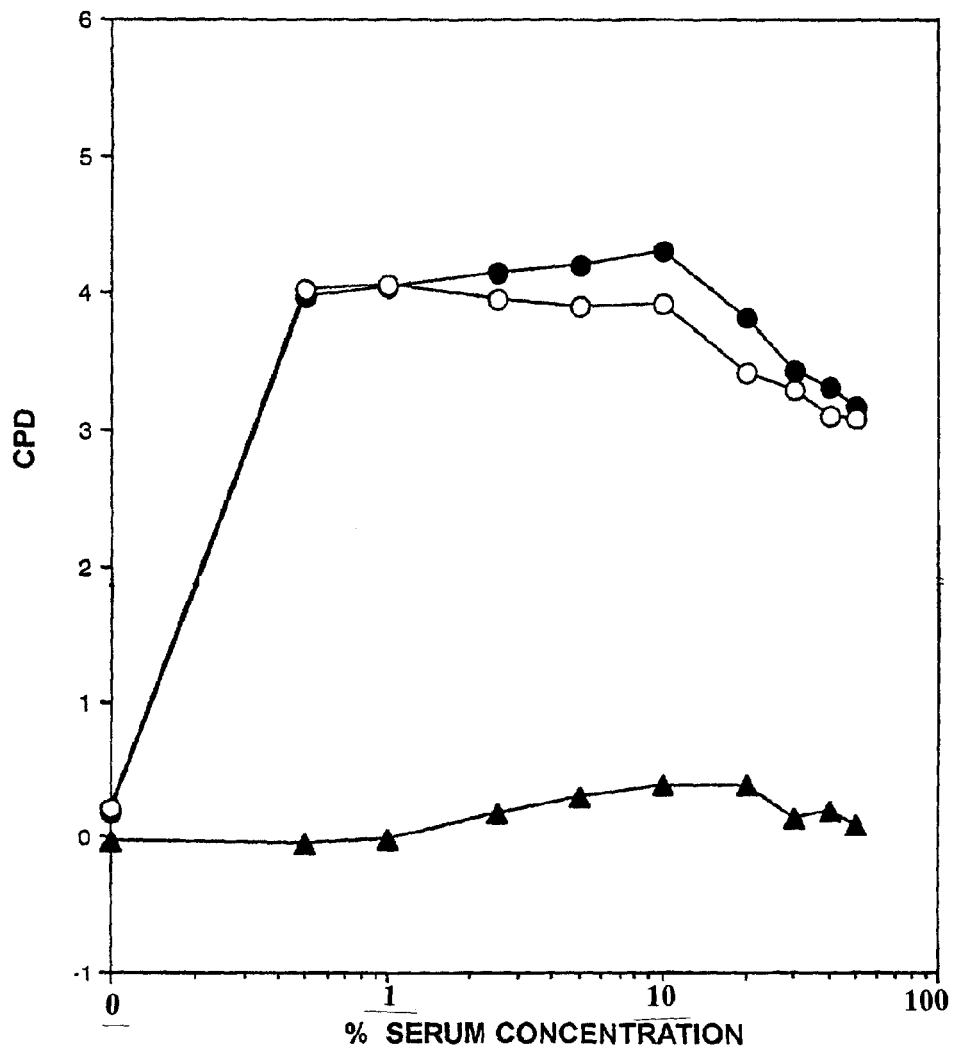
FIG. 55. Growth of the ALVA-4 Cells in CDE-horse Serum±DHT.

Correlation Between Hormone Autonomy and Lack of Iron Effects. In the next series of studies, data was sought supporting the concept that loss of steroid hormone dependence correlates positively with loss of Fe (III) effects. As shown in FIG. 39, LNCaP cells grew better in "low-Fe" serum-free defined medium than in defined medium based on "standard" D-MEM/F-12. This difference was also evaluated with the androgen insensitive DU145 (FIG. 51) and PC3 (FIG. 52) cells. The results were clear. The autonomous lines grew equally well in CAPM based on both types of D-MEM/F-12. The presence of the higher Fe (III) level in CAPM based on standard D-MEM/F-12 had no effect. To confirm that these cell lines were androgen autonomous as defined by the loss of steroid and inhibitor growth regulation in CDE-serum, the next studies were done. DU145 cells showed no inhibition of growth in 50% CDE-serum (FIG. 53). There was no androgenic effect whatsoever. A similar assay with PC3 cells showed essentially the same results (FIG. 54). There was no inhibition even in 50% CDE-horse serum, and no androgenic effect. Additionally, ALVA41 cells are not iron sensitive (results not shown), and also are not sensitive to the serum-borne inhibitor (FIG. 55).

Discussion of Example 12. Together with the studies presented above, it appears that $AR^+$ cells are sensitive to the serum-borne inhibitor, sensitive to the positive effects of steroid hormone and sensitive to Fe (III) inhibition. In contrast, the DU145 and PC3 cells are insensitive to the serum-borne inhibitor, insensitive to the positive effects of androgen, and insensitive to Fe (III). The results presented in this example continue to demonstrate the requirement for the action of a serum-borne mediator to demonstrate steroid hormone responsive cell growth in culture. The use of CDE-serum was essential for the demonstration of androgen and other steroid hormone responsiveness in culture, but its use limits the understanding of stimulatory or inhibitory roles of hormones or factors on prostate and other cancer cells because of the inclusion of an undetermined amount of undefined components. A serum-free medium circumvents this problem, as shown in subsequent Examples.

In addition, autonomy may be the loss of the receptor for the serum factor and/or the loss of the intracellular steroid hormone receptor. If this hypothesis is correct it should be possible to identify cells that possess steroid receptors but still have lost "sensitivity" to the hormone by virtue of the lack of the effect of the inhibitor. Most notably, this is the case with DU145 and ALVA-41 cells. As defined by immunohistochemistry, the DU145 cells are definitely $AR^+$ (Brolin J et al. (1992) *The Prostate* 20, 281-295). As defined by a number of criteria, the ALVA41 cells are $AR^+$ (Nakhla A M and Rosner W (1994) *Steroids* 59, 586-589). A new concept explaining the progression of normal tissue cells to hormone autonomous cancers is discussed in more detail in an Example below.

Exposure of androgen responsive prostate cancer cells to Fe (III) results in cell death. Compounds containing available Fe (III) offer the possibility of new therapies for prostate cancer localized to the tissue. It is proposed that deprivation of iron will be a highly effective means of eliminating the most dangerous hormone autonomous forms of prostate cancer. The measurement of thyroid hormone receptors in prostate cancer should be initiated as a diagnostic tool to determine iron sensitivity. Moveover, new therapy mode for tumors containing mixtures of both hormone responsive and autonomous cells is suggested, based on the observation that deprivation of iron can equally kill both types of cancer. This suggests that systemic Fe (III) therapy for disseminated prostate cancer may be efficacious.

It is definitely possible that iron in the Fe (III) form and compounds containing it will be effective anti-prostate cancer treatments, and that direct injection (or painting) of localized prostate tumors or metastasis at other sites (e.g. bone) might effectively kill these cancers without concomitant systemic effects. This therapy potentially could replace such protocols as systemic chemotherapy (physically damaging), radiotherapy (damage to collateral tissues) or the use of locally acting radioactive gold chips that are complex to handle in the surgical environment and must be implanted and removed surgically. Furthermore, iron therapies can be repeated frequently by application via transrectal or transurethral access, using conventional techniques. This approach is unique and has not been discussed or suggested anywhere else in the literature. Such iron treatments may be a useful therapy for benign prostatic hypertrophy (BPH). As discussed above, this condition is very common in older men and is treated usually by surgery. Application of iron compounds is a new approach to treatment of BPH. Similarly, a Fe (III) solution could be applied to breast cancer lumpectomy or mastectomy sites at the time of surgery, and/or applied by injection to the sites subsequent to surgery.

Example 13

Growth in Serum-free Defined Medium versus Growth in CDE-Serum±$E_2$

The defined media described in Example 10 were used to verify the presence of a serum-borne inhibitor. The growth of six different $ER^+$ cell lines was compared in serum-free defined media (TABLE 7) to the effects seen in cultures supplemented with CDE-horse serum. These studies are shown in FIGS. 56 and 57. Estrogenic effects are recorded for each set of conditions with each cell line.

MCF-7K Cells in Serum-free and Serum Containing Medium±$E_2$. The first studies were done with steroid hormone responsive human cancer cell lines. FIG. 56A shows MCF-7K cell growth in serum-free DDM-2MF±10 nM $E_2$. The population replicated logarithmically for 12 days. $E_2$ had no effect on growth rate or saturation density. These results were in contrast to assays done in D-MEM/F-12 supplemented with CDE horse serum (FIG. 56B). Above 10% (v/v) serum, growth was progressively inhibited. The inhibition caused by any serum concentration was reversed by $E_2$. Measured on assay day 10, a 3 CPD estrogenic effect was observed which was a $2^3$ or 8-fold cell number increase. The experiments were also done with MCF-7A cells with similar results (data not shown). This effect in CDE-serum was as great as that reported for a special response clone of the MCF-7 cell line (Wiese T E et al. (1992) *In Vitro Cell Dev Biol* 28A, 595-602).

T47D Cells in Serum-free and Serum Containing Medium±$E_2$. FIG. 56C shows the growth of T47D cells in serum-free defined DDM-2MF±10 nM $E_2$. Although a small effect of estrogen was observed on growth rate, the most significant effect was an increase in stationary densities by 0.5 to 1.0 CPD. In contrast, the effect of $E_2$ was much greater in medium containing CDE horse serum (FIG. 56D). At 50% (v/v) CDE-serum, growth was completely inhibited. The estrogenic effect under these conditions was>5 CPD. This was more than a $2^5$ or 32-fold hormone effect on cell number. Comparison of these results with those of others (Chalbos D et al. (1982) *J Clin Endocrinol Metab* 55, 276-283; Schatz R W et al. (1985) *J Cell Physiol* 124, 386-390); Soto A M et al. (1986) *Cancer Res* 46, 2271-2275; Soto A M and Sonnenschein C (1987) *Endocr Rev* 8, 44-52;Reese C C et al. (1988) *Ann N.Y. Acad Sci* 538, 112-121) confirmed that the conditions in FIG. 56D were substantially more effective. Comparable experiments with the ZR-75-1 line gave results intermediate between MCF-7 and T47D cells (data not shown). ZR-75-1 cells showed no effect of $E_2$ in serum-free defined DDM-2MF. This line grows more slowly than MCF-7 or T47D cells in defined medium and in serum-supplemented cultures (Ogasawara M and Sirbasku D A (1988) *In Vitro Cell Dev Biol* 24, 911-920). The maximum estrogenic effects of the preferred embodiment recorded with ZR-75-1 cells in D-MEM/F-12 with 50% (v/v) CDE-horse serum ranged between 3 and 4 CPD after 14 days. This was greater than reported by others in serum containing (Darbre P et al. (1983) *Cancer Res* 43, 349-355; Kenney N J et al. (1993) *J Cell Physiol* 156, 497-514) or "serum-free" medium (Allegra J C and Lippman M E (1978) *Cancer Res* 38, 3823-3829; Darbre P D et al. (1984) *Cancer Res* 44, 2790-2793).

LNCaP Cells in Serum-free and Serum Containing Medium±$E_2$. In another study, the effects of $E_2$ on the growth of the LNCaP human prostatic carcinoma cell lines in defined medium and in serum-supplemented culture were compared. This cell line bears a point mutation in the AR that permits high affinity binding of estrogens to the altered receptor (Veldscholte J et al. (1990) *Biochem Biophys Res Commun* 173, 534-540; Veldscholte J et al. (1990) *Biochim Biophys Acta* 1052, 187-194). In addition, it is possible that estrogens cause LNCaP growth via a separate functional ER (Castagnetta LA and Carruba G (1995) *Ciba Found Symp* 191, 269-286). Irrespective of mechanism, estrogens are known to promote LNCaP growth (Bélanger C et al. (1990) *Ann N.Y.*

*Acad Sci* 595, 399-402; Veldscholte J et al. (1990) *Biochem Biophys Res Commun* 173, 534-540; Veldscholte J et al. (1990) *Biochim Biophys Acta* 1052, 187-194; Castagnetta L A and Carruba G (1995) *Ciba Found Symp* 191, 269-286). As presented herein (FIG. 56E), this cell line in serum-free defined CAPM showed essentially no $E_2$ effect on growth rate and $\leq 1.0$ CPD on saturation density. When LNCaP growth assays were done in medium with CDE-horse serum, the mitogenic effect of $E_2$ was>5 CPD (FIG. 56F). Estrogenic effects herein were larger than reported by others with LNCaP cells in serum containing culture (Belanger C et al. (1990) *Ann N.Y. Acad Sci* 595, 399-402; Castagnetta L A and Carruba G (1995) *Ciba Found Symp* 191, 269-286).

Figure 58:
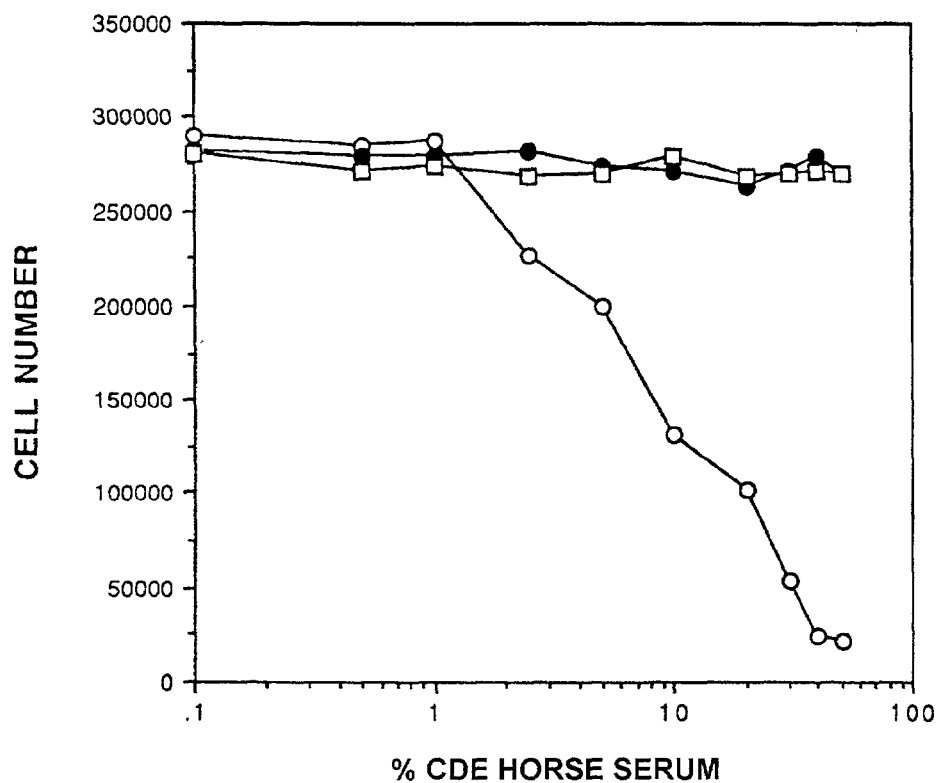
FIG. 58. Effect of CDE-horse Serum on LNCaP Cell Growth in Serum-free CAPM±E$_2$ and±DHT.

LNCaP Cell Growth in CAPM Defined Medium with CDE-Horse Serum and±DHT or $E_2$. To confirm that the serum-borne inhibitor can be assessed even in the presence of all of the components of serum-free defined medium, an example experiment is shown in FIG. 58. The LNCaP cells were grown in serum-free CAPM supplemented with increasing concentrations of CDE-horse serum without steroids and in assay dishes with the CDE-serum plus 10 nM $E_2$ or 10 nM DHT. Without steroid, the CDE-horse serum showed the expected progressive inhibition. Both the estrogen and androgen reversed this inhibition completely at every serum concentration. Clearly, the inhibitor in serum possesses a very special quality that blocks the action of the many mitogenic agents present in defined media.

$GH4C_1$ Cells in Serum-free and Serum Containing Medium±$E_2$. In the next studies, shown in FIG. 57A, the growth of rodent $ER^+$ cell lines in defined medium and CDE serum-containing medium with and without $E_2$ were compared. The study was with the $GH_4C_1$ rat pituitary tumor cell line. In serum-free PCM-9, $E_2$ had no effect on growth rate or saturation density (FIG. 57A). In contrast, the cells were highly estrogen responsive in CDE-horse serum (FIG. 57B). In $\geq 30\%$ (v/v) CDE-serum, the estrogenic effect was $\geq 4.5$ CPD (i.e.>22-fold cell number increase). The $GH_4C_1$ response obtained was substantially greater than that previously reported in cultures containing serum from a gelded horse (Amara J F and Dannies P S (1983) *Endocrinology* 112, 1141-1143). Replicate studies with the $GH_1$ and $GH_3$ rat pituitary tumor cells gave results equivalent to those shown in FIGS. 57A and 57B (results not shown).

MTW9/PL2 Cells in Serum-free and Serum Containing Medium±$E_2$. FIG. 57C shows the effect of $E_2$ on growth of the MTW9/PL2 rat mammary tumor cells in serum-free DDM-2A. There was a small effect on growth rate and a $\leq 1.0$ CPD effect on saturation density. When the same cells were assayed in D-MEM/F-12 containing CDE horse serum, the effect of $E_2$ was remarkable (FIG. 57D). Cell number differences of $2^6$ (i.e. 64-fold) were recorded in 50% (v/v) serum in a seven-day assay. This result agrees with those presented above in this disclosure. Furthermore, comparison of MTW9/PL2 responses (FIG. 57D) to those of the human breast cancer cells (FIGS. 56B and 56D) confirms that the $ER^+$ rat cells are the most estrogen responsive mammary origin line yet developed.

H301 Cells in Serum-free and Serum Containing Medium±$E_2$. In the final studies, the effect of $E_2$ on the growth of the H301 hamster kidney tumor cells in serum-free medium was compared to that in CDE horse serum containing medium. Estrogen had no effect on H301 cell growth in serum-free defined CAPM (FIG. 57E). In contrast, $E_2$ induced H-301 cell number increases of>$2^4$ (i.e.>16-fold) were recorded in D-MEM/F-12 containing $\geq 30\%$ (v/v) CDE serum (FIG. 57F). The H301 response was similar to the MCF-7 cells in that 50% (v/v) CDE-serum did not fully inhibit. The magnitude of the estrogenic effect with H301 cells was equal to that reported by others studying this line in cultures supplemented with CDE serum prepared by different methods (Soto A M et al. (1988) *Cancer Res* 48, 3676-3680).

Discussion of Example 13. The new serum-free defined medium serves as part of a model system for identifying physiologically relevant new molecules. When completely serum-free defined conditions were employed in the past, the effects of estrogens were either marginal or insignificant as has been discussed above. The earlier observations in completely serum-free defined culture medium have been extended in the present investigation. Direct comparisons were made between estrogenic effects in serum-free defined culture and estrogenic effects in medium containing CDE serum. The results were unequivocal. With every cell line tested, CDE serum was required to demonstrate significant estrogenic effects on logarithmic cell growth rates. A major advance provided was the clear demonstration that high concentrations of serum are required to observe large magnitude estrogenic effects. Furthermore, the inhibitory effects of serum are dose dependent even in the presence of the components used to formulate serum-free medium. This indicates that growth is progressively negatively regulated. This observation has physiological implications. Changes in the serum concentration of the inhibitor, or changes in availability to target tissues, will have direct effects on the rate of cell replication. The results in FIGS. 56-58 point to serum as the best source yet identified to obtain the component that regulates sex steroid responsive growth. The tissue origin of the serum regulator remains to be investigated.

Example 14

Action of DES on Human $AR^+$LNCaP Prostate Cancer Cells

In this Example, it is demonstrated that DES does not inhibit steroidogenic cell growth and may be suitable for use in cancer therapies, including but not limited to other therapies disclosed herein.

LNCaP Cells and DES Action. Diethylstilbestrol (DES) is now used as one of the primary treatments for prostatic cancer (Seidenfeld J et al. (2000) *Ann Intern Med* 132, 566-577). Its action is likely mediated through the hypothalamus-pituitary axis (Seidenfeld J et al. (2000) _i Ann Intern Med 132, 566-577). DES causes suppression of anterior pituitary gonadotrophins and therefore suppresses testicular output of androgens. Although it is thought that DES has no direct effects on prostate cancer cells, the development of the assay methodology set out herein permitted a direct assessment of this issue. The $AR^+$ LNCaP cells were used as a model for these tests (FIG. 59). As shown in FIG. 59A, 10 nM DHT effectively reversed the inhibition caused by higher concentrations of CDE-horse serum in D-MEM/F-12. Likewise, 10 nM $E_2$ also reversed the CDE-serum caused inhibition completely (FIG. 59B). However, the same concentration of DES was entirely ineffective (FIG. 59C). DES did not reverse the serum caused inhibition. The synthetic estrogen had no direct positive effect on LNCaP cell growth. In the final study of this series, DES addition to medium containing DHT or $E_2$ did not affect the reversal caused by these two natural steroids (FIG. 59D). Therefore, DES is not a direct inhibitor of androgen or estrogen promoted LNCaP cell growth. The view that DES acts indirectly to cause chemical castration is consistent with the present results. These results are supported by other studies indicating that DES does not bind to the AR of LNCaP cells (Montgomery B T et al. (1992) *The Prostate* 21, 63-73).

Discussion of Example 14. The fact that DES is a major treatment for prostate cancer but does not act directly on the tissue has therapeutic implications. For prostate cancer localized to the organ, or specific metastases in other locations (e.g. bone, liver or lung), direct application of Fe (III) offers a therapy with a different mode of action. It is also possible that local Fe (III) therapy (as described in Example 12) can be used in conjunction with conventional systemic DES treatment to increase effectiveness above that with either treatment alone. There is another potential advantage of local Fe (III) treatment over systemic DES treatment. DES has many side-effects in males. Some present considerable discomfort or medical problems. Locally applied Fe (III) is absorbed by the body to form non-toxic mono ferric and diferric transferrin by chelation with the large pool of available apotransferrin. The iron containing proteins formed are no problem for the body because they are the natural physiological forms of iron delivered to all tissues.

Example 15

Preparation of Inhibitor Depleted Serum for Control Studies and Stability Properties of the Inhibitor This Example, lists several acceptable techniques for useful inactivated immunoglobulin inhibitors, and distinguishes the inhibitors from the classical "estrocolyone."

Figure 60:
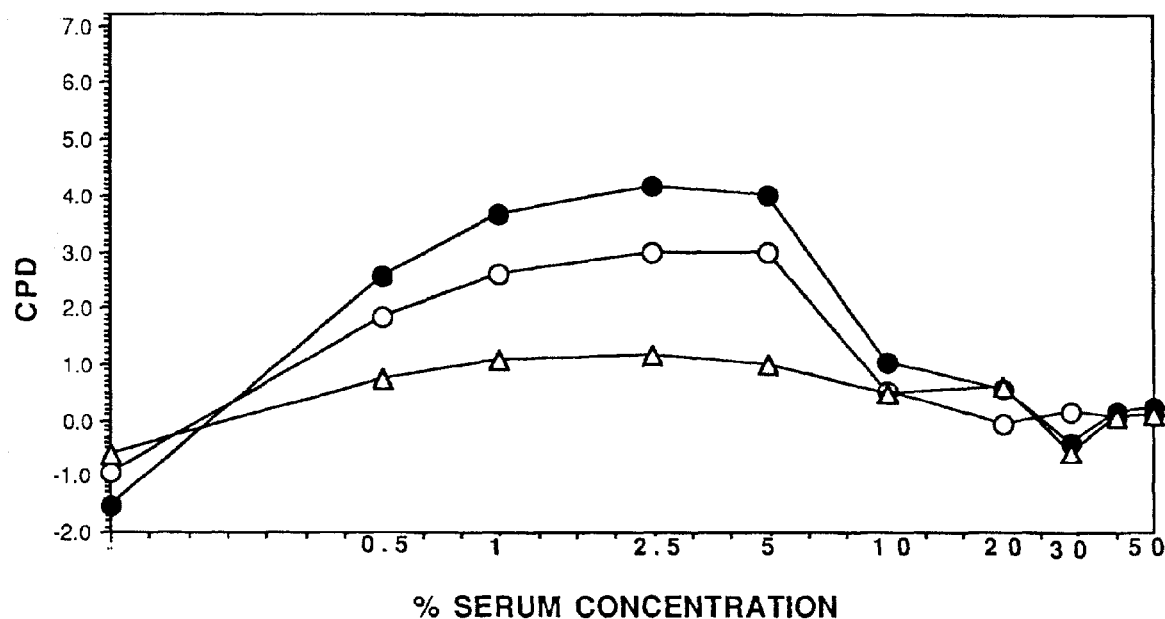
FIG. 60. Effect of Tris Buffer (pH 7.4) Dialysis on the Estrogen Reversible Inhibitor Activity of CDE-horse Serum Assayed with MTW9/PL2 Cell±E$_2$.

Effect of Dialysis on Estrogenic Effects. CDE-horse serum was dialyzed at 4° C. against 0.05M Tris-HCl, pH 7.4, for up to 72 hours with buffer changes every 24 hours using a Spectropor dialysis membrane. The resulting serum was tested for estrogenic effects with MWT9/PL2 cells as shown in FIG. 60. There was near a total loss of estrogen reversible inhibitory activity accompanying this treatment. It was found consistently (N=14) that this treatment resulted in the appearance of an estrogen irreversible inhibitor at serum concentrations above 10% (v/v). It was possible that the estrogen reversible inhibitor was low molecular weight and had passed through the dialysis membrane.

Figure 61:
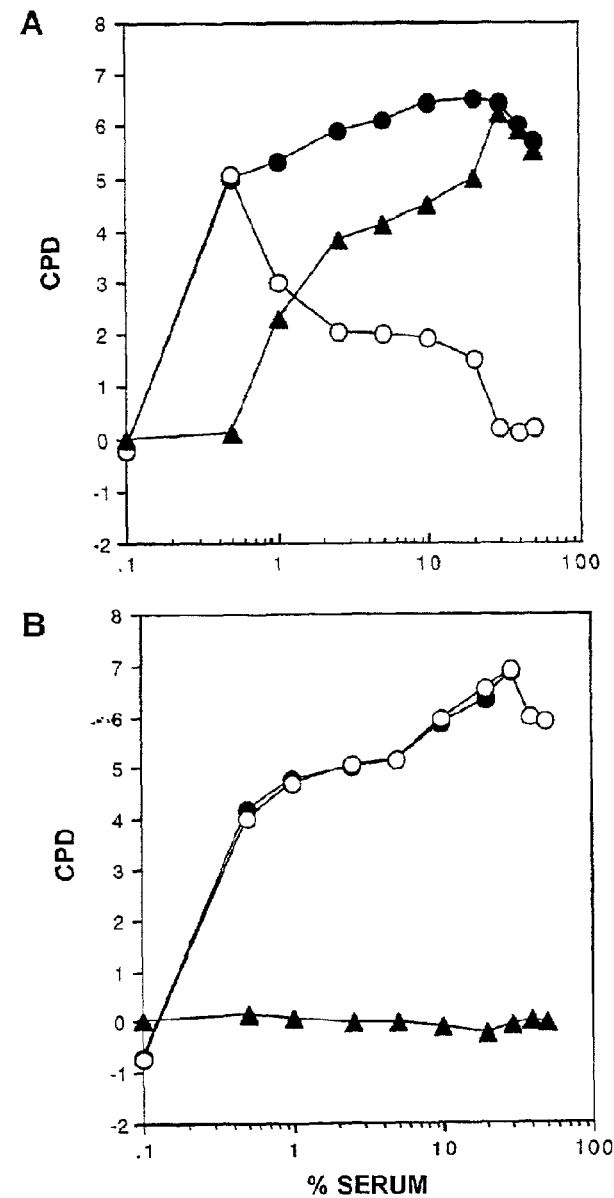
FIG. 61. Ultrafiltration of CDE-horse Serum and Assay of the Filtrate and Retentate with MTW9/PL2 Cells±E$_2$.

Ultrafiltration of CDE-Serum and Estrogenic Effects. CDE-horse serum was submitted to nitrogen gas pressure ultrafiltration using an Amicon unit and an YM-30 membrane (i.e. a 30,000 molecular weight cut-off). The filtrate was assayed with MTW9/PL2 cells directly whereas the retentate was diluted to the original volume with normal saline before assay. The filtrate (FIG. 61B) supported growth but without any estrogenic effect. The retentate (FIG. 61A) demonstrated the usual high estrogenic effect (i.e. 6 CPD) seen in the other MTW9/PL2 cell assays presented in this Example. It is unlikely the Tris dialysis results described above came from passage of the inhibitor through the membrane. The ultrafiltration results confirm a molecular weight>30,000 daltons. The combined results of dialysis and ultrafiltration suggest a lower molecular weight cofactor that might help stabilize the estrogen reversible inhibitor.

Figure 62:
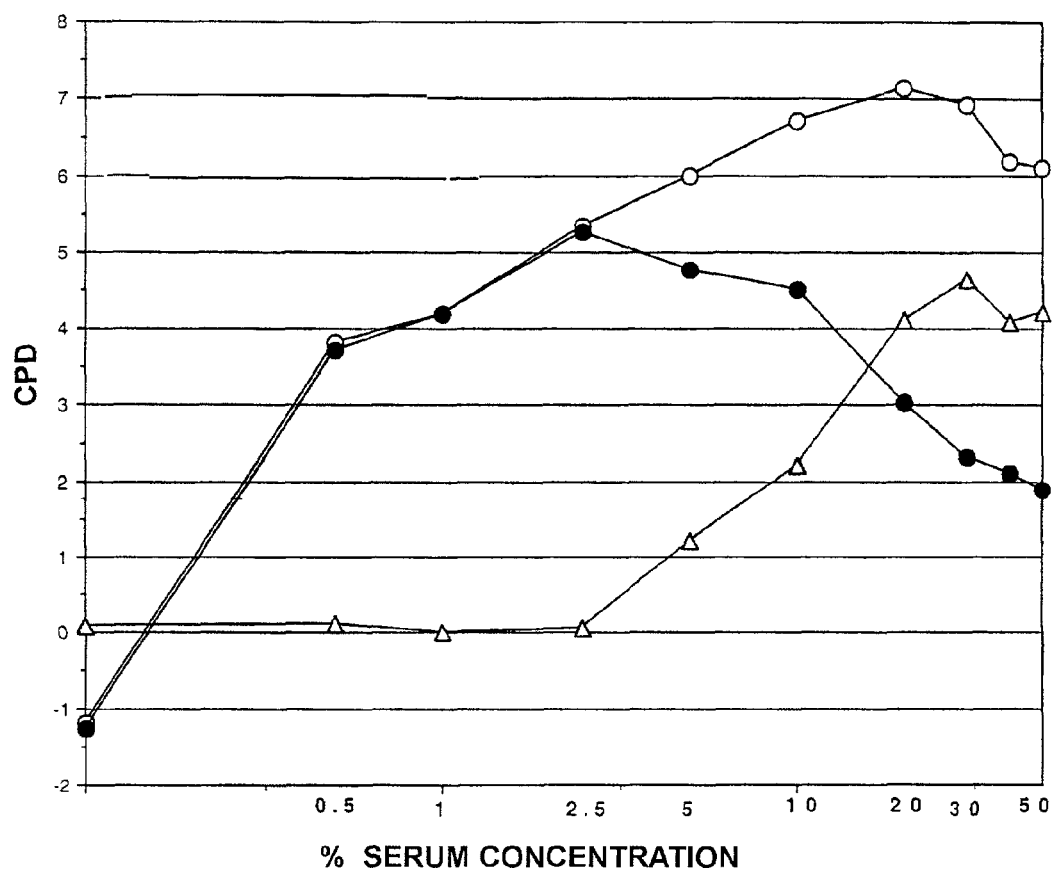
FIG. 62. 50° C. Treatment of CDE-horse Serum for 30 minutes and Assay with MTW9/PL2 Cells±E$_2$.
Figure 63:
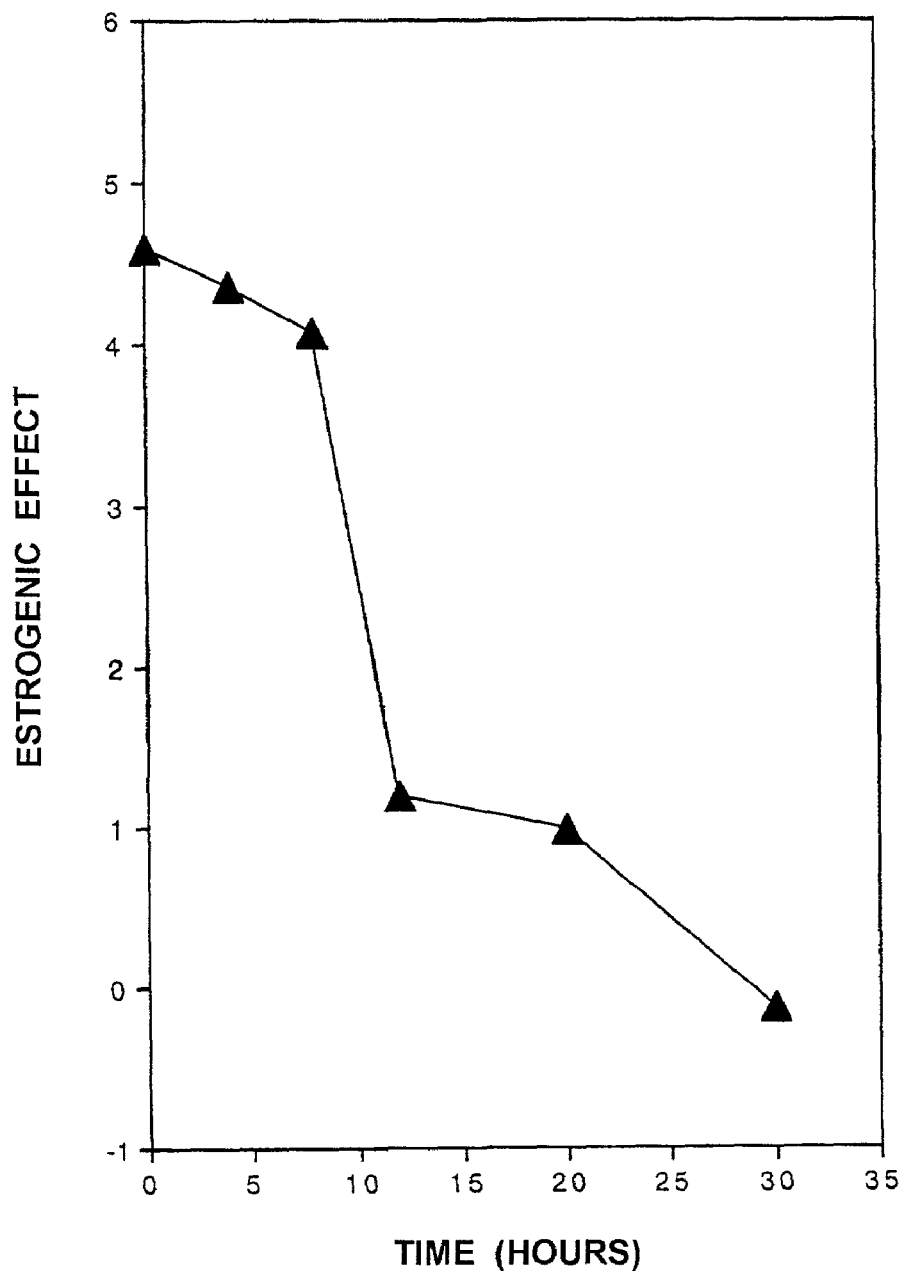
FIG. 63. Time Course of Heat Treatment of CCDE-horse serum at 50° C. and Measurement of Estrogenic Effects with MTW9/PL2 Cells.
Figure 64:
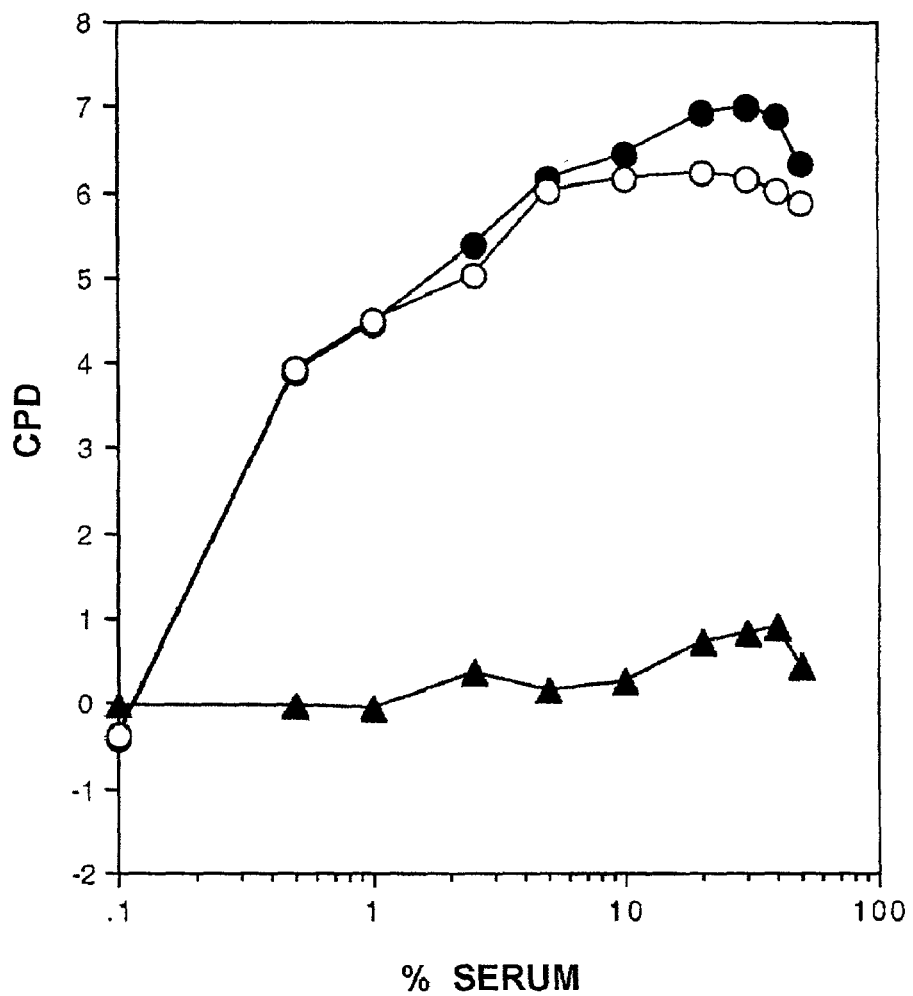
FIG. 64. 50° C. Treatment of CDE-horse Serum for 20 hours and Assay with MTW9/PL2 Cells±E$_2$.
Figure 65:
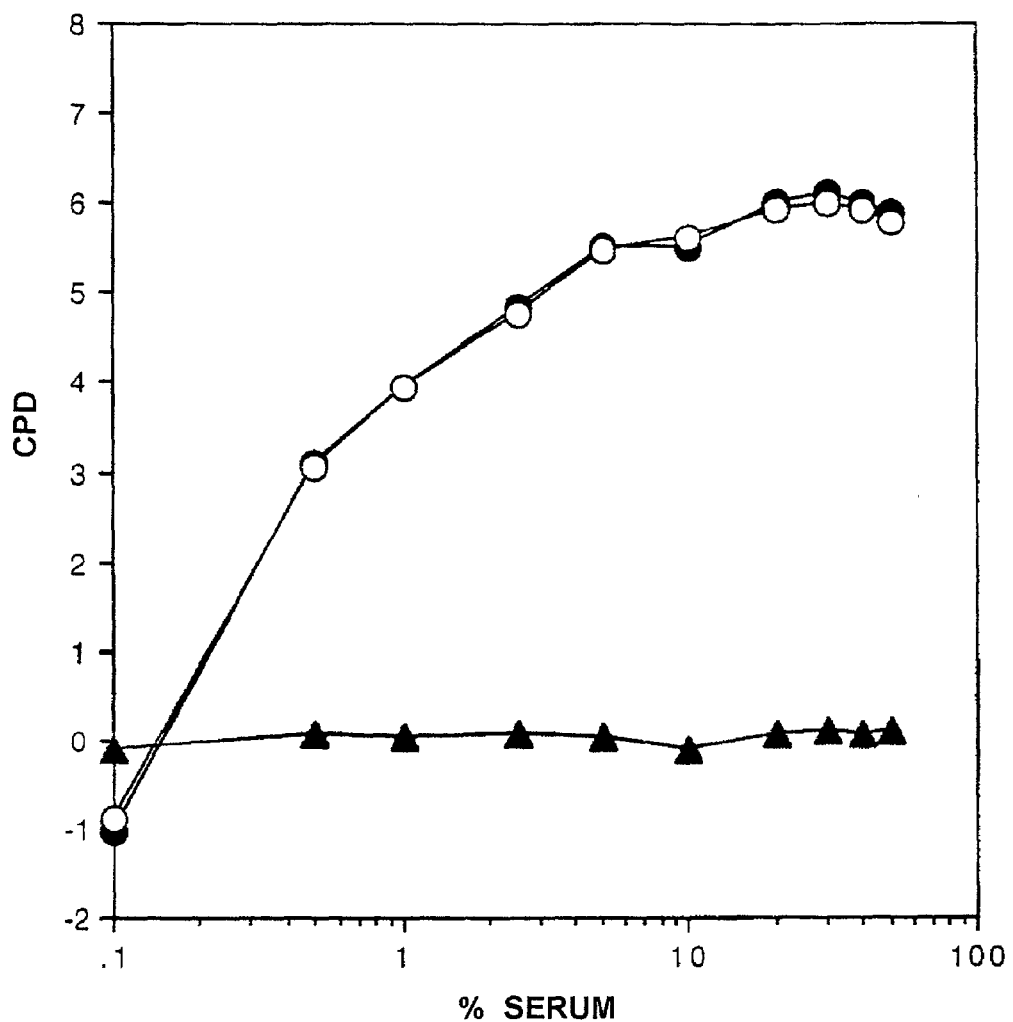
FIG. 65. 60° C. Treatment of CDE-horse Serum for 90 minutes and Assay with MTW9/PL2 Cells±E$_2$.

Heat Treatment and Estrogenic Effects/Inhibitor Content of CDE-serum. The heat stability of the estrogen reversible inhibitor of CDE-horse serum was investigated at 50° C. and 60° C. with the MTW9/PL cells. Heating at 50° C. for 30 minutes reduced the estrogen effect to 4.6 CPD (FIG. 62) instead of the usual 5 to 6 CPD. The effect of heating at 50° C. for up to 30 hours is shown in FIG. 63. By 20 hours, the estrogenic effect with MTW9/PL2 cells was reduced to $\leq 1.0$ CPD. Nonetheless, this serum still supported full growth of the MTW9/PL2 cells (FIG. 64). Another effective method requiring less time is shown in (FIG. 65). Heating at 60° C. for 90 minutes yielded serum that supported high levels of growth (i.e. $\geq 6$ CPD) but had lost all inhibitor activity. This easy treatment, which is especially fast and inexpensive to perform, provides a control serum that has applications in assay of test substances.

Figure 66:
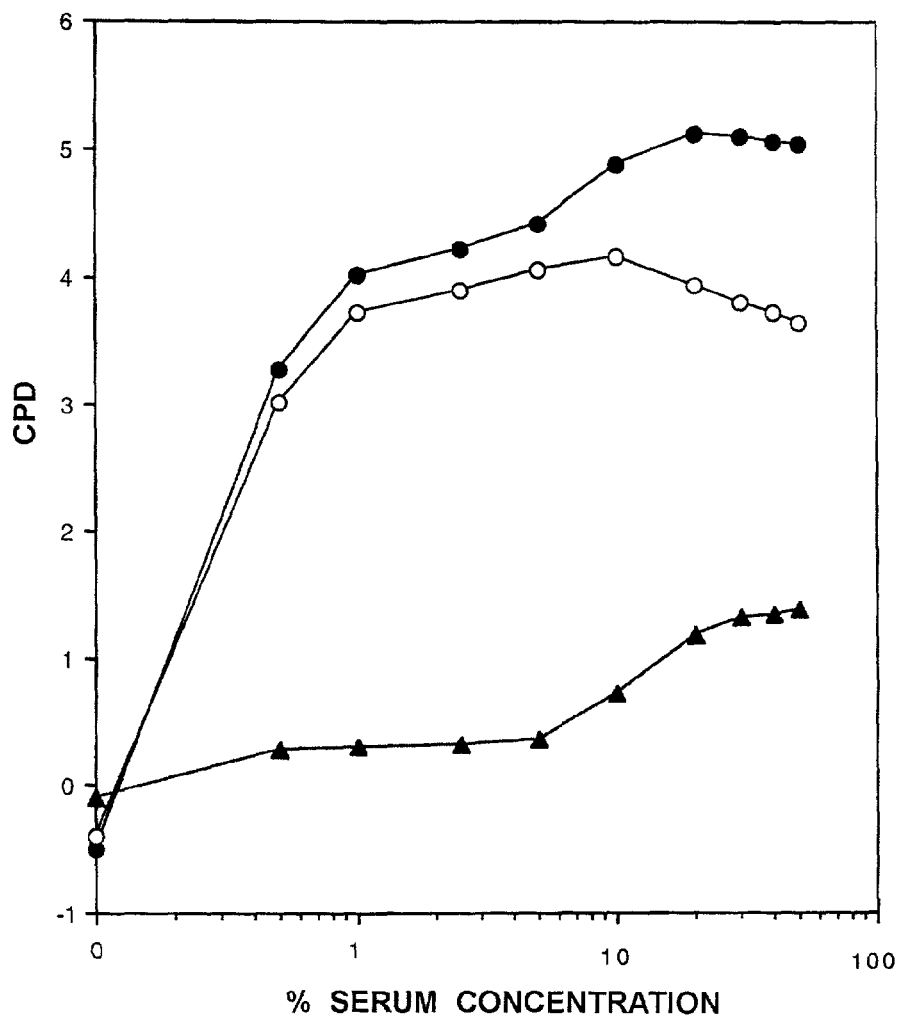
FIG. 66. Affi-Gel Blue Treatment of CDE-horse Serum and Assay with MTW9/PL2 Cells±E$_2$.

Affi-Gel Blue Extraction of CDE-Serum. An aliquot of CDE-horse serum was passed through a 5 mL Affi-Gel Blue™ affinity chromatography column (Bio-Rad, Inc.), prepared according to the manufacturer's instructions. The flow through fraction was tested in the assay for estrogen mitogenic activity at 0 to 50% (v/v). The results are shown in FIG. 66. The 5 mL Affi-Gel Blue™ column removed more than 80% of the inhibitory activity in the serum. Increasing the column bed to 10 mL resulted in removal of more than 90% of the inhibitory activity in the serum.

Acid Treatment of CDE-serum. CDE-horse serum was adjusted to pH 4.5 with HCl and incubated for 16 hrs at 4° C. The resulting serum readjusted to pH 7.4 and tested as previously done with MTW9/PL2 cells. Acid treated CDE-serum promoted only limited MTW9/PL2 cell growth and an estrogenic effect of<0.5 CPD. Not only was the inhibitor acid labile, but the serum components that support growth at<10% (v/v) were also adversely affected (data not shown).

Figure 67:
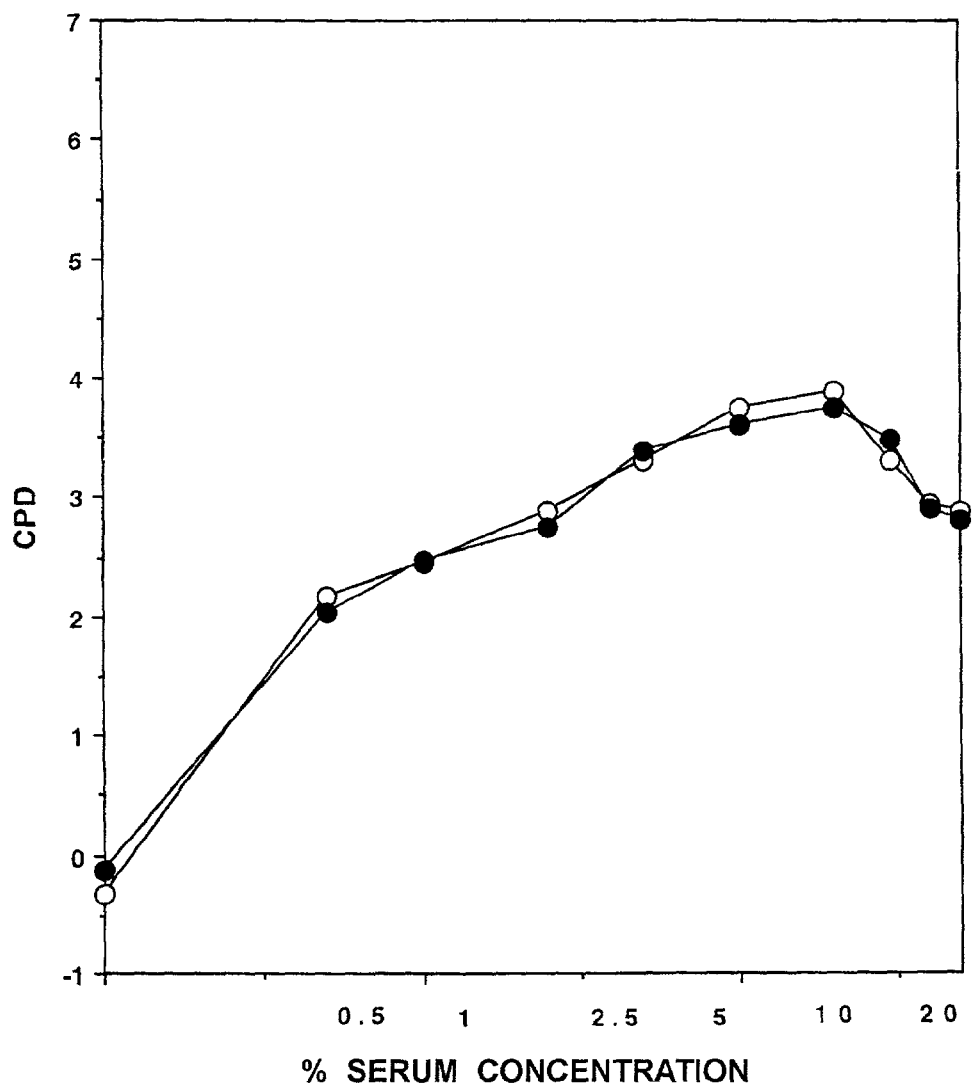
FIG. 67. Effect of 6 M Urea on the Estrogenic Activity of CDE-horse Serum Assayed with MTW9/PL2 Cells±E$_2$.

Urea Treatment of CDE-serum. CDE-horse serum was dialyzed against 0.05 M Tris-HCl, pH 7.4, with 50 mM calcium chloride and 6 M urea for 16 hours at 4° C. The urea was removed by dialysis against the buffer without urea. The addition of $CaCl_2$ to the Tris buffer protects the activity (see results below). The resulting serum was tested as previously described. As shown in FIG. 67, the inhibitory activity was inactivated. Also, the growth promoting activity of<10% (v/v) was also adversely affected.

Discussion of Example 15. The preparation of inhibitor-depleted serum has applications with regard to testing compounds that might possess cytotoxic activity independent of any steroid hormone-like cell growth stimulating ("steroidogenic") effects or other hormone-like properties. The methods outlined will permit assays of commercial, environmental, industrial and medical compounds, substances and mixtures for inhibitor-like activity and/or cytotoxic activity in the same preparations.

There is another very important application of this technology. Development of compounds with estrogen reversible and estrogen irreversible inhibitor-like activity, including peptides, recombinant DNA products, or synthetic organic or inorganic compounds can be sought using inhibitor-depleted serum as the assay base. The new agents can be compared directly to the purified serum inhibitor to determine their efficacy and potency. It is anticipated that this technology will yield compounds that mimic the serum inhibitor and can be used to treat various forms of mucosal cancers including breast and prostate and colon. This method is expected to allow rapid examination of many compounds. The preferred preparation method for control serum is heating at 50° C. for about 20 to 30 hours or 60° C. for about 90 minutes. Affi-Gel Blue treatment is effective, but only with small volumes of serum (e.g. 1 to 2 liters). Affi-Gel Blue is more expensive and time consuming than the heating methods. Tris dialysis, acid pH treatment and urea treatment are not as satisfactory but can be applied as required under special circumstances.

The results presented herein distinguish the estrogen reversible inhibitor sought here from estrocolyone 1 (Soto A M et al. (1992) *J Steroid Biochem Mol Biol* 43, 703-712). Estrocolyone 1 is stable to treatment with 6 M urea, stable at 60° C. for 2 hours, and stable in 2 M acetic acid. Furthermore, estrocolyone does not bind to Affi-Gel Blue. The serum-borne inhibitor described herein does not share any of these properties.

Example 16

Effects of Conventional Purification Methods on the Properties of the Estrogen Reversible Serum-Borne Inhibitor This Example demonstrates the mainly adverse effects of conventional purification techniques on the desired properties of the present inhibitors. This Example also illustrates that the conventional purification techniques can be used to produce certain desired effects on the inhibitors.

Figure 68:
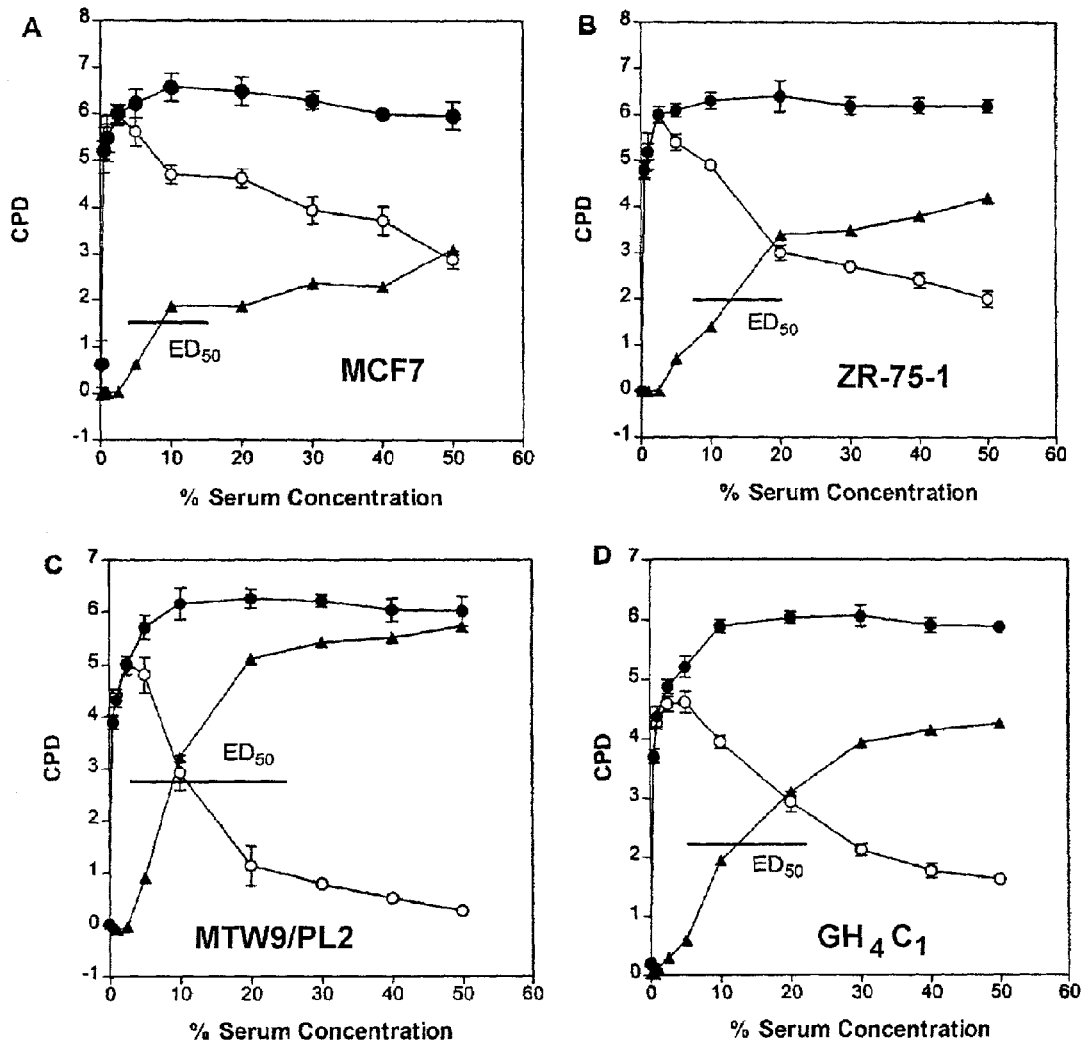
FIG. 68. ED$_{50}$ Estimations for Purification Quantification of Beginning with Serum. (A) MCF-7K Cells ED$_{50}$ of CDE-horse Serum±E$_2$; (B) ZR-75-1 Cells ED$_{50}$ of CDE-horse Serum±E$_2$; (C) MTW9/PL2 Cells ED$_{50}$ of CDE-horse Serum E$_2$; (D) GH$_4$C$_1$ Cells ED$_{50}$ of CDE-horse Serum±E$_2$.

CDE-horse Serum Effects Used to Calculate the $ED_{50}$ Required for Purification Quantification. Conduct of purifications requires measurement of specific activity (i.e. $ED_{50}$) and definition of units of activity. The results in FIG. 68 present examples of how estimates of the $ED_{50}$ concentrations protein required for half-maximum estrogenic effects were determined. Two representative commonly studied estrogen sensitive human cell lines and two established rodent lines were selected for presentation. FIGS. 68A, 68B, 68C and 68D show assay results with the MCF-7K and ZR-75-1 human breast cancer cells, the MTW9/PL2 rat mammary tumor cells, and the $GH_4C_1$ rat pituitary tumor cells, respectively. With all four lines, the maximum estrogen reversible inhibition was observed at 50% (v/v) CDE-serum. Under these conditions, estrogen reversed cell number increases (i.e. estrogenic effects) ranged from $2^{3.1}$ to $2^{5.5}$ (i.e. $2^{CPD}$) or 8-fold with MCF-7K cells to 45-fold with MMW9/PL2 cells. Serum concentrations of 8 to 16% (v/v) supported $ED_{50}$ effects. This corresponded to protein concentrations of 2.4 to 4.8 mg/mL (TABLE 8). One unit of activity is the amount that achieves $ED_{50}$. To achieve maximum inhibition, 15±2.5 mg/mL of protein were required (i.e. 50% serum). The experiments presented here support the previous conclusion that serum contains an estrogen reversible inhibitor.

TABLE 8

Inhibitor Purification by General Methods

| Chromatography/ Separation Method | Pool Elution Conditions | $ED_{50}$ of Pools | % Activity Recovered | Activity Half-life |
|---|---|---|---|---|
| 1. CDE-horse serum | — | 2.4 to 4.8 mg/ml | (100%) | ≦24 days |
| 2. Ammonium Sulfate | 40 to 75% saturation | 6.7 mg/ml | 80% | ≦14 days |
| 3. DEAE-Sepharose; Pool | 0.05 M Tris-HCl, pH 8.6, with NaCl elution steps | | | |
| I | | 133 μg/ml | 278% | ≦14 days |
| II | | 30 μg/ml | 111% | ≦14 days |
| III | | 2.2 mg/ml | 23% | ND |
| IV | | 390 μg/ml | 0% | ND |
| V | | 2.9 mg/ml | 3% | ND |
| VI | | 223 μg/ml | 1042% | ≦14 days |
| VII | | 1.7 mg/ml | 19% | ND |
| 4. Phenyl Sepharose | 0.05 M Tris-HCl, pH 7.4, with a 3.0 M NaCl to buffer gradient | | | |
| Pooled fractions 100-130 | | 94 μg/ml | 33% | ≦14 days |
| 5. Bio-Gel HTP Pool | 0.01 M sodium phosphate, pH 7.2, with a linear gradient of the buffer | | | |
| I | | 224 μg/ml | 18% | ND |
| II | | 70 μg/ml | 0.7% | ≦14 days |
| III | | 421 μg/ml | 20% | ND |
| IV | | 260 μg/ml | 10.2% | ND |
| V | | 36 μg/ml | 2.7% | ≦14 days |

Figure 69:
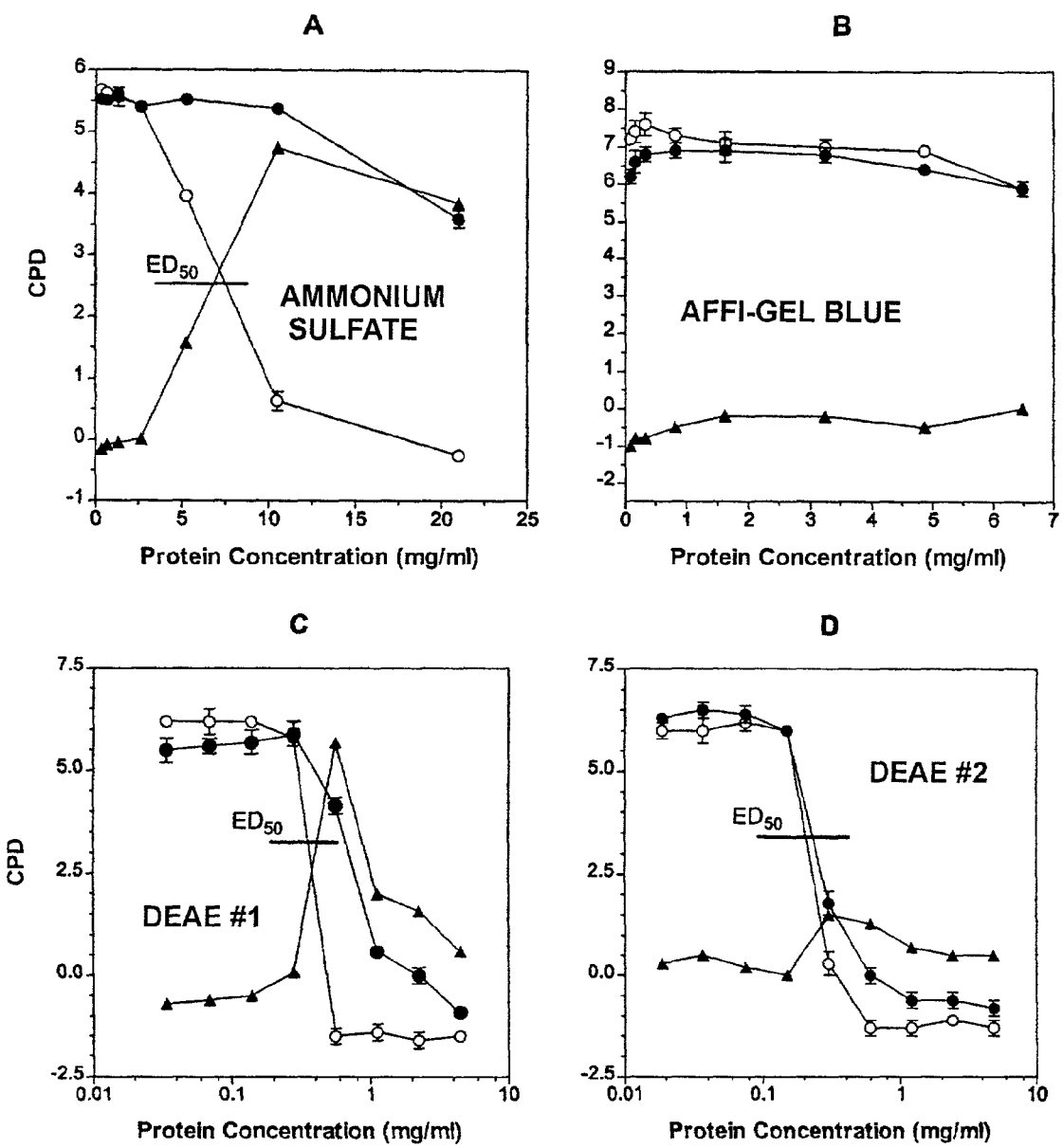
FIG. 69. Assay of Estrogenic Activity (ED$_{50}$) of Chromatographic Pools. (A) Ammonium Sulfate Active Fraction; (B)Affi-Gel BlueGel Albumin Rich Fraction; (C) DEAE Sepharose Pool IV Active Fraction Assay #1; (D) DEAE Sepharose Pool IV Active Fraction Assay #2.

Ammonium Sulfate Precipitation. Ammonium sulfate precipitation was studied both to increase specific activity and to decease the volume of the serum. The activity precipitated over a broad concentration range. The precipitate from 0 to 40% saturated ammonium sulfate contained<30% of the protein and activity of whole CDE-serum. Replicate 40 to 75% saturation precipitates contained approximately 80% of the total activity units and 60% of the serum protein. The $ED_{50}$ of this fraction ranged between 3.0 to 6.7 mg/ml (FIG. 69A). The ammonium sulfate results are summarized in TABLE 8. The ammonium sulfate fractions were not stable to freezing and thawing nor were they stable during storage at 4 C. or 23 C. To best preserve activity, the precipitated material had to be used immediately in the next isolation step. Our results differ from those in another report (Soto A M et al. (1992) *J Steroid Biochem Mol Biol* 43, 703-712) indicating that the estrogen reversible inhibitory activity was stable in ammonium sulfate.

Proteinase Inhibitors. In replicate studies, the addition of the proteinase inhibitors 4-anidinophenylmethanesulfonyl fluoride (0.01 mg/ml), phenylmethylsulfonyl flouride (0.10 mg/ml), N-tosyl-L-phenylalanine chloromethyl ketone (0.1 mg/ml), and leupeptin (0.01 mg/ml) to the serum before precipitation, or to the 40 to 75% precipitated fraction, was not beneficial. Although effective as a metaloproteinase inhibitor, EDTA was not used because it was expected to remove stabilizing calcium.

Affi-Gel Blue Chromatography—General Considerations. Affi-Gel Blue fractionation of CDE-horse serum was done as described by the manufacturer for the isolation of albumin (Bio-Rad Affi-Gel® BlueGel, 50 to 100 mesh, Instruction Manual, Catalog Numbers 153-7301 and 153-7302). This study addressed two issues. First, it was important to establish that the inhibitor localized as a single protein, or at most only a few proteins. This issue has not been addressed directly before. Affi-Gel BlueGel is a mild method that effectively separates functionally active serum proteins (Sirbasku D A et al. (1991) *Biochemistry* 30, 295-304; Travis J et al. (1976) *Biochem J* 157, 301-306; Gianazza E and Arnaud P (1982) *Biochem J* 201, 129-136; Iqbal M J and Johnson M W et al. (1977) *J Steroid Biochem* 8, 977-983). Second, Affi-Gel BlueGel offers a reliable and convenient means of isolating relatively pure native serum albumin (Travis J et al. (1976) *Biochem J* 157, 301-306; Gianazza E and Arnaud P (1982) *Biochem J* 201, 129-136). This is especially significant because reports from other laboratories have cited albumin as "the" serum inhibitor (Laursen I et al. (1990) *Anticancer Res* 10, 703-712; Sonnenschein C et al. (1996) *J Steroid Biochem Mol Biol* 59, 147-154).

Figure 70:
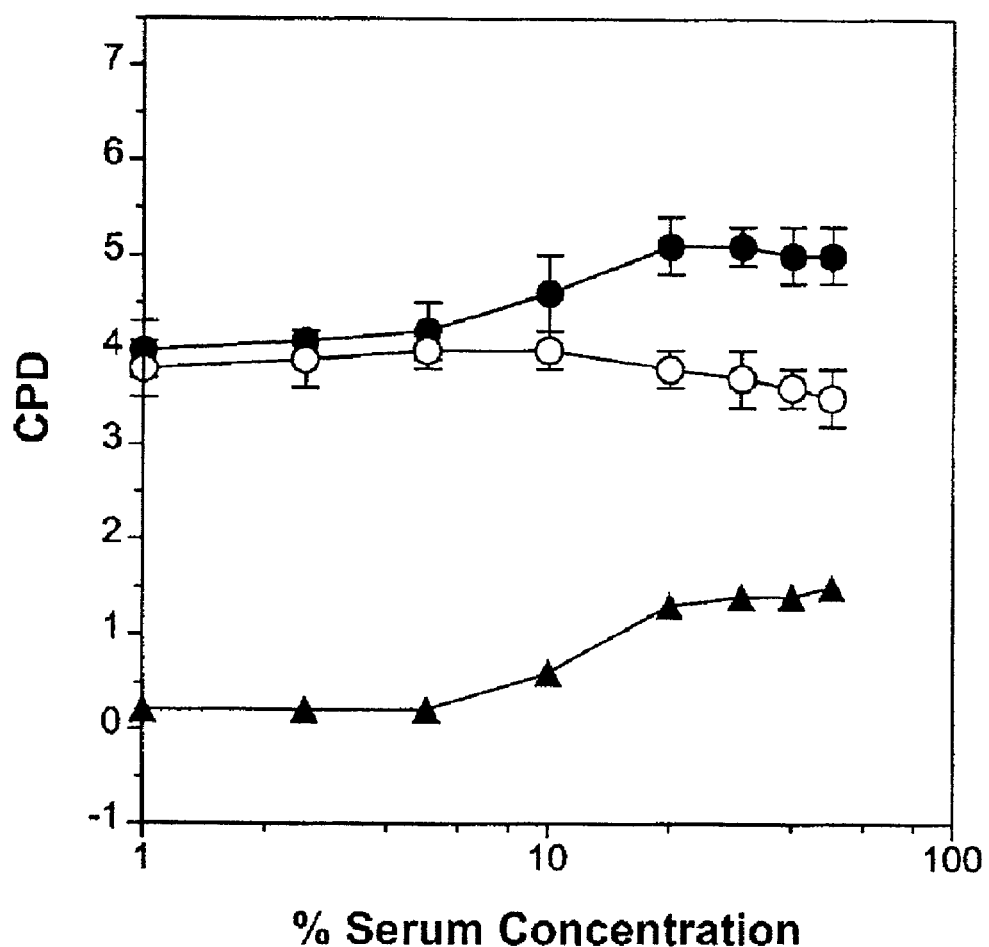
FIG. 70. Assay of Affi-Gel BlueGel By-Pass Fraction±E$_2$.

Affi-Gel Blue Chromatography—Technical Applications. A one-liter column (5 cm×51 cm) was equilibrated with 0.05 M Tris-HCl, pH 7.4. The 40 to 75% ammonium sulfate precipitated material (438 mL, with 23.5 grams of protein) was dialyzed against this buffer and applied to the column. After washing with equilibration buffer, elution was done with increasing step concentrations of 0.15, 1.0 and 3.0 M NaCl in the buffer. The four pools contained 3.7, 3.2, 27.3 and 26.8% of the protein applied, respectively. The flow-through and the 0.15 M NaCl pools did not contain albumin, as expected (Travis J et al. (1976) *Biochem J* 157, 301-306; Gianazza E and Arnaud P (1982) *Biochem J*201, 129-136). The 1.0 and 3.0 M NaCl pools contained 70% albumin (Travis J et al. (1976) *Biochem J* 157, 301-306; Gianazza E and Arnaud P (1982) *Biochem J*201, 129-136). SDS-PAGE and Coomassie Blue staining confirmed albumin in these pools (results not shown). Assay of the four pools showed no inhibitory activity (TABLE 8). Affi-Gel BlueGel either retained the activity even with a 3.0 M NaCl wash, or it caused inactivation. FIG. 69B shows an example assay of an albumin rich pool. The same results were obtained with whole CDE-serum applied to the same column (results not presented). The same four pools shown in TABLE 8 also showed no recovery of the estrogen reversible inhibitory activity. The Affi-Gel BlueGel results in TABLE 8 suggested another use for this matrix. Passage of CDE-horse serum through Affi-Gel Blue removed the majority of the estrogen reversible inhibitory activity for MTW9/PL2 cells (FIG. 70). This was effective even though the volume of serum applied was more than five times the volume of the resin. The maximum estrogenic effect seen with Affi-Gel BlueGel treated serum as 1.5 CPD (FIG. 70) whereas the maximum effect in control CDE-serum was 5.5 CPD (FIG. 68C) with MTW9/PL2 cells. The residual activity in the by-pass fraction is likely due to IgA/IgM. Small amounts of these immunoglobulins are usually in the by-pass of this column (Gianazza E and Arnaud P (1982) *Biochem J* 201, 129-136).

Human Serum Albumin as Inhibitor. In studies not presented, three preparations of human serum albumin were assayed for estrogen reversible inhibitory activity with $ER^+$ human and rodent cell lines. Globulin containing (96 to 99% albumin), crystalline, and Cohn's fraction V human serum albumin (all from Sigra) were not inhibitory at concentrations up to 12 mg/mL. The assays showed the same pattern as in FIG. 69B. These results further support our earlier conclusion that albumin was not the estrogen reversible inhibitor.

DEAE Sepharose Chromatography—General Considerations. We next applied DEAE Sepharose chromatography. Because ammonium sulfate precipitation provided no benefit beyond sample concentration (TABLE 8), we instead used whole CDE-serum. The DEAE Sepharose column was eluted with both step increases in NaCl concentration and with linear gradients of NaCl. Eight permutations of pH, NaCl elution concentrations, and gradient protocols were analyzed. The results presented in FIG. 71 were the optimum conditions identified.

Figure 71:
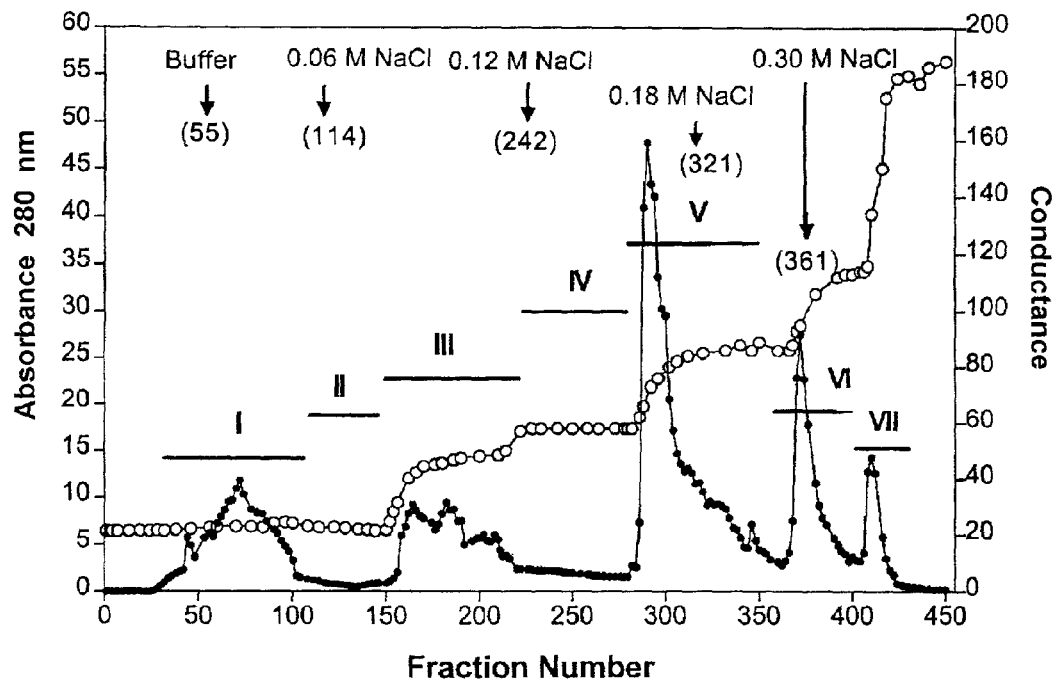
FIG. 71. DEAE Sepharose Chromatography Elution Profile with Whole CDE-horse Serum.

DEAE Sepharose Chromatography—Technical Considerations. DEAE Sepharose used at pH 8.6 provided the best separations. Seven pools were obtained (FIG. 71). Activity assays of each pool are summarized in TABLE 8. The flow-through fraction (pool I) and the wash with equilibration buffer (pool II) together contained 389% of the applied activity and 5.6% of the protein applied. Pool II was particularly active, with the lowest $ED_{50}$ concentration of any from general chromatography (i.e. 30 µg/mL). Pools III, IV and V were less active although they still contained 126% of the units and 37.7% of the protein. Pool VI contained 1042% of the activity applied and 32% of the protein. Pool VI alone contained 10 times more activity than applied to the column (TABLE 8). Pool VII was markedly less active with only 19% of the activity and 4.5% of the protein. Although 79.8% of the applied protein was recovered, more than 15 times the expected units were recovered. Although the reason(s) for the apparent increase is not clear, other investigators (Dell' Aquila M L and Gaffney E V (1984) *J Natl Cancer Inst* 73, 397-403) have reported identification of estrogen irreversible inhibitors of the $ER^+$ MCF-7, T47D and ZR-75-1 human breast cancer cell lines in fractions from DEAE Sepharose. It is possible that the higher pH conditions have inactivated these inhibitors and thereby allow greater effect of the estrogen reversible form(s). It is also possible that exposure to high pH alters the inhibitor to yield a more active form.

DEAE Sepharose Chromatography—Stability Considerations and Evidence of more than one Activity. Activity was found in pools I, II and VI. This suggested more than one estrogen reversible inhibitor. In any case, there was a stability problem. An example of this is shown in replicate assays of pool VI over a period of 21 days. The first assay of activity immediately after isolation is shown in FIG. 69C. The effects on $ER^+$ cell growth were biphasic. At lower protein concentrations, estrogen reversible inhibition was observed. At higher concentrations, the pool material became irreversibly inhibitory. With all active DEAE pools, this biphasic pattern was consistent. Additional sequential assays initiated after 14 days storage at 4° C. or 23° C. showed another consistent finding. The maximum estrogenic effect caused by $E_2$ decrease>90% (FIG. 69D). As estrogen reversible inhibition decayed, only the estrogen irreversible inhibition remained (FIG. 69D). From these results, decay most likely resulted in formation of an altered inhibitor that was estrogen irreversible.

Figure 72:
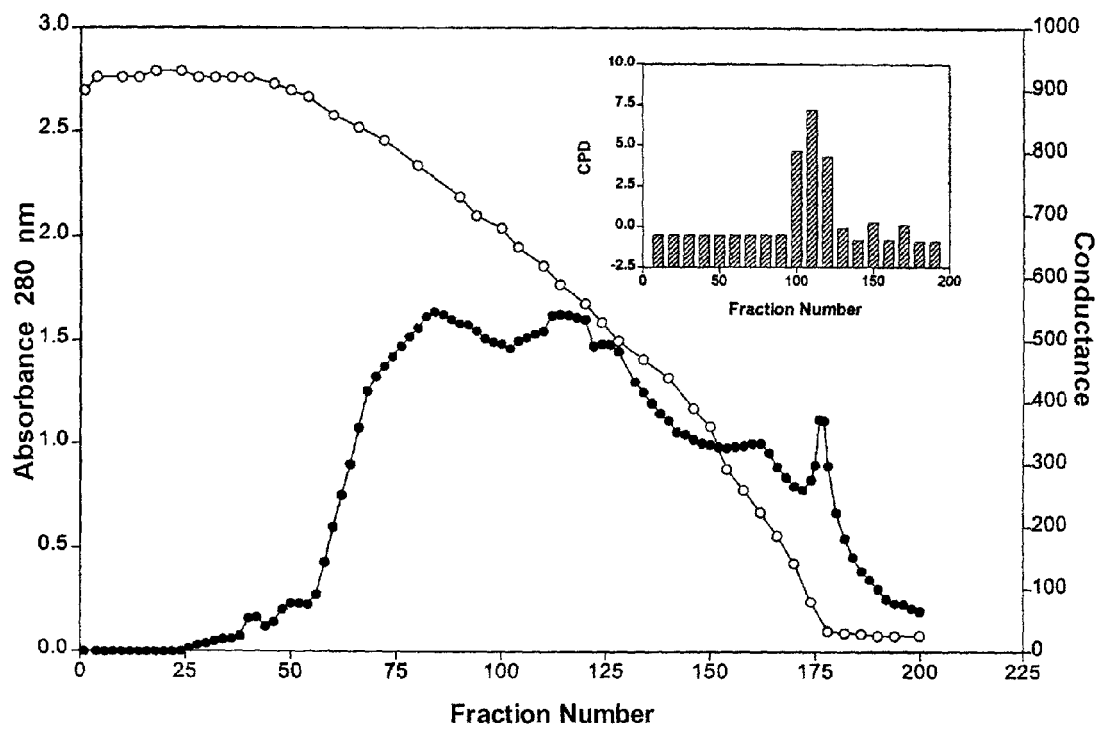
FIG. 72. Phenyl Sepharose Chromatography Elution Profile with DEAE Sepharose Pool IV.

Phenyl Sepharose Chromatography. Phenyl Sepharose chromatography has been previously reported to effectively enrich human serum-derived estrocolyone 1 (Soto A M et al. (1992) *J Steroid Biochem Mol Biol* 43, 703-712). When samples of that estrogen reversible activity were applied under high salt conditions, and the elution done with decreasing salt concentrations, a single inhibitory fraction was separated from the bulk of the proteins (Soto A M et al. (1992) *J Steroid Biochem Mol Biol* 43, 703-712). In the present studies, further purification of DEAE Sepharose pool VI was investigated using phenyl Sepharose. FIG. 72 presents the results of the optimum of four elution protocols investigated. Activity was located in fractions 100 through 130 that contained 12% of the applied protein. The specific activity increased 2.3-fold compared to DEAE Sepharose pool VI (TABLE 8). The initial assay results (data not shown) were similar to those in FIG. 69C. Sequential assays again confirmed a rapid inactivation ending with estrogen irreversible inhibition similar to that shown in FIG. 69D. As seen before, an estrogen irreversible inhibitor was generated upon standing in buffer.

Figure 73:
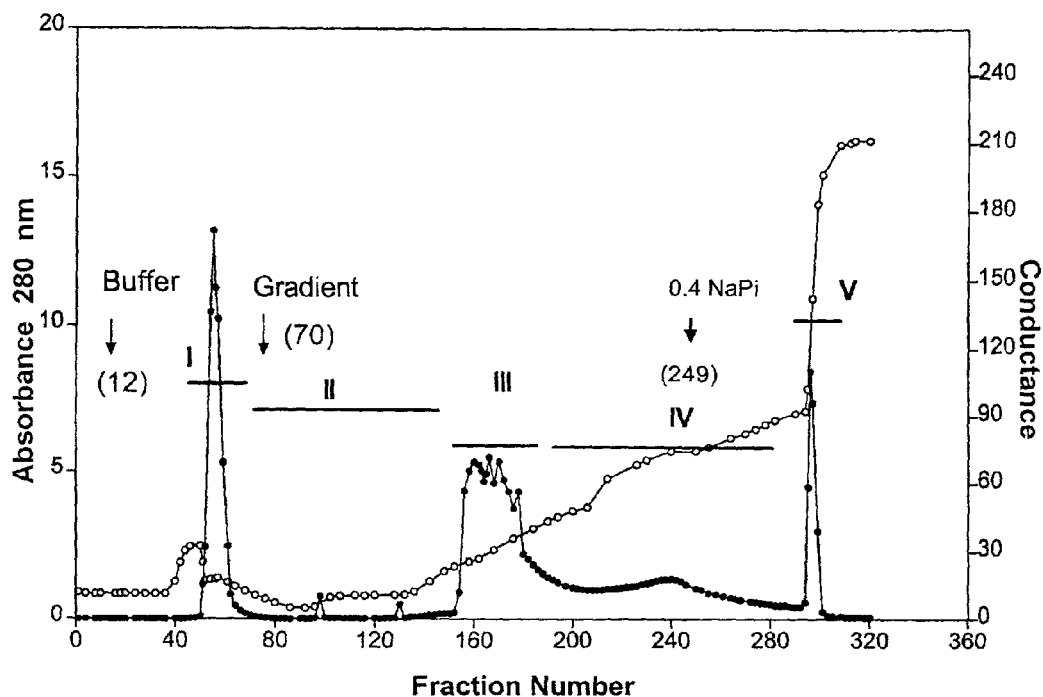
FIG. 73. HTP Bio-Gel (hydroxylapatite) Elution Profile with DEAE Sepharose Pool IV.

HTP Bio-Gel Chromatography and other Methods. Further purification of DEAE Sepharose pool VI was also attempted using HTP Bio-Gel (hydroxylapatite). FIG. 73 shows the results of the most effective of three HTP Bio-Gel elution protocols attempted. The protein and total units of activity recovered from this column were 69.6% and 51.6% respectively. As summarized in TABLE 8, the specific activities (i.e. $ED_{50}$) of pools I, III and V were not improved compared to DEAE pool VI. The specific activities of pools II and V were significantly improvement. Sequential assays of these showed responses similar to those in FIGS. 69C and 69D. The initial estrogen reversible activity decayed within 14 days to irreversible inhibition. In studies not presented, Concanavalin A Sepharose and metal ($Zn^{2+}$) chelate affinity chromatography were also attempted with whole serum, the active fractions from DEAE Sepharose and with the 40 to 75% ammonium sulfate precipitate. These methods were not effective. When activity was obtained, it decayed within two to three weeks in the same pattern as shown in FIGS. 69C and 69D. Analysis of the report (Soto A M et al. (1992) *J Steroid Biochem Mol Biol* 43, 703-712) attempting estrocolyone isolation confirmed substantially the same instability and low yield problems. In the studies described in this Example, it is very clear that purification of the inhibitor had not yet been achieved using conventional purification methods, although useful ways of producing irreversible inhibitor compositions were revealed.

Discussion of Example 16. All of the methods described in this Example are conventional protein purification methods in general use today. They commonly yield high specific activity or high purity protein preparations. Because they were carried out under what are considered non-denaturating conditions and non-reducing conditions, the expected outcome was isolation of an active estrogen reversible inhibitor. It is clear that a spectrum of the usual methods will not yield the estrogen reversible inhibitor in an active, stable form.

It should be noted that the ammonium sulfate experiments alone clearly differentiate the present serum described inhibitor from that described in U.S. Pat. Nos. 4,859,585 (Sonnenschein) and 5,135,849 (Soto). Those patents teach the use of a stable inhibitor obtained by ammonium sulfate fractionation. In the present case, however, an ammonium sulfate fraction yields unstable activity.

Affi-Gel BlueGel has usefulness as a method of preparation of inhibitor depleted serum. It may be preferred under circumstances where heating (the other very effective method) might destroy some component in serum needed for a specialized mucosal or other origin cancer cells. The Affi-Gel Blue results, and others presented herein, support the view that serum albumin is not the serum-borne estrogen reversible inhibitor activity sought herein.

The results of the DEAE chromatography indicate that there is more than one inhibitor. The number cannot be established by that method, but elution localization suggests at least two and possibly more. Further, in light of the results shown in Example 20, the DEAE elution pattern shown in FIG. 69D is consistent with the two or more inactivated inhibitors being denatured forms of immunoglobulins IgA/IgM/IgG1/IgG2 may be very potent antitumor agents and worthy of consideration as new treatment modalities. It should be noted that these fractions were very freeze-thaw sensitive, especially in the absence of calcium. In every case where activity was localized to a chromatographic pool, the activity decayed within 21 to 28 days to an estrogen irreversible agent. This suggests that a denaturation process is ongoing in buffers mostly without calcium, and that a potentially important product is formed that may have cancer therapeutic value. This may be a means of generating very high potency irreversible inhibitors of mammary cancers and other types of mucosal cancers.

Example 17

Calcium Stabilization and Correlation with $^3$H-DHT Binding and Immunoprecipitation by Antibodies Raised to Human SHBG General Protein Isolation Principals. Before continuing the isolation attempts described above, principals common to all protein isolation attempts were applied. Information was sought about the conditions that would best stabilize the activity, and in doing so an understanding of new/appropriate methods of purification was gained.

Figure 74:
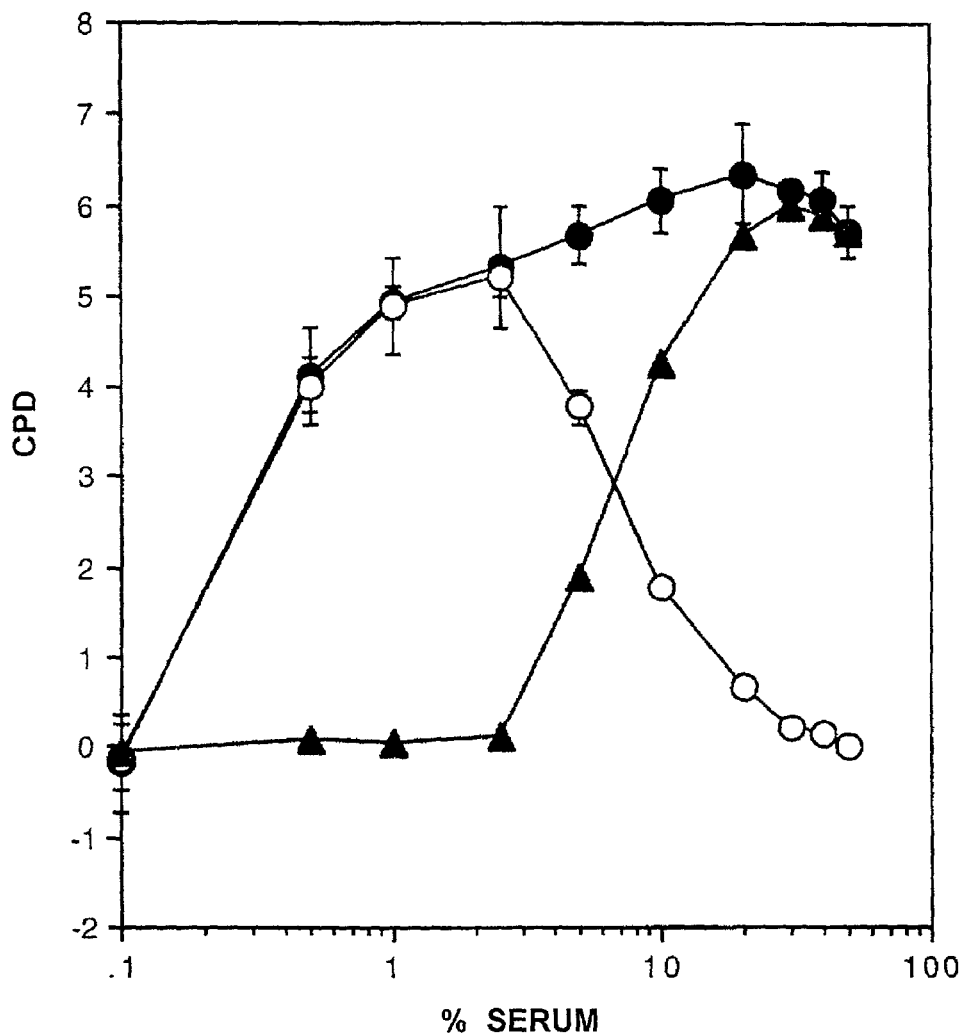
FIG. 74. MTW9/PL2 Cell Assay of CDE-horse Serum Estrogenic Activity after Dialysis in Tris-HCl, pH 7.4, plus 50 mM CaCl$_2$.

Effect of Calcium on Tris-HCl Dialysis Retention of Estrogenic Activity. CDE-horse serum was dialyzed against 0.05M Tris-HCl, pH 7.4, with 50 mM $CaCl_2$ for 72 hrs, buffer changes every 24 hrs at 4° C. using a 6000-8000 molecular weight cut-off dialysis membrane. The resulting serum was assayed with MTW9/PL2 cells±10 nM $E_2$. As shown in FIG. 74, the usual large magnitude estrogenic effects were identified. The presence of calcium in the buffer completely prevented the inactivation found when dialysis was done in buffer without calcium (compare to FIG. 60).

Chelex™ Treatment and Protective Effects of Calcium Ions Against Heat Inactivation. CDE-horse serum was treated with Chelex™ resin beads to remove free metal ions including calcium. This was done to continue the evaluation of calcium as a stabilizer. The serum was incubated with 10%

(w/v) prewashed Chelex™ 100 resin (100-200 mesh, sodium form) (Bio-Rad) for 2 hrs at room temperature. At the end of the incubation, the serum was separated from the Chelex beads by 0.2 µm pore filtration. Calcium concentrations were determined with a calcium-detecting probe. They were<10 nM. Next the Chelex treated serum was incubated at 50° C. either without added calcium or in the presence of 1.0, 10 and 50 mM $CaCl_2$. The serum was assayed with MTW9/PL2 cells at the designated times shown in FIG. 75 (30% Chelex treated serum±10 nM $E_2$) to determine estrogenic effects. Without calcium, total activity was lost within 3 hours. In the presence of increasing calcium, the activity was progressively stabilized. At 50 mM $CaCl_2$,<15 % of the activity was lost even after 30 hours at 50° C. A control with CDE-horse serum is shown. CDE-serum alone lost complete activity by 20 hours at 50° C. as expected from the results in FIG. 64. Clearly, the addition of calcium stabilized the activity.

Figure 76:
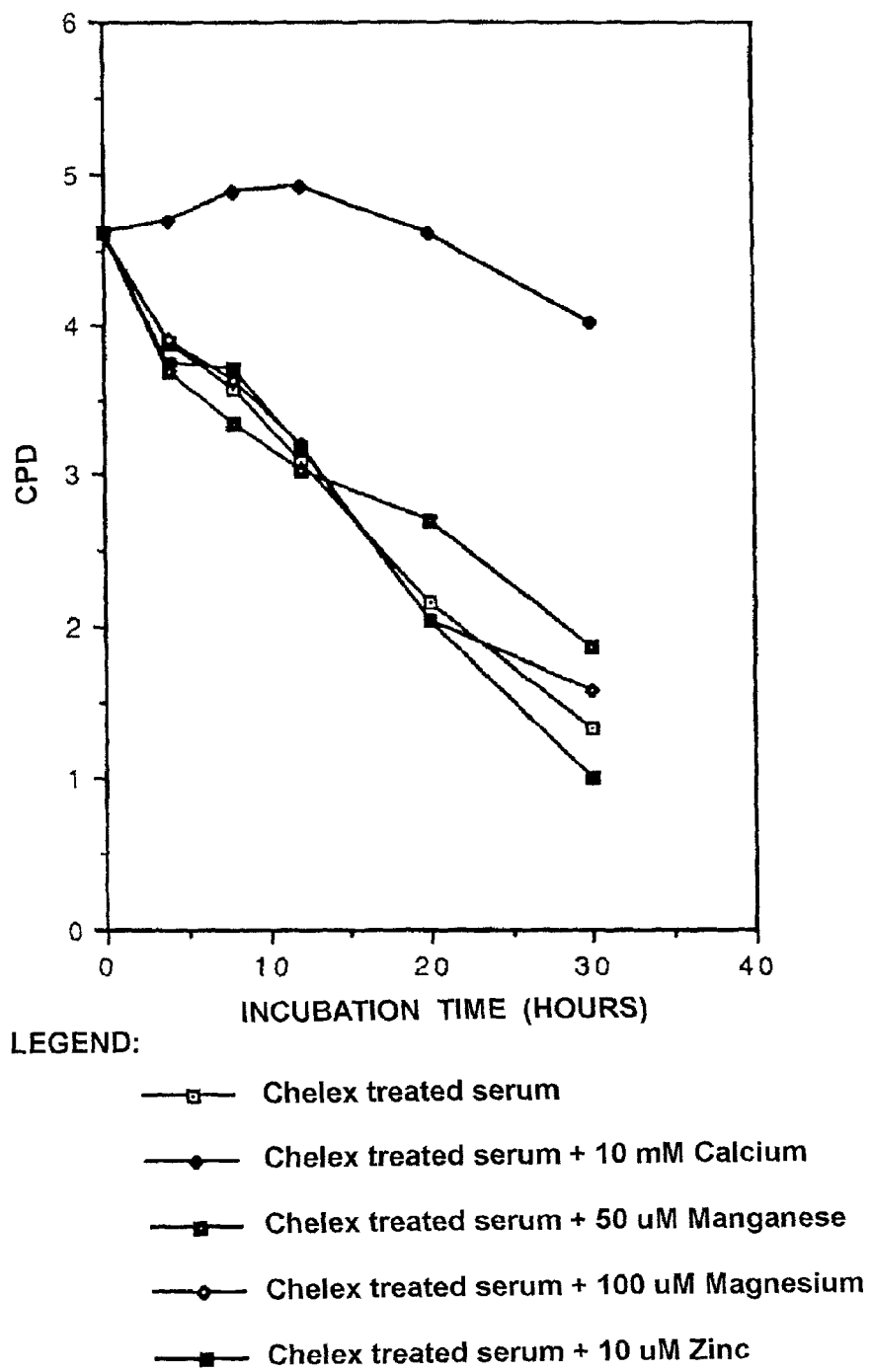
FIG. 76. Effect of Zn, Mn, Mg and Ca on the 37° C. Heat Stability of the Estrogenic Activity in Chelex Treated CDE-horse Serum Assayed with MTW9/PL2 Cells.

Chelex™ Treatment and Protective Effects of Metal Ions Against Heat Inactivation. CDE-horse serum was treated with Chelex™ resin beads to remove free metal ions including calcium. This was a continuation of the study above but with other metal ions to determine if they substituted for calcium. The experiment was conducted as described in the paragraph above but with the change that the incubation temperature was lowered to 37° C. to permit more accurate estimation of the early kinetics of inactivation. Chelex treated serum lost 80% activity in 30 hours at this temperature (FIG. 76). With 10 mM $CaCl_2$, protection was nearly complete at this temperature for 30 hours. However, zinc, magnesium and manganese ions offered no protection. Because these are expected to be common substitutes for calcium, it is likely that stabilization by calcium is quite specific.

Figure 77:
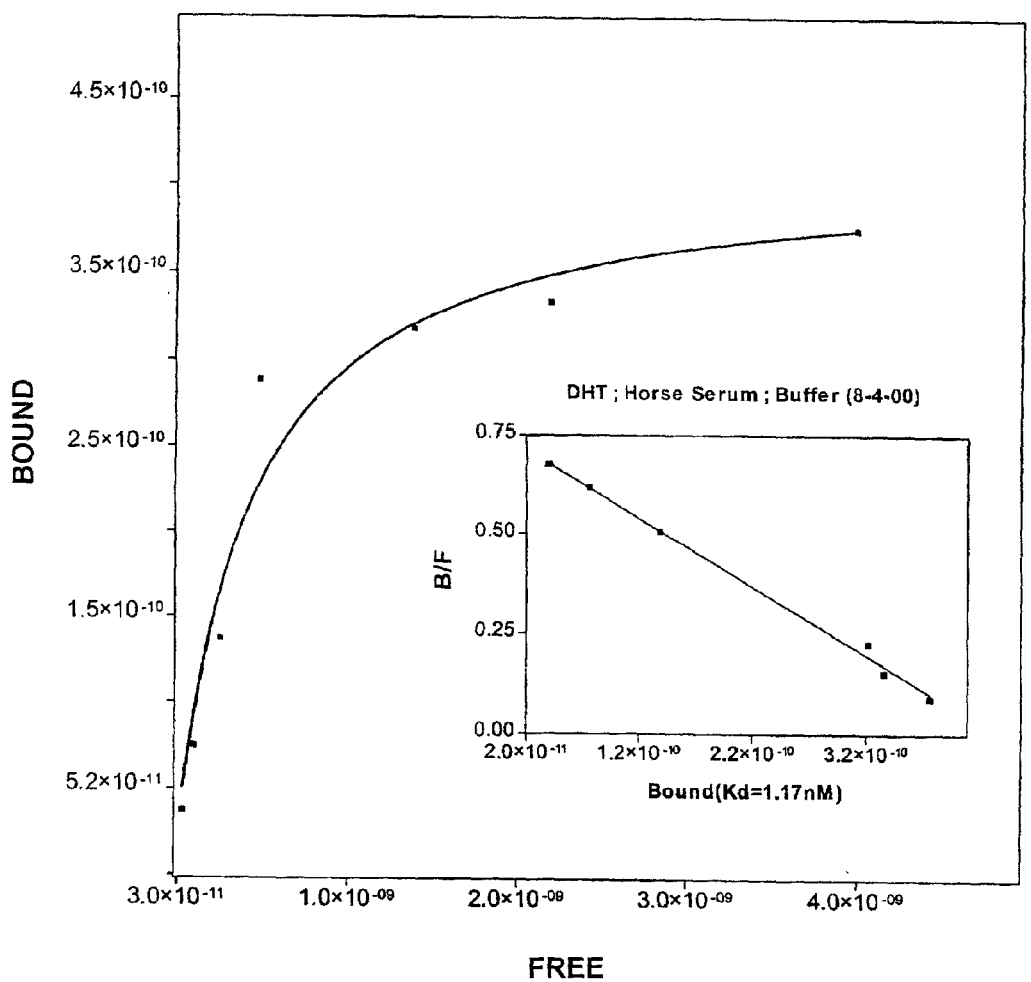
FIG. 77. Binding Affinity (K$_d$) of $^3$H-DHT to CDE-horse Serum.

Labeled Steroid Hormone Binding in CDE-Serum and Scatchard Analysis. One of the basic tenets of the estrocolyone hypothesis is that there are serum proteins that bind sex steroid hormones at affinities (i.e. $K_d$) in the picomolar range (Soto A M et al. (1986) *Cancer Res* 46, 2271-2275). However, what was found instead with CDE-horse serum is specific binding of $^3$H-DHT in the of $K_d$ range 1 to 5 nM as determined by Scatchard analysis (Scatchard G (1949) *Ann N.Y. Acad Sci* 51, 660-672) (FIG. 77). The binding methods are presented in the General Materials and Methods section. With CDE-rat serum the binding affinities were even higher (results not shown). Routinely, the affinities for specific binding of $^3$H-DHT with CDE-rat serum were in the $K_d$ range 15 to 40 nM. With both CDE-horse and CDE-rat serum, binding $K_d$ for $^3$H-$E_2$ was about two to five times higher concentrations (results not presented). CDE-serum shows specific binding of sex steroid hormones, but the affinity was not sufficiently high to support the conclusions of others (Soto A M et al. (1986) *Cancer Res* 46, 2271-2275) concerning picomolar affinities and the estrocolyone hypothesis.

Figure 75:
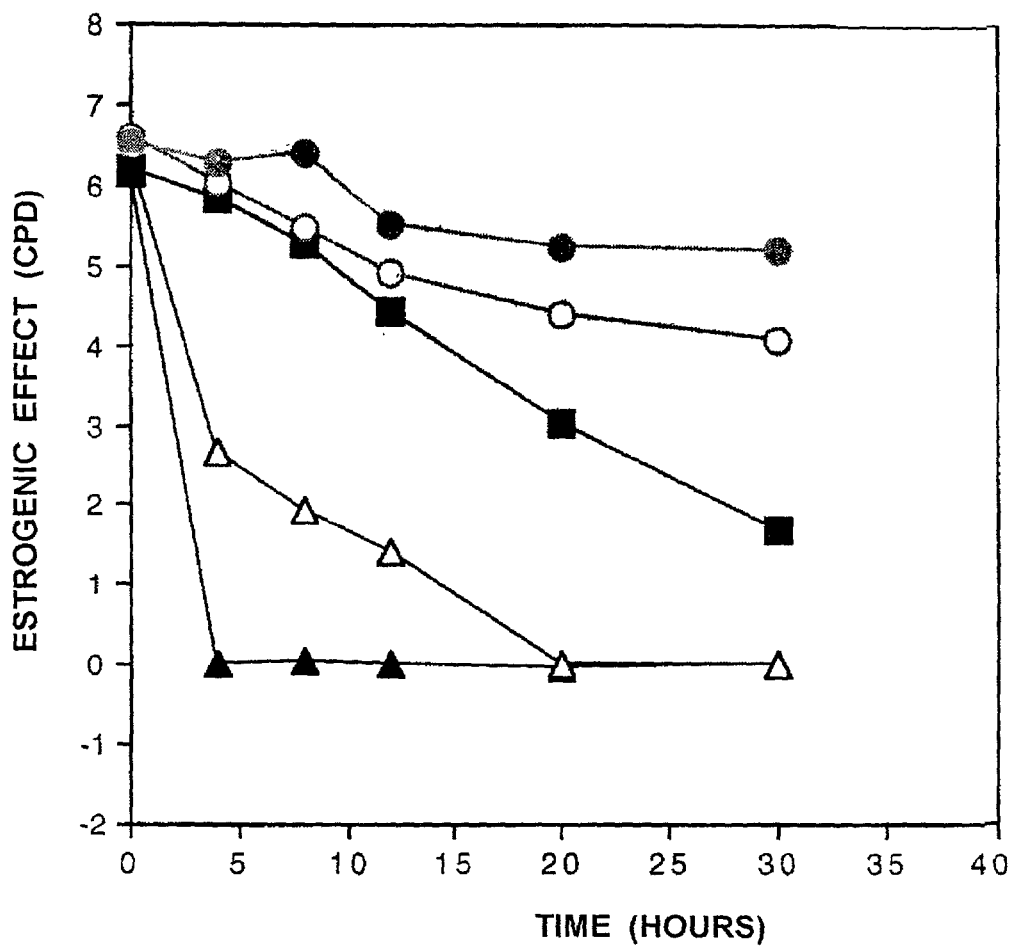
FIG. 75. Effect of Calcium on the 50° C. Heat Stability of the Estrogenic Activity in Chelex Treated CDE-horse Serum Assayed with MTW9/PL2 Cells.
Figure 78:
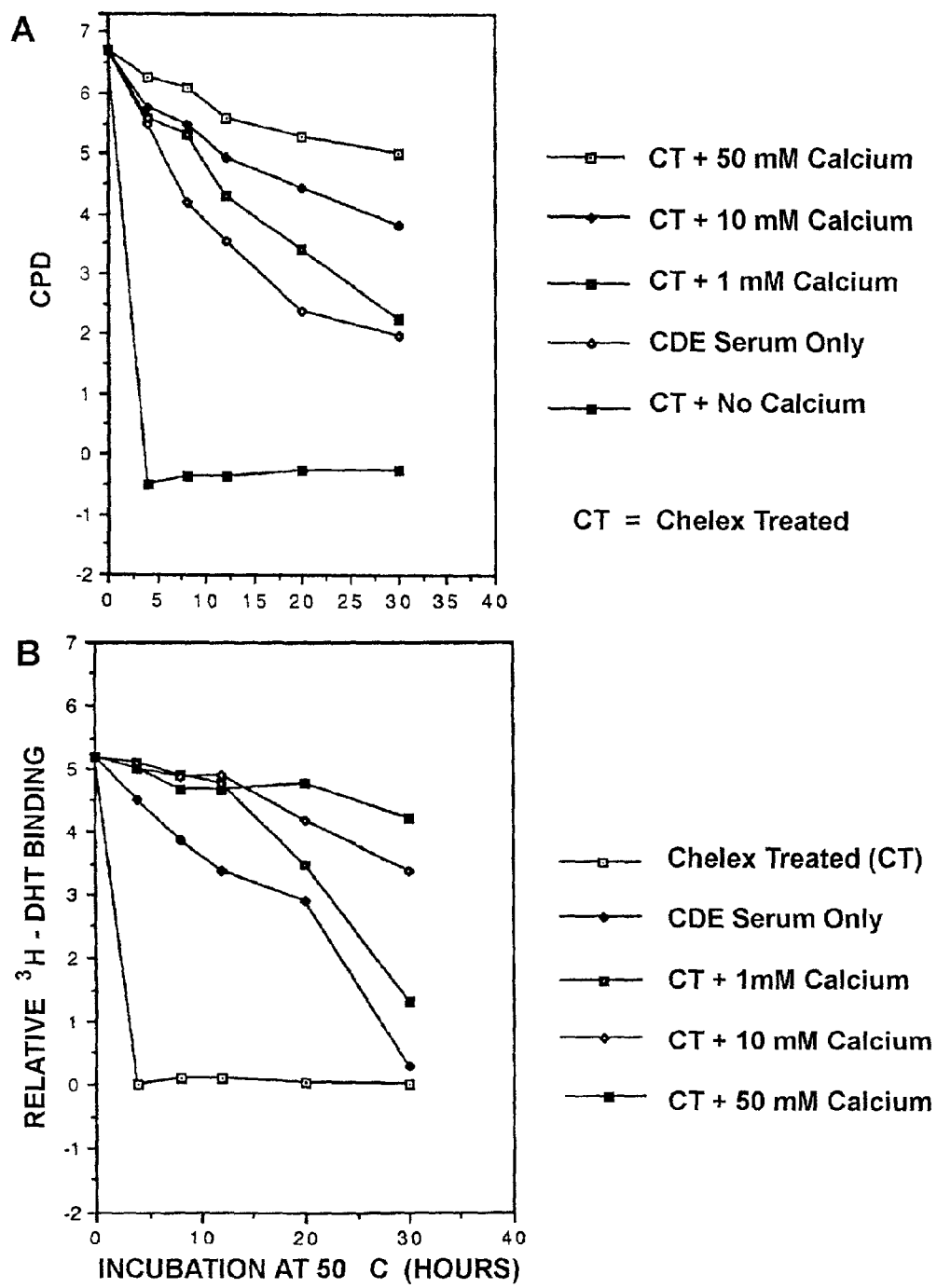
FIG. 78. Calcium Protection of both the Estrogenic Effect with MTW9/PL2 Cell and the Binding of $^3$H-DHT with Chelex Treated CDE-horse Serum. (A) Estrogenic Effect Protection by Calcium; (B) Calcium Protection of $^3$H-DHT Binding.

Correlation between Calcium Stabilization of Inhibitor Activity and Calcium Stabilization of $^3$H-DHT Binding to CDE-horse Serum. As shown in FIG. 75 with CDE-serum that had been Chelex treated, calcium protected the inhibitor activity from heat inactivation. This study was repeated with another batch of Chelex treated CDE-horse serum (FIG. 78). This study showed essentially the same results as presented in FIG. 75. However, in parallel, the Chelex treated serum was also assayed for $^3$H-DHT binding (FIG. 78B). Clearly, as the calcium concentration was increased in the serum, there was protection of $^3$H-DHT binding that paralleled the protection of the estrogenic effect shown in FIG. 78A. These results implied a relationship between the estrogen reversible inhibitor activity being sought and a sex steroid hormone binding protein.

Immunoprecipitation of the $^3$H-DHT Binding Activity and Estrogenic Activity in CDE-horse Serum. In the final studies of this series, rabbit antibodies against human SHBG (Accurate Chemicals) were assayed for immunoprecipitation of the $^3$H-DHT binding activity of CDE-horse serum. After incubation of the serum with the designated dilutions antiserum, Protein A/G-Sepharose (Pierce Kit) was added to absorb the immune complexes, and the resulting serum assayed for binding under conditions described in General Materials and Methods. The results of this study are shown in FIG. 79A. Increasing antibody decreased the steroid binding activity. In parallel, the same samples were used to assess estrogenic effects with MTW9/PL2 cells (FIG. 79B). Increasing anti-SHBG decreased the estrogenic effect by decreasing the concentration of the inhibitor in the serum. There appeared to be some type of cross-reaction, but it was still not clear that this proved SHBG-like properties for the estrogen reversible inhibitor. In both FIGS. 79A and 79B, addition of control rabbit serum had no effect.

Discussion of Example 17. The effect of calcium on both the estrogenic activity and the binding of $^3$H-DHT to CDE-serum was remarkably similar to data presented by others concerning the stability of human SHBG (Rosner W et al. (1974) *Biochim Biophys Acta* 351, 92-98). Other investigators have raised the issue of classical SHBG as the sex hormone reversible inhibitor of target cell growth. This seems highly unlikely, however, in light of the results presented above. Both CDE horse serum and CDE rat serum contain concentrations of inhibitor about equal to any of the other serum types investigated. Furthermore, it is accepted knowledge that horse and adult rat serum do not contain SHBG (Corvol P and Bardin C W (1973) *Biol Reprod* 8, 277-282; Renior J-M et al. (1980) *Proc Natl Acad Sci* USA 77, 4578-4582; Wenn R V et al. (1977) *Endokinologie* 69, 151-156). Nevertheless, anti-human SHBG purchased from Accurate Chemicals not only immunoprecipitated the activity in serum, but also the $^3$H-DHT binding activity. This data initially suggested that the inhibitor was a SHBG like activity (Sirbasku D A et al. "Serum factor regulation of estrogen responsive mammary tumor cell growth." Proceedings of the 1997 Meeting of the "Department of Defense Breast Cancer Research Program: An Era of Hope", (Abstract) pp. 739-740, Washington, D.C., Oct. 31-Nov. 4, 1997). However, there were enough physical differences to indicate that the activity was not actually SHBG and that the cross-reaction with anti-SHBG was possibly misleading.

Despite the ambiguity in its identity at that point, it was clear that the estrogen reversible inhibitor sought by herein had different properties than that described in U.S. Pat. Nos. 4,859,585 (Sonnenschein) and 5,135,849 (Soto). In those patents, the activity was not shown to cross-react with anti-human SHBG nor was it stated to share SHBG-like properties. The putative kinship to SHBG provided impetus to use a method that had already been applied to the purification of SHBG in order to identify the inhibitor. In Example 18 the purification of the estrogen reversible inhibitor activity is described, performing the first, and third through sixth isolation.

Example 18

Cortisol Affinity and Phenyl Sepharose Isolation of the "SHBG-like" Estrogen Reversible Inhibitor from CDE-Horse Serum Outcome of the Search for the Estrogen Reversible Inhibitors. As cited above, neither horse or rat serum contains SHBG. Therefore, these were the preferred sera to begin isolation. Partial purification of the inhibitor from serum has been achieved initially by a two-step procedure. The partially purified inhibitor fractions are different than the serum derived inhibitor described in U.S. Pat. No. 4,859,585 (issued to Sonnenschein and Soto), which has been more recently identified as a subtype domain of albumin. By contrast, it has been discovered that IgA and IgM, preferably in dimeric/polymeric form, are steroid hormone reversible inhibitors of cell growth.

Two-step Cortisol-agarose and Phenyl Sepharose Isolation Method. Based on the perceived SHBG-like properties described above, a new approach to the purification was taken. This method used a two-step cortisol-agarose affinity and phenyl-Sepharose chromatography protocol. It had been employed by others to simultaneously yield purified human cord serum CBG and SHBG (Femlund P and Laurell C-B (1981) *J Steroid Biochem* 14, 545-552). The method first required the synthesis of the cortisol affinity matrix. The cortisol-agarose affinity matrix was synthesized and the initial purifications done as described (Fernlund P and Larell C-B (1981) *J Steroid Biochem* 14, 545-552). An 80 mL bed volume cortisol-agarose column (2.5 cm×17.8 cm) was equilibrated with a buffer containing 0.05 M piperazine, pH 5.5, with 0.2 M NaCl. Two liters of horse serum were charcoal-dextran extracted at 34° C. as described above. For two of the six preparations used in these studies, the serum was depleted of steroid hormones by the Amberlite™ XAD-4 resin method. There was no resulting difference in the purifications. After removing a 30 mL sample for pre-column activity assay, the remaining volume was adjusted to pH 5.5 with 1.0 N HCl. This was applied to the column at a flow rate of 30 to 40 mL per hour. Throughout the purification, the flow rates were maintained with a peristaltic pump. The effluent was collected and a sample and adjusted to pH 7.2 for post-column assessment of estrogen reversible inhibitory activity. After all of the serum had been applied, the column was washed for 7 days at the same flow rate with the equilibration buffer until the $A_{280nm}$ of the effluent was<0.06 versus water.

To recover the activity, the cortisol-agarose column was eluted with a 500 mL linear gradient formed with 250 mL of the piperazine/NaCl buffer and 250 mL of the buffer with 1.0 mg/mL cortisol and 10% (v/v) methanol. After completion of the gradient, the column was washed with one volume of the cortisol/methanol buffer. A total volume of 600 mL was collected as 10 mL fractions. As reported by Femlund & Laurell (Femlund P and Laurell C-B (1981) *J Steroid Biochem* 14, 545-552), two separate $A_{280nm}$ or protein concentration ranges could be recognized, but their separation and individual chromatography on phenyl-Sepharose was no more effective than pooling the entire 600 mL gradient elution and using it for the next step. The total volume from the cortisol gradient was reduced 5 to 8-fold by nitrogen gas pressure Amicon ultrafiltration (YM-10 membrane) and applied directly to the next column without dialysis or pH adjustment.

A 28 mL bed volume phenyl-Sepharose (1.5 cm×16 cm) was equilibrated with 0.05 M Tris-HCl, pH 7.5, containing 0.5 M NaCl. The concentrated cortisol gradient volume was applied at a flow rate of 60 mL/hour (10 mL fractions). The first $A_{280nm}$ peak observed was a mixture of cortisol and CBG (Femlund P and Laurel C-B (1981) *J Steroid Biochem* 14, 545-552). These fractions were combined as cortisol affinity-phenyl Sepharose pool I (CA-PS-pool I). The column was then washed with equilibration buffer until the $A_{280nm}$ was reduced to 0.002 versus water. The next buffer applied was 0.05 M Tris-HCl, pH 7.5 (60%, v/v) containing 40% (v/v) ethylene glycol. The $A_{280nm}$ peak observed with this wash was combined to form CA-PS-pool II that corresponded to SHBG from human serum (Femlund P and Laurell C-B (1981) *J Steroid Biochem* 14, 545-552). The two pools were separately concentrated to approximately 40 mL each and dialyzed separately against storage buffer which was 0.05 M Tris-HCl, pH 7.5, containing 0.15 NaCl, 0.05 M $CaCl_2$ and 60% (v/v) glycerol. The dialysis further concentrated each sample. As last additions, 0.1 mM cortisol was added to CA-PS-pool I and 0.1 mM DHT to CS-PS-pool II. The pools were stored unfrozen at −20 C. Six replicate isolations were done. The protein yields ranged from 22.8 to 37.7 for CA-PS-pool I and 5.82 to 12.2 mg for Ca-PS-pool II. Based on an average of 60 grams of protein per two liters of CDE-horse serum (i.e. 30 mg/mL), CA-PS-pool II represented about 0.013% of the total protein in serum.

Figure 80:
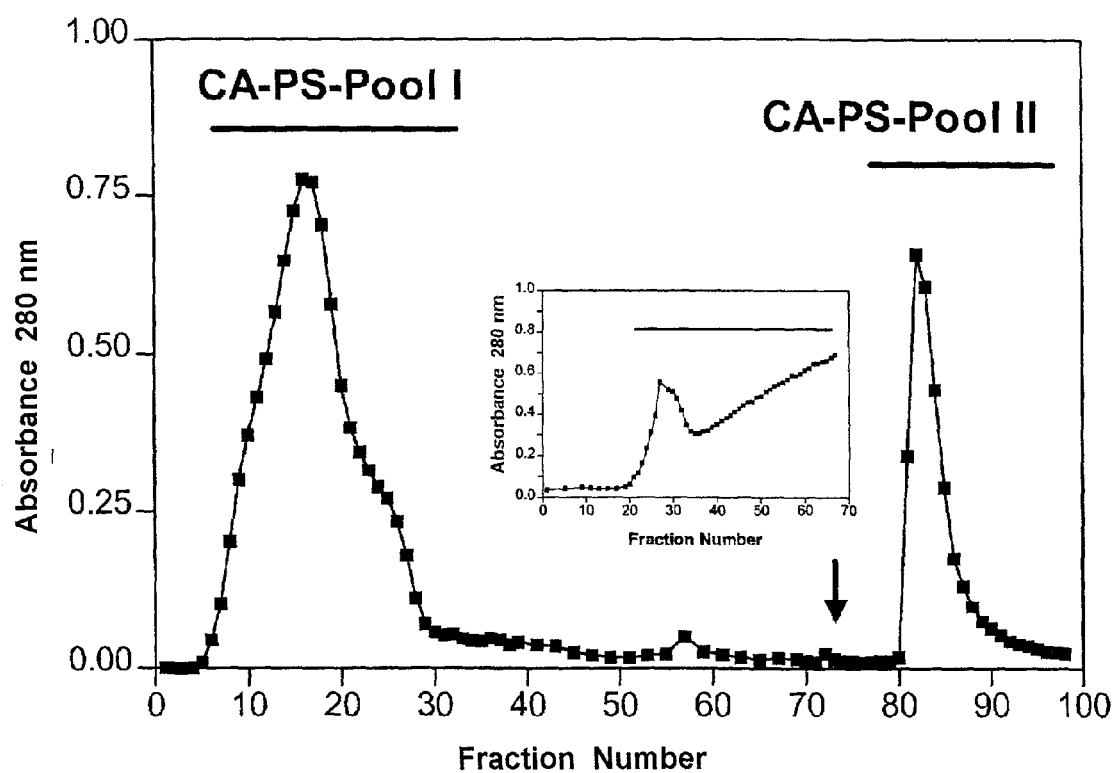
FIG. 80. Column Elution Profiles of the Two-step Cortisol Affinity and Phenyl Sepharose Elution of CA-PA-pool I and CA-PS-pool II.
Figure 81:
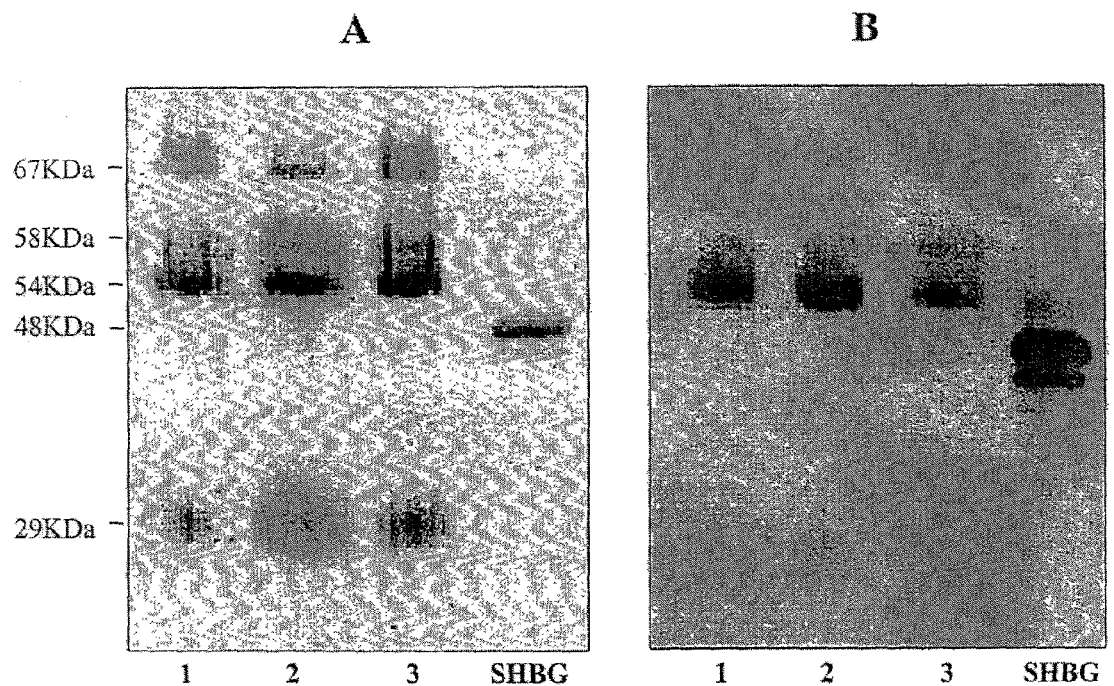
FIG. 81. Identification of the Molecular Forms Present in Active CA-PS-pool II. (A) SDS-PAGE with Coomassie Blue Staining; (B) Western Analysis with Anti-human SHBG.

Cortisol affinity and phenyl Sepharose Isolation Results and SDS-PAGE Molecular Weight Estimation. The chromatography profiles from the two-step cortisol affinity and phenyl Sepharose isolation of the inhibitor(s) activity from CDE-horse serum are shown in FIG. 80. The elution from phenyl Sepharose gave the CA-PS-pools I and II. CA-PS-pool I contained predominantly 58 kDa CBG (Rosner W and Bradlow HL (1971) *J Clin Endocrinol Metab* 33, 193-198) as confirmed by SDS-PAGE and Western immunoblotting with rabbit anti-horse CBG as well as by partial $N^\alpha$ amino acid sequencing of the first 10 to 20 residues (results not presented). SDS-PAGE analyses of three example preparations of CA-PS-pool II are shown in FIG. 81A. Components of 67, 58, 54, and 29 kDa were identified. These were compared to the 48 and 46 kDa units identified for purified human SHBG (Khan M S et al. (1985) *Steroids* 45, 463-472) (FIG. 81A).

Native Molecular Weight Estimation. Analyzes done under non-reducing and non-denaturing conditions using Superdex molecular sieve FPLC at neutral pH in buffers identified components CA-PS-pool I in the exclusion volume at≧900 kDa, and components approximately 350 and 168 kDa (Sirbasku D A et al. "Serum factor regulation of estrogen responsive mammary tumor cell growth." Proceedings of the 1997 Meeting of the "Department of Defense Breast Cancer Research Program: An Era of Hope", (Abstract) pp. 739-740, Washington, D.C., Oct. 31-Nov. 4, 1997). Comparison of the results from denaturing and non-denaturing conditions confirmed that the CA-PS-pool II was still heterogeneous and that the activity was most likely a subunit containing high molecular weight protein(s).

Removal of Storage Solution Components before Bioassay. Before conducting bioassays of the inhibitory activity in the phenyl-Sepharose pools, the glycerol and steroid hormones in the storage buffers were removed. If DHT is not removed completely from CA-PS-pool II, the inhibitory activity was substantially diminished or eliminated entirely. Samples (0.5 to 15 mL) were introduced into Slide-A-Lyzer® (Pierce) cassettes of molecular weight cutoff 10,000. The cassettes were incubate twice with stirring in two liters of Tris-HCl, pH 7.4, containing 10 mM $CaCl_2$ for four hours at 34° C. to remove excess free steroids and glycerol. Next, the cassettes were transferred to the same buffer containing 20% (v/v) of a charcoal-dextran mixture prepared as described above. After 18 hours at 37° C., the cassettes were transferred to another two-liter volume of the same buffer containing 10% (v/v) of the charcoal-dextran mixture and dialysis continued with stirring for another 6 to 8 hours. Finally, the cassettes were rinsed lightly with water and the dialyzed material recovered according to manufacturers instructions. The contents were sterilized by 0.2-μm-pore membrane filtration and stored at 4° C. These preparations were usually used within a few weeks.

Assay of CA-PS-pool I Estrogen Reversible Inhibitory Activity with MTW9/PL2 Cells. When assayed with MTW9/PL2 cells, CA-PS-pool I contained 20 to 25% of the units of estrogen reversible inhibitory activity recovered from the phenyl Sepharose column (data not shown). With two preparations not presented, the cortisol gradient pool shown in FIG. 80 was made 1.5 M NaCl before application to the phenyl Sepharose column equilibrated at the same higher salt concentration. Under these conditions, the CA-PS-pool I contained >90% CBG, as estimated by SDS-PAGE, but showed either no estrogen reversible activity or only traces (results not presented). Irrespective of the ionic strength or pH of the cortisol affinity pool applied to phenyl Sepharose, ethylene glycol was required to elute the majority of the activity.

Figure 82:
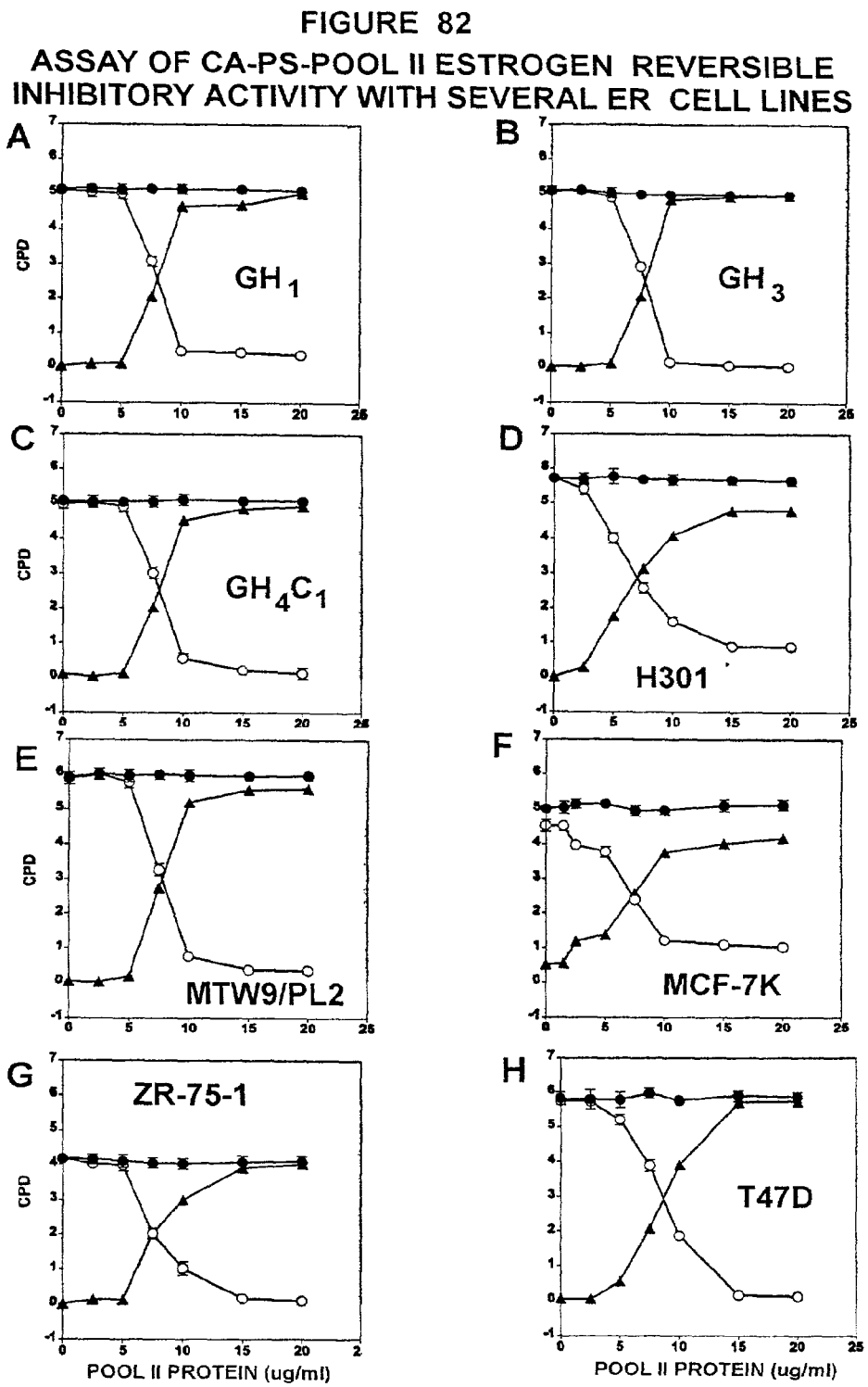
FIG. 82. CA-PS-pool II Effect on ER$^+$) Cell Growth in 2.5% CDE-horse Serum±E$_2$. (A) GH$_1$ Cells; (B) GH$_3$ Cells; (C) GH$_4$C$_1$ Cells; (D) H301 Cells; (E) MTW9/PL2 Cells; (F) MCF-7K Cells; (G) ZR-75-1 Cells; (H) T47D Cells.

Assay of CA-PS-pool II Estrogen Reversible Inhibitory Activity with Several ER$^+$ Cell Lines. Despite method variations with phenyl Sepharose, CA-PS-pool II always contained ≧75% of the activity recovered. In a crucial test of significance, CA-PS-pool II was assayed to determine if it replaced the effects of CDE-serum with eight different ER$^+$ cell lines. The results are shown in FIG. 82. The estrogen reversible inhibitory effects of CA-PS-pool II were investigated with five rodent tumor cell lines derived from three different estrogen target tissue tumors, and three separate estrogen sensitive human breast cancer cell lines. The cells were added to medium with 2.5% (v/v) CDE-horse serum plus increasing concentrations of CA-PS-pool II ±10 nM $E_2$. The first lines evaluated were the $GH_1$, $GH_3$, and $GH_4C_1$ rat pituitary tumor cells (FIGS. 82A, 82B and 82C, respectively). They were chosen first because these lines are well known for hormone regulation of differentiated tissue specific functions in culture and exceptional sensitivity to a variety of hormones including estrogens (Tashjian A H Jr (1979) *Methods Enzymol* 58, 527-535; Haug E and Gautvik K M (1976) *Endocrinology* 99, 1482-1489; Haug E (1979) *Endocrinology* 104, 429-437; Amara J F and Dannies P S (1983) *Endocrinology* 112, 1141-1143). At 10 μg/mL, CA-PS-pool II was fully inhibitory with all three GH lines. Growth was reduced to near seed density levels (i.e.<0.5 CPD). By this measure,>1,700-fold increase in potency had been achieved versus full CDE-serum. The $ED_{50}$ with the GH cells was 6 to 8 μg/mL which was a 300 to 800-fold specific activity increase compared to full serum. $E_2$ reversed the effects of the CA-PS-pool II at every inhibitory concentration. CA-PS-pool II replaced the effects of full CDE-serum with these cells. FIGS. 82D and 82E show similar experiments with the estrogen sensitive H301 hamster kidney tumor cells and the MTW9/PL2 rat mammary cells, respectively. CA-PS-pool II was most inhibitory at 15 μg/mL with both lines. The $ED_{50}$ were in the range of 5 to 10 μg/mL. As with the GH lines, $E_2$ completely reversed the effects of the inhibitor. Again, CA-PS-pool II replaced the effects of full CDE-serum with these cells. With human breast cancer cell lines MCF-7K, ZR-75-1 and T47D, the results were similar (FIGS. 82F, 82G, and 82H, respectively). Addition of 10 to 15 μg/mL of CA-PS-pool II caused maximum inhibition. The $ED_{50}$ concentrations were 6 to 9 μg/mL. As with ER$^+$ rodent cell lines, $E_2$ completely reversed the inhibition caused by CA-PS-pool II. Again, CA-PS-pool II replaced the effects of full CDE-serum with these cells.

Figure 83:
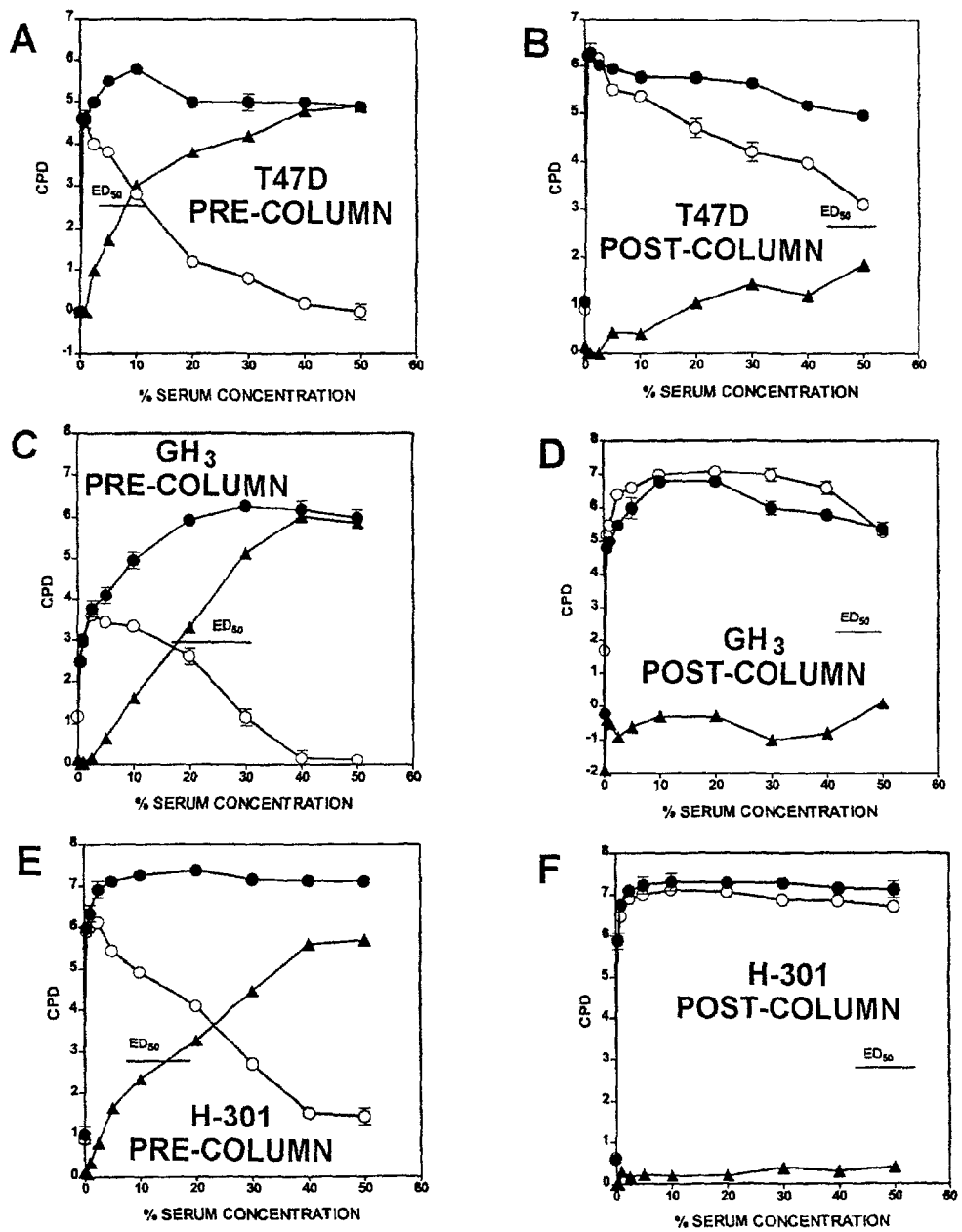
FIG. 83. Cortisol Affinity Column Depletion of the Estrogenic Activity in CDE-horse Serum Assayed with ER$^+$ Cell Lines±E$_2$. (A) T47D Cells Pre-Column; (B) T47D Cells Post-Column; (C) GH$_3$ Cells Pre-Column; (D) GH$_3$ Cells Pre-Column; (E) H301 Cells Pre-Column; (F) H301 Cells Post-Column.

Cortisol-agarose Affinity Removal of the Inhibitor from CDE-serum. Next it was determined if the cortisol affinity chromatography had not removed the majority of the activity from serum. To test this, three cell lines were analyzed with pre-and post cortisol column samples. FIGS. 83A and 83B show the effect of a single column passage on the inhibitory activity for T47D human breast cells. The $ED_{50}$ of the pre-column CDE-serum was 7% (v/v). Post column, even 50% (v/v) serum did not achieve $ED_{50}$. FIGS. 83C and 83D show the same studies with the $GH_3$ rat pituitary cells. In this case, a single column passage completely depleted the activity. Complete depletion was also observed with the H-301 hamster kidney cell line (FIGS. 83E and 83F).

Storage Conditions and SHBG Related Properties. At completion of the two-step isolation, the pools were stored in the presence of sufficient glycerol to prevent freezing at −20° C. In experiments not shown, the estrogen reversible inhibitor was progressively less stable without addition of glycerol, calcium and/or steroid hormone. Dialysis against buffers without calcium is most definitely to be avoided. Freeze/thaw is very harmful, even with calcium and DHT present. Assays of −20° C. glycerol stored CA-PS-pool II over a two year period indicated no decay in activity. Clearly, the storage conditions known to stabilize functional SHBG (Femlund P and Laurell C-B (1981) *J Steroid Biochem* 14, 545-552; Rosner W et al. (1974) *Biochim Biophys Acta* 351, 92-98) also favored retention of estrogen reversible inhibitor activity in CA-PS-pool II.

Labeled Steroid Hormone Binding to CA-PS-pool I. CA-PS-pool I was determined to contain CBG by criteria cited above. Additionally, this pool was examined by Scatchard analysis for binding of tritium labeled steroid hormones. The results are summarized in TABLE 9. The association constants ($K_a$) of the ilabeled hormones showed the order cortisol>progesterone>>>sex steroid hormones. The $K_a$ of cortisol binding at 34° C. was $1.41 \times 10^9$ M$^{-1}$ that was equal to that of native rat CBG when analyzed at 4° C. (Rosner W (1990) *Endocr Rev* 11, 80-91). However, it was higher than the $K_a$ of $5.2 \times 10^7$ M$^{-1}$ for human CBG measured at 23° C. (Rosner W and Bradlow H L (1971) *J Clin Endocrinol Metab* 33, 193-198). The binding characteristics of steroids to CBG from several species have been studied (Rosner W (1972) *J Steroid Biochem* 3, 531-542). The similarity of the results further supports the conclusion that CA-PS-pool I contains predominantly CBG.

Labeled Steroid Hormone Binding to CA-PS-pool II. The estrogen reversible inhibitor activity in CDE-serum correlated with the binding of tritium labeled sex steroid hormones. This suggested a relationship between the estrogen reversible inhibitor and SHBG. However, the $K_a$ for $^3$H-DHT binding to CDE-serum at 34° C. was $3.90 \times 10^7$ M$^{-1}$. However, it is important to note that this was at least 20 times lower than that of purified human SHBG at $0.99 \times 10^9$ M$^{-1}$ for DHT or $2.2 \times 10^8$ M$^{-1}$ for $E_2$ at 37° C. (Rosner W and Smith R N (1975) *Biochemistry* 14, 4813-4820). To determine if CA-PS-pool II possessed the same sex hormone binding properties as whole CDE-serum, and/or human SHBG, the next study was conducted. Scatchard analysis of $^3$H-DHT binding to CA-PS-pool II was done at 34° C. The estimated $K_a$ was $5.88 \times 10^7$ M$^{-1}$. Replicates (N=3) gave a $K_a$ range $4.5 \times 10^7$ M$^{-1}$. Computer analysis indicated a single class of binding sites although correlation coefficients were approximately 0.7. Similar analyses were done with $^3$H-$E_2$, $^3$H-progesterone and $^3$H-cortisol. The results with all four labeled steroids are summarized in TABLE 9. The $K_a$ order was DHT>$E_2$>>>cortisol>progesterone. The $K_a$ for sex steroid hormone binding to the CA-PS-pool II was similar to whole CDE-serum but 20 to 50-fold lower than human SHBG.

TABLE 9

Summary of the Scatchard Analysis of phenyl-Sepharose pools I and II with four labeled steroid hormones

| Steroid Hormone | CA-PS-Pool I | | CA-PS-Pool II | |
|---|---|---|---|---|
| (3H-labeled) | $K_d(M)$ | $K_a(M^{-1})$ | $K_d(M)$ | $K_a(M^{-1})$ |
| Cortisol | $7.10 \times 10^{-10}$ | $1.41 \times 10^9$ | $1.89 \times 10^{-6}$ | $5.30 \times 10^5$ |
| Progesterone | $1.70 \times 10^{-9}$ | $5.90 \times 10^8$ | $7.89 \times 10^{-6}$ | $1.17 \times 10^5$ |
| 17β-estradiol | $1.05 \times 10^{-5}$ | $9.51 \times 10^4$ | $2.83 \times 10^{-8}$ | $3.55 \times 10^7$ |
| Dihydrotestosterone | $6.05 \times 10^{-6}$ | $1.64 \times 10^5$ | $1.43 \times 10^{-8}$ | $6.99 \times 10^7$ |

Western Immunoblotting with anti-human SHBG. The above shows that the estrogen reversible inhibitor shared immunological properties with human SHBG. To investigate further, Western immunoblotting of CA-PS-pool II was done with anti-human SHBG. The results are presented in FIG. 81B. Western analysis with the anti-SHBG recognized the same four components seen with Coomassie Blue staining in FIG. 81A. These same four components have also been identified with whole CDE-serum using Western analysis with anti-human SHBG (data not shown). In Western immunoblotting studies not presented, anti-human SHBG did not identify horse serum albumin. This confirmed that the 67 kDa Coomassie Blue stained component present in the CA-PS-pool II was not 68 kDa horse serum albumin. These results provided additional support for the conclusion that albumin is not the estrogen reversible inhibitor activity of serum. These results also very clearly demonstrated that the SHBG used to raise antibodies in rabbit had not been purified to homogeneity, but rather had been used at a more crude state. (It was also confirmed by the manufacturer of the anti-SHBG antibody that the SHBG fraction used for antibody production was not highly purified and had not been size fractionated.)

Discussion of Example 18. There has been one very critical problem with the estrocolyone hypothesis. Estrocolyone has never been purified and shown to act as described (Soto A M and Sonnenschein C (1987) Endocr Rev 8, 44-52). The active pool isolated from the two-step procedure (i.e. CA-PS-pool II) certainly does not bind steroid hormones with sufficient affinity to act as estrocolyones (TABLE 9). Growth is activated at picomolar concentrations while the affinity ($K_d$) of $E_2$ with CA-Pool II is about $10^{-8}$ M. This discrepancy is simply far too large to accept the role of estrogens in growth as binding the inhibitor and thereby preventing its action on target cells (Soto A M and Sonnenschein C (1987) Endocr Rev 8, 44-52). The fact that proteins in CA-PS-pool II bind steroids is not germane to the mechanism of action of these hormones in growth regulation under physiological conditions.

The results of steroid hormone binding may however be germane to the use of high dose treatments of breast cancer. Care must be taken when considering that high doses of estrogen, androgen, progesterone and cortisol all have the potential for binding the active agent in CA-PS-pool II and therefore may reduce the effective concentration of inhibitor. The assays described in this Example can be applied to biological fluids and plasma to determine if steroid concentrations are excessive and to evaluate proper levels with changes in treatment regimes.

The results presented herein indicate that the proposed new model of cell growth is a favored mechanism. Steroid hormones appear to act as positive agents via internal high affinity receptors (e.g. ERγ) whereas serum-borne inhibitors act at the surface to block growth. The combination of the two signals dictates cell proliferation rates. This data further supports the assertion that the ERγ can be used for diagnostic purposes in ER+ cancers in the same way that conventional ER receptor screening is now performed.

A highly enriched fraction of serum protein was prepared whose estrogen reversible inhibitory activity is stable and whose effects replicate those seen with full serum with a variety of sex steroid hormone target tumor cell types in culture. Because early studies mistakenly indicated that the inhibitor shared various properties with SHBG, a two-step cortisol-agarose affinity and phenyl-Sepharose chromatography protocol was applied. A highly enriched "SHBG-like" preparation was obtained. At 10 to 15 μg/mL, it replicated the $E_2$ reversible inhibition caused by 30 to 50% (v/v) serum with steroid responsive human breast cancer cells, and responsive rat mammary, rat pituitary and Syrian hamster kidney tumor cells in culture. The inhibitor retained full activity for more than one year when stored unfrozen at −20° C. in the presence of calcium, dihydrotestosterone and glycerol. This study demonstrated that the longstanding problem of inhibitor stability has been overcome and that a high specific activity preparation was now available to further probe molecular identity. These results clearly differentiate this inhibitor preparation from any previously described type of estrogen reversible inhibitor (i.e. estrocolyone). Moreover, no previous inhibitor composition, at a concentration≦15 μg/mL, can supplant the effects of full serum to give estrogenic effects≦3 CPD with several ER+ cell lines from different tissues and different species.

The most active inhibitor preparation obtained in this study appeared to have multiple components present. The separation and identification of these components, as discussed in Example 20, would yield additional assays and preferred reagents and methodologies for testing new hormone-like and anti-hormone like substances. The active serum-derived inhibitor fraction can be used directly in tests of new compounds, substances, mixtures and preparations from natural and synthetic sources to estimate both estrogenic and androgenic activity in culture. Large-scale preparation of this purified serum fraction is possible by using larger affinity columns and proportionately increased serum volumes, similar to existing technology employed for purifying other biological products. It is advantageous that only small quantities of the purified serum fraction are needed for cell growth assays.

Example 19

Serum-free Assay Systems for Measuring Large Magnitude Steroid Hormone Mitogenic Responses with the Two-Step Purified Inhibitor The above-described studies with several different sex steroid sensitive cell lines demonstrated that the effects of a partially purified estrogen reversible inhibitor could readily be assayed in the presence of a low concentration (i.e. 2.5%) of CDE-serum. The next step was to eliminate the serum completely and to show estrogen responsiveness under far more defined conditions.

Figure 84:
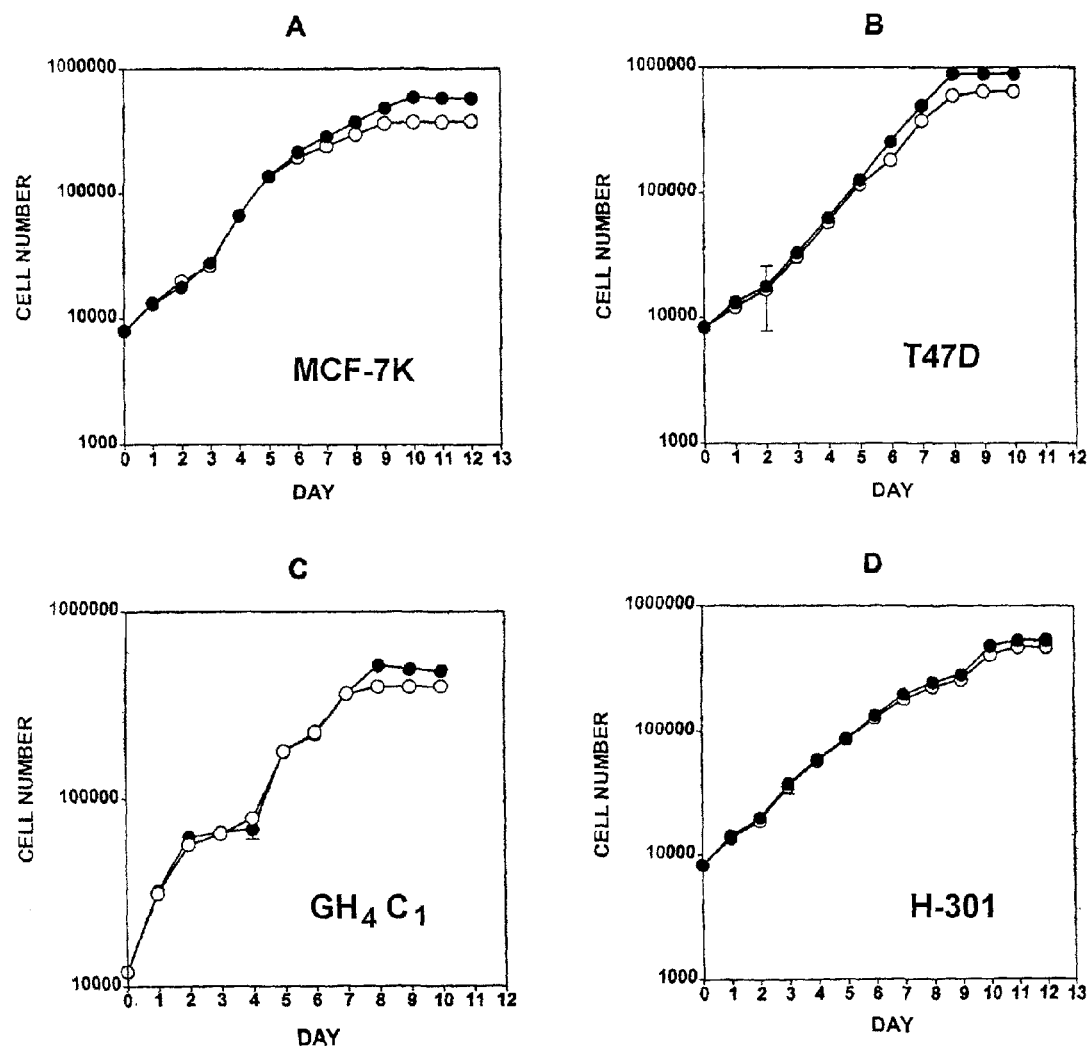
FIG. 84. Serum-free Growth of Cells in Four Different Defined Media±E$_2$. (A) MTW9/PL2 Cells in DDM-2A; (B) T47D Cells in DDM-2MF; (C) GH$_4$C$_1$ Cells in PCM-9; (D) H301 Cells in CAPM.

Second Analysis of Serum-free Growth±$E_2$. Experiments were conducted using completely serum-free medium, and the magnitude of the estrogenic effects observed in defined medium was again compared to those seen in medium containing CDE-serum. ER+ tumor cell growth was measured first in serum-free defined culture±10 nM $E_2$. Similar experiments have been reported in FIGS. 56 and 57. The reassays are included because the first experiments were done two years earlier. The results show the stability of the cell lines used and the fact that serum-free defined medium is highly reproducible. More recent results are shown with the MCF-7K human breast cancer cells (FIG. 84A), the T47D human breast cancer cells (FIG. 84B), the $GH_4C_1$ rat pituitary tumor cells (FIG. 84C), and the H301 Syrian hamster kidney tumor cells (FIG. 84D). All four-cell lines grew logarithmically for several days in defined and reached densities of 0.5 to $1.0 \times 10^6$ cells per 35-mm dish. The media formulations were based on standard D-MEM/F-12 as described in TABLE 7. Growth rates were optimized to 70% or more of D-MEM/F-12 containing 10% (v/v) fetal bovine serum. The results presented in FIG. 84 show little or no $E_2$ effect on growth in defined medium. Barnes and Sato (Barnes D and Sato G (1980) *Nature* (Lond) 281, 388-389) have reported similar negative results with another strain of MCF-7 cells in a different formulation of defined medium. Considering the variety of cell types assayed herein, the present results and the results of others, the lack of estrogenic effects in serum-free defined medium is not related to chemical composition of any one medium nor is there a major problem with time dependent variation of cell line properties.

Figure 85:
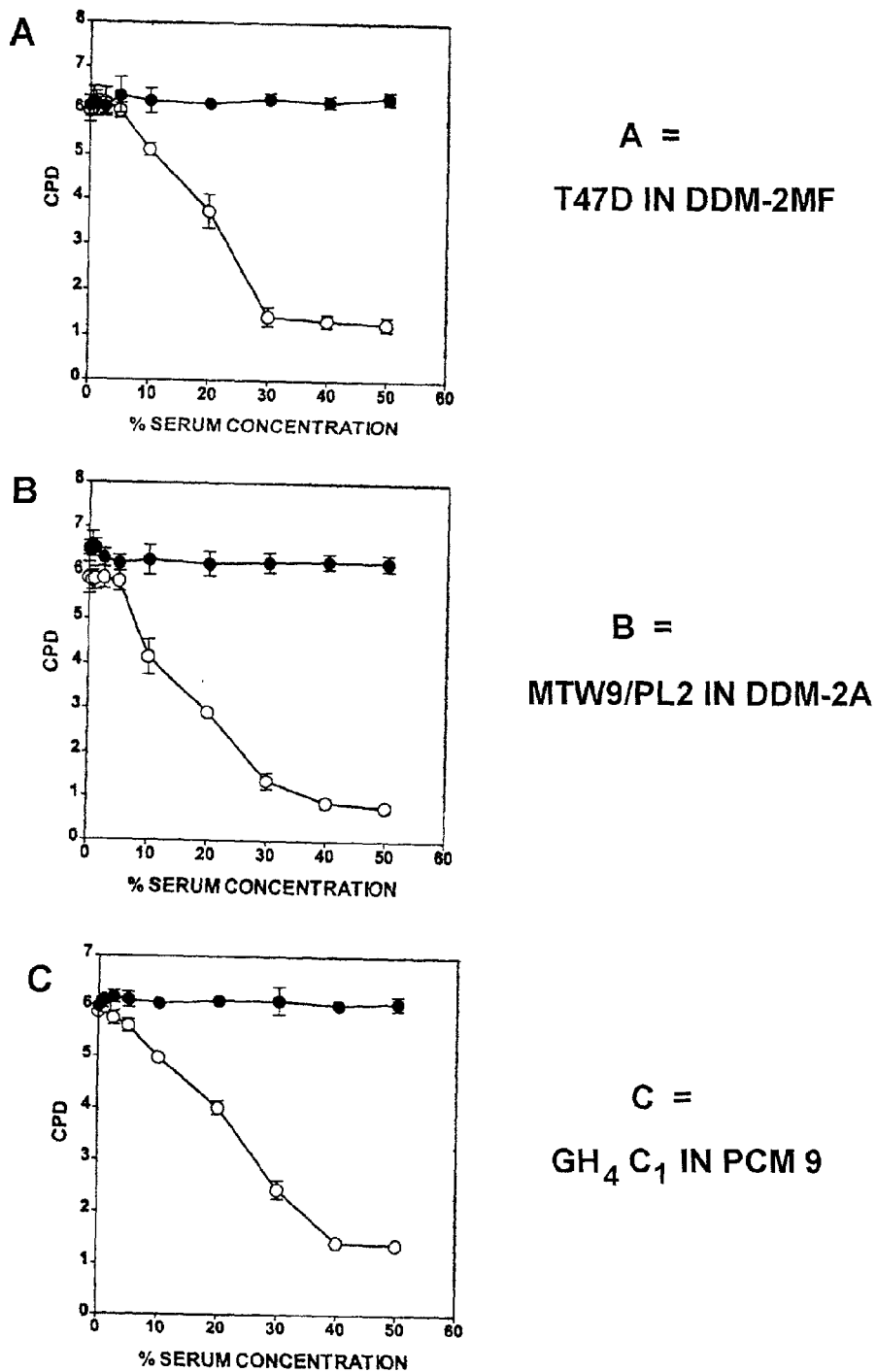
FIG. 85. Effects of CDE-horse Serum on Estrogen Responsiveness of Three ER$^+$ Cell Lines Growing in Serum-free Defined Media. (A) T47D Cells in DDM-2MF; (B) MTW9/PL2 Cells in DDM-2A; (C) GH$_4$C$_1$ Cells in PCM-9.

Effects of CDE-Serum on ER+ Cells in Different Formulations of Serum-free Defined Medium. The experiments in FIG. 85 were done to show that serum could be added to different formulations of defined medium and still cause estrogen reversible inhibition. Effects are shown with CDE-horse serum±10 nM $E_2$ and T47D cells DDM-2MF (FIG. 85A), MTW9/PL2 cells in DDM-2A (FIG. 85B) and $GH_4C_1$ cells in PCM-9 (FIG. 85C). Definitely, the serum-borne inhibitor(s) was fully effective in three different formulations of defined medium and with three different estrogen target tissue cell types.

Figure 86:
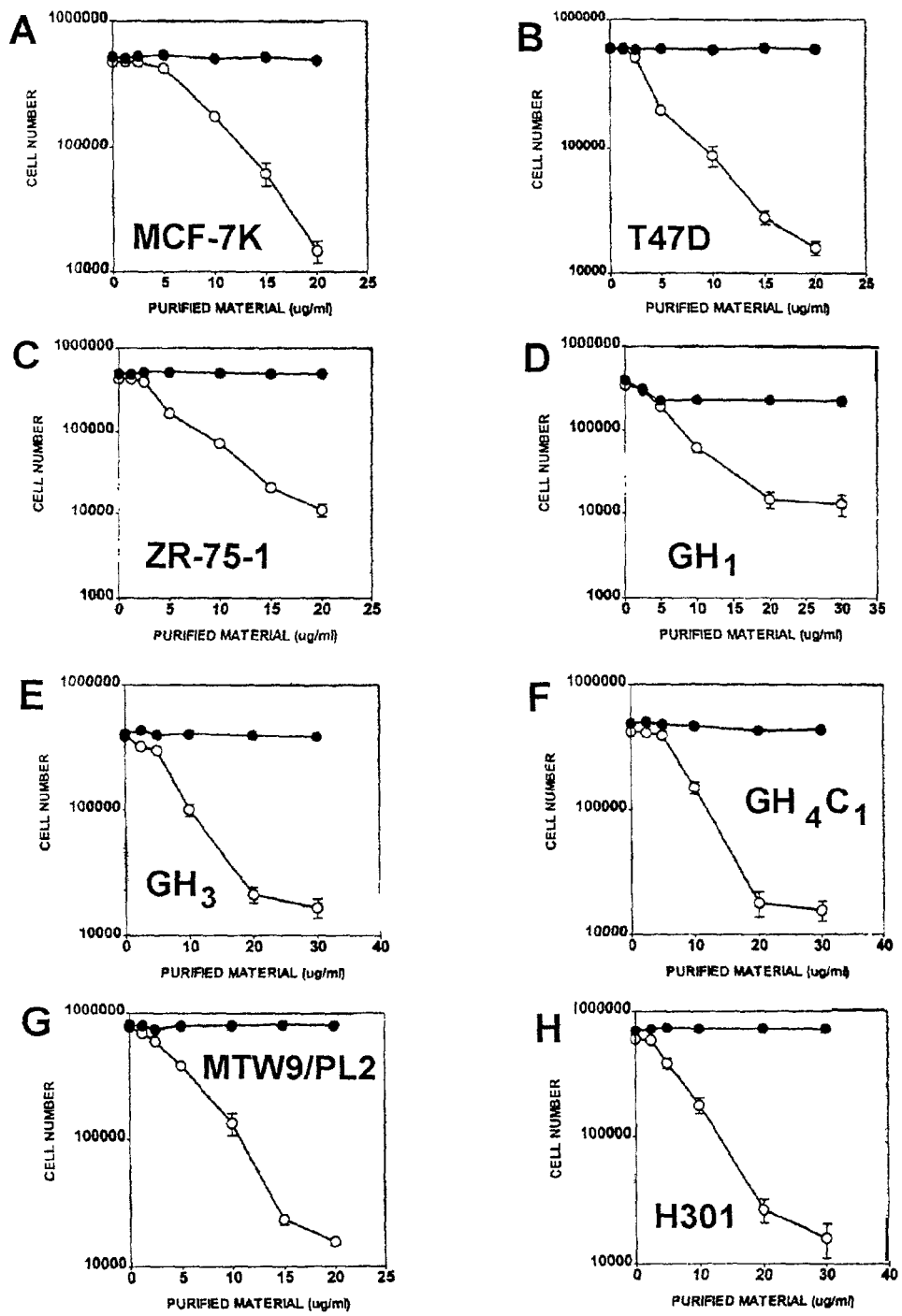
FIG. 86. Effects of CA-PS-pool II on the Growth of Eight ER$^+$ Cell Lines in Serum-free Defined Medium±E$_2$.

Effects of CA-PS-pool II on ER+ Cell Growth in Serum-free Defined Medium. The estrogen reversible inhibitory effects of CA-PS-pool II were examined with eight ER+ cell lines growing in different serum-free defined media (FIG. 86). The cell lines were the MCF-7K cells (FIG. 86A), the T47D cells (FIG. 86B), the ZR-75-1 human breast cancer cells (ATCC# CRL-1500) (FIG. 86C), the $GH_1$ (ATCC# CCL-82) (FIG. 86D), $GH_3$ (ATCC# CCL-82.1) (FIG. 86E), and $GH_4C_1$, (FIG. 86F) rat pituitary tumor cells, the MTW9/PL2 rat mammary tumor cells (FIG. 86G), and the H301 Syrian hamster kidney tumor cells (FIG. 86H). At 20 to 30 µg/mL, this fraction completely inhibited growth. The inhibition was totally reversed by 10 nM $E_2$. The $E_2$ effects on cell number were in the range from 33 to 72-fold (i.e. CPD $=2^{5.04}$ to $2^{6.18}$). The activity was not replaced by serum albumin at 5 mg/mL (data not shown). The estrogen mitogenic effects seen in defined medium containing only a few µg/mL of protein were equal to or greater than those seen in medium containing 30 to 50% (v/v) CDE-horse serum with every ER+ cell line tested (TABLE 10). Plainly, the serum-free conditions established herein are the most defined model assay systems yet established to demonstrate estrogen responsiveness in vitro.

TABLE 10

Summary of the Maximum Estrogenic Effects in D-MEM/F-12 plus CDE-horse Serum ± 10 nM E2 versus those in Serum-free Defined Medium Supplemented with CA-PS-pool II

| CELL LINES | MAXIMUM ESTROGENIC EFFECTS IN CDE-SERUM | MAXIMUM ESTROGENIC EFFECTS IN SERUM-FREE MEDIUM PLUS CA-PS-POOL II |
|---|---|---|
| MCF-7K | 3.40 CPD ($2^{3.40}$ = 10.5-fold) | 5.84 CPD ($2^{5.84}$ = 57.3-fold) |
| T47D | 5.38 CPD ($2^{5.38}$ = 41.6-fold) | 5.88 CPD ($2^{5.88}$ = 58.9-fold) |
| ZR-75-1 | 3.84 CPD ($2^{3.84}$ = 14.3-fold) | 5.21 CPD ($2^{5.21}$ = 37.0-fold) |
| $GH_1$ | 4.71 CPD ($2^{4.71}$ = 26.2-fold) | 5.04 CPD ($2^{5.04}$ = 32.9-fold) |
| $GH_3$ | 4.78 CPD ($2^{4.78}$ = 27.4-fold) | 5.04 CPD ($2^{5.04}$ = 32.9-fold) |
| $GH_4C_1$ | 4.82 CPD ($2^{4.82}$ = 28.2-fold) | 5.11 CPD ($2^{5.11}$ = 34.5-fold) |
| MTW9/PL2 | 6.22 CPD ($2^{6.22}$ = 74.5-fold) | 6.18 CPD ($2^{6.18}$ = 72.5-fold) |
| H-301 | 4.33 CPD ($2^{4.33}$ = 20.1-fold) | 6.01 CPD ($2^{6.01}$ = 64.4-fold) |

CPD ($2^{CPD}$ = Fold Cell Number Increases Above Controls Without Estrogen)

Discussion of Example 19. The studies presented in FIG. 86 and Table 10 summarized unequivocally, and for the very first time, that large magnitude estrogen mitogenic responses can be observed in completely serum-free defined media containing 2 mg/mL total protein. Furthermore, the responses shown in FIG. 86 either equal or exceed others previously observed in partially serum-free media with ZR-75-1 human breast cancer cells (Allegra J C and Lippman M E (1978) *Cancer Res* 38, 3823-3829; Darbe P D et al. (1984) *Cancer Res* 44, 2790-2793) or with a variety of other estrogen sensitive (ER+) human and rodent cell lines in medium with hormone depleted or deficient serum (Amara J F and Dannies P S (1983) *Endocrinology* 112, 1141-1143; Natoli C et al. (1983) *Breast Cancer Res Treat* 3, 23-32; Soto A M et al. (1986) *Cancer Res* 46, 2271-2275; Wiese T E et al. (1992) *In Vitro Cell Dev Biol* 28A, 595-602).

These results have a number of important implications. First, they support the aspect of the estrocolyone hypothesis (Soto A M and Sonnenschein C (1987) *Endocr Rev* 8, 44-52) that relates to the presence in serum of a meaningful inhibitor(s). Also, there is no doubt that the inhibitor(s) is completely estrogen reversible. However, the present experiments do not confirm that the steroid hormones interact with sufficient affinity with the inhibitor to support that aspect of the estrocolyone hypothesis. The results in TABLE 9 indicate that this aspect of the estrocolyone hypothesis is highly unlikely.

The estrogen reversibility of the inhibitor with every target cell type studied under the rigorous conditions of serum-free defined culture suggests physiologic relevance. The large magnitude of the effects is a strong statement in favor of significance. This is especially clear when considering the fact that the first experiments with 30 to 50% (v/v) serum contained 15 to 25 mg/mL of protein, whereas the later tests using serum-free medium required only 20 µg/mL of isolated protein.

The active fraction isolated from horse serum represented only 0.01 to 0.04% (w/w) of the total protein. Nonetheless, it effectively regulated eight ER+ cell lines derived from three species and three different target tissues. These observations are evidence that a broadly applicable serum fraction has been identified. Furthermore, the serum-free medium results suggest that a common agent(s) may coordinately regulate estrogen responsive tissue growth in vivo and that the concept of estrogen reversible negative control may be far-reaching. The results support the conclusion that in vitro studies can be used to identify important new aspects of in vivo endocrine physiology.

The results in defined medium have practical applications. Cells in serum-free medium grow in response to nutrients, growth factors, metal delivery proteins, adhesion proteins, and various classes of hormones. All of these components are mitogenic in the sense that they contribute to cell replication. Nonetheless, the addition of only 20 µg/mL of inhibitor to block growth completely bears directly on the question of the progression of normal steroid target cells to fully hormone autonomous cancers.

The inhibitor preparation used herein has the properties of a family of tissue regulators first named "chalones". These proposed cell regulators are water-soluble and tissue specific (but not species specific) proliferation inhibitors that are reversible by physiologic stimuli including hormones (Bullough W S (1975) Life Sci 16, 323-330; Finkler N and Acker P (1978) Mt Sinai J Med 45, 258-264). The studies presented here support this classic concept as it applies to sex steroid hormone target tissues. As further demonstrated in subsequent Examples, the molecular identification of the serum inhibitor(s) promises not only to further support the role of estrogens as "necessary", but also to establish that "chalone-like" entities likely are the missing "sufficient" components that account for estrogen regulation of tissue growth. The application of serum-free defined medium conditions along with the use of a high specific activity fraction to demonstrate estrogen responsiveness in culture is unique.

Example 20

Chemical and Immunological Properties of the Partially Purified CA-PS-Pool II Inhibitors and Identification as IgA and IgM This Example describes chemical and physical confirmation that the sought-after serum-borne cancer cell growth inhibitor(s) include at least IgA and IgM.

Proteinase and Chemical Fragmentation followed by HPLC and Amino Acid Sequencing. Although it was clear from SDS-PAGE (FIG. 81A) that the CA-PS-pool II preparation was not homogeneous, chemical fragmentation with cyanogen bromide and proteolytic enzymes was used for protein/peptide sequencing in an attempt to identify at least some of the proteins present, employing standard techniques (Work T S and Burton R H, eds (1981) Laboratory Techniques in Biochemistry and Molecular Biology, Volume 9, G. Allen, Sequencing of Proteins and Peptides, Elsevier/North-Holland, Amsterdam, pp 43-71). This set of protocols yielded many peptides. These were applied to reverse phase HPLC columns in trifluoroacetic acid and eluted with organic solvents as described (Ogasawara M et al. (1989) Biochemistry 28, 2710-2721). The separated peptides were sequenced. The analyses of several peptides are shown in FIG. 87. Attempts were made to align these sequences with human SHBG (hm SHBG) (Walsh K A et al. (1986) Biochemistry 25, 7584-7590), rabbit SHBG (rb SHBG) (Griffin P R et al. (1989) J Biol Chem 264, 19066-19075), rat androgen binding protein (rt ABP) (GENBANK registration) and a partial sequence of hamster androgen binding protein (hs ABP) (GENBANK registration). A BLAST SEARCH match showed ≦30% homology for the peptides sequenced. If the material in CA-PS-pool II had significant shared primary structure with SHBG, it could not be confirmed.

Figure 88:
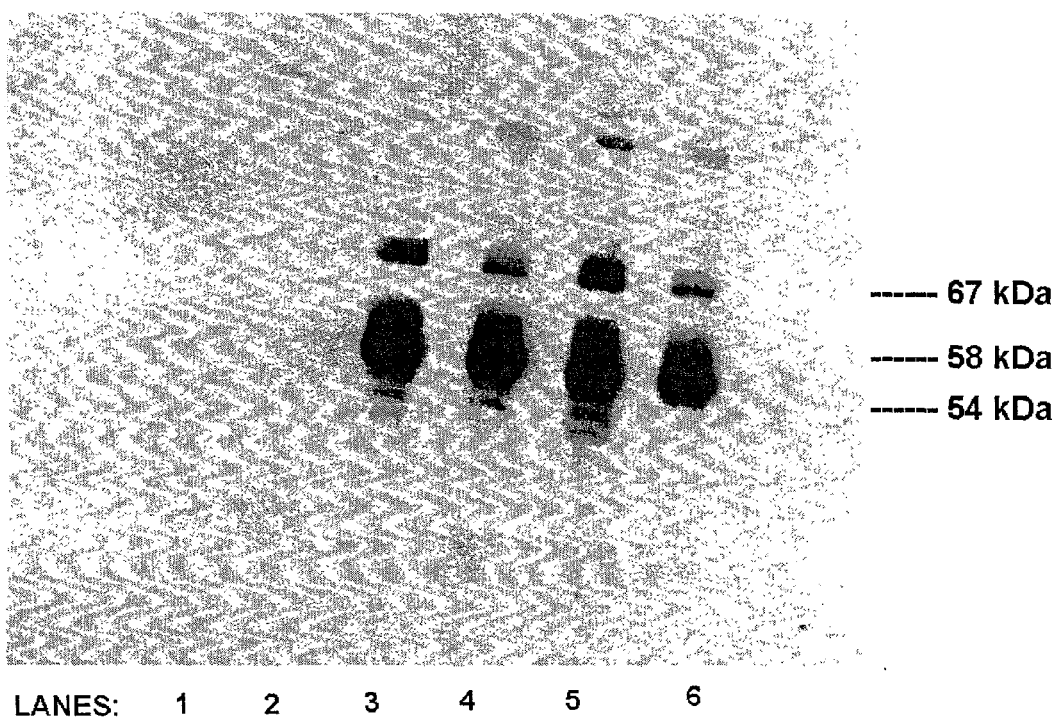
FIG. 88. Western Analysis of CA-PS-pool I and CA-PS-pool II with the Antibody Raised to the 54 kDa Band.

Antibodies Against the CA-PS-Pool II Components. Preparative SDS-PAGE was done on the Ca-PS-pool II fraction, and after localization of the 54 kDa band, the 54 kDa band was eluted and prepared for rabbit antibody production by HTI (Ramona, Calif.). The antibodies raised were very potent and reacted with CA-PS-pool II (FIG. 88). They did not cross react with CBG (CA-PS-pool I). However, despite great care, it was evident that the anti-54 kDa was raised against a mixture of 67, 58 and 54 kDa subunits (FIG. 88). The reaction was definitely strongest with the 54 kDa component, but clearly identifiable with the 67 kDa and 58 kDa bands as well. This apparent problem turned out to be an advantage, and allowed positive identification of the active agents in CA-PS-pool II. It was investigated whether the activity in CA-PS-pool II might have been isolated because of affinity for the agarose matrix rather than as a consequence of the steroid hormone ligand attached to agarose, noting from interpretation of unrelated studies, that agarose alone can bind immunoglobulins and give SDS-PAGE bands at 67, 58 and 54 kDa. Therefore, it was thought possible that IgG was the estrogen reversible inhibitor.

Figure 89:
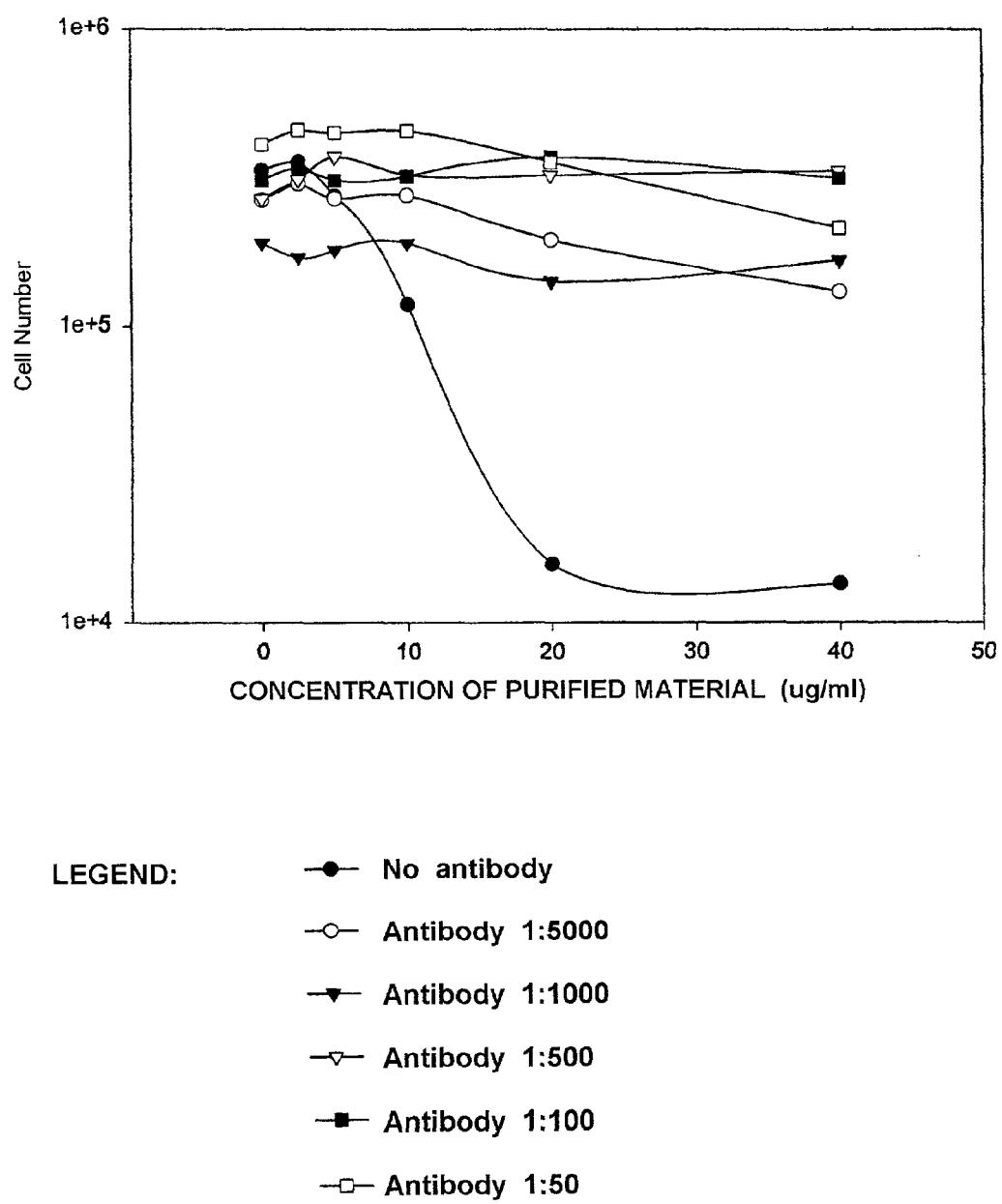
FIG. 89. Effect of the Anit-54 kDa Antiserum on the Inhibition of MWT9/PL2 Cell Growth by the Isolated Fraction CS-PS-Pool II.

Antibodies Against the 54 kDa Component of CA-PS-Pool II and Blocking of the Estrogen Reversible Inhibitor Activity. Based on the results in FIG. 88, it was apparent that the 54 kDa antiserum might be used to determine if the biological activity resided in any of the 67, 58 or 54 kDa bands. The next study was done to resolve this important issue. The results were pivotal. FIG. 89 shows that the purified material in CA-PS-pool II was completely inhibitory at 20 to 40 µg/mL. Addition of even a 1:5000 dilution of anti-54 kDa blocked the effect of the inhibitor. In control studies, rabbit pre-immune serum had no effect even at 1:100 a dilution (data not shown). It was evident that anti-54 kDa serum contained the antibody to the activity.

Figure 90:
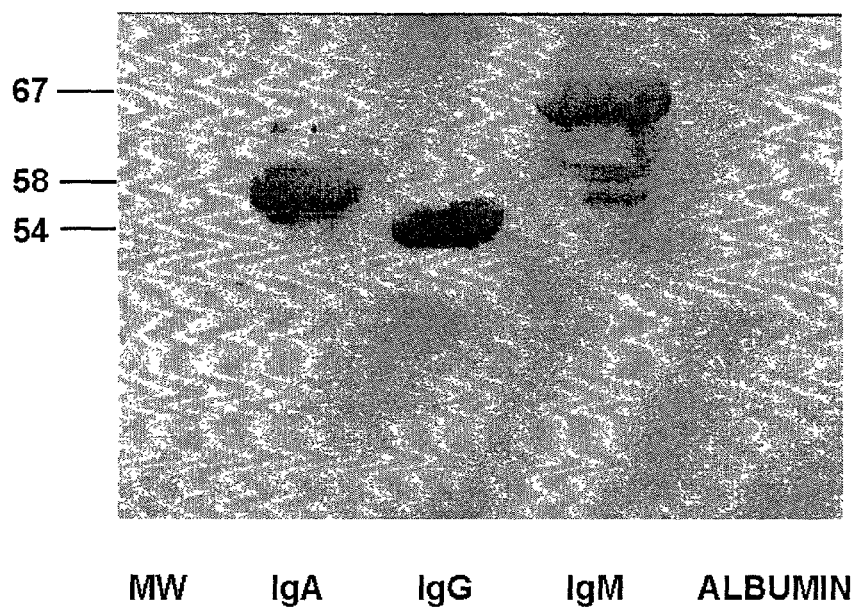
FIG. 90. Western Immunoblotting of Commercially Prepared Horse IgG, IgA and IgM with anti-54 kDa Antiserum.

Anti-54 kDa Serum Recognizes Authentic Horse IgA, IgM and IgG. Next, authentic horse IgA was obtained from Accurate Chemicals, and horse IgM was obtained from Accurate Chemicals and Custom Monoclonal International. The material from Custom Monoclonals was custom purified by an affinity method with a monoclonal antibody against horse IgM Fc and further purified by molecular sieve chromatography to be sure of elimination of other immunoglobulins (a common problem). IgGs were obtained from Zymed (San Francisco, Calif.), Sigma (St. Louis, Mo.) or The Binding Site (San Diego, Calif.). The Western analysis shown in FIG. 90 demonstrates these results. The results show clear cross-reaction with 67 kDa IgM heavy chain, 58 kDa IgA heavy chain and 54 kDa IgG heavy chain but no reaction with horse albumin.

Figure 91:
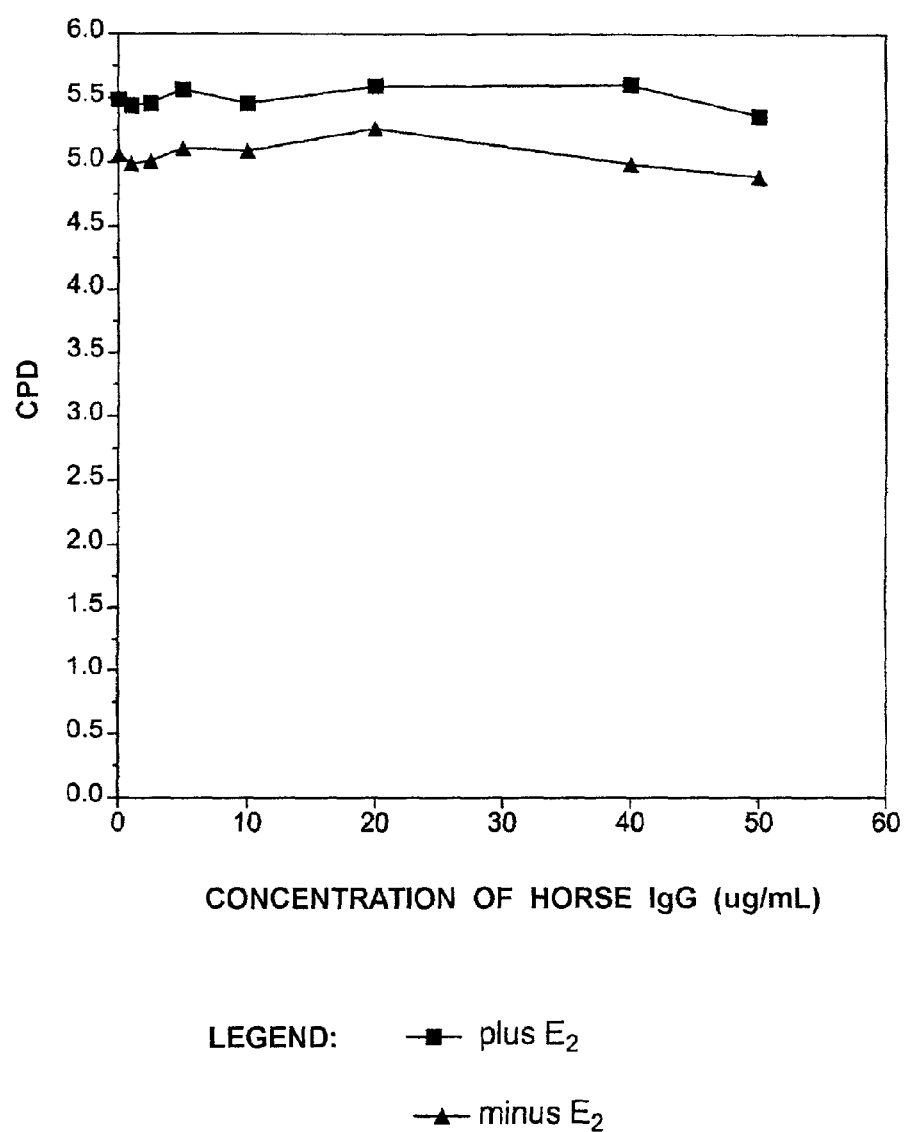
FIG. 91. Effect of Horse IgG on MTW9/PL2 Cell Growth in 2.5% CDE-horse Serum±E$_2$.
Figure 92:
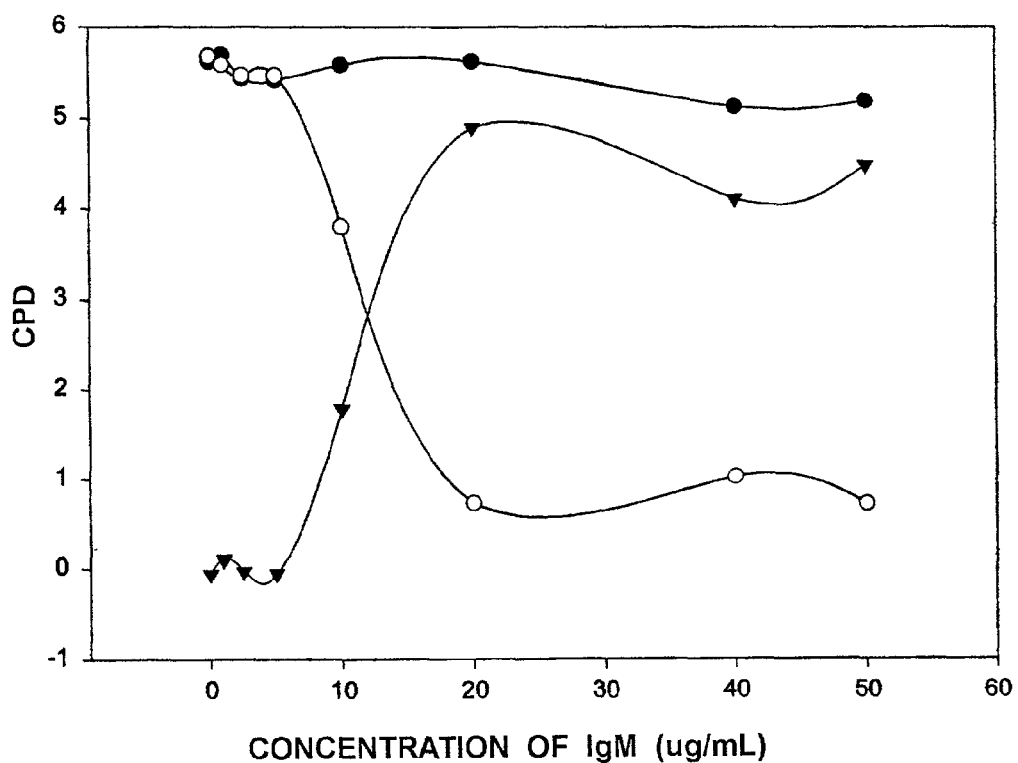
FIG. 92. Effect of Horse IgM on MTW9/PL2 Cell Growth in 2.5% CDE-horse Serum±E$_2$.
Figure 93:
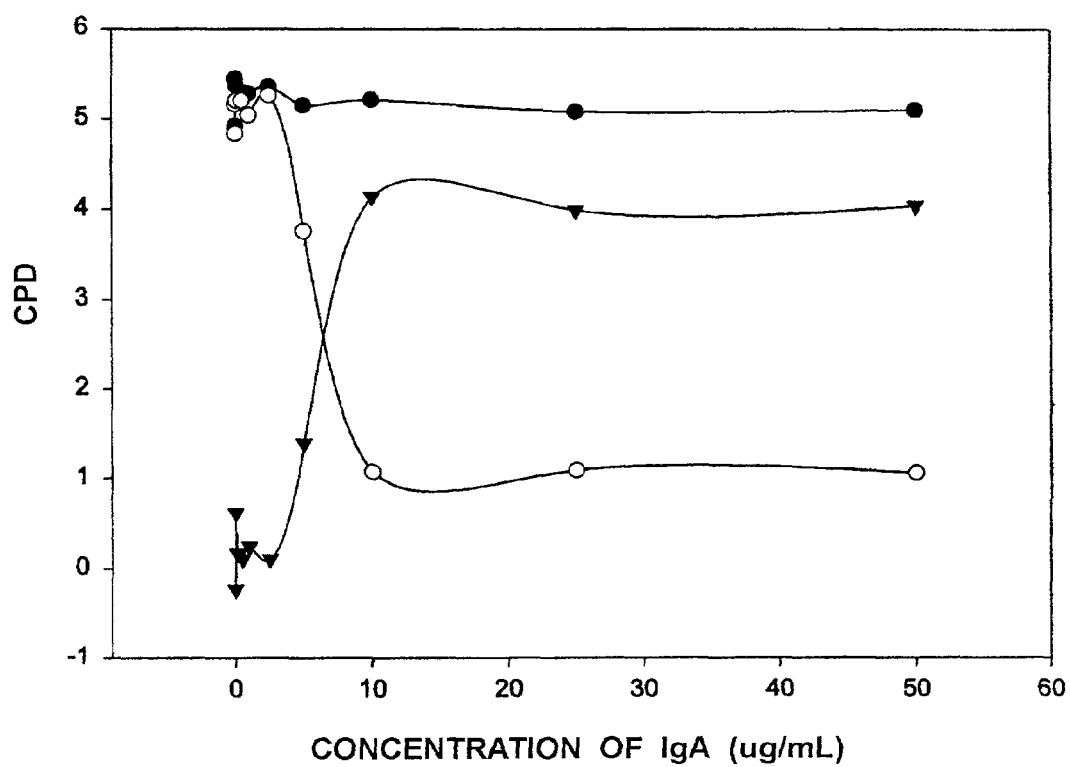
FIG. 93. Effect of Horse IgA on MTW9/PL2 Cell Growth in 2.5% CDE-horse Serum±E$_2$.

Assay of Estrogenic Effects Controlled by Commercially Purchased Horse IgG, IgA and IgM in 2.5% CDE-horse Serum with MTW9/PL2 Cells. FIG. 91 demonstrates that at concentrations up to 59 µg/mL, horse IgG did not cause inhibition of MTW9/PL2 cell growth in 2.5% CDE-horse serum. There was no significant estrogenic effect caused by IgG. FIG. 92 shows very clearly that commercially prepared horse serum derived IgM (Custom Monoclonals), was very active. At concentrations of 20 to 50 µg/mL, IgM completely inhibited the growth of the MTW9/PL2 cells (i.e.<1.0 CPD). Addition of 10 nM $E_2$ reversed the inhibition nearly completely. Estrogenic effects of 4 to 5 CPD were seen (FIG. 92). FIG. 93 shows the same general results with commercially prepared horse serum derived IgA (Accurate). The only apparent difference was that IgA was slightly more effective than IgM. These results clearly proved that the active components in CA-PS-pool II were IgA and IgM. That these Igs would prove to be the inhibitor was completely unexpected. Although these two active classes of immunoglobulins (IgA and IgM) are well-established secretory products of normal breast cells, there was no previous suggestion in the prior art that they play a role in the negative regulation of estrogen-dependent cell growth. These immunoglobulins are major proteins in milk whose hormone-related local production in breast tissue is well documented, and their function in the body's secretory immune system is well known.

Alternate Methods of Obtaining Horse Serum IgG, IgM and IgA. IgG can be purified using a Hytrap matrix, which is a mixture of immobilized Protein A and Protein G, employing a technique described by others (Lindmark R et al. (1983) *J Immunol Meth* 62, 1-13; Kronvall G et al. (1969) *J Immunol* 103, 828-833; Akerstrom B et al. (1986) *J Biol Chem* 261, 10240-10247). IgM can be obtained using a mannan binding protein isolation method normally applied with human serum (Nevens J R et al. (1992) *J Chrom* 597, 247-256). However, yields are low. Another method based on anti-IgM immunoglobulins linked covalently to Sepharose is far more effective. This same procedure with immobilized anti-IgA immunoglobulins can be used to isolate IgA (Tharakan J In: Antibody Techniques, Malik V S & Lillehoj E P, Eds, 1994, Academic Press, San Diego, Calif., Chapter 15). Horse IgA can also be purified using an immobilized Jacalin lectin method usually reserved for human samples (Roque-Barreira M C et al. (1986) *Braz J Med Biol Res* 19, 149-157). However, it can be modified for non-human species. The buffers are modified to contain 10 to 50 mM $CaCl_2$ to bind IgA from other species. Even then, yields are not high. The preferred methods for horse IgA and IgM use immobilized antibodies.

Figure 95:
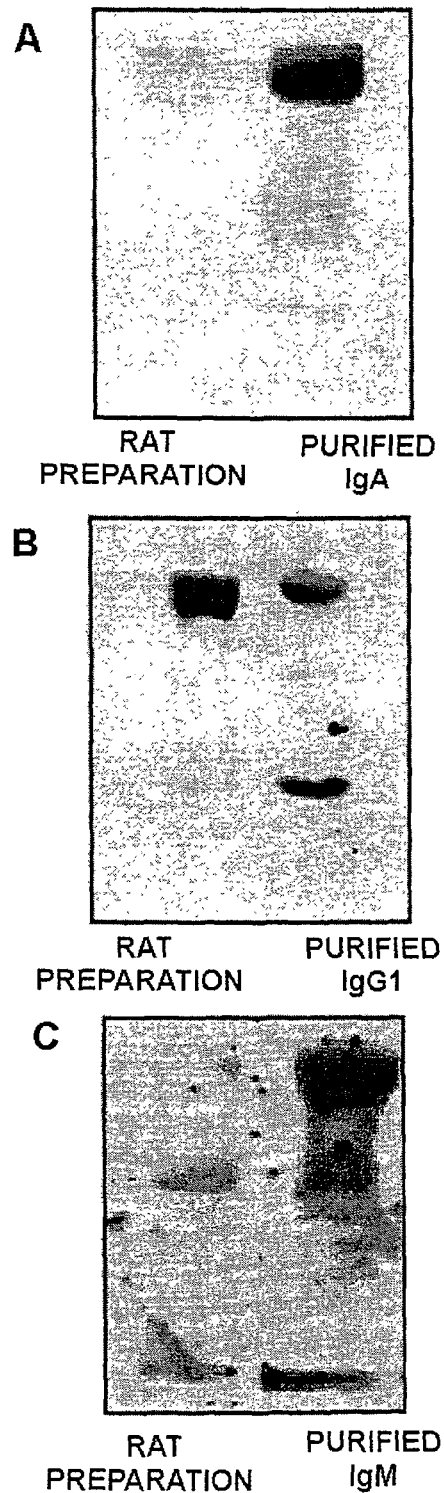
FIG. 95. Western Analysis of a Rat Purified "SHBG-like" Preparation. (A) Western with Anti-rat IgA with Purified IgA Control; (B) Western with Anti-rat IgG1 with Purified IgG1 Control; (C) Western with Anti-rat IgM with Purified IgM Control.

Purification of Rat Serum Immunoglobulins. Three isolations of the estrogen reversible inhibitor from separate one-liter batches of adult rat serum were conducted. This was done for two important reasons. First, the estrogen reversible activity in all types of adult serum, including rat, were assayed with a highly estrogen sensitive MTW9/PL2 rat mammary tumor cell line. It was useful to confirm the horse serum purification results with a homologous experimental system. Second, the confirmation that rat IgA and IgM regulated rat mammary tumor cell growth would open the possibility of combined testing of new therapeutic substances both in vitro and in vivo. To summarize, the same "CBG" and "SHBG" fractions were obtained from rat serum by the methods of Fernlund & Laurell as had been obtained from horse serum. The chromatography profiles of the rat separations (not presented) were very similar to those presented in FIG. 80. The only major difference was that no rat CBG was obtained. At pH 5.5, rat CBG did not significantly bind to the affinity matrix. Rat serum CA-PS-pool I and CA-PS-pool II both contained only two Coomassie Blue stained bands when analyzed by SDS-PAGE (FIG. 94A). These were approximately 55 kDa and 54 kDa. They were somewhat lower molecular weights than found with horse, and there were fewer bands. To test if either rat band was IgG, a Western analysis was performed with rabbit anti-rat IgG (FIG. 94B). The antibody did not recognize the Coomassie stained bands but did react with control IgG. However, when examined with very specific heavy chain monoclonal antibodies raised to rat IgG1, IgA, and IgM (purchased from Zymed), the Western analysis was clear (FIG. 95). Both the commercially purified rat immunoglobulins (purchased from Zymed) and the two-step purified pools showed cross-reaction with anti-IgA (weakly), anti-IgG1 subtype (strong reaction) and anti-IgM (moderate reaction) (FIGS. 95A, 95B, and 95C, respectively).

Rat and Horse Serum Active Pools Isolated by the Two-Step Procedure of Fernlund and Laurel have the Same Classes of Immunoglobulins. The same classes of immunoglobulins obtained by the two-step procedure of Fernlund and Laurell (Fernlund P and Laurell C-B (1981) *J Steroid Biochem* 14, 545-552) with horse serum were found when rat serum was the starting material. This was considered to be further confirmation that binding to the agarose matrix was more important than to the immobilized cortisol. It should be noted that in the original Fernlund and Laurell report using human cord serum does not address possible immunoglobulin contamination, however (Fernlund P and Laurell C-B (1981) *J Steroid Biochem* 14, 545-552). This is particularly curious because human immunoglobulins bind to agarose (Smith R L and Griffin C A (1985) *Thombosis Res* 37, 91-101).

Amino Acid Sequencing Of Rat "SHBG-Like" Proteins. Protein fragmentation and amino acid sequencing of rat "SHBG-like" proteins were done as described above for horse CA-PS-pool II. The analyses of several peptides are shown in FIG. 96. Attempts were made to align these sequences with human SHBG (hm SHBG) (Walsh K A et al. (1986) *Biochemistry* 25, 7584-7590), rabbit SHBG (rb SHBG) (Griffin P R et al. (1989) *J Biol Chem* 264, 19066-19075), rat androgen binding protein (rt ABP) (GENBANK registration) and a partial sequence of hamster androgen binding protein (hs ABP) (GENBANK registration). A BLAST SEARCH match showed≦30% homology for the peptides sequenced. If the rat "SHBG-like" pools have significant shared primary structure with SHBG or rat androgen binding protein, it could not be confirmed by these studies.

Labeled Steroid Hormone Binding to The "SHBG-like" Pools from Rat Serum. As described in TABLE 9, CA-PS-pool II from horse serum binds sex steroids with an affinity of about $10^{-8}$ M. This same Scatchard analysis was done with an active fraction from rat serum. TABLE 11 shows the results of these studies with four labeled steroid hormones. It is clear that sex steroid hormones bind with a higher affinity than progesterone or cortisol. The binding affinities of rat and horse preparations were very similar. In both cases, the affinities tend to rule out the estrocolyone hypothesis because it requires $E_2$ binding in the picomolar range.

TABLE 11

Summary of the Scatchard Analysis of the "SHBG-like" Pools from Rat Serum with Labeled Steroid Hormones

| Steroid Hormone | CA-PS-Pool II | |
|---|---|---|
| (3H-labeled) | $K_d$ (M) | $K_a$ (M$^{-1}$) |
| Cortisol | $5.7 \times 10^{-6}$ | $1.8 \times 10^5$ |
| Progesterone | $6.9 \times 10^{-6}$ | $1.4 \times 10^5$ |
| 17β-estradiol | $4.1 \times 10^{-8}$ | $2.4 \times 10^7$ |
| Dihydrotestosterone | $2.4 \times 10^{-8}$ | $4.1 \times 10^7$ |

Evaluation of the Rabbit Anti-SHBG Cross-Reaction with the Active Pools from the Two-Step Isolation of Fernlund and Laurell. As shown above in FIG. 81B, Western analysis with the anti-SHBG detected horse IgA, IgM and IgG. Additionally, anti-SHBG immunoprecipitated the estrogenic activity of horse serum (FIG. 79B). To extend these results, it was established that rabbit anti-human SHBG recognized a number of the major classes and subclasses of rat immunoglobulins. SDS-PAGE with Coomassie blue staining (FIG. 97A) was compared to identification of the same proteins by Western analysis with anti-SHBG (FIG. 97B). These results leave very little doubt that the SHBG used to raise antibodies in rabbits was not homogeneous but in fact was a "crude" preparation contaminated with several immunoglobulins.

Figure 98:
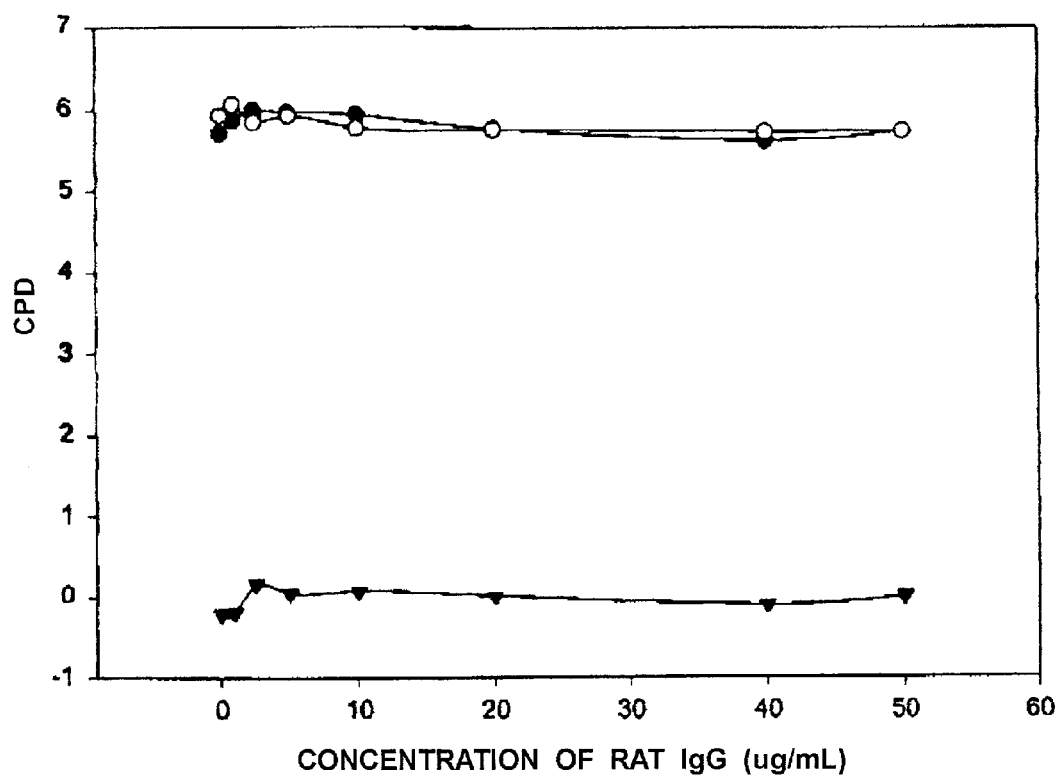
FIG. 98. Effect of Rat IgG on MTW9/PL2 Cell Growth in Medium with 2.5% CDE-rat Serum±$E_2$.
Figure 99:
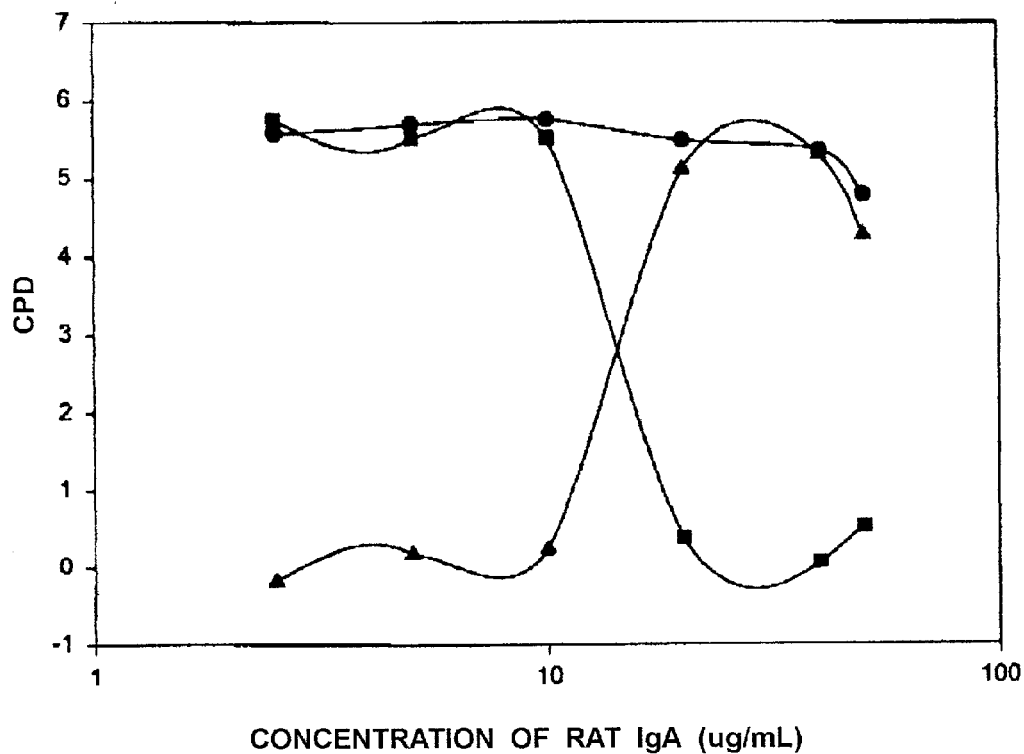
FIG. 99. Effect of Rat IgA on MTW9/PL2 Cell Growth in Medium with 2.5% CDE-rat Serum±$E_2$.
Figure 100:
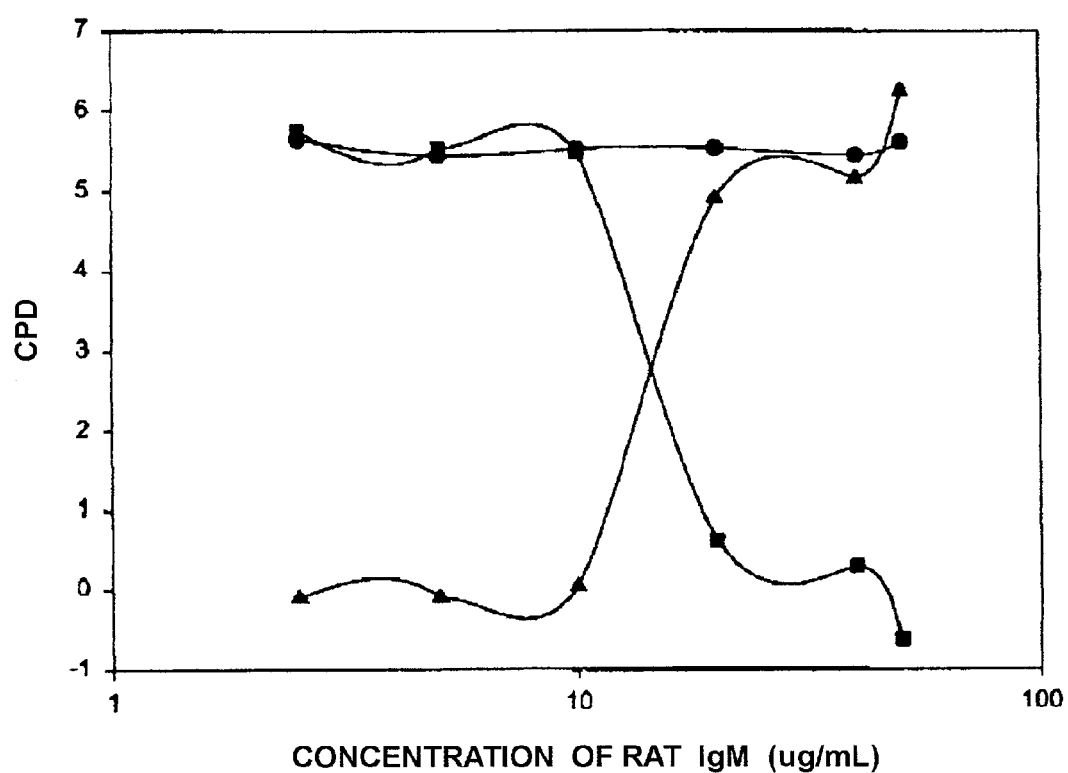
FIG. 100. Effect of Rat IgM on MTW9/PL2 Cell Growth in Medium with 2.5% CDE-rat Serum±$E_2$.

Test of Rat IgG, IgA and IgM for Estrogen Reversible Inhibitory Activity with MTW9/PL2 Rat Mammary Tumor Cells. All of the rat immunoglobulins described in this section were purchased from Zymed as the highest quality available. Their activity was assessed with MTW9/PL2 cells in 2.5% (v/v) CDE-rat serum, as described above. The activity of rat IgG (all subclasses combined) was assessed (FIG. 98). There was no inhibitory effect at up to 50 μg/mL. Rat IgA was a potent estrogen reversible inhibitor (FIG. 99). At 20 to 50 µg/mL, it completely inhibited growth. Addition of 10 nM $E_2$ completely reversed the inhibition. The estrogenic effects recorded were>5 CPD. The results with rat IgM were very similar (FIG. 100). At 20 to 50 µg/mL, it completely inhibited growth. Addition of 10 nM $E_2$ reversed the inhibition. The estrogenic effects recorded were>5 CPD. It is essential to note that IgA or IgM replaced the effect of full CDE-rat serum with MTW9/PL2 cells. With a completely homologous system (i.e. cell line, basal 2.5% CDE-serum, and immunoglobulins), the results were clear. IgA and IgM were the sought after serum-borne inhibitors from rat.

Discussion of Example 20. The identification of IgA and IgM as serum-borne inhibitors fully separates these inhibitors from the teachings of U.S. Pat. Nos. 4,859,585 (Sonnenschein) and U.S. Pat. No. 5,135,849 (Soto), which arrived at no molecular identification of the inhibitor. The series of investigations presented above demonstrate that a very long-standing problem has been solved. While the solution is significant, an even more an important consequence of this knowledge is the fact that for the very first time, mucosal cell hormone dependent growth has been linked to a natural immune regulation. Moreover, this information has direct application to the diagnosis, genetic screening, prevention and therapy of breast and prostate cancer and a high likelihood of applications to other mucosal cancers, as described in more detail in U.S. patent application Ser. No. 09/852,547 /PCT/US2001/015171 entitled "Compositions and Methods for the Diagnosis, Treatment and Prevention of Steroid Hormone Responsive Cancers," which is hereby incorporated herein by reference.

During the purification of both the horse serum and the rat serum estrogen reversible activity, SUPERDEX™ (Pharmacia) molecular sieve chromatography of the final mixtures indicated the presence of<20% 160 kDa monomeric immunoglobulins. The majority of the material was of much larger mass. Because IgA exists naturally as monomer, dimer and polymers, there was a question concerning which of these is/are inhibitory form(s). The SUPERDEX™ results strongly favor the dimer/polymer form. This was confirmed also with commercially prepared IgA that was obtained from hybridoma and myeloma cell lines. The IgA from these was>80% dimer/polymer. It was very active as an inhibitor. In light of these results, it is suggested that these forms are the "good" type of IgA in the body, and that direct measurement of their concentration in plasma and body fluids has diagnostic and prognostic applications.

The introduction of test methods done with minimum serum plus purified immunoglobulin inhibitor ("spiked serum") provides a new approach to substances, mixtures and compounds that might be influenced by serum components. For example, a serum composition might contain steroid hormone free serum, such as a standard, commercially available fetal bovine serum preparation, and a predetermined amount of an immunoglobulin inhibitor, i.e., one or more of IgA, IgM or IgG. Testing under these conditions, with a known amount of inhibitor in the serum, may be desirable or required when the substance has potential for inactivation/activation by a serum component or when it has lipophilic properties that require a minimum protein concentration in the medium to prevent loss.

Another valuable application of the immunoglobulin inhibitors will be in identifying substances that may have direct effects on the action of the immunoglobulins to cause inactivation. An assay of this nature is unique in the sense that incubation of substances with the immunoglobulin can be done before the assay to determine effects on natural immune responses. Changes in environmental/chemical factors that affect the body's immune system are of major medical concern. They also are of great concern to veterinary medicine. Chemicals/nutritional supplements may affect immune function of domestic animals and thereby affect human food supplies.

This series of investigations demonstrate at least two immunoglobulin inhibitors in serum. More than one inhibitor was suggested by the conventional purification data in a preceding Example, and was proved true in succeeding examples. There may still be other useful estrogen reversible immunoglobulin inhibitors in serum that are yet to be identified from serum or tissue sources. The methods described in this Example have direct application to the search for new compounds that mimic the effect of the immunoglobulins as estrogen reversible inhibitors. Such application opens a new avenue of search for anticancer drugs.

Example 21

Regulation of Steroid Hormone-Responsive and Thyroid Hormone-Responsive Cancer Cell Growth in Serum-free Defined Medium by Secretory and Plasma Forms of IgA and Plasma and Cell Culture Derived IgM This Example demonstrates that the determination of whether purified IgA and IgM from several species mimic the sex steroid hormone reversible inhibitors isolated from horse in serum was sought. These studies included $ER^+$ tumor cells derived from rodents as well $ER^+$ and $AR^+$ cells from human cancers. Completely serum-free defined culture conditions were used to perform cell growth assays using the purified inhibitors. The total protein concentration in the media was<2 mg/mL. The estrogenic and androgenic effects observed in these assays are unique, as like effects have not been achieved previously in completely serum-free defined medium.

Figure 101:
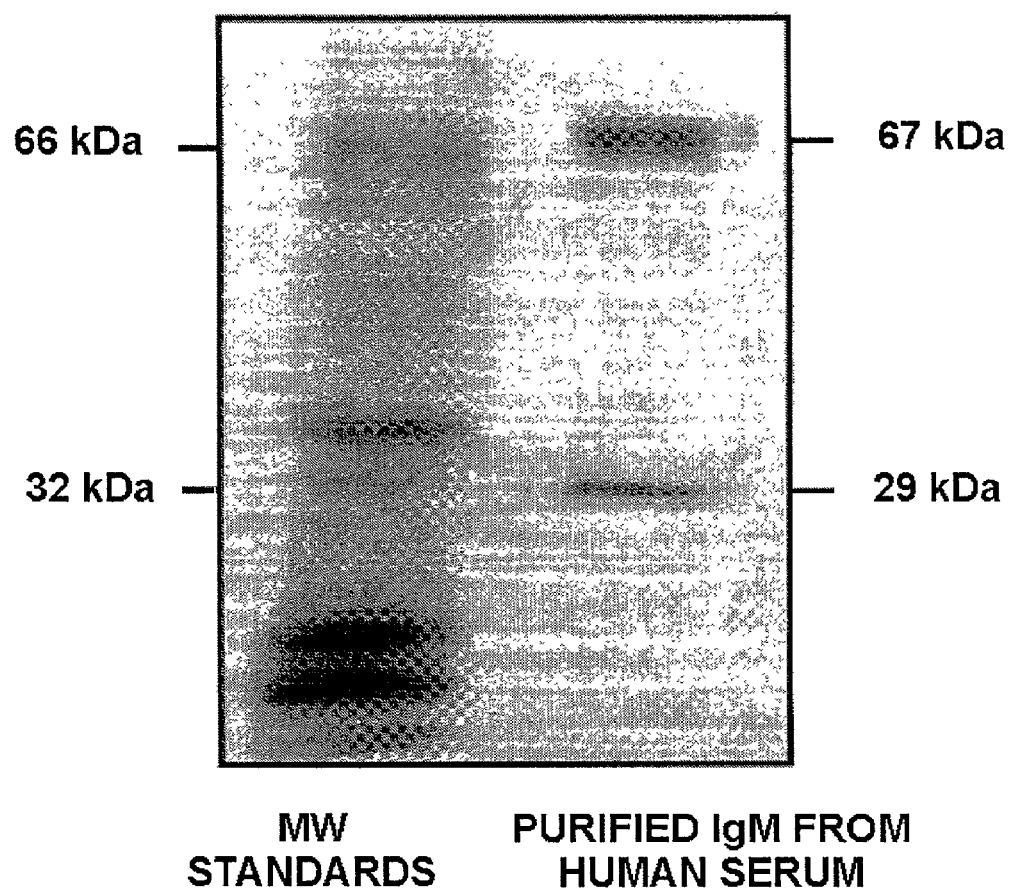
FIG. 101. Mannan Binding Protein Isolation of Human Plasma/Serum IgM.
Figure 102:
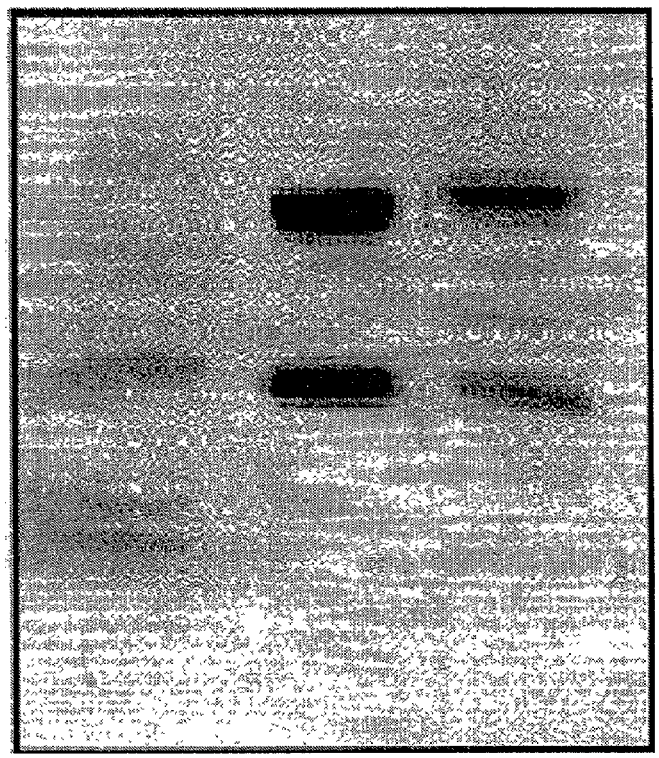
FIG. 102. Jacalin Lectin Purification of Human Plasma/Serum IgA.

Sources of Purified IgA and IgM. Human IgM was purified from human plasma as described using immobilized mannan-binding protein (Nevens J R et al. (1992) *J Chromatography* 597, 247-256). As an example of the effectiveness of this isolation, FIG. 101 shows SDS-PAGE and Coomassie Blue Staining with two preparations of human plasma IgM prepared. Human IgA1 and IgA2 were purified using immobilized Jacalin (Roque-Barreira M C and Campos-Neto A (1985) *J Immunol* 134, 1740-1743; Kondoh H et al. (1986) *J Immunol Methods* 88, 171-173; Pack T D (1999) *American Biotechnology Laboratory* 17, 16-19; Loomes L M et al. (1991) *J Immunol Methods* 141, 209-218). Rat IgA and IgM were purchased from Zymed. The effectiveness of the Jacalin method with human plasma is shown in FIG. 102. Horse IgA and IgM were purchased from Accurate, Sigma and Custom Monoclonals. IgA and IgM from other species or as products from cell culture are purchased from Sigma or Accurate. Human IgA and IgM were bought also from Sigma and Accurate. Human secretory (milk) IgA (sIgA) was purchased from Sigma or Accurate.

Figure 103:
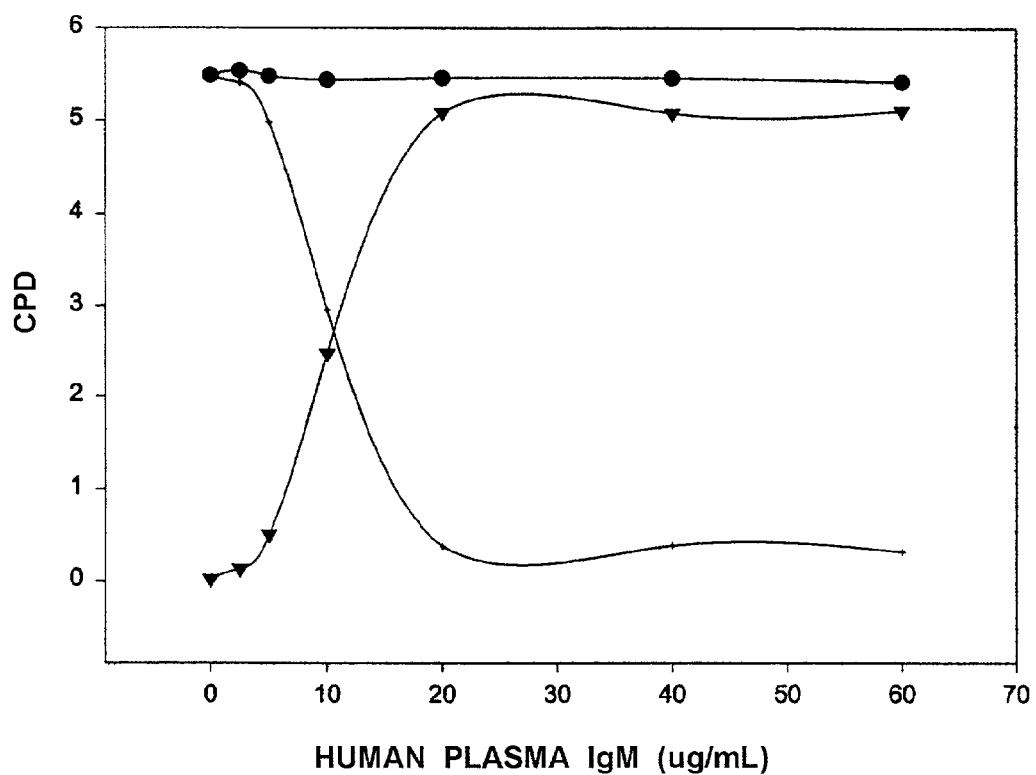
FIG. 103. Effect of Human IgM on MTW9/PL2 Cell Growth $E_2$ in Serum-free Defined Medium.
Figure 104:
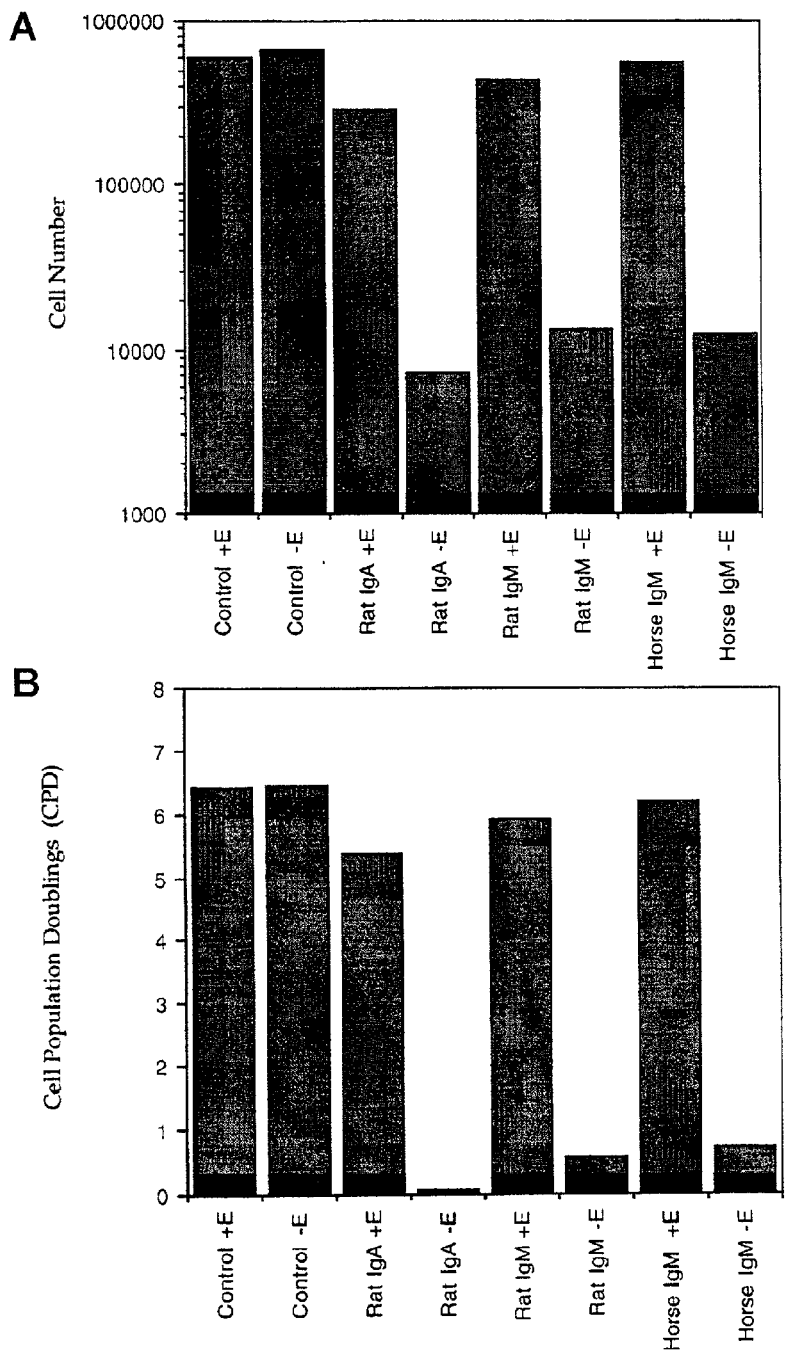
FIG. 104. Comparison of the Effects of Rat and Horse IgA and IgM on MTW9/PL2 Cell Growth±$E_2$ in Serum-free Defined Medium Expressed in Cell Number and CPD.

A. MTW9/PL2 rat mammary tumor cells. For this series of experiments the serum-free defined medium was the preferred formulation of DDM-2A described in TABLE 7. The cell growth assays with this cell line in DDM-2A testing increasing concentrations of human plasma IgM is shown in FIG. 103. Human plasma IgM completely inhibited growth by 20 to 60 µg/mL. The $ED_{50}$ was about 12 µg/mL. Based on an IgM $M_r$ of 950,000, the $ED_{50}$ concentration was $1.3 \times 10^{-8}$ M. Complete inhibition was at $2.2 \times 10^{-8}$ M. These concentrations are certainly within the physiological range of IgM in the plasma and body fluids such as breast milk. Based on these studies, a comparison was done in completely serum-free defined DDM-2A medium of the effects of 40 µg/mL of rat plasma IgA±$E_2$, rat plasma IgM±$E_2$, and horse plasma IgM±$E_2$ (FIG. 104, expressed as (A) cell numbers and (B) CPD). From the CPD calculations it was clear that no matter the species source, IgA and IgM were very potent estrogen reversible inhibitors of MTW9/PL2 cell growth.

One problem occurred with the MTW9/PL2 cell assays that initially caused concern. Human IgA was purchased from Sigma as the milk derived immunoglobulin. It was far less expensive than plasma IgA. For reasons that at first were not clear, this material was at best only partially inhibitory and often not inhibitory. As will be discussed below with $GH_1$ cells, this turned out to be a significant clue to the mechanism of action of the immunoglobulins. Nonetheless, it is known that the heavy chains of IgM and IgA from different species share primary structure homology. This is not true of the variable regions of the light chains. The results presented support the possibility of Fc-like receptor mediation of the IgA and IgM effects on MTW9/PL2 cells.

Figure 105:
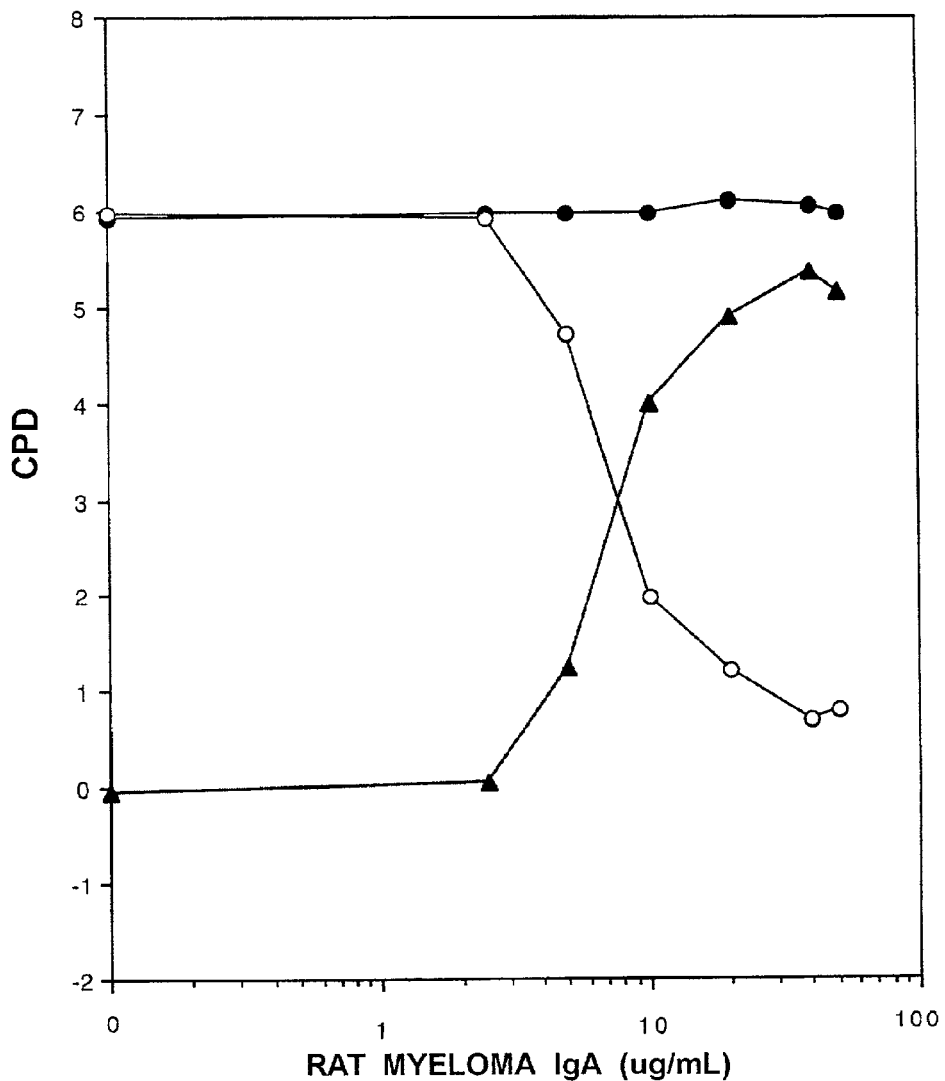
FIG. 105. Effect of Rat Myeloma IgA on $GH_1$ Cell Growth in Serum-free Defined Medium±$E_2$.
Figure 106:
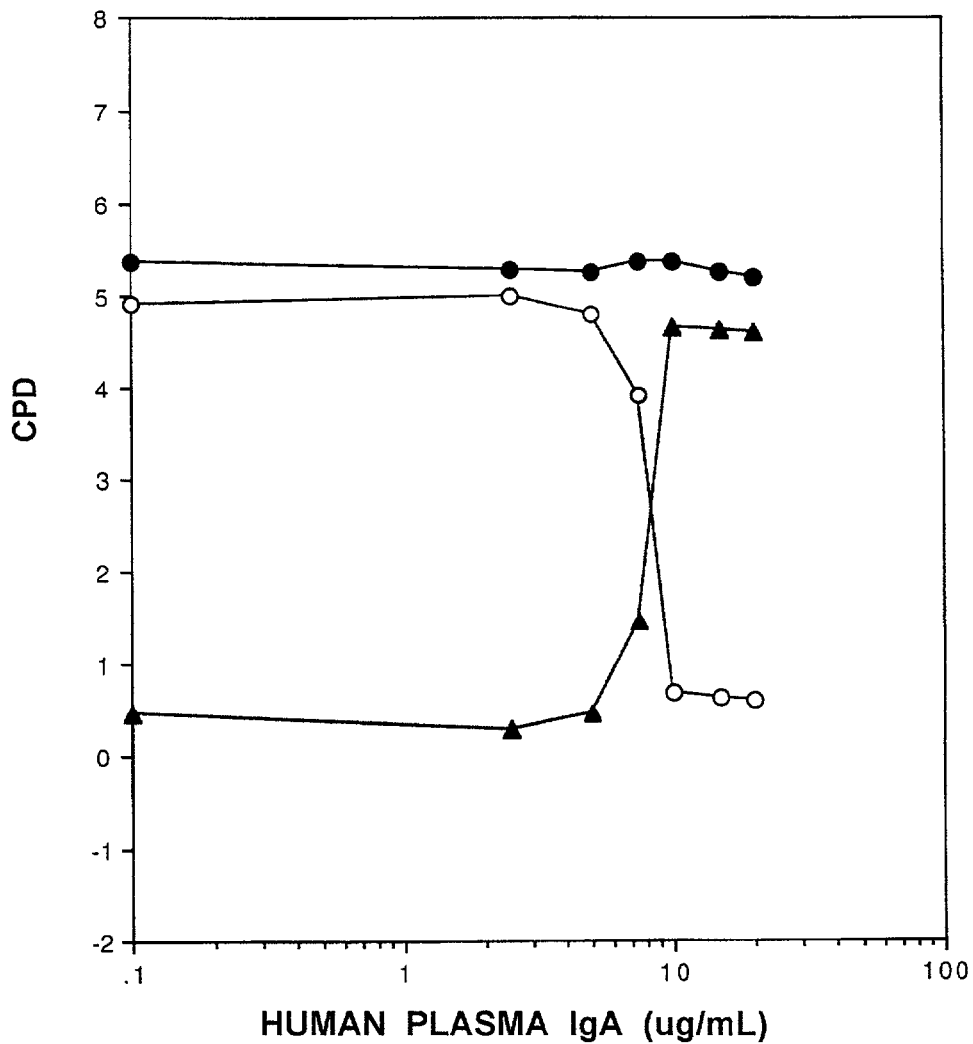
FIG. 106. Effect of Human Plasma IgA on $GH_1$ Cell Growth in Serum-free Defined Medium±$E_2$.
Figure 107:
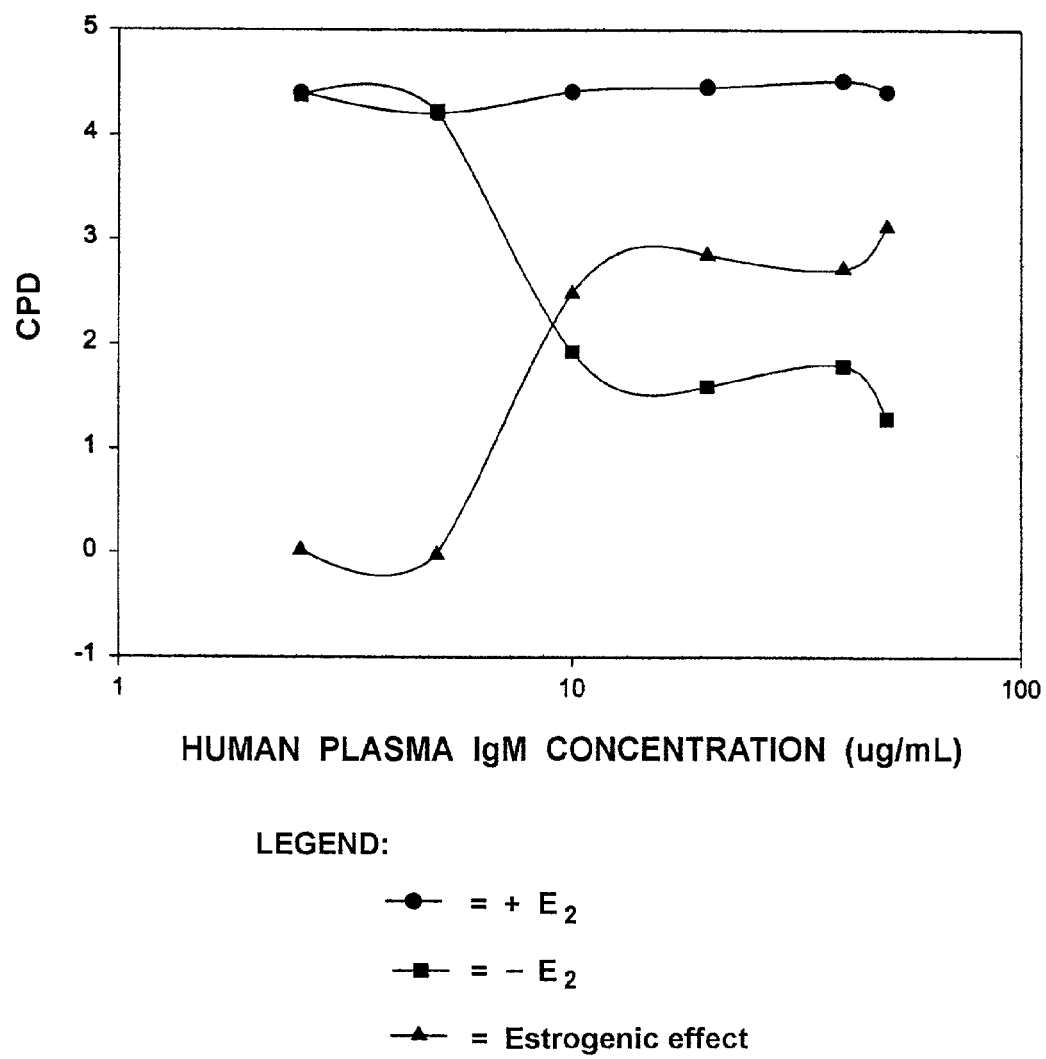
FIG. 107. Effect of Human Plasma IgM on $GH_1$ Cell Growth in Serum-free Defined Medium±$E_2$.
Figure 108:
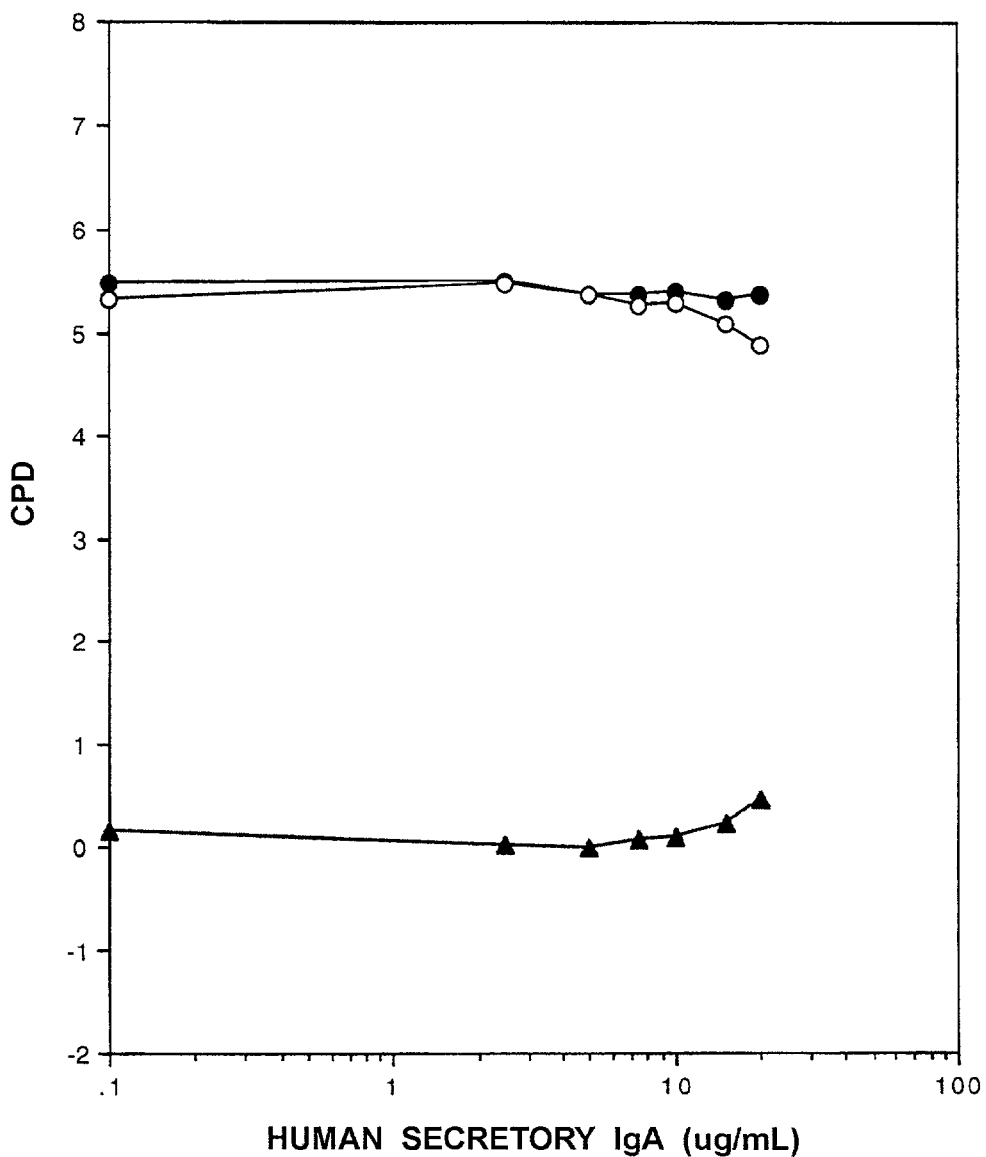
FIG. 108. Effects of sIgA a on $GH_1$ Cell Growth in Serum-free Defined Medium±$E_2$.
Figure 109:
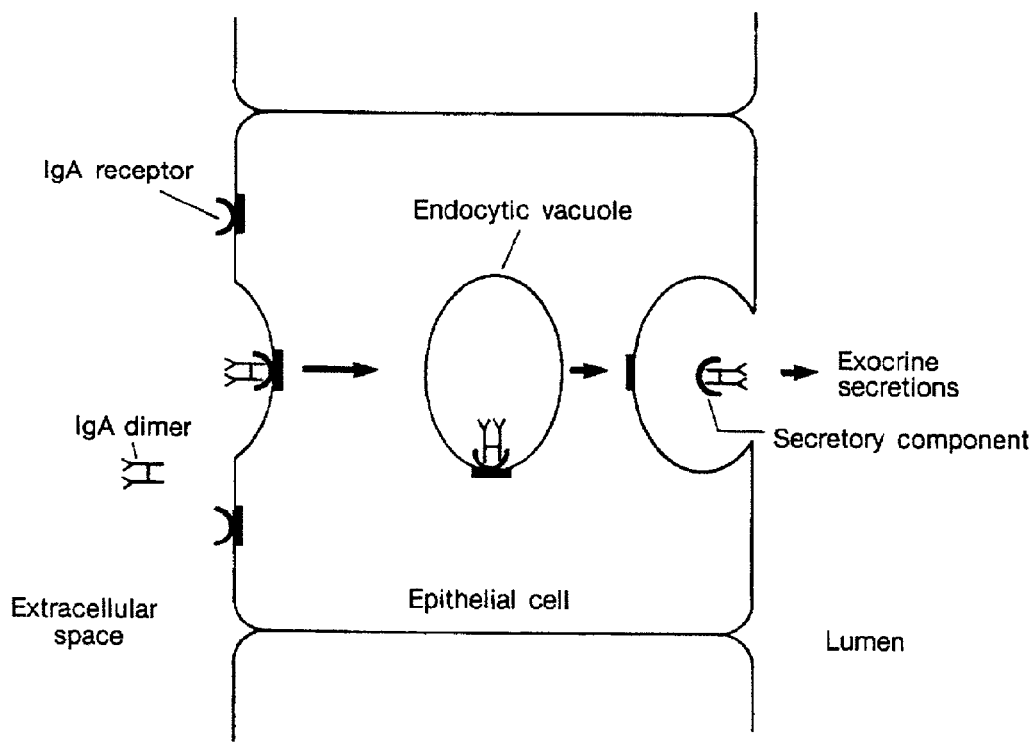
FIG. 109. Model of Mucosal Epithelial Cell Transport of IgA/IgM.

B. $GH_1$, $GH_3$ and $GH_4C_1$ rat pituitary tumor cells. For this series of experiments the serum-free defined medium was the preferred formulation of PCM-9 described in TABLE 7. The next serum-free defined medium studies were done with $GH_1$ cells. Example assays are shown. This cell line was highly estrogen responsive in the presence of homologous rat myeloma derived IgA (FIG. 105). Maximum estrogenic effect was>5 CPD or more than a 32-fold estrogen-induced increase in cell number in 10 days. A similar assay with human plasma derived IgA showed nearly the same results (FIG. 106). Indeed, human IgA showed greater inhibition at 10 µg/mL. Another study with human IgM demonstrated that it was also an estrogen reversible inhibitor of $GH_1$ cell growth (FIG. 107). It was not as inhibitory as IgA with this cell line, but certainly still effective. As discussed above, in the Background of the Invention, during the secretion process a fragment of about 80% of the poly-Ig receptor (including the five extracellular domains) becomes attached to the dimeric/polymeric form of IgA to form secretory IgA or sIgA. The receptor fragment is called the "secretory component". After secretion, sIgA can be readily isolated from human milk. The effect of milk derived secretory IgA (sIgA) was evaluated with the $GH_1$ cells in PCM-9, and the results of a representative study are shown in FIG. 108. These results were strikingly different than those obtained with plasma derived IgA (pIgA) (FIG. 106). SIgA was not inhibitory even at 20 µg/mL. Considering why the two different forms of IgA behaved so differently, the poly-Ig receptor was recognized as a potential candidate for the mediator of the action of IgA/IgM. As discussed in the Introduction of this Detailed Description, this receptor has not been previously associated with any growth related function. The poly-Ig receptor is concerned with process of transcytosis of IgA/IgM, as conceptually illustrated in FIG. 109. SIgA already has the receptor bound in the sense of the secretory piece in association with the Fc domains of the dimer. FIG. 110 illustrates schematically the structures of inactive monomeric IgA, the connecting or joining "J" chain, the structure of the active dimer with "J" chain, the secretory piece or secretory component, and the dimeric IgA structure plus secretory component attached, as generally understood. The illustration shows that the Fc domains of dimeric IgA are blocked by the secretory piece/component. Access to the Fc domains is required for binding to the poly-Ig receptor.

Figure 111:
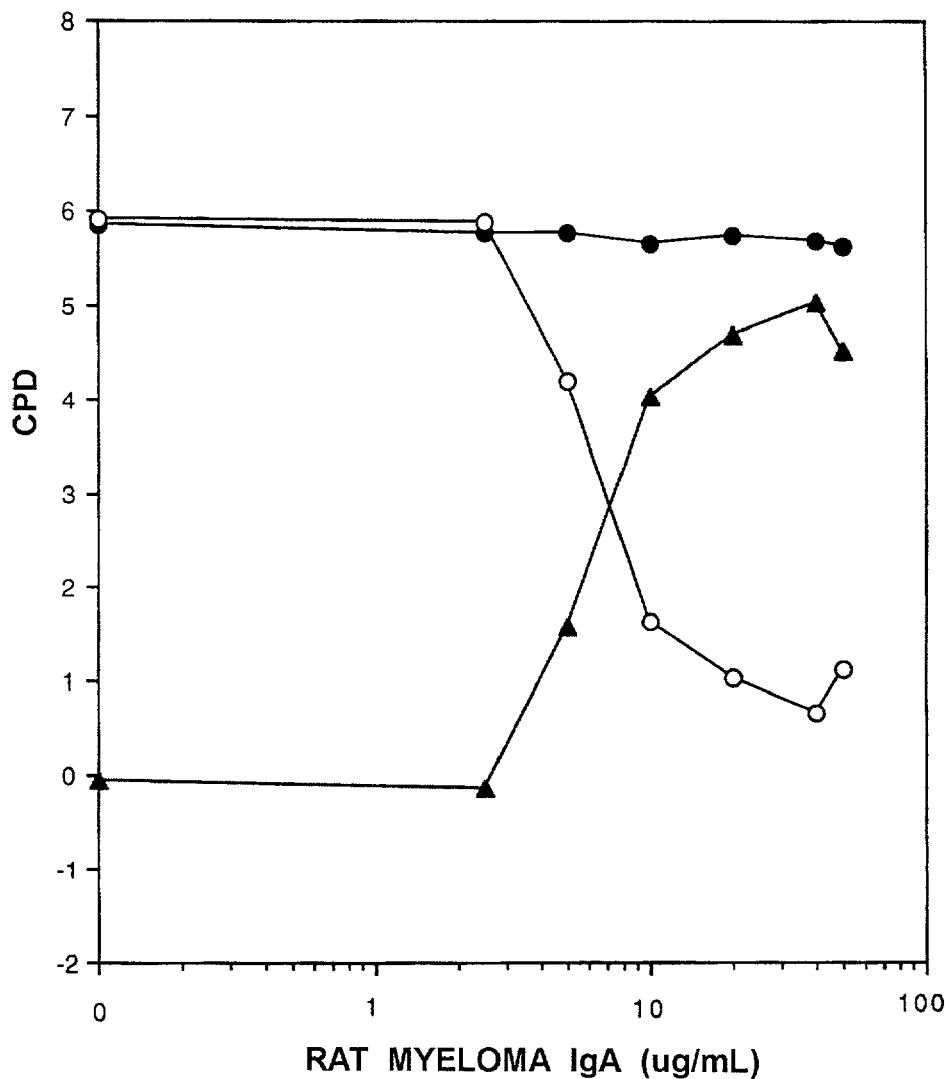
FIG. 111. Effect of Rat Myeloma IgA on $GH_3$ Cell Growth in Serum-free Defined Medium±$E_2$.
Figure 112:
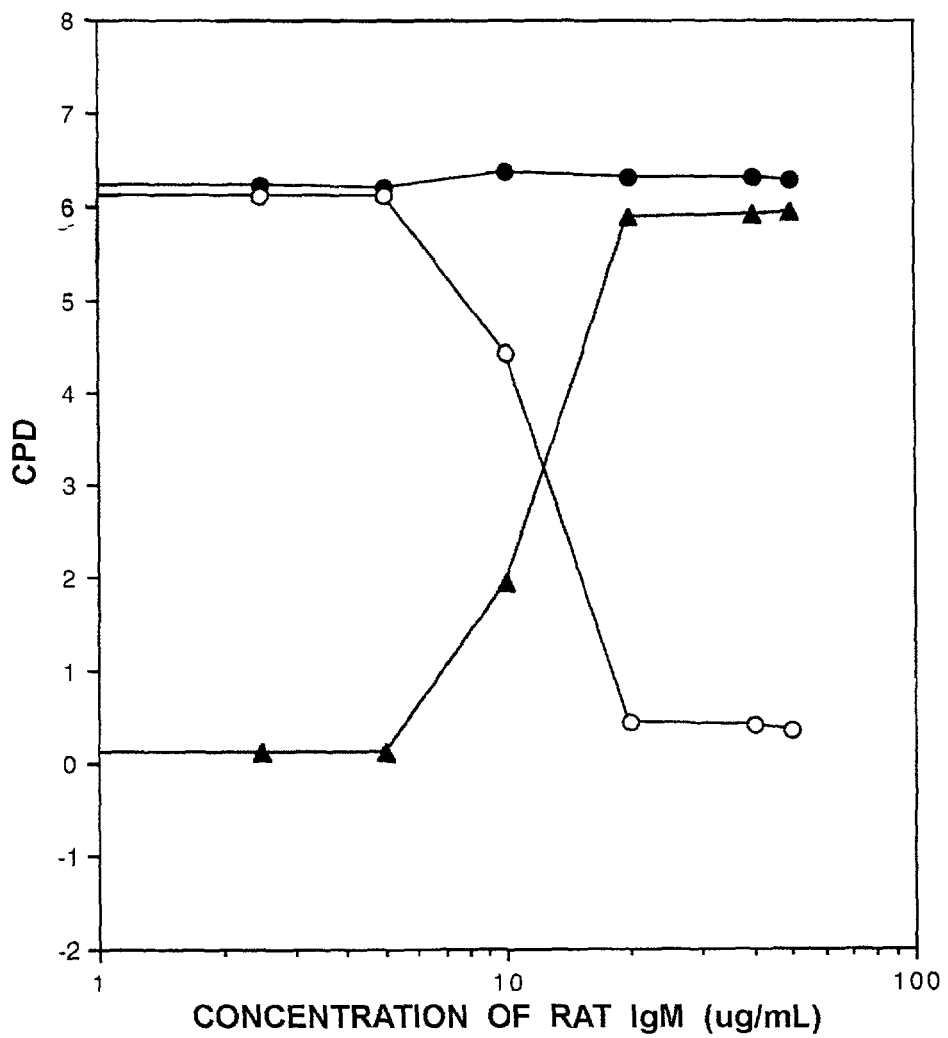
FIG. 112. Effect of Rat IgM on $GH_3$ Cell Growth in Serum-free Defined Medium±$E_2$.
Figure 113:
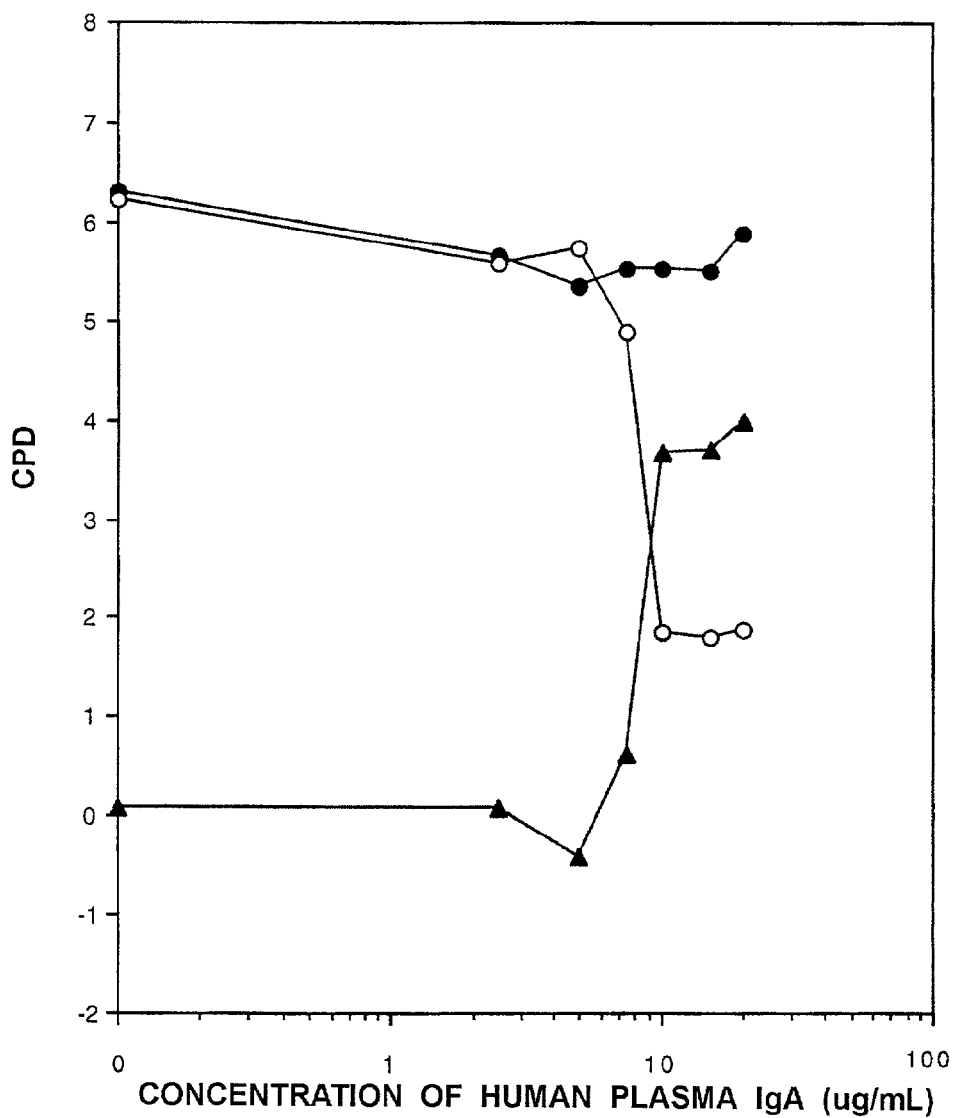
FIG. 113. Effect of Human Plasma IgA on $GH_3$ Cell Growth in Serum-free Defined Medium±$E_2$.
Figure 114:
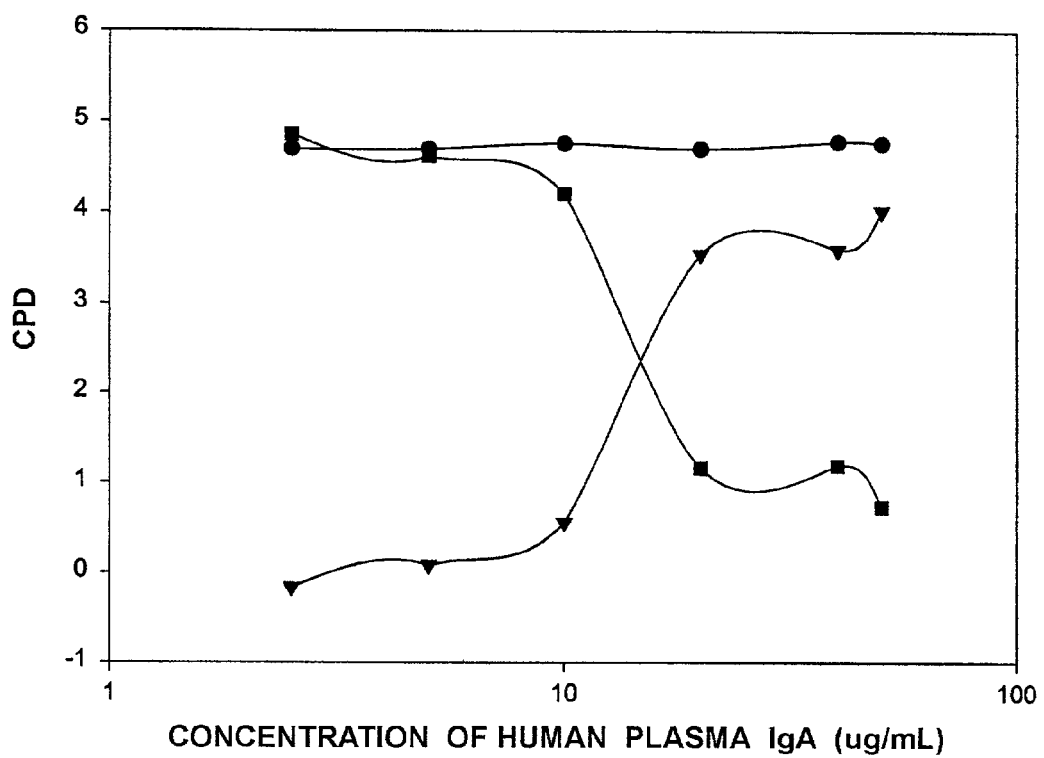
FIG. 114. Effe ct of Human Plasma IgM on $GH_3$ Cell Growth in Serum-free Defined Medium±$E_2$.
Figure 115:
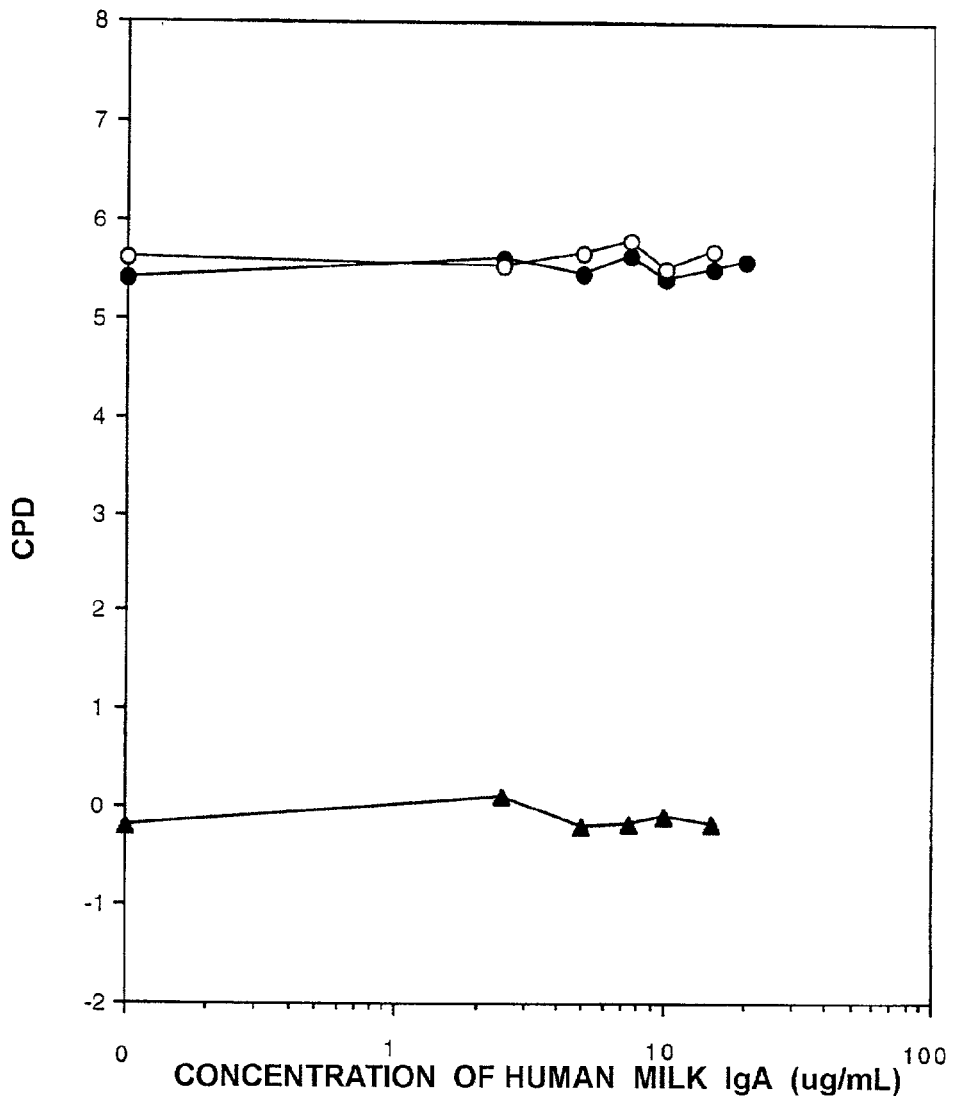
FIG. 115. Effect of Human Secretory IgA on $GH_3$ Cell Growth in Serum-free Defined Medium±$E_2$.

The present series of cell growth assays above were continued with the related $GH_3$ cells, again in serum-free defined the preferred formulation of PCM-9 medium. Rat myeloma derived IgA was an effective estrogen reversible inhibitor of these cells in a 9 day growth assay (FIG. 111). The maximum estrogenic effect exceeded 5 CPD. A similar assay with rat IgM was conducted (FIG. 112). It showed even greater inhibition at 10 µg/mL than with IgA. The estrogenic effect recorded in 10 days was nearly 6 CPD. These same assays were next repeated with the human immunoglobulins. Human pIgA was an estrogen reversible inhibitor of $GH_3$ cell growth (FIG. 113). It was not as effective as its rat counterpart, but the estrogenic effect with the human immunoglobulin was still 4 CPD. Also, human IgM was effective with $GH_3$ cells (FIG. 114). Again the estrogenic effect was about 4 CPD. In the final study with $GH_3$ cells, it was again apparent that human milk derived sIgA was not inhibitory (FIG. 115).

Figure 116:
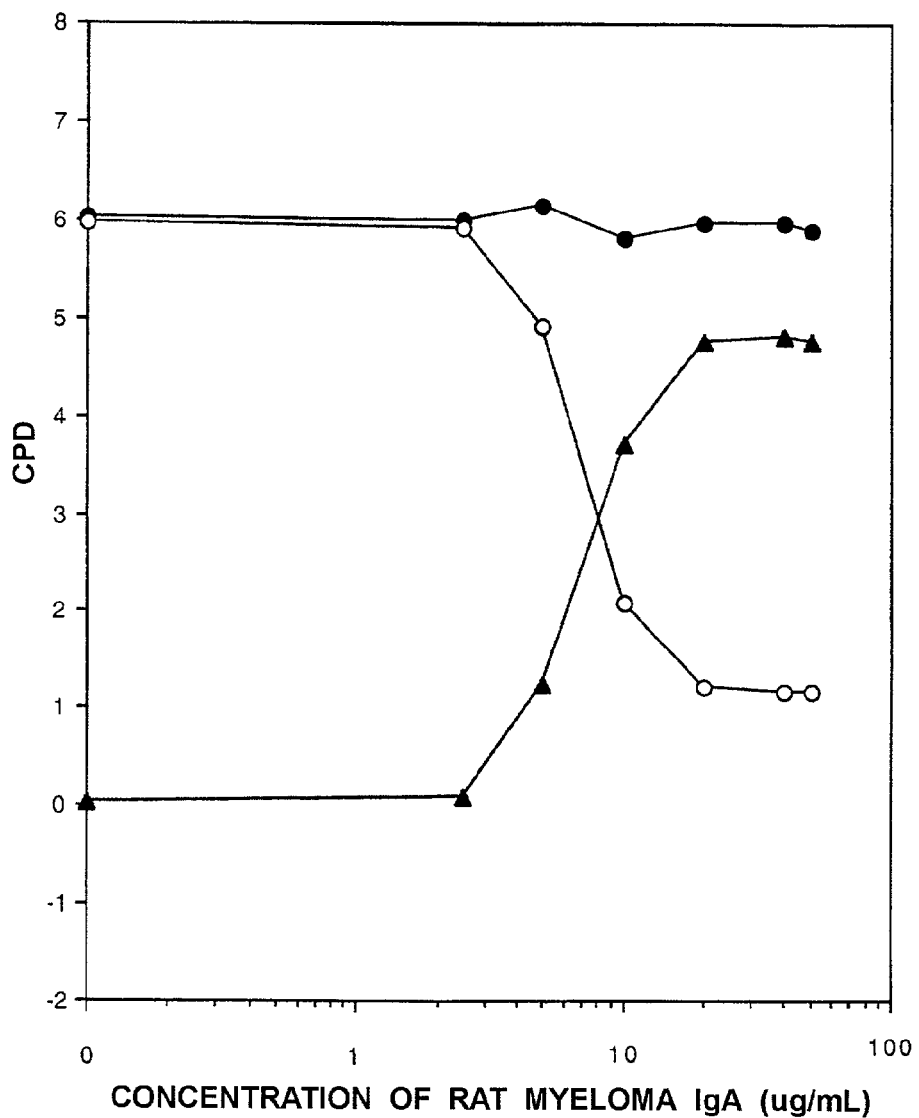
FIG. 116. Effect of Rat Myeloma IgA on $GH_4C_1$ Cell Growth in Serum-free Defined Medium±$E_2$.
Figure 117:
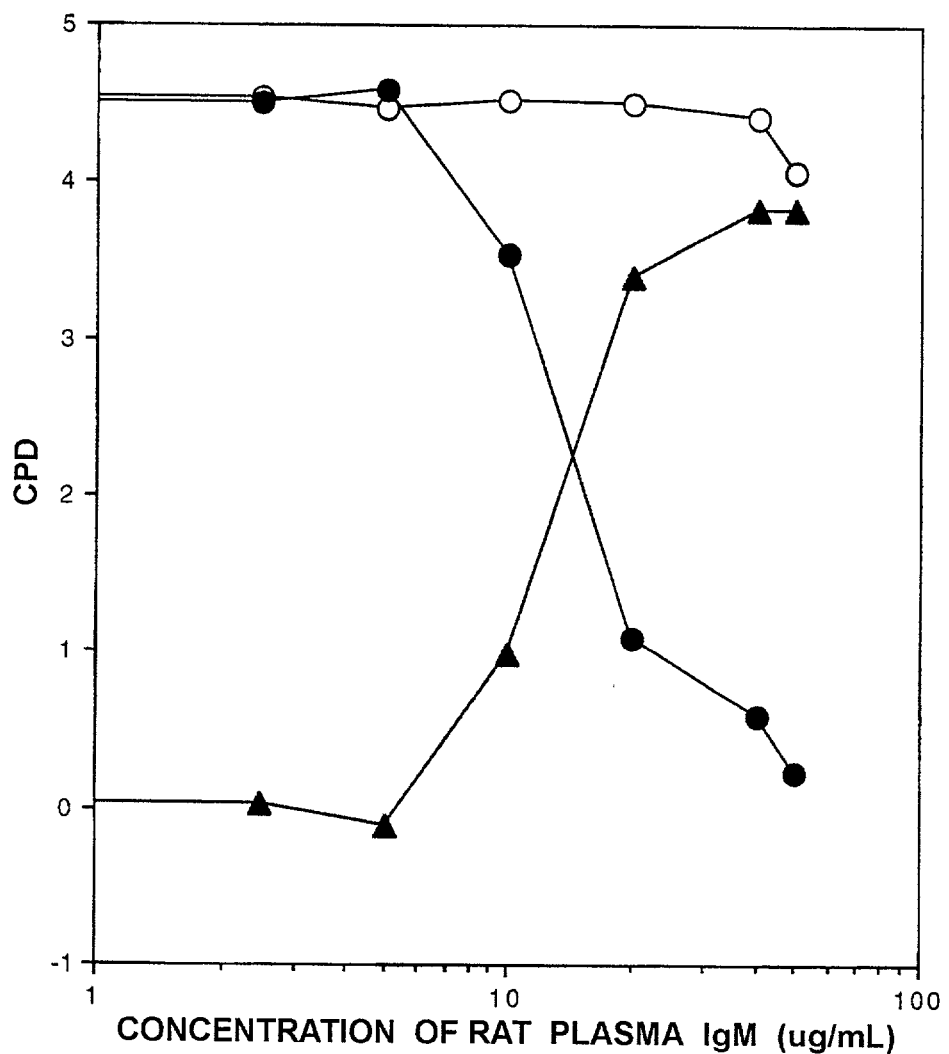
FIG. 117. Effect of Rat Plasma IgM on $GH_4C_1$ Cell Growth in Serum-free Defined Medium±$E_2$.
Figure 118:
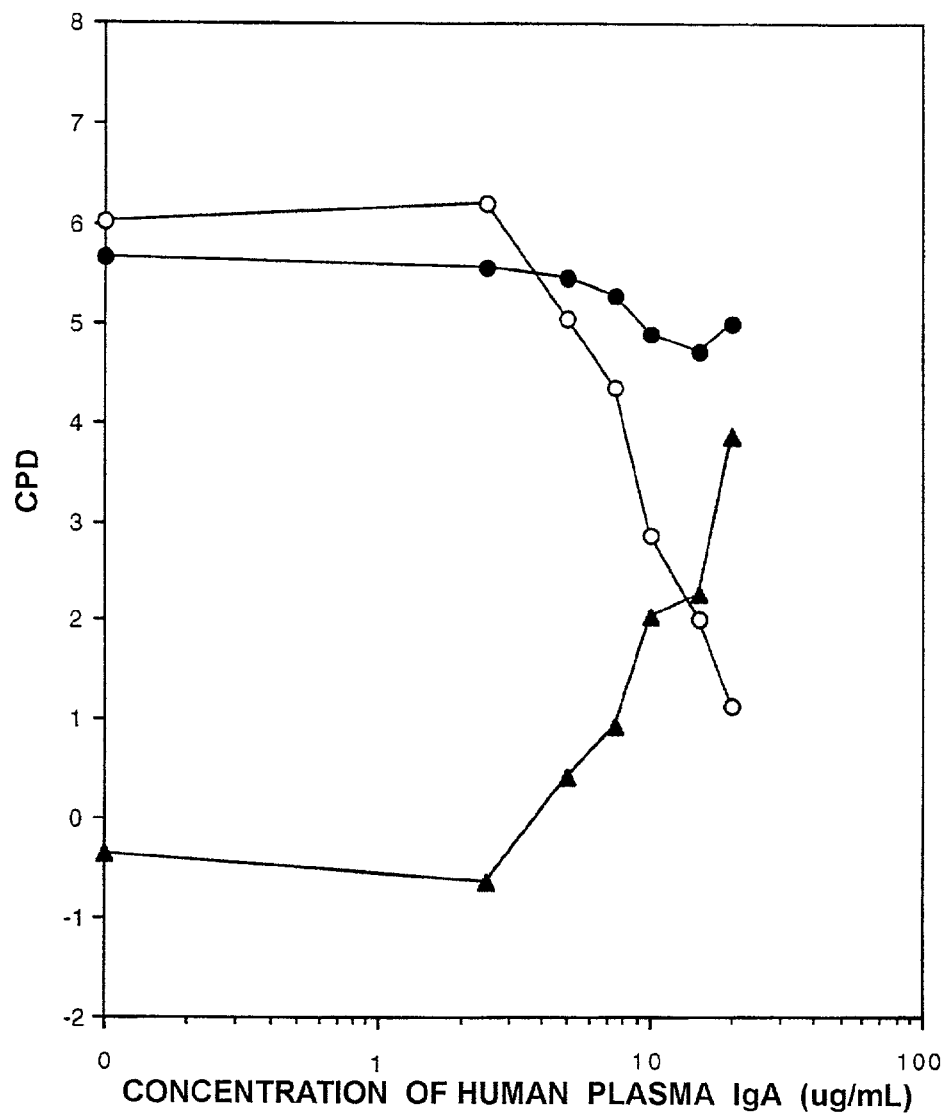
FIG. 118. Effect of Human Plasma IgA on $GH_4C_1$ Cell Growth in Serum-free Defined Medium±$E_2$.
Figure 119:
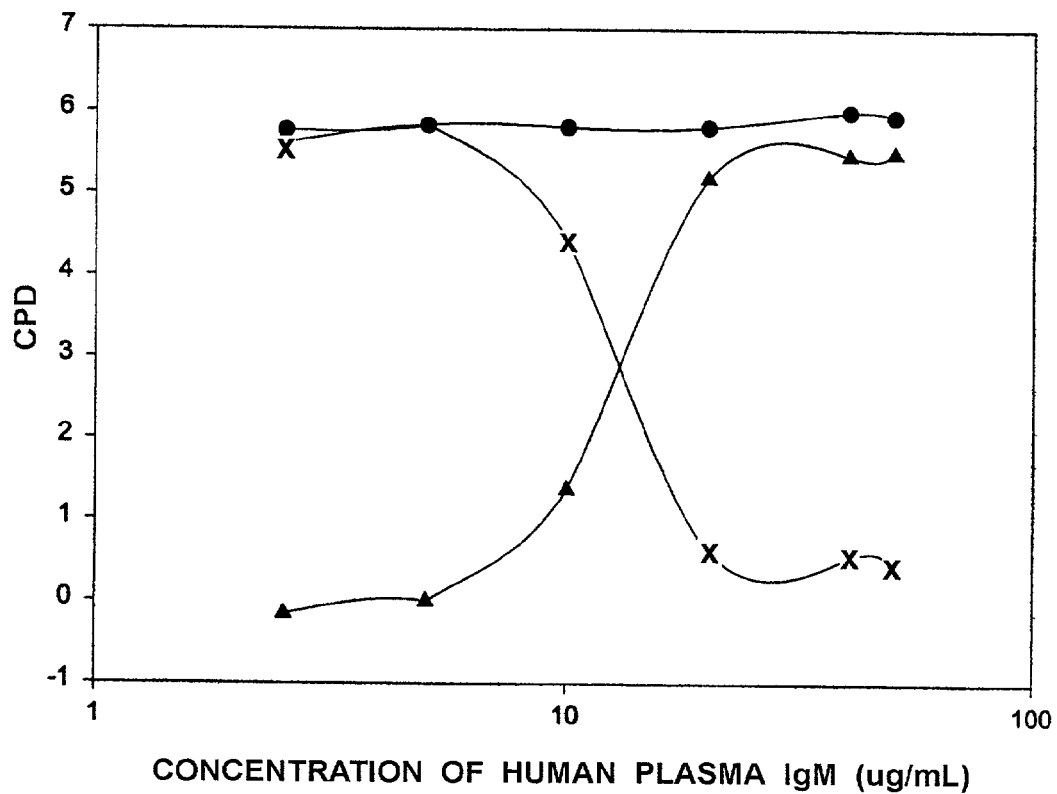
FIG. 119. Effect of Human Plasma IgM on $GH_4C_1$ Cell Growth in Serum-free Defined Medium±$E_2$.

The studies above with $GH_1$ and $GH_3$ cells were continued with the related $GH_4C_1$ line, again in serum-free defined PCM-9 medium. Rat myeloma derived IgA was an effective estrogen reversible inhibitor of these cells in a 9 day growth assay (FIG. 116). The maximum estrogenic effect approached 5 CPD. A similar assay with rat plasma IgM was conducted (FIG. 117). It showed slightly less inhibition than IgA. The estrogenic effect recorded in 10 days was nearly 4 CPD. These same assays were next repeated with the human immunoglobulins. Human pIgA was an estrogen reversible inhibitor of $GH_4C_1$ cell growth (FIG. 118). It was not as effective as its rat counterpart, but the estrogenic effect with the human immunoglobulin was still almost 4 CPD. Also, human pIgM was effective with $GH_4C_1$ cells (FIG. 119). The estrogenic effect was about 5 CPD. In the final study with $GH_4C_1$ cells it was again apparent that human milk derived sIgA was not inhibitory (FIG. 120).

C. H301 Syrian hamster kidney tumor cells. The studies with this cell line were done in the preferred formulation of CAPM defined medium described in TABLE 7. Because hamster IgA and IgM were not available, these experiments began with plasma IgA from mouse (FIG. 121). Mouse IgA was very effective with hamster H301 cells. The estrogenic effect was>5 CPD. Human plasma IgA was also effective (FIG. 122A). The maximum estrogenic effect reached 4 CPD. Secretory IgA was inactive (FIG. 122B). With this cell line, human IgM also was an estrogen reversible inhibitor. As shown in FIG. 123, a dose-response study demonstrated that in serum-free defined medium with 40 µg/mL of human plasma IgM, concentrations of 0.1 to 1.0 picomolar $E_2$ caused significant growth (p<0.01). This data demonstrate the extraordinary sensitivity of the serum-free defined cell growth assays in the presence of immunoglobulin. The data in FIG. 123 provide strong support for the view that the H301 cells can be used to characterize the new ERγ and characterized in preceding Examples.

D. MCF-7A and MCF-7K human breast cancer cells. For this series of experiments the serum-free defined medium was the preferred formulation of DDM-2MF described in TABLE 7. Two highly applied MCF-7 human breast cancer cell strains were applicable to this series of investigations. As shown with MCF-7A cells in DDM-2MF serum-free defined medium, plasma IgA was highly effective as an estrogen reversible inhibitor. The estrogenic effect exceeded 4 CPD in 10 days (FIG. 124A). In contrast, sIgA was inactive (FIG. 124B). With the MCF-7K strain, the results were nearly identical. Plasma IgA was effective (FIG. 125A) and sIgA was inactive (FIG. 125B). The estrogenic effects caused by pIgA were replicated by substitution of plasma IgM. With MCF-7A and MCF-7K, pIgM was an effective estrogen reversible sustaining estrogenic effects of>4 CPD (FIGS. 126 and 127, respectively). In a final study of this series, an $E_2$ dose-response experiment was conducted with MCF-7K cells in DDM-2MF plus 40 µg/mL of plasma IgM. The results were remarkable. Estrogen at as low as 0.1 picomolar caused more than one-half maximum growth response (FIG. 128). The extraordinary sensitivity of this assay methodology is clearly established. These results add more evidence that a very high affinity estrogen receptor (i.e. ERγ) regulates growth and is yet to be defined in human breast cancer cells.

E. T47D human breast cancer cells. The T47D cell line was assayed for immunoglobulin effects in the preferred formulation of serum-free defined medium DDM-2MF described in TABLE 7. As shown in FIG. 129A, human plasma IgA was a very effective estrogen reversible inhibitor with T47D cells. The maximum estrogenic effect was 6 CPD or a 72-fold cell number increase in 12 days. In contrast, sIgA was inactive at up to 20 µg/mL (FIG. 129B). Likewise, human plasma IgM is effective (FIG. 130), demonstrating complete inhibition of cell growth by 20 µg/mL IgM. The estrogenic effect was 5 CPD in 12 days. In experiments not shown, the effects of plasma derived IgM were compared to myeloma derived IgM. This study yielded the same estrogenic effects with both sources of IgM. Again, the antigenic determinant appears to be unimportant. The results support the view that the heavy chains dictate the activity. In other studies with T47D cells in defined medium containing 40 µg/mL, the dose-response effects with $E_2$ showed more than one-half maximum growth at 0.1 picomolar (FIG. 131). These results continue to fortify the theme that the methods described in this Example allow investigation of potential estrogenic compounds and substances that might be present in samples of industrial or biological materials at very low concentrations. It is also apparent that the data supports the view that a high affinity ERγ regulates growth.

F. ZR-75-1 human breast cancer cells. For these experiments the serum-free medium was the preferred formulation of DDM-2MF described in TABLE 7. Plasma IgA was an estrogen reversible inhibitor with ZR-75-1 cells (FIG. 132A). The estrogenic effect was recorded at 5 CPD in 14 days. As seen before with the other $ER^+$ cell lines above, sIgA was not an inhibitor with ZR-75-1 cells (FIG. 132B). Plasma IgM was also assayed with the ZR-75-1 cells (FIG. 133). It was a potent estrogen reversible inhibitor under these completely serum-free defined conditions. As discussed above, this line had been thought to be estrogen responsive in serum-free culture. However, the former methods were not serum-free. As disclosed herein, it has now been established in entirely different culture conditions and shown that this line is truly estrogen growth responsive in culture.

G. HT-29 human colon cancer cells. For this series of experiments the serum-free defined medium was the preferred formulation of CAPM described in TABLE 7. As expected from endocrine physiology, colon is not a sex steroid hormone growth regulated tissue as are others such as breast, uterus, ovary and pituitary. However, it was discovered that this tissue is thyroid hormone growth responsive. As shown in FIG. 134, HT-29 human colonic carcinoma cells grow in CAPM independently of the presence of thyroid hormone. This growth is promoted by the other factors present in CAPM minus $T_3$. However addition of plasma IgM at 40 µg/mL had a dramatic effect. In the absence of $T_3$ HT-29 cell growth was inhibited to ≦1.0 CPD in 10 days. Addition of increasing concentrations of $T_3$ restored growth (FIG. 134). This demonstrates that colonic cancer cells respond to thyroid hormones in the same manner that $ER^+$ cells respond to $E_2$. Estrogens and thyroid hormones belong to the same superfamily of receptors and both are required for normal physiologic growth and development (Williams G R and Franklyn J A (1994) *Baillieres Clin Endocinol Metab* 8, 241-266; Tsai M J and O'Malley B W (1994) *Annu Rev Biochem* 63, 451486). This is the first demonstration of a secretory immunoglobulin acting directly as a thyroid hormone reversible growth inhibitor of a human origin colon cancer cell line.

H. LNCaP human prostatic carcinoma cells. For this series of experiments the serum-free defined medium was the preferred formulation of CAPM described in TABLE 7. LNCaP cells were negatively regulated by plasma IgA (FIG. 135A). The immunoglobulin was a DHT reversible inhibitor that was completely effective at 10 µg/mL. The androgenic effect was >5 CPD in 12 days. As seen with the $ER^+$ cell lines above, sIgA was not inhibitory with LNCaP cells (FIG. 135B). Two different types of human IgM were also compared with LNCaP cells (FIG. 136). They were plasma derived and myeloma derived IgM. Despite the differences in antigen binding domains, both forms were equally inhibitory and both forms were reversed by 10 nM DHT. These results indicate that the Fc/heavy chain of IgM is the functional activator of the inhibition.

Summary of the estrogenic effects of IgM on $ER^+$ cell growth. FIG. 137 presents a summary of the effects of IgM derived from different species with a variety of $ER^+$ cell lines. This summary presents the maximum estrogenic effects recorded under conditions described above in serum-free defined medium with each cell line±10 nM $E_2$. Estrogenic effects ranged from 4 to >7 CPD. Comparison of the results in FIG. 137 with those in TABLE 10 show in general that the results achieved in completely defined medium are equal to or greater than those seen in CDE-serum cultures.

Discussion of Example 21. These methods will permit evaluation of industrial, environmental, biological, medical, veterinary medicine and other potential sources of estrogenic or androgenic activity under the most sensitive conditions yet developed. Estrogenic activity is measurable at ≦1.0 picomolar concentrations. Two cell lines, MTW9/PL2 and H301, are preferred potential sources of identification of the new growth regulatory ERγ. The evidence presented with MCF-7 and T47D human breast cancer cells support the presence of a new growth regulatory ERγ. Because the purified IgA and IgM described herein are as effective as serum-borne inhibitors, the serum-free methods described herein provide unique tools to search for ERγ. Assays conducted under these conditions permit estimation of estrogen sensitivities in ranges not approachable by other technology. These methods can also be adapted to measurement of the inhibitor in biological fluids available in only small supply. For example, coupled with use of XAD-4 resin extraction to remove steroids, bodily fluids and other source materials can be assayed on small scale to determine the concentration of effective inhibitor. This is of particular interest because IgA in plasma is >90% inactive monomer and <10% active dimer/polymer. Measurement of IgA by conventional methods gives total concentrations, and does not determine the concentration/presence of active inhibitor. The present biological activity method has distinct features and advantages, and can serve as an adjunct measurement.

Serum-free defined medium assays can be used to search for new compounds that mimic the action of immunoglobulins to block cancer cell growth in its early stages. This screening can be done under conditions in which serum proteins might interfere. Compounds so-identified can next be evaluated by addition of CDE-serum or XAD-4 treated serum to determine if serum proteins interfere and to determine drug efficacy in vitro under both serum-free defined medium conditions and serum supplemented conditions. Serum-free defined medium method can be used for screening of compounds that may either enhance or inhibit immune function at the epithelial cell level. Compounds with these activities may have utility as immune enhancers to help reduce the risk of cancer development. These assay methods offer a screening tool for such compounds that has not been available before. Larger magnitude effects permit greater accuracy with the new assay methods when estimating effects of substances that are less potent than natural estrogens.

Example 22

Effect of Tamoxifen Antiestrogen in Serum-free Defined Medium

This Example illustrates the use of one of the present assays to detect the estrogenic or anti-estrogenic effect of a substance. In particular, the classical antiestrogen was assayed as a demonstration of the usefulness of the present assay system.

Background of Tamoxifen Effects and Clinical Applications. The antiestrogenic effects of tamoxifen are well documented. Most evidence suggests this compound and its active metabolite 4-hydroxyl-tamoxifen prevent growth of ERα positive cells via interaction with the receptor (Coezy E et al. (1982) *Cancer Res* 42, 317-323; Bardon S et al. (1984) *Mol Cell Endocrinol* 35, 89-96; Reddel R R et al. (1985) *Cancer Res* 45, 1525-1531). However, it has also been suggested that tamoxifen blocks growth factor promoted MCF-7 breast cancer cell growth (Vignon F et al. (1987) *Biochem Biophys Res Commun* 146, 1502-1508). Also, tamoxifen has high affinity binding sites and actions distinct from the estrogen receptor (Sutherland R L et al. (1980) *Nature* (Lond) 288, 273-275; Phaneuf S et al. (1995) *J Reprod Fertil* 103, 121-126). Despite its complex actions, tamoxifen has widespread use as a treatment for breast cancer (Fisher B et al. (1998) *J Natl Cancer Inst* 90, 1371-1388; Jaiyesimi I A et al (1995) *J Clin Oncol* 13, 513-529; Clinical Trial Report (1997) *J Clin Oncol* 15, 1385-1394; Clinical Trial Report (1987) *Lancet* 2(8552), 171-175; Forrest A P et al. (1996) Lancet 348(9029), 708-713; Tormey D C et al. (1996) *J Natl Cancer Inst* 88, 1828-1833; Gundersen S et al. (1995) *Breast Cancer Res Treat* 36, 49-53; Gelber R D et al. (1996) *Lancet* 347(9008), 1066-1071; Raabe N K et al. (1997) *Acta Oncol* 36, 2550260).

Serum-free Medium Effects of Tamoxifen. The effects of tamoxifen (TAM) were reexamined under completely serum-free defined conditions. It is very important to note that throughout the Examples herein, data is presented showing that estrogens have either had no effect on growth in defined medium or at most a 1.0 CPD effect that was related to saturation density. This was true no matter if phenol red was present or absent from the medium, as shown in Example 8 and reported (Moreno-Cuevas J E and Sirbasku D A (2000) *In Vitro Cell Dev Biol* 36, 447-464). In similar assays, $1.0 \times 10^{-7}$ M tamoxifen was completely inhibitory with T47D cells in culture, as shown in FIG. 138. The study shown in FIG. 138 examined the concentrations of tamoxifen needed to fully inhibit T47D cell growth in the preferred formulation of DDM-2MF serum-free defined medium without any source of estrogens. The expected outcome was no tamoxifen inhibition. As shown, estrogen alone had only a 1.0 CPD effect in serum-free defined medium. However, tamoxifen had unexpected effects revealed by the use of serum-free defined medium. Tamoxifen effectively arrested growth at $1.0 \times 10^{-7}$ M. Higher concentrations were cytotoxic. It should be noted that tamoxifen had the same effect as immunoglobulins IgA and IgM. To demonstrate this fact another way, the experiment in FIG. 139 shows that estrogens completely reverse the effect of $1.0 \times 10^{-7}$ M tamoxifen. This sequence of experiments shows the same results as that shown above with plasma IgA and IgM and ER$^+$ cell lines.

Discussion of Example 22. The observation of inhibition of cell growth by a classical antiestrogen demonstrates the usefulness of this technology to search for other antiestrogenic compounds. Furthermore, because of the current intense focus on the search for SERMs (i.e. Selective Estrogen Receptor Modulators) the serum-free technology disclosed herein has particularly useful applications. Specific types of SERMS can be sought for different cell types. Those SERMs that do not cause breast cancer cell growth can be readily identified by this technology. Those SERMs with multiple activities can be identified before conducting expensive animal testing.

The technology presented permits a clear definition of antiestrogens with "mixed" functions (e.g. tamoxifen-like, that act at several sites) versus those with a "pure" function mediated only by the estrogen receptor. To date, no similar easily applied in vitro method based on serum-free defined medium and secretory immunoglobulins is available that produces growth as an endpoint of the assay. An entirely new function for the drug tamoxifen is proposed, in which the tamoxifen mimics the immune system effects on ER$^+$ cancers thereby inhibiting growth. Estrogen reverses these effects, not as a consequence of interaction with the classical ERα, but as a consequence of the ERγ. Tamoxifen may also be an antagonist of ERγ, and this possible use for tamoxifen is now proposed.

The serum-free defined medium technology presented herein has direct application to the assay of a great variety of drugs now in use by women either before the onset of breast cancer or after the onset. Drugs or preparations such as anti-depressants, herbal extracts, soy products, other food, plant or microorganism extracts, estrogenic creams and cosmetic preparations can be assessed for anti-estrogenic or estrogenic activity.

Serum-free assay methods are also applicable to exploration of additional antiandrogenic compounds. Furthermore, in view of the possible role of estrogens as well as androgens in prostate growth, this technology can be used to search for compounds with both activities.

Example 23

IgG1 and IgG2 as Immunoglobulin Regulators of Estrogen and Androgen Responsive Cancer Cell Growth This Example investigates and discusses the relative effectiveness of certain IgGs as inhibitors of steroid hormone responsive cancer cell growth.

The IgG Subclasses and the Importance of Assessing Each for Activity. As reviewed above, in the Background of the Invention, three classes of immunoglobulins are secreted by mucosal tissues. The IgG class is lowest in concentration in secretions, but still physiologically important because of its capacity to neutralize pathogens by different mechanisms. Additionally, the studies above showed that bulk purified mixtures of all subclasses of horse and rat IgG were not estrogen reversible inhibitors for MTW9/PL2 rat mammary tumor cells. The human clinical importance of understanding and measuring IgG subclasses has been growing steadily. From a few clinical reports per year in 1970, the literature now exceeds four hundred reports a year. These assays are significant for several reasons. (i) They provide a clearer picture of an individual's susceptibility to disease. (ii) An awareness that treatment for subclass deficiencies is important. (iii) The subclasses can be used to assess the state of a number of diseases. (iv) The importance of IgG subclass difference between ethnic groups and different races is a potential area for expanded control of disease.

Figure 140:
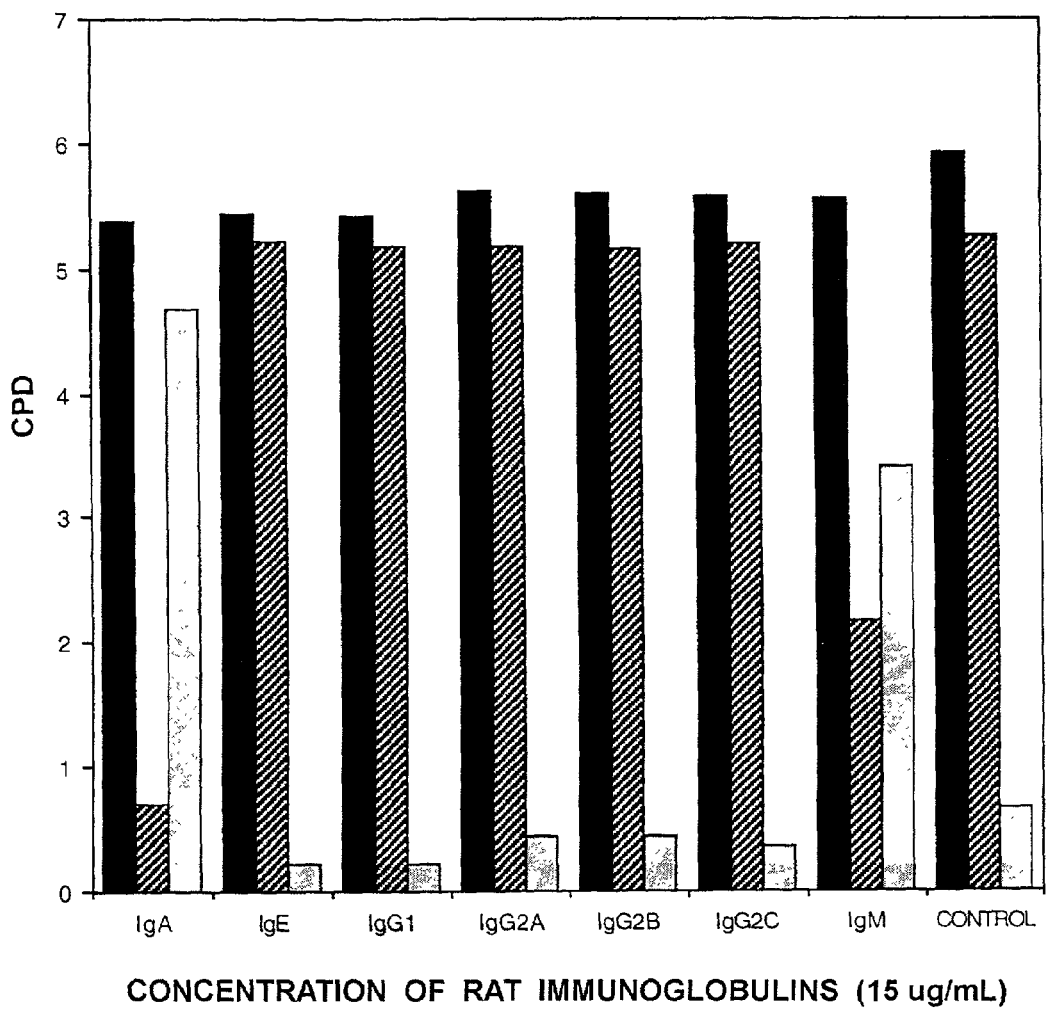

Test of Rat IgG Subclasses as Estrogen Reversible Inhibitors of MTW9/PL2 Rat Mammary Tumor Cell Growth. The IgG subclasses of rat are IgG1, IgG2A, IgG2B and IgG2C. These IgGs, obtained from commercial sources previously identified herein, were tested at 15 µg/mL with MTW9/PL2 cells in DDM-2A serum-free defined medium (FIG. 140). All four IgG subclasses were compared to rat pIgA and rat pIgM. The latter two were estrogen reversible inhibitors, as expected (FIG. 140). However, the four IgG subclasses were not inhibitors at a concentration that was effective with IgA or IgM. The estrogenic effects recorded in cultures with them were no larger than seen in serum-free defined medium alone (FIG. 140). Clearly, IgG are not effective steroid hormone modulators in rat.

Test of Human IgG Subclasses as Estrogen Reversible Inhibitors of Breast and Prostate Cancer Cell Growth. The subclasses of human IgG are IgG1, IgG2, IgG 3 and IgG4. They are formed with both λ and κ light chains. A series of studies was performed, and it was found that with human breast cancer cells, only IgG1κ was a significant estrogen reversible inhibitor. FIG. 141 shows a comparison of its activity to human pIgA and pIgM. At 40 µg/mL, it was 37% as effective as pIgA. A similar study with LNCaP cells showed that only IgG1κ had activity greater than the estrogenic effect seen in CAPM serum-free defined medium only (FIG. 142). In some experiments with prostate cells, IgG2κ also showed androgen reversible inhibitory activity (data not shown).

Discussion of Example 23. The effect of IgG1κ raises an issue not encountered with IgA or IgM. The preference for the κ light chain implies that a different receptor mediates the effects of this immunoglobulin. This immunoglobulin may have greater effect on normal breast or prostate cells as an inhibitor. It is also believed that part of the transformation/ progression process leading to hormone responsive cancers is an attenuation of the effectiveness of IgG1κ as an inhibitor. The present IgG1 observations have other applications, as well, including the measurement of the IgG1κ subclass in different populations such as black American, Asian, white, Native American and Hispanic with contrasting susceptibilities to breast and prostate cancer, or individuals within any one ethnic group, may provide additional information and confirmation of the usefulness of such measurements. These measurements can be made in bodily fluids or plasma. Measurement in milk and breast fluid may provide an indication of susceptibility to the development of breast cancer.

Irrespective of the receptor that mediates the growth response of IgG1κ, this receptor will be a candidate for the missing transcytosis receptor for IgG. Its molecular identification has utility in diagnostic specimens of breast, prostate and other cancers and can be used to determine new uses of the immune system for therapeutic applications. Once it is completely identified, the receptor that mediates the IgG1 growth inhibition effect will provide another target for development of compounds that mimic the immune system inhibition of cancer cell growth.

Example 24

Mediation of IgA/IgM Effects by the Poly-Ig Receptor

In this Example, it was determined that a poly-Ig receptor or a poly-Ig like receptor mediates the inhibition of cell growth by IgA and IgM. The negative response to IgA and IgM is mediated by the mucosal poly-Ig receptor or a very similar structure with the same immunoglobulins specificity as well as the same immunological and $M_r$ properties. The known poly-Ig receptor is a $M_r$ 100,000 transmembrane protein with several properties that place it in the Ig superfamily of receptors (Krajči P et al. (1992) *Eur J Immunol* 22, 2309-2315; Williams A F and Barclay A N (1988) *Annu Rev Immunol* 6, 381-405).

Genetic Properties of the Poly-Ig Receptor. The complete genomic and cDNA sequences of the poly-Ig receptor have been determined (Krajči P et al. (1991) *Hum Genet* 87, 642-648; Krajči P et al. (1992) *Eur J Immunol* 22, 2309-2315). Poly-Ig receptor gene has been localized to chromosome 1 at 1q3 1-q42 locus Krajči P et al. (1991) *Hum Genet* 87, 642-648; Krajči P et al. (1992) *Eur J Immunol* 22, 2309-2315; Karjči P et al. (1995) *Adv Exp Med Biol* 371A, 617-623). The long arm of chromosome 1 had initially been described as the location of the most frequent ctyogenetic abnormalities found in human breast carcinoma (Bieche I et al. (1995), *Clin Cancer Res* 1, 123-127). More recently this conclusion was modified to state that distal alterations of the short arm of chromosome 1 are the most frequent cytogenetic abnormalities in human breast carcinoma (Bieche I et al. (1999) *Genes Chromosomes Cancer* 24, 255-263). The gene encoding the poly-Ig receptor is linked to D1S58 on the long arm of chromosome 1 (Karjči P et al. (1992) *Hum Genet* 90, 215-219). This locus (i.e. D1S58) is a known site for "allelic imbalances" in a remarkable 75% of all breast cancers (Loupart M-L et al. (1995) *Genes Chromosomes Cancer* 12, 16-23). Allelic imbalances include "Allelic Loss, Allelic Gain, and Imbalances". Loss of heterozygosity (LOH) is consistently high along the length of the long arm of chromosome 1 at D1S58 (i.e. 46%) in breast cancers (Loupart M-L et al. (1995) *Genes, Chromosomes & Cancer* 12, 16-23). LOH is strongly associated with development of cancer. Viewed in light of the present invention, these published published reports gain new meaning and significance. The report describing changes in D1S58 did not specify what gene or type of gene or function might be impaired by damage to this locus (Loupart M-L et al. (1995) *Genes, Chromosomes & Cancer* 12, 16-23). The present results indicate that this "hot spot" is either the authentic poly-Ig receptor acting in its new capacity as a growth regulator, or a very closely related receptor with similar molecular weight, ligand binding and immunological properties. However, it must be recognized that the functional form of the growth regulatory receptor may arise from alternate splicing of the poly-Ig receptor gene. Alternate splicing of the poly-Ig receptor gene is known in rabbit (Deitcher D L and Mostov K E (1986) *Mol Cell Biol* 6, 2712-2715; Frutiger S (1987) *J Biol Chem* 262, 1712-1715) and bovine tissue (Kulseth M A et al. (1995) *DNA Cell Biol* 14, 251-256). It has yet to be proven (or disproven) in humans. Certainly this possibility is still open with hormone responsive cancer cells. Alternately the 1q31-q41 region of chromosome 1 contains several other genes of immunological interest (Krajči P et al. (1991) *Hum Genet* 87, 642-648; Karjči P et al. (1992) *Eur J Immunol* 22, 2309-2315; Bruns G A P and Sherman S L (1989) *Cytogenet Cell Genet* 51, 67-77). There can be little doubt that the discovery of immune negative regulation of growth mediated by the poly-Ig receptor, or one very related, is an advance. It was arrived at not by the genetic approach described above which screens genes without regard for function, but instead by a functional approach based on the biochemical, endocrine and cell biology studies described above.

Structural Properties of the Poly-Ig Receptor. A very detailed structural analysis of the human poly-Ig receptor has been presented by others (Krajči P et al. (1992) *Eur J Immunol* 22, 2309-2315). Altogether, eleven exons cover the entire coding sequence. The five extracellular domains designated D1, D2, D3, D4 and D5 were coded for by exons E3, E4, E5 (D3 & D4), E5 and E6, respectively. The five extracellular domains are repeating disulfide stabilized Ig-like domains with homology to the Ig superfamily of receptors. The functions of D2, D3 and D4 are not well defined. The functions of D1 and D5 are well studied. D1 is the binding site for the Fc domains of IgA and IgM (Frutiger S et al. (1986) *J Biol Chem* 262, 1712-1715; Bakos M-A et al. (1993) *J Immunol* 151, 1346-1352; Røe M et al. (1999) *J Immunol* 162, 6046-6052). The presence of a "J" chain in the immunoglobulins appears essential for receptor binding and secretion (Vaerman J-P et al. (1998) *Eur J Immunol* 28, 171-182). D1 is highly conserved among species. The amino acid sequence of the D1 loop responsible for IgA/IgM binding has been established as residues 15→37 (Bakos M-A et al. (1991) *J Immunol* 147, 3419-3426; Bakos M-A et al. (1993) *J Immunol* 151, 1346-1352; Bakos M-A et al. (1994) *Mol Immunol* 31, 165-168). A monoclonal antibody recognizing this sequence blocks the binding of the immunoglobulins. Also, anti-J chain blocks binding (Vaerman J-P et al. (1998) *Eur J Immunol* 28, 171-182). The D5 domain forms a covalent disulfide bond with IgA to form secretory sIgA. Exon 8 codes for the membrane spanning sequence/domain. Exons 9, 10 and 11 code for the three cytoplasmic domains that regulate various aspects of transcytosis (Breitfeld P P et al. (1990) *J Biol Chem* 265, 13750-13757; Reich V et al. (1996) *J Cell Sci* 109, 2133-2139; Karjči P et al. (1992) *Eur J Immunol* 22, 2309-2315). These domains are highly conserved (Banting G et al. (1989) *FEBS Lett* 254, 177-183). One serine residue is particularly important for transcytosis (Hirt R P et al. (1993) *Cell* 74, 245-255).

Clinical Studies of Secretory Component (Poly-Ig Receptor) Expression in Breast and Colon Cancer. Others have performed a study of the protein and mRNA expression of the poly-Ig receptor with a sample of human colon cancers (Karjči P et al. (1996) *Br J Cancer* 73, 1503-1510). Expression of secretory component was found in 33 colorectal adenomas (31 patients) and in 19 colorectal carcinomas from 19 patients. Although that study provides evidence that colon adenomas (i.e. a predisposition to colon cancer) and confirmed cancers express poly-Ig receptor, the investigators did not attempt to translate the observations further than to propose a role in "cellular dysplasia".

Likewise, the levels of secretory component have been measured by others in breast tumors from 95 patients with primary or metastatic disease (Stem J E et al. (1985) *Cancer Immunol Immunother* 19, 226-230). These authors proposed that low levels of secretory component (SC) were found in metastatic lesions and that this "could indicate a potential for SC involvement in immune regulation of tumor growth," referring to conventional antigen-antibody recognition immune effects. However, it was not undertaken to identify growth effects related to either the immunoglobulins IgA/IgM or to identify a role of the poly-Ig receptor directly. Furthermore, this study was incomplete. There was no attempt made to determine the estrogen receptor status of the primary or metastatic disease. Therefore, there was no correlation to growth state based on the most accepted criterion of steroid hormone receptor status. This line of study appears to have stopped with 1985 observation. The present invention has directly addressed the problem by demonstrating growth regulation by the secretory immune system using several different $ER^+$ cancers.

Lines of Evidence Supporting Poly-Ig Receptor or a Poly-Ig-like Receptor in Negative Growth Regulation. The present series of studies and observations indicate that the IgA/IgM mediating receptor has the properties of the poly-Ig receptor. Supporting facts include the following: (1) The source of the active IgA is not the deciding factor. Plasma or myeloma derived IgA are equally effective. Also, species makes little or no apparent difference in activity. IgA isolated from various species has major sequence homology in the α heavy chains but differences in the variable chains. This is consistent with mediation by an Fc superfamily receptor. (2) IgA purchased commercially from myeloma cell sources contains predominantly dimeric and polymeric immunoglobulin. It is highly active as an inhibitor. This is consistent with mediation by the poly-Ig receptor. (3) Cultures containing the active CA-PS-pool II material (see Examples 18 and 20) are predominantly dimeric/polymeric forms of immunoglobulins. These preparations are active in serum-supplemented and serum-free defined medium. This is consistent with the expected binding to the poly-Ig receptor. (4) IgM is at least as active, or more active than IgA on a molar basis. The source of the IgM can be from plasma or myeloma cells. They are equally effective. This is also expected of the poly-Ig receptor. (5) Anti-secretory component antibodies completely blocked the inhibitory effects of IgA and IgM. This not only indicates poly-Ig receptor mediation, it supports the view that IgA and IgM act via the same receptor. The poly-Ig receptor is known to conduct transcytosis of both of these immunoglobulins.

Secretory IgA is invariably inactive as an inhibitor. It has the five extracellular domains of poly-Ig receptor attached. By contrast, plasma derived IgA is fully active. To prove that pIgA does not have the secretory component whereas sIgA contains the 80 kDa receptor fragment, the Western analysis in FIG. 143 was done. Secretory IgA shows an 80 kDa cross-reaction band with anti-secretory component whereas pIgA shows no reaction. This was the expected result and provides additional support for the view that the poly-Ig receptor is the mediator. Because secretory component is isolated from milk sIgA, these results show that the secretory component used for immunization of the rabbits was free of the other subunits in IgA. This was a good control for the next experiments.

In the next experiments, anti-human secretory component antiserum was used to block the inhibiting effects of IgA and IgM. FIG. 144 shows the results with the T47D cells in serum-free defined medium DDM-2MF with human plasma IgM alone and with a series of dilutions of the antiserum. As shown, 10 nM $E_2$ completely reversed the IgM inhibition. Dilutions of 1:500 to 1:5000 also blocked the inhibition. In the insert in FIG. 144, a control study with pre-immune rabbit serum demonstrated it had no inhibitor blocking activity. A similar study was done with LNCaP cells in serum-free defined CAPM with human pIgA (FIG. 145). As shown, 10 nM $E_2$ completely reversed the pIgA inhibition. Anti-serum dilutions of 1:00 and 1:1000 also reversed the inhibition. Differences between the effective dilutions with T47D and LNCaP cells is due to changes in lots of commercially prepared antiserum.

To determine if IgA/IgM responsive cells expressed 1 00 kDa poly-Ig receptor, the Western analysis shown in FIG. 146 was done. Amounts of extracts of the designated cell types were analyzed with a 1:1000 dilution of rabbit anti-human secretory component. As expected MDCK cells were positive. This cell line has been studied for several years as a model of poly-Ig receptor sorting and function. LNCaP cells showed the same receptor (FIG. 146). Cell lines that were negative were ALVA-41, DU145, human fibroblasts, and PC3 cells (FIG. 146). As shown in multiple experiments in preceding Examples, LNCaP cells are IgA/IgM inhibited. The results of the Western analyses show that they express the poly-Ig receptor.

In the final experiments of this series, pIgA was tested with two of the cell lines that were poly-Ig receptor negative by the Western analysis shown in FIG. 146. The results with DU145 cells are shown in FIG. 147. Plasma IgA was not an inhibitor. A similar study with PC3 cells is shown in FIG. 148. Again, pIgA was not an inhibitor even at 50 µg/mL. These results demonstrate cells that lack the poly-Ig receptor are also insensitive to pIgA. The HT-29 colon cancer cells are known to express only the authentic form of the poly-Ig receptor. They are also negatively growth regulated by IgM.

Discussion of Example 24. For the first time a relationship between immunoglobulin growth regulation and the poly-Ig receptor is demonstrated. This receptor has in the past been studied only from the perspective of a transcytosis receptor. In view of all these results, the poly-Ig receptor very likely has more function than transcytosis only. Ongoing investigations are directed to identifying gene changes in the authentic poly-Ig receptor gene, which may include point mutations, deletions, insertions, and premature termination. The receptor mediating the effects of IgA/IgM may be an alternate splicing form of the original transcytosis receptor. Alternatively, changes in the regulation of expression may influence the presence or absence of this receptor. The positive correlation between the presence of ER and AR, and expression of the growth regulating poly-Ig receptor indicates regulation or positive influence by steroid hormones.

One of the primary themes of cancer research has been that loss of "tumor suppressor genes" causes the release of cells from negative regulation and thereby contributes to the progression to cancer. The present invention indicates that the poly-Ig receptor has a "tumor suppressor" function. It is present in cells that are regulated by IgA/IgM and absent in cells that are insensitive to immune inhibitors. This is a new aspect of cancer immunology not recognized before the present invention. For the first time, the poly-Ig receptor is connected to the D1S58 linked locus that is a "hot spot" for genetic changes in breast cancer. It is now proposed that this locus or near neighbors contain the growth regulating form of authentic transcytosis poly-Ig receptor or a very similar immunoglobulin superfamily receptor. Alternately the 1q31-q41 region of chromosome 1 contains several other genes of immunological interest that include the receptor for IgA/IgM. Those genes can be employed as screens for breast and other mucosal cell cancers. They are expected to indicate susceptibility and may be useful in prognosis and other diagnostic applications with human tissue and cancer samples. Analyses of allelic imbalances in the receptor gene are also foreseen as a new tool to determine susceptibility and prognosis for development of breast and other mucosal cancers, as will be the detection of mutations in the growth regulating intracellular domains of the receptor. The known amino acid sequence of the poly-Ig receptor does not contain the immunoreceptor tyrosine-based inhibitory motif (ITIM) common to a new family of inhibitory motif receptors (Cambier J C (1997) *Proc Natl Acad Sci* USA 94, 5993-5995). Other amino acid sequences may serve this same function.

Example 25

Mediation of IgG1κ Effects by a Fc-like Receptor

In this Example, it is shown that the inhibiting effects of IgG1κ were mediated by an Fc receptor or Fcγ-type receptor. It is highly unlikely that IgG1 acts via the poly-Ig receptor. The poly-Ig receptor has a requirement for "J" chain for binding (hence its specificity for dimeric/polymeric IgA or pentameric IgM each of which have one J chain). Also, as shown in TABLE 12, Fcγ receptors are localized in leukocyte series or bone marrow origin cells. There is no convincing evidence of their presence in epithelial cells or in secretory cells of the mucosa. It is now proposed that the receptor being sought is one analogous to the Fcγ in at least two significant properties. First, it binds monomeric IgG1 via the Fc domain of the immunoglobulin with some participation of the κ light chain. Second, that the receptor has inhibitory activity akin to a new family of Fc receptors. The amino acid sequence of the new IgG1κ receptor is expected to have an immunoreceptor tyrosine-based inhibitory motif (ITIM) (VxYxxL) (SEQ ID NO:1 and SEQ ID NO:2) common to the new family of inhibitory motif receptors (Cambier JC (1997) *Proc Natl Acad Sci* USA 94, 5993-5995). Other amino acid sequences may serve this same function.

It is proposed that the Fcγ family of receptors contains members that possess the very special property of mediating cell growth inhibition. The methods of identification are outlined below.

TABLE 12

Properties of the Fcγ Family of Receptors

| | FcγR1 (CD 64) | FcγRII (CD 32) | FcγRIII (CD 16) |
|---|---|---|---|
| IgG1 Binding | $K_a = 10^8 \, M^{-1}$ | $K_a = 2 \times 10^6 \, M^{-1}$ | $K_a = 5 \times 10^5 \, M^{-1}$ |
| Binding Order | IgG1> | IgG1> | IgG1= |
| | IgG3= | IgG3= | IgG3 |
| | IgG4> | IgG4> | |
| | IgG2 | IgG2 | |
| Found in these Cell Types | Macrophages Neutrophils Eosinophils | Macrophages Neutrophils Eosinophils Platelets B Cells | Natural Killer Cells Macrophages Neutrophils Eosinophils |

Discussion of Example 25.

The amino acid sequence of a new Fc family receptor may include immunoreceptor tyrosine-based inhibitory motif (ITIM) common to a new family of inhibitory motif receptors (Cambier J C (1997) *Proc Natl Acad Sci* USA 94, 5993-5995). The results obtained in the present studies support the involvement of Fc receptors of mucosal cells that include one of the known members of the family of ITIMs or other amino acid sequences that serve this same function. Ongoing work includes genetic mapping to a specific chromosome number and locus. The genomic DNA sequence of the new receptor (or existing receptor if already known), introns and exons, will be obtained. This receptor may be used for diagnostic and clinical proposes, and as a screen for genetic susceptibility to breast and prostate and other mucosal cancers, as described in more detail in U.S. patent application Ser. No. 09/852,547 entitled "Compositions and Methods for the Diagnosis, Treatment and Prevention of Steroid Hormone Responsive Cancers," which is hereby incorporated herein by reference. Identification of mutations and changes associated with progression from normal cells to autonomous cancer cells is also expected, and, along with detection of changes in regulation of expression and allelic imbalances in the receptor gene, will have very useful research, diagnostic and clinical applications.

Example 26

Immunoglobulin Inhibitors as Tools for Identifying the Receptors that Mediate the IgA/IgM/IgG Cell Growth Regulating Effects As shown by Examples 24 and 25, the present Immunoglobulin Inhibitors can be used as reagents for identifying their mediating receptors.

The Mediating Receptors—Inhibitory Function.

As discussed above, serum contains a great variety of mitogenic agents. On this point the present results in 50% (v/v) serum were especially relevant. This concentration of serum is a rich source of mitogens including insulin and the insulin-like growth factors. Nutrients and other serum components also have growth-promoting effects. Examples include diferric transferrin, unsaturated fatty acids bound to albumin, complex lipids and ethanolamine. Clearly, the inhibitor(s) also blocks their growth effects, which lends support to the conclusion that the mediating receptor for the serum-borne agent must have special properties. For instance, the immunoreceptor tyrosine-based inhibitory motif (ITIM) class of Fc receptors is of particular interest with respect to identifying the mediator(s) of immunoglobulin inhibition of cancer cell growth, because the hallmark of the ITIM receptors is that they have an intracellular amino acid sequence motif I/Vx-YxxL (SEQ ID NO:1 and SEQ ID NO:2) that signals cell growth shutdown after ligand binding, and therefore shuts off growth factor dependent growth. In the preceding Examples it is demonstrated that steroid hormones are selectively capable of reversing the effects of the serum inhibitor(s). Plainly, as predicted by the estrocolyone hypothesis, serum contains an inhibitor(s) that has a dominant role in the regulation of proliferation of steroid hormone target cells. The isolated IgA and IgM blocked growth factor dependent growth in serum-free defined medium. Because of its "master switch" character, the newly identified immunoglobulin inhibitors have many important and useful applications. Moreover, the results of the present investigations support the view that the inhibitor(s) will have biological implications extending well beyond estrogen and androgen target tissues.

The Receptor Mediating IgA/IgM/IgG Inhibitory Effects

The results shown in the foregoing Examples strongly indicate that the IgA/IgM growth inhibition is mediated either by the poly-Ig receptor or a very closely related receptor. Establishing a growth regulating function for this "transcytosis" receptor will open new directions in medical diagnosis, treatment and prevention of cancers of mucosal epithelial tissues. It will be determined whether the poly-Ig receptor, or a poly-Ig like receptor mediates the growth regulating effects of IgA on human breast and prostate cancer cells in culture. For this study, the poly-Ig receptor in these cancer cells will be identified using well-known PCR cloning technology, $^{125}$I-labeled IgA chemical cross-linking and Western and immunohistochemistry methods described in the literature.

Next, blocking polyclonal antibodies or blocking monoclonal antibodies will be employed to show that the poly-Ig receptor mediates the growth response. The antibodies will be raised against the poly-Ig receptor using known techniques. Reversal of the inhibitory effect of IgA and IgM by blocking the poly-Ig receptor will suggest that the poly-Ig receptor is not just a simple transport receptor, but that it has a central role in breast and prostate cancer cell growth regulation. There is no existing paradigm for breast or prostate cell growth regulation that involves the poly-Ig receptor or for that matter any receptor specific for the IgA class of immunoglobulins including Fcα receptors (Fridman W H (1991) *FASEB J* 5, 2684-2690).

The different forms and domains of IgG, IgA and IgM that act as inhibitors of normal prostate and breast and other mucosal epithelial cell growth and the hormone responsive and hormone autonomous forms of these cancers in serum-free defined culture medium will be determined and used as tools to evidence or confirm the identity of the receptor(s) responsible for mediating the growth regulatory effect. The properties of the ligand that elicits a response will be evidence supporting the identity of the receptor. Poly-Ig receptor is activated by Fc-domains as are Fcγ receptors. Normal cells are likely to be most inhibited by IgG, IgA and IgM, whereas the $ER^+$ and $AR^+$ cells will likely be inhibited primarily by IgA/IgM, and $ER^-$ and $AR^-$ cells will likely not be inhibited by any of the three classes of immunoglobulins, as predicted by the conceptual model described below. The methods employed will include direct tests of the activity of IgG, IgA and IgM on cell growth as well as assessment of the activity of specific size forms and Fc versus Fab fragments. Antibodies such as anti-J chain and anti-Fc will be used to extend these studies to demonstrate that the Fc is the active domain and that Fc binding receptors are involved.

More specifically, $AR^+$ LNCaP cells, the $AR^-$ PC3 and DU145 cells, and the $AR^+$ ALVA41 cells will be studied. Normal human prostate and breast epithelial cells will be obtained from Clonetics. Growth assays will be done in completely serum-free CAPM (prostate) and DDM-2MF (breast), as described above. IgA1 and IgA2 will be purified from human serum and colostrum, using techniques that are well known and have been described in the literature. Initial small samples will be obtained from a commercial supplier such as The Binding Site (San Diego, Calif.). The monomeric, dimeric and polymeric forms of IgA will be separated using techniques that are well known and have been described in the literature. If only IgA2 has activity, it will be further separated into the A2(m)1 and A2(m)2 allotypes, using well-known techniques that have been described in the literature. Because the initial IgA/IgM inhibitor preparations evaluated were mostly dimeric and monomeric, those forms are expected to be the most active in these series of tests. Confirmation that the most active forms are dimeric/polymeric IgA/IgM will be strong evidence for poly-Ig receptor mediation. Should the monomers be revealed as the only active inhibitor forms, however, it would favor Fc or Fc superfamily receptors, in which case the Fcα will be investigated as a possible mediator.

IgA will be fragmented with a specific protease to yield Fc and Fab fragments from IgA, using techniques that are well known and have been described in the literature. The Fab and Fc fragments of IgM will be obtained using a Pierce Chemicals kit based on immobilized trypsin. Fab and Fc fragments of IgG1 will be obtained using another Pierce kit. If only Fc fragments of IgA and IgM are active, mediation by the poly-Ig receptor is likely. If the Fc of IgG1 is active, it will indicate an Fc receptor as the mediator.

The immunoglobulin inhibitors will also be used as tools or biological reagents to confirm whether IgG acts via a receptor different than IgA/IgM. Based on the results reported above, identification of Fcγ like receptors and the poly-Ig receptor (or related receptor) with normal cells, $ER^+$ cells and $AR^+$ cells is expected, and no functional receptors are expected in $ER^-$ cells or $AR^-$ cells. $^{125}$I-labeled IgG1, IgA and IgM will be prepared using chloramine T or Iodogen beads or coated tube (Pierce Chemicals kits). Binding parameters, binding constants, analyses of the effects of reciprocal additions of labeled and unlabeled immunoglobulins to identify separate or similar binding sites, and determination of the effects of addition of purified secretory component on IgA and IgM binding will be performed as previously described or using well known published techniques. Specific binding will be as total binding minus binding in a 100-fold excess of unlabeled protein. For each form with activity, time, concentration and temperature dependence of binding will be assessed. Scatchard analysis will be used to estimate the number of sites per cell and the association constants ($K_a$). Reciprocal competitions with unlabeled and labeled immunoglobulins will be used to define interaction with the same or different receptors. This latter point is important because binding of both IgA and IgM to the same site strongly favors the poly-Ig receptor and plainly contra-indicates Fcα (IgA) or Fcμ (IgM) receptors, which are members of a superfamily in which each member is specific for a (monomer) class of immunoglobulins. In addition, the effects of blocking antibodies such as anti-secretory component, anti J chain and anti Fc will be assessed with all three cell types. Where indicated, chemical cross-linking with $^{125}$I-labeled Ig will be performed to define the mass of the receptors. Optionally, metabolic labeling and/or immunoprecipitation techniques will be used instead, employing well-known techniques.

Western immunoblotting with normal, steroid hormone receptor positive and steroid hormone receptor negative cell types will be performed to identify the receptors present. Immunohistochemistry will be applied to identify the poly-Ig receptor and Fcγ receptors on all three types of cells using the blocking antibodies. Using a full-length human poly-Ig receptor cDNA clone, S1 nuclease protection assays will be conducted with RNA from normal prostate and breast cells, ER$^+$ and ER$^-$ breast cancer cells, and AR$^+$ and AR$^-$ prostate cancer cells to identify mRNA. In the cases of ER$^+$ and AR$^+$ or ER$^-$ or AR$^-$ cells, this method will help to identify truncated or otherwise altered receptors or non-functional receptors. As described in certain of the preceding examples, Western blots have already been conducted, as well as cell growth assays with receptor blocking antibodies. The remaining analyses will be done with normal cells as well as all other ER$^-$ or AR$^-$ lines. All blocking antibodies are dialyzed against buffer containing charcoal to remove interfering steroid hormones. Rabbit polyclonal anti secretory component will be raised (e.g., by HTI BioProducts, Ramona, Calif.) and rabbit polyclonal anti-human J chain and specific antibodies against the Fc receptors for IgG and IgA are commercially available (Accurate). The specificity of all antiserum will be checked by Western analysis.

To identify the receptors mediating the androgen reversible inhibition of normal and/or AR$^+$ cells, PCR cloning methods will additionally be used to determine the cDNA sequences of the poly-Ig receptor and Fcγ receptors from normal, AR$^+$ and, if indicated, from AR$^-$ cells. This method will provide clear answers to the question of the relationship of the human poly-Ig receptor and Fcγ receptors to immune system negative regulation. It is expected that the receptors will be found to be either identical to known sequences or altered in sequence to convert them to "inhibitory motif" receptors. Based on the known cDNA sequence of the poly-Ig receptor from HT-29 cells, PCR cloning technology will be applied to obtain a full-length clone from the LNCaP and T47D cells. Ongoing investigations are directed to comparing receptor sequences from normal prostate and breast cells to identify any changes. Based on the known sequence of the FcγRIIB1 receptor, these same studies will be repeated. The receptors identified by cloning will be examined for the immunoreceptor tyrosine-based inhibitory motif (ITIM) amino acid sequence I/VxYxxL (SEQ ID NO:1 and SEQ ID NO:2) or related sequences. Concomitantly, the cells will be examined by Western analysis for SHP-1 and SHP-2 phosphatase mediators of the inhibition of growth factor activity. These markers are not only associated with the inhibitory motif but also other inhibitory receptors. More specifically, an LNCaP and T47D full-length poly-Ig receptor clone will be prepared and compared to the reported sequence of the poly-Ig receptor. The same technology will be applied to the poly-Ig receptor from normal prostate cells, and, if indicated, from the AR$^+$ lines. Because these cell lines are expected to express the known poly-Ig receptor, or a related form, the PCR approach is applicable. The same approach will be used with the Fcγ like receptor. However, in this case, because these receptors are predominantly lymphoid origin, the form in epithelial cells may be substantially different. Standard cloning methods will be employed to obtain the complete cDNA sequence of the Fcγ like receptor from normal and LNCaP cells. Total RNA will be extracted and mRNA purified by oligo dT cellulose chromatography (also for Northern analysis). cDNA synthesis will be done with oligo dT primers and AMV reverse transcriptase followed by Rnase H to remove RNA. Second strand synthesis will be done with hexameric random primers and DNA pol. I. Treatment with T4 DNA pol, Rnase H and Rnase A creates blunt ends. EcoR1 methylation is followed by EcoR1 linkers and ligation into a cloning vector. (Stragene) vectors based on λgt10 (hybridization screening) and λgt 10 (secretory component antibody screening). Both vectors will accept inserts larger than the receptor. The cDNA sequence of human poly-Ig receptor known is the genomic sequence. These will be used to prepare sequence specific primers for PCR. The primers will encompass the 5' and 3' non-coding sequences to ensure a complete cDNA. The PCR products will be subcloned using the TA kit from Invitrogen. The sequencing of PCR clones will be done by the dideoxy chain termination method (Lone Star Labs, Houston, TX). From these, determination of whether there have been significant alterations in the receptor during the transition from normal to ER$^-$ and AR$^-$ cancer cells is expected. From sequence data, the ITIM amino acid sequences indicating an inhibitory motif receptor will be sought. It is important to note, however, that the absence of these sequences does not necessarily rule out an inhibitory function. The Western analyses for SHP-1 and SHP-2 will be valuable for indicating an inhibitory function even in the absence of ITIM or when the ITIM is in a modified form.

Discussion of Example 26. Without wishing to be bound by a particular theory, it is proposed that the inhibitory effect of IgG1 is more marked with normal cells than with ER$^+$ or AR$^+$ cancer cell lines and an early step in the pathway to malignancy involves loss by the cell of IgG1 regulation. From preliminary investigations, it is suggested that the IgA and IgM receptors are likely to be a common poly-Ig receptor or poly-Ig like receptor, which in normal cells is expected to be the same as in steroid hormone receptor positive cell lines. In contrast, the IgG1 receptor, likely an Fc gamma type receptor, is expected to either be altered or its expression greatly reduced in ER$^+$ and AR$^+$ cell lines. The demonstration that IgG1 has a major growth inhibiting effect on normal cells may lead to immunization against breast cancer by administering or enhancing IgG1 in at-risk tissues. Characterization of an inhibitory role for IgG1 via an Fcγ-like receptor is expected to lead to important innovations in medical diagnosis, treatment and prevention of cancers of mucus epithelial tissues.

Example 27

Conceptual Model for Cascading Loss of Cell Growth Inhibition in Cancer Cells Concept. The isolated inhibitors, now identified as IgA, IgM and IgG1, controlled breast and prostate cell growth by acting as a steroid hormone reversible inhibitor even when tested under the very rigorous conditions of serum-free defined culture. These active natural inhibitors are present in blood, bodily secretions and mucosal epithelial tissues. The isolated inhibitors readily prevented the growth of these types of cancer cells when they were still in the early (i.e., hormone responsive) stage, but not in the late, non-hormone responsive stage. These results have many implications with regard to the diagnosis, genetic screening, treatment and prevention of breast, prostate, colon and other mucosal cancers. Without wishing to be bound by a particular theory, considering the present experimental results and discoveries, a new conceptual model for understanding how estrogens cause $ER^+$ breast cancer cell growth and for understanding how the natural progression of breast cancers occurs to give rise to highly malignant (and dangerous) hormone autonomous forms is proposed. This same model is applicable to other mucosal tissues that respond to the steroid hormone family of hormones, including androgens and thyroid hormones.

Progression Concept Based on the Breast Cancer Model—Generally Applicable to Mucosal Tissue Cancers. It is well established that breast cancers pass through a characteristic natural history that involves a gradual evolution from near normal growth patterns into cancers that are completely steroid hormone autonomous (i.e. they are no longer stimulated by steroid hormones). These are usually designated estrogen receptor negative ($ER^-$). As disclosed herein, it has been found that autonomous ($ER^-$) breast cancer is accompanied by a loss in sensitivity to IgA or IgM. Fully autonomous breast cancers are not inhibited by these secretory immunoglobulins. In light of the outcome of the present investigations, it appears that autonomous breast cancers lack the poly-Ig receptor that mediates the growth inhibiting effects of IgA and IgM. These results are of extraordinary significance because for the first time they pinpoint a specific genetic change (i.e. in the poly-Ig receptor) that might account for the majority (i.e. approximately 75%) of breast cancers termed "sporadic" and for which there is as yet no clear genetic change identified. Indeed, these results also provide an excellent opportunity to implement gene therapy based on reintroduction of the poly-Ig or poly-Ig like receptor into completely autonomous cancers to regain immunological regulation.

It is well established in the literature that IgG1 is present in serum during childhood, when breast tissue growth is precisely regulated to body size (isometric growth). The other inhibitors, IgA and IgM, are very low at this time, but increase in serum at puberty. Because adult women have increased positive stimuli for breast cell proliferation due to estrogen production, the presence of IgA and IgM may provide additional protection.

It is now proposed that alterations in immune regulation lead to the progression of breast and prostate cells from normal control to $ER^+$ and $AR^+$ cancer cells and that additional alternations in immune control contribute to the development of fully autonomous cancers, according to the following model presented in TABLE 13:

TABLE 13

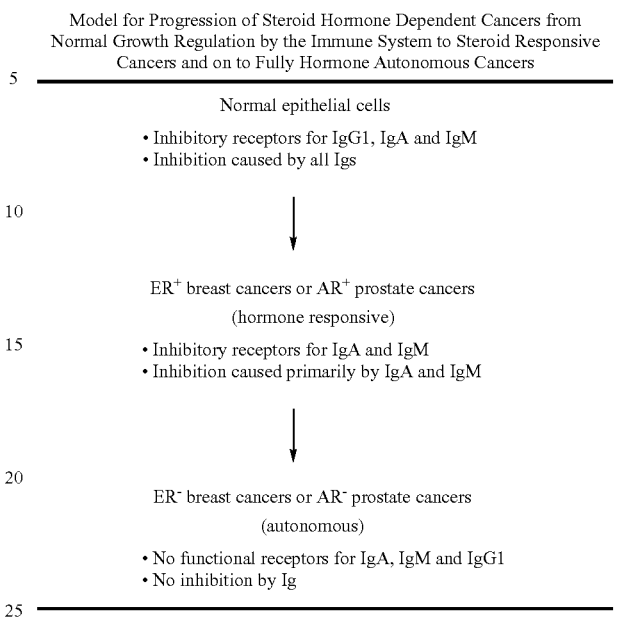

Model for Progression of Steroid Hormone Dependent Cancers from Normal Growth Regulation by the Immune System to Steroid Responsive Cancers and on to Fully Hormone Autonomous Cancers Normal epithelial cells
- Inhibitory receptors for IgG1, IgA and IgM
- Inhibition caused by all Igs

↓

$ER^+$ breast cancers or $AR^+$ prostate cancers
(hormone responsive)
- Inhibitory receptors for IgA and IgM
- Inhibition caused primarily by IgA and IgM

↓

$ER^-$ breast cancers or $AR^-$ prostate cancers
(autonomous)
- No functional receptors for IgA, IgM and IgG1
- No inhibition by Ig Inhibitory Motif Receptors.

The receptors mediating the immune response regulation must be at or very near the beginning of the onset of breast cancer. Using the tools developed in the present series of investigations, it is expected that inhibitory motif receptors for these immunoglobulins will be identified. It is now proposed that the mediating receptors are members of the Ig superfamily, which includes Fc receptors and a new class of Ig inhibitory motif receptors. This new class of receptors has emerging importance because of the increasing recognition of the role of negative regulation of cell growth. These receptors have both common and unique properties. They bind immunoglobulins via the Fc domains and hence can be classified as Fc receptors. One of these is, in fact, FcγRIIB that binds IgG1 (TABLE 12) and causes inhibition of antigen activation of B cells. There are many other examples (Cambier JC (1997) *Proc Natl Acad Sci USA* 94, 5993-5995). Among these are more than 15 receptors now designated Signal-Regulatory Proteins (SIRPs). These all express a special inhibitor motif of six amino acids (I/VxYxxL) (SEQ ID NO:1 and SEQ ID NO:2) that is now referred to as the "immunoreceptor tyrosine-based inhibitory motif" or ITIM. One of the most marked characteristics of the ITIM containing SIRPs is that this motif recruits two phosphatases (SHP-1 and SHP-2) to result in the inhibition of all growth factor dependent proliferation. This is similar to what was observed with IgG1, IgA and IgM and $ER^+$ breast cancer cells and $AR^+$ prostate cancer cells serum-free defined medium. This work is expected to aid in the identification of the missing genes for sporadic breast cancers and a more complete understanding of the cascade of gene changes that lead to complete loss of immune control of breast cell growth.

Similarly, it is suggested that alterations in immune regulation also lead to the progression of prostate cells from normal control to $AR^+$ cancer cells and that additional alterations in immune control contribute to the development of $AR^-$ fully autonomous cancers. Further studies are directed at identifying a cascade of gene changes leading to complete loss of immune control of cell proliferation.

Similarly, it is also proposed that alterations in immune regulation also lead to the progression of colon cancer cells from thyroid hormone receptor (THR) normal control to THR+ cancer cells and that additional alterations in immune control contribute to the development of THR⁻ fully autonomous cancers. Further studies are directed at identifying a cascade of gene changes leading to complete loss of immune control of cell proliferation In continuing investigations, tests to determine whether steroid hormone independent breast and prostate cancer cell growth results from either the loss of the poly-Ig receptor or an inactivation of its function are being carried out. A series of steroid hormone dependent and steroid hormone independent breast and prostate cancer cell lines will be compared for their inhibitory growth responses to IgA, the presence of poly-Ig receptor m-RNA, the expression of the receptor by $^{125}$I-IgA binding analysis and immunohistochemistry localization of receptor. Detection of an absence of the receptor or an inability to bind IgA will suggest that cancer cell autonomy arises due to a loss of secretory immune system regulation. Such a result would be entirely new in the field of hormone dependent cancers and would provide a new immune mechanism responsible for conversion from hormone dependence to autonomy. New immunotherapies can be developed based on activating the receptor in hormone responsive cancers and new gene therapies based on reestablishing the function of this receptor in autonomous breast cancers.

Ongoing investigation is directed at resolving whether hormone autonomous breast cancer cell lines have functional poly-Ig receptors. The ER⁻ cell lines to be studied are the MDA-MB-231, BT-20, MDA-MB-330 the non-tumorus HBL-100, and the Hs578t and Hs578Bst. Each will be evaluated for growth in serum-free medium±IgA and±$E_2$. This study will determine if autonomous cells have lost immune system negative regulation. To determine if the receptor is lost, the S1 nuclease protection assays will be used to seek its mRNA. A kit from AMBION will be used. In addition, 125I-I labeled IgA will be used to determine specific binding characteristics as described above. Immunohistochemistry will be employed to confirm and/or extend the binding data. If the receptor mRNA and protein are absent, these methods should confirm that fact. If they are present but nonfunctional, these methods should confirm that fact as well.

Discussion of Example 27.

The proposed model for progression of mucosal cancers from normal cells to fully autonomous cancers is based on the experimental results presented and is unique. No previous recognition has been published of the roles of IgA, IgM and IgG1 in breast, prostate, or other mucosal cancers. Application of this model has diagnostic implications. Breast, prostate and other cancers can be examined for content of the receptors for IgA, IgM and IgG1 to determine stage of the cancer. This information can be compared to the determination of estrogen receptor and progesterone receptor status to aid in decisions regarding immunotherapy with immune modulators or the immunoglobulins or the use of combined anti-hormone and immune therapy modalities. Tumors that are negative for all of the immunoglobulin receptors are prime candidates for gene therapy to replace the receptors and thereby reestablish immune surveillance, as further described in U.S. patent application Ser. No. 09/852,547 PCT/US2001/015171 entitled "Compositions and Methods for the Diagnosis, Treatment and Prevention of Steroid Hormone Responsive Cancers," which is incorporated herein by reference.

Example 28

IgA/IgM Based Test to Detect Lowered Levels of Steroid Hormone Reversible Cell Growth Inhibitors in Plasma or Body Secretions Toward identifying individuals with high susceptibility to breast cancer or prostate cancer, the level of the inhibitory form of IgA (i.e., IgA dimer) will be measured in an individual's plasma, or the secretory IgA and polymeric IgM will be measured in a bodily secretion. Decreases in plasma levels of IgA or decreased secretory capacity into milk or structural alterations in IgA may confer greater susceptibility to breast cancer. Levels are expected to be low in susceptible individuals and to fall with increasing age in normal individuals, substantially mirroring the age distribution pattern associated with breast and prostate cancer incidence. An antibody raised against the D5 domain disulfide regions, with IgA attached, is an example of an assay for the dimeric/polymeric IgA. In secretory fluids, direct measure of sIgA can be done along with a measure of secretory component by radioimmunoassay or other methods using ELISA or biotin-avidin technology. The levels of IgM can be measured directly although their levels are more subject to wide variations. Also, "J" chain can be measured, but only in samples treated to remove the free (unbound) form known to be in plasma.

Another useful test process is use of rectal or nasal passage antigen challenge and measurement of the appearance of the specific antibody against the antigen in plasma and secretory fluids by standard high capacity clinical test methods. This will directly measure the immune status of the individual. Those with optimum capacity can be separated from individuals with impaired secretory immune system function. Impaired function of the secretory immune system may indicate susceptibility to cancer.

The testing is carried out by first treating a plasma specimen to deplete or substantially remove the steroid hormone content without inactivating or removing the endogenous poly IgA dimer and poly IgM molecules. The hormone depleted specimen is then tested for cell growth inhibitory activity in the presence of added steroid hormone in an in vitro assay employing cultured tumor cells incubated in a defined serum-free medium. Procedures for preparing the steroid hormone depleted plasma or serum and for conducting the assay are described in the preceding examples. XAD™-4 is particularly suited for treating small biological specimens. These extraction methods yield steroid hormone depleted serum that allows identification of 30 to 100-fold estrogen and androgen growth effects (cell number measurement) in culture in 7 to 14 days with human breast and human prostate cancer cells as well at rat mammary, rat pituitary and Syrian hamster kidney tumor cells.

The results are compared to similar tests using positive and negative control plasmas or serums, which have defined levels of IgA dimer and poly IgM. In this way the tumor cell growth inhibitory activity of the individual's plasma is measured. Because the in vitro assay system employs a cell line that forms breast or prostate tumors when implanted in vivo, the in vitro assay results are believed to be suggestive of the in vivo condition of the individual.

Alternatively, or additionally, plasma and bodily fluids may be monitored for autoimmune antibodies that block the inhibitory action of IgA and IgM. An expected increase in autoimmune antibodies with increasing age is expected to coincide with increased cancer incidence, or the incidence of cancer may be high in individuals with early onset disease.

Each and every claim is incorporated into the specification as an embodiment of the present invention. Thus the claims are a further description and are an addition to the preferred embodiments of the present invention. While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims. The disclosures U.S. Provisional Patent Application Nos. 60/203,314; 60/208,348; 60/208,111; 60/229,071 and 60/231,273, and all patents, patent applications and publications cited herein are hereby incorporated herein by reference.

---

What is claimed is:

1. An in vitro assay method for detecting cancer cell growth stimulation by a substance of interest, the method comprising:

maintaining a predetermined population of steroid hormone-responsive mucosal epithelial cancer cells in a steroid hormone-free nutrient medium comprising a basal nutrient fluid devoid of unbound Fe (III) and comprising calcium ions and an amount of at least one immunoglobulin chosen from the group consisting of non-monomeric plasma IgA and polymeric IgM sufficient to inhibit cell growth in the absence of an inhibition-reversing amount of a steroid hormone, said cells also being steroid hormone dependent for proliferation in vivo when implanted into a suitable host;

adding said substance of interest to said cells and nutrient medium to yield a test mixture;

incubating said test mixture for a predetermined period of time under cell growth promoting conditions; and determining the cell population in said test mixture after said predetermined period of time, a measurable increase in said cell population indicating a cancer cell growth stimulating effect by said substance of interest.

2. The assay method of claim 1 comprising maintaining serum-free assay conditions.

3. The assay method of claim 1 wherein the nutrient medium further includes steroid-hormone depleted serum.

4. The assay method of claim 1 wherein the nutrient medium further includes serum that has not been subjected to heat inactivation.

5. The assay method of claim 1 wherein said immunoglobulin is polymeric IgM.

6. The assay method of claim 1 wherein said substance of interest is suspected of containing proteolytic activity, in which said immunoglobulin resists protease degradation.

7. The assay method of claim 1 wherein said immunoglobulin is non-monomeric plasma IgA.

8. The assay method of claim 1 further comprising:

maintaining a second predetermined population of said steroid hormone-responsive mucosal epithelial cancer cells in a steroid hormone-free nutrient medium, said cells also being steroid hormone responsive for proliferation in vivo when implanted into a suitable host;

adding said substance of interest to said cells and nutrient medium, to yield a control mixture;

incubating said control mixture for a predetermined period of time under cell growth promoting conditions;

determining the cell population in said control mixture after said predetermined period of time, a measurable increase in said cell population indicating a control level cell growth stimulating effect by said substance of interest.

9. The method of claim 1 comprising:

maintaining a predetermined population of estrogen responsive mucosal epithelial cancer cells in a steroid hormone-free nutrient medium comprising an amount of at least one immunoglobulin chosen from the group consisting of non-monomeric plasma IgA and polymeric IgM sufficient to inhibit cancer growth in the absence of an inhibition-reversing amount of estrogen, said cell also being estrogen responsive for proliferation in vivo when implanted into a suitable host;

adding a defined amount of said substance of interest to said cells and medium, to yield a test culture;

incubating said test culture for a predetermined period of time under cell growth promoting conditions; and determining the cell population in said test culture after said predetermined period of time, a measurable increase in said cell population indicating cell growth stimulating effect by said substance of interest, whereby an estrogenic substance is detected.

10. The method of claim 9 further comprising testing said substance of interest for cytotoxic effects on said cells.

11. The method of claim 1 wherein said nutrient medium comprises a Fe (III) chelating agent.

12. The method of claim 1 wherein said nutrient medium comprises a cell attachment promoting protein.

13. The method of claim 1 wherein said nutrient medium contains about 1-50 mM calcium ion.

14. The method of claim 1 wherein said basal nutrient fluid comprises D-MEM/F-12.

15. The method of claim 1 wherein said nutrient medium comprises 100 ng/mL to 10 μg/mL insulin, 0.3-10 nM tri-iodothyronine, 2- 50μg/mL diferric transferrin, 5-100 μM ethanolamine, 0.2-5.0 mg/mL bovine serum albumin (BSA), 5-20 ng/mL selenium, 2-10 μM deferoxamine, and, optionally, at least one component chosen from the group consisting of 1-50ng/mL EGF, 0.2-20ng/mL aFGF, 5-50μM phosphoethanolamine, 50-500 μg/mL linoleic acid-BSA, 1-50 μg/mL reduced glutathione, 0.5-2.0 mM glutamine, 1-10 μg/mL heparin, and 20-50 μg human fibronectin.

16. The assay method of claim 1 wherein the steroid hormone-responsive mucosal epithelial cancer cells are selected from the group consisting of GH4C1, GH1 and GH3 rat pituitary cells, ZR-75-1 human breast cancer cells, MCF-7A human breast cancer cells, T47D human breast cancer cells, LNCaP human prostate cancer cells, and HT-29 human colon cancer cells.

17. The assay method of claim 1 wherein the steroid hormone is selected from the group consisting of Estrogens, Androgens, Progesterone, and Glucocorticoids.

18. The assay method of claim 17 wherein the steroid hormone-responsive mucosal epithelial cancer cells are selected from the group consisting of GH4C1, GH1 and GH3 rat pituitary cells, ZR-75-1 human breast cancer cells, MCF-7A human breast cancer cells, T47D human breast cancer cells, LNCaP human prostate cancer cells, and HT-29 human colon cancer cells.

19. The assay method of claim 3 wherein the steroid hormone-responsive mucosal epithelial cancer cells are selected from the group consisting of GH4C1, GH1 and GH3 rat pituitary cells, ZR-75-1 human breast cancer cells, MCF-7A human breast cancer cells, T47D human breast cancer cells, LNCaP human prostate cancer cells, and HT-29 human colon cancer cells.

20. The assay method of claim 3 wherein the steroid hormone is selected from the group consisting of Estrogens, Androgens, Progesterone, and Glucocorticoids.

21. The assay method of claim 20 wherein the steroid hormone-responsive mucosal epithelial cancer cells are selected from the group consisting of GH4C1, GH1 and GH3 rat pituitary cells, ZR-75-1 human breast cancer cells, MCF-7A human breast cancer cells, T47D human breast cancer cells, LNCaP human prostate cancer cells, and HT-29 human colon cancer cells.

22. An in vitro assay method for detecting steroid hormone cancer cell growth stimulation by a substance of interest, the method comprising:

maintaining a predetermined population of steroid hormone-responsive mucosal epithelial cancer cells in a steroid hormone-free nutrient medium comprising a basal nutrient fluid devoid of unbound Fe (III) and comprising calcium ions and an amount of at least one immunoglobulin chosen from the group consisting of non-monomeric plasma IgA and polymeric IgM sufficient to inhibit cell growth in the absence of an inhibition-reversing amount of a steroid hormone, said cells also being steroid hormone dependent for proliferation in vivo when implanted into a suitable host;

adding said substance of interest to said cells and medium to yield a test mixture;

incubating said test mixture for a predetermined period of time under cell growth promoting conditions; and determining the cell population in said test mixture after said predetermined period of time, wherein a measurable increase in said cell population indicates a steroid hormone dependent cancer cell growth stimulating effect by said substance of interest.

23. The method of claim 22 wherein the non-monomeric plasma IgA is dimeric/polymeric IgA.

24. An in vitro assay method for detecting estrogenic cancer cell growth stimulation by a substance of interest, the method comprising:

maintaining a predetermined population of estrogen-responsive mucosal epithelial cancer cells in a steroid hormone-free nutrient medium comprising a basal nutrient fluid devoid of unbound Fe (III) and comprising calcium ions and an amount of at least one immunoglobulin chosen from the group consisting of non-monomeric plasma IgA and polymeric IgM sufficient to inhibit cell growth in the absence of an inhibition-reversing amount of an estrogen, said cells also being estrogen dependent for proliferation in vivo when implanted into a suitable host;

adding said substance of interest to said cells and medium to yield a test mixture;

incubating said test mixture for a predetermined period of time under cell growth promoting conditions; and determining the cell population in said test mixture after said predetermined period of time, wherein a measurable increase in said cell population indicates an estrogenic dependent cancer cell growth stimulating effect by said substance of interest.

25. The method of claim 24 wherein the non-monomeric plasma IgA is dimeric/polymeric IgA.

26. The method of claim 7 wherein the non-monomeric plasma IgA is dimeric/polymeric IgA.

\* \* \* \* \*

SEQUENCE LISTING

```
<160> NUMBER OF SEQ ID NOS: 26

<210> SEQ ID NO 1
<211> LENGTH: 7
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 1

Ile Leu Xaa Tyr Xaa Xaa Leu
1               5

<210> SEQ ID NO 2
<211> LENGTH: 7
<212> TYPE: PRT
<213> ORGANISM: homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 2

Val Leu Xaa Tyr Xaa Xaa Leu
1               5

<210> SEQ ID NO 3
<211> LENGTH: 381
<212> TYPE: PRT
<213> ORGANISM: homo sapiens
<220> FEATURE:
<221> NAME/KEY: mat_peptide
<222> LOCATION: (1)..(381)

<400> SEQUENCE: 3

Arg His Thr Arg Gln Gly Trp Ala Leu Arg Pro Val Leu Pro Thr Gln
1               5                   10                  15

Ser Ala His Asp Pro Pro Ala Val His Leu Ser Asn Gly Pro Gly Gln
                20                  25                  30

Glu Pro Ile Ala Val Met Thr Phe Asp Leu Thr Lys Ile Thr Lys Thr
            35                  40                  45

Ser Ser Ser Phe Glu Val Arg Thr Trp Asp Pro Glu Gly Val Ile Phe
        50                  55                  60

Tyr Gly Asp Thr Asn Pro Lys Asp Asp Trp Phe Met Leu Gly Leu Arg
65                  70                  75                  80

Asp Gly Arg Pro Glu Ile Gln Leu His Asn His Trp Ala Gln Leu Thr
                85                  90                  95

Val Gly Ala Gly Pro Arg Leu Asp Asp Gly Arg Trp His Gln Val Glu
                100                 105                 110
```

Val Lys Met Glu Gly Asp Ser Val Leu Leu Glu Val Asp Gly Glu
            115                 120                 125

Val Leu Arg Leu Arg Gln Val Ser Gly Pro Leu Thr Ser Lys Arg His
            130                 135                 140

Pro Ile Met Arg Ile Ala Leu Gly Gly Leu Leu Phe Pro Ala Ser Asn
145                 150                 155                 160

Leu Arg Leu Pro Leu Val Pro Ala Leu Asp Gly Cys Leu Arg Arg Asp
                165                 170                 175

Ser Trp Leu Asp Lys Gln Ala Glu Ile Ser Ala Ser Ala Pro Thr Ser
            180                 185                 190

Leu Arg Ser Cys Asp Val Glu Ser Asn Pro Gly Ile Phe Leu Pro Pro
            195                 200                 205

Gly Thr Gln Ala Glu Phe Asn Leu Arg Asp Ile Pro Gln Pro His Ala
            210                 215                 220

Glu Pro Trp Ala Phe Ser Leu Asp Leu Gly Leu Lys Gln Ala Ala Gly
225                 230                 235                 240

Ser Gly His Leu Leu Ala Leu Gly Thr Pro Glu Asn Pro Ser Trp Leu
                245                 250                 255

Ser Leu His Leu Gln Asp Gln Lys Val Leu Ser Ser Gly Ser Gly
            260                 265                 270

Pro Gly Leu Asp Leu Pro Leu Val Leu Gly Leu Pro Leu Gln Leu Lys
            275                 280                 285

Leu Ser Met Ser Arg Val Val Leu Ser Gln Gly Ser Lys Met Lys Ala
            290                 295                 300

Leu Ala Leu Pro Pro Leu Gly Leu Ala Pro Leu Leu Asn Leu Trp Ala
305                 310                 315                 320

Lys Pro Gln Gly Arg Leu Phe Leu Gly Ala Leu Pro Gly Glu Asp Ser
                325                 330                 335

Ser Thr Ser Phe Cys Leu Asn Gly Leu Trp Ala Gln Gly Gln Arg Leu
            340                 345                 350

Asp Val Asp Gln Ala Leu Asn Arg Ser His Glu Ile Trp Thr His Ser
            355                 360                 365

Cys Pro Gln Ser Pro Gly Asn Gly Thr Asp Ala Ser His
            370                 375                 380

<210> SEQ ID NO 4
<211> LENGTH: 367
<212> TYPE: PRT
<213> ORGANISM: Oryctolagus cuniculus

<400> SEQUENCE: 4

Thr Gln Arg Ala Gln Asp Ser Pro Ala Val His Leu Ile Asn Gly Leu
1               5                   10                  15

Gly Gln Glu Pro Ile Gln Val Leu Thr Phe Asp Leu Thr Arg Leu Val
            20                  25                  30

Lys Ala Ser Ser Ser Phe Glu Leu Arg Thr Trp Asp Ser Glu Gly Val
            35                  40                  45

Ile Phe Tyr Gly Asp Thr Ser Pro Lys Asp Asp Trp Phe Met Leu Gly
            50                  55                  60

Leu Arg Asp Gly Arg Pro Glu Ile Gln Met His Asn Pro Trp Ala Gln
65                  70                  75                  80

Leu Thr Val Gly Ala Gly Pro Arg Leu Asp Asp Gly Ser Trp His Gln
                85                  90                  95

Val His Val Lys Ile Arg Gly Asp Ser Val Leu Leu Glu Val Asp Gly
            100                 105                 110

```
Lys Glu Val Leu Arg Leu Ser Gln Val Ser Gly Thr Leu His Asp Lys
            115                 120                 125

Pro Gln Pro Val Met Lys Leu Ala Val Gly Gly Leu Leu Phe Pro Pro
        130                 135                 140

Ser Ser Leu Arg Leu Pro Leu Val Pro Ala Leu Asp Gly Cys Leu Arg
145                 150                 155                 160

Arg Gly Ser Trp Leu Asp Pro Gln Ala Gln Ile Ser Ala Ser Ala His
                165                 170                 175

Ala Ser Arg Arg Ser Cys Asp Val Glu Leu Gln Pro Gly Ile Phe Phe
            180                 185                 190

Pro Pro Gly Thr His Ala Glu Phe Ser Leu Gln Asp Ile Pro Gln Pro
        195                 200                 205

Gln Thr Glu Pro Trp Ala Phe Ser Leu Asp Leu Glu Leu Lys Pro Ser
    210                 215                 220

Glu Gly Ser Gly Arg Leu Leu Ala Leu Gly Thr Pro Glu Asp Pro Asn
225                 230                 235                 240

Trp Leu Ser Leu His Leu Gln Asp Gln Lys Val Val Leu Ser Ser Gly
                245                 250                 255

Met Glu Pro Gly Leu Asp Leu Pro Leu Ala Trp Gly Leu Pro Leu Gln
            260                 265                 270

Leu Lys Leu Gly Val Ser Thr Ala Val Leu Ser Gln Gly Ser Lys Lys
        275                 280                 285

Gln Ala Leu Gly Leu Pro Pro Ser Gly Leu Gly Pro Leu Leu Asn Leu
    290                 295                 300

Trp Ala Gln Pro Gln Gly Arg Leu Phe Leu Gly Ala Leu Pro Gly Glu
305                 310                 315                 320

Asp Ser Ser Ala Ser Phe Cys Leu Asp Gly Leu Trp Ala Gln Gly Gln
                325                 330                 335

Lys Leu Asp Met Asp Lys Ala Leu Asn Arg Ser Gln Asp Ile Trp Thr
            340                 345                 350

His Ser Cys Pro Ser Ser Pro Gly Asn Gly Thr Asp Thr Ser His
        355                 360                 365

<210> SEQ ID NO 5
<211> LENGTH: 373
<212> TYPE: PRT
<213> ORGANISM: Rattus norvegicus

<400> SEQUENCE: 5

Leu Arg His Ile Asp Pro Ile Gln Ser Ala Gln Asp Ser Pro Ala Lys
1               5                   10                  15

Tyr Leu Ser Asn Gly Pro Gly Gln Glu Pro Val Thr Val Leu Thr Ile
            20                  25                  30

Asp Leu Thr Lys Ile Ser Lys Pro Ser Ser Phe Glu Phe Arg Thr
        35                  40                  45

Trp Asp Pro Glu Gly Val Ile Phe Tyr Gly Asp Thr Asn Thr Glu Asp
    50                  55                  60

Asp Trp Phe Met Leu Gly Leu Arg Asp Gly Gln Leu Glu Ile Gln Leu
65                  70                  75                  80

His Asn Leu Trp Ala Arg Leu Thr Val Gly Phe Gly Pro Arg Leu Asn
                85                  90                  95

Asp Gly Arg Trp His Pro Val Glu Leu Lys Met Asn Gly Asp Ser Leu
            100                 105                 110

Leu Leu Trp Val Asp Gly Lys Glu Met Leu Cys Leu Arg Gln Val Ser
        115                 120                 125
```

```
Ala Ser Leu Ala Asp His Pro Gln Leu Ser Met Arg Ile Ala Leu Gly
    130                 135                 140
Gly Leu Leu Leu Pro Thr Ser Lys Leu Arg Phe Pro Leu Val Pro Ala
145                 150                 155                 160
Leu Asp Gly Cys Ile Arg Arg Asp Ile Trp Leu Gly His Gln Ala Gln
                165                 170                 175
Leu Ser Thr Ser Ala Arg Thr Ser Leu Gly Asn Cys Asp Val Asp Leu
            180                 185                 190
Gln Pro Gly Leu Phe Phe Pro Pro Gly Thr His Ala Glu Phe Ser Leu
        195                 200                 205
Gln Asp Ile Pro Gln Pro His Thr Asp Pro Trp Thr Phe Ser Leu Glu
    210                 215                 220
Leu Gly Phe Lys Leu Val Asp Gly Ala Gly Arg Leu Leu Thr Leu Gly
225                 230                 235                 240
Thr Gly Thr Asn Ser Ser Trp Leu Thr Leu His Leu Gln Asp Gln Thr
                245                 250                 255
Val Val Leu Ser Ser Glu Ala Glu Pro Lys Leu Ala Leu Pro Leu Ala
            260                 265                 270
Val Gly Leu Pro Leu Gln Leu Lys Leu Asp Val Phe Lys Val Ala Leu
        275                 280                 285
Ser Gln Gly Pro Lys Met Glu Val Leu Ser Thr Ser Leu Leu Arg Leu
    290                 295                 300
Ala Ser Leu Trp Arg Leu Trp Ser His Pro Gln Gly His Leu Ser Leu
305                 310                 315                 320
Gly Ala Leu Pro Gly Glu Asp Ser Ser Ala Ser Phe Cys Leu Ser Asp
                325                 330                 335
Leu Trp Val Gln Gly Gln Arg Leu Asp Ile Asp Lys Ala Leu Ser Arg
            340                 345                 350
Ser Gln Asp Ile Trp Thr His Ser Cys Pro Gln Ser Pro Ser Asn Asp
        355                 360                 365
Thr His Thr Ser His
    370

<210> SEQ ID NO 6
<211> LENGTH: 353
<212> TYPE: PRT
<213> ORGANISM: Phodopus sungorus

<400> SEQUENCE: 6

Asn Gly Pro Gly Gln Glu Pro Val Ala Val Met Thr Ile Asp Leu Thr
1               5                   10                  15
Gln Met Ser Lys Pro Tyr Ser Ser Phe Glu Phe Arg Thr Leu Asp Pro
            20                  25                  30
Glu Gly Val Ile Phe Tyr Gly Asp Thr Asn Thr Lys Asp Asp Trp Phe
        35                  40                  45
Met Leu Gly Leu Arg Asp Gly Gln Leu Glu Ile Gln Met His Asn Pro
    50                  55                  60
Trp Ala Gln Leu Thr Val Gly Phe Gly Pro Arg Leu Asn Asp Gly Arg
65                  70                  75                  80
Trp His Gln Val Glu Leu Lys Met Ser Gly Asp Ser Leu Gln Leu Trp
                85                  90                  95
Val Asp Gly Lys Glu Leu Leu Cys Leu Arg Gln Ile Ser Gly Thr Leu
            100                 105                 110
Ala Asn Asn Ser Trp Pro Ser Met Arg Ile Ala Leu Gly Gly Leu Leu
        115                 120                 125
```

```
Leu Pro Thr Ser Ser Leu Arg Phe Pro Leu Val Pro Ala Leu Asp Gly
    130                 135                 140

Cys Leu Arg Arg Asp Thr Trp Leu Gly His Gln Val His Leu Ser Pro
145                 150                 155                 160

Ser Ala Pro Asn Leu Gly Asn Cys Asp Val Asp Leu Gln Pro Gly Leu
                165                 170                 175

Phe Phe Pro Gln Gly Thr His Ala Glu Phe Ser Leu Gln Asp Ile Pro
            180                 185                 190

Gln Pro Arg Thr Asp Pro Trp Ser Phe Ser Leu Glu Leu Gly Leu Lys
                195                 200                 205

Leu Val Asp Gly Ser Gly Cys Leu Leu Ala Leu Gly Thr Arg Thr Asn
    210                 215                 220

Ser Ser Trp Leu Ser Leu His Leu Gln Asp Gln Lys Val Val Leu Ser
225                 230                 235                 240

Ser Gly Val Glu Pro Lys Leu Val Leu Ala Leu Asp Met Gly Leu Pro
                245                 250                 255

Leu Gln Leu Lys Leu Asp Ile Leu Lys Val Val Leu Ser Gln Gly Pro
                260                 265                 270

Lys Thr Glu Val Leu Gly Ala Ser Ala Ser Arg Leu Ala Ala Leu Arg
                275                 280                 285

Thr Leu Trp Ser His Pro Gln Gly Leu Ser Leu Gly Ala Leu Ala
    290                 295                 300

Gly Asp Asn Ser Ser Ala Ser Phe Cys Leu Ser Asp Leu Trp Val Gln
305                 310                 315                 320

Gly Gln Arg Leu Asp Ile Asp Gln Ala Leu Asn Arg Ser Gln Asn Ile
                325                 330                 335

Trp Thr His Ser Cys Pro His Ser Pro Asn Asn Val Ser His Ile Ser
                340                 345                 350

His

<210> SEQ ID NO 7
<211> LENGTH: 7
<212> TYPE: PRT
<213> ORGANISM: Artificial
<220> FEATURE:
<223> OTHER INFORMATION: Motif #40 of SHBG

<400> SEQUENCE: 7

Ile Pro Gly Val Ile Leu Lys
1               5

<210> SEQ ID NO 8
<211> LENGTH: 9
<212> TYPE: PRT
<213> ORGANISM: artificial
<220> FEATURE:
<223> OTHER INFORMATION: Motif #25 of SHBG

<400> SEQUENCE: 8

Val Val Ser Val Leu Pro Ile Gln Val
1               5

<210> SEQ ID NO 9
<211> LENGTH: 10
<212> TYPE: PRT
<213> ORGANISM: artificial
<220> FEATURE:
<223> OTHER INFORMATION: Motif #31 of SHBG

<400> SEQUENCE: 9
```

```
Ile Glu Gly Val Ile Pro Ile Pro Ser Val
1               5                   10

<210> SEQ ID NO 10
<211> LENGTH: 10
<212> TYPE: PRT
<213> ORGANISM: Artificial
<220> FEATURE:
<223> OTHER INFORMATION: Motif # 22 of SHBG

<400> SEQUENCE: 10

Ser Leu Val Tyr Val Thr Asn Val Ala Lys
1               5                   10

<210> SEQ ID NO 11
<211> LENGTH: 10
<212> TYPE: PRT
<213> ORGANISM: Artificial
<220> FEATURE:
<223> OTHER INFORMATION: Motif # 26 of SHBG

<400> SEQUENCE: 11

Val Val Val Ile Leu Ala Ile Val Pro Lys
1               5                   10

<210> SEQ ID NO 12
<211> LENGTH: 10
<212> TYPE: PRT
<213> ORGANISM: Artificial
<220> FEATURE:
<223> OTHER INFORMATION: Motif # 34 of SHBG

<400> SEQUENCE: 12

Ser Val Pro Gly Leu Val Ser Pro Ser Gln
1               5                   10

<210> SEQ ID NO 13
<211> LENGTH: 10
<212> TYPE: PRT
<213> ORGANISM: Artificial
<220> FEATURE:
<223> OTHER INFORMATION: Motif # 37 of SHBG
<220> FEATURE:
<221> NAME/KEY: misc_feature
<222> LOCATION: (5)..(5)
<223> OTHER INFORMATION: Xaa can be any naturally occurring amino acid

<400> SEQUENCE: 13

Ala Thr Val Val Xaa Leu Ile Ser Asp Phe
1               5                   10

<210> SEQ ID NO 14
<211> LENGTH: 7
<212> TYPE: PRT
<213> ORGANISM: Artificial
<220> FEATURE:
<223> OTHER INFORMATION: Motif # 20 of SHBG

<400> SEQUENCE: 14

Val Gln Leu Ser Pro Ser Glu
1               5

<210> SEQ ID NO 15
<211> LENGTH: 11
<212> TYPE: PRT
<213> ORGANISM: Artificial
<220> FEATURE:
<223> OTHER INFORMATION: Motif # 10 of SHBG
```

```
<400> SEQUENCE: 15

Val Ala Gln Phe Leu Ser Thr Tyr Val Ile Thr
1               5                   10

<210> SEQ ID NO 16
<211> LENGTH: 9
<212> TYPE: PRT
<213> ORGANISM: Artificial
<220> FEATURE:
<223> OTHER INFORMATION: Motif # 34.1 of SHBG

<400> SEQUENCE: 16

Ser Val Pro Gly Leu Val Ser Pro Ser
1               5

<210> SEQ ID NO 17
<211> LENGTH: 12
<212> TYPE: PRT
<213> ORGANISM: Artificial
<220> FEATURE:
<223> OTHER INFORMATION: Motif # 41 of SHBG

<400> SEQUENCE: 17

Val Phe Ala Leu Ala Pro Ile Pro Gly Val Leu Lys
1               5                   10

<210> SEQ ID NO 18
<211> LENGTH: 10
<212> TYPE: PRT
<213> ORGANISM: Artificial
<220> FEATURE:
<223> OTHER INFORMATION: Motif # 26.1 of SHBG

<400> SEQUENCE: 18

Val Val Val Ile Leu Ala Ile Val Pro Lys
1               5                   10

<210> SEQ ID NO 19
<211> LENGTH: 6
<212> TYPE: PRT
<213> ORGANISM: Artificial
<220> FEATURE:
<223> OTHER INFORMATION: Motif # 9 of SHBG

<400> SEQUENCE: 19

Leu Ala Val Gln Val Arg
1               5

<210> SEQ ID NO 20
<211> LENGTH: 11
<212> TYPE: PRT
<213> ORGANISM: Artificial
<220> FEATURE:
<223> OTHER INFORMATION: Motif # 37.2 of SHBG

<400> SEQUENCE: 20

Gly Pro Phe Val Thr Pro Val Thr Val Thr Lys
1               5                   10

<210> SEQ ID NO 21
<211> LENGTH: 9
<212> TYPE: PRT
<213> ORGANISM: Artificial
<220> FEATURE:
<223> OTHER INFORMATION: Motif # 9.1 of SHBG
<220> FEATURE:
<221> NAME/KEY: misc_feature
```

```
<222> LOCATION: (5)..(5)
<223> OTHER INFORMATION: Xaa can be any naturally occurring amino acid

<400> SEQUENCE: 21

Ile Glu Gln Tyr Xaa Ser Thr Phe Lys
1               5

<210> SEQ ID NO 22
<211> LENGTH: 10
<212> TYPE: PRT
<213> ORGANISM: Artificial
<220> FEATURE:
<223> OTHER INFORMATION: Motif # 29 of SHBG
<220> FEATURE:
<221> NAME/KEY: misc_feature
<222> LOCATION: (6)..(6)
<223> OTHER INFORMATION: Xaa can be any naturally occurring amino acid

<400> SEQUENCE: 22

Ile Phe Tyr Pro Ile Xaa Ile Tyr Thr Gln
1               5                   10

<210> SEQ ID NO 23
<211> LENGTH: 16
<212> TYPE: PRT
<213> ORGANISM: Artificial
<220> FEATURE:
<223> OTHER INFORMATION: Motif # 21 of SHBG

<400> SEQUENCE: 23

Glu Val Gln Leu Val Glu Ile Gly Gly Gly Leu Val Gln Pro Gly Arg
1               5                   10                  15

<210> SEQ ID NO 24
<211> LENGTH: 9
<212> TYPE: PRT
<213> ORGANISM: Artificial
<220> FEATURE:
<223> OTHER INFORMATION: Motif # 18 of SHBG

<400> SEQUENCE: 24

Val Val Ser Gly Leu Phe Pro Val Pro
1               5

<210> SEQ ID NO 25
<211> LENGTH: 8
<212> TYPE: PRT
<213> ORGANISM: Artificial
<220> FEATURE:
<223> OTHER INFORMATION: Motif of SHBG

<400> SEQUENCE: 25

Ile Ser Gly Ala Phe Ile Ala Phe
1               5

<210> SEQ ID NO 26
<211> LENGTH: 17
<212> TYPE: PRT
<213> ORGANISM: Artificial
<220> FEATURE:
<223> OTHER INFORMATION: Motif # 18 of SHBG

<400> SEQUENCE: 26

Val Val Ser Gly Leu Phe Val Pro Pro Ile Ser Gly Ala Phe Ile Ala
1               5                   10                  15

Phe
```